United States Patent
Lanquar et al.

(10) Patent No.: US 12,148,506 B2
(45) Date of Patent: Nov. 19, 2024

(54) COMPOSITIONS AND METHODS FOR EXPRESSING GENES OF INTEREST IN HOST CELLS

(71) Applicant: Nobell Foods, Inc., South San Francisco, CA (US)

(72) Inventors: Viviane Lanquar, San Carlos, CA (US); Leyla Hathwaik, South San Francisco, CA (US); Yaxin Wang, South San Francisco, CA (US)

(73) Assignee: Nobell Foods, Inc., South San Francisco, CA (US)

( * ) Notice: Subject to any disclaimer, the term of this patent is extended or adjusted under 35 U.S.C. 154(b) by 0 days.

(21) Appl. No.: 18/519,995

(22) Filed: Nov. 27, 2023

(65) Prior Publication Data

US 2024/0177797 A1    May 30, 2024

Related U.S. Application Data

(63) Continuation of application No. PCT/US2022/031424, filed on May 27, 2022.

(60) Provisional application No. 63/194,424, filed on May 28, 2021.

(51) Int. Cl.
   *G01N 33/48* (2006.01)
   *G16B 15/10* (2019.01)

(52) U.S. Cl.
   CPC .................................... *G16B 15/10* (2019.02)

(58) Field of Classification Search
   None
   See application file for complete search history.

(56) References Cited

U.S. PATENT DOCUMENTS

| | | |
|---|---|---|
| 10,894,812 B1 | 1/2021 | Lanquar et al. |
| 10,947,552 B1 | 3/2021 | Lanquar et al. |
| 10,988,521 B1 | 4/2021 | Lanquar et al. |
| 11,034,743 B1 | 6/2021 | Lanquar et al. |
| 11,072,797 B1 | 7/2021 | Lanquar et al. |
| 11,142,555 B1 | 10/2021 | Lanquar et al. |
| 11,401,526 B2 | 8/2022 | Lanquar et al. |
| 11,685,928 B2 | 6/2023 | Lanquar et al. |
| 11,840,717 B2 | 12/2023 | Lanquar et al. |
| 11,952,606 B2 | 4/2024 | Lanquar et al. |
| 2007/0292918 A1 | 12/2007 | Stelman et al. |
| 2008/0313776 A1 | 12/2008 | Li |
| 2018/0291392 A1 | 10/2018 | El-Richani et al. |
| 2020/0123556 A1 | 4/2020 | El-Richani et al. |
| 2021/0010017 A1 | 1/2021 | El-Richani et al. |
| 2021/0222186 A1 | 7/2021 | El-Richani et al. |
| 2022/0098259 A1 | 3/2022 | Lanquar et al. |
| 2022/0098608 A1 | 3/2022 | Lanquar et al. |
| 2022/0169690 A1 | 6/2022 | Lanquar et al. |
| 2022/0372504 A1 | 11/2022 | Lanquar et al. |
| 2023/0146346 A1 | 5/2023 | Lanquar et al. |
| 2023/0203556 A1 | 6/2023 | Lanquar et al. |
| 2023/0265139 A1 | 8/2023 | Lanquar et al. |
| 2024/0035041 A1 | 2/2024 | El-Richani et al. |
| 2024/0043900 A1 | 2/2024 | Lanquar et al. |
| 2024/0102072 A1 | 3/2024 | Lanquar et al. |

FOREIGN PATENT DOCUMENTS

| | | |
|---|---|---|
| WO | WO-2018187754 A1 | 10/2018 |
| WO | WO-2022251263 A1 | 12/2022 |

OTHER PUBLICATIONS

Yang, Lina, et al. "Graph-based analysis of RNA secondary structure similarity comparison." Complexity 2021 (2021): 1-15.*
Agius, Phaedra, Kristin P. Bennett, and Michael Zuker. "Comparing RNA secondary structures using a relaxed base-pair score." RNA 16.5 (2010): 865-878.*
Bindewald et al., RNA secondary structure prediction from sequence alignments using a network of k—nearest neighbor classifiers. RNA 12(3):342-352 (2006).
Hofacker et al., "Automatic detection of conserved RNA structure elements in complete RNA virus genomes.," Nucleic Acids Res 1998_26_16_3824_3836 (1998).
Ruan et al., "An iterated loop matching approach to the prediction of RNA secondary structures with pseudoknots," Bioinformatics. 20(1):58-66 (2004).
Abrahams et al., "Expression patterns of three genes in the stem of lucerne (*Medicago sativa*)," Plant Mol. Biol. 27:513-528 (1995).
Akiyama et al., "A max-margin training of RNA secondary structure prediction integrated with the thermodynamic model," J Bioinform Comput Biol. 2018; 16(6):1840025 (15 pages).
Andronescu et al., "Computational approaches for RNA energy parameter estimation," RNA 16(12):2304-2318 (2010).
Andronescu et al., "Efficient parameter estimation for RNA secondary structure prediction," Bioformatics. 23(13):119-128 (2007).
Apolloni et al., "RNA Secondary Structure Prediction by MFT Neural Networks," Psychol Forsch. 143-148 (2013.
Bajusz, Dávid, et al. "Why is Tanimoto index an appropriate choice for fingerprint-based similarity calculations?" Journal of Cheminformatics 7.1, pp. 1-13 (2015).
Barsacchi et al., "SwiSpot: modeling riboswitches by spotting out switching sequences," Bioinformatics. 32 (21): 3252-3259 (Nov. 2016).
Bindewald, "CyloFold: secondary structure prediction including pseudoknots". Nucleic Acids Research. 38 (Web Server issue): W368-W372. (Jul. 2010).
Calonaci et al., "Machine learning a model for RNA structure prediction," NAR Genomics and Bioinformatics 2(4), pp. 1-12 (2020).

(Continued)

*Primary Examiner* — Anna Skibinsky
(74) *Attorney, Agent, or Firm* — COOLEY LLP

(57) ABSTRACT

Provided herein are compositions and methods for stabilizing RNA, increasing protein expression, and combinations thereof. Also provided are compositions and methods for utilizing stabilized RNA or increased protein levels to generate chordate proteins in a host cell, such as a plant cell.

14 Claims, 29 Drawing Sheets

Specification includes a Sequence Listing.

(56) References Cited

OTHER PUBLICATIONS

Chen et al., "A DNA sequence element that confers seed-specific enhancement to a constitutive promoter," The EMBO Journal 7(2):297-302 (1988).
Chen et al., "RNA Secondary Structure Prediction By Learning Unrolled Algorithms," International Conference on Learning Representations. 2020, 19 pages.
Chin et al., "Codon Optimization OnLine (COOL): a web-based multi-objective optimization platform for synthetic gene design." Bioinformatics 30(15):2210-2212 (2014).
Colot et al., "Localization of sequences in wheat endosperm protein genes which confer tissue-specific expression in tobacco," EMBO J. 6:3559-3564 (1987).
Daly and Hearn, "Expression of heterologous proteins in Pichia pastoris: a useful experimental tool in protein engineering and production," J. Mol. Recognition 18:119-38 (Nov. 26, 2004).
Dawson et al., "Prediction of RNA pseudoknots using heuristic modeling with mapping and sequential folding". PLOS ONE. 2 (9): e905, 7 pages. (Sep. 2007).
Ding Y, Lawrence CE (Dec. 2003). "A statistical sampling algorithm for RNA secondary structure prediction". Nucleic Acids Research. 31 (24): 7280-7301.
Do et al., "CONTRAfold: RNA secondary structure prediction without physics-based models," Bioinformatics. 22 (14): e90-e98 (Jul. 2006).
Fox et al., "Chemistry and biochemistry of milk constituents," Food Biochemistry and Food Processing 2:442-464 (2006).
Garbarino et al., "Isolation of a ubiquitin-ribosomal protein gene (ubi3) from potato and expression of its promoter in transgenic plants," Plant Molecular Biology 24(1):119-127 (Feb. 1994).
Gaspar et al., "EuGene: maximizing synthetic gene design for heterologous expression," Bioinformatics 28(20):2683-2684 (2012).
GenBank Accession No. X00806.1, dated Nov. 14, 2006, 2 pages.
GenBank Accession No. EF030816, dated Nov. 11, 2006, 2 pages.
GenBank Accession No. EF030817, dated Nov. 11, 2006, 2 pages.
GenBank Accession No. KJ787649.1, dated Aug. 11, 2014, 2 pages.
GenBank accession No. L22576.1, dated Dec. 28, 2007, 2 pages.
GenBank accession No. X51514.1 dated Apr. 18, 2005, 2 pages.
GenBank Accession No. X59836.1, dated Jul. 20, 1992, 2 pages.
Giegerich et al., "Abstract shapes of RNA". Nucleic Acids Research. 32 (16):4843-4851 (2004).
Grey et al. "A viral microRNA down-regulates multiple cell cycle genes 10 through mRNA 5' UTRs." PLoS Pathog 6(6):e1000967, pp. 1-9 (2010).
Grote et al., "JCat: a novel tool to adapt codon usage of a target gene to its potential expression host," Nucleic Acids Res. 33, W526-W531 (Jul. 1, 2005).
Gruber "The Vienna RNA Websuite," Nucleic Acids Research, vol. 36, Issue suppl. 2, Jul. 1, 2008, pp. W70-W74.
Guignon et al., "RNA StrAT: RNA Secondary Structure Analysis Toolkit," 2008, 1 page. [Retrieved on Sep. 10, 2020]. Retrieved from the internet: http://www.cecm.sfu.ca/-cchauve/Publications/RCG08_74.pdf.
Guimaraes et al., "D-Tailor: automated analysis and design of DNA sequences," Bioinformatics 30, 1087-1094 (2014).
Hamada et al., "Prediction of RNA secondary structure using generalized centroid estimators". Bioinformatics. 25 (4):465-473 (Feb. 2009).
Hamada et al., "Predictions of RNA secondary structure by combining homologous sequence information". Bioinformatics. 25 (12): i330-i338, (2009).
Hattori et al., "High-level expression of tuberous root storage protein genes of sweet potato in stems of plantlets grown in vitro on sucrose medium," Plant Mol. Biol. 14:595-604 (1990).
Haynes et al., "Using a neural network to identify secondary RNA structures quantified by graphical invariants," Match Commun Math Comput Chem. 60(2):277-90 (2008).
Higgins et al., "The sequence of a pea vicilin gene and its expression in transgenic tobacco plants," Plant Mol Biol. 11:683-695 (1989).
Hofacker et al., "Fast Folding and Comparison of RNA Secondary Structures". Monatshefte für Chemie. 125 (2):167-188 (1994).
Hoover et al., "DNAWorks: an automated method for designing oligonucleotides for PCR-based gene synthesis," Nucleic Acids Res. 30(10):e43, pp. 1-7 (May 15, 2002).
Hor et al., "A Tool Preference Choice Method for RNA Secondary Structure Prediction by SVM with Statistical Tests," Evol Bioinformatics Online. 9:163-84 (2013).
International Search Report and Written Opinion for PCT Application No. PCT/US2022/31424, mailed Oct. 27, 2022, 17 pages.
Jofuku and Goldberg, "Kunitz Trypsin Inhibitor Genes Are Differentially Expressed during the Soybean Life Cycle and in Transformed Tobacco Plants," The Plant Cell 1:1079-1093 (Nov. 1989).
Jung et al., "Visual gene developer: a fully programmable bioinformatics software for synthetic gene optimization," BMC Bioinformatics 12, 340, 13 pages (2011).
Knudsen B, Hein J. RNA secondary structure prediction using stochastic context-free grammars and evolutionary history. Bioinformatics. 15(6):446-54 (1999).
Knudsen, "Pfold: RNA secondary structure prediction using stochastic context-free grammars," Nucleic Acids Res. 31(13):3423-8 (2003).
Koessler et al., "A predictive model for secondary RNA structure using graph theory and a neural network," BMC Bioinformatics. 2010; 11(Suppl 6):521.
Laxa, "Intron-mediated enhancement: a tool for heterologous gene expression in plants?." Frontiers in plant science 7:1977, 13 pages, (Jan. 6, 2017).
Liu et al., "A Hopfield Neural Network based algorithm for RNA secondary structure prediction," 1st International Multi Symposium on Computer and Computational Sciences; Hangzhou, China: IEEE; 2006, 7 pages.
Lu et al., "Activity of the 5' regulatory regions of the rice polyubiquitin rubi3 gene in transgenic rice plants as analyzed by both GUS and GFP reporter genes," Plant Cell Rep 27, 1587-1600 (2008).
Lu et al. Predicting RNA secondary structure via adaptive deep recurrent neural networks with energy-based filter, BMC Bioinformatics. 2019; 20(Suppl 25):684, 10 pages.
Mann et al., "Switchgrass (*Panicum virgatum* L.) polyubiquitin gene (PvUbi1 and PvUbi2) promoters for use in plant transformation," BMC Biotechnol 11:74, pp. 1-14 (2011).
Markham et al., UNAFold: software for nucleic acid folding and hybridization. Methods in Molecular Biology 453:3-31 (2008).
Marris et al., "The 5' flanking region of a barley B hordein gene controls tissue and developmental specific CAT expression in tobacco plants," Plant Mol. Biol. 10:359-366 (1988).
Mathews et al. Folding and finding RNA secondary Spring Harbor perspectives in biology vol. 2,12 (2010): a003665, 15 pages.
Mathews et al., "Incorporating chemical modification constraints into a dynamic programming algorithm for prediction of RNA secondary structure". Proceedings of the National Academy of Sciences of the United States of America. 101(19): 7287-7292 (May 2004).
Newbigin et al, "Pea convicilin: structure and primary sequence of the protein and expression of a gene in the seeds of transgenic tobacco," Planta 180:461-470 (1990).
Nikolova et al., Approaches to Measure Chemical Similarity—a Review. QSAR Comb. Sci., 22: 1006-1026 (2003).
O'Leary et al., "RNA structural analysis of the MYC mRNA reveals conserved motifs that affect gene expression" PLoS ONE, Jun. 17, 2019, vol. 14, No. 6, article e0213758, pp. 1-19, [Retrieved on Sep. 10, 2022]. Retrieved from the internet: https://doi.org/10.1371/journal.pone.0213758.
Orom et al., "MicroRNA-10a binds the 5'UTR of ribosomal protein mRNAs and enhances their translation," Mol Cell. May 23, 2008; 30(4):460-71.
Ortega et al., "The 5' untranslated region of the soybean cytosolic glutamine synthetase p 1 gene contains prokaryotic translation initiation signals and acts as a translational enhancer in plants," Molecular genetics and genomics 287(11):881-893 (Dec. 2012).
Puigbo et al., "OPTIMIZER: a web server for optimizing the codon usage of DNA sequences. Nucleic Acids Res. Jul. 2007; 35(Web Server issue): W126-31", Epub Apr. 16, 2007.

(56) References Cited

OTHER PUBLICATIONS

Qasim et al., "Secondary Structure Prediction of RNA using Machine Learning Method," Int J Comput Appl. 2011; 10(6):0975-8887, 8 pages.
Quan et al., "Developing parallel ant colonies filtered by deep learned constrains for predicting RNA secondary structure with pseudo-knots," Neurocomputing. 2020; 384:104-14.
Reeder et al. "pknotsRG: RNA ps including near-optimal structures and sliding windows". Nucleic Acids Research. 35:W320-W324 (Jul. 2007).
Rerie et al. , "Developmental and environmental regulation of pea legumin genes in transgenic tobacco," Mol Gen Genet. Jan. 1991;225(1):148-57.
Richardson et al., "GeneDesign: rapid, automated design of multikilobase synthetic genes," Genome Res. 16, 550-556 (2006).
Rivas et l., "A dynamic programming algorithm for RNA structure prediction including pseudoknots," Journal of Molecular Biology. 285 (5): 2053-2068 (Feb. 1999).
Rocha-Sosa et al., "Both developmental and metabolic signals activate the promoter of a class I patatin gene," EMBO J. 8(1):23-29 (1989).
Sakakibara et al., "Stochastic context free grammars for tRNA modeling," Nucleic Acids Research 22(23):5112-5120 (1994).
Sato et al., "IPknot: fast and accurate prediction of RNA secondary structures with pseudoknots using integer programming". Bioinformatics. 27(13): i85-i93 (Jul. 2011).
Sato et al., "RNA secondary structure prediction using deep learning with thermodynamic integration," Nat Commun. (2021) 12:945, pp. 1-9.
Schemthaner et al., "Endosperm-specific activity of a zein gene promoter in transgenic tobacco plants," EMBO J. 7:1249-1255 (1988).
Schroeder et al., "Ensemble of secondary structures for encapsidated satellite tobacco mosaic virus RNA consistent with chemical probing and crystallography constraints". Biophysical Journal. 101(1):167-175 (Jul. 2011).
Segupta Gopalan et al., "Developmentally regulated expression of the bean f8-phaseolin gene in tobacco seed," Proc. Natl. Acad. Sci.U.S.A. 82:3320-3324 (1985).
Singh et al., "SPOT-RNA: RNA Secondary Structure Prediction using an Ensemble of Two-dimensional Deep Neural Networks and Transfer Learning," Nat Commun. 2019; 10 (1):1-13.
Singh et al., "RNA secondary structure prediction using an ensemble of two-dimensional deep neural networks and transfer learning". Nature Communications 10(1):5407, pp. 1-13. (Nov. 27, 2019).
Steeg, "Neural networks, adaptive optimization, and RNA secondary structure prediction," Artificial intelligence and molecular biology. 121-60 (1993).
Strixner et al., "Egg proteins," In Handbook of food proteins (pp. 150-209 (2011). Woodhead publishing.
Swenson et al. "GTfold: enabling parallel RNA secondary structure prediction on multi-core desktops," BMC Research Notes. 5: 341 (Jul. 2012).
Takaiwa et al., "Compensatory rebalancing of rice prolamins by production of recombinant prolamin/bioactive peptide fusion proteins within ER-derived protein bodies," Plant Cell Rep 37:209-223 (2018).
Takefuji et al., "Parallel algorithms for finding a near-maximum independent set of a circle graph," IEEE Trans Neural Netw. 1990; 1(3):263- 7.
Theis et all., "Prediction of RNA Secondary Structure Including Kissing Hairpin Motifs". In Moulton, Vincent and Singh, Mona (ed.). Algorithms in Bioinformatics. vol. 6293 (Lecture Notes in Computer Science ed.). Springer Berlin Heidelberg. pp. 52-56 (2010).
Tian et al., "Ubiquitin fusion expression and tissue-dependent targeting of hG-CSF in transgenic tobacco," BMC biotechnology 11, No. 91, 14 pages (Oct. 11, 2011).
Tsang et al., "SARNA-Predict: accuracy improvement of RNA secondary structure prediction using permutation-based simulated annealing". IEEE/ACM Transactions on Computational Biology and Bioinformatics. 7(4):727-740 (2010).
Tschofen et al., "Plant molecular farming: much more than medicines," Annual Review of Analytical Chemistry 9 (2016):271-294.
UniProtKB/Swiss-Prot No. P02666, updated Nov. 8, 2023, created Jul. 21, 1989, 7 pages.
U.S. Appl. No. 18/066,604, filed Dec. 15, 2022, by El-Richini et al.
Vanegas et al., "RNA CoSSMos: Characterization of Secondary Structure Motifs—a searchable database of secondary structure motifs in RNA three-dimensional structures," Nucleic Acids D439-D444 (2012).
Villalobos et al., "Gene Designer: a synthetic biology tool for constructing artificial DNA segments," BMC Bioinformatics 2006, 7:285, 8 pages.
Voelker et al., "Differences in expression between two seed lectin alleles obtained from normal and lectin-deficient beans are maintained in transgenic tobacco," EMBO J. 6:3571-3577) (Dec. 1, 1987).
Wang et al., "DMfold: A Novel Method to Predict RNA Secondary Structure With Pseudoknots Based on Deep Learning and Improved Base Pair Maximization Principle," Front Genet.2019; 10:143, pp. 1-12.
Westhof, "twenty years of RNA crystallography," RNA. 2015; 21(4):486-487.
Willmott et al., "Improving RNA secondary structure prediction via state inference with deep recurrent neural networks," Comput Math Biophys. 2020; 8:36-50.
Wong et al., "Improved co-expression of multiple genes in vectors containing internal ribosome entry sites (IRESes) from human genes," Gene Therapy 9:337-344 (2002).
Wu et al., "RNA Secondary Structure Prediction Based on Long Short-Term Memory Model," 14th International Conference on Intelligent Computing (ICIC); 2018; Wuhan, China, xx pages.
Wu et al., "The synthetic gene designer: a flexible web platform to explore sequence space of synthetic genes for heterologous expression," in 2005 IEEE Computational Systems Bioinformatics Conference, Workshops and Poster Abstracts, Aug. 8-11, 2005, 2 pages. (California: Stanford University, (Sep. 2005).
Xayaphoummine et al., "Kinefold web server for RNA/DNA folding path and structure prediction including pseudoknots and knots". Nucleic Acids Research. 33 (Web Server issue): W605-W610. (Jul. 2005).
Xia et al.,"Thermodynamic parameters for an expanded nearest-neighbor model for formation of RNA duplexes with Watson-Crick Base Pairs," Biochemistry. 37(42):14719-35 (1998).
Xu et al., "Characterization of a rice gene family encoding root-specific proteins," Plant Mol. Biol. 27:237-248 (1995).
Yamamoto et al., "Characterization of cis-acting sequences regulating root-specific gene expression in tobacco," Plant Cell. Apr. 1991;3(4):371-82.
Yamauchi et al., "Promoter regions of cysteine endopeptidase genes from legumes confer germination-specific expression in transgenic tobacco seeds," Plant Mol Biol. 30:321-9 (Jan. 1996).
Yang et al., "Tools for the automatic identification and classification of RNA base pairs," Nucleic Acids Research 31:3450-3460 (2003).
Yonemoto et al., "A semi-supervised learning approach for RNA secondary structure prediction," Comput Biol Chem. 57:72-9 (2015).
Zakov et al., "Rich parameterization improves RNA structure prediction," Journal of Computational Biology. 18 (11):1525-1542. (Nov. 2011).
Zhang et al., "A New Method of RNA Secondary Structure Prediction Based on Convolutional Neural Network and Dynamic Programming," Front Genet. 2019; 10:467, 12 pages.
Zhao et al., "Review of machine learning methods for RNA secondary structure prediction," PLoS Comput Biol 17(8): e1009291. (Aug. 26, 2021), 22 pages.
Zhu et al., "Research on folding diversity in statistical learning methods for RNA secondary structure prediction," Int J Biol Sci. 14(8):872-82, (2018).
Zou et al., "The stem-loop region of the tobacco psbA 5' UTR is an important determinant of mRNA stability and translation efficiency," Molecular genetics and genomics 269, No. 3 (2003): 340-349.

(56) References Cited

OTHER PUBLICATIONS

Zuker et al., "Optimal computer folding of large RNA sequences using thermodynamics and auxiliary information". Nucleic Acids Research. 9 (1): 133-148 (Jan. 1981).

* cited by examiner

N indicates the number of seeds analyzed.

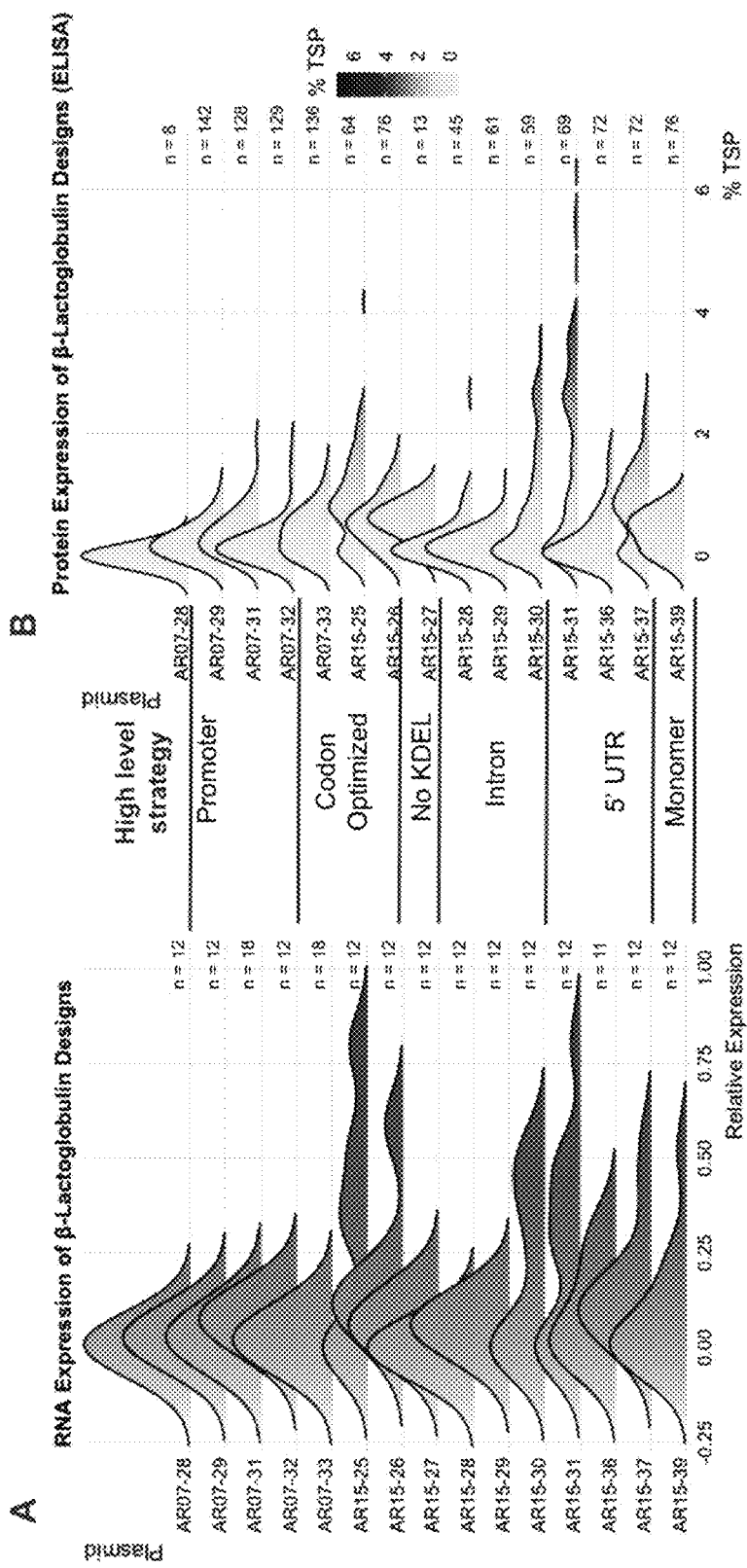

| Name | Predicted Structure | Highest RNA Expression |
|---|---|---|
| OLG1 (SEQ ID NO: 683) | 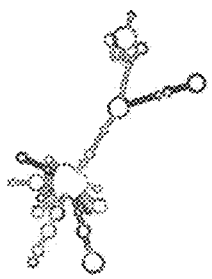 | 0.08 |
| OLG2 (SEQ ID NO: 685) | 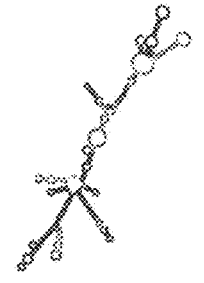 | 0.78 |
| OLG3 (SEQ ID NO: 687) | 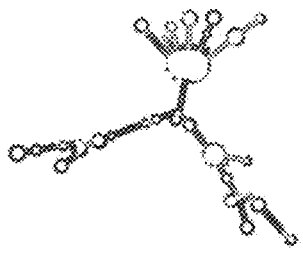 | 0.60 |
| OLG4 (SEQ ID NO: 689) | 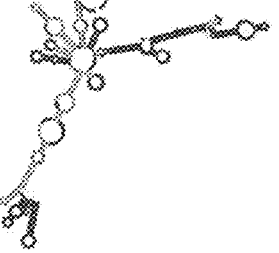 | 0.14 |
FIG. 8

| Name | Predicted MFE Structure | Predicted Centroid Structure | Highest RNA Expression |
|---|---|---|---|
| OLG1 (SEQ ID NO: 683) | 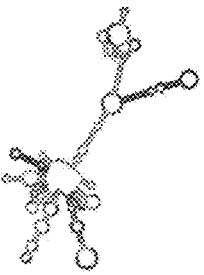 | 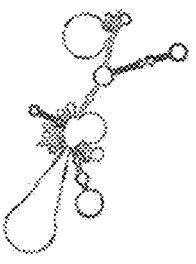 | 0.08 |
| OLG2 (SEQ ID NO: 685) | 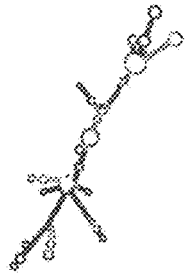 | 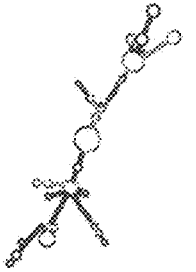 | 0.78 |
| OLG3 (SEQ ID NO: 687) | 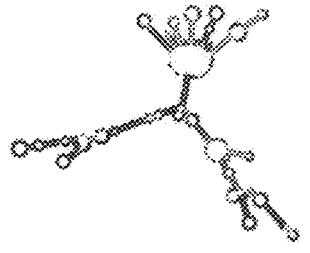 | 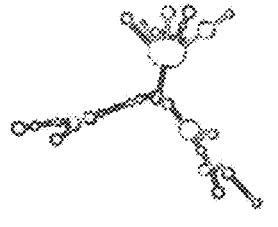 | 0.60 |
| OLG4 (SEQ ID NO: 689) | 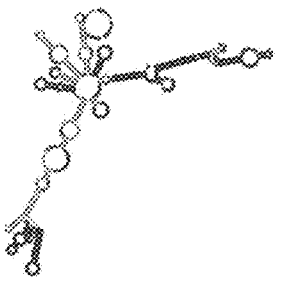 | 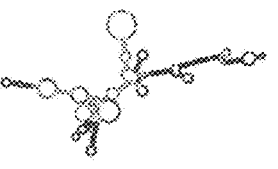 | 0.14 |
FIG. 9

FIG. 10A
| Name (SEQ ID) | MFE structure | Centroid Structure |
|---|---|---|
| OLG1 (683) |  |  |
| OLG2 (685) |  |  |

FIG. 10C

| Name (SEQ ID) | Curve Length Measure and (Visual Score) | Highest RNA Expression | RNA Expression Fold Change | Qualitative RNA Category |
|---|---|---|---|---|
| OLG1 (683) | 7.8 (4) | 0.08 | 1 | Low |
| OLG2 (685) | 1.8 (1) | 0.78 | 10 | High |

FIG. 10D
| Name (SEQ ID) | MFE structure | Centroid Structure |
|---|---|---|
| OLG3 (687) | 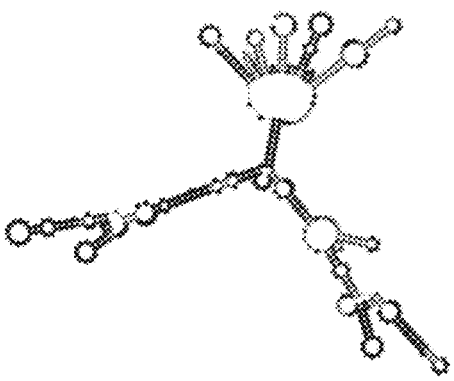 | 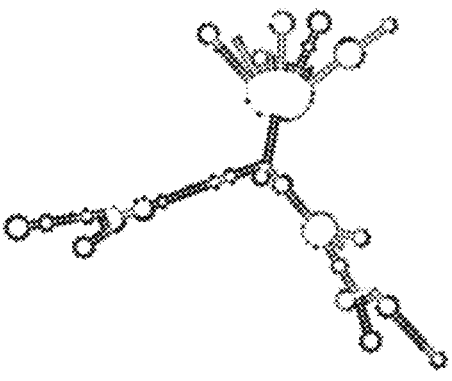 |
| OLG4 (689) |  | 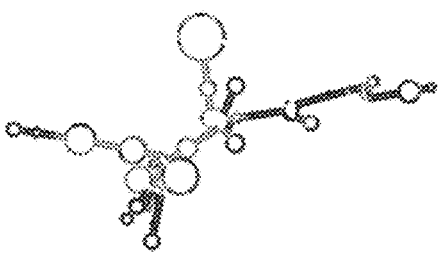 |

FIG. 10F

| Name (SEQ ID) | Curve Length Measure and (Visual Score) | Highest RNA Expression | RNA Expression Fold Change | Qualitative RNA Category |
|---|---|---|---|---|
| OLG3 (687) | 2.2 (2) | 0.60 | 8 | High |
| OLG4 (689) | 7.7 (3) | 0.14 | 2 | Low |

FIG. 11A
| Name (SEQ ID) | MFE structure | Centroid Structure |
|---|---|---|
| OOVAL1 (693) | 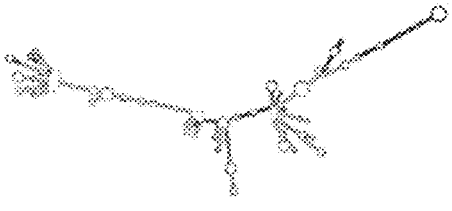 | 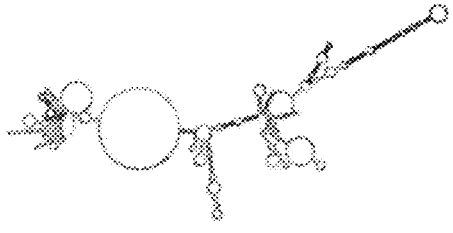 |
| OOVAL2 (695) | 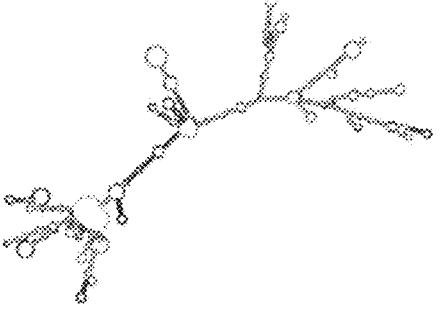 |  |

FIG. 11C

| Name (SEQ ID) | Curve Length Measure and (Visual Score) | Highest RNA Expression | RNA Expression Fold Change | Qualitative RNA Category |
|---|---|---|---|---|
| OOVAL1 (693) | 16.5 (4) | 0.033 | 1 | Low |
| OOVAL2 (695) | 9.9 (1) | 0.108 | 4 | High |

FIG. 11D
| Name (SEQ ID) | MFE structure | Centroid Structure |
|---|---|---|
| OOVAL3 (697) | 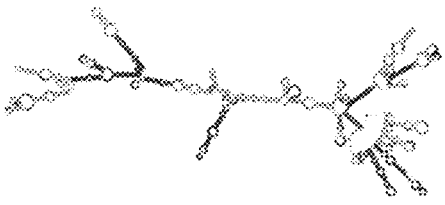 | 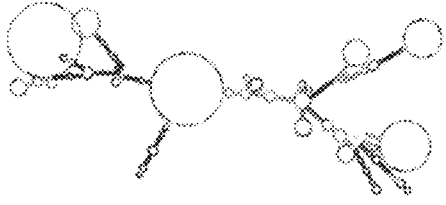 |
| OOVAL4 (699) | 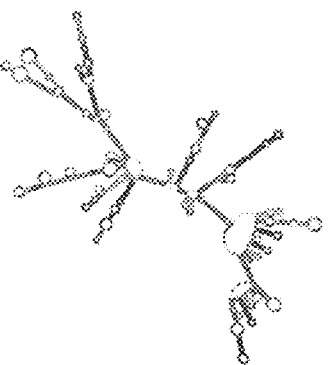 | 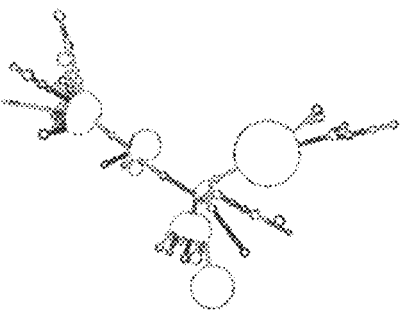 |

FIG. 11F

| Name (SEQ ID) | Curve Length Measure and (Visual Score) | Highest RNA Expression | RNA Expression Fold Change | Qualitative RNA Category |
|---|---|---|---|---|
| OOVAL3 (697) | 11.7 (2) | 0.083 | 3 | High |
| OOVAL4 (699) | 16.3 (3) | 0.035 | 1 | Low |

FIG. 12A
| Name | MFE structure | Centroid Structure |
|---|---|---|
| eGFP1 (SEQ ID NO: 830) | 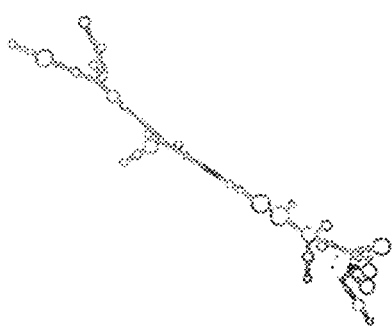 | 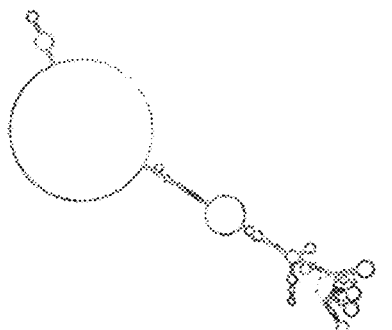 |
| eGFP2 (SEQ ID NO: 831) | 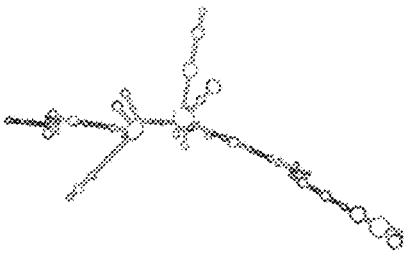 | 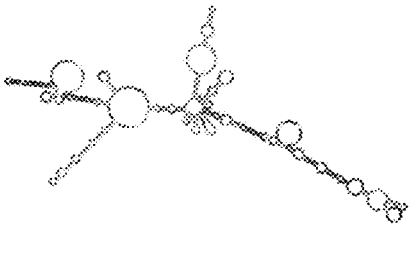 |

FIG. 12C

| Name | Curve Length Measure and (Visual Score) | Highest RNA Expression | RNA Expression Fold Change | Qualitative RNA Category |
|---|---|---|---|---|
| eGFP1 (SEQ ID NO: 830) | 10.1 (3) | 0.033 | 1 | Low |
| eGFP2 (SEQ ID NO: 831) | 5.2 (2) | 0.230 | 7 | High |

FIG. 12D
| Name | MFE structure | Centroid Structure |
|---|---|---|
| eGFP (SEQ ID NO: 829) | 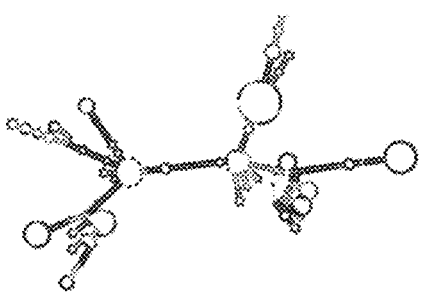 | 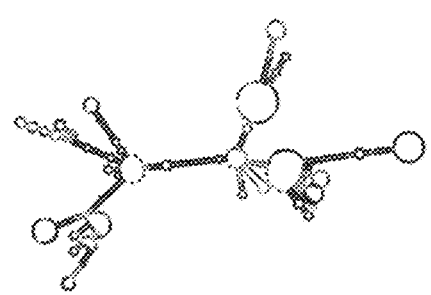 |

FIG. 12F

| Name | Curve Length Measure and (Visual Score) | Highest RNA Expression | RNA Expression Fold Change | Qualitative RNA Category |
|---|---|---|---|---|
| eGFP (SEQ ID NO: 829) | 2.7 (1) | 0.650 | 19 | High |

COMPOSITIONS AND METHODS FOR EXPRESSING GENES OF INTEREST IN HOST CELLS

CROSS REFERENCE TO RELATED APPLICATION

This application is a continuation of International Application No. PCT/US2022/031424 filed May 27, 2022, which claims priority to U.S. Provisional Patent Application No. 63/194,424 filed May 28, 2021, the contents of each of which are incorporated herein by reference in their entireties.

REFERENCE TO AN ELECTRONIC SEQUENCE LISTING

The contents of the electronic sequence listing (ALRO_009_01US_SeqList_ST26.xml; Size: 1,019,910 bytes; and Date of Creation: Nov. 7, 2023) are herein incorporated by reference in its entirety.

TECHNICAL FIELD

The present disclosure is related to compositions and methods for expressing exogenous proteins in host cells.

BACKGROUND

The global population is estimated to reach 9.1-9.7 billion by 2050, with an approximately 1.8-fold increase in income per capita. Food consumption is predicted to become increasingly based on animal derived products—mainly due to increased wealth in developing countries. Thus, population growth and increased demand for high-protein diets will require dramatic changes in the food industry.

Proteins used as ingredients in the food industry have traditionally been based on isolates from natural sources, such bovine milk. However, it is rapidly becoming unsustainable to produce animal-derived food products, given their environmental impact and limited resources for production thereof. Recombinant protein production could provide an alternative source of protein for use in food applications. However, in order to make the use of recombinant proteins in food economically feasible, high levels of protein expression must be achieved in one or more host cells. Achieving such high expression levels poses numerous technical challenges.

Ovalbumin (OVAL) and β-Lactoglobulin (LG) are two proteins that play an important role in the food industry. OVAL is the main protein found in egg white that comprises 54% of the total protein. It is a globular monomeric protein that comprises a single polypeptide chain of 385 amino acids with a 42.7 kDa molecular weight which exist as a tetramer. OVAL is widely used in the food industry for its ability to foam and to form gels. On the other hand, LG is the major whey protein of milk in most mammals, making up approximately 52% of the whey protein. It is an 18.2 kDa highly structured globular protein that can exist as monomers, dimers and multimers depending on the pH of the medium. LG is a valuable ingredient in formulating food products because it can improve properties such as emulsification, gelling, biding and can provide increased nutritional value for health and wellbeing.

There is an urgent need to develop compositions and methods that allow for production of recombinant proteins at high levels in one or more host cells, so that the proteins may be used as ingredients in food compositions. Specifically, there is a need in the art to develop compositions and methods that increase expression of OVAL and LG in various transgenic organisms, cells, and the like.

BRIEF SUMMARY

Provided is a method for selecting a nucleic acid sequence, said method comprising the steps of a) providing data on a plurality of nucleic acid sequences; b) predicting secondary structure of the plurality of nucleic acid sequences, with a plurality of RNA folding models, such that each nucleic acid sequence in the plurality of nucleic acid sequences is associated with at least two predicted secondary structures; c) determining a structural similarity score for the at least two predicted secondary structures associated with each nucleic acid sequence; and d) selecting a nucleic acid sequence with a higher structural similarity score than at least one other nucleic acid sequence in the plurality of nucleic acid sequences; wherein the selected nucleic acid sequence is predicted to accumulate at higher levels when expressed in a host cell.

Provided is a method for selecting a nucleic acid sequence, said method comprising the steps of: a) providing data on a plurality of nucleic acid sequences, each nucleic acid sequence in the plurality of nucleic acid sequences being associated with at least two predicted secondary structures from different RNA folding models; b) determining a structural similarity score for the at least two predicted secondary structures associated with each nucleic acid sequence; c) selecting a nucleic acid sequence with a higher structural similarity score than at least one other nucleic acid sequence in the plurality of nucleic acid sequences; wherein the selected nucleic acid sequence is predicted to accumulate at higher levels when expressed in a host cell. In some embodiments, at least one of the RNA folding models employs machine learning. In some embodiments, the plurality of nucleic acid sequences encode the same amino acid sequence. In some embodiments, the plurality of nucleic acid sequences encode amino acids sharing at least 90%, 91%, 92%, 93%, 94%, 95%, 96%, 97%, 98%, or 99% sequence identity. In some embodiments, the method comprises manufacturing the selected nucleic acid sequence into a nucleic acid. In some embodiments, the method comprises expressing the selected nucleic acid sequence in a host cell. In some embodiments, the method comprises expressing the manufactured nucleic acid in a host cell. In some embodiments, the nucleic acid sequence encodes for a messenger RNA. In some embodiments, the RNA folding models comprise a model selected from the group consisting of Cocke-Younger Kasami model, inside and outside models, loop-based energy model, minimum free energy, suboptimal folding, centroid, and any combination thereof. In some embodiments, the at least two predicted secondary structures are a minimum free energy structure and a centroid structure. In some embodiments, the structural similarity score is determined via tool selected from the group consisting of Consan, Dynalign, PMcomp, Stemloc, Foldalign, locARNA, SPARSE, MARNA, FoldAlignM, Murlet, CARNA, RAF, RNAforester, RNAdistance, RNAStrAt, RNApdist, and any combination thereof. In some embodiments, the structure similarity score is based on visual inspection of the predicted secondary structures. In some embodiments, the structure similarity score is a ranking of the plurality of nucleic acid sequences based on the relative similarity of each nucleic acid sequences' predicted secondary structures. In some embodiments, the similarity score is based on degree of curve overlap in a graph depicting number of base pairs at each position of the predicted secondary structures. In some embodiments, the similarity score is based on the degree of curve overlap of the predicted secondary structures plotted in a mountain plot. In some embodiments, the similarity score is based on the correlation of curves representing the predicted secondary structures in a graph depicting number of base pairs at each position. In some embodiments, the degree of curve overlap is calculated by methodology selected from the group consisting of least squares, curve length measure, and any combination thereof.

Provided is a method of manufacturing a nucleic acid, said method comprising: a) manufacturing a selected nucleic acid sequence to produce a nucleic acid, wherein the selection of the nucleic acid sequence was based on the selected nucleic acid sequence having a higher structural similarity score than at least one other nucleic acid sequence in a plurality of nucleic acid sequences; wherein the structural similarity score is based on the structural similarity between at least two predicted secondary structures for each nucleic acid sequence, the predicted secondary structures produced by different RNA folding models. In some embodiments, at least one of the RNA folding models employs machine learning. In some embodiments, the plurality of nucleic acid sequences encode the same amino acid sequence. In some embodiments, the plurality of nucleic acid sequences encode amino acids sharing at least 90%, 91%, 92%, 93%, 94%, 95%, 96%, 97%, 98%, or 99% sequence identity. In some embodiments, the method comprises expressing the manufactured nucleic acid in a host cell. In some embodiments, the manufactured nucleic acid expresses at a higher level than other nucleic acids containing other nucleic acid sequences from the plurality of nucleic acid sequences. In some embodiments, the RNA folding models comprise a model selected from the group consisting of Cocke-Younger Kasami model, inside and outside models, loop-based energy model, minimum free energy, suboptimal folding, centroid, and any combination thereof. In some embodiments, the at least two predicted secondary structures are a minimum free energy structure and a centroid structure. In some embodiments, the structural similarity score is determined via tool selected from the group consisting of Consan, Dynalign, PMcomp, Stemloc, Foldalign, locARNA, SPARSE, MARNA, FoldAlignM, Murlet, CARNA, RAF, RNAforester, RNAdistance, RNAStrAt, RNApdist, and any combination thereof. In some embodiments, the structure similarity score is based on visual inspection of the predicted secondary structures. In some embodiments, the structure similarity score is a ranking of the plurality of nucleic acid sequences based on the relative similarity of each nucleic acid sequences' predicted secondary structures. In some embodiments, the similarity score is based on degree of curve overlap in a graph depicting number of base pairs at each position of the predicted secondary structures. In some embodiments, the similarity score is based on the degree of curve overlap of the predicted secondary structures plotted in a mountain plot.

Provided is a nucleic acid comprising a nucleic acid sequence selected in a method of the disclosure.

Provided is a host cell comprising a nucleic acid comprising a sequence of Table 11, Table 12, or Table 15. In some embodiments, the nucleic acid comprises a sequence selected from the group consisting of: SEQ ID NO: 757, 760, 762, 763, 765, 772, 773, 778, and 780.

Provided is a host cell comprising a nucleic acid encoding any one of SEQ ID NO: 685, 687, and 695.

Provided herein is a host cell that comprises an exogenous RNA sequence that encodes a chordate protein, wherein the exogenous RNA sequence is stabilized as determined by increased expression of the chordate protein as compared to an otherwise comparable host cell lacking the exogenous RNA sequence that is stabilized, and wherein the chordate protein is expressed in the amount of at least 1% or higher per total protein weight of soluble protein extractable from the host cell.

In some embodiments, the chordate is a vertebrate. In some embodiments, the vertebrate is a mammal. In some embodiments, the mammal is a bovine. In some embodiments, the vertebrate is a bird. In some embodiments, the bird is a chicken.

In some embodiments, the chordate protein is an egg protein or a milk protein. In some embodiments, the chordate protein is a milk protein. In some embodiments, the milk protein is β-lactoglobulin. In some embodiments, the chordate protein is an egg protein. In some embodiments, the egg protein is ovalbumin. In some embodiments, the chordate protein is expressed in the amount of at least 2%, at least 3%, at least 4%, or at least 5% per total protein weight of soluble protein extractable from the host cell. In some embodiments, the chordate protein is expressed in the amount of about 1 to about 2%, about 2 to about 3%, or about 2 to about 5% per total protein weight of soluble protein extractable from the host cell.

In some embodiments, provided herein is a plant that comprises a host cell. In some embodiments, the plant is a soybean plant.

In some embodiments, provided is a DNA construct for expression of a transgene in a host cell, wherein the DNA construct comprises: (a) a codon-optimized transgene sequence that comprises at least 90% identity to a sequence selected from the group consisting of SEQ ID NO: 1, 3, 5, 7, 9-13, 83, 617-621, 683-690, and 693-700; and (b) an exogenous intron sequence, wherein the exogenous intron sequence comprises at least 90% identity to a sequence selected from the group consisting of: SEQ ID NO: 679-682. In some embodiments, the codon-optimized transgene sequence comprises a sequence selected from SEQ ID NO: 1, 3, 5, 7, 9-13, 83, 617-621, 683-690, and 693-700. In some embodiments, the exogenous intron sequence comprises a sequence selected from SEQ ID NO: 679-682.

In some embodiments, provided is a DNA construct for expression of a transgene in a host cell, wherein the DNA construct comprises: (a) a codon-optimized transgene sequence that comprises at least 90% identity to a sequence selected from the group consisting of SEQ ID NO: 1, 3, 5, 7, 9-13, 83, 617-621, 683-690, and 693-700; and (b) an exogenous intron sequence, wherein the exogenous intron sequence comprises at least 90% identity to a sequence selected from the group consisting of: SEQ ID NO: 679-682. In some embodiments, the codon-optimized transgene sequence comprises a sequence selected from SEQ ID NO: 1, 3, 5, 7, 9-13, 83, 617-621, 683-690, and 693-700. In some embodiments, the exogenous intron sequence comprises a sequence selected from SEQ ID NO: 679-682. In some embodiments, the DNA construct further comprises a signal peptide sequence. In some embodiments, the signal peptide sequence is selected from the group consisting of: SEQ ID NO: 616, 707-717. In some embodiments, the DNA construct further comprises a sequence encoding a KDEL sequence. In some embodiments, the DNA construct further comprises a sequence encoding at least one of a 5' UTR and a 3' UTR. In some embodiments, the DNA construct further comprises a sequence encoding a ubiquitin monomer. In some embodiments, the DNA construct further comprises an exogenous promoter sequence. In some embodiments, the exogenous promoter sequence is isolated or derived from a plant promoter sequence. In some embodiments, the exogenous promoter sequence is isolated or derived from a seed promoter sequence. In some embodiments, the DNA construct further comprises an exogenous terminator sequence.

Provided herein is also a composition that comprises a DNA construct.

Provided herein is also a method of transforming a host cell, the method comprising contacting a host cell with a composition provided herein, thereby transforming the host cell. In some embodiments, the host cell is a plant cell. In some embodiments, the method comprises bombardment or *agrobacterium*-mediated transformation. In some embodiments, the method further comprises cultivating the plant cell after the transforming.

Provided herein is an RNA generated from a DNA construct provided herein.

Provided herein is also a method of expressing ovalbumin or β-lactoglobulin in a plant, the method comprising: contacting at least a portion of a plant with a DNA construct of the disclosure, wherein the method is effective in increasing expression of the ovalbumin or β-lactoglobulin as compared to an otherwise comparable method lacking the contacting. In some embodiments, the method is effective in increasing expression of the ovalbumin or β-lactoglobulin by at least about 1-fold as compared to an otherwise comparable method lacking the contacting.

Provided herein is also a method of stably expressing a chordate protein in a plant cell, the method comprising: (a) contacting a plant cell with a DNA construct that comprises at least 90% identity to a sequence selected from the group consisting of SEQ ID NO: 752-766, thereby generating a transformed plant cell; and (b) cultivating a plant that comprises the transformed plant cell, thereby generating a transformed plant, wherein the chordate protein is expressed in the amount of 1% or higher per total protein weight of soluble protein extractable from the transformed plant cell. In some embodiments, the DNA construct comprises at least 95%, at least 97%, or at least 99% identity to a sequence selected from the group consisting of SEQ ID NO: 752-766.

Provided herein is also a method of stably expressing a chordate protein in a plant cell, the method comprising: (a) contacting a plant cell with a DNA construct that comprises at least 90% identity to a sequence selected from the group consisting of SEQ ID NO: 767-781, thereby generating a transformed plant cell; and (b) cultivating a plant that comprises the transformed plant cell, thereby generating a transformed plant, wherein the chordate protein is expressed in the amount of 1% or higher per total protein weight of soluble protein extractable from the transformed plant cell. In some embodiments, the DNA construct comprises at least 95%, at least 97%, or at least 99% identity to a sequence selected from the group consisting of SEQ ID NO: 767-781. In some embodiments, the chordate protein is expressed in the amount of at least 1%, at least 2%, at least 3%, at least 4%, or at least 5% per total protein weight of soluble protein extractable from the transformed plant cell. In some embodiments, the plant cell is from a soybean plant. In some embodiments, the contacting comprises bombardment or *agrobacterium*-mediated transformation. In some embodiments, a level of a transcript of a transgene encoded by the DNA construct is increased by at least 1-fold as compared to an otherwise comparable method lacking the contacting. In some embodiments, a level of the chordate protein encoded by the DNA construct is increased by at least 1-fold as measured by ELISA and as compared to an otherwise comparable method lacking the contacting. In some embodiments, the level is increased by at least 3-fold, at least 5-fold, at least 10-fold, at least 30-fold, or at least 50-fold. In some embodiments, the method further comprises isolating a seed from the transformed plant.

Provided herein is also a nutraceutical that comprises a chordate protein isolated from a transformed plant cell generated by a method of the disclosure.

BRIEF DESCRIPTION OF THE DRAWINGS

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 3A shows gradient plots summarizing RNA expression of exemplary (3-Lactoglobulin designs. FIG. 3B shows gradient plots summarizing protein expression of exemplary β-Lactoglobulin designs. Protein expression is shown as a function of relative expression and % TSP, respectively. Boxes indicate the designs that led to an increase in both RNA expression and protein accumulation. In between FIG. 3A and FIG. 3B is a breakdown of the designs based on high level strategy. n=number of seeds analyzed. Cassette details: AR07-28 BnNap:sig11:OLG1:KDEL:nos, AR07-29 GmSeed2:sig2:OLG1:KDEL:nos, AR07-31 GmSeed12:coixss:OLG1:KDEL:nos, AR07-32 GmSeed12:sig12:OLG1:KDEL:nos, AR07-33 PvPhas:arcUTR:sig10:OLG1:KDEL:arcT, AR15-25 GmSeed2: sig2:OLG2:KDEL:EUT:Rb7T, AR15-26GmSeed2:sig2:OLG3:KDEL:EUT:Rb7T, AR15-27 GmSeed2:sig2:OLG4:KDEL:EUT:Rb7T, AR15-28 GmSeed2:sig2:OLG2:EUT:Rb7T, AR15-29 GmSeed2 (intron 1):sig2:OLG2:KDEL:EUT:Rb7T, AR15-30 GmSeed2:sig2:OLG2 (intron 1):KDEL:EUT:Rb7T, AR15-31 GmSeed2:sig2:OLG2 (intron 2):KDEL:EUT:Rb7T, AR15-36 GmSeed2:lgUTR:sig2:OLG2:KDEL:EUT:Rb7T, AR15-37 GmSeed2:glnB1UTR:sig2:OLG2: KDEL: EUT: Rb7T, AR15-39 GmSeed2:Ubimonomer:sig2:OLG2:KDEL:EUT:Rb7T. See also, Table 12.

FIG. 8—depicts the predicted minimum free energy secondary structures for several codon optimized β-Lactoglobulin-encoding nucleic acid sequences. Highest RNA expression among transformants also depicted. There was no obvious correlation between expression and any single secondary structure.

FIG. 9—depicts the predicted minimum free energy and centroid secondary structures for several codon optimized β-Lactoglobulin-encoding nucleic acid sequences. Highest RNA expression among transformants also depicted. It was observed that higher expressing sequences had similar predicted structures between different prediction algorithms.

FIG. 10A-FIG. 10F—depict the predicted minimum free energy (MFE) and centroid secondary structures for several codon optimized β-Lactoglobulin-encoding nucleic acid sequences. Mountain plot graphs for both the MFE and centroid structures are shown, together with curve length distance between the curves for each predicted secondary structure. Highest RNA expression among transformants based on empirical measurements, as well as overall RNA fold expression increase over lowest expressing sequence is shown.

FIG. 11A-FIG. 11F—depict the predicted minimum free energy (MFE) and centroid secondary structures for several codon optimized ovalbumin-encoding nucleic acid sequences. Mountain plot graphs for both the MFE and centroid structures are shown, together with curve length distance between the curves for each predicted secondary structure. Highest RNA expression among transformants based on empirical measurements, as well as overall RNA fold expression increase over lowest expressing sequence is shown.

FIG. 12A-FIG. 12F—depict the predicted minimum free energy (MFE) and centroid secondary structures for several codon optimized green fluorescent protein-encoding nucleic acid sequences. Mountain plot graphs for both the MFE and centroid structures are shown, together with curve length distance between the curves for each predicted secondary structure. Highest RNA expression among transformants based on empirical measurements, as well as overall RNA fold expression increase over lowest expressing sequence is shown.

FIG. 13A depicts RNA expression in the X-Axis and curve length on the Y-Axis and includes a linear regression trendline for reference. FIG. 13B depicts curve length measure in the X-Axis and RNA expression in the Y-Axis. A Logarithmic trendline is added for the correlation between the two variables.

DETAILED DESCRIPTION

Figure 1:
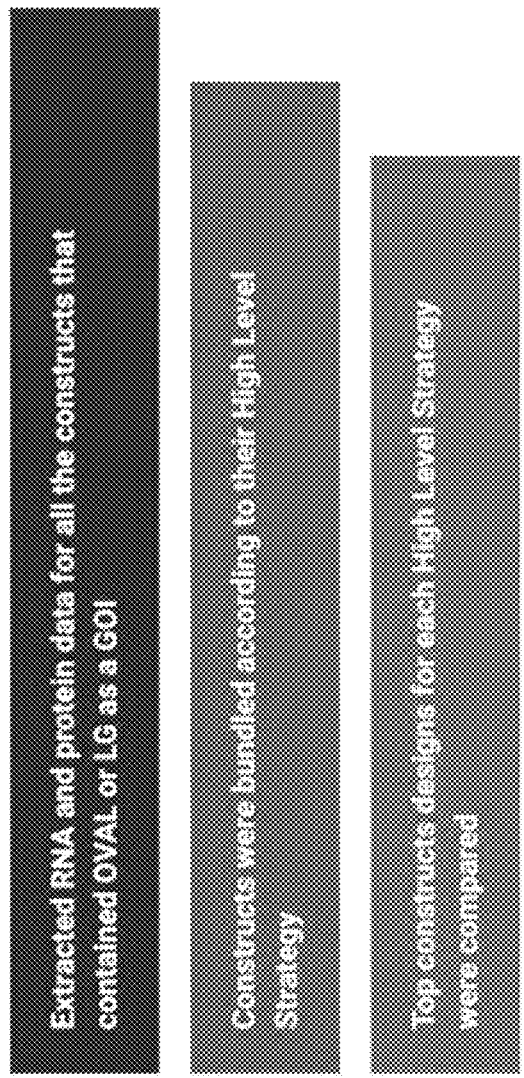
FIG. 1 is a schematic showing an exemplary strategy to compare RNA stabilization of constructs encoding ovalbumin (OVAL) and/or lactoglobulin (LG) and their respective protein data. Data was bundled using different categories in order to evaluate strategies and/or construct designs that can lead to RNA stability and higher protein accumulation.

The following description includes information that may be useful in understanding the present disclosure. It is not an admission that any of the information provided herein is prior art or relevant to the presently claimed disclosures, or that any publication specifically or implicitly referenced is prior art.

Provided herein are compositions and methods for increasing expression levels in a host cell of one or more proteins encoded by transgenes by way of RNA stabilization. These compositions and methods may be used to express one or more proteins, such as ovalbumin (OVAL) and β-Lactoglobulin (LG), at high levels in a host cell. Also provided are various transgenic organisms, animals, crops, and cells that comprise stabilized RNA and/or enhanced levels of proteins encoded by the stabilized RNA. The compositions and methods may be used to generate transgenic cells, organisms, crops, animals, and the like, and to produce recombinant protein therein.

Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art.

As used herein, the singular forms "a," "an," and "the: include plural referents unless the content clearly dictates otherwise.

The term "about" or "approximately" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. When used in conjunction with a range or series of values, the term "about" applies to the endpoints of the range or each of the values enumerated in the series, unless otherwise indicated. Similarly, the term "about" when preceding a series of numerical values or a range of values (e.g., "about 10, 20, 30" or "about 10-30") refers, respectively to all values in the series, or the endpoints of the range.

As used herein, "mammalian milk" can refer to milk derived from any mammal, such as bovine, human, goat, sheep, camel, buffalo, water buffalo, dromedary, llama and any combination thereof. In some embodiments, a mammalian milk is a bovine milk.

As used herein, "rennet" refers to a set of enzymes typically produced in the stomachs of ruminant mammals. Chymosin, its key component, is a protease enzyme that cleaves κ-casein (to produce para-κ-casein and a macropeptide). In addition to chymosin, rennet contains other enzymes, such as pepsin and lipase. Rennet is used to separate milk into solid curds (for cheesemaking) and liquid whey. Rennet or rennet substitutes are used in the production of many cheeses.

The term "plant" includes reference to whole plants, plant organs, plant tissues, and plant cells and progeny of same, but is not limited to angiosperms and gymnosperms such as *Arabidopsis*, potato, tomato, tobacco, alfalfa, lettuce, carrot, strawberry, sugar beet, cassava, sweet potato, soybean, lima bean, pea, chickpea, maize (corn), turf grass, wheat, rice, barley, sorghum, oat, oak, *eucalyptus*, walnut, palm and duckweed as well as fern and moss. Thus, a plant may be a monocot, a dicot, a vascular plant reproduced from spores such as fern or a nonvascular plant such as moss, liverwort, hornwort and algae. The word "plant," as used herein, also encompasses plant cells, seeds, plant progeny, propagule whether generated sexually or asexually, and descendants of any of these, such as cuttings or seed. Plant cells include suspension cultures, callus, embryos, meristematic regions, callus tissue, leaves, roots, shoots, gametophytes, sporophytes, pollen, seeds and microspores. Plants may be at various stages of maturity and may be grown in liquid or solid culture, or in soil or suitable media in pots, greenhouses or fields. Expression of an introduced leader, trailer or gene sequences in plants may be transient or permanent.

The term "vascular plant" refers to a large group of plants that are defined as those land plants that have lignified tissues (the xylem) for conducting water and minerals throughout the plant and a specialized non-lignified tissue (the phloem) to conduct products of photosynthesis. Vascular plants include the clubmosses, horsetails, ferns, gymnosperms (including conifers) and angiosperms (flowering plants). Scientific names for the group include Tracheophyta and Tracheobionta. Vascular plants are distinguished by two primary characteristics. First, vascular plants have vascular tissues which distribute resources through the plant. This feature allows vascular plants to evolve to a larger size than non-vascular plants, which lack these specialized conducting tissues and are therefore restricted to relatively small sizes. Second, in vascular plants, the principal generation phase is the sporophyte, which is usually diploid with two sets of chromosomes per cell. Only the germ cells and gametophytes are haploid. By contrast, the principal generation phase in non-vascular plants is the gametophyte, which is haploid with one set of chromosomes per cell. In these plants, only the spore stalk and capsule are diploid.

The term "non-vascular plant" refers to a plant without a vascular system consisting of xylem and phloem. Many non-vascular plants have simpler tissues that are specialized for internal transport of water. For example, mosses and leafy liverworts have structures that look like leaves but are not true leaves because they are single sheets of cells with no stomata, no internal air spaces and have no xylem or phloem. Non-vascular plants include two distantly related groups. The first group are the bryophytes, which is further categorized as three separate land plant Divisions, namely Bryophyta (mosses), Marchantiophyta (liverworts), and Anthocerotophyta (hornworts). In all bryophytes, the primary plants are the haploid gametophytes, with the only diploid portion being the attached sporophyte, consisting of a stalk and sporangium. Because these plants lack lignified water-conducting tissues, they can't become as tall as most vascular plants. The second group is the algae, especially the green algae, which consists of several unrelated groups. Only those groups of algae included in the Viridiplantae are still considered relatives of land plants.

The term "plant part" refers to any part of a plant including but not limited to the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like. The two main parts of plants grown in some sort of media, such as soil or vermiculite, are often referred to as the "above-ground" part, also often referred to as the "shoots", and the "below-ground" part, also often referred to as the "roots".

The term "plant tissue" refers to any part of a plant, such as a plant organ. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

The term "seed" is meant to encompass the whole seed and/or all seed components, including, for example, the coleoptile and leaves, radicle and coleorhiza, scutellum, starchy endosperm, aleurone layer, pericarp and/or testa, either during seed maturation and seed germination.

The term "transgenic plant" means a plant that has been transformed with one or more exogenous nucleic acids. "Transformation" refers to a process by which a nucleic acid is integrated into the genome of a plant cell. "Stably integrated" refers to the permanent, or non-transient retention and/or expression of a polynucleotide in and by a cell genome. Thus, a stably integrated polynucleotide is one that is a fixture within a transformed cell genome and can be replicated and propagated through successive progeny of the cell or resultant transformed plant. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols, viral infection, whiskers, electroporation, heat shock, lipofection, polyethylene glycol treatment, micro-injection, and particle bombardment.

As used herein, the terms "stably expressed" or "stable expression" when used in reference to a protein refer to expression and accumulation of a protein in a host cell, such as a plant cell. In some embodiments, a protein may accumulate in a cell because it is not degraded by endogenous host cell proteases. In some embodiments, a protein is considered to be stably expressed in a plant if it is present in the plant in an amount of 1% or higher per total protein weight of soluble protein extractable from the plant.

The term "recombinant" refers to nucleic acids or proteins formed by laboratory methods of genetic recombination (e.g., molecular cloning) to bring together genetic material from multiple sources, creating sequences that would not otherwise be found in the genome. A recombinant fusion protein is a protein created by combining sequences encoding two or more constituent proteins, such that they are expressed as a single polypeptide. Recombinant fusion proteins may be expressed in vivo in various types of host cells, including plant cells, bacterial cells, fungal cells, mammalian cells, etc. Recombinant fusion proteins may also be generated in vitro.

The term "promoter" or a "transcription regulatory region" refers to nucleic acid sequences that influence and/or promote initiation of transcription. Promoters are typically considered to include regulatory regions, such as enhancer or inducer elements. The promoter will generally be appropriate to the host cell in which the target gene is being expressed. The promoter, together with other transcriptional and translational regulatory nucleic acid sequences (also termed "control sequences"), is necessary to express any given gene. In general, the transcriptional and translational regulatory sequences include, but are not limited to, promoter sequences, ribosomal binding sites, transcriptional start and stop sequences, translational start and stop sequences, and enhancer or activator sequences.

The term signal peptide—also known as "signal sequence", "targeting signal", "localization signal", "localization sequence", "transit peptide", "leader sequence", or "leader peptide", is used herein to refer to an N-terminal peptide which directs a newly synthesized protein to a specific cellular location or pathway. Signal peptides are often cleaved from a protein during translation or transport and are therefore not typically present in a mature protein.

The term "proteolysis" or "proteolytic" or "proteolyze" means the breakdown of proteins into smaller polypeptides or amino acids. Uncatalyzed hydrolysis of peptide bonds is extremely slow. Proteolysis is typically catalyzed by cellular enzymes called proteases but may also occur by intramolecular digestion. Low pH or high temperatures can also cause proteolysis non-enzymatically. Limited proteolysis of a polypeptide during or after translation in protein synthesis often occurs for many proteins. This may involve removal of the N-terminal methionine, signal peptide, and/or the conversion of an inactive or non-functional protein to an active one.

The term "purifying" is used interchangeably with the term "isolating" and generally refers to the separation of a particular component from other components of the environment in which it was found or produced. For example, purifying a recombinant protein from plant cells in which it was produced typically means subjecting transgenic protein containing plant material to biochemical purification and/or column chromatography.

When referring to expression of a protein in a specific amount per the total protein weight of the soluble protein extractable from the plant ("TSP"), it is meant an amount of a protein of interest relative to the total amount of protein that may reasonably be extracted from a plant using standard methods. Methods for extracting total protein from a plant are known in the art. For example, total protein may be extracted from seeds by bead beating seeds at about 15000 rpm for about 1 min. The resulting powder may then be resuspended in an appropriate buffer (e.g., 50 mM Carbonate-Bicarbonate pH 10.8, 1 mM DTT, 1× Protease Inhibitor Cocktail). After the resuspended powder is incubated at about 4° C. for about 15 minutes, the supernatant may be collected after centrifuging (e.g., at 4000 g, 20 min, 4° C.). Total protein may be measured using standard assays, such as a Bradford assay. The amount of protein of interest may be measured using methods known in the art, such as an ELISA or a Western Blot.

When referring to a nucleic acid sequence or protein sequence, the term "identity" is used to denote similarity between two sequences. Unless otherwise indicated, percent identities described herein are determined using the BLAST algorithm available at the world wide web address: blast.ncbi.nlm.nih.gov/Blast.cgi using default parameters.

As used herein, the terms "dicot" or "dicotyledon" or "dicotyledonous" refer to a flowering plant whose embryos have two seed leaves or cotyledons. Examples of dicots include, but are not limited to, *Arabidopsis*, tobacco, tomato, potato, sweet potato, cassava, alfalfa, lima bean, pea, chickpea, soybean, carrot, strawberry, lettuce, oak, maple, walnut, rose, mint, squash, daisy, *Quinoa*, buckwheat, mung bean, cow pea, lentil, lupin, peanut, fava bean, French beans (i.e., common beans), mustard, or cactus.

The terms "monocot" or "monocotyledon" or "monocotyledonous" refer to a flowering plant whose embryos have one cotyledon or seed leaf. Examples of monocots include, but are not limited to turf grass, maize (corn), rice, oat, wheat, barley, sorghum, orchid, iris, lily, onion, palm, and duckweed.

As used herein, a "low lactose product" is any food composition considered by the FDA to be "lactose reduced", "low lactose", or "lactose free".

As used herein, a "milk protein" is any protein, or fragment or variant thereof, that is typically found in one or more mammalian milks.

As used herein, a "non-milk" protein is any protein that is not typically found in any mammalian milk. One non-limiting example of a non-milk protein is green fluorescent protein (GFP).

As used herein, an "exogenous intron" refers to an intronic sequence, or portion thereof, derived from a first cell type that is introduced into a second cell type. Thus, exogenous introns are not native to a host cell and/or host plant. Exogenous introns may, in some embodiments, comprise synthetic sequences and chimeric sequences. Exogenous introns do not typically code for amino acids, and are removed (i.e., spliced) by the host cell during translation of a protein from the transgene.

As used herein, a "nucleic acid" refers to a physical nucleic acid chemical structure. A nucleic acid is a polymeric form of nucleotides of any length, either deoxyribonucleotides or ribonucleotides or analogs thereof. The term also refers to both double and single stranded nucleic acid molecules. The following are non-limiting examples of a nucleic acid: a gene or gene fragment (for example, a probe, primer), an exon, an intron, intergenic DNA (including, without limitation, heterochromatic DNA), messenger RNA (mRNA), transfer RNA (tRNA), ribosomal RNA (rRNA), a ribozyme, cDNA, a recombinant polynucleotide, a branched polynucleotide, a plasmid, a vector, isolated DNA of a sequence, isolated RNA of a sequence, sgRNA, guide RNA, a nucleic acid probe, a primer, an snRNA, a long non-coding RNA, a snoRNA, a siRNA, a miRNA, a tRNA-derived small RNA (tsRNA), an antisense RNA, an shRNA, or a small rDNA-derived RNA (srRNA). A nucleic acid can comprise modified nucleotides, such as methylated nucleotides and nucleotide analogs. If present, modifications to the nucleotide structure can be imparted before or after assembly of the nucleic acid. The sequence of nucleotides can be interrupted by non-nucleotide components. A nucleic acid can be further modified after polymerization, such as by conjugation with a labeling component. A nucleic acid can also have secondary or tertiary structure. A nucleic acid can base pair, such as by way of Watson Crick base pairing.

As used herein, a "nucleic acid sequence" refers to a non-physical succession of bases indicating the order of nucleotides of a nucleic acid. A nucleic acid sequence is observable in written form such as on a machine (in silico) or handwritten. A nucleic acid sequence can be input or obtained from databases in a computer having a central processing unit As used herein, the term "machine learning" refers to use of mathematical algorithms/models and related software that leverage data to improve performance of a task (e.g., predictions). Machine learning encompasses learning models capable of supervised learning, unsupervised learning, semi-supervised learning, and reinforcement learning. In some embodiments, machine learning utilizes alignment data and/or empirical data regarding RNA secondary or tertiary structure to improve RNA folding predictions or RNA structural comparisons. In a non-limiting example, the predictions made by machine learning algorithms and models of the present disclosure can inform selection of nucleic acid sequences for manufacture of a nucleic acid.

Nucleic Acid Sequence Selection Based on Predicted Structures

In some embodiments, the present disclosure teaches methods for selecting a nucleic acid sequence based on differences in the predicted or empirically-determined structures of those sequences. Specifically, the present disclosure teaches a method of selecting nucleic acid sequences that result in similar predicted secondary structures from different RNA folding models. This invention is based in part, on the inventor's discovery that nucleic acid sequences that produce more similar predicted secondary structures across different RNA folding models, result in higher or more stable expression/accumulation of nucleic acids in vivo compared to nucleic acid sequences that produce more dissimilar predicted secondary structures.

Without wishing to be bound by any one theory, it is hypothesized that differences in predicted secondary structure produced from different RNA folding models are associated with decreased structural stability of the manufactured nucleic acid in vivo. That is, it is hypothesized that the differences in predicted structures from different models is indicative or suggestive that the sequence may take on different- or multiple-structures, when expressed in vivo, which may have deleterious effects on nucleic acid expression or accumulation in vivo.

In some embodiments, the present disclosure teaches a method comprising the steps of a) providing a plurality of nucleic acid sequences for evaluation; b) predicting secondary structure of the plurality of nucleic acid sequences, with a plurality of RNA folding models, such that each nucleic acid sequence in the plurality of nucleic acid sequences is associated with at least two predicted secondary structures; c) assessing structural similarity for the at least two predicted secondary structures associated with each nucleic acid sequence (e.g., via assignment of a structural similarity score); and d) selecting a nucleic acid sequence with higher structural similarity between predicted secondary structures than at least one other nucleic acid sequence in the plurality of nucleic acid sequences. In some embodiments, the selected nucleic acid sequence with higher similarity in its predicted secondary structures is predicted to express or accumulate at higher levels when expressed in vivo. In some embodiments, the predicted secondary structures are provided, and need not be predicted. The various aspects of the presently-disclosed invention are discussed in more detail, below.

Plurality of Nucleic Acid Sequences

The present disclosure provides techniques for selecting a nucleic acid sequence from amongst a plurality of nucleic acid sequences. In some embodiments, the methods of the present disclosures are most effective when the selection is made within a group of related nucleic acid sequences. In some embodiments, it is hypothesized that selection of related nucleic acid sequences permits for selection based on predicted structure, while reducing potential confounding effects related to non-structural issues, such as the presence of RNAi targets, binding, or shuttling of nucleic acids in vivo, or other potential expression regulatory controls that may vary between highly disparate sequences. Thus, in some embodiments, the techniques of the present disclosure are more effective (i.e. are expected to produce the most accurate expression predictions), when applied to related sequences, including but not limited to: nucleic acid variants encoding the same or similar amino acid sequence (e.g., codon variants, or other sequence variations that in non-coding regions) or comprising other nucleic acid sequence variations that encode for amino acid chains that are at least 90%, 91%, 92%, 93%, 94%, 95%, 96%, 97%, 98%, or 99% sequence identity.

In some embodiments, the plurality of nucleic acid sequences are codon variants encoding the same or similar amino acid sequence. In some embodiments, the plurality of sequences encode for nucleic acids comprising RNAi hairpins, wherein the sequences vary in nucleic acids, but continue to be processed into small RNAs capable of interacting with the same target nucleotide. In some embodiments, the plurality of nucleic acid sequences are sequence other sequence variants that do not exhibit a biological function. For example, in some embodiments, the presently disclosed techniques can be applied to nucleic acid sequences encoding nucleic acids with laboratory applications, including probes, primers, linkers, bar codes, etc. In some embodiments the plurality of nucleic acid sequences are variants of riboswitches, aptamers, rRNAs or other non-coding RNAs.

In some embodiments, the plurality of nucleic acid sequences can be from any source, including, without limitation, randomly generated sequences, sequences derived from natural diversity (e.g., related sequences from related species), sequence rearrangements, artificial sequences, mutational library sequences, etc. Disclosure related to various types of plurality of nucleic acids is provided in this document, and is also known to those with skill in the art.

Secondary Structures

Provided are nucleic acids with secondary structure. RNA secondary structure is represented by a sequence of bases, paired by hydrogen bonding, within its nucleotide sequence. Stacking these base pairs forms the scaffold driving the folding of RNA three-dimensional structures. As a result, the knowledge of the RNA secondary structure is useful for modeling RNA structures and understanding any functional mechanisms. The present disclosure provides in silico and wet lab approaches to determining secondary structures.

RNA Folding Models

The present disclosure provides methods for predicting nucleic acid expression based on the similarity of secondary (or tertiary structures) developed from different RNA folding models. In some embodiments, the methods of the present disclosure are compatible with any RNA folding model. Persons having skill in the art are familiar with a variety of RNA folding models.

In some embodiments the RNA folding model utilizes comparative sequence analysis. Comparative sequence analysis is considered by some to be the most accurate computational method for determining the RNA secondary structure. This method assumes that the RNA secondary structure is evolutionarily conserved to a greater extent than the RNA sequence. This method usually finds the base pairs that covary to maintain Watson-Crick and wobble base pairs (compensatory mutations) of a given sequence using a set of homologous sequences. In some embodiments, comparative sequence analysis can be combined with score-based methods (See e.g., RNAalifold-Hofacker I L, Fekete M, Flamm C, Huynen M A, Rauscher S, Stolorz P E, et al. Automatic detection of conserved RNA structure elements in complete RNA virus genomes. Nucleic Acids Res. 1998; 26 (16): 3825-36; KnetFold-Bindewald E, Shapiro B A. RNA secondary structure prediction from sequence alignments using a network of k-nearest neighbor classifiers. RNA. 2006; 12(3):342-52; and IL-Ruan J, Stormo G D, Zhang W. An iterated loop matching approach to the prediction of RNA secondary structures with pseudoknots. Bioinformatics. 2004; 20(1):58-66).

Other RNA folding models are based on score assignment, where only a single RNA sequence is required as the input. These methods assume that the native RNA structure is a structure with a minimum/maximum total score, depending on the hypothesis of RNA folding mechanism or its simplification. Hence, the problem of RNA secondary structure prediction is transformed into an optimization problem. Since the RNA secondary structure can be recursively broken down into smaller elements with independent score contributions, the dynamic programming (DP) algorithm is often employed to identify the optimal structure. Evaluation of the score for structure elements requires a score scheme of many parameter.

In some embodiments, any RNA folding model can be utilized in a method of the disclosure. Exemplary, non-limiting methods are provided in Table 1.

TABLE 1

Exemplary RNA Folding Models

| Name | Description | References |
|---|---|---|
| CentroidFold | Secondary structure prediction based on generalized centroid estimator | Hamada M, Kiryu H, Sato K, Mituyama T, Asai K (February 2009). "Prediction of RNA secondary structure using generalized centroid estimators". Bioinformatics. 25 (4): 465-473. doi: 10.1093/bioinformatics/btn601. PMID 19095700. |
| CentroidHomfold | Secondary structure prediction by using homologous sequence information | Hamada M, Sato K, Kiryu H, Mituyama T, Asai K (June 2009). "Predictions of RNA secondary structure by combining homologous sequence information". Bioinformatics. 25 (12): i330-i338. doi: 10.1093/bioinformatics/btp228. PMC 2687982. PMID 19478007. |
| Context Fold | An RNA secondary structure prediction software based on feature-rich trained scoring models. | Zakov S, Goldberg Y, Elhadad M, Ziv-Ukelson M (November 2011). "Rich parameterization improves RNA structure prediction". Journal of Computational Biology. 18 (11): 1525-1542. Bibcode: 2011LNCS.6577 . . . 546Z. doi: 10.1089/cmb.2011.0184. PMID 22035327. |
| CONTRAfold | Secondary structure prediction method based on conditional log-linear models (CLLMs), a flexible class of probabilistic models which generalize upon SCFGs by using discriminative training and feature-rich scoring. | Do C B, Woods D A, Batzoglou S (July 2006). "CONTRAfold: RNA secondary structure prediction without physics-based models". Bioinformatics. 22 (14): e90-e98. doi: 10.1093/bioinformatics/btl246. PMID 16873527. |
| Crumple | Simple, cleanly written software to produce the full set of possible secondary structures for one sequence, given optional constraints. | Schroeder S J, Stone J W, Bleckley S, Gibbons T, Mathews D M (July 2011). "Ensemble of secondary structures for encapsidated satellite tobacco mosaic virus RNA consistent with chemical probing and crystallography constraints". Biophysical Journal. 101 (1): 167-175. Bibcode: 2011BpJ . . . 101 . . . 167S. doi: 10.1016/j.bpj.2011.05.053. PMC 3127170. PMID 21723827. |

TABLE 1-continued

Exemplary RNA Folding Models

| Name | Description | References |
|------|-------------|------------|
| CyloFold | Secondary structure prediction method based on placement of helices allowing complex pseudoknots. | Bindewald E, Kluth T, Shapiro B A (July 2010). "CyloFold: secondary structure prediction including pseudoknots". Nucleic Acids Research. 38 (Web Server issue): W368-W372. doi: 10.1093/nar/gkq432. PMC 2896150. PMID 20501603. |
| E2Efold | A deep learning based method for efficiently predicting secondary structure by differentiating through a constrained optimization solver, without using dynamic programming. | Chen X, Li Y, Umarov R, Gao X, Song L (2020). "RNA Secondary Structure Prediction By Learning Unrolled Algorithms". arXiv: 2002.05810 [cs.LG]. |
| GTFold | Fast and scalable multicore code for predicting RNA secondary structure. | Swenson M S, Anderson J, Ash A, Gaurav P, Sükösd Z, Bader D A, et al. (July 2012). "GTfold: enabling parallel RNA secondary structure prediction on multi-core desktops". BMC Research Notes. 5: 341. doi: 10.1186/1756-0500-5-341. PMC 3748833. PMID 22747589. |
| IPknot | Fast and accurate prediction of RNA secondary structures with pseudoknots using integer programming. | Sato K, Kato Y, Hamada M, Akutsu T, Asai K (July 2011). "IPknot: fast and accurate prediction of RNA secondary structures with pseudoknots using integer programming". Bioinformatics. 27 (13): i85-i93. doi: 10.1093/bioinformatics/btr215. PMC 3117384. PMID 21685106. |
| KineFold | Folding kinetics of RNA sequences including pseudoknots by including an implementation of the partition function for knots. | Xayaphoummine A, Bucher T, Isambert H (July 2005). "Kinefold web server for RNA/DNA folding path and structure prediction including pseudoknots and knots". Nucleic Acids Research. 33 (Web Server issue): W605-W610. doi: 10.1093/nar/gki447. PMC 1160208. PMID 15980546. |
| Mfold | (Minimum Free Energy) RNA structure prediction algorithm. | Zuker M, Stiegler P (January 1981). "Optimal computer folding of large RNA sequences using thermodynamics and auxiliary information". Nucleic Acids Research. 9 (1): 133-148. doi: 10.1093/nar/9.1.133. PMC 326673. PMID 6163133. |
| pKiss | A dynamic programming algorithm for the prediction of a restricted class (H-type and kissing hairpins) of RNA pseudoknots. | Theis, Corinna and Janssen, Stefan and Giegerich, Robert (2010). "Prediction of RNA Secondary Structure Including Kissing Hairpin Motifs". In Moulton, Vincent and Singh, Mona (ed.). Algorithms in Bioinformatics. Vol. 6293 (Lecture Notes in Computer Science ed.). Springer Berlin Heidelberg. pp. 52-64. doi: 10.1007/978-3-642-15294-8_5. ISBN 978-3-642-15293-1. |
| Pknots | A dynamic programming algorithm for optimal RNA pseudoknot prediction using the nearest neighbour energy model. | Rivas E, Eddy S R (February 1999). "A dynamic programming algorithm for RNA structure prediction including pseudoknots". Journal of Molecular Biology. 285 (5): 2053-2068. arXiv: physics/9807048. doi: 10.1006/jmbi.1998.2436. PMID 9925784. S2CID 2228845. |
| PknotsRG | A dynamic programming algorithm for the prediction of a restricted class (H-type) of RNA pseudoknots. | Reeder J, Steffen P, Giegerich R (July 2007). "pknotsRG: RNA pseudoknot folding including near-optimal structures and sliding windows". Nucleic Acids Research. 35 (Web Server issue): W320-W324. doi: 10.1093/nar/gkm258. PMC 1933184. PMID 17478505. |

TABLE 1-continued

Exemplary RNA Folding Models

| Name | Description | References |
|---|---|---|
| RNA123 | Secondary structure prediction via thermodynamic-based folding algorithms and novel structure-based sequence alignment specific for RNA. | RNA123 |
| RNAfold | MFE RNA structure prediction algorithm. Includes an implementation of the partition function for computing basepair probabilities and circular RNA folding. | I. L. Hofacker; W. Fontana; P. F. Stadler; S. Bonhoeffer; M. Tacker; P. Schuster (1994). "Fast Folding and Comparison of RNA Secondary Structures". Monatshefte für Chemie. 125 (2): 167-188. doi: 10.1007/BF00818163. S2CID 19344304. |
| RNAshapes | MFE RNA structure prediction based on abstract shapes. Shape abstraction retains adjacency and nesting of structural features, but disregards helix lengths, thus reduces the number of suboptimal solutions without losing significant information. Furthermore, shapes represent classes of structures for which probabilities based on Boltzmann-weighted energies can be computed. | Giegerich R, Voss B, Rehmsmeier M (2004). "Abstract shapes of RNA". Nucleic Acids Research. 32 (16): 4843-4851. doi: 10.1093/nar/gkh779. PMC 519098. PMID 15371549. |
| RNAstructure | A program to predict lowest free energy structures and base pair probabilities for RNA or DNA sequences. Programs are also available to predict maximum expected accuracy structures and these can include pseudoknots. Structure prediction can be constrained using experimental data, including SHAPE, enzymatic cleavage, and chemical modification accessibility. Graphical user interfaces are available for Windows, Mac OS X, Linux. Programs are also available for use with Unix-style text interfaces. Also, a C++ class library is available. | Mathews D H, Disney M D, Childs J L, Schroeder S J, Zuker M, Turner D H (May 2004). "Incorporating chemical modification constraints into a dynamic programming algorithm for prediction of RNA secondary structure". Proceedings of the National Academy of Sciences of the United States of America. 101 (19): 7287-7292. Bibcode: 2004PNAS . . . 101.7287M. doi: 10.1073/pnas.0401799101. PMC 409911. PMID 15123812. |
| SARNA-Predict | RNA Secondary structure prediction method based on simulated annealing. It can also predict structure with pseudoknots. | Tsang H H, Wiese K C (2010). "SARNA-Predict: accuracy improvement of RNA secondary structure prediction using permutation-based simulated annealing". IEEE/ACM Transactions on Computational Biology and Bioinformatics. 7 (4): 727-740. doi: 10.1109/TCBB.2008.97. PMID 21030739. S2CID 12095376. |
| seqfold | Predict the minimum free energy structure of nucleic acids. seqfold is an implementation of the Zuker, 1981 dynamic programming algorithm, the basis for UNAFold/mfold, with energy functions from SantaLucia, 2004 (DNA) and Turner, 2009 (RNA). MIT license. Python CLI or module. | seqfold, Lattice Automation, 2022 Mar. 27, retrieved 2022 Mar. 27 |
| Sfold | Statistical sampling of all possible structures. The | Ding Y, Lawrence C E (December 2003). "A statistical sampling |

TABLE 1-continued

Exemplary RNA Folding Models

| Name | Description | References |
| --- | --- | --- |
| | sampling is weighted by partition function probabilities. | algorithm for RNA secondary structure prediction". Nucleic Acids Research. 31 (24): 7280-7301. doi: 10.1093/nar/gkg938. PMC 297010. PMID 14654704. |
| Sliding Windows & Assembly | Sliding windows and assembly is a tool chain for folding long series of similar hairpins. | Schroeder S J, Stone J W, Bleckley S, Gibbons T, Mathews D M (July 2011). "Ensemble of secondary structures for encapsidated satellite tobacco mosaic virus RNA consistent with chemical probing and crystallography constraints". Biophysical Journal. 101 (1): 167-175. Bibcode: 2011BpJ . . . 101 . . . 167S. doi: 10.1016/j.bpj.2011.05.053. PMC 3127170. PMID 21723827. |
| SPOT-RNA | SPOT-RNA is first RNA secondary structure predictor which can predict all kind base pairs (canonical, noncanonical, pseudoknots, and base triplets). | Singh J, Hanson J, Paliwal K, Zhou Y (November 2019). "RNA secondary structure prediction using an ensemble of two-dimensional deep neural networks and transfer learning". Nature Communications. 10 (1): 5407. Bibcode: 2019NatCo . . . 10.5407S. doi: 10.1038/s41467-019-13395-9. PMC 6881452. PMID 31776342. |
| SwiSpot | Command-line utility for predicting alternative (secondary) configurations of riboswitches. It is based on the prediction of the so-called switching sequence, to subsequently constrain the folding of the two functional structures. | Barsacchi M, Novoa E M, Kellis M, Bechini A (November 2016). "SwiSpot: modeling riboswitches by spotting out switching sequences". Bioinformatics. 32 (21): 3252-3259. doi: 10.1093/bioinformatics/btw401. PMID 27378291. |
| UNAFold | The UNAFold software package is an integrated collection of programs that simulate folding, hybridization, and melting pathways for one or two single-stranded nucleic acid sequences. | Markham N R, Zuker M (2008). UNAFold: software for nucleic acid folding and hybridization. Methods in Molecular Biology. Vol. 453. pp. 3-31. doi: 10.1007/978-1-60327-429-6_1. ISBN 978-1-60327-428-9. PMID 18712296. |
| vsfold/vs subopt | Folds and predicts RNA secondary structure and pseudoknots using an entropy model derived from polymer physics. The program vs_subopt computes suboptimal structures based on the free energy landscape derived from vsfold5. | Dawson W K, Fujiwara K, Kawai G (September 2007). "Prediction of RNA pseudoknots using heuristic modeling with mapping and sequential folding". PLOS ONE. 2 (9): e905. Bibcode: 2007PLoSO . . . 2 . . . 905D. doi: 10.1371/journal.pone.0000905. PMC 1975678. PMID 17878940. |
| Cocke-Younger Kasami | It employs bottom-up parsing and dynamic programming to predict structure. | Walter, H. K., Brandt, U. (2000). The Cocke-Younger-Kasami Algorithm. Germany: Techn. Univ., Fachbereich Informatik. |
| loop-based energy | Determines RNAs having more favorable folding by way of free energies. | Mathews, David H et al. "Folding and finding RNA secondary structure." Cold Spring Harbor perspectives in biology vol. 2, 12 (2010): a003665. doi: 10.1101/cshperspect.a003665 |

In some embodiments, an RNA folding model is selected from (and/or is contained within the software identified in) Table 1. In some embodiments, an RNA folding model comprises a model selected from the group consisting of Cocke-Younger Kasami model, inside and outside model, loop-based energy model, minimum free energy, centroid, CONTRAfold, CentroidFold, ContextFold, and combinations thereof. In some embodiments, an RNA structure is determined by a model selected from the group consisting of minimum free energy, centroid (e.g., centroidFold), suboptimal folding, and any combination thereof.

In some embodiments, a nearest-neighbor (NN) model, and variants derived therefrom, is utilized to predict RNA structure. The NN model can be used for the calculation of energy changes of any structure of a given RNA molecule, and the DP algorithm can be also employed to efficiently find the MFE structure. For predicting a structure with noncanonical base pairs, some other score schemes can be employed as scoring functions, such as nucleotide cyclic motifs score system or equilibrium partition function. In an exemplary approach for RNA secondary-structure prediction, a single RNA sequence is folded according to an appropriate scoring function. In this approach, RNA structure can be divided into substructures such as loops and stems according to the nearest-neighbor model. Dynamic programming algorithms can then be employed for locating the global minimum or probabilistic structures from these substructures. The scoring parameters of each substructure can be obtained experimentally (e.g., RNAfold, RNAstructure, and RNAshapes) or by machine learning (e.g., CONTRAfold, CentroidFold, ContextFold, and the like). In some embodiments, RNAfold is utilized. In some embodiments, CentroidFold is utilized.

In some embodiments, RNA expression can be associated with predicted secondary or tertiary structures across multiple RNA folding models. In some embodiments, methods disclosed herein comprise use of one or more models. In some embodiments, methods disclosed herein comprise use of two or more models. In some embodiments, from about 0, 1, 2, 3, 4, or 5 models are employed.

In some embodiments, nucleic acid sequences having increased RNA and/or protein expression comprise similar or identical predicted secondary or tertiary structure across two or more models. In some embodiments, nucleic acid sequences comprising a codon variation comprise increased RNA and/or protein expression. The nucleic acid sequences comprising the codon variation may also have similar or identical predicted secondary or tertiary structure across two or more models. Exemplary codon variations are provided herein and any of which can be employed to increase expression.

ML-based methods for RNA secondary structure prediction can generally be divided into 3 categories according to the subprocess that ML participates in, i.e., score scheme based on ML, preprocessing and postprocessing based on ML, and prediction process based on ML. In some embodiments, the ML-based models learn functions that map inputs (features) to outputs by adjusting model parameters based on the known input-output pairs. Many of them employ free energy parameters, encoded RNA sequences, sequence patterns, or evolutionary information as key features, and their outputs can be classification labels (such as paired or unpaired) or continuous values (such as free energy). When a new input is fed to the trained model, the model can classify a corresponding label or predict a corresponding value. A non-limiting list of ML RNA folding models is provided in Table 2, below. In some embodiments, an RNA folding model of Table 1 also employs machine learning.

TABLE 2

Non-Limiting List of ML-based RNA Secondary Structure Prediction Methods.

| Category | | ML Technique | Reference |
| --- | --- | --- | --- |
| Score scheme based on ML model | Free energy parameter-refining approach based on ML | Linear regression | Xia T B, SantaLucia J, Burkard M E, Kierzek R, Schroeder S J, Jiao X Q, et al. Thermodynamic parameters for an expanded nearest-neighbor model for formation of RNA duplexes with Watson-Crick base pairs. Biochemistry. 1998; 37(42): 14719-35. |
| | | Constraint generation | Andronescu M, Condon A, Hoos H H, Mathews D H, Murphy K P. Efficient parameter estimation for RNA secondary structure prediction. Bioinformatics. 2007; 23(13): i19-i28. |
| | | Loss-augmented max-margin constraint generation model, Boltzmann-likelihood model | Andronescu M, Condon A, Hoos H H, Mathews D H, Murphy K P. Computational approaches for RNA energy parameter estimation. RNA. 2010; 16(12): 2304-18. |
| | Weighted approach based on ML | Discriminative structured-prediction learning framework combined, online learning algorithm | Zakov S, Goldberg Y, Elhadad M, Ziv-Ukelson M. Rich parameterization improves RNA structure prediction. J Comput Biol. 2011; 18(11): 1525-42. |
| | | SSVM | Akiyama M, Sato K, Sakakibara Y. A max-margin training of RNA secondary structure prediction integrated with the thermodynamic model. J Bioinform Comput Biol. 2018; 16(6): 1840025. |
| | | Deep neural network | Sato K, Akiyama M, Sakakibara Y. RNA secondary structure prediction using deep learning with thermodynamic integration. Nat Commun. 2021; 12(1): 945 |
| | Probabilistic approach based on ML | EM method | Sakakibara Y, Brown M, Hughey R, Mian I S, Sjölander K, Underwood R C, et al. Stochastic contextfree grammars for tRNA modeling. Nucleic Acids Res. 1994; 22(23): 5112-20 |
| | | EM method | Knudsen B, Hein J. RNA secondary structure prediction using stochastic context-free grammars and evolutionary history. Bioinformatics. 1999; 15(6): 446-54. |
| | | EM method | Knudsen B, Hein J. Pfold: RNA secondary structure prediction using stochastic context-free grammars. Nucleic Acids Res. 2003; 31(13): 3423-8. |
| | | CLLM | Do C B, Woods D A, Batzoglou S. CONTRAfold: RNA secondary structure prediction without physicsbased models. Bioinformatics. 2006; 22(14): e90-e8. |
| | | Semi-supervised learning algorithm | Yonemoto H, Asai K, Hamada M. A semi-supervised learning approach for RNA secondary structure prediction. Comput Biol Chem. 2015; 57: 72-9. |

TABLE 2-continued

Non-Limiting List of ML-based RNA Secondary Structure Prediction Methods.

| Category | | ML Technique | Reference |
| --- | --- | --- | --- |
| Preprocessing and postprocessing based on ML model | Preprocessing based on ML model | SVM | Hor C-Y, Yang C-B, Chang C-H, Tseng C-T, Chen H-H. A Tool Preference Choice Method for RNA Secondary Structure Prediction by SVM with Statistical Tests. Evol Bioinformatics Online. 2013; 9: 163-84. |
| | | Statistical context-free grammar model | Zhu Y, Xie Z Y, Li Y Z, Zhu M, Chen Y P P. Research on folding diversity in statistical learning methods for RNA secondary structure prediction. Int J Biol Sci. 2018; 14(8): 872-82. |
| | Postprocessing based on ML model | MLP | Haynes T, Knisley D, Knisley J. Using a neural network to identify secondary RNA structures quantified by graphical invariants. Match Commun Math Comput Chem. 2008; 60(2): 277-90. |
| | | MLP | Koessler D R, Knisley D J, Knisley J, Haynes T. A predictive model for secondary RNA structure using graph theory and a neural network. BMC Bioinformatics. 2010; 11(Suppl 6): S21. |
| Predicting process based on ML model | End-to-end approach | System composed of several interactional neurons | Takefuji Y, Chen L L, Lee K C, Huffman J. Parallel algorithms for finding a near-maximum independent set of a circle graph. IEEE Trans Neural Netw. 1990; 1(3): 263-7. |
| | | Hopfield networks | Liu Q, Ye X, Zhang Y. A Hopfield Neural Network based algorithm for RNA secondary structure prediction. 1st International Multi Symposium on Computer and Computational Sciences; Hangzhou, China: IEEE; 2006. |
| | | MLP | Qasim R, Kauser N, Jilani T. Secondary Structure Prediction of RNA using Machine Learning Method. Int J Comput Appl. 2011; 10(6): 0975-8887. |
| | | MFT network | Steeg E W. Neural networks, adaptive optimization, and RNA secondary structure prediction. Artificial intelligence and molecular biology. 1993: 121-60. |
| | | MFT network with mean field approximation to update network's nodes | Apolloni B, Lotorto L, Morpurgo A, Zanaboni A. RNA Secondary Structure Prediction by MFT Neural Networks. Psychol Forsch. 2003: 143-8. |
| | | Compound deep neural networks, transfer learning | Singh J, Hanson J, Paliwal K, Zhou Y Q. SPOT-RNA: RNA Secondary Structure Prediction using an Ensemble of Two-dimensional Deep Neural Networks and Transfer Learning. Nat Commun. 2019; 10 (1): 1-13. |
| | | Compound deep neural networks | Chen X, Li Y, Umarov R, Gao X, Song L. RNA Secondary Structure Prediction By Learning Unrolled Algorithms. International Conference on Learning Representations. 2020. |
| | | CNN, MLP | Calonaci N, Jones A, Cuturello F, Sattler M, Bussi G. Machine learning a model for RNA structure prediction. 2020; 2(4): lqaa090. |
| | Hybrid approach | Hierarchical network of k-nearest neighbor model | Bindewald E, Shapiro B A. RNA secondary structure prediction from sequence alignments using a network of k-nearest neighbor classifiers. RNA. 2006; 12(3): 342-52. |
| | | Bi-LSTM | Quan L, Cai L, Chen Y, Mei J, Sun X, Lyu Q. Developing parallel ant colonies filtered by deep learned constrains for predicting RNA secondary structure with pseudo-knots. Neurocomputing. 2020; 384: 104-14. |
| | | Bi-LSTM | Wu H, Tang Y, Lu W, Chen C, Huang H, Fu Q, editors. RNA Secondary Structure Prediction Based on Long Short-Term Memory Model. 14th International Conference on Intelligent Computing (ICIC); 2018; Wuhan. China. |
| | | Bi-LSTM | Lu W, Tang Y, Wu H, Huang H, Fu Q, Qiu J, et al. Predicting RNA secondary structure via adaptive deep recurrent neural networks with energy-based filter. BMC Bioinformatics. 2019; 20(Suppl 25): 684. |
| | | CNN | Zhang H, Zhang C, Li Z, Li C, Wei X, Zhang B, et al. A New Method of RNA Secondary Structure Prediction Based on Convolutional Neural Network and Dynamic Programming. Front Genet. 2019; 10: 467. |
| | | Bi-LSTM | Wang L, Liu Y, Zhong X, Liu H, Lu C, Li C, et al. DMfold: A Novel Method to Predict RNA Secondary Structure With Pseudoknots Based on Deep Learning and Improved Base Pair Maximization Principle. Front Genet. 2019; 10: 143. |

TABLE 2-continued

Non-Limiting List of ML-based RNA Secondary Structure Prediction Methods.

| Category | ML Technique | Reference |
|---|---|---|
| | Bi-LSTM | Willmott D, Murrugarra D, Ye Q. Improving RNA secondary structure prediction via state inference with deep recurrent neural networks. Comput Math Biophys. 2020; 8: 36-50. |

CLLM, conditional log-linear model; CNN, convolutional neural network; EM, expectation-maximization; MFT, mean field theory; ML, machine learning; MLP, multilayer perceptron; SSVM, structured support vector machine; SVM, support vector machine.
Adapted from Zhao Q, Zhao Z, Fan X, Yuan Z, Mao Q, Yao Y (2021) Review of machine learning methods for RNA secondary structure prediction. PLOS Comput Biol 17(8): e1009291.

Wet-Lab Nucleic Acid Structures

In some embodiments, a wet lab method is utilized to predict or determine RNA structure. X-ray crystallography and nuclear magnetic resonance (NMR) are exemplary approaches for determining RNA structures, both of which can offer structural information at a single base pair resolution.

In some embodiments, a wet lab method comprises X-ray crystallography, see Westhof E. Twenty years of RNA crystallography. RNA. 2015; 21(4):486-7, included by reference herein in its entirety. In some embodiments, a wet lab method comprises NMR, see Westhof E. Twenty years of RNA crystallography. RNA. 2015; 21(4):486-7, herein incorporated by reference in its entirety.

In some embodiments, a method employing a wet-lab approach can precede a method comprising machine learning. In other words, structural predictions obtained from a wet-lab method can be input into a method employing machine learning. In some embodiments, images of a structure from a wet-lab analysis can be loaded onto a software of the disclose for nucleic acid structural comparison to inform a selection.

In some embodiments, the present disclosure teaches a modified method for nucleic acid structures determined via wet lab methods. Rather than reciting at least two predicted secondary structures from different RNA folding models, wet lab approaches seek to identify possible folding variants actually identified/observed using the wet lab technique. Thus in some embodiments, the step of predicting secondary structure is replaced with determining structure, and the step of determining structure similarity between predicted structures is replaced with determining structural similarity between actually observed structures.

Assessing Similarity of Nucleic Acid Sequence Structures (Structural Similarity Scores)

The presently disclosed methods can employ any method for assessing similarity between secondary structures of a nucleic acid sequence. In some embodiments, the secondary structure comprises RNA structure. In some embodiments the secondary structure comprises single stranded DNA. In some embodiments, secondary structures of nucleic acids can be compared visually, or can be assessed entirely in silico. In some embodiments, the secondary structures are assessed via hybrid approaches. In some embodiments, similarity scores are saved/recorded/written down to permit further review/analysis. In some embodiments, similarity scores are assessed, but never recorded.

In-Silico Similarity

In some embodiments, a comparison between predicted secondary or tertiary structures is determined. A comparison can employ in silico methods. In some embodiments, an in-silico method utilizes software that is configured to accept information (e.g., an image or other data file conveying information about a chemical structure of a nucleic acid or a nucleic acid sequence) and provide an output related to secondary structure and optionally a comparison of secondary structures of a plurality of nucleic acid sequences. Table 3 provides a summary of exemplary software that quantifies differences between nucleic acid sequences. Any of the software of Table 1 can also be utilized to analyze similarity of structures of nucleic acids.

TABLE 3

Exemplary software that quantifies differences. Additional software is provided in Table 1, many of which are also capable of structural comparisons.

| Software | Reference |
|---|---|
| RNAstructure | rna.urmc.rochester.edu/RNAstructureWeb/ |
| CoSSMos | Vanegas, P. L., Hudson, G. A., Davis, A. R., Kelly, S. C., Kirkpatrick, C. C., and Znosko, B. M. (2012) RNA CoSSMos: Characterization of Secondary Structure Motifs- a searchable database of secondary structure motifs in RNA three-dimensional structures, Nucleic Acids D439-D444. |
| RNAView | Yang, H., Jossinet, F., Leontis, N., Chen, L., Westbrook, J., Berman, H. M. and Westhof, E. (2003) Tools for the automatic identification and classification of RNA base pairs. Nucleic Acids Res, 31, 3450-3460 |

In some embodiments, structural similarity is determined by any other algorithmic/computational method known to persons having skill in the art, including those disclosed in Nikolova, N. and Jaworska, J. (2003), Approaches to Measure Chemical Similarity—a Review. QSAR Comb. Sci., 22: 1006-1026.

In some embodiments, structural similarity of the NP is evaluated by calculating the pairwise nucleic acid sequence secondary structure based on the Tanimoto coefficient and using the python library RDKit (www.rdkit.org). Briefly, morgan fingerprints are prepared for the at least two secondary structures. These fingerprints are then compared to assess similarity.

In some embodiments, the Tanimoto coefficient is calculated with the formula for dichotomous variables.

$$S_{AB} = \frac{C}{A + B - C}$$

In some embodiments, the Tanimoto Coefficient is calculated using formula 1 for continuous variables.

$$S_{A,B} = \frac{\left[\sum nj = 1 XjAXjB\right]}{\left[\sum nj = 1 (xjA)2 + \sum nj = 1 (xjB)2 - \sum nj = 1 XjAXjB\right]} \quad \text{Formula 1}$$

Wherein the SAB similarity score between molecules A and B is calculated by dividing the "C" features in common between two structures, by the "A" the features of a first structure plus the "B" features of a second structure, minus C. That is, A is the number of on bits in molecule A, B is number of on bits in molecule B, while C is the number of bits that are on in both molecules. $x_{j,A}$ means the j-th feature of molecule A. $x_{j,B}$ means the j-th feature of molecule B. For more information on how to calculate the Tanimoto coefficient, see Bajusz, D., Rácz, A. & Héberger, K. Why is Tanimoto index an appropriate choice for fingerprint-based similarity calculations?. *J Cheminform* 7, 20 (2015).

In some embodiments Tanimoto coefficients range from 0 to 1 with 0 being no similarity and 1 being an identical molecule. In some embodiments. In some embodiments, two natural product structures are considered similar if they have a Tanimoto similarity coefficient of at least 0.6, 0.7, 0.8, 0.9, or 0.95, including all ranges and subranges therebetween.

Visual (or Observed/Perceived) Similarity

In some embodiments, secondary structures of nucleic acid sequences are assessed visually or observationally. In some embodiments, the assessment results are quantitative. In some embodiments, the assessment is qualitative. The examples of the present disclosure identify a strong correlation between differences in secondary structures of the same nucleic acid sequence, and the resulting nucleic acid's expression/stability in vivo. Thus, in some embodiments, selecting a nucleic acid sequence with superior expression/stability can be done by picking out a sequence with secondary structures that are less different compared to the secondary structures of at least one other nucleic acid sequence. In some embodiments, this type of distinction can be achieved visually/observationally. For example, at least two secondary structures (e.g., a predicted minimum free energy structure and a predicted centroid structure) can be visually compared and optionally ranked according to perceived similarity. This visual analysis can be completed, for example, by stacking the predicted structure figures with about 50% translucency in a suitable computer program (e.g., Microsoft Word or the like), and visually assessing the amount of overlap. In some embodiments, the predicted structure figures are stacked with about 20%, 30%, 40%, 50%, 60%, 70%, 80%, or up to about 90% translucency, including all ranges and subranges therebetween. In some embodiments, the visual analysis can be conducted by comparing the structures side-by-side, such as on different columns of a table, or sequentially, such as in a flip book.

The visual assessment can be conducted purely on qualitative perception of differences, or can be done by counting number and size of different structures, such as number of loops, steps, helices, and the number of nucleic acids within them. In some embodiments the analysis can be done by assigning a score to each set of structures, or by instead ranking sets based on their similarity. Regardless of whether structure sets are assigned individual scores, or relative scores (e.g., ranking), these are considered a sequence similarity score within the context of this disclosure.

In some embodiments, a visual structure similarity analysis can be supplemented with an in silico analysis. For example, in some embodiments, the assessment of differences between two or more secondary structures can be conducted on the structure itself. In some embodiments, the assessment of differences can be conducted on a representation of structures. For example, in some embodiments, the secondary structures are assessed with the nucleotides represented in the structure. In some embodiments the secondary structures are assessed against wire models of the structures that do not identify individual nucleic acids. In some embodiments, the structures are assessed via shadow (e.g., silhouette) cutout representations of the space occupied by a structure. In some embodiments, structure similarity assessments can also be conducted on more abstract representations of structure. For example, in some embodiments, the structural similarity comparison can be conducted on mountain plot curves, representing the number of nucleic acid residues per position in a predicted structure (see discussion on mountain plots in the disclosure and also in Andreas R. Gruber, Ronny Lorenz, Stephan H. Bernhart, Richard Neuböck, Ivo L. Hofacker, The Vienna RNA Websuite, Nucleic Acids Research, Volume 36, Issue suppl_2, 1 Jul. 2008, Pages W70-W74).

Similarity Variation of Wet-Lab Nucleic Acid Structures

In some embodiments, a wet-lab method is used to predict a structure of a nucleic acid sequence. Wet-lab methods such as X-ray crystallography and nuclear magnetic resonance (NMR) can offer structural information at a single base pair resolution. Although many methods have been developed to infer the state of nucleotides (paired or unpaired) in an RNA molecule using enzymatic or chemical probes coupled with next-generation sequencing most of them can only be used to capture the RNA secondary structure in vitro. The obtained structure may differ markedly from the in vivo conformation. Accordingly, wet-lab methods can be combined with at least one other structural prediction method disclosed herein. In some embodiments, a method comprises a wet-lab method (X-ray crystallography or NMR) and at least one other RNA structure prediction method (e.g., any from Table 1).

Structures obtained from wet-lab techniques can be evaluated in the same way as those developed from RNA folding models. In some embodiments differences in structures observed via wet lab techniques can be assessed visually (observationally) as described herein. In some embodiments differences in structures observed via wet lab techniques can be assessed in silico, using any known structure comparison strategy, including those described herein.

Selection of Nucleic Acid Sequence

In some embodiments, the methods of the present disclosure recite selecting a nucleic acid sequence from amongst the plurality of nucleic acid sequences based on the similarity of the predicted secondary structure. In some embodiments, a nucleic acid sequence is selected if it has a structural similarity score that is higher (i.e., more similar) than at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more, other nucleic acid sequence(s) in the plurality of nucleic acid sequences. In some embodiments, a nucleic acid sequence is selected if it has the highest structural similarity score (i.e., most similar) than at least one other nucleic acid sequence in the plurality of nucleic acid sequences. In some embodiments, the selection is supervised or unsupervised. In some embodiments the selection is done in silico based on a set of pre-existing rules. In some embodiments, the selection is made by a user. As noted above, selection may utilize any appropriate scale for evaluating similarity. Exemplary means comprise, scoring, ranking, percent ranking, and combinations thereof.

In some embodiments, a selection can consider further elements beyond the similarity score. For example, in some embodiments, selection of the nucleic acid sequence can take into account presence or absence of a desired sequence, presence or absence of base pairing or base pairing potential, distance of predicted structural features (e.g., bulge, hairpin, internal loop), relaxed base-pair score, and combinations thereof. For example, in some embodiments, a nucleic acid sequence with a similarity score higher than at least one other nucleic acid sequence may further be evaluated/selected based on the presence of a desired loop length or the presence of other structures. In some embodiments, a nucleic acid sequence is selected due to the presence of an loops with optimal loop length of about 4-8 bp, and/or containing a tetraloop UUCG. In some embodiments a nucleic acid would be less likely to be selected if it exhibited unstable structures that would be expected to present pseudo-knots such as large loops with no secondary structure of their own and loops of less than 4 and more than 8 bp. Selection can also take into amount the frequency of any of the aforementioned aspects.

Scoring can comprise assigning a number from 0-1000. In some embodiments, a selection of a nucleic acid sequence is based on a lower number. In some embodiments a selection is based on a nucleic acid sequence having a higher number. In some embodiments, a sequence is selected having a score of about 0-5, 1-5, 1-10, 0-10, 5-15, 5-20, 15-30, 15-45, 0-50, 5-10, 1-20, 10-30, 15-75, and any subrange in between. In some embodiments, a sequence is selected having a score of about 50-200, 50-150, 100-200, 250-500, 300-500, or 500-1000, and any subrange in between.

In some embodiments, a selection comprises ranking a plurality of nucleic acid sequences according to their score. A selection can comprise selecting lower ranked nucleic acid sequences or higher ranked nucleic acid sequences. Percent ranking can also be employed. Percentile rank of a given score is the percentage of scores in its frequency distribution that are less than that score.

In some embodiments, selection of a nucleic acid sequence can be based on a nucleic acid sequence having a higher structural similarity score than at least one other nucleic acid sequence in a plurality of nucleic acid sequences. In some embodiments, methods comprised herein comprise an analysis comprising a mountain plot. Krouwer and Monti (1995) devised the mountain plot (also known as a folded empirical cumulative distribution plot) as a complementary representation of the difference plot. It shows the distribution of the differences with an emphasis on the center and the tails of the distribution. A mountain plot can be used to estimate the median of the differences, the central 95% interval, the range, and the percentage of observations outside the total allowable error bands. The mountain plot is a useful complementary plot to the Bland & Altman plot which can also be employed in any of the methods provided herein.

A structural similarity score can be increased by any amount. In some embodiments, a structural similarity score is increased by at least about or at most about 1-fold, 5-fold, 10-fold, 15-fold, 25-fold, 50-fold, 75-fold, 100-fold, 125-fold, 150-fold, 175-fold, 200-fold, 225-fold, 250-fold, 275-fold, 300-fold, 325-fold, 350-fold, 375-fold, 400-fold, 425-fold, 450-fold, 475-fold, or up to about 500-fold, including all ranges and subranges therebetween. In some embodiments, a structural similarity score is increased by at least about or at most about 5%, 10%, 20%, 30%, 40%, 50%, 60%, 70%, 80%, 90%, 100%, 110%, 120%, 130%, 140%, 150%, or up to about 200%, including all ranges and subranges therebetween.

In some embodiments, a method provided herein comprises determining a structural similarity score. A structural similarity score can be determined by way of any of the RNA structure prediction models provided herein.

In some embodiments, an in silico structural similarity analysis can inform selection of a nucleic acid sequence, from a plurality of nucleic acid sequences, to be manufactured into a nucleic acid. In some embodiments, provided methods comprise selecting a nucleic acid sequence with a higher structural similarity score than at least one other nucleic acid sequence in a plurality of nucleic acid sequences. In some embodiments, a selected nucleic acid sequence comprises an optimized codon sequence.

In some embodiments, manufactured nucleic acids can be evaluated for expression in host cells. In some embodiments, a structural similarity score obtained from an in silico analysis is plotted against empirical expression data obtained from manufacture. In some embodiments, nucleic acids showing high expression, comprise a logarithmic correlation between an in silico structural similarity analysis and a related empirical analysis. In some embodiments, a logarithmic correlation comprises an R2 correlation coefficient of at least about or at most about 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, or up to about 1, including all ranges and subranges therebetween.

Manufacturing

Provided herein are methods of manufacturing a nucleic acid. Persons having skill in the art will be familiar with the multiple strategies for manufacturing nucleic acids. In some embodiments, a selected nucleic acid sequence is manufactured into a nucleic acid. In some embodiments, the manufactured nucleic acid exhibits greater expression in a host cell as compared to a non-selected nucleic acid, if the non-selected nucleic acid were manufactured. In some embodiments, the increased expression is at least about or at most about: 0.5-fold, 1-fold, 3-fold, 5-fold, 7-fold, 10-fold, 12-fold, 15-fold, 20-fold, 30-fold, 40-fold, 50-fold, 60-fold, 70-fold, 80-fold, 90-fold, 100-fold, 110-fold, 120-fold, 130-fold, 140-fold, 150-fold, or up to about 200-fold, including all ranges and subranges therebetween.

In some embodiments, a nucleic acid comprises a sequence with at least about or at most about 85%, 90%, 95%, 96%, 97%, 98%, 99%, or 100% identity to any one of SEQ ID NO: 757, 760, 762, 763, 765, 772, 773, 778, and 780. In some embodiments, a nucleic acid comprises a sequence selected from the group consisting of: SEQ ID NO: 757, 760, 762, 763, 765, 772, 773, 778, and 780. In some embodiments, a nucleic acid comprises SEQ ID NO: 757. In some embodiments, a nucleic acid comprises SEQ ID NO: 760. In some embodiments, a nucleic acid comprises SEQ ID NO: 762. In some embodiments, a nucleic acid comprises SEQ ID NO: 763. In some embodiments, a nucleic acid comprises SEQ ID NO: 765. In some embodiments, a nucleic acid comprises SEQ ID NO: 772. In some embodiments, a nucleic acid comprises SEQ ID NO: 773. In some embodiments, a nucleic acid comprises SEQ ID NO: 778. In some embodiments, a nucleic acid comprises SEQ ID NO: 780. In some embodiments, a host cell comprises a nucleic acid encoding any one of SEQ ID NO: 685, 687, and 695. In some embodiments, a host cell comprises a nucleic acid encoding a sequence comprising at least about 85%, 90%, 95%, 96%, 97%, 98%, 99%, or 100% identity to any one of SEQ ID NO: 685, 687, and 695.

In some embodiments, a plurality of nucleic acid sequences that undergo a method to inform a selection encode for the same amino acid sequence (e.g., a protein with comparable identity and/or function). In some embodiments, the amino acid sequences comprise at least about or at most about 75%, 80%, 85%, 90%, 95%, 96%, 97%, 98%, 99%, or 100% sequence identity, including all ranges and subranges therebetween.

Computer and Robotic System

In some embodiments, a method of the disclosure comprises a computer system and optionally a robotic system.

In addition, any or call of the methods of the disclosure can comprise automation, for example the systems may be at least partially automated or fully automated. In some embodiments, a system of the disclosure can comprise one or more work modules (e.g., a DNA/RNA synthesis module, a vector cloning module, a selection module, a sequencing module, and combinations thereof).

As will be appreciated by those in the art, an automated system can include a wide variety of components, including, but not limited to: liquid handlers; one or more robotic arms; plate handlers for the positioning of microplates; plate sealers, plate piercers, automated lid handlers to remove and replace lids for wells on non-cross contamination plates; disposable tip assemblies for sample distribution with disposable tips; washable tip assemblies for sample distribution; 96 well loading blocks; integrated thermal cyclers; cooled reagent racks; microtiter plate pipette positions (optionally cooled); stacking towers for plates and tips; magnetic bead processing stations; filtrations systems; plate shakers; barcode readers and applicators; and one or more computer systems. Provided systems can comprise use of a microtiter plate (e.g., a 96- or 384-well plate), optionally configured for automated systems.

In some embodiments, the robotic systems of the present disclosure comprise automated handling (e.g., a robotic arm) enabling high-throughput pipetting to perform any or all of the steps in a method described herein. Exemplary methods can comprise aspiration, dispensing, mixing, diluting, washing, accurate volumetric transfers; retrieving and discarding of pipette tips; and repetitive pipetting of identical volumes for multiple deliveries from a single sample aspiration. These manipulations can be cross-contamination free.

In some embodiments, the automated systems of the present disclosure are compatible with platforms for multi-well plates, deep-well plates, square well plates, reagent troughs, test tubes, mini tubes, microfuge tubes, cryovials, filters, micro array chips, optic fibers, beads, agarose and acrylamide gels, and other solid-phase matrices or platforms are accommodated on an upgradeable modular deck. In some embodiments, the automated systems of the present disclosure contain at least one modular deck for multi-position work surfaces for placing source and output samples, reagents, sample and reagent dilution, assay plates, sample and reagent reservoirs, pipette tips, and an active tip-washing station.

In some embodiments, an integrated thermal cycler and/or thermal regulators are used for stabilizing the temperature of heat exchangers such as controlled blocks or platforms to provide accurate temperature control of incubating samples from 0° C. to 100° C.

In some embodiments, an automated system of the present disclosure is designed to be flexible and adaptable with multiple hardware add-ons to allow the system to carry out multiple applications. In some embodiments, a software program module can allow creation, modification, and running of methods. A system's diagnostic modules can allow setup, instrument alignment, and motor operations. The customized tools, labware, and liquid and particle transfer patterns allow different applications to be programmed and performed. A database can allow method and parameter storage. Robotic and computer interfaces allow communication between instruments.

Persons having skill in the art will recognize the various robotic platforms capable of carrying out any of the methods of the present disclosure. Table 3.5 below provides a non-exclusive list of scientific equipment capable of carrying out steps of the disclosure.

TABLE 3.5

Exemplary equipment that can be comprised in a method of the disclosure.

| Equipment Type | Operation(s) performed | Compatible Equipment |
| --- | --- | --- |
| liquid handlers | Hitpicking (combining by transferring) primers/templates for PCR amplification of DNA parts | Hamilton Microlab STAR, Labcyte Echo 550, Tecan EVO 200, Beckman Coulter Biomek FX, or equivalents |
| Thermal cyclers | PCR amplification of DNA parts | Inheco Cycler, ABI 2720, ABI Proflex 384, ABI Veriti, or equivalents |
| Fragment analyzers (capillary electrophoresis) | gel electrophoresis to confirm PCR products of appropriate size | Agilent Bioanalyzer, AATI Fragment Analyzer, or equivalents |
| Sequencer (sanger: Beckman) | Verifying sequence of parts/templates | Beckman Ceq-8000, Beckman GenomeLab ™, or equivalents |
| NGS (next generation sequencing) instrument | Verifying sequence of parts/templates | Illumina MiSeq series sequences, illumina Hi-Seq, Ion torrent, pac bio or other equivalents |
| nanodrop/plate reader | assessing concentration of DNA samples | Molecular Devices SpectraMax M5, Tecan M1000, or equivalents. |
| liquid handlers | Hitpicking (combining by transferring) DNA parts for assembly along with cloning vector, addition of reagents for assembly reaction/process | Hamilton Microlab STAR, Labcyte Echo 550, Tecan EVO 200, Beckman Coulter Biomek FX, or equivalents |

TABLE 3.5-continued

Exemplary equipment that can be comprised in a method of the disclosure.

| Equipment Type | Operation(s) performed | Compatible Equipment |
|---|---|---|
| Colony pickers | for inoculating colonies in liquid media | Scirobotics Pickolo, Molecular Devices QPix 420 |
| liquid handlers | Hitpicking primers/templates, diluting samples | Hamilton Microlab STAR, Labcyte Echo 550, Tecan EVO 200, Beckman Coulter Biomek FX, or equivalents |
| Fragment analyzers (capillary electrophoresis) | gel electrophoresis to confirm assembled products of appropriate size | Agilent Bioanalyzer, AATI Fragment Analyzer |
| Sequencer (sanger: Beckman) | Verifying sequence of assembled plasmids | ABI3730 Thermo Fisher, Beckman Ceq-8000, Beckman GenomeLab ™, or equivalents |
| NGS (next generation sequencing) instrument | Verifying sequence of assembled plasmids | Illumina MiSeq series sequences, illumina Hi-Seq, Ion torrent, pac bio or other equivalents |
| centrifuge | spinning/pelleting cells | Beckman Avanti floor centrifuge, Hettich Centrifuge |
| Electroporators | electroporative transformation of cells | BTX Gemini X2, BIO-RAD MicroPulser Electroporator |
| Ballistic transformation | ballistic transformation of cells | BIO-RAD PDS1000 |
| Incubators, thermal cyclers | for chemical transformation/heat shock | Inheco Cycler, ABI 2720, ABI Proflex 384, ABI Veriti, or equivalents |
| Liquid handlers | for combining DNA, cells, buffer | Hamilton Microlab STAR, Labcyte Echo 550, Tecan EVO 200, Beckman Coulter Biomek FX, or equivalents |
| Colony pickers | for inoculating colonies in liquid media | Scirobotics Pickolo, Molecular Devices QPix 420 |
| Liquid handlers | For transferring cells onto Agar, transferring from culture plates to different culture plates (inoculation into other selective media) | Hamilton Microlab STAR, Labcyte Echo 550, Tecan EVO 200, Beckman Coulter Biomek FX, or equivalents |
| Platform shaker-incubators | incubation with shaking of microtiter plate cultures | Kuhner Shaker ISF4-X, Infors-ht Multitron Pro |
| Colony pickers | for inoculating colonies in liquid media | Scirobotics Pickolo, Molecular Devices QPix 420 |
| liquid handlers | Hitpicking primers/templates, diluting samples | Hamilton Microlab STAR, Labcyte Echo 550, Tecan EVO 200, Beckman Coulter Biomek FX, or equivalents |
| Thermal cyclers | cPCR verification of strains | Inheco Cycler, ABI 2720, ABI Proflex 384, ABI Veriti, or equivalents |
| Fragment analyzers (capillary electrophoresis) | gel electrophoresis to confirm cPCR products of appropriate size | Infors-ht Multitron Pro, Kuhner Shaker ISF4-X |
| Sequencer (sanger: Beckman) | Sequence verification of introduced modification | Beckman Ceq-8000, Beckman GenomeLab ™, or equivalents |
| NGS (next generation sequencing) instrument | Sequence verification of introduced modification | Illumina MiSeq series sequences, illumina Hi-Seq, Ion torrent, pac bio or other equivalents |
| Liquid handlers | For transferring from culture plates to different culture plates (inoculation into production media) | Hamilton Microlab STAR, Labcyte Echo 550, Tecan EVO 200, Beckman Coulter Biomek FX, or equivalents |
| Colony pickers | for inoculating colonies in liquid media | Scirobotics Pickolo, Molecular Devices QPix 420 |
| Platform shaker-incubators | incubation with shaking of microtiter plate cultures | Kuhner Shaker ISF4-X, Infors-ht Multitron Pro |
| Liquid handlers | For transferring from culture plates to different culture plates (inoculation into production media) | Hamilton Microlab STAR, Labcyte Echo 550, Tecan EVO 200, Beckman Coulter Biomek FX, or equivalents |

TABLE 3.5-continued

Exemplary equipment that can be comprised in a method of the disclosure.

| Equipment Type | Operation(s) performed | Compatible Equipment |
|---|---|---|
| Platform shaker-incubators | incubation with shaking of microtiter plate cultures | Kuhner Shaker ISF4-X, Infors-ht Multitron Pro |
| liquid dispensers | Dispense liquid culture media into microtiter plates | Well mate (Thermo), Benchcel2R (velocity 11), plateloc (velocity 11) |
| microplate labeler | apply barcoders to plates | Microplate labeler (a2+ cab - agilent), benchcell 6R (velocity 11) |
| Liquid handlers | For transferring from culture plates to different culture plates (inoculation into production media) | Hamilton Microlab STAR, Labcyte Echo 550, Tecan EVO 200, Beckman Coulter Biomek FX, or equivalents |
| Platform shaker-incubators | incubation with shaking of microtiter plate cultures | Kuhner Shaker ISF4-X, Infors-ht Multitron Pro |
| liquid dispensers | Dispense liquid culture media into multiple microtiter plates and seal plates | well mate (Thermo), Benchcel2R (velocity 11), plateloc (velocity 11) |
| microplate labeler | Apply barcodes to plates | microplate labeler (a2+ cab - agilent), benchcell 6R (velocity 11) |
| Liquid handlers | For processing culture broth for downstream analytical | Hamilton Microlab STAR, Labcyte Echo 550, Tecan EVO 200, Beckman Coulter Biomek FX, or equivalents |
| UHPLC, HPLC | quantitative analysis of precursor and target compounds | Agilent 1290 Series UHPLC and 1200 Series HPLC with UV and RI detectors, or equivalent; also any LC/MS |
| LC/MS | highly specific analysis of precursor and target compounds as well as side and degradation products | Agilent 6490 QQQ and 6550 QTOF coupled to 1290 Series UHPLC |
| Spectrophotometer | Quantification of different compounds using spectrophotometer based assays | Tecan M1000, spectramax M5, Genesys 10S |
| Fermenters: | incubation with shaking | Sartorius, DASGIPs (Eppendorf), BIO-FLOs (Sartorius-stedim). Applikon |
| Platform shakers | | innova 4900, or any equivalent |
| Fermenters: DASGIPs (Eppendorf), BIO-FLOs (Sartorius-stedim) | | |
| Liquid handlers | For transferring from culture plates to different culture plates (inoculation into production media) | Hamilton Microlab STAR, Labcyte Echo 550, Tecan EVO 200, Beckman Coulter Biomek FX, or equivalents |
| UHPLC, HPLC | quantitative analysis of precursor and target compounds | Agilent 1290 Series UHPLC and 1200 Series HPLC with UV and RI detectors, or equivalent; also any LC/MS |
| LC/MS | highly specific analysis of precursor and target compounds as well as side and degradation products | Agilent 6490 QQQ and 6550 QTOF coupled to 1290 Series UHPLC |
| Flow cytometer | Characterize strain performance (measure viability) | BD Accuri, Millipore Guava |
| Spectrophotometer | Characterize strain performance (measure biomass) | Tecan M1000, Spectramax M5, or other equivalents |

Computer System Hardware

Provided herein is hardware that can be used with any of the computer systems described herein. A computer system may be used to execute program code stored in a non-transitory computer readable medium (e.g., memory) in accordance with any of the embodiments of the disclosure. A computer system can comprise an input/output subsystem, which may be used to interface with human users and/or other computer systems depending upon the application. The system may include, e.g., a keyboard, mouse, graphical user interface, touchscreen, or other interfaces for input, and, e.g., an LED or other flat screen display, or other interfaces for output, including application program interfaces (APIs). Other elements of embodiments of the disclosure, such as the components of the LIMS system, may be implemented with a computer system.

Program code may be stored in non-transitory media such as persistent storage in secondary memory or main memory or both. Main memory may include volatile memory such as random access memory (RAM) or non-volatile memory such as read only memory (ROM), as well as different levels of cache memory for faster access to instructions and data. Secondary memory may include persistent storage such as solid state drives, hard disk drives or optical disks. One or more processors can read program code from one or more non-transitory media and execute the code to enable the computer system to accomplish a method herein. Those skilled in the art will understand that the processor(s) may ingest source code, and interpret or compile the source code into machine code that is understandable at the hardware gate level of the processor(s). The processor(s) may include graphics processing units (GPUs) for handling computationally intensive tasks. Particularly in machine learning, one or more CPUs may offload the processing of large quantities of data to one or more GPUs.

In some embodiments, a processor(s) may communicate with external networks via one or more communications interfaces, such as a network interface card, WiFi transceiver, etc. A bus communicatively couples the I/O subsystem, the processor(s), peripheral devices, communications interfaces, memory, and persistent storage. Embodiments of the disclosure are not limited to this representative architecture.

As used herein, the term component in this context refers broadly to software, hardware, or firmware (or any combination thereof) component. Components are typically functional components that can generate useful data or other output using specified input(s). A component may or may not be self-contained. An application program (also called an "application") may include one or more components, or a component can include one or more application programs.

The term "memory" can be any device or mechanism used for storing information. In accordance with some embodiments of the present disclosure, memory is intended to encompass any type of, but is not limited to: volatile memory, nonvolatile memory, and dynamic memory. For example, memory can be random access memory, memory storage devices, optical memory devices, magnetic media, floppy disks, magnetic tapes, hard drives, SIMMs, SDRAM, DIMMs, RDRAM, DDR RAM, SODIMMS, erasable programmable read-only memories (EPROMs), electrically erasable programmable read-only memories (EEPROMs), compact disks, DVDs, and/or the like. In accordance with some embodiments, memory may include one or more disk drives, flash drives, databases, local cache memories, processor cache memories, relational databases, flat databases, servers, cloud-based platforms, and/or the like. In addition, those of ordinary skill in the art will appreciate many additional devices and techniques for storing information can be used as memory.

In some embodiments, memory may be used to store instructions for running one or more applications or modules on a processor. For example, memory could be used in some embodiments to house all or some of the instructions needed to execute the functionality of one or more of the modules and/or applications disclosed in this application.

Strategies for Stabilization of RNA

Provided herein are nucleic acids that may be used to for stable expression of RNAs in one or more host cells. As described herein, stable expression of RNAs may refer to mechanisms that increase one or more of (i) transcription levels of RNA, (ii) half-life of RNA in a cell, or (iii) efficiency of RNA translation.

In some embodiments, a DNA construct comprises a transgene that encodes one or more proteins. Accordingly, also provided are methods of expressing one or more proteins in a host cell, using the DNA constructs and/or stabilized RNAs disclosed herein. In some embodiments, use of the DNA constructs and/or stabilized RNAs may lead to (i) increased levels of protein expression in a host cell, (ii) increased half-life of the protein in a host cell, and/or (iii) increased accumulation of the protein in a host cell.

Stabilization of RNA can be achieved using a variety of approaches, such as any of those previously described. Exemplary methodologies comprise the use of elements in the construct which modulate transcriptional regulation and/or translational regulation. Illustrative methods for modulation of transcriptional regulation include codon optimization. Illustrative methods for modulation of translational regulation include modification of a promoter and/or terminator, codon optimization, modification of an intron sequence, insertion of exogenous intron sequences, insertion or modification of a 5' and/or 3' untranslated region (UTR), the use of a ubiquitin monomer, and any combination thereof.

In some embodiments, the DNA constructs of the disclosure can comprise one or more elements, and the elements may be provided in any order. For example, a DNA construct may comprise the following elements, in order from 5' to 3': promoter-signal sequence-transgene-KDEL-terminator. In some embodiments, a DNA construct may comprise an intron. In some embodiments, the intron is located within the transgene sequence, or 5' or 3' thereto. In some embodiments, the intron is located between the promoter and the signal sequence, between the signal sequence and the transgene, between the transgene and the KDEL, or between the KDEL and the terminator.

Promoters

In some embodiments, stabilization of RNA in a host cell can be achieved via transcriptional regulation. For example, in some embodiments, transcriptional regulation of an RNA may be achieved by modulation of a promoter sequence in a DNA construct encoding the RNA. Modulation of a promoter can refer to modulation of an endogenous promoter, such as making one or more nucleotide substitutions relative to an endogenous promoter. In some embodiments, modulation of a promoter may refer to the addition of one or more exogenous promoters to a DNA construct.

In some embodiments, a DNA construct comprises a promoter that is capable of stably expressing an RNA in a cell. In some embodiments, a DNA construct comprises a promoter that is capable of increasing the level of RNA in a cell. In some embodiments, a DNA construct comprises a promoter that leads to increased half-life of an RNA in a cell. The promoters described herein may be derived in their entirety from a native gene or be composed of different elements derived from different promoters found in nature, or even comprise synthetic DNA segments.

In some embodiments, the promoter may be a plant promoter. A "plant promoter" is a promoter capable of initiating transcription in plant cells and can drive or facilitate transcription of a nucleotide sequence or fragment thereof of the instant invention. Such promoters need not be of plant origin. For example, promoters derived from plant viruses, such as the CaMV35S promoter or from *Agrobacterium tumefaciens*, such as the T-DNA promoters, can be plant promoters. A typical example of a plant promoter of plant origin is the maize ubiquitin-1 (ubi-1) promoter known to those of skill. Plant promoters can be from a monocot, dicot, *Arabidopsis*, rice, modified versions thereof, or combinations thereof.

Promoters can be selected based on the desired outcome, and may include constitutive, tissue-specific, inducible, or other promoters for expression in the host organism. In some embodiments, a promoter is a constitutive promoter. Promoters referred to herein as "constitutive promoters" actively promote transcription under most, but not necessarily all, environmental conditions and states of development or cell differentiation. Promoters from viral (Verdaguer et al., 1998; Schenk et al., 1999; Bohorova et al., 2001; Samac et al., 2004; Davies et al., 2014) and plant polyubiquitin (UBQ) genes (Lu et al., 2008; Mann et al., 2011) can be used to obtain enhanced constitutive transgene expression. Exemplary constitutive plant promoters comprise: Cauliflower Mosaic Virus 35S (35S), 1' or 2' promoter derived from T-DNA of *Agrobacterium tumefaciens*, maize ubiquitin-1, or modified versions of any of these.

In choosing a promoter to use in the methods of the disclosure, it may be desirable to use a tissue-specific or developmentally regulated promoter. In some cases, a promoter is a specific promoter. A specific promoter refers to a promoter that has a high preference for being active in a specific tissue or cell and/or at a specific time during development of a plant. By "high preference" is meant at least a 3-fold, preferably 5-fold, more preferably at least 10-fold still more preferably at least a 20-fold, 50-fold or 100-fold increase in transcription in the desired tissue over the transcription in any other tissue. Typical examples of temporal and/or tissue specific promoters of plant origin that can be used with the polynucleotides of the present invention, are: SH-EP from *Vigna mungo* and EP-C1 from *Phaseolus vulgaris* (Yamauchi et al. (1996) Plant Mol Biol. 30:321-9.); RCc2 and RCc3, promoters that direct root-specific gene transcription in rice (Xu et al. (1995) Plant Mol. Biol. 27:237) and TobRB27, a root-specific promoter from tobacco (Yamamoto et al. (1991) Plant Cell 3:371).

Promoters which are seed or embryo-specific and may be useful in disclosure include soybean Kunitz trypsin inhibitor (Kti3, Jofuku and Goldberg, Plant Cell 1:1079-1093 (1989)), patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259:149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), β-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol. Biol. 14:595-604).

In some embodiments, a promoter can be a soybean promoter. In some cases, a promoter can be a soybean seed specific promoter. Exemplary suitable soybean promoters comprise: AtOle1, GmBg7S1, Gm2S-1, GmBBId-II, GmCons4, GmCons6, GmCons10, GmRoot1, GmRoot2, GmRoot3, GmRoot5, GmRoot6, GmRoot7, GmRoot8, GmSeed2, GmSeed3, GmSeed5, GmSeed6, GmSeed7, GmSeed8, GmSeed10, GmSeed11, GmSeed12, GmCEP1-L, GmGRD, GmFAB1, GmFAB2, GmFAB3, GmFAB5, GmFAB8, GmFAB9, GmFAB10, GmFAB11, GmFAB17, GmTHIC, GmOLEA, GmOLEB, GmWRKY13, GmWRKY17, GmWRKY21, GmWRKY27, GmWRKY43, GmWRKY54, GmWRKY67, GmWRKY79, GmWRKY80, GmWRKY82, GmWRKY85, GmWRKY162, PvDlec2, PvPhas, pBCON, LfKCS3, FAE1, BoACP, BnNap, BnaNapinC, SSPRO2745.1, SSPRO2743.1, modifications thereof, and any combination thereof.

In some embodiments, a promoter is selected from those provided in Table 4 or Table 11. In some embodiments, a promoter comprises a sequence having at least 70%, at least 80%, at least 85%, at least 90%, at least 95%, at least 97%, at least 98%, at least 99%, or 100% identity, including all ranges and subranges therebetween, with a sequence selected from Table 4 or Table 11. In some embodiments, a promoter is selected from the group that consists of: gmSeed2, gmSeed12, and pvPhas. In some embodiments, a DNA construct for stably expressing RNA in a host cell comprises a gmSeed2 promoter operably linked to a transgene. In some embodiments, a DNA construct for stably expressing RNA in a host cell comprises a gmSeed12 promoter operably linked to a transgene. In some embodiments, a DNA construct for stably expressing RNA in a host cell comprises a pvPhas promoter operably linked to a transgene.

In some embodiments, the promoter is an inducible promoter. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Additional promoters for regulating the expression of the transgenes of the present disclosure in plants are stalk-specific promoters. Such stalk-specific promoters include the alfalfa S2A promoter (GenBank Accession No. EF030816; Abrahams et al., Plant Mol. Biol. 27:513-528 (1995)) and S2B promoter (GenBank Accession No. EF030817) and the like, herein incorporated by reference.

The location of promoters used in the DNA constructs designed herein may be selected to increase RNA expression, and/or downstream protein expression. For example, in some embodiments, the promoter may be located proximal to the transcriptional start site. In some embodiments, the promoter may be located distal to the transcriptional start site (i.e., it may be located thousands and more nucleotides adjacent, typically upstream, of the transcriptional start site.) In some embodiments, the promoter may be a minimal promoter. A "minimal promoter" may be, for example, a truncated or modified version of a wildtype promoter that includes substantially only those sequences required to properly initiate transcription.

In some cases, a promoter can be paired with a transcription terminator to achieve improved RNA stability and/or transgene expression in plants. Transcriptional termination is the process by which RNA synthesis by RNA polymerase is substantially stopped, and both the processed messenger RNA and the enzyme are released from the DNA template. In some cases, improper termination of an RNA transcript can affect the stability of the RNA, and hence can affect protein expression. Variability of transgene expression is sometimes attributed to variability of termination efficiency.

Terminator

A "transcriptional terminator" or "terminator" is a nucleic acid sequence that can halt transcription. It comprises a DNA sequence involved in specific termination of RNA transcription by RNA polymerase. Transcriptional terminator sequences can prevent transcriptional activation of downstream nucleic acid sequences by upstream promoters. A transcriptional terminator may be required in vivo to achieve the desired level of expression or to avoid transcription of a particular sequence. A transcription terminator is considered operably linked to a nucleotide sequence if it can reduce or eliminate transcription of the sequence to which it is linked. In some embodiments, the terminator is a forward terminator. Normally, a forward terminator interrupts transcription when placed upstream of a nucleic acid sequence to be transcribed. In some embodiments, the terminator is a bi-directional terminator. A bi-directional terminator may stop transcription for both the forward and reverse strands and may have the capability of terminating transcription in both 5' to 3', and 3' to 5' orientations. A single sequence element that acts as a bidirectional terminator can terminate transcription initiated from two convergent promoters.

In some embodiments, the terminator is a reverse transcription terminator, which typically terminates transcription upon reverse strand swallowing.

Terminator sequences can contain polyadenylation (poly (A)) signals, which control the steps involved in 3' end formation: recognition, endonucleolytic cleavage, and polyadenylation of primary RNA (pre-mRNA). These steps can impact gene expression by influencing mRNA termination, stability, localization, export to cytoplasm, and/or translation efficiency. In some embodiments, a terminator is selected from those provided in Table 4 or Table 11. In some embodiments, a terminator comprises a sequence having from 70%, 80%, 85%, 90%, 95%, 97%, 98%, 99%, or 100% identity, including all ranges and subranges therebetween, with a sequence selected from Table 4 or Table 11.

In eukaryotic systems, such as in plants, a terminator may contain special DNA sequences that allow site-specific cleavage of new transcripts to expose polyadenylation sites. This signals a specialized endogenous polymerase, adding a stretch of about 200 A residues (polyA) to the 3' end of the transcript. RNA molecules modified with this poly A tail are believed to be more stable and more efficiently translated. Thus, in some embodiments, the terminator may include a signal for RNA cleavage. In some embodiments, the terminator signal promotes polyadenylation of the message. Terminators and/or elements of the polyadenylation site can serve to enhance the output nucleic acid levels and/or to minimize readthrough between nucleic acids.

In some embodiments, a DNA construct comprises a terminator that promotes stable expression of an RNA in a cell. In some embodiments, a DNA construct comprises a terminator that is capable of increasing the level of RNA in a cell. In some embodiments, a DNA construct comprises a terminator that leads to increased half-life of an RNA in a cell. In some embodiments, a DNA construct comprises a combination of a promoter and a terminator that is capable of increasing the level of RNA in a cell. In some embodiments, a DNA construct comprises a combination of a promoter and a terminator that leads to increased half-life of an RNA in a cell.

In some embodiments, terminators for use in accordance with the present disclosure include any terminators described herein or known to those of skill in the art. Examples of terminators include, but are not limited to, termination sequences of genes such as, for example, bovine growth hormone terminator, and, for example, NOS, ARC, EU, Rb7, HSP, ATHSP, AtUbi10, Stubi3, TM6, Octopine Synthase (OCS), SV40 terminator, spy, yejM, secG-leuU, thrLABC, rnB T1, hisLGDCBHAFI, metZWV, rnC, xapR, aspA, EU:Rb7, AtHSP:AtUbi10, EU:StUbi3, EU:TM6. In some embodiments, the terminator comprises a virus termination sequences such as an arcA terminator. In some embodiments, the terminator may be a sequence that cannot be transcribed or translated, such as that resulting from sequence truncation. In some embodiments, a terminator is a dual terminator and is selected from the group consisting of: EU:Rb7, AtHSP:AtUbi10, EU:StUbi3, and EU:TM6. In some embodiments, a terminator is selected from the group consisting of NOS, ARC, EU, Rb7, HSP, AtHSP, AtUbi10, Stubi3, and TM6.

Any heterologous polynucleotide of interest can be operably linked to a terminator sequence provided in the disclosure. Examples of polynucleotides of interest that can be operably linked to the terminator sequences described herein include, but are not limited to, polynucleotides comprising regulatory elements such as introns, enhancers, promoters, translation leader sequences, protein-coding regions from disease and insect resistance genes, genes conferring nutritional value, genes conferring yield and heterosis increase, genes that confer male and/or female sterility, antifungal, antibacterial or antiviral genes, selectable marker genes, herbicide resistance genes and the like.

In embodiments, RNA stabilization can be achieved via combination of a terminator and promoter provided herein. In some embodiments, a synergistic effect on RNA stabilization is observed when a terminator and a promoter are present in a DNA construct of the disclosure. In some embodiments, RNA stabilization is increased by at least about 1-fold, about 2-fold, about 3-fold, about 5-fold, about 10-fold, about 20-fold, about 50-fold, about 100-fold, about 300-fold, about 500-fold, or about 1000-fold, including all ranges and subranges therebetween, when a promoter and terminator are present in a DNA construct as compared to an otherwise comparable construct lacking at least one of the promoter or terminator.

Intron

In some embodiments, RNA stabilization can be achieved or improved via the addition or removal of endogenous or exogenous intronic sequences in a DNA construct. Introns are non-coding sections of an RNA transcript that can be removed by RNA splicing during maturation of the final RNA product.

Intron sequences may be incorporated at any location within a DNA construct, including but not limited to a 5' end, 3' end, within or adjacent to a transgene sequence, and any combination thereof. In some cases, an intron sequence is added within a transgene sequence. In some cases, an intron is located within about 0-5, 1-10, 5-25, or 10-30 bases from a start of a transgene sequence. In some cases, an intron is located up to about 0, 5, 10, 15, 20, 30, 40, 50, 70, 90, or 100 bases from a start of a transgene sequence. In some embodiments, an intron is placed adjacent to a 5'UTR. In some embodiments, an intron is placed within a coding sequence of a transgene. In some embodiments, an intron is placed after a promoter sequence. In some embodiments, an intron is placed between a promoter sequence and a coding sequence. In some cases, an endogenous or native intron is replaced with an exogenous intron. Replacement may be full replacement or partial replacement. In cases comprising partial intron replacement, a portion of an endogenous intron remains and can be adjacent to an exogenous intron sequence.

In some embodiments, an intron sequence used in a DNA construct is isolated or derived from a eukaryote. For example, the intron may be isolated or derived from an intronic sequence of a eukaryote selected from animals, plants, and fungi. In some cases, an intron sequence may be isolated or derived from a plant. The plant intronic sequence may be from the same plant species as a host cell, a different plant species as compared to a host cell, or a hybrid species. In some embodiments, an intron sequence isolated or derived from *glycine max, Arabidopsis thaliana*, or both. In some embodiments, an intron sequence is isolated or derived from a soybean (*Glycine max*). In some embodiments, an intron sequence is isolated or derived from elongation factor TA.

The DNA constructs described herein may comprise any number of introns. For example, a DNA construct may comprise 1, 2, 3, 4, 5, 6, 7, 8, 9, 10, or more introns. In some embodiments, a DNA construct comprises a transgene, wherein the transgene comprises 1, 2, 3, 4, 5, 6, 7, 8, 9, 10, or more introns. In some embodiments, a transgene may comprise a reduced number of introns relative to the wild-type gene. For example, in some embodiments, 1, 2, 3, 4, 5, 6, 7, 8, 9, 10, or more introns may be removed from a wildtype gene to produce a transgene as described herein. In some embodiments, a transgene sequence comprises about 1 to about 3 intronic sequences. In some cases, a transgene comprises one intron, two introns, or three introns.

In some embodiments, an intron comprises a sequence having at least 70%, at least 80%, at least 85%, at least 90%, at least 95%, at least 97%, at least 98%, at least 99%, or 100% identity, including all ranges and subranges therebetween, with a sequence selected from Table 11 or Table 14.

Untranslated Regions (UTRs)

In some embodiments, RNA stabilization can be achieved or improved via addition or removal of 5' or 3' untranslated regions (5'UTR or 3'UTR) to a DNA construct. UTRs are known to control gene expression and protein function via a wide range of mechanisms. Exemplary mechanisms include: (A) Alternative polyadenylation: either more than one polyA site is utilized to produce mRNA variants that differ in 3'UTR length or, if the polyA is located upstream of the stop codon, truncated transcripts are produced; (B) Riboswitching: 3' or 5'UTRs form folding structures that sense a metabolite and modulate transcript stability; (C) Adenosine methylation (m6A): The presence of m6A in 5'UTR promotes CAP-independent translation; (D) Short-peptide translation: A short open reading frame in 5'UTR (uORF) can either repress the translation of the main ORF or induce mRNA decay via the NMD pathway; (E) Nonsense-mediated decay (NMD): A pre-mature termination codon (PTC) upstream of the regular termination codon (TC) recruits NMD factors that mediate mRNA decay; (F) Alternative splicing: Retention of intronic elements in 5'UTR can either promote or repress translation, while retention of intronic elements in 3'UTR can modulate miRNA-mediated cleavage. In some embodiments, a 5'UTR and/or 3' UTR is modulated to regulate (increase or decrease) the transport of an mRNA out of a plant nucleus. Any one of the aforementioned mechanisms can be employed in disclosed strategies to stabilize RNA in a plant.

5' untranslated regions (UTRs) play an important role in optimizing gene expression. 5'UTR are short sequences (~65 bp) upstream of the start codon (AUG) that can affect translation initiation by its secondary structure and the existence of the AUG. The κ' UTR can have a positive or negative effect on translation since they are the target for the binding of microRNAs. Additionally, 5' UTRs can have a role in mRNA stabilization. In some embodiments, a DNA construct described herein comprise a 5' UTR. In some embodiments, a DNA construct described herein comprises a 3' UTR. In some embodiments, a DNA construct described herein comprises a 5' UTR and a 3'UTR.

In some embodiments, a UTR (e.g., a 5' UTR or a 3' UTR) comprises a sequence that is isolated or derived from a plant. For example, in some embodiments, a UTR can comprise a sequence that is isolated or derived from a soybean plant. In some embodiments, a UTR comprises a sequence that is isolated or derived from a mammal, such as any of the mammals described herein. In some embodiments, a UTR comprises a sequence that is isolated or derived from a gene encoding a milk protein, such as β-Lactoglobulin. In some embodiments, a UTR comprises a sequence that is isolated or derived from a gene encoding an egg protein, such as ovalbumin. In some embodiments, a DNA construct described herein comprise a 5'UTR selected from: Arc5'UTR, glnB1UTR, native UTRs of ovalbumin, native UTR of β lactoglobulin, and combinations thereof. In some embodiments, a UTR is selected from those provided in Table 4, or Table 11. In some embodiments, a UTR comprises a sequence having at least 70%, at least 80%, at least 85%, at least 90%, at least 95%, at least 97%, at least 98%, at least 99%, or 1000 identity, including all ranges and subranges therebetween, with a sequence selected from Table 4 or Table 11.

TABLE 4

Exemplary promoters, 5' UTRs, signal peptides and terminators. Disclosed are also variants thereof, homologues thereof, and modified versions thereof.

| Type | Name | Description | Native Species | Illustrative Accession No. (Glyma, GenBank) |
|---|---|---|---|---|
| Promoter | PvPhas | Phaseolin-1 (aka β-phaseolin) | Common bean (*Phaseolus vulgaris*) | J01263.1 |
| | BnNap | Napin-1 | Rapeseed (*Brassica napus*) | J02798.1 |
| | AtOle1 | Oleosin-1 (Ole1) | Arabidopsis (*Arabidopsis thaliana*) | X62353.1, AT4G25140 |
| | GmSeed2 | Gy1 (Glycinin 1) | Soybean (*Glycine max*) | Glyma.03G163500 |
| | GmSeed3 | cysteine protease | Soybean (*Glycine max*) | Glyma.08G116300 |
| | GmSeed5 | Gy5 (Glycinin 5) | Soybean (*Glycine max*) | Glyma.13G123500 |

TABLE 4-continued

Exemplary promoters, 5' UTRs, signal peptides and terminators. Disclosed are also variants thereof, homologues thereof, and modified versions thereof.

| Type | Name | Description | Native Species | Illustrative Accession No. (Glyma, GenBank) |
|---|---|---|---|---|
| | GmSeed6 | Gy4 (Glycinin 4) | Soybean (*Glycine max*) | Glyma.10G037100 |
| | GmSeed7 | Kunitz trypsin protease inhibitor | Soybean (*Glycine max*) | Glyma.01G095000 |
| | GmSeed8 | Kunitz trypsin protease inhibitor | Soybean (*Glycine max*) | Glyma.08G341500 |
| | GmSeed10 | Legume Lectin Domain | Soybean (*Glycine max*) | Glyma.02G012600 |
| | GmSeed11 | β-conglycinin a subunit | Soybean (*Glycine max*) | Glyma.20G148400 |
| | GmSeed12 | β-conglycinin a' subunit | Soybean (*Glycine max*) | Glyma.10G246300 |
| | pBCON | β-conglycinin β subunit | Soybean (*Glycine max*) | Glyma.20G148200 |
| | GmCEP1-L | KDEL-tailed cysteine endopeptidase CEP1-like | Soybean (*Glycine max*) | Glyma06g42780 |
| | GmTHIC | phosphomethylpyrimidine synthase | Soybean (*Glycine max*) | Glyma11g26470 |
| | GmBg7S1 | Basic 7S globulin precursor | Soybean (*Glycine max*) | Glyma03g39940 |
| | GmGRD | glucose and ribitol dehydrogenase-like | Soybean (*Glycine max*) | Glyma07g38790 |
| | GmOLEA | Oleosin isoform A | Soybean (*Glycine max*) | Glyma.19g063400 |
| | GmOLEB | Oleosin isoform B | Soybean (*Glycine max*) | Glyma.16g071800 |
| | Gm2S-1 | 2S albumin | Soybean (*Glycine max*) | Glyma13g36400 |
| | GmBBId-II | Bowman-Birk protease inhibitor | Soybean (*Glycine max*) | Glyma16g33400 |
| 5'UTR | Arc5'UTR | arc5-1 gene | *Phaseolus vulgaris* | J01263.1 |
| | glnB1UTR | 65 bp of native glutamine synthase | Soybean (*Glycine max*) | AF301590.1 |
| Signal peptide | GmSCB1 | Seed coat BURP domain protein | Soybean (*Glycine max*) | Glyma07g28940.1 |
| | StPat21 | Patatin | Tomato (*Solanum lycopersicum*) | CAA27588 |
| | 2Sss | 2S albumin | Soybean (*Glycine max*) | Glyma13g36400 |
| | Sig2 | Glycinin G1 N-terminal peptide | Soybean (*Glycine max*) | Glyma.03G163500 |
| | Sig12 | Beta-conglycinin alpha prime subunit N-terminal peptide | Soybean (*Glycine max*) | Glyma.10G246300 |
| | Sig8 | Kunitz trypsin inhibitor N-terminal peptide | Soybean (*Glycine max*) | Glyma.08G341500 |
| | Sig10 | Lectin N-terminal peptide from Glycine max | Soybean (*Glycine max*) | Glyma.02G012600 |
| | Sig11 | Beta-conglycinin alpha subunit N-terminal peptide | Soybean (*Glycine max*) | Glyma.20G148400 |
| | Coixss | Alpha-coixin N-terminal peptide from Coix lacryma-job | *Coix lacryma-job* | |
| | KDEL | C-terminal amino acids of sulfhydryl endopeptidase | *Phaseolus vulgaris* | |
| Terminator | NOS | Nopaline synthase gene termination sequence | *Agrobacterium tumefaciens* | |
| | ARC | arc5-1 gene termination sequence | *Phaseolus vulgaris* | J01263.1 |
| | EU | Extensin termination sequence | *Nicotiana tabacum* | |
| | Rb7 | Rb7 matrix attachment region termination sequence | *Nicotiana tabacum* | |
| | HSP or AtHSP | Heat shock termination sequence | *Arabidopsis thaliana* | |
| | AtUbi10 | Ubiquitin 10 termination sequence | *Arabidopsis thaliana* | |
| | Stubi3 | Ubiquitin 3 termination | *Solanum tuberosum* | |
| | TM6 | M6 matrix attachment region termination sequence | *Nicotiana tabacum* | |

TABLE 4-continued

Exemplary promoters, 5' UTRs, signal peptides and terminators. Disclosed are also variants thereof, homologues thereof, and modified versions thereof.

| Type | Name | Description | Native Species | Illustrative Accession No. (Glyma, GenBank) |
|---|---|---|---|---|
| Dual terminators | EU:Rb7 | Extensin termination sequence:Rb7 matrix attachment region termination sequence | *Nicotiana tabacum* | |
| | AtHSP:AtUbi10 | Heat shock termination sequence:Ubiquitin 10 termination sequence | *Arabidopsis thaliana* | |
| | EU:StUbi3 | Rb7 matrix attachment region termination sequence:Ubiquitin 3 termination | *Nicotiana tabacum*, *Solanum tuberosum* | |
| | EU:TM6 | Rb7 matrix attachment region termination sequence:M6 matrix attachment region termination sequence | *Nicotiana tabacum* | |

Ubiquitin Monomer

In some embodiments, RNA can be stabilized via use of a ubiquitin monomer. Ubiquitin is a small protein that can be covalently linked to lysine residues of proteins targeted for intracellular degradation by proteasomes. Expression of recombinant/transgenic proteins fused with a ubiquitin monomer can be an advantageous strategy to enhance protein accumulation. The ubiquitin monomer may act as a chaperone for the incorporation of the ribosomal protein into the ribosome. During translation, ubiquitin can be accurately cleaved from the protein by endogenous ubiquitin-specific proteases, leaving the protein of interest free of unnecessary sequences.

In some embodiments, ubiquitin monomers from plants can be utilized in DNA constructs in order to enhance protein expression. The ubiquitin monomer is cleaved either immediately after or during translation improving translational regulation.

In some embodiments, a ubiquitin monomer is from a plant, a mammal, or a fungus. Any of the disclosed plants provided herein can be the source of a ubiquitin monomer, including but not limited to soybean, potato, wheat, corn, and the like. In some cases, the ubiquitin monomer is isolated or derived from a potato.

A ubiquitin monomer sequence can be located at any position of a transgene. In some cases, a monomer is at a 5' end, 3' end, in or adjacent to a coding sequence or promoter sequence, and combinations thereof. In some embodiments, a monomer is adjacent to a promoter sequence. In some embodiments, a monomer is located 3' to a promoter sequence. In some embodiments, a promoter is located 5' to any sequence provided herein. In some embodiments, a monomer is located within about 0-5, 1-10, 5-25, or 10-30 bases 5' or 3' of any sequence provided herein. In some embodiments, a monomer is located between a promoter and a signal peptide.

In some embodiments, a ubiquitin monomer comprises a sequence having at least 70%, at least 80%, at least 85%, at least 90%, at least 95%, at least 96%, at least 97%, at least 98%, at least 99%, or 100% identity, including all ranges and subranges therebetween, with a sequence selected from Table 11.

Codon Optimization

In some embodiments, the present disclosure teaches that RNA stabilization can also be achieved through codon optimization of the DNA sequence encoding the RNA. In some embodiments, codon optimized variants of genes produce pluralities of nucleic acid sequences that can be evaluated for expression potential and stability via the methods of the present disclosure.

The genetic code consists of three-nucleotide units called codons. There are 64 possible codons, each specifying one of twenty amino acids or an end to translation ("STOP codons"). Therefore, at least some codons are redundant. In the coding system used by the vast majority of organisms, two amino acids are each encoded by a single codon, whereas all other amino acids are separately encoded by two, three, four, or six codons, with three STOP codons. For amino acids represented by two, three, or four codons, the codons typically differ from each other at the third nucleotide position. For amino acids represented by two codons, the third position is either a purine (A, G) or pyrimidine (C, T) in both cases. For the three amino acids that are represented by six codons (Arg, Leu, and Ser), each has one block of four codons that follows this pattern by differing in the third position, plus one additional set of two codons. Arg and Leu are each represented by a two-codon block different from each other by a change in the first and second nucleotide positions. The two-codon representation of serine (Ser) is different from that of the Arg two-codon block only in the third nucleotide position.

For a particular amino acid, a given organism does not use the possible codons equally. Organisms each have a bias in codon usage. The pattern of bias in codon usage is distinct for an organism and its close relatives throughout the genome. For example, in *Streptomyces* spp., frequent codons generally include G or C in the third nucleotide position. Rare codons generally include A or T in the third position. In other organisms, A or T is preferred in the third position. Within a particular species, there can be distinct categories of genes with their own codon bias. In *E. coli*, for example, there are roughly three classes of genes, each with a distinctive codon usage signature. One class is rich in important proteins that are abundantly expressed; the second class includes proteins that are expressed at relatively low levels; and the third class includes proteins likely to have been recently acquired from other species.

In most synthetic gene design strategies, the process attempts to match the codon composition of a synthetic gene to the codon compositions of genes of a host in which the synthetic gene will be expressed. See, e.g., U.S. Patent Publication No. US2007/0292918. Such strategies may in some situations lead to increased expression of the synthetic gene in the host. For example, codon optimization in yeast may significantly improve the translation of heterologous gene transcripts due to minimizing the effects of, e.g., limiting aminoacyl-tRNAs and transcription termination at AT-rich sequences. See, e.g., Daly and Hearn (2004) J. Mol. Recognition 18:119-38.

Codon optimization comprises a variety of approaches that involve synonymous substitutions to increase protein expression. One strategy that is preferred by some is to maximize the use of frequent codons in the expression host species during the design of heterologous genes. A second strategy preferred by others is to place maximum value on the context of particular codons, and therefore to maximize the use of codon pairs that occur frequently in the expression host. For example, in some embodiments, codon optimization pursues a codon harmonization approach, which seeks to maintain regions of slow translation that are thought to be important for protein folding.

A third strategy is to make the codon usage of the new coding sequence in the new species resemble the codon usage of the reference coding sequence in the species of origin. This third strategy places high value on the recognition of possible requirements for rare codons to ensure proper secondary structure of transcript RNA molecules. A further strategy is to make the codon composition of the heterologous gene resemble the overall codon composition of expressed genes of the new host. Sequence changes resulting in synonymous codons can also be used to alter numerous features of mRNA coding sequences that can inhibit expression, including putative splice donor and acceptor sites. Additionally, simply using the same frequently-occurring codon repeatedly in a heterologous sequence is expected to eventually have the same effect as selecting a rare codon, e.g., overuse of the corresponding tRNA will limit the availability of the tRNA. Thus, in some embodiments codon optimization should also seek to balance these strategies and their underlying concerns in order to produce best results.

Persons having skill in the art will be familiar with how to deploy codon-optimization techniques. Codon usage tables for almost all characterized organisms can be found online, including, the Kazusa database (world wide web at.kazusa.or.jp/codon/) and hive database (hive.biochemistry.gwu.edu/review/codon). In addition, a non-limiting list of software tools capable of generating codon optimized sequence variants is provided in Table 5, below.

TABLE 5

Codon Optimization Tools

| Codon Optimization Tool | Relevant Citation |
| --- | --- |
| DNAWorks | Hoover D. M., Lubkowski J. (2002). DNAWorks: an automated method for designing oligonucleotides for PCR-based gene synthesis. Nucleic Acids Res. 30, e43. 10.1093/nar/30.10.e43 |
| Jcat | Grote A., Hiller K., Scheer M., Munch R., Nortemann B., Hempel D. C., et al. (2005). JCat: a novel tool to adapt codon usage of a target gene to its potential expression host. Nucleic Acids Res. 33, W526-W531 10.1093/nar/gki376 |
| Synthetic gene designer | Wu G., Bashir-Bello N., Freeland S. (2005). "The synthetic gene designer: a flexible web platform to explore sequence space of synthetic genes for heterologous expression," in 2005 IEEE Computational Systems Bioinformatics Conference, Workshops and Poster Abstracts, 2005 Aug. 8-11. (California: Stanford University;), 258-259 |
| GeneDesign | Richardson S. M., Wheelan S. J., Yarrington R. M., Boeke J. D. (2006). GeneDesign: rapid, automated design of multikilobase synthetic genes. Genome Res. 16, 550-556 10.1101/gr.4431306 |
| Gene Designer 2.0 | Villalobos A., Ness J. E., Gustafsson C., Minshull J., Govindarajan S. (2006). Gene designer: a synthetic biology tool for constructing artificial DNA segments. BMC Bioinformatics 7, 285. 10.1186/1471-2105-7-285 |
| OPTIMIZER | Puigbò P., Guzmán E., Romeu A., Garcia-Vallvé S. (2007). Optimizer: a web server for optimizing the codon usage of DNA sequences. Nucleic Acids Res. 35, W126-W131 10.1093/nar/gkm219 |
| Visual gene developer | Jung S.-K., McDonald K. (2011). Visual gene developer: a fully programmable bioinformatics software for synthetic gene optimization. BMC Bioinformatics 12, 340. 10.1186/1471-2105-12-340 |
| Eugene | Gaspar P., Oliveira J. L., Frommlet J., Santos M. A. S., Moura G. (2012). EuGene: maximizing synthetic gene design for heterologous expression. Bioinformatics 28, 2683-2684 10.1093/bioinformatics/bts465 |
| COOL | Chin J. X., Chung B. K.-S., Lee D.-Y. (2014). Codon optimization on-line (COOL): a web-based multi-objective optimization platform for synthetic gene design. Bioinformatics 30, 2210-2212 10.1093/bioinformatics/btu192 |
| D-Tailor | Guimaraes J. C., Rocha M., Arkin A. P., Cambray G. (2014). D-Tailor: automated analysis and design of DNA sequences. Bioinformatics 30, 1087-1094 10.1093/bioinformatics/btt742 |

Nucleic Acid Secondary Structure

Codon changes also have the potential to affect structure of nucleic acids in vivo. Specifically changes in primary sequence can affect folding, and therefore RNA stability. Therefore, in some embodiments, the present disclosure teaches methods for selecting primary transcript sequences based on their predicted secondary structures. Codon usage bias can be analyzed and optimized using various techniques. In some embodiments, a plurality of different codon optimized transgenes can be generated and evaluated for their RNA structure in silico, using publicly available programs such as RNAfold. Different parameters, such as thermodynamic parameters, can be analyzed including but not limited to minimum free energy structures (MFE), base pair probabilities, and energy mountain plot. In addition, locations of 5' regions and/or start codons within different structures, such as MFE, can be determined to further analyze RNA structure within those regions to optimize as necessary. In some embodiments, using information gathered from thermodynamic parameter analysis, codon optimized sequences can be selected that yield RNA sequences that comprise a stable structure. Exemplary stable structures can comprise secondary structures, such as loops, bulges, base pair mismatches, hairpin loops, internal loops, helices, multibranch loops, terminal mismatches, dangling ends, and combinations thereof.

In some embodiments, a stable RNA structure comprises a loop. A loop of the disclosure can be of any length. In some cases, a loop of the disclosure that confers increased stability comprises at least about 4, 5, 6, 7, 8, 9, 10, 11, 12, 13, 14, 15, 16, 17, 18, 19, 20, 21, 22, 23, 24, 25, 26, 27, 29, 29, 30, or more base pairs. In some embodiments, a stable structure comprises a loop with a length of about 4 to about 8 base pairs. Additional exemplary stable structures can contain tetraloops, such as UUCG (SEQ ID NO: 615). In some embodiments, a stable structure comprises two or more hairpin loops, wherein the hairpin loops are each less than 8 base pairs.

In some embodiments, codon usage bias can be utilized to reduce or prevent unstable structures. An unstable structure can comprise a loop of less than about 4 base pairs or over 8 base pairs. In some embodiments, an unstable structure may lack a secondary structure. In some embodiments, an unstable structure comprises at least one of a pseudo-knot (e.g. a loop with no secondary structure), a loop of less than 4 base pairs or over 8 base pairs, or a large hairpin loop (e.g. over than about 8 base pairs).

In some embodiments, a sequence can be codon optimized for expression in a host cell, such as a plant cell. Other host cells are also contemplated. For example, a sequence can be codon optimized for expression in any of the plants of the disclosure. In some embodiments, a sequence is codon optimized for expression in a soybean plant (*Glycine max*).

KDEL (Lys-Asp-Glu-Leu, SEQ ID NO: 616) and Related Sequences

Additionally, stabilization of RNA can be achieved through the use of a KDEL sequence. KDEL is a target peptide sequence in mammals and plants located on the C-terminal end of an amino acid structure of a protein. The KDEL sequence reduces or eliminates a protein from being secreted from the endoplasmic reticulum (ER) and can facilitate its return if it is exported. A protein with a functional KDEL motif will be retrieved from the Golgi apparatus by retrograde transport to the ER lumen. It also targets proteins from other locations (such as the cytoplasm) to the ER. Proteins can leave the ER after this sequence has been cleaved off. The instant inventors have surprisingly discovered that the presence of a KDEL sequence in an RNA may increase the stability thereof. Accordingly, provided herein are stably expressed RNA sequences comprising a sequence encoding a KDEL sequence. Also provided herein are DNAs comprising a KDEL sequence, that are capable of stably expressing an RNA in a host cell.

Homologues of KDEL are also contemplated in the present disclosure. A homologue may be a similar sequence employed in other organisms. For example, the sequence HDEL (His-Asp-Glu-Leu) performs the same function in yeasts as KDEL. In some embodiments, a DNA sequence described herein may comprise a sequence encoding any one of a KDEL, HDEL, and the like. In some embodiments, a DNA sequence described herein may comprise a sequence selected from the group consisting of: KDEL (SEQ ID NO: 616), HDEF (SEQ ID NO: 632), HDEL (SEQ ID NO: 633), RDEF (SEQ ID NO: 634), RDEL (SEQ ID NO: 635), WDEL (SEQ ID NO: 636), YDEL (SEQ ID NO: 637), HEEF (SEQ ID NO: 638), HEEL (SEQ ID NO: 639), KEEL (SEQ ID NO: 640), REEL (SEQ ID NO: 641), KAEL (SEQ ID NO: 642), KCEL (SEQ ID NO: 643), KFEL (SEQ ID NO: 644), KGEL (SEQ ID NO: 645), KHEL (SEQ ID NO: 646), KLEL (SEQ ID NO: 647), KNEL (SEQ ID NO: 648), KQEL (SEQ ID NO: 649), KREL (SEQ ID NO: 650), KSEL (SEQ ID NO: 651), KVEL (SEQ ID NO: 652), KWEL (SEQ ID NO: 653), KYEL (SEQ ID NO: 654), KEDL (SEQ ID NO: 655), KIEL (SEQ ID NO: 656), DKEL (SEQ ID NO: 657), FDEL (SEQ ID NO: 658), KDEF (SEQ ID NO: 659), KKEL (SEQ ID NO: 660), HADL (SEQ ID NO: 661), HAEL (SEQ ID NO: 662), HIEL (SEQ ID NO: 663), HNEL (SEQ ID NO: 664), HTEL (SEQ ID NO: 665), KTEL (SEQ ID NO: 666), HVEL (SEQ ID NO: 667), NDEL (SEQ ID NO: 668), QDEL (SEQ ID NO: 669), REDL (SEQ ID NO: 670), RNEL (SEQ ID NO: 671), RTDL (SEQ ID NO: 672), RTEL (SEQ ID NO: 673), SDEL (SEQ ID NO: 674), TDEL (SEQ ID NO: 675), SKEL (SEQ ID NO: 676), STEL (SEQ ID NO: 677), and EDEL (SEQ ID NO: 678).

In some embodiments, a sequence of the disclosure can be modified to add a KDEL sequence or a homologue thereof. In some embodiments, a sequence is modified to remove a KDEL sequence or homologue thereof. In some embodiments, a sequence can be modulated to potentiation, reduce, or otherwise strengthen or dampen an existing KDEL sequence or homologue thereof.

Transgenes, Including Chordate Proteins

The DNA constructs described herein may comprise one or more transgenes. The transgenes may encode one or more of a protein or RNA of interest. In some embodiments, the transgene encodes a protein. In some embodiments, the transgene encodes a chordate protein. The chordate proteins provided herein may comprise proteins of a variety of chordates. Chordates are divided into three subphyla: Vertebrata (fish, amphibians, reptiles, birds, and mammals); *Tunicata* or Urochordata (sea squirts, salps); and Cephalochordata (which includes lancelets). Proteins from any of the aforementioned chordates can be utilized in compositions and methods of the disclosure.

In some embodiments, the chordate is a mammal. Accordingly, in some embodiments, the transgene is a mammalian protein. In some embodiments, the mammalian protein can comprise one or more milk proteins. As used herein the term "milk protein" refers to any protein, or fragment or variant thereof, that is typically found in one or more mammalian milks. Caseins and whey proteins are the major proteins of milk. Casein constitutes approximately 80% (29.5 g/L) of the total protein in bovine milk, and whey protein accounts for about 20% (6.3 g/L). Casein is chiefly phosphate-conjugated and mainly consists of calcium phosphate-micelle complexes. It is a heterogeneous family of 4 major components including alpha- (αs1- and αs2-casein), beta-, gamma-, para-κ-casein, and kappa-casein.

Illustrative milk proteins that may be used in a transgene of the disclosure include members of the casein family of proteins, such as α-S1 casein, α-S2 casein, β-casein, and κ-casein. The caseins are phosphoproteins and make up approximately 80% of the protein content in bovine milk and about 20-45% of the protein in human milk. Caseins form a multi-molecular, granular structure called a casein micelle in which some enzymes, water, and salts, such as calcium and phosphorous, are present. The micellar structure of casein in milk is significant in terms of a mode of digestion of milk in the stomach and intestine and a basis for separating some proteins and other components from cow milk. In practice, casein proteins in bovine milk can be separated from whey proteins by acid precipitation of caseins, by breaking the micellar structure by partial hydrolysis of the protein molecules with proteolytic enzymes, or microfiltration to separate the smaller soluble whey proteins from the larger casein micelle. Caseins are relatively hydrophobic, making them poorly soluble in water.

In some embodiments, the casein proteins described herein (e.g., α-S1 casein, α-S2 casein, β-casein, and/or κ-casein) are isolated or derived from cow (*Bos taurus*), goat (*Capra hircus*), sheep (*Ovis aries*), water buffalo (*Bubalus bubalis*), dromedary camel (*Camelus dromedaries*), bactrian camel (*Camelus bactrianus*), wild yak (*Bos mutus*), horse (*Equus caballus*), donkey (*Equus asinus*), reindeer (*Rangifer tarandus*), eurasian elk (*Alces alces*), alpaca (*Vicugna pacos*), zebu (*Bos indicus*), llama (*Lama glama*), or human (*Homo sapiens*). In some embodiments, a casein protein (e.g., α-S1 casein, α-S2 casein, β-casein, or κ-casein) has at least 80%, at least 85%, at least 90%, at least 95%, at least 96%, at least 97%, at least 98%, or at least 99% identity with a casein protein from one or more of cow (*Bos taurus*), goat (*Capra hircus*), sheep (*Ovis aries*), water buffalo (*Bubalus bubalis*), dromedary camel (*Camelus dromedaries*), bactrian camel (*Camelus bactrianus*), wild yak (*Bos mutus*), horse (*Equus caballus*), donkey (*Equus asinus*), reindeer (*Rangifer tarandus*), eurasian elk (*Alces alces*), alpaca (*Vicugna pacos*), zebu (*Bos indicus*), llama (*Lama glama*), or human (*Homo sapiens*).

As used herein, the term "α-S1 casein" refers to not only the α-S1 casein protein, but also fragments or variants thereof α-S1 casein is found in the milk of numerous different mammalian species, including cow, goat, and sheep. The sequence, structure and physical/chemical properties of α-S1 casein derived from various species is highly variable. An illustrative sequence for bovine α-S1 casein can be found at Uniprot Accession No. P02662, and an illustrative sequence for goat α-S1 casein can be found at GenBank Accession No. X59836.1. The terms "α-S1 casein" and "alpha-S1-casein" (and similar terms) are used interchangeably herein.

As used herein, the term "α-S2 casein" refers to not only the α-S2 casein protein, but also fragments or variants thereof α-S2 is known as epsilon-casein in mouse, Gamma-casein in rat, and casein-A in guinea pig. The sequence, structure and physical/chemical properties of α-S2 casein derived from various species is highly variable. An illustrative sequence for bovine α-S2 casein can be found at Uniprot Accession No. P02663, and an illustrative sequence for goat α-S2 casein can be found at Uniprot Accession No. P33049. The terms "α-S2 casein" and "alpha-S2-casein" (and similar terms) are used interchangeably herein.

As used herein, the term "β-casein" refers to not only the β-casein protein, but also fragments or variants thereof. For example, A1 and A2 β-casein are genetic variants of the β-casein milk protein that differ by one amino acid (at amino acid 67, A2 β-casein has a proline, whereas A1 has a histidine). Other genetic variants of β-casein include the A3, B, C, D, E, F, H1, H2, I and G genetic variants. The sequence, structure and physical/chemical properties of β-casein derived from various species is highly variable. Exemplary sequences for bovine β-casein can be found at Uniprot Accession No. P02666 and GenBank Accession No. MI5132.1. The terms "β-casein", "beta-casein" and "B-casein" (and similar terms) are used interchangeably herein.

As used herein, the term "κ-casein" refers to not only the κ-casein protein, but also fragments or variants thereof. κ-casein is cleaved by rennet, which releases a macropeptide from the C-terminal region. The remaining product with the N-terminus and approximately two-thirds of the original peptide chain is referred to as para-κ-casein. The sequence, structure and physical/chemical properties of κ-casein derived from various species is highly variable. Illustrative sequences for bovine κ-casein can be found at Uniprot Accession No. P02668 and GenBank Accession No. CAA25231. The terms "κ-casein", "κ-casein" and "kappa-casein" (and similar terms) are used interchangeably herein.

In some embodiments, the milk protein comprises from about: 75-85%, 80%-85%, 80%-90%, 85%-95%, 90%-95%, or 95%-100%, including all ranges and subranges therebetween, identity to a sequence selected from SEQ ID NO: 1-SEQ ID NO: 614. Provided milk proteins of the disclosure can have from about: 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, including all ranges and subranges therebetween to sequence provided and/or referenced in Table 17.

In some embodiments, the milk protein is a casein protein, for example, α-S1 casein, α-S2 casein, β-casein, and or κ-casein. In some embodiments, the milk protein is κ-casein and comprises the sequence of SEQ ID NO: 4, or a sequence at least 90%, at least 95%, at least 96%, at least 97%, at least 98%, or at least 99% identical thereto. In some embodiments, the milk protein is para-κ-casein and comprises the sequence of SEQ ID NO: 2, or a sequence at least 90%, at least 95%, at least 96%, at least 97%, at least 98%, or at least 99% identical thereto. In some embodiments, the milk protein is β-casein and comprises the sequence of SEQ ID NO: 6, or a sequence at least 90%, at least 95%, at least 96%, at least 97%, at least 98%, or at least 99% identical thereto. In some embodiments, the milk protein is α-S1 casein and comprises the sequence SEQ ID NO: 8, or a sequence at least 90%, at least 95%, at least 96%, at least 97%, at least 98%, or at least 99% identical thereto. In some embodiments, milk protein is α-S2 casein and comprises the sequence SEQ ID NO: 84, or a sequence at least 90%, at least 95%, at least 96%, at least 97%, at least 98%, or at least 99% identical thereto.

In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 4. In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 2. In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 6. In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 8. In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 84.

In some embodiments, α-S1 casein is encoded by the sequence of SEQ ID NO: 7, or a sequence at least 90%, at least 95%, at least 96%, at least 97%, at least 98%, or at least 99% identical thereto. In some embodiments, α-S2 casein is encoded by the sequence of SEQ ID NO: 83, or a sequence at least 90%, at least 95%, at least 96%, at least 97%, at least 98%, or at least 99% identical thereto. In some embodiments, β-casein is encoded by the sequence of SEQ ID NO: 5, or a sequence at least 90%, at least 95%, at least 96%, at least 97%, at least 98%, or at least 99% identical thereto. In some embodiments, κ-casein is encoded by the sequence of SEQ ID NO: 3, or a sequence at least 90%, at least 95%, at least 96%, at least 97%, at least 98%, or at least 99% identical thereto. In some embodiments, para-κ-casein is encoded by the sequence of SEQ ID NO: 1, or a sequence at least 90%, at least 95%, at least 96%, at least 97%, at least 98%, or at least 99% identical thereto.

In some embodiments, the milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 7. In some embodiments, the milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 83. In some embodiments, the milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 3. In some embodiments, the milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 1. In some embodiments, the milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 5.

In some embodiments, the milk protein is a casein protein, and comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 85-133, or 148-563. In some embodiments, the milk protein is a casein protein and comprises the sequence of any one of SEQ ID NO: 85-133 or 148-563.

In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 85-98 or 148-340. In some embodiments, the milk protein comprises the sequence of any one of SEQ ID NO: 85-98 or 148-340.

In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 99-109 or 341-440. In some embodiments, the milk protein comprises the sequence of any one of SEQ ID NO: 99-109 or 341-440.

In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 110-120 or 441-494. In some embodiments, the milk protein comprises the sequence of any one of SEQ ID NO: 110-120 or 441-494.

In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 121-133 or 495-563. In some embodiments, the milk protein comprises the sequence of any one of SEQ ID NO: 121-133 or 495-563 or 495-563.

In some embodiments, the milk protein is not a casein protein. Examples of non-casein milk proteins include, for example, β-lactoglobulin, α-lactalbumin, lysozyme, lactoferrin, lactoperoxidase, serum albumin, or an immunoglobulin.

In some embodiments, a chordate protein comprises whey. As used herein "whey" refers to the liquid remaining after milk has been curdled and strained, for example during cheesemaking. Whey comprises a collection of globular proteins, typically a mixture of β-lactoglobulin, α-lactalbumin, bovine serum albumin, and immunoglobulins. The term "whey protein" may be used herein to refer to a milk protein which heat labile and is soluble in milk at about pH 4.6 in its undenatured state. Alpha-Lactalbumin (α-LA) and beta-lactoglobulin (β-LG) are the predominant whey proteins and comprise about 70-80% of the total whey proteins. Other types of whey proteins include, immunoglobulins (Igs) (e.g., IgA, IgG, IgM, IgE), serum albumin, lysozyme, lactoferrin (LF), lactoperoxidase (LP), and protease-peptones.

In some embodiments, the milk protein is a protein typically found in whey. In some embodiments, the milk protein is β-lactoglobulin or a functional fragment thereof. In some embodiments, the milk protein is β-lactoglobulin and comprises the sequence of SEQ ID NO: 10, or a sequence at least 90%, at least 95%, at least 96%, at least 97%, at least 98%, or at least 99% identical thereto. In some embodiments, the milk protein is β-lactoglobulin and is encoded by the sequence of any one of SEQ ID NO: 9, 11, 12, or 13, or a sequence at least 90%, at least 95%, at least 96%, at least 97%, at least 98%, or at least 99% identical to any one of SEQ ID NO: 9, 11, 12, or 13. In some embodiments, the milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 9-13 or 564-614. In some embodiments, the milk protein comprises the sequence of any one of SEQ ID NO: 10 or 564-614.

In an aspect, a chordate protein is an egg protein. In some embodiments, an egg protein used in the compositions and methods described herein is an egg white protein. Egg white is made up of at least 40 different kinds of proteins. Ovalbumin is the major egg white protein, along with ovotransferrin and ovomucoid. Other proteins of interest include flavoprotein, which binds riboflavin; avidin, which can bind and inactivate biotin; and lysozyme, which has lytic action against bacteria.

In some embodiments, an egg protein used in the compositions and methods described herein is an egg yolk protein. Exemplary egg yolk proteins comprise: Phosvitins, vitellin, lipophorin, and combinations thereof.

In some embodiments, an egg protein is any one of: ovalbumin, ovotransferrin, ovomucoid, ovoglobulin G2, ovoglobulin G3, alpha-ovomucin, beta-ovomucin, lysozyme, ovoinhibitor, ovoglycoprotein, flavoprotein, ovomacroglobulin, avidin, cystatin, ovostatin, ovalbumin related protein X, ovalbumin related protein Y, vitellogenin, alpha-lipovitellin, beta-lipovitellin, alpha-livetin, beta-livetin, gamma-livetin, phosvitin, apovitellenin I, apovitellenin II, apovitellenin III, apovitellenin IV, apovitellenin V, apovitellenin VI, VLDL-II, apo-B, and any combination thereof. In other embodiments, an egg protein is selected from the group consisting of ovalbumin, ovotransferrin, ovomucoid, lysozyme, ovoglobulin G2, ovoglobulin G3, alpha-ovomucin, beta-ovomucin, apovitellenin-1, alpha-lipovitellin, beta-lipovitellin and any combination thereof. In some embodiments, an egg protein used in the DNA constructs described herein may include apolipoproteins, egg yolk globulin, or riboflavin binding protein. In some embodiments, a transgene construct described herein comprises a transgene encoding an ovalbumin protein. In some embodiments, an egg protein comprises a sequence or is encoded by a sequence selected from Table 6-Table 8. In some embodiments, an egg protein comprises a sequence or is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to, including all ranges and subranges therebetween, a sequence selected from Table 6-Table 8.

In some embodiments, the chordate protein is ovalbumin or a functional fragment thereof. In some embodiments, the disclosure teaches ovalbumin protein sequence that is encoded by codon-optimized SEQ ID NO: 617. In a particular embodiment, the ovalbumin protein comprising an amino acid sequence having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, sequence identity to SEQ ID NO:622 is provided. In some embodiments, the ovalbumin protein has the amino acid sequence of SEQ ID NO: 622.

In some embodiments, the disclosure teaches ovotransferrin protein sequence that is encoded by codon-optimized SEQ ID NO: 618. In a particular embodiment, the ovotransferrin protein comprising an amino acid sequence having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, sequence identity to SEQ ID NO:623 is provided. In some embodiments, the ovotransferrin protein has the amino acid sequence of SEQ ID NO: 623.

In other embodiments, the disclosure teaches ovomucoid protein sequence that is encoded by codon-optimized SEQ ID NO: 619. In a particular embodiment, the ovomucoid protein comprising an amino acid sequence having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, sequence identity to SEQ ID NO:624 is provided. In some embodiments, the ovomucoid protein has the amino acid sequence of SEQ ID NO: 624.

In other embodiments, the disclosure teaches lysozyme sequence that is encoded by codon-optimized SEQ ID NO: 620. In a particular embodiment, the lysozyme protein comprising an amino acid sequence having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, sequence identity to SEQ ID NO:625 is provided. In some embodiments, the lysozyme protein has the amino acid sequence of SEQ ID NO: 625.

In other embodiments, the disclosure teaches apovitellenin-1 protein sequences that is encoded by codon-optimized SEQ ID NO: 621. In a particular embodiment, the apovitellenin-1 protein comprising an amino acid sequence having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, sequence identity to SEQ ID NO:626 is provided. In some embodiments, the apovitellenin-1 protein has the amino acid sequence of SEQ ID NO: 626.

TABLE 6

Exemplary codon-optimized DNA sequences of egg proteins.

| Egg Protein | Sequence Identifier | Nucleotide Sequence |
| --- | --- | --- |
| Ovalbumin | SEQ ID NO: 617 | ATGGGATCAATCGGT GCTGCCAGCATGGAG TTTTGCTTTGATGTAT TTAAGGAACTCAAAG TACATCACGCTAACG AAAATATTTTCTACT |

TABLE 6-continued

Exemplary codon-optimized DNA sequences of egg proteins.

| Egg Protein | Sequence Identifier | Nucleotide Sequence |
|---|---|---|
| | | GTCCTATAGCTATAA
TGTCCGCACTTGCTAT
GGTCTATTTGGGCGC
CAAGGATTCTACACG
CACCCAGATTAATAA
GGTGGTTCGTTTTGA
CAAACTTCCAGGCTT
TGGTGATTCAATAGA
GGCCCAATGTGGGAC
AAGTGTCAACGTACA
CAGCTCTTTGCGTGA
TATACTCAACCAAAT
AACTAAACCCAATGA
CGTGTATAGTTTTCC
CTTGCCTCCCGTCTTT
ATGCTGAAGAACGTT
ACCCAATATTGCCCG
AATACCTCCAATGTG
TCAAGGAACTGTATC
GCGGCGGACTTGAAC
CAATAAATTTTCAGA
CCGCAGCCGATCAGG
CCAGGGAGCTCATAA
ACTCATGGGTCGAAA
GTCAAACAAATGGGA
TCATACGTAATGTGC
TCCAGCCTTCTAGCG
TTGATTCACAAACCG
CCATGGTGTTGGTCA
ATGCCATCGTATTTA
AAGGTCTCTGGGAAA
AGACATTTAAGGATG
AAGATACTCAGGCAA
TGCCTTTCCGTGTAAC
CGAGCAGGAGTCCAA
ACCCGTTCAAATGAT
GTACCAGATAGGGTT
GTTTAGGGTAGCCAG
TATGGCCTCTGAGAA
AATGAAGATACTGGA
ATTGCCCTTTGCCAGT
GGTACCATGTCCATG
CTTGTACTGTTGCCA
GATGAAGTTTCTGGC
CTGGAGCAGCTTGAG
TCTATAATAAACTTC
GAGAAGTTGACAGAG
TGGACATCATCTAAC
GTTATGGAAGAACGT
AAAATAAAAGTGTAT
TTGCCTCGCATGAAG
ATGGAGGAGAAATAC
AACCTTACCAGTGTA
CTGATGGCAATGGGC
ATAACCGATGTTTTTT
CTAGTTCCGCAAACC
TTTCTGGTATCTCCTC
AGCAGAATCTCTGAA
GATATCCCAAGCAGT
TCATGCAGCACACGC
AGAAATAAACGAGGC
AGGACGTGAAGTGGT
AGGATCAGCCGAGGC
AGGCGTTGATGCAGC
ATCCGTGAGCGAAGA
GTTTCGTGCCGATCA
CCCTTTCCTTTTCTGC
ATCAAACACATTGCT
ACCAATGCCGTTCTTT
TCTTCGGGCGCTGTG
TATCCCCTTAA |
| Ovotransferrin | SEQ ID NO: 618 | ATGAAACTGATTTTG
TGTACCGTCCTGTCA
CTTGGGATTGCCGCA
GTATGTTTTGCCGCC |

TABLE 6-continued

Exemplary codon-optimized DNA sequences of egg proteins.

| Egg Protein | Sequence Identifier | Nucleotide Sequence |
|---|---|---|
| | | CCACCCAAGAGTGT |
| | | TATCCGTTGGTGTAC |
| | | CATCTCTAGCCCTGA |
| | | GGAGAAGAAATGTA |
| | | ACAACCTCAGGGAC |
| | | TTGACCCAGCAAGA |
| | | GAGGATAAGCCTGA |
| | | CATGTGTCCAGAAG |
| | | GCTACCTATCTCGAC |
| | | TGTATCAAAGCCAT |
| | | AGCCAACAACGAGG |
| | | CCGACGCAATATCC |
| | | CTTGATGGAGGACA |
| | | GGTGTTCGAGGCCG |
| | | GACTTGCCCCTTATA |
| | | AATTGAAGCCTATA |
| | | GCTGCTGAAATCTAC |
| | | GAGCATACTGAGGG |
| | | TTCTACCACTAGTTA |
| | | TTATGCCGTAGCCGT |
| | | AGTTAAAAAGGGGA |
| | | CCGAGTTTACAGTCA |
| | | ACGATCTCCAGGGT |
| | | AAAAATAGCTGCCA |
| | | TACTGGTCTTGGTAG |
| | | GAGTGCTGGGTGGA |
| | | ATATACCTATCGGTA |
| | | CACTCCTCCACTGGG |
| | | GCGCTATCGAGTGG |
| | | GAGGGTATCGAAAG |
| | | TGGAAGCGTGGAAC |
| | | AGGCAGTCGCTAAG |
| | | TTTTTTTCCGCCTCTT |
| | | GCGTACCCGGCGCT |
| | | ACTATAGAGCAGAA |
| | | ACTTTGCCGTCAGTG |
| | | CAAAGGAGATCCCA |
| | | AGACCAAGTGTGCC |
| | | CGTAACGCCCCCTAT |
| | | AGTGGATATTCCGG |
| | | CGCTTTCCACTGCTT |
| | | GAAGGATGGAAAGG |
| | | GGGACGTAGCCTTC |
| | | GTGAAACACACTAC |
| | | AGTGAATGAAAACG |
| | | CCCCCGATCTCAATG |
| | | ACGAGTATGAGTTG |
| | | CTTTGCCTGGATGGT |
| | | AGTCGCCAACCAGT |
| | | CGATAATTACAAAA |
| | | CCTGTAACTGGGCTC |
| | | GTGTTGCTGCACATG |
| | | CCGTCGTTGCACGCG |
| | | ATGACAATAAAGTG |
| | | GAGGATATCTGGTC |
| | | CTTTCTGTCAAAAGC |
| | | CCAAAGCGATTTTG |
| | | GCGTAGATACCAAG |
| | | TCAGATTTCCATCTG |
| | | TTTGGGCCACCTGGA |
| | | AAGAAAGACCCTGT |
| | | GCTTAAGGACTTCTT |
| | | GTTCAAAGACAGTG |
| | | CCATAATGCTCAAA |
| | | CGCGTTCCTAGCCTT |
| | | ATGGATTCTCAACTG |
| | | TATCTCGGGTTCGAA |
| | | TATTACTCAGCCATA |
| | | CAATCAATGAGGAA |
| | | GGACCAGCTCACTC |
| | | CTAGCCCTAGAGAG |
| | | AATAGAATTCAATG |
| | | GTGTGCTGTTGGAA |
| | | AAGACGAGAAATCT |
| | | AAATGCGACCGTTG |
| | | GAGCGTCGTCAGCA |

TABLE 6-continued

Exemplary codon-optimized DNA sequences of egg proteins.

| Egg Protein | Sequence Identifier | Nucleotide Sequence |
|---|---|---|
| | | ACGGTGATGTTGAG
TGTACTGTAGTTGAT
GAAACTAAGGATTG
CATTATTAAGATTAT
GAAGGGGGAGGCCG
ATGCCGTCGCATTGG
ATGGAGGGCTGGTT
TATACCGCAGGTGTC
TGTGGACTGGTGCCT
GTCATGGCAGAAAG
ATATGATGATGAAT
CACAATGCAGTAAA
ACAGACGAACGTCC
AGCCTCATATTTTGC
TGTCGCCGTCGCCCG
CAAGGATTCCAATG
TGAATTGGAATAATT
TGAAGGGAAAAAAA
TCCTGCCACACTGCT
GTAGGGCGTACAGC
AGGTTGGGTGATCC
CAATGGGACTGATT
CACAATAGGACCGG
TACTTGCAACTTTGA
TGAATATTTCTCCGA
GGGGTGTGCTCCCG
GTAGCCCCCCCAAC
AGCCGCTTGTGCCA
GCTGTGCCAAGGTA
GTGGAGGTATTCCCC
CTGAGAAATGCGTC
GCTTCCTCTCACGAG
AAATACTTTGGTTAT
ACTGGTGCCTTGCGT
TGCCTCGTAGAAAA
AGGTGACGTCGCTTT
TATCCAACACAGTA
CTGTAGAGGAGAAT
ACAGGGGGAAGAA
CAAAGCTGACTGGG
CTAAGAATCTTCAG
ATGGACGATTTCGA
ACTGTTGTGTACCGA
TGGTAGAAGGGCTA
ATGTTATGGATTATC
GTGAGTGCAATCTTG
CAGAAGTACCAACC
CATGCTGTAGTTGTC
AGACCCGAGAAAGC
AAATAAAATTAGAG
ACCTTTTGGAGAGA
CAAGAGAAACGTTT
CGGTGTAAACGGCT
CAGAGAAGTCTAAA
TTCATGATGTTTGAA
AGTCAAAATAAGGA
TCTGTTGTTCAAAGA
CTTGACTAAATGCCT
GTTTAAAGTCAGGG
AAGGCACCACTTAT
AAAGAATTTCTGGG
AGATAAATTCTACA
CAGTAATAAGCAAC
TTGAAAACATGCAA
TCCTTCCGATATCCT
GCAAATGTGCAGTTT
CCTTGAAGGGAAAT
AA |
| Ovomucoid | SEQ ID NO: 619 | ATGGCTATGGCCGGA
GTCTTTGTTCTTTTCT
CTTTCGTGCTTTGTGG
TTTTTTGCCTGACGCC
GCCTTCGGAGCCGAG
GTTGACTGCTCTCGCT
TCCCAAATGCAACCG |

TABLE 6-continued

Exemplary codon-optimized DNA sequences of egg proteins.

| Egg Protein | Sequence Identifier | Nucleotide Sequence |
|---|---|---|
| | | ATAAAGAGGGAAAG GACGTTCTTGTTTGCA ACAAGGACCTGCGTC CTATCTGTGGGACAG ATGGCGTTACATATA CTAACGACTGCCTTTT GTGTGCATATTCTATT GAATTTGGTACTAAC ATATCTAAGGAGCAT GATGGGAATGCAAA GAAACAGTTCCCATG AACTGTAGTTCTTAT GCTAATACCACTAGT GAGGACGGCAAGGTC ATGGTATTGTGCAAT AGGGCTTTCAATCCT GTATGCGGGACAGAT GGTGTCACTTACGAC AATGAATGTTTGCTG TGTGCTCACAAGGTC GAACAAGGAGCTTCT GTCGATAAGAGGCAT GATGGGGGTTGCAGA AAAGAATTGGCTGCA GTATCAGTTGACTGC TCTGAGTATCCCAAG CCAGATTGCACCGCC GAGGACCGCCCATTG TGTGGAAGCGATAAT AAGACTTATGGAAAT AAATGCAACTTCTGC AATGCCGTTGTGGAA |
| Lysozyme | SEQ ID NO: 620 | ATGAGGAGCTTGTT GATACTTGTGCTTTG TTTCCTTCCCCTTGC AGCATTGGGGAAAG TTTTCGGTAGGTGCG AGCTTGCCGCCGCA ATGAAAAGACACGG CTTGGACAATTATCG TGGATACTCTCTCGG CAATTGGGTTTGTGT AGCAAAGTTCGAGA GCAATTTTAACACCC AGGCTACTAATAGA AATACCGACGGATC TACCGACTACGGGA TTCTGCAAATAAAC AGCCGCTGGTGGTG TAATGACGGGCGTA CTCCCGGTAGCCGC AATCTCTGTAACATC CCCTGTAGTGCATTG CTTAGTTCTGACATT ACAGCTAGCGTGAA CTGTGCTAAAAAGA TAGTTTCTGACGGTA ATGGAATGAGTGCT TGGGTTGCCTGGAG GAACCGTTGTAAGG GGACCGACGTTCAA GCATGGATTAGAGG GTGTCGTCTGTGA |
| Apovitellenin-1 | SEQ ID NO: 621 | AGCAACGGCACTCTG ACTTTGAGTCATTTCG GAAAATGCTGA ATGGTACAATACAGA GCACTCGTGATTGCC GTAATTTTGCTTCTTT CCACTACCGTCCCTG AGGTACATAGCAAGT CCATCATTGACAGAG AACGCAGGGACTGGC TGGTGATTCCTGATG |

TABLE 6-continued

Exemplary codon-optimized DNA sequences of egg proteins.

| Egg Protein | Sequence Identifier | Nucleotide Sequence |
|---|---|---|
| | | CTGCTGCTGCCTATAT TTATGAAGCCGTCAA CAAGGTATCACCACG CGCAGGTCAGTTCTT GCTCGACGTTTCTCA AACCACAGTCGTGTC TGGAATCAGGAACTT TCTCATCAACGAAAC AGCTAGGCTTACTAA GCTGGCCGAGCAACT TATGGAGAAAATTAA GAACCTTTGCTATAC TAAAGTGTTGGGCTA CTAG |

TABLE 7

Exemplary protein sequences of egg proteins which are a translated version of the codon-optimized nucleotide sequences of Table 6.

| Protein Name | Sequence Identifier | Protein Sequence (Amino Acid) |
|---|---|---|
| Ovalbumin | SEQ ID NO: 622 | MGSIGAASMEFCFDV FKELKVHHANENIFY CPIAIMSALAMVYLG AKDSTRTQINKVVRF DKLPGFGDSIEAQCG TSVNVHSSLRDILNQI TKPNDVYSFSLASRL YAEERYPILPEYLQCV KELYRGGLEPINFQT AADQARELINSWVES QINGIIRNVLQPSSVD SQTAMVLVNAIVFKG LWEKTFKDEDTQAM PFRVTEQESKPVQMM YQIGLFRVASMASEK MKILELPFASGTMSM LVLLPDEVSGLEQLES INFEKLTEWTSSNVM EERKIKVYLPRMKME EKYNLTSVLMAMGIT DVFSSSANLSGISSAE SLKISQAVHAAHAEI NEAGREVVGSAEAG VDAASVSEEFRADHP FLFCIKHIATNAVLFF GRCVSP |
| Ovotransferrin | SEQ ID NO: 623 | MKLILCTVLSLGIAAV CFAAPPKSVIRWCTISS PEEKKCNNLRDLTQQE RISLTCVQKATYLDCI KAIANNEADAISLDGG QVFEAGLAPYKLKPIA AEIYEHTEGSTTSYYA VAVVKKGTEFTVNDL QGKNSCHTGLGRSAG WNIPIGTLLHWGAIEW EGIESGSVEQAVAKFF SASCVPGATIEQKLCR QCKGDPKTKCARNAP YSGYSGAFHCLKDGK GDVAFVKHTTVNENA PDLNDEYELLCLDGSR QPVDNYKTCNWARV AAHAVVARDDNKVE DIWSFLSKAQSDFGVD TKSDFHLFGPPGKKDP VLKDFLFKDSAIMLKR VPSLMDSQLYLGFEYY SAIQSMRKDQLTPSPR |

TABLE 7-continued

Exemplary protein sequences of egg proteins which are a translated version of the codon-optimized nucleotide sequences of Table 6.

| Protein Name | Sequence Identifier | Protein Sequence (Amino Acid) |
|---|---|---|
| | | ENRIQWCAVGKDEKS KCDRWSVVSNGDVEC TVVDETKDCIIKIMKG EADAVALDGGLVYTA GVCGLVPVMAERYDD ESQCSKTDERPASYFA VAVARKDSNVNWNN LKGKKSCHTAVGRTA GWVIPMGLIHNRTGTC NEDEYFSEGCAPGSPP NSRLCQLCQGSGGIPP EKCVASSHEKYFGYT GALRCLVEKGDVAFIQ HSTVEENTGGKNKAD WAKNLQMDDFELLCT DGRRANVMDYRECNL AEVPTHAVVVRPEKA NKIRDLLERQEKRFGV NGSEKSKFMMFESQN KDLLFKDLTKCLFKVR EGTTYKEFLQDKFYTV ISNLKTCNPSDILQMCS FLEGK |
| Ovomucoid | SEQ ID NO: 624 | MAMAGVFVLFSFVL CGFLPDAAFGAEVDC SRFPNATDKEGKDVL VCNKDLRPICGTDGV TYTNDCLLCAYSIEFG TNISKEHDGECKETV PMNCSSYANTTSEDG KVMVLCNRAFNPVC GTDGVTYDNECLLCA HKVEQGASVDKRHD GGCRKELAAVSVDCS EYPKPDCTAEDRPLC GSDNKTYGNKCNFC NAVVESNGTLTLSHF GKC |
| Lysozyme | SEQ ID NO: 625 | MRSLLILVLCFLPLAA LGKVFGRCELAAAMK RHGLDNYRGYSLGNW VCVAKFESNENTQAT NRNTDGSTDYGILQIN SRWWCNDGRTPGSRN LCNIPCSALLSSDITAS VNCAKKIVSDGNGMS AWVAWRNRCKGTDV QAWIRGCRL |
| Apovitellenin-1 | SEQ IDN O: 626 | MVQYRALVIAVILLL STTVPEVHSKSHIDRE RRDWL VIPDAAAA YI YEAVNKVSPRAGQFL LDVSQTTVVSGIRNFL INETARLTKLAEQLM EKIKNLCYTKVLGY |

TABLE 8

Additional exemplary ovalbumin protein sequences of the disclosure

| SEQ ID NO | Description | Species (Common Name) | Accession Number | Protein Sequence (Amino Acid) |
|---|---|---|---|---|
| 810 | Ovalbumin | Meleagris gallopavo (wild turkey) | XP_010706723.1 | MGSIGAVSMEFCFDVFKELK VHHANENIFYSPFTIISALA MVYLGAKDSTRTQINKVVRF DKLPGFGDSVEAQCGTSVNV |

TABLE 8-continued

*Additional exemplary ovalbumin protein sequences of the disclosure*

| SEQ ID NO | Description | Species (Common Name) | Accession Number | Protein Sequence (Amino Acid) |
|---|---|---|---|---|
| | | | | HSSLRDILNQITKPNDVYSF SLASRLYAEETYPILPEYLQ CVKELYRGGLESINFQTAAD QARGLINSWVESQTNGMIKN VLQPSSVDSQTAMVLVNAIV FKGLWEKAFKDEDTQAIPFR VTEQESKPVQMMYQIGLFKV ASMASEKMKILELPFASGTM SMWVLLPDEVSGLEQLETTI SFEKMTEWISSNIMEERRIK VYLPRMKMEEKYNLTSVLMA MGITDLFSSSANLSGISSAG SLKISQAVHAAYAEIYEAGR EVIGSAEAGADATSVSEEFR VDHPFLYCIKHNLTNSILFF GRCISP |
| 811 | | | NP_001290119.1 | MGSIGAVSMEFCFDVFKELK VHHANENIFYSPFTIISALA MVYLGAKDSTRTQINKVVRF DKLPGFGDSVEAQCGTSVNV HSSLRDILNQITKPNDVYSF SLASRLYAEETYPILPEYLQ CVKELYRGGLESINFQTAAD QARGLINSWVESQTNGMIKN VLQPSSVDSQTAMVLVNAIV FKGLWEKAFKDEDTQAIPFR VTEQESKPVQMMYQIGLFKV ASMASEKMKILELPFASGTM SMWVLLPDEVSGLEQLETTI SFEKMTEWISSNIMEERRIK VYLPRMKMEEKYNLTSVLMA MGITDLFSSSANLSGISSAG SLKISQAAHAAYAEIYEAGR EVIGSAEAGADATSVSEEFR VDHPFLYCIKHNLTNSILFF GRCISP |
| 812 | Ovalbumin | *Coturnix japonica* (Japanese quail) | P19104.2 | MGSIGAASMEFCFDVFKELK VHHANDNMLYSPFAILSTLA MVFLGAKDSTRTQINKVVHF DKLPGFGDSIEAQCGTSVNV HSSLRDILNQITKQNDAYSF SLASRLYAQETYTVVPEYLQ CVKELYRGGLESVNFQTAAD QARGLINAWVESQTNGIIRN ILQPSSVDSQTAMVLVNAIA FKGLWEKAFKAEDTQTIPFR VTEQESKPVQMMYQIGSFKV ASMASEKMKILELPFASGTM SMLVLLPDDVSGLEQLESII SFEKLTEWTSSSIMEERKVK VYLPRMKMEEKYNLTSLLMA MGITDLFSSSANLSGISSVG SLKISQAVHAAHAEINEAGR DVVGSAEAGVDATEEFRADH PFLFCVKHIETNAILLFGRC VSP |
| 813 | Ovalbumin | *Bambusicola thoracicus* (Chinese bamboo partridge) | P0I27989.1 | YYRVPCMVLCTAFHPYIFIV LLFALDNSEFTMGSIGAVSM EFCFDVFKELRVHHPNENIF FCPPFAIMSAMAMVYLGAKDS TRTQINKVIRFDKLPGFGDS TEAQCGKSANVHSSLKDILN QITKPNDVYSFSLASRLYAD ETYSIQSEYLQCVNELYRGG LESINFQTAADQARELINSW VESQINGIIRNVLQPSSVDS QTAMVLVNAIVFRGLWEKAF KDEDTQTMPFRVTEQESKPV QMMYQIGSFKVASMASEKMK ILELPLASGTMSMLVLLPDE VSGLEQLETTISFEKLTEWT |

TABLE 8-continued

Additional exemplary ovalbumin protein sequences of the disclosure

| SEQ ID NO | Description | Species (Common Name) | Accession Number | Protein Sequence (Amino Acid) |
|---|---|---|---|---|
| | | | | SSNVMEERKIKVYLPRMKME EKYNLTSVLMAMGITDLFRS SANLSGISLAGNLKISQAVH AAHAEINEAGRKAVSSAEAG VDATSVSEEFRADRPFLFCI KHIATKVVFFFGRYTSP |
| 814 | Ovalbumin | Numida Meleagris (Helmeted guineafowl) | XP_021241976.1 | MASIGAVSTEFCVDVYKELR VHHANENIFYSPFTIISTLA MVYLGAKDSTRTQINKVVRF DKLPGFGDSIEAQCGTSVNV HSSLRDILNQITKPNDVYSF SLASRLYAEETYPILPEYLQ CVKELYRGGLESINFQTAAD QARELINSWVESQTSGIIKN VLQPSSVNSQTAMVLVNAIY FKGLWERAFKDEDTQAIPFR VTEQESKPVQMMSQIGSFKV ASVASEKVKILELPFVSGTM SMLVLLPDEVSGLEQLESTI STEKLTEWTSSSIMEERKIK VFLPRMRMEEKYNLTSVLMA MGMTDLFSSSANLSGISSAE SLKISQAVHAAYAEIYEAGR EVVSSAEAGVDATSVSEEFR VDHPFLLCIKHNPTNSILFF GRCISP |
| 815 | | | XP_021241975.1 | MALCKAFHPYIFIVLLFDVD NSAFTMASIGAVSTEFCVDV YKELRVHHANENIFYSPFTI ISTLAMVYLGAKDSTRTQIN KVVRFDKLPGFGDSIEAQCG TSVNVHSSLRDILNQITKPN DVYSFSLASRLYAEETYPIL PEYLQCVKELYRGGLESINF QTAADQARELINSWVESQTS GIIKNVLQPSSVNSQTAMVL VNAIYFKGLWERAFKDEDTQ AIPFRVTEQESKPVQMMSQI GSFKVASVASEKVKILELPF VSGTMSMLVLLPDEVSGLEQ LESTISTEKLTEWTSSSIME ERKIKVFLPRMRMEEKYNLT SVLMAMGMTDLFSSSANLSG ISSAESLKISQAVHAAYAEI YEAGREVVSSAEAGVDATSV SEEFRVDHPFLLCIKHNPTN SILFFGRCISP |
| 816 | Ovalbumin | Odontophorus gujanensis (Marbled wood quail) | NXJ07552.1 | RILCMAFHPYIFIVLLFAPD NSEFTMGSIGAVSTEFCFDV FKELKVHHANENIFYSPFTI ISALAMVYLGAKDSTRTQIN KVVRFDKLPGFGDSIEAQCG TSVNVHSSLRDILNQITKPN DFYSFSLASRLYADEAYPIL PEYLQCVKELYRGGLESINF QTAADQARELINSWVESQTS GIIRNVLQPSSVDSQTAIVL VNAIYFKALWKKGFKNEDTQ AIPFRVTEQESKSVQMMQQI GTFKVASVASEKMKILELPF ASGTMSMWVLLPDEVSDLEQ LETTISFEKLTEWTSSNIME ERKIKVFLPRMKMEEKYNLT SVLMAMGMTDLFSSSANLSG ISSAESLKISQAVHAAYAEI YEAGSEVVGSAEAGVDATSA TEEFRVDRPFLFCIKHNPTN SILFFGRCISP |

TABLE 8-continued

Additional exemplary ovalbumin protein sequences of the disclosure

| SEQ ID NO | Description | Species (Common Name) | Accession Number | Protein Sequence (Amino Acid) |
|---|---|---|---|---|
| 817 | Ovalbumin | Coturnix japonica (Japanese quail) | XP_015709965.1 | MGSIGAASMEFCFDVFKELK VHHANDNMLYSPFAILSTLA MVFLGAKDSTRTQINKVVHF DKLPGFGDSIEAQCGTSANV HSSLRDILNQITKQNDAYSF SLASRLYAQETYTVVPEYLQ CVKELYRGGLESVNFQTAAD QARGLINAWVESQINGIIRN ILQPSSVDSQTAMVLVNAIA FKGLWEKAFKAEDTQTIPFR VTEQESKPVQMMHQIGSFKV ASMASEKMKILELPFASGTM SMLVLLPDDVSGLEQLESTI SFEKLTEWTSSSIMEERKVK VYLPRMKMEEKYNLTSLLMA MGITDLFSSSANLSGISSVG SLKISQAVHAAYAEINEAGR DVVGSAEAGVDATEEFRADH PFLFCVKHIETNAILLFGRC VSP |
| 818 | | | XP_015709964.1 | MGLCTAFHPYIFIVLLFALD NSEFTMGSIGAASMEFCFDV FKELKVHHANDNMLYSPFAI LSTLAMVFLGAKDSTRTQIN KVVHFDKLPGFGDSIEAQCG TSANVHSSLRDILNQITKQN DAYSFSLASRLYAQETYTVV PEYLQCVKELYRGGLESVNF QTAADQARGLINAWVESQTN GIIRNILQPSSVDSQTAMVL VNAIAFKGLWEKAFKAEDTQ TIPFRVTEQESKPVQMMHQI GSFKVASMASEKMKILELPF ASGTMSMLVLLPDDVSGLEQ LESTISFEKLTEWTSSSIME ERKVKVYLPRMKMEEKYNLT SLLMAMGITDLFSSSANLSG ISSVGSLKISQAVHAAYAEI NEAGRDVVGSAEAGVDATEE FRADHPLFCVKHIETNAIL LFGRCVSP |
| 819 | Ovalbumin | Coturnix coturnix (European quail) | Q6V115.3 | MGSIGAASMEFCFDVFKELK VHHANDNMLYSPFAILSTLA MVFLGAKDSTRTQINKVVHF DKLPGFGDSIEAQCGTSANV HSSLRDILNQITKQNDAYSF SLASRLYAQETYTVVPEYLQ CVKELYRGGLESVNFQTAAD QARGLINAWVESQINGIIRN ILQPSSVDSQTAMVLVNAIA FKGLWEKAFKAEDTQTIPFR VTEQESKPVQMMHQIGSFKV ASMASEKMKILELPFASGTM SMLVLLPDDVSGLEQLESTI SFEKLTEWTSSSIMEERKVK VYLPRMKMEEKYNLTSLLMA MGITDLFSSSANLSGISSVG SLKIPQAVHAAYAEINEAGR DVVGSAEAGVDATEEFRADH PFLFCVKHIETNAILLFGRC VSP |
| 820 | Ovalbumin | Phasianus colchicus (Pheasant) | XP_031445133.1 | MGSIGAVSMEFCFDVLKELK VHHANENYFYAPFTMFSALA MIYLGAKDSTRAQINKVVRF DKLPGFGDSIEAQCGTSADP QVHSSLRDILNQITKPNDAY SFSLASRLYADEKYSIVPEY LKCVKELYRGDVESINFQTA ADQARGLINSWVESQTNGMI KNVLQPSSVDSQTAMVLVNA |

TABLE 8-continued

Additional exemplary ovalbumin protein sequences of the disclosure

| SEQ ID NO | Description | Species (Common Name) | Accession Number | Protein Sequence (Amino Acid) |
|---|---|---|---|---|
| | | | | VVFKGLWEKAFKEEDTQAIP FRVTEQESKPVQMMHQIGLF KVASVPSEKMKILELPFASG TMSMWVLLPDEVSGLEQLET TISFEKMTEWTSSNIMEERK IRVYLPRMKMEEKYNLTSIL MAMGMTDLFSSSANLSGISS VGSLKISQAVHAAYAEIYEA GREVAGSAEAMDATSVSEE FRVDHPFLYCIKHNPSNTLL FLGRCIFP |
| 821 | | | XP_031445132.1 | MALCTAFHPYVFIILLFALD NSEFTMGSIGAVSMEFCFDV LKELKVHHANENYFYAPFTM FSALAMIYLGAKDSTRAQIN KVVRFDKLPGFGDSIEAQCG TSADPQVHSSLRDILNQITK PNDAYSFSLASRLYADEKYS IVPEYLKCVKELYRGDVESI NFQTAADQARGLINSWVESQ TNGMIKNVLQPSSVDSQTAM VLVNAVVFKGLWEKAFKEED TQAIPFRVTEQESKPVQMMH QIGLFKVASVPSEKMKILEL PFASGTMSMWVLLPDEVSGL EQLETTISFEKMTEWTSSNI MEERKIRVYLPRMKMEEKYN LTSILMAMGMTDLFSSSANL SGISSVGSLKISQAVHAAYA EIYEAGREVAGSAEAAMDAT SVSEEFRVDHPFLYCIKHNP SNTLLFLGRCIFP |
| 822 | Ovalbumin | *Penelope pileate* (White-crested guan) | NXC49292.1 | IALRTAYPPYIVIVLLFALD NSEFTMASIGAVSTEFCFNV FRELKVQHANENIFYCPFTI FSALAFAYLGAKENTRTQIN KVAHFDKLPGFGDSIEAQCG TSANVHSSLRDILNQITKPS DNYSLSLASRLYVDERYPIL PEYLQCVKELYRGGVEPITF QTAADQARELINSWVESQTN GMIKNILQPSSVDSQTAMVL VNAVYFKGMWQKAFKNEDTQ EMPFRITENESKPVQMMHQI GSFKIATVASEKLKILELPY ASGMMSMLVLLPDQASGLEQ LENTISFEKLNEWTSSNMVE ERRIKVYLPRMKMEEKYNLT AVLTALGITDLFSPSANLSG ISSAASLKISQAVHAAYAEI YEAGRDVVGSAEAGVDATSV TDEFRVDHPFLFCMKHNPSN SIVFLGKCVSP |
| 823 | Ovalbumin | *Anseranas semipalmata* (Magpie goose) | NXI67304.1 | CTAFHHYIVIVLLLFALDNS DFTMGSIGAASAEFCFDVFK ELKVHHANENICYSPLSIIS ALAMVYLGARDNTRTQIDKV VHFDQIPGFGESIESQCGTS VSVHSSLTDILTQITKPSDN YSFSLASRLYAEETYPILPE YLQCVKELYKGGLESISFQT AADQARELINSWVESQTNGI IKNILQPSSVDSQTAMVLVN AIYFKGMWEKAFKDENTQEM PFRVTEQESKPVQMMFQFGS FKVATVASEKVKILELPYAS GMISMCVLLPDEVSGLEQIE NTISLEKLTEWTSSNMMEER RMKVYLPRMKLEEQYNLTSV LMALGMTDLFSPSANLSGIS SAESLKISEAVHAAYVEIYE |

TABLE 8-continued

_Additional exemplary ovalbumin protein sequences of the disclosure_

| SEQ ID NO | Description | Species (Common Name) | Accession Number | Protein Sequence (Amino Acid) |
|---|---|---|---|---|
| | | | | AGREVVGSAEAGMDVSSVSE EFRVDHPFLFLIKHNPSNSI LFFGRLISP |
| 824 | Ovalbumin | Chauna torquata (Southern screamer) | NXK52213.1 | HYVCTAFHHHTVIVLLLFAL DNSDFTMGSIGAASTEFCFD VFKELKVQHVNGNIFYSPLS IISALAMVYLGARDNTRTQI DKVVHFDKIPGFGESIEAQC GTSESVHSSLKDILTQITKP SDNFSLSLASRLYAEETYPI LPEYLQCVKELYKGGLESVS FQTAADQARELISSWVESQT NGIIKNILQPSSVDSQTEMV LVNAIYFKGMWEKAFKDEDT QTMPFRITEQESKPMQMMYQ VGSFKVAVVASEKMKILELP YASGMMSMWVLLPDEVSGLE QLETTISFEKLTEWTSSNMM EERRMKVYLPRMKMEEKYNL TSVLIALGMTDLFSSSANLS GISSAESLKMSEAVHAAYVE IYEAGREVVGSAEAGMDVTS VSEEFKADRPFLFLIKHNPT NSILFFGRWISP |
| 825 | Ovalbumin | Anas platyrhynchos (Mallard) | NP_001298098.1 | MGSIGAASTEFCFDVFRELR VQHVNENIFYSPFSIISALA MVYLGARDNTRTQIDKVVHF DKLPGFGESMEAQCGTSVSV HSSLRDILTQITKPSDNFSL SFASRLYAEETYAILPEYLQ CVKELYKGGLESISFQTAAD QARELINSWVESQTNGIIKN ILQPSSVDSQTTMVLVNAIY FKGMWEKAFKDEDTQAMPFR MTEQESKPVQMMYQVGSFKV AMVTSEKMKILELPFASGMM SMFVLLPDEVSGLEQLESTI SFEKLTEWTSSTMMEERRMK VYLPRMKMEEKYNLTSVFMA LGMTDLFSSSANMSGISSTV SLKMSEAVHAACVEIFEAGR DVVGSAEAGMDVTSVSEEFR ADHPFLFFIKHNPTNSILFF GRWMSP |
| 826 | | | XP_038031283.1 | MGSIGAASTEFCFDVFRELR VQHVNENIFYSPFSIISALA MVYLXARDNTRTQIDKVVHF DKLPGFGESMEAQCGTSVSV HSSLRDILTQITKPSDNFSL SFASRLYAEETYAILPEYLQ CVKELYKGGLESISFQTAAD QARELINSWVESQTNGIIKN ILQPSSVDSQTTMVLVNAIY FKGMWEKAFKDEDTQAMPFR MTEQESKPVQMMYQVGSFKV AMVTSEKMKILELPFASGMM SMFVLLPDEVSGLEQLESTI SFEKLTEWTSSTMMEERRMK VYLPRMKMEEKYNLTSVFMA LGMTDLFSSSANMSGISSTV SLKMSEAVHAACVEIFEAGR DVVGSAEAGMDVTSVSEEFR ADHPFLFFIKHNPTNSILFF GRWMSP |
| 827 | Ovalbumin-like | Cygnus atratus (Black swan) | XP_035408641.1 | MGSIGAASTEFCFDVFRELK VQHVNENIFYSPLSIISALA MVYLGARDNTRAQIDKVVHF DKIPGFGESMESQCGTSVSV HSSLRDILTEITKPSDNFSL SFASRLYAEETYTILPEYLQ |

TABLE 8-continued

Additional exemplary ovalbumin protein sequences of the disclosure

| SEQ ID NO | Description | Species (Common Name) | Accession Number | Protein Sequence (Amino Acid) |
|---|---|---|---|---|
| | | | | CVKELYKGGLESISFQTAAD QARELINSWVESQINGIIKN ILQPSSVDSQTTMVLVNAIY FKGMWEKAFKDEDTQTMPFR MTEQESKPVQMMYQVGSFKV ATVTSEKVKILELPFASGMM SMCVLLPDEVSGLEQLETTI SFEKLTEWTSSTMMEERRMK VYLPRMKMEEKYNLTSVFMA LGMTDLFSSSANMSGISSTV SLKMSEAVHAACVEIFEAGR DVVGSAEAGMDVTSVSEEFR ADHPPLFFIKHNPTNSILFF GRWISP |
| 828 | Ovalbumin-like | *Anser cygnoides domesticus* (Domastic goose) | XP_013056574.1 | MGSIGAASTEFCFDVFRELK VQHVNENIFYSPLSIISALA MVYLGARDNTRTQIDQVVHF DKIPGFGESMEAQCGTSVSV HSSLRDILTEITKPSDNFSL SFASRLYAEETYTILPEYLQ CVKELYKGGLESISFQTAAD QARELINSWVESQTNGIIKN ILQPSSVDSQTTMVLVNAIY FKGMWEKAFKDEDTQTMPFR MTEQESKPVQMMYQVGSFKL ATVTSEKVKILELPFASGMM SMCVLLPDEVSGLEQLETTI SFEKLTEWTSSTMMEERRMK VYLPRMKMEEKYNLTSVFMA LGMTDLFSSSANMSGISSTV SLKMSEAVHAACVEIFEAGR DVVGSAEAGMDVTSVSEEFR ADHPPLFFIKHNPSNSILFF GRWISP |

In some embodiments, an egg protein can be a protein that is typically found in an egg without a yolk. Yolkless eggs can comprise wind eggs, dwarf eggs, or fart eggs. Egg proteins may include proteins present in the yolk portion of an egg. In some embodiments, the egg protein is typically found in a fertilized egg.

Chordates

In some embodiments, a transgene of the disclosure encodes a chordate protein, wherein the chordae is a vertebrate. Illustrative vertebrates are described below.

In some embodiments, a vertebrate is a mammal. For example, in some embodiments, the vertebrate is a bovine. Illustrative bovine species includes, but are not limited to: Holstein, jersey, brown swiss, guernsey, Ayrshire, red and white Holstein, milking shorthorn, simmental, French brown, tux-zillertal, marnau-werdenfel, Icelandic, Danish jersey, aldemey, abigar, Chinese black, agerolese, Australian milking zebu, achham, aulie-ata, Australian Friesian, Jamaica hope, burlina, and butana and kenana. In some cases, the bovine is selected from the group consisting of: Holstein, Jersey, Brown Swiss, Guernsey, Ayrshire, Milking Shorthorn, and Red and White Holstein.

In some embodiments, the vertebrate is a placental mammal. The placental mammals belong to the sub-class Eutheria. In some embodiments, a mammal of the disclosure is a placental mammal selected from the group consisting of a: camel, goat, cow, yak, buffalo, horse, donkey, zebu, sheep, reindeer, giraffe, and cockroach.

In some embodiments, the vertebrate is a bird. Exemplary birds comprise any one of a: chicken, turkey, duck, goose, pheasant, quail, ostrich, guinea fowl, rhea, bantam, pigeon, emu, and dodo, penguin. In some embodiments, the vertebrate is a domesticated bird and/or a bird that are bred to produce eggs for consumption.

In some embodiments, the vertebrate is a chicken. In some embodiments, the vertebrate is a hybrid chicken. Hybrid chickens are bred to lay more eggs than their unmodified or unbred counterparts. In some embodiments, the vertebrate is a chicken selected from a golden comet, Rhode Island red, leghorn, Sussex, Plymouth rock, Ancona, barnevelder, hamburg, maran, buff orpington, easter egger, Ameraucana, Australorp, Delaware, Euskal oiloa, Faverolle, Golden laced Wyandotte, Isa brown, Jaerhon, New Hampshire red, Red sex link, or Welsummer. In some embodiments, the vertebrate is a chicken selected from: australorp, white leghom, Sussex, goldline, hybrid, Plymouth Rock, and Rhode Island Red.

In some embodiments, the vertebrate is a non-bird animal such as a turtle, *iguana*, alligator, snake, platypus, echidna, reptile, fish, amphibian, insect, lizard, crocodile, alligator, crab, shrimp, ant eater, and modified versions thereof.

In some embodiments, the vertebrate is a marsupial. Marsupials give birth to barely formed offspring, and the baby grows in a pouch on the mother's belly. Marsupial mammals belong to the Sub-class Metatheria.

Host Cells

Also provided herein are host cells for expressing a transgene of interest. In some embodiments, a protein encoded by a transgene of interest accumulates at a high level in the host cell. In some embodiments, an RNA of interest accumulates at a high level in the host cell. In some embodiments, an RNA of interest has an increased half-life in the host cell.

In some embodiments, the host cell may be a plant cell. For example, the host cell may be a plant cell isolated or derived from any one of the plant species described above. In some embodiments, the host cell can be isolated or derived from a species which is not a plant.

Provided herein are plants, transgenic plants, and portions thereof (for example host cells from plants) that comprise any of the transgene or modifications disclosed herein. Plants may be in any condition including but not limited to dead, alive, pre-germination, post-germination, flowering, seed stage, and combinations thereof. A plant may be edible. A plant may be inedible or poisonous. In some cases, a plant is a crop.

In some embodiments, a plant is a monocot. For example, in some embodiments, the plant may be a monocot selected from turf grass, maize (corn), rice, oat, wheat, barley, sorghum, orchid, iris, lily, onion, palm, and duckweed.

In some embodiments, a plant is a dicot. For example, in some embodiments, the plant may be a dicot selected from *Arabidopsis*, tobacco, tomato, potato, sweet potato, cassava, alfalfa, lima bean, pea, chickpea, soybean, carrot, strawberry, lettuce, oak, maple, walnut, rose, mint, squash, daisy, *Quinoa*, buckwheat, mung bean, cow pea, lentil, lupin, peanut, fava bean, French beans (i.e., common beans), mustard, or cactus. In some embodiments, the plant is a soybean (*Glycine max*). In some embodiments, the plant is *Arabidopsis thaliana*.

In some embodiments, a plant is a non-vascular plant selected from moss, liverwort, hornwort or algae. In some embodiments, the plant is a vascular plant reproducing from spores (e.g., a fern).

Exemplary plants that can be used with the compositions and methods of the disclosure include but are not limited to: spermatophytes (spermatophyta), acrogymnospermae, angiosperms (magnoliophyta), ginkgoidae, pinidae, mesangiospermae, cycads, Ginkgo, conifers, gnetophytes, *Ginkgo biloba*, cypress, junipers, *thuja*, cedarwood, pines, *angelica*, caraway, coriander, cumin, fennel, parsley, dill, dandelion, helichrysum, marigold, mugwort, safflower, camomile, lettuce, wormwood, calendula, citronella, sages, thyme, chia seed, mustard, olive, coffee, *capsicum*, eggplant, paprika, cranberry, kiwi, vegetable plants (e.g., carrot, celery), *tagetes*, tansy, tarragon, sunflower, wintergreen, basil, hyssop, lavender, lemon *verbena*, marjoram, melissa, patchouli, pennyroyal, peppermint, rosemary, sesame, spearmint, primroses, samara, pepper, pimento, potato, sweet potato, tomato, blueberry, nightshades, *petunia*, morning glory, lilac, jasmin, honeysuckle, snapdragon, *psyllium*, wormseed, buckwheat, amaranth, chard, *quinoa*, spinach, rhubarb, jojoba, cypselea, *chlorella*, manila, hazelnut, canola, kale, bok choy, rutabaga, frankincense, myrrh, elemi, hemp, pumpkin, squash, curcurbit, manioc, *dalbergia*, legume plants (e.g., alfalfa, lentils, beans, clovers, peas, fava coceira, frijole bola roja, frijole negro, *lespedeza*, licorice, lupin, mesquite, carob, soybean, peanut, tamarind, *wisteria, cassia*, chickpea, garbanzo, fenugreek, green pea, yellow pea, snow pea, lima bean, fava bean), geranium, flax, pomegranate, cotton, okra, neem, fig, mulberry, clove, *eucalyptus*, tea tree, niaouli, fruiting plants (e.g., apple, apricot, peach, plum, pear, nectarine), strawberry, blackberry, raspberry, cherry, prune, rose, tangerine, citrus (e.g., grapefruit, lemon, lime, orange, bitter orange, mandarin), mango, citrus bergamot, buchu, grape, broccoli, brussels, sprout, camelina, cauliflower, rape, rapeseed (canola), turnip, cabbage, cucumber, watermelon, honeydew melon, zucchini, birch, walnut, cassava, baobab, allspice, almond, breadfruit, sandalwood, macadamia, taro, tuberose, aloe vera, garlic, onion, shallot, vanilla, *yucca*, vetiver, galangal, barley, corn, *curcuma aromatica*, ginger, lemon grass, oat, palm, pineapple, rice, rye, sorghum, triticale, turmeric, yam, bamboo, barley, cajuput, *canna*, cardamom, maize, oat, wheat, cinnamon, *sassafras, lindera benzoin*, bay laurel, avocado, ylang-ylang, mace, nutmeg, moringa, horsetail, oregano, cilantro, chervil, chive, aggregate fruits, grain plants, herbal plants, leafy vegetables, non-grain legume plants, nut plants, succulent plants, land plants, water plants, delbergia, millets, drupes, schizocarps, flowering plants, non-flowering plants, cultured plants, wild plants, trees, shrubs, flowers, grasses, herbaceous plants, brushes, lianas, cacti, green algae, tropical plants, subtropical plants, temperate plants, and derivatives and crosses thereof.

In some embodiments, the host cell comprises a non-plant cell. Exemplary non-plant host cells can be isolated or derived from a microbe, algae, fungi, yeast, and the like. Examples of microbes that may be used as host cells include but are not limited to firmicutes, cyanobacteria (blue-green algae), oscillatoriophcideae, bacillales, lactobacillales, oscillatoriales, bacillaceae, lactobacillaceae, *Acetobacter* suboxydans, *Acetobacter xylinum, Actinoplane missouriensis, Arthrospira platensis, Arthrospira maxima, Bacillus cereus, Bacillus coagulans, Bacillus subtilus, Bacillus cerus, Bacillus licheniformis, Bacillus stearothermophilus, Bacillus subtilis, Escherichia coli, Lactobacillus acidophilus, Lactobacillus bulgaricus, Lactococcus lactis, Lactococcus lactis* Lancefield Group N, *Lactobacillus reuteri, Leuconostoc citrovorum, Leuconostoc dextranicum, Leuconostoc mesenteroides* strain NRRL B-512(F), *Micrococcus* lysodeikticus, *Spirulina, Streptococcus cremoris, Streptococcus lactis, Streptococcus lactis* subspecies diacetylactis, *Streptococcus thermophilus, Streptomyces chattanoogensis, Streptomyces griseus, Streptomyces natalensis, Streptomyces olivaceus, Streptomyces olivochromogenes, Streptomyces rubiginosus*, Tetrahymena thermophile, Tetrahymena hegewischi, Tetrahymena hyperangularis, Tetrahymena *malaccensis*, Tetrahymena pigmentosa, Tetrahymena pyriformis, and Tetrahymena vorax, and *Xanthomonas campestris*, and derivatives and crosses thereof.

Examples of algae that may be used as host cells include but are not limited to green algae (e.g., *Chlorella*), brown algae (e.g., Alaria *marginata, Analipus japonicus*, Ascophyllum nodosum, Ecklonia sp, Eisenia bicyclis, Hizikia *fusiforme, Kjellmaniella gyrata, Laminaria angustata, Laminaria longirruris, Laminaria Longissima, Laminaria* ochotensis, *Laminaria* claustonia, *Laminaria saccharina, Laminaria digitata, Laminaria japonica*, Macrocystis pyrifera, Petalonia fascia, Scytosiphon lome), red algae (e.g., Gigartinaceae, Soliericeae, *Chondrus crispus, Chondrus ocellatus*, Eucheuma *cottonii*, Eucheuma *spinosum, Furcellaria fastigiata*, Gracilaria *bursa-pastoris, Gracilaria lichenoides, Gloiopeltis furcata, Gigartina acicularis*, Gigartina *bursa-pastoris*, Gigartina pistillata, Gigartina radula, Gigartina *skottsbergii, Gigartina stellata, Palmaria palmata, Porphyra columbina, Porphyra crispata*, Porhyra deutata, Porhyra perforata, Porhyra suborbiculata, *Porphyra tenera*, Porphyridium cruentum, Porphyridium *purpureum*, Porphyridium aerugineum, Rhodella maculate, Rhodella *reticulata, Rhodella violacea*, Rhodophyceae, Rhodymenia *palmata*), and derivatives and crosses thereof.

Examples of fungi that may be used as host cells include but are not limited to *Aspergillus* sp., *Aspergillus nidulans, Aspergillus niger, Aspergillus niger* var. *awamori, Aspergil-*

*lus oryzae, Candida albicans, Candida etchellsii, Candida guilliermondii, Candida humilis, Candida lipolytica, Candida pseudotropicalis, Candida utilis, Candida versatilis, Chrysosporium lucknowense, Debaryomyces hansenii, Endothia parasitica, Eremothecium ashbyii, Fusarium* sp., *Fusarium gramineum, Fusarium moniliforme, Fusarium venenatum, Hansenula polymorpha, Kluyveromyces* sp., *Kluyveromyces lactis, Kluyveromyces marxianus, Kluyveromyces marxianus* var. *lactis, Kluyveromyces thermotolerans, Morteirella vinaceae* var. *raffinoseutilizer, Mucor miehei, Mucor miehei* var. *Cooney et Emerson, Mucor pusillus* LindtMyceliophthora thermophile, *Neurospora crassa, Penicillium roquefortii, Physcomitrella patens, Pichia* sp., *Pichia pastoris, Pichia finlandica, Pichia trehalophila, Pichia koclamae, Pichia membranaefaciens, Pichia minuta* (*Ogataea minuta, Pichia* lindneri), *Pichia opuntiae, Pichia thermotolerans, Pichia salictaria, Pichia guercuum, Pichia pijperi, Pichia stiptis, Pichia methanolica, Rhizopus niveus, Rhodotorula* sp., *Saccharomyces* sp., *Saccharomyces bayanus, Saccharomyces beticus, Saccharomyces cerevisiae, Saccharomyces chevalieri, Saccharomyces diastaticus, Saccharomyces ellipsoideus, Saccharomyces exiguus, Saccharomyces florentinus, Saccharomyces fragilis, Saccharomyces pastorianus, Saccharomyces pombe, Saccharomyces sake, Saccharomyces uvarum, Sporidiobolus johnsonii, Sporidiobolus salmonicolor, Sporobolomyces roseus, Trichoderma, Trichoderma reesei, Xanthophyllomyces dendrorhous, Yarrowia lipolytica, Zygosaccharomyces rouxii*, and derivatives and crosses thereof.

Exemplary yeast that may be used as host cells include but are not limited to: a *Kluyveromyces* sp., *Pichia* sp., *Saccharomyces* sp., Tetrahymena sp., *Yarrowia* sp., *Hansenula* sp., Blastobotrys sp., *Candida* sp., *Zygosaccharomyces* sp., and *Debaryomyces* sp. Additional non-limiting examples of yeast strains that can be used as the host cell are *Kluyveromyces lactis, Kluyveromyces marxianus, Saccharomyces cerevisiae*, and *Pichia pastoris*. Additional species of yeast strains that can be used as host cells are known in the art.

Also provided herein are non-plant host cells that can be cultivated. The culturing of transgenic host cells can be performed in any fermentation vessel, including but not limited to a culture plate, a flask, or a fermentor (e.g., stirred tank fermentor, an airlift fermentor, a bubble column fermentor, a fixed bed bioreactor, or any combination thereof), and at any scale known in the art. Culture media for use in such fermentations processes may include any culture medium in which the recombinant host cells provided herein can grow and/or remain viable. In some embodiments, the culture media are aqueous media comprising carbon, nitrogen (e.g., anhydrous ammonia, ammonium sulfate, ammonium nitrate, diammonium phosphate, monoammonium phosphate, ammonium polyphosphate, sodium nitrate, urea, peptone, protein hydrolysates, yeast extract), and phosphate sources. The culture media can further comprise salts, minerals, metals, other nutrients, emulsifying oils, and surfactants. Non-limiting examples of carbon sources include monosaccharides, disaccharides, polysaccharides, acetate, ethanol, methanol, methane, or one or more combinations thereof. Non-limiting examples of monosaccharides include dextrose (glucose), fructose, galactose, xylose, arabinose, and combinations thereof. Non-limiting examples of disaccharides include sucrose, lactose, maltose, trehalose, cellobiose, and combinations thereof. Non-limiting examples of polysaccharides include starch, glycogen, cellulose, amylose, hemicellulose, and combinations thereof. Conditions for production of the recombinant proteins are those under which the recombinant host cells provided herein can grow and/or remain viable. Non-limiting examples of such conditions include suitable pH, suitable temperature, and suitable oxygenation. In some embodiments, the culture media further comprise proteases (e.g., plant-based proteases) that can prevent degradation of the recombinant proteins, protease inhibitors that reduce the activity of proteases that can degrade the recombinant proteins, and/or sacrificial proteins that siphon away protease activity.

Transgenic Organisms, Including Plants and Host Cells

Also provided herein are transgenic organisms, such as plants, comprising or expressing one or more chordate proteins of the disclosure. In some embodiments, the transgenic host cells comprise an exogenous RNA sequence that encodes a chordate protein selected from ovalbumin, β-Lactoglobulin, or combinations thereof.

In some embodiments, the transgenic plants stably express the chordate protein. In some embodiments, the transgenic plants transiently express the chordate protein. In some embodiments, the transgenic plants and/or host cell stably express the chordate protein in the plant or cell thereof in an amount of at least 1% per the total protein weight of the soluble protein extractable from the plant or cell thereof. For example, the transgenic plants and/or host cell may stably express the chordate protein in an amount of at least 1%, at least 1.5%, at least 2%, at least 2.5%, at least 3%, at least 3.5%, at least 4%, at least 4.5%, at least 5%, at least 5.5%, at least 6%, at least 6.5%, at least 7%, at least 7.5%, at least 8%, at least 8.5%, at least 9%, at least 9.5%, at least 10%, at least 10.5%, at least 11%, at least 11.5%, at least 12%, at least 12.5%, at least 13%, at least 13.5%, at least 14%, at least 14.5%, at least 15%, at least 15.5%, at least 16%, at least 16.5%, at least 17%, at least 17.5%, at least 18%, at least 18.5%, at least 19%, at least 19.5%, at least 20%, including all ranges and subranges therebetween, or more of total protein weight of soluble protein extractable from the plant and/or host cell.

In some embodiments, the transgenic plants and/or host cell thereof may stably express the chordate protein in an amount of less than about 1% of the total protein weight of soluble protein extractable from the plant or cell thereof. In some embodiments, the transgenic plants or cell thereof stably express the chordate protein in the range of about 1% to about 2%, about 3% to about 4%, about 4% to about 5%, about 5% to about 6%, about 6% to about 7%, about 7% to about 8%, about 8% to about 9%, about 9% to about 10%, about 10% to about 11%, about 11% to about 12%, about 12% to about 13%, about 13% to about 14%, about 14% to about 15%, about 15% to about 16%, about 16% to about 17%, about 17%, to about 18%, about 18% to about 19%, about 19% to about 20%, or more than about 20%, including all ranges and subranges therebetween, of the total protein weight of soluble protein extractable from the plant and/or host cell thereof.

In some embodiments, the transgenic plant or host cell stably expresses the chordate protein in an amount in the range of about 0.5% to about 3%, about 1% to about 4%, about 1% to about 5%, about 2% to about 5%, about 1% to about 10%, about 2% to about 10%, about 3% to about 10%, about 5 to about 12%, about 4% to about 10%, or about 5% to about 10%, about 4% to about 8%, about 5% to about 15%, about 5% to about 18%, about 10% to about 20%, or about 1% to about 20%, including all ranges and subranges therebetween, of the total protein weight of soluble protein extractable from the plant and/or host cell thereof. In some embodiments, the chordate protein is ovalbumin or β-Lactoglobulin expressed from about 1% to 3% of the total protein weight of soluble protein extractable from the plant and/or host cell thereof.

In some embodiments, the chordate protein is expressed at a level at least 2-fold higher than a protein expressed without a method comprising RNA stabilization in a plant or host cell thereof. For example, in some embodiments, the chordate protein is expressed at a level at least 2-fold, at least 2.5-fold, at least 3-fold, at least 3.5-fold, at least 4-fold, at least 4.5-fold, at least 5-fold, at least 5.5-fold, at least 6-fold, at least 7-fold, at least 7.5-fold, at least 8-fold, at least 8.5-fold, at least 9-fold, at least 9.5-fold, at least 10-fold, at least 25-fold, at least 50-fold, or at least 100-fold higher, including all ranges and subranges therebetween, than a protein expressed without RNA stabilization in a plant and/or host cell thereof.

In some embodiments, the chordate protein allows for accumulation of a chordate protein in a host cell at least 2-fold higher than a casein protein expressed without RNA stabilization in a plant or host cell. For example, in some embodiments, a chordate protein accumulates in a host cell and/or plant at least 2-fold, at least 2.5-fold, at least 3-fold, at least 3.5-fold, at least 4-fold, at least 4.5-fold, at least 5-fold, at least 5.5-fold, at least 6-fold, at least 7-fold, at least 7.5-fold, at least 8-fold, at least 8.5-fold, at least 9-fold, at least 9.5-fold, at least 10-fold, at least 25-fold, at least 50-fold, or at least 100-fold higher, including all ranges and subranges therebetween, than a chordate protein expressed without any of the RNA stabilization methods provided herein.

In some embodiments, the chordate protein is stably expressed in the plant and/or host cell in an amount of 1% or higher per the total protein weight of the soluble protein extractable from the plant and/or host cell. In some embodiments, the chordate protein is stably expressed in the plant and/or host cell in an amount of 2% or higher per the total protein weight of the soluble protein extractable from the plant and/or host cell. In some embodiments, the chordate protein is stably expressed in the plant and/or host cell in an amount of 3% or higher per the total protein weight of the soluble protein extractable from the plant and/or host cell. In some embodiments, the chordate protein is stably expressed in the plant and/or host cell in an amount of 4% or higher per the total protein weight of the soluble protein extractable from the plant and/or host cell. In some embodiments, the chordate protein is stably expressed in the plant and/or host cell in an amount of 5% or higher per the total protein weight of the soluble protein extractable from the plant and/or host cell. In some embodiments, the chordate protein is stably expressed in the plant and/or host cell in an amount of 6% or higher per the total protein weight of the soluble protein extractable from the plant and/or host cell. In some embodiments, the chordate protein is stably expressed in the plant and/or host cell in an amount of 7% or higher per the total protein weight of the soluble protein extractable from the plant and/or host cell. In some embodiments, the chordate protein is stably expressed in the plant and/or host cell in an amount of 8% or higher per the total protein weight of the soluble protein extractable from the plant and/or host cell. In some embodiments, the chordate protein is stably expressed in the plant and/or host cell in an amount of 9% or higher per the total protein weight of the soluble protein extractable from the plant and/or host cell. In some embodiments, the chordate protein is stably expressed in the plant and/or host cell in an amount of 10% or higher per the total protein weight of the soluble protein extractable from the plant and/or host cell. In some embodiments, the chordate protein is stably expressed in the plant and/or host cell in an amount of 110% or higher per the total protein weight of the soluble protein extractable from the plant and/or host cell. In some embodiments, the chordate protein is stably expressed in the plant and/or host cell in an amount of 12% or higher per the total protein weight of the soluble protein extractable from the plant and/or host cell. In some embodiments, the chordate protein is stably expressed in the plant and/or host cell in an amount of 13% or higher per the total protein weight of the soluble protein extractable from the plant and/or host cell. In some embodiments, the chordate protein is stably expressed in the plant and/or host cell in an amount of 14% or higher per the total protein weight of the soluble protein extractable from the plant and/or host cell. In some embodiments, the chordate protein is stably expressed in the plant and/or host cell in an amount of 15% or higher per the total protein weight of the soluble protein extractable from the plant and/or host cell. In some embodiments, the chordate protein is stably expressed in the plant and/or host cell in an amount of 16% or higher per the total protein weight of the soluble protein extractable from the plant and/or host cell. In some embodiments, the chordate protein is stably expressed in the plant and/or host cell in an amount of 17% or higher per the total protein weight of the soluble protein extractable from the plant and/or host cell. In some embodiments, the chordate protein is stably expressed in the plant and/or host cell in an amount of 18% or higher per the total protein weight of the soluble protein extractable from the plant and/or host cell. In some embodiments, the chordate protein is stably expressed in the plant and/or host cell in an amount of 19% or higher per the total protein weight of the soluble protein extractable from the plant and/or host cell. In some embodiments, the chordate protein is stably expressed in the plant and/or host cell in an amount of 20% or higher per the total protein weight of the soluble protein extractable from the plant and/or host cell.

In some embodiments, a transformed plant and/or host cell comprises in its genome: a recombinant DNA construct encoding a chordate protein, wherein the chordate protein comprises lysozyme, ovalbumin, ovotransferrin, or ovoglobulin. In some embodiments, the chordate protein is ovalbumin. A subject DNA construct encoding ovalbumin can comprise any of the aforementioned stabilization elements and/or modifications within any of the elements including but not limited to a promoter, terminator, codon optimization, KDEL, intron, ubiquitin monomer, 5'UTR, 3'UTR, and combinations thereof. In some embodiments, a DNA construct encoding ovalbumin comprises a promoter selected from the group consisting of: BnNap, gmSeed2, gmSeed12, pvPhas, and combinations thereof. In some embodiments, a DNA construct encoding ovalbumin comprises a signal peptide selected from the group consisting of: sig11, sig 2, coixss, sig12, and combinations thereof. In some embodiments, no signal peptide is comprised within the DNA construct. In some embodiments, a DNA construct encoding ovalbumin comprises a terminator sequence selected from the group consisting of arcT, Rb7T, EUT, and combinations thereof. In some embodiments, a double terminator is used. A double terminator can be EUT:Rb7T. In some embodiments, a DNA construct encoding ovalbumin comprises a KDEL sequence. In some embodiments, a DNA construct encoding ovalbumin comprises an exogenous or ectopically located intron sequence. In some embodiments, a DNA construct encoding ovalbumin comprises an exogenous or ectopically located glnB1 sequence.

In some embodiments, a transformed plant and/or host cell comprises in its genome a recombinant DNA construct encoding a β-Lactoglobulin protein. A subject DNA construct encoding β-Lactoglobulin can comprise any of the aforementioned stabilization elements and/or modifications within any of the elements including but not limited to a promoter, terminator, codon optimization, KDEL, intron, ubiquitin monomer, 5'UTR, 3'UTR, and combinations thereof. In some embodiments, a DNA construct encoding β-Lactoglobulin comprises a promoter selected from the group consisting of: BnNap, gmSeed2, gmSeed12, pvPhas, and combinations thereof. In some embodiments, a DNA construct encoding β-Lactoglobulin comprises a signal peptide selected from the group consisting of: sig11, sig 2, coixss, sig12, and combinations thereof. In some embodiments, a signal peptide is selected from a sequence in Table 4 or Table 11. In some embodiments, a signal peptide comprises a sequence having about 70%, about 75%, about 80%, about 85%, about 90%, about 95%, about 96%, about 97%, about 98%, about 99%, or 100%, including all ranges and subranges therebetween, identity from a sequence in Table 4 or Table 11. In some embodiments, no signal peptide is comprised within the DNA construct. In some embodiments, a DNA construct encoding β-Lactoglobulin comprises a terminator sequence selected from the group consisting of arcT, Rb7T, EUT, and combinations thereof. In some embodiments, a double terminator is used. A double terminator can be EUT: Rb7T. In some embodiments, a DNA construct encoding β-Lactoglobulin comprises a KDEL sequence. In some embodiments, a DNA construct encoding β-Lactoglobulin comprises an exogenous or ectopically located intron sequence. In some embodiments, a DNA construct encoding β-Lactoglobulin comprises an exogenous or ectopically located glnB1 sequence. In some embodiments, the milk protein is β-lactoglobulin and comprises the sequence of SEQ ID NO: 10, or a sequence at least 90% identical thereto.

In some embodiments, constructs encoding ovalbumin or β-Lactoglobulin can comprise a sequence provided in Table 11, Table 12 and/or Table 15 or a sequence having from about: 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, including all ranges and subranges therebetween, relative thereto.

In some embodiments, a transformed plant and/or host cell comprises in its genome a recombinant DNA construct encoding a milk protein. In some embodiments, the milk protein is α-lactalbumin, lysozyme, lactoferrin, lactoperoxidase, or an immunoglobulin (e.g., IgA, IgG, IgM, or IgE).

In some embodiments, a transformed plant and/or host cell comprises in its genome: a recombinant DNA construct encoding a casein protein. In some embodiments, a transformed plant and/or host cell comprises in its genome: a recombinant DNA construct encoding a casein protein selected from α-S1 casein, α-S2 casein, β-casein, and κ-casein. In some embodiments, the milk protein is α-S1 casein. In some embodiments, the milk protein is α-S1 casein and comprises the sequence SEQ ID NO: 8, or a sequence at least 90% identical thereto. In some embodiments, the milk protein is α-S2 casein. In some embodiments, the milk protein is α-S2 casein and comprises the sequence SEQ ID NO: 84, or a sequence at least 90% identical thereto. In some embodiments, the milk protein is β-casein. In some embodiments, the milk protein is β-casein and comprises the sequence of SEQ ID NO: 6, or a sequence at least 90% identical thereto. In some embodiments, the casein protein is κ-casein. In some embodiments, the casein protein is κ-casein and comprises the sequence of SEQ ID NO: 4, or a sequence at least 90% identical thereto. In some embodiments, the casein protein is para-κ-casein. In some embodiments, the casein protein is para-κ-casein and comprises the sequence of SEQ ID NO: 2, or a sequence at least 90% identical thereto.

In some embodiments, a transformed plant and/or host cell comprises in its genome: a recombinant DNA construct encoding hemoglobin, collagen, IgM, or IgE.

The transgenic plants and/or host cells described herein may be generated by various methods known in the art. For example, a DNA construct encoding a chordate protein may be contacted with a plant, or a portion thereof, and the plant may then be maintained under conditions wherein the chordate protein is expressed. In some embodiments, the DNA construct is introduced into the plant, or part thereof, using one or more methods for plant transformation known in the art, such as Agrobacterium-mediated transformation, particle bombardment-medicated transformation, electroporation, and microinjection.

In some embodiments, a method for expressing a chordate protein in a plant cell comprises: (a) contacting a plant cell with a DNA construct, thereby generating a transformed plant cell; and (b) cultivating a plant that comprises the transformed plant cell, thereby generating a transformed plant. In some embodiments, the chordate protein is expressed in the amount of at least about 1%, at least 2%, at least 3%, at least 4%, or at least 5% or higher per total protein weight of soluble protein extractable from the transformed plant cell. In some embodiments, the chordate protein is expressed in the amount of at least about 1%-3%, 3%-5%, 1-5%, 2-5%, 5-10%, including all ranges and subranges therebetween, or higher per total protein weight of soluble protein extractable from the transformed plant cell. In embodiments, a method can further comprise isolating a portion of the transformed plant including but not limited to any plant tissue: leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, seed, pericarp, endosperm, placenta, berry, stamen, and/or leaf sheath. In some cases, a method comprises isolating a seed from a transformed plant.

In some cases, a transgenic plant and/or host cell comprises a level of a chordate protein encoded by any of the DNA constructs provided herein that can be measured via an in vitro assay. A person of skill in the art will readily identify suitable in vitro assays to measure protein levels including but not limited to: ELISA, western blot, protein quantitation ratioing, mass spectrometry, and the like. In embodiments, a level of a chordate protein encoded by a provided transgene construct is increased by at least about: 0.5 fold, 1-fold, 2-fold, 3-fold, 4-fold, 5-fold, 8-fold, 10-fold, 15-fold, 20-fold, 30-fold, 40-fold, 50-fold, 70-fold, 100-fold, 120-fold, 150-fold, 175-fold, 200-fold, 300-fold, 400-fold, or up to about 500-fold as compared to an otherwise comparable host cell or transgenic plant lacking modification with any of the disclosed transgenes and/or RNA stabilization methods.

Methods of Processing Chordate Proteins from Host Cells

The chordate protein may be extracted from a host cell, such as from a plant, using standard methods known in the art. Any chordate protein can be expressed in a host cell and/or transgenic plant. In some embodiments, the chordate protein is ovalbumin and/or β-Lactoglobulin expressed in a soybean plant.

In some embodiments, the protein may be extracted using solvent or aqueous extraction. In some embodiments, the oil may be separated from the protein using hexane or ethanol extraction to produce a white flake. The protein may be extracted from the white flake using controlled temperature in an aqueous buffered environment (e.g., carbonate, citrate), in order to control the pH. The chordate protein can be separated from the host cell proteins using selective precipitation of one or more of the proteins with centrifugation or filtration methods. In some embodiments, one or more additives may be used to aid the extraction processes (e.g., salts, protease/peptidase inhibitors, osmolytes, solvents, reducing agents, etc.) The following step is processing the chordate protein into a food product. In some embodiments, only one protein from a chordate is used in a product. In some embodiments, more than one chordate protein is used in a product. In some embodiments, all chordate proteins may be used in a product. In some embodiments, a chordate protein may be used itself in a food product. The product is then formulated as desired.

In some embodiments a method comprises collecting seeds from a host cell plant. After seeds are collected, hulled and/or ground, and chordate protein has been extracted, the chordate protein is separated from other seed protein. In some embodiments, this separation is not 100% efficient, meaning that the "other seed protein" fraction may still contain some residual host cell protein. For example, in some embodiments, the other seed protein fraction may comprise about 0.1%, about 0.3%, about 0.5%, about 0.7%, about 1%, about 2%, about 3%, about 4%, about 5%, about 6%, about 7%, about 8%, about 9%, about 20%, about 20%, about 30%, or about 50%, including all ranges and subranges therebetween, chordate protein by weight. The other seed protein fraction may then be used directly in a food composition. Alternatively, the other seed protein fraction may be combined with concentrated chordate protein. In some embodiments, the other seed protein fraction is combined with one or more of the constituent proteins from the chordate protein. In some embodiments, the other seed protein fraction is combined with all of the constituent proteins from the chordate protein.

It may be advantageous to use a seed processing composition comprising plant protein and a chordate protein (e.g., about 0.1%, about 0.3%, about 0.5%, about 0.7%, about 1%, about 2%, about 3%, about 4%, about 5%, about 6%, about 7%, about 8%, about 9%, about 20%, about 20%, about 30%, or about 50%, including all ranges and subranges therebetween, chordate protein by weight) as an ingredient in a food composition. Using both (i) a chordate protein produced by a seed and (ii) other protein extracted from the seed allows for efficient use of resources and reduces waste. Such processes may simplify food manufacturing processes and reduce the unit cost to manufacture each product. Thus, provided herein is a method of making a food composition, the method comprising: (i) expressing a chordate protein in a transformed plant; and (ii) preparing a food composition comprising the chordate protein and plant protein from the same transformed plant in which the chordate protein was produced. In some embodiments, the transformed plant is a soybean. In some embodiments, the transformed plant is pea.

Food Compositions

Any of the compositions and methods provided herein can be used to generate a food composition. In some embodiments, host cells of the disclosure are modified to comprise and/or express transgene sequences that encode for a chordate protein. In some embodiments, a host cell is a mammalian host cell. In some embodiments, a host cell is a plant cell. Any one of a mammalian or plant cell can be modified to comprise or express a chordate protein. In some embodiments, a plant expresses a chordate protein selected from ovalbumin and β-Lactoglobulin.

In some embodiments, a plant protein composition comprising a chordate protein is used to produce a food composition. The food composition may be, for example, a meat analog, a nutritional bar, a bakery product, a beverage, mashed potatoes, or candy. In some embodiments, the food composition is for a human. In some embodiments, the food composition is for a companion animal (e.g., a dog, cat, rabbit, hamster, guinea pig, horse, etc.) For example, the food composition may be pet food. In some embodiments, the food composition is for a pediatric human.

Also provided herein are various compositions prepared during a method of making a food composition. For example, in some embodiments, a seed processing composition is provided comprising ovalbumin and/or β-Lactoglobulin. In some embodiments, a seed processing composition comprises (a) a chordate protein comprising i) a full-length ovalbumin component; and ii) a β-lactoglobulin component; and (b) plant seed tissue. In some embodiments, a seed processing composition comprises (a) a chordate protein comprising i) an ovalbumin component; and ii) a β-lactoglobulin component; and (b) plant seed tissue. In some embodiments, a seed processing composition comprises (a) a chordate protein comprising i) an egg or milk protein (e.g., an ovalbumin or β-Lactoglobulin protein); and ii) a second protein (i.e., a fusion partner); and (b) plant seed tissue. In some embodiments, the plant seed tissue is ground. In some embodiments, the plant seed tissue is from soybean. In some embodiments, the seed processing composition comprises at least one member selected from the group consisting of: enzyme (e.g., chymosin), protease, extractant, solvent, buffer, additive, salt, protease inhibitor, peptidase inhibitor, osmolyte, and reducing agent.

In some embodiments, a protein concentrate composition is provided. In some embodiments, the protein concentrate composition comprises: a chordate protein, comprising i) a full-length ovalbumin component; and/or ii) a β-lactoglobulin component. In some embodiments, the protein concentrate composition comprises: a chordate protein, comprising i) an ovalbumin component; and/or ii) a β-lactoglobulin component. In some embodiments, the protein concentrate composition comprises: a chordate protein, comprising i) an egg or milk protein (e.g., ovalbumin or β-Lactoglobulin protein); and ii) a second protein. In some embodiments, the chordate protein is present in an enriched amount, relative to other components present in the composition. In some embodiments, there is substantially no plant seed tissue present in the protein concentrate composition. In some embodiments, the protein concentrate composition further comprises at least one member selected from the group consisting of: enzyme (e.g., chymosin), protease, extractant, solvent (e.g., ethanol, hexane, phenol), buffer, additive, salt, protease inhibitor, peptidase inhibitor, osmolyte, and reducing agent.

In some embodiments, the food composition is a solid. In some embodiments, the food composition is a liquid. In some embodiments, the food composition is a powder.

In some embodiments, the food composition is a solid phase, protein-stabilized emulsion. In some embodiments, the food composition is a colloidal suspension.

In some embodiments, the chordate proteins and transgenic plants described herein may be used to prepare a food composition such as a meat composition. A meat composition of the disclosure can comprise a milk protein (e.g., β-lactoglobulin protein). In some embodiments, meat compositions of the disclosure can comprise β-lactoglobulin isolated from a plant, for example a soybean plant. In some embodiments, meat compositions of the disclosure can comprise β-lactoglobulin isolated from a plant, for example a soybean plant, and a combination of methylcellulose and a casein protein of the disclosure. In some embodiments, a meat composition comprises reduced methylcellulose as compared to an otherwise comparable meat composition lacking a casein protein comprised within the meat composition. Various meat compositions are contemplated including, but not limited to: burger, patty, sausage, hot dog, nugget, finger, salad, bouillon powder, bouillon cube, flavor packet, meat ball, meatloaf, and the like.

In some embodiments, the chordate proteins and transgenic plants described herein may be used to prepare a food composition such as one or more egg substitute compositions. An egg substitute composition of the disclosure can comprise an egg protein (e.g., ovalbumin). In some embodiments, egg substitute compositions of the disclosure can comprise ovalbumin isolated from a plant, for example a soybean plant. Various egg substitutes are contemplated including but not limited to: an egg-based sauce (e.g. mayonnaise), dressing or custard; a scramble, omelet, or quiche; or an egg white composition.

In some embodiments, the chordate proteins and transgenic plants described herein may be used to prepare a food composition such as one or more baked goods. A baked good composition of the disclosure can comprise an egg protein (e.g., ovalbumin). In some embodiments, baked goods of the disclosure can comprise ovalbumin isolated from a plant, for example a soybean plant. Various baked goods are contemplated including but not limited to: bars, breads (bagels, buns, rolls, biscuits and loaf breads), cookies, desserts (brownies, cakes, cheesecakes and pies), muffins, pizza, snack cakes, sweet goods (doughnuts, Danish, sweet rolls, cinnamon rolls and coffee cake) and tortillas.

In some embodiments, the chordate proteins and transgenic plants described herein may be used to prepare a food composition such as cheese or processed cheese products. In some embodiments, the food composition is an alternative dairy composition selected such as milk, cream, or butter. The alternative milk composition may be used to prepare alternative dairy compositions such as yogurt and fermented dairy products, directly acidified counterparts of fermented dairy products, cottage cheese, dressing, curds, creme fraiche, toppings, icings, fillings, low-fat spreads, dairy-based dry mixes, frozen dairy products, frozen desserts, desserts, baked goods, soups, sauces, salad dressing, geriatric nutrition, creams and creamers, analog dairy products, follow-up formula, baby formula, infant formula, milk, dairy beverages, acid dairy drinks, smoothies, milk tea, butter, margarine, butter alternatives, growing up milks, low-lactose products and beverages, medical and clinical nutrition products, protein/nutrition bar applications, sports beverages, confections, meat products, analog meat products, meal replacement beverages, and weight management food and beverages.

In some embodiments, the chordate proteins and transgenic plants described herein may be used to prepare a food composition such as tofu or processed tofu products.

In some embodiments the chordate proteins and transgenic plants described herein may be used to prepare a dairy product. In some embodiments, the dairy product is a fermented dairy product. An illustrative list of fermented dairy products includes cultured buttermilk, sour cream, yogurt, skyr, leben, lassi, or kefir. In some embodiments the chordate proteins and transgenic plants described herein may be used to prepare cheese products.

In some embodiments the chordate proteins and transgenic plants described herein may be used to prepare a powder containing a milk protein. In some embodiments, the chordate proteins and transgenic plants described herein may be used to prepare a low-lactose product.

In some embodiments, a method for making a food composition comprises, expressing a recombinant chordate protein of the disclosure in a plant, extracting the recombinant chordate protein from the plant, optionally separating the ovalbumin and/or β-Lactoglobulin from the mammalian or plant protein, and creating a food composition using the chordate protein and/or the milk protein.

In some embodiments, a method of expressing, extracting, and making a food composition from a chordate protein, comprises: expressing a chordate protein in a host cell, the chordate protein comprising a first protein and a second protein; extracting the chordate protein from the host cell; and processing the chordate protein into a food composition. The food composition may be, for example, cheese, processed cheese product, yogurt, fermented dairy product, directly acidified counterpart of fermented dairy product, cottage cheese dressing, frozen dairy product, frozen dessert, dessert, baked good, topping, icing, filling, low-fat spread, dairy-based dry mix, soup, sauce, salad dressing, geriatric nutrition, cream, creamer, analog dairy product, follow-up formula, baby formula, infant formula, milk, dairy beverage, acid dairy drink, smoothie, milk tea, butter, margarine, butter alternative, growing up milk, low-lactose product, low-lactose beverage, medical and clinical nutrition product, protein bar, nutrition bar, sport beverage, confection, meat product, analog meat product, meal replacement beverage, weight management food and beverage, dairy product, cultured buttermilk, sour cream, yogurt, skyr, leben, lassi, kefir, powder containing a milk protein, and low-lactose product. In some embodiments, the food composition is a dairy product. In some embodiments, the food composition is a cheese.

In some embodiments, a method for making a food composition comprises, expressing a recombinant chordate protein of the disclosure in a plant, extracting one or both of the proteins, and creating a food composition using the chordate protein. In some embodiments, the first protein and the second protein are separated from one another in the plant cell, prior to extraction. In some embodiments, the first protein is separated from the second protein after extraction, for example by contacting the chordate protein with an enzyme that cleaves the chordate protein. The enzyme may be, for example, chymosin. In some embodiments, the chordate protein is cleaved using rennet.

Provided herein are also nutraceuticals generated using any of the compositions or methods provided herein. Nutraceuticals are products derived from food sources that can provide extra health benefits, in addition to the basic nutritional value found in foods. Nutraceutical products may prevent chronic diseases, improve health, delay the aging process, increase life expectancy, and/or support the structure or function of the body. In some embodiments, a nutraceutical comprises any one of a: drug, dietary supplement, herbal supplement, food ingredient, antioxidants, fortified dairy products, citrus fruits, vitamins, minerals, herbals, milk, and/or cereals.

Kits, Containers, and the Like

Provided are also containers, kits, encasements, and the like that comprise any of the compositions provided herein.

In some embodiments, a kit is provided for stabilizing RNA in host cells. A kit can also comprise any of the DNA constructs provided, sequences, transgenic cells, transgenic plants, and/or any of the in bulk. For instance, a bushel of a transgenic plant can be provided in contained form. In some embodiments, a DNA construct comprises GmSeed2:sig2: OOVAL2 (intron 1):KDEL:EUT:Rb7T. In some embodiments, a container, kit, and the like comprise a nucleic acid encoding any one of SEQ ID NO: 685, 687, and 695. In some embodiments, a container, kit, and the like comprise a nucleic acid encoding a sequence comprising at least about 85%, 90%, 95%, 96%, 97%, 98%, 99%, or 100% identity to any one of SEQ ID NO: 685, 687, and 695. Transgenic plants manufactured using any of the aforementioned nucleic acids can also be provided in any of the kits, containers, and the like of the disclosure.

Any of the containment forms provided can also comprise additional components such as media, water, soil, plant supplements, and the like to generate and/or cultivate transgenic host cells or transgenic plants.

Some examples of the kits further include instructions for making any of the compositions described herein.

EXAMPLES

The following experiments demonstrate different strategies employing engineered constructs to increase RNA stability and protein expression, as well as methods of generating and testing the same. While the examples below describe expression in plants, it will be understood by those skilled in the art that the constructs and methods disclosed herein may be tailored for expression in any host organism.

Example 1: Strategies to Increase RNA Stability and Protein Generation and Study Methodology Outline of Exemplary Strategies Various strategies were tested in order to either increase RNA levels or improve RNA stability, which in turn lead to an increased protein accumulation in soybean seeds. These strategies are listed in Table 9.

TABLE 9

Summary of strategies that were tested to increase RNA stability and recombinant protein accumulation in soybean seeds.

Figure 7:
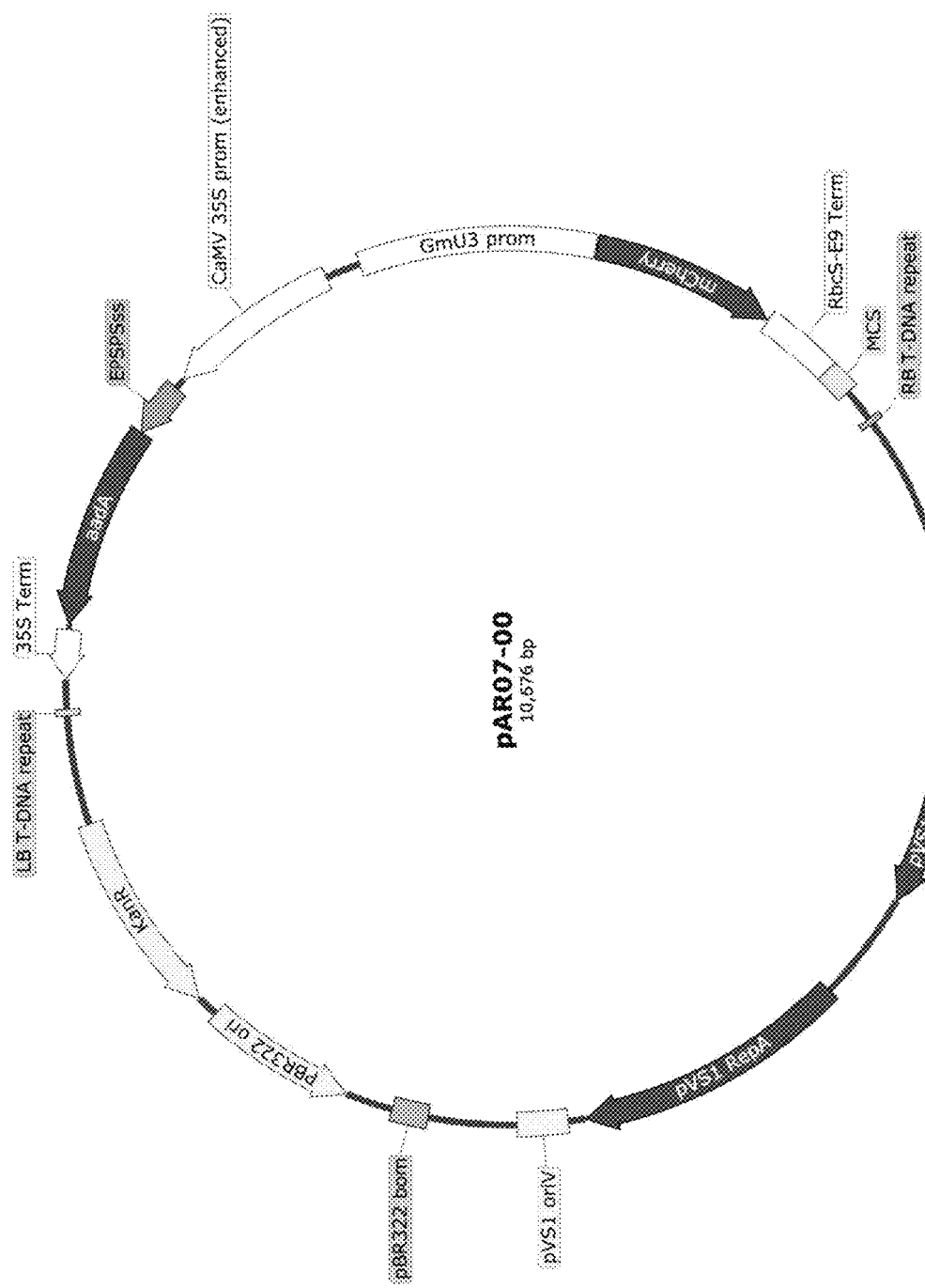
FIG. 7 is a graphic of the pAR07-00 cloning vector containing a selectable marker cassette conferring spectinomycin resistance in plants. The pAR07-00 cloning vector is a modified binary pCAMBIA3300 vector containing the Aminoglycoside-3"-adenyltransferase (aadA) gene fused to a *petunia* EPSPS chloroplast transit peptide (CTP), that confers resistance to spectinomycin driven by the 35S promoter, which is followed by the 35S terminator. A BamHI restriction enzyme site was available to insert the expression cassette into the vector between the antibiotic resistance gene and the mCherry marker gene.

| Category | High level strategy | Details |
| --- | --- | --- |
| Transcriptional regulation | Promoter/Terminator | Tested different combinations of promoter and terminator. |
| Transcriptional/Translational Regulation/RNA stability | Codon optimization | Different transgenes were designed and inserted into the plasmid of FIG. 7 with different codon optimization versions. |
| RNA stability | +/− KDEL | Constructs were designed that either contained (+) or did not contain (−) a KDEL sequence. KDEL acts on the stability of the RNA, and can have positive effects on the expression of some transgenes. |
| Transcriptional regulation | Intron | Constructs containing one or more exogenous introns were designed. Splicing can have a positive effect on RNA stability. It was hypothesized that by reintroducing introns in specific locations of the transgene, RNA levels can be enhanced. |
| Transcriptional regulation | 5' UTR/3' UTR | The 5' or 3' untranslated region (UTR) may act on the stability of the mRNA and translation efficiency, and may also play a role in regulating the transport of mRNAs out of the nucleus. Accordingly, constructs were designed that either contain or do not contain a 5' and/or a 3' UTR. |
| Translational regulation | Monomer | Ubiquitin monomers from certain plant species were transcriptionally fused to a transgene in order to enhance protein expression. The ubiquitin monomer is separated from the transgene either immediately after or during translation, improving translational regulation. |

Example 2: Use of Promoter and Terminators to Enhance Stability of RNA and Increase Protein Levels Study Design and Methodology Protein accumulation may be increased by modulating levels of gene expression. Since promoter selection is an important factor in determining level of gene expression, various promoters were tested to determine which is able to drive optimal transcription of RNA encoding a desired protein. Specifically, to express OVAL and LG in soybean seeds, several seed specific promoters (BnNap, GmSeed2, GmSeed12 and PvPhas) were tested. Except for PvPhas, most of the promoters were used in combination with the nopaline synthase terminator (nosT) to control for the effect of that element in protein expression.

The first strategy tested use of seed-specific promoters to modulate expression of OVAL or LG in soybean seeds. Various seed-specific promoters BnNap, GmSeed2, GmSeed12 and PvPhas were implemented. Except for PvPhas, most of the promoters were accompanied with the nopaline synthase terminator (nosT) to control for the effect of that element in protein expression.

qPCR analysis was used to determine RNA levels, and enzyme-linked immunosorbent assays (ELISA) or western blots were used to quantify protein expression. qPCR and ELISA data was extracted for all the plasmid constructs that contained OVAL or LG as the transgene.

RNA and protein quantification data was analyzed as follows: (1) ELISA protein quantifications of ovalbumin and β-Lactoglobulin are summarized in Table 10 and Table 12 except for AR07-22 and AR07-23 where the seed samples were only analyzed using western blot; (2) Seed samples for each construct were separated into 3 categories based on their protein expression levels: WT seeds that have below detection threshold expressions; Low expression seeds that have above detection threshold but below 1% TSP expressions; or High expression seeds that have above 1% TSP expressions. ELISA detection thresholds for ovalbumin and 0-Lactoglobulin are 0.023% TSP and 0.063% TSP respectively. The numbers of seeds in the three categories for each construct are summarized in Table 10 and Table 12.

Results

As described below, Table 10 provides data summarizing relative expression of the ovalbumin (i.e., RNA levels), which is the transcript level of the ovalbumin transgene relative to the native Glycinin 1 gene of all the seeds that were analyzed per construct design (n=number of seeds). Analyzed seeds were collected around 90 days after plants were transferred to soil. Table 10 also shows protein levels (i.e., % Total Soluble protein (% TSP)) of the ovalbumin transgene in all the seeds that were analyzed per construct design (n=number of seeds). Analyzed seeds were collected between 90-120 days after plants were transferred to soil.

Figures 2A, 2B:
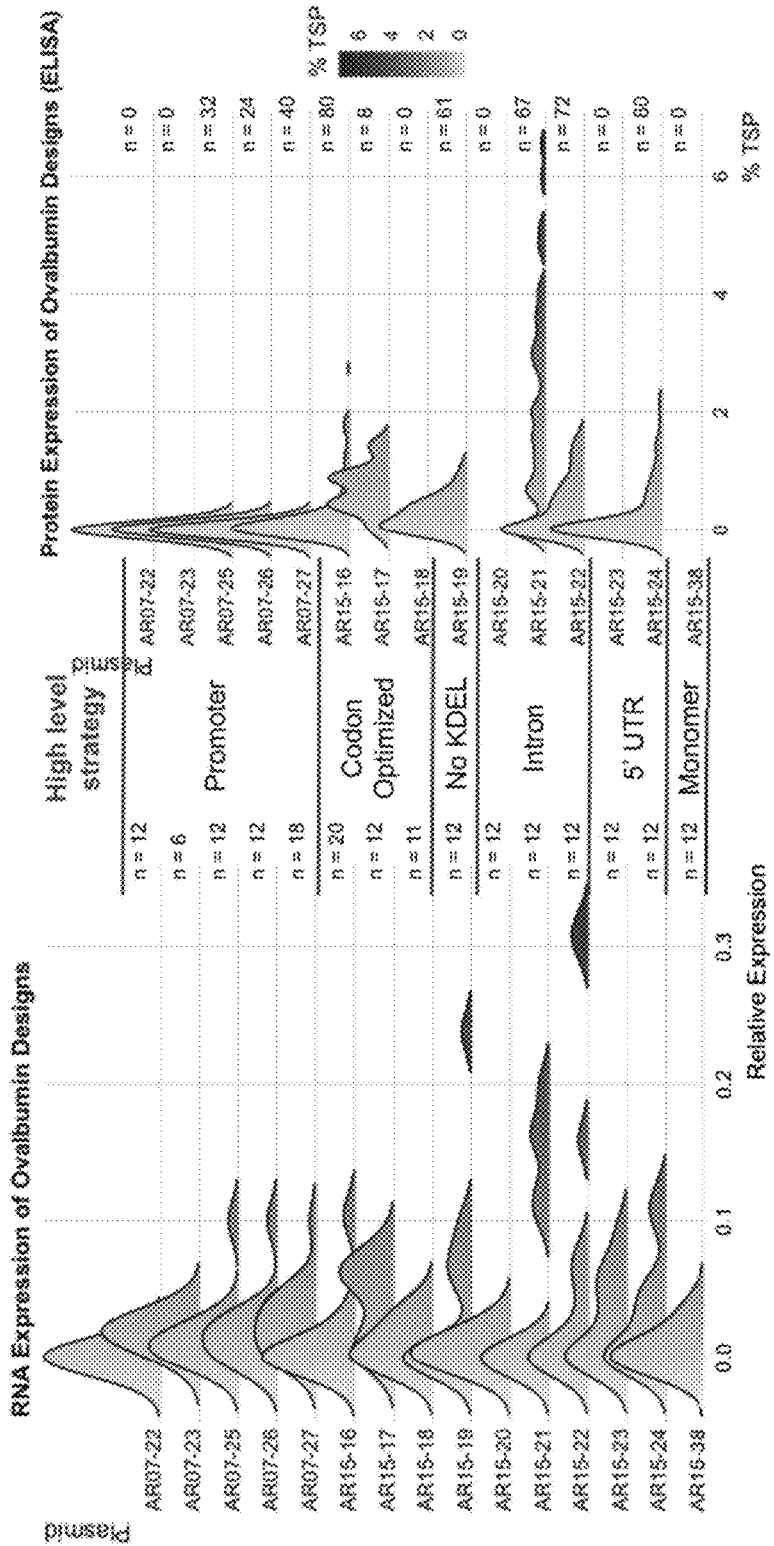
FIG. 2A shows RNA expression of exemplary constructs encoding ovalbumin.
FIG. 2B shows protein expression of exemplary constructs encoding ovalbumin as determined by ELISA. Protein expression is shown as a function of relative expression and percent total soluble protein (% TSP), respectively. Boxes indicate the designs that led to an increase in both RNA expression and protein accumulation. In between FIG. 2A and FIG. 2B, a breakdown of the designs based on "high level strategy" is shown. n=number of seeds analyzed. Note: Since the RNA level (cut off <0.1) was low for plants transformed with constructs AR07-22 and AR07-23 as well as AR15-18, -20, -23 and -38, the plants were discarded, and no protein data was collected for these constructs (n=0).

Results show that OVAL expressed under different seed specific promoters (AR07-22, -23, -25, -26 and -27) accumulated at low RNA levels (FIG. 2A), leading to low protein accumulation (FIG. 2B). GmSeed12:sig12 (AR07-27) and PvPhas (AR07-27) were the two designs that had the highest RNA and protein level (Table 10, plasmid ID AR07-26). The highest RNA and protein level recorded was 0.11 times the level of glycinin1 and 0.08% TSP for design containing GmSeed12 promoter (Table 10, plasmid ID AR07-26).

TABLE 10

Summary of RNA and protein quantification of exemplary OVAL constructs.

| Construct ID | Details | Highest RNA level | Max % TSP | # of all plants analyzed for ELISA | # of all seeds analyzed for ELISA | # of seeds below detection level | # of seeds with 0.023-1% TSP | # of seeds with over 1% TSP |
|---|---|---|---|---|---|---|---|---|
| AR07-22 | BnNap:sig11:OOVAL1:KDEL:nos | 0.002 | 0.000 | 3 | 31 | 31* | 0* | 0* |
| AR07-23 | GmSeed2:sig2:OOVAL1:KDEL:nos | 0.03 | 0.004 | 4 | 32 | 32* | 0* | 0* |
| AR07-25 | GmSeed12:coixss:OOVAL1:KDEL:nos | 0.1 | 0.009 | 4 | 32 | 32 | 0 | 0 |
| AR07-26 | GmSeed12:sig12:OOVAL1:KDEL:nos | 0.06 | 0.08 | 3 | 24 | 21 | 3 | 0 |
| AR07-27 | PvPhas:arcUTR:sig10:OOVAL1:KDEL:arcT | 0.08 | 0.06 | 5 | 40 | 38 | 2 | 0 |
| AR15-16 | GmSeed2:sig2:OOVAL2:KDEL:EUT:Rb7T | 0.11 | 2.74 | 10 | 80 | 37 | 36 | 7 |
| AR15-17 | GmSeed2:sig2:OOVAL3:KDEL:EUT:Rb7T | 0.08 | 1.43 | 1 | 8 | 0 | 7 | 1 |
| AR15-18 | GmSeed2:sig2:OOVAL4:KDEL:EUT:Rb7T | 0.04 | * | * | * | — | — | — |
| AR15-19 | GmSeed2:sig2:OOVAL2:EUT:Rb7T | 0.24 | 1.08 | 8 | 61 | 12 | 47 | 2 |
| AR15-20 | GmSeed2 (intron 1):sig2:OOVAL2:KDEL:EUT:Rb7T | 0.03 | * | * | * | — | — | — |
| AR15-21 | GmSeed2:sig2:OOVAL2 (intron 1):KDEL:EUT:Rb7T | 0.22 | 6.64 | 9 | 67 | 14 | 10 | 43 |
| AR15-22 | GmSeed2:sig2:OOVAL2 (intron 2):KDEL:EUT:Rb7T | 0.32 | 1.69 | 9 | 72 | 36 | 26 | 10 |
| AR15-23 | GmSeed2:ovalUTR:sig2:OOVAL2:KDEL:EUT:Rb7T | 0.09 | * | * | * | — | — | — |

TABLE 10-continued

Summary of RNA and protein quantification of exemplary OVAL constructs.

| Construct ID | Details | Highest RNA level | Max % TSP | # of all plants analyzed for ELISA | # of all seeds analyzed for ELISA | # of seeds below detection level | # of seeds with 0.023-1% TSP | # of seeds with over 1% TSP |
|---|---|---|---|---|---|---|---|---|
| AR15-24 | GmSeed2:glnB1UTR:sig2: OOVAL2:KDEL:EUT: Rb7T | 0.12 | 2.28 | 10 | 80 | 47 | 25 | 8 |
| AR15-38 | GmSeed2: Ubimonomer:sig2: OOVAL2:KDEL:EUT:Rb7T | 0.05 | ❋ | ❋ | ❋ | — | — | — |

*Protein amount was determined using a western blot. No seeds were analyzed by ELISA for constructs AR07-22 and AR07-23.
❋Plants were all discarded due to low RNA expression and not further analyzed.
(—) No data available.

TABLE 11

Sequences for exemplary introns, β-Lactoglobulin, ovalbumin, signal peptide, terminators, monomers, and promoters.

| | SEQ ID NO | Sequence |
|---|---|---|
| Introns | | |
| Intron 1 | 679 | GTTCGTTATCTACCACCGTTCTATGGATTTTATTCCTTCTATTCG TGTTTATTCTATTGGTTTATGTTGCTTGCAATATGTTTTTTCTGA ATCTGTCGTCGTTGTCTTCAATTTTATCCATGTTTCAGAGATCAA TTTTGTTTGTGTAGTATGTGCTTATTCTTCTTCTTTTCGTTCGAG TTGTTAATAACGGTGCTATGGTGTTTTCAAAAGTGTTTTTTTAT TACTTTTGATTTAAAGTTTTTTTGGTAAGGCTTTTATTTGCTTGT TATATTCAAATCTTTGGATCCAGATCTTATATAAGTTTTTGGTTC AAGAAAGTTTTTGGTTACTGATGAATAGATCTATTAACTGTTACT TTAATCGATTCAAGCTAAAGTTTTTTGGTTACTGATGAATAGATC TATTATCTGTTACTTTTAATCGGTTCAAGCTCAAGTTTTTTGGTT ACTGATGAATAGATCTATATACGTCACAGTGTGCTAAACATGCCC TTGTTTTATCTCGATCTTATGTATGGGAGTGCCATAAATTTTGTT ATGTCTATTTTTTATCTGTTGGAATCATACTGAGTTTGATGCGT TACGATTGAGCATACCTATTTTTGGGCTTGTTGTATGGTGGGTAT TTAGATCTTAATCTTTTTATGCTTATGAAAGGTTTTGTAATGACA AAGGTCTTAATGTTGTTAAACTTTTATTTTTACTTTATATGGTGT GTTGATGTGTTATGGTTTTGACAACTTTTTTTTTTCTGGATTTT TGCAG |
| Intron 2 | 680 | GTAACCATATCTTTCATCTGTTATGTGACTACACATTGCTTCTCT TTTTGTGTTCTGTCTCATTAATTGCGGTTTGTTACATGTTGTTTG TAG |
| Intron 3 | 681 | GTAAGCAACCAACACACCATCTAATACGCTAGCAAATTCAATATT ATCATTATCCTTATATTTGTTTCCGCGCTTGATTTTATAG |
| Intron 4 | 682 | GTTTGTATTTACTCAAATGTTGATCAGTAGTGTTTTAGGACATT GATTAAGAAACCCAAAAAATAATTATTTTTATTGAAACGCATAAA TTTATACTAGCCGTGACTGTTTTTATGTCCTTATATGATCTTCGC AATATATATTTTCTATTATAAGTTTCTTAACCAATGCACTAACTT ACTGTTAACAAGACCTTATTATTAAACATCATCTATCACTTGGTT AATTGTATTCATTTGATGCATGGTAATGCATTACATATATACAG |
| LG Codon optimized | | |
| OLG1 | 683 | TTGATCGTAACACAGACTATGAAGGGTCTTGATATACAGAAGGTG GCCGGGACTTGGTACAGTTTGGCAATGGCCGCATCCGACATCTCC TTGTTGGACGCACAATCAGCCCCATTGCGTGTGTACGTAGAAGAG CTTAAACCAACTCCCGAGGGGGATCTGGAAATTCTGCTCCAGAAA TGGGAGAACGGTGAGTGCGCCCAGAAGAAGATCATCGCAGAGAAG ACCAAAATTCCAGCAGTATTCAAAATCGACGCATTGAACGAAAAT AAGGTGCTCGTACTGGACACTGATTATAAGAAGTATCTCCTTTTC |

TABLE 11-continued

Sequences for exemplary introns, β-Lactoglobulin, ovalbumin, signal peptide, terminators, monomers, and promoters.

| | SEQ ID NO | Sequence |
|---|---|---|
| | | TGTATGGAGAACTCAGCAGAGCCTGAACAGAGTCTTGCCTGCCAA TGCCTTGTTCGTACCCCAGAGGTAGATGATGAAGCTCTGGAAAAG TTCGATAAGGCCCTTAAGGCTCTGCCTATGCACATTAGGCTTTCT TTCAATCCAACTCAACTTGAGGAACAATGTCACATT |
| OLG1 | 684 | LIVTQTMKGLDIQKVAGTWYSLAMAASDISLLDAQSAPLRVYVEE LKPTPEGDLEILLQKWENGECAQKKIIAEKTKIPAVFKIDALNEN KVLVLDTDYKKYLLFCMENSAEPEQSLACQCLVRTPEVDDEALEK FDKALKALPMHIRLSFNPTQLEEQCHI |
| OLG2 | 685 | CTTATTGTGACCCAAACCATGAAGGGCCTCGACATTCAAAAGGTT GCCGGAACCTGGTACTCCCTTGCTATGGCTGCTTCCGATATCTCC TTGCTCGATGCTCAATCCGCTCCACTTAGGGTGTACGTGGAAGAG TTGAAGCCAACTCCAGAGGGCGATCTTGAGATCTTGCTTCAAAAG TGGGAGAACGATGAGTGCGCCCAGAAGAAGATTATCGCCGAAAAG ACCAAGATTCCCGCCGTGTTCAAGATCGATGCTCTCAACGAGAAC AAGGTGCTCGTGCTCGATACCGACTACAAGAAGTACCTTCTCGTC TGCATGGAAAACTCCGCTGAGCCAGAGCAATCTCTTGTTTGCCAA TGCCTTGTGAGGACCCCAGAGGTTGACGATGAAGCTCTTGAGAAG TTCGACAAGGCTCTCAAGGCTTTGCCTATGCACATCCGCCTTAGC TTCAACCCAACTCAGCTTGAGGAACAGTGCCACATC |
| OLG2 | 686 | LIVTQTMKGLDIQKVAGTWYSLAMAASDISLLDAQSAPLRVYVEE LKPTPEGDLEILLQKWENDECAQKKIIAEKTKIPAVFKIDALNEN KVLVLDTDYKKYLLVCMENSAEPEQSLVCQCLVRTPEVDDEALEK FDKALKALPMHIRLSFNPTQLEEQCHI |
| OLG3 | 687 | CTCATTGTTACACAAACCATGAAGGGTCTTGACATTCAGAAGGTT GCTGGGACATGGTATTCACTAGCGATGGCTGCTTCTGATATCTCC CTGTTGGATGCACAGTCTGCCCCCCTGAGAGTGTATGTTGAAGAA CTGAAACCGACACCTGAAGGAGACTTGGAAATTTTACTCCAGAAA TGGGAAATGATGAGTGTGCCCAAAGAAGATAATAGCCGAGAAG ACCAAAATTCCTGCTGTGTTTAAGATTGATGCTTTGAATGAGAAC AAAGTACTAGTCCTCGACACTGATTACAAGAAATACTTATTAGTG TGCATGGAAAACAGCGCAGAGCCAGAACAATCACTTGTTTGTCAA TGTTTGGTCCGTACTCCAGAGGTAGATGATGAAGCATTGGAGAAA TTTGATAAAGCATTGAAGGCACTTCCAATGCATATAAGGCTTAGT TTCAATCCTACTCAGCTTGAAGAGCAATGCCACATC |
| OLG3 | 688 | LIVTQTMKGLDIQKVAGTWYSLAMAASDISLLDAQSAPLRVYVEE LKPTPEGDLEILLQKWENDECAQKKIIAEKTKIPAVFKIDALNEN KVLVLDTDYKKYLLVCMENSAEPEQSLVCQCLVRTPEVDDEALEK FDKALKALPMHIRLSFNPTQLEEQCHI |
| OLG4 | 689 | CTTATAGTAACTCAAACCATGAAGGGACTTGATATCCAAAAGTT GCAGGAACCTGGTACTCACTGGCTATGGCAGCTTCCGACATCTCC TTGTTGGACGCACAATCCGCACCATTGCGCGTCTACGTTGAGGAG TTGAAACCTACACCAGAGGGGGATCTTGAGATTTTGCTCCAGAAA TGGGAGAACGACGAGTGTGCCCAGAAAAAAATTATAGCAGAGAAG ACTAAAATTCCTGCTGTTTTTAAGATTGATGCCCTGAACAGAAT AAGGTACTGGTCCTCGACACTGATTATAAAAAGTATTTGCTGGTG TGTATGGAGAACAGTGCTGAACCTGAACAGAGCCTGGTCTGTCAA TGTCTTGTAAGGACACCTGAGGTTGATGACGAGGCACTTGAAAAA TTCGACAAGGCCCTTAAGGCTCTGCCTATGCACATCCGTCTGAGT TTCAACCCTACTCAGTTGGAGGAACAATGTCATATT |
| OLG4 | 690 | LIVTQTMKGLDIQKVAGTWYSLAMAASDISLLDAQSAPLRVYVEE LKPTPEGDLEILLQKWENDECAQKKIIAEKTKIPAVFKIDALNEN KVLVLDTDYKKYLLVCMENSAEPEQSLVCQCLVRTPEVDDEALEK FDKALKALPMHIRLSFNPTQLEEQCHI |
| OLG2 (intron 1) | 691 | CTTATTGTGACCCAAACCATGAAGGGCCTCGACATTCAAAAGGTT CGTTATCTACCACCGTTCTATGGATTTTATTCCTTCTATTCGTGT TTATTCTATTGGTTTATGTTGCTTGCAATATGTTTTTTCTGAATC TGTCGTCGTTGTCTTCAATTTTATCCATGTTTCAGAGATCAATTT TGTTTGTGTAGTATGTGCTTATTCTTCTTTTCGTTCGAGTTG TTAATAACGGTGCTATGGTGTTTTCAAAAGTGTTTTTTTATTAC TTTTGATTTAAAGTTTTTTTTGGTAAGGCTTTTATTTGCTTGTTAT ATTCAAATCTTTGGATCCAGATCTTATATAAGTTTTTGGTTCAAG AAAGTTTTTGGTTACTGATGAATAGATCTATTAACTGTTACTTTA ATCGGATTCAAGCTAAAGTTTTTTGGTTACTGATGAATAGATCTAT TATCTGTTACTTTTAATCGGTTCAAGCTCAAGTTTTTTGGTTACT |

TABLE 11-continued

Sequences for exemplary introns, β-Lactoglobulin,
ovalbumin, signal peptide, terminators,
monomers, and promoters.

| Name | SEQ ID NO | Sequence |
|---|---|---|
| | | GATGAATAGATCTATATACGTCACAGTGTGCTAAACATGCCCTTG
TTTTATCTCGATCTTATGTATGGGAGTGCCATAAATTTTGTTATG
TCTATTTTTTTATCTGTTGGAATCATACTGAGTTTGATGCGTTAC
GATTGAGCATACCTATTTTTGGGCTTGTTGTATGGTGGGTATTTA
GATCTTAATCTTTTTATGCTTATGAAAGGTTTTGTAATGACAAAG
GTCTTAATGTTGTTAAACTTTTATTTTTACTTTATATGGTGTGTT
GATGTGTTATGGTTTTGACAACTTTTTTTTTTTCTGGATTTTTGC
AGGTTGCCGGAACCTGGTACTCCCTTGCTATGGCTGCTTCCGATA
TCTCCTTGCTCGATGCTCAATCCGCTCCACTTAGGGTGTACGTGG
AAGAGTTGAAGCCAACTCCAGAGGGCGATCTTGAGATCTTGCTTC
AAAAGTGGGAGAACGATGAGTGCGCCCAGAAGAAGATTATCGCCG
AAAAGACCAAGATTCCCGCCGTGTTCAAGATCGATGCTCTCAACG
AGAACAAGGTGCTCGTGCTCGATACCGACTACAAGAAGTACCTTC
TCGTCTGCATGGAAAACTCCGCTGAGCCAGAGCAATCTCTTGTTT
GCCAATGCCTTGTGAGGACCCCAGAGGTTGACGATGAAGCTCTTG
AGAAGTTCGACAAGGCTCTCAAGGCTTTGCCTATGCACATCCGCC
TTAGCTTCAACCCAACTCAGCTTGAGGAACAGTGCCACATC |
| OLG2 (intron 2) | 692 | CTTATTGTGACCCAAACCATGAAGGGCCTCGACATTCAAAAGGTA
ACCATATCTTTCATCTGTTATGTGACTACACATTGCTTCTCTTTT
TGTGTTCTGTCTCATTAATTGCGGTTTGTTACATGTTGTTTGTAG
GTTGCCGGAACCTGGTACTCCCTTGCTATGGCTGCTTCCGATATC
TCCTTGCTCGATGCTCAATCCGCTCCACTTAGGGTGTACGTGGAA
GAGTTGAAGCCAACTCCAGAGGGCGATCTTGAGATCTTGCTTCAA
AAGTGGGAGAACGATGAGTGCGCCCAGAAGAAGATTATCGCCGAA
AAGACCAAGATTCCCGCCGTGTTCAAGATCGATGCTCTCAACGAG
AACAAGGTGCTCGTGCTCGATACCGACTACAAGAAGTACCTTCTC
GTCTGCATGGAAAACTCCGCTGAGCCAGAGCAATCTCTTGTTTGC
CAATGCCTTGTGAGGACCCCAGAGGTTGACGATGAAGCTCTTGAG
AAGTTCGACAAGGCTCTCAAGGCTTTGCCTATGCACATCCGCCTT
AGCTTCAACCCAACTCAGCTTGAGGAACAGTGCCACATC |
| Oval Codon optimized | | |
| OOVAL1 | 693 | GGTAGCATTGGGGCTGCTTCTATGGAATTTTGTTTCGATGTCTTT
AAAGAACTTAAGGTACACCATGCAAATGAGAACATTTTCTACTGT
CCCATCGCTATAATGTCTGCACTTGCAATGGTTTACCTTGGGGCT
AAAGACAGTACTCGTACACAAATAAATAAAGTAGTGAGATTCGAT
AAGTTGCCTGGGTTCGGGGATTCTATCGAAGCTCAATGTGGGACC
AGTGTTAACGTACATAGCTCCTTGCGCGATATCTTGAATCAAATA
ACAAAGCCTAATGATGTATACTCATTTTCATTGGCCTCTCGCTTG
TATGCCGAGGAAAGATACCCCATTCTGCCAGAATACCTTCAGTGC
GTCAAGGAACTCTACCGCGGAGGACTCGAGCCCATAAATTTCCAG
ACTGCAGCAGACCAGGCCAGGGAGCTGATTAACTCTTGGGTAGAG
AGCCAGACAAATGGCATAATCAGGAATGTGCTGCAGCCATCATCA
GTTGATTCACAAACAGCTATGGTGCTGGTTAATGCAATCGTCTTC
AAAGGGTTGTGGGAAAAGGCTTTTAAGGACGAAGATACTCAAGCT
ATGCCTTTCCGTGTAACAGAGCAAGAAAGCAAGCCTGTACAAATG
ATGTATCAGATTGGTCTGTTTCGTGTTGCCTCTATGGCTTCAGAG
AAAATGAAGATACTCGAACTTCCCTTCGCATCAGGGACTATGAGC
ATGTTGGTTTTGTTGCCTGATGAGGTATCTGGTTTGGAACAGCTG
GAATCAATAATCAATTTCGAGAAGTTGACAGAATGGACCAGTTCT
AATGTTATGGAAGAGCGTAAGATAAAAGTATATTTGCCTCGTATG
AAAATGGAAGAAAAGTACAATTTGACCAGCGTTTTGATGGCTATG
GGCATCACTGACGTTTTTTCATCTTCTGCTAATCTCAGCGGCATA
TCCAGCGCAGAGAGCCTCAAAATATCCCAAGCCGTCCATGCTGCA
CATGCAGAGATAAATGAGGCTGGTAGGGAAGTGGTCGGGAGCGCT
GAAGCTGGGGTAGATGCAGCCAGTGTAAGTGAAGAGTTCAGGGCT
GACCATCCCTTCCTGTTCTGCATTAAGCACATTGCAACTAACGCA
GTACTCTTTTTTGGACGTTGCGTGAGCCCC |
| OOVAL1 | 694 | GSIGAASMEFCFDVFKELKVHHANENIFYCPIAIMSALAMVYLGA
KDSTRTQINKVVRFDKLPGFGDSIEAQCGTSVNVHSSLRDILNQI
TKPNDVYSFSLASRLYAEERYPILPEYLQCVKELYRGGLEPINFQ
TAADQARELINSWVESQTNGIIRNVLQPSSVDSQTAMVLVNAIVF
KGLWEKAFKDEDTQAMPFRVTEQESKPVQMMYQIGLFRVASMASE
KMKILELPFASGTMSMLVLLPDEVSGLEQLESIINFEKLTEWTSS
NVMEERKIKVYLPRMKMEEKYNLTSVLMAMGITDVFSSSANLSGI
SSAESLKISQAVHAAHAEINEAGREVVGSAEAGVDAASVSEEFRA
DHPFLFCIKHIATNAVLFFGRCVSP |

TABLE 11-continued

Sequences for exemplary introns, β-Lactoglobulin, ovalbumin, signal peptide, terminators, monomers, and promoters.

| | SEQ ID NO | Sequence |
|---|---|---|
| OOVAL2 | 695 | GGATCAATTGGCGCCGCATCTATGGAGTTCTGCTTCGATGTTTTT AAAGAGCTTAAAGTGCACCATGCCAACGAGAATATCTTCTATTGC CCAATTGCCATTATGTCTGCCCTTGCTATGGTGTACTTGGGTGCT AAAGACTCTACTAGGACCCAGATAAACAAGGTAGTCAGATTCGAC AAGCTGCCTGGGTTTGGCGACTCTATTGAAGCTCAGTGTGGTACT TCTGTTAATGTCCACTCATCCCTCCGCGACATACTTAATCAAATT ACAAAACCAAATGATGTGTACTCATTTAGTCTGGCCAGCCGTTTG TACGCAGAGGAACGCTACCCTATCCTGCCAG AGTATTTGCAATGTGTGAAGGAACTTTACAGGGGTGGGCTTGAGC CAATAAACTTTCAAACAGCAGCCGACCAAGCTAGGGAGCTTATCA ATTCTTGGGTCGAGAGCCAAACTAACGGAATCATCCGCAACGTCC TCCAGCCAAGTTCCGTTGATTCCCAGACCGCTATGGTACTTGTGA ATGCCATTGTCTTCAAGGGGCTTTGGGAGAAGGCATTTAAAGACG AGGACACTCAGGCAATGCCCTTTCGTGTGACCGAGCAGGAGTCAA AACCTGTTCAAATGATGTACCAAATTGGGCTGTTCAGAGTTGCTA GTATGGCCTCTGAGAAAATGAAGATCCTTGAACTCCCATTTGCCT CCGGGACAATGTCTATGCTTGTCCTCCTGCCAGATGAAGTCAGTG GGCTCGAACAGCTCGAAAGCATAATAAACTTTGAGAAACTTACCG AATGGACTTCTTCCAATGTTATGGAGGAGCGTAAAATTAAGGTCT ATCTGCCCCGCATGAAAATGGAGGAAAAGTATAATCTCACTAGCG TCCTCATGGCTATGGGAATTACTGATGTATTCTCCTCTAGCGCTA ATCTGAGTGGAATCTCCAGCGCCGAGTCTCTCAAGATAAGCCAGG CCGTGCACGCTGCTCATGCTGAAATCAACGAAGCCGGCAGAGAGG TGGTGGGGTCAGCTGAGGCAGGTGTAGATGCAGCCAGTGTCTCTG AGGAATTTAGAGCCGATCACCCTTTCCTTTTTTGCATTAAACATA TCGCTACAAATGCCGTTTTGTTTTTCGGTCGTTGCGTTAGTCCA |
| OOVAL2 | 696 | GSIGAASMEFCFDVFKELKVHHANENIFYCPIAIMSALAMVYLGA KDSTRTQINKVVRFDKLPGFGDSIEAQCGTSVNVHSSLRDILNQI TKPNDVYSFSLASRLYAEERYPILPEYLQCVKELYRGGLEPINFQ TAADQARELINSWVESQTNGIIRNVLQPSSVDSQTAMVLVNAIVF KGLWEKAFKDEDTQAMPFRVTEQESKPVQMMYQIGLFRVASMASE KMKILELPFASGTMSMLVLLPDEVSGLEQLESIINFEKLTEWTSS NVMEERKIKVYLPRMKMEEKYNLTSVLMAMGITDVFSSSANLSGI SSAESLKISQAVHAAHAEINEAGREVVGSAEAGVDAASVSEEFRA DHPLFLFCIKHIATNAVLFFGRCVSP |
| OOVAL3 | 697 | GGGTCCATCGGTGCCGCCTCAATGGAATTCTGCTTTGACGTCTTC AAGGAACTTAAGGTACATCATGCCAACGAGAATATTTTTTACTGT CCAATAGCTATCATGAGTGCACTTGCTATGGTGTACCTTGGAGCC AAAGACTCAACCCGTACCCAGATCAACAAGGTGGTCCGCTTTGAC AAACTGCCAGGGTTTGGGGATTCTATTGAGGCCCAATGCGGAACA AGTGTGAACGTCCACTCTAGCTTGCGCGATATACTTAATCAAATA ACTAAACCAATGATGTGTATTCATTCTCTCGCCAGCAGACTG TACGCAGAAGAAAGGTATCCCATTCTCCCCGAGTACCTCCAATGC GTAAAGGAGTTGTACAGAGGCGGCCTGGAACCCATAAATTTCCAA ACTGCCGCAGATCAGGCTCGTGAGCTGATAAATTCATGGGTCGAG AGCCAAACTAACGGTATCATTCGTAATGTCCTTCAACCCTCAAGT GTGGACAGTCAGACAGCCATGGTCCTCGTCAATGCTATAGTCTTC AAAGGCCTGTGGGAAAAGACCTTTAAGGATGAAGATACTCAAGCA ATGCCCTTTAGAGTCACAGAGCAAGAAAGCAAACCCGTGCAAATG ATGTATCAAATCGGGCTCTTTCGTGTTGCATCCATGGCATCTGAA AAGATGAAGAT ATTGGAACTCCCCTTCGCCTCTGGAACAATGAGTATGTTGGTACT TCTGCCCGATGAGGTCTCTGGGTTGGAACAGCTTGAATCTATTAT TAACTTCGAGAAACTGACCGAGTGGACTAGTAGTAATGTCATGGA GGAGAGAAAGATTAAGGTTTATTTGCCACGCATGAAGATGGAAGA GAAATATAACTTGACATCTGTACTGATGGCAATGGGTATAACCGA CGTATTTAGCAGTAGCGCCAATCTGTCAGGGATTTCTTCAGCCGA AAGTCTCAAGATTTCTCAGGCAGTTCACGCAGCCCATGCAGAGAT AAACGAAGCAGGCCGCGAAGTTGTCGGATCTGCAGAAGCCGGCGT GGATGCAGCCAGTGTCTCCGAAGAGTTCAGAGCAGACCACCCTTT CCTCTTCTGCATTAAGCACATCGCAACCAACGCAGTACTTTTTTT CGGACGTTGCGTGTCCCCA |
| OOVAL3 | 698 | GSIGAASMEFCFDVFKELKVHHANENIFYCPIAIMSALAMVYLGA KDSTRTQINKVVRFDKLPGFGDSIEAQCGTSVNVHSSLRDILNQI TKPNDVYSFSLASRLYAEERYPILPEYLQCVKELYRGGLEPINFQ TAADQARELINSWVESQTNGIIRNVLQPSSVDSQTAMVLVNAIVF KGLWEKAFKDEDTQAMPFRVTEQESKPVQMMYQIGLFRVASMASE KMKILELPFASGTMSMLVLLPDEVSGLEQLESIINFEKLTEWTSS NVMEERKIKVYLPRMKMEEKYNLTSVLMAMGITDVFSSSANLSGI |

TABLE 11-continued

Sequences for exemplary introns, β-Lactoglobulin, ovalbumin, signal peptide, terminators, monomers, and promoters.

| | SEQ ID NO | Sequence |
|---|---|---|
| | | SSAESLKISQAVHAAHAEINEAGREVVGSAEAGVDAASVSEEFRA DHPFLFCIKHIATNAVLFFGRCVSP |
| OOVAL4 | 699 | GGTTCAATAGGAGCTGCGTCTATGGAGTTTTGTTTGATGTCTTT AAGGAACTCAAAGTCCACCACGCCAATGAAAATATTTTCTATTGC CCTATTGCAATCATGAGTGCGCTAGCCATGGTTTACTTGGGTGCA AAAGACAGTACGCGTACTCAAATAAACAAGGTTGTTCGTTTGAC AAGCTTCCTGGATTTGGAGATAGTATTGAAGCACAATGTGGAACT AGCGTAAACGTCCACAGCTCATTGAGGGACATTCTTAACCAAATT ACCAAGCCAAATGATGTATATAGTTTTTCCTTGGCATCACGACTG TATGCAGAAGAAAGATATCCTATCCTCCCGGAATATCTTCAGTGC GTGAAAGAATTATACAGAGGTGGGCTAGAGCCAATCAATTTTCAA ACCGCTGCTGATCAAGCTCGCGAGTTGATTAACTCATGGGTTGAG AGCCAGACAAATGGGATAATAAGAAATGTTCTTCAACCATCTAGT GTGGACTCTCAAACAGCAATGGTGCTCGTCAATGCGATAGTTTTT AAAGGCTTGTGGGAGAAAACATTCAAAGATGAGGATACTCAGGCA ATGCCATTCCGTGTAACTGAACAGGAATCTAAGCCTGTTCAAATG ATGTATCAGATTGGTTTGTTCAGAGTTGCCTCTATGGCATCTGAA AAAATGAAAATTTTGGAGCTTCCATTTGCTAGTGGAACAATGTCA ATGTTAGTTTTACTGCCTGATGAAGTGTCCGGTTTAGAACAATTG GAATCAATTATCAACTTTGAAAAGTTGACCGAGTGGACTTCCTCC AATGTGATGGAGGAGAGGAAGATTAAGGTGTACCTTCCCAGAATG AAGATGGAAGAGAAATATAACCTGACTTCGGTCCTAATGGCTATG GGGATCACAGATGTGTTTTCTTCCTCGGCAAACCTTTCAGGCATA TCAAGCGCCGAGTCATTGAAAATTTCACAGGCTGTTCATGCAGCT CATGCTGAAATCAATGAGGCCGGGCGGGAGGTTGTGGGCAGTGCT GAAGCTGGAGTTGATGCTGCCTCAGTGTCTGAGGAATTTAGAGCA GATCATCCTTTCCTCTTCTGCATTAAGCATATTGCTACCAATGCT GTACTGTTCTTCGGTAGGTGTGTTAGCCCC |
| OOVAL4 | 700 | GSIGAASMEFCFDVFKELKVHHANENIFYCPIAIMSALAMVYLGA KDSTRTQINKVVRFDKLPGFGDSIEAQCGTSVNVHSSLRDILNQI TKPNDVYSFSLASRLYAEERYPILPEYLQCVKELYRGGLEPINFQ TAADQARELINSWVESQTNGIIRNVLQPSSVDSQTAMVLVNAIVF KGLWEKTFKDEDTQAMPFRVTEQESKPVQMMYQIGLFRVASMASE KMKILELPFASGTMSMLVLLPDEVSGLEQLESIINFEKLTEWTSS NVMEERKIKVYLPRMKMEEKYNLTSVLMAMGITDVFSSSANLSGI SSAESLKISQAVHAAHAEINEAGREVVGSAEAGVDAASVSEEFRA DHPFLFCIKHIATNAVLFFGRCVSP |
| OOVAL2 (intron 1) | 701 | GGATCAATTGGCGCCGCATCTATGGAGTTCTGCTTCGATGTTTTT AAAGAGCTTAAAGTGCACCATGCCAACGAGAATATCTTCTATTGC CCAATTGCCATTATGTCTGCCCTTGCTATGGTGTACTTGGGTGCT AAAGACTCTACTAGGACCCAGATAAACAAGGTTCGTTATCTACCA CCGTTCTATGGATTTTATTCCTTCTATTCGTGTTTATTCTATTGG TTTATGTTGCTTGCAATATGTTTTTTCTGAATCTGTCGTCGTTGT CTTCAATTTTATCCATGTTTCAGAGATCAATTTTGTTTGTGTAGT ATGTGCTTATTCTTCTTCTTTTCGTTCGAGTTGTTAATAACGGTG CTATGGTGTTTTCAAAAGTGTTTTTTTTATTACTTTTGATTTAAA GTTTTTTTGGTAAGGCTTTTATTTGCTTGTTATATTCAAATCTTT GGATCCAGATCTTATATAAGTTTTTGGTTCAAGAAAGTTTTTGGT TACTGATGAATAGATCTATTAACTGTTACTTTAATCGATTCAAGC TAAAGTTTTTTGGTTACTGATGAATAGATCTATTATCTGTTACTT TTAATCGGTTCAAGCTCAAGTTTTTTGGTTACTGATGAATAGATC TATATACGTCACAGTGTGCTAAACATGCCCTTGTTTTATCTCGAT CTTATGTATGGGAGTGCCATAAATTTTGTTATGTCTATTTTTTTA TCTGTTGGAATCATACTGAGTTTGATGCGTTACGATTGAGCATAC CTATTTTTGGGCTTGTTGTATGGTGGGTATTTAGATCTTAATCTT TTTATGCTTATGAAAGGTTTTGTAATGACAAAGGTCTTAATGTTG TTAAACTTTTATTTTTACTTTATATGGTGTGTTGATGTGTTATGG TTTTGACAACTTTTTTTTTTCTGGATTTTTGCAGGTAGTCAGAT TCGACAAGCTGCCTGGGTTGGCGACTCTATTGAAGCTCAGTGTG GTACTTCTGTTAATGTCCACTCATCCCTCCGCACATACTTAATC AAATTACAAAACCAAATGATGTGTACTCATTTAGTCTGGCCAGCC GTTTGTACGCAGAGGAACGCTACCCTATCCTGCCAGAGTATTTGC AATGTGTGAAGGAACTTTACAGGGGTGGGCTTGAGCCAATAAACT TTCAAACAGCAGCCGACCAAGCTAGGGAGCTTATCAATTCTTGGG TCGAGAGCCAAACTAACGGAATCATCCGCAACGTCCTCCAGCCAA GTTCCGTTGATTCCCAGACCGCTATGGTACTTGTGAATGCCATTG TCTTCAAGGGGCTTTGGGAGAAGGCATTTAAAGACGAGGACACTC AGGCAATGCCCTTTCGTGTGACCGAGCAGGAGTCAAAACCTGTTC AAATGATG |

TABLE 11-continued

Sequences for exemplary introns, β-Lactoglobulin, ovalbumin, signal peptide, terminators, monomers, and promoters.

| | SEQ ID NO | Sequence |
|---|---|---|
| OOVAL2 (intron 2) | 702 | TACCAAATTGGGCTGTTCAGAGTTGCTAGTATGGCCTCTGAGAAA ATGAAGATCCTTGAACTCCCATTTGCCTCCGGGACAATGTCTATG CTTGTCCTCCTGCCAGATGAAGTCAGTGGGCTCGAACAGCTCGAA AGCATAATAAACTTTGAGAAACTTACCGAATGGACTTCTTCCAAT GTTATGGAGGAGCGTAAAATTAAGGTCTATCTGCCCCGCATGAAA ATGGAGGAAAAGTATAATCTCACTAGCGTCCTCATGGCTATGGGA ATTACTGATGTATTCTCCTCTAGCGCTAATCTGAGTGGAATCTCC AGCGCCGAGTCTCTCAAGATAAGCCAGGCCGTGCACGCTGCTCAT GCTGAAATCAACGAAGCCGGCAGAGAGGTGGTGGGGTCAGCTGAG GCAGGTGTAGATGCAGCCAGTGTCTCTGAGGAATTTAGAGCCGAT CACCCTTTCCTTTTTTGCATTAAACATATCGCTACAAATGCCGTT TTGTTTTTCGGTCGTTGCGTTAGTCCAGGATCAATTGGCGCCGCA TCTATGGAGTTCTGCTTCGATGTTTTTAAAGAGCTTAAAGTGCAC CATGCCAACGAGAATATCTTCTATTGCCCAATTGCCATTATGTCT GCCCTTGCTATGGTGTACTTGGGTGCTAAAGACTCTACTAGGACC CAGATAAACAAGGTAACCATATCTTTCATCTGTTATGtgactaca cattgcttctcttttttgtgttctgtctcattaattgCGGTTTGTT ACATGTTGTTTGTAGGTAGTCAGATTCGACAAGCTGCCTGGGTTT GGCGACTCTATTGAAGCTCAGTGTGGTACTTCTGTTAATGTCCAC TCATCCCTCCGCGACATACTTAATCAAATTACAAAACCAAATGAT GTGTACTCATTTAGTCTGGCCAGCCGTTTGTACGCAGAGGAACGC TACCCTATCCTGCCAGAGTATTTGCAATGTGTGAAGGAACTTTAC AGGGGTGGGCTTGAGCCAATAAACTTTCAAACAGCAGCCGACCAA GCTAGGGAGCTTATCAATTCTTGGGTCGAGAGCCAAACTAACGGA ATCATCCGCAACGTCCTCCAGCCAAGTTCCGTTGATTCCCAGACC GCTATGGTACTTGTGAATGCCATTGTCTTCAAGGGGCTTTGGGAG AAGGCATTTAAAGACGAGGACACTCAGGCAATGCCCTTTCGTGTG ACCGAGCAGGAGTCAAAACCTGTTCAAATGATGTACCAAATTGGG CTGTTCAGAGTTGCTAGTATGGCCTCTGAGAAAATGAAGATCCTT GAACTCCCATTTGCCTCCGGGACAATGTCTATGCTTGTCCTCCTG CCAGATGAAGTCAGTGGGCTCGAACAGCTCGAAAGCATAATAAAC TTTGAGAAACTTACCGAATGGACTTCTTCCAATGTTATGGAGGAG CGTAAAATTAAGGTCTATCTGCCCCGCATGAAAATGGAGGAAAAG TATAATCTCACTAGCGTCCTCATGGCTATGGGAATTACTGATGTA TTCTCCTCTAGCGCTAATCTGAGTGGAATCTCCAGCGCCGAGTCT CTCAAGATAAGCCAGGCCGTGCACGCTGCTCATGCTGAAATCAAC GAAGCCGGCAGAGAGGTGGTGGGGTCAGCTGAGGCAGGTGTAGAT GCAGCCAGTGTCTCTGAGGAATTTAGAGCCGATCACCCTTTCCTT TTTTGCATTAAACATATCGCTACAAATGCCGTTTTGTTTTTCGGT CGTTGCGTTAGTCCA |

Promoters

| | | |
|---|---|---|
| GmSeed2 | 703 | AACACAAGCTTCAAGTTTTAAAAGGAAAAATGTCAGCCAAAAACT TTAAATAAAATGGTAACAAGGAAATTATTCAAAAATTACAAACCT CGTCAAAATAGGAAAGAAAAAAAGTTTAGGGATTTAGAAAAAACA TCAATCTAGTTCCACCTTATTTTATAGAGAGAAGAAACTAATATA TAAGAACTAAAAAACAGAAGAATAGAAAAAAAAAGTATTGACAGG AAAGAAAAAGTAGCTGTATGCTTATAAGTACTTTGAGGATTTGAA TTCTCTCTTATAAAACACAAACACAATTTTTAGATTTTATTTAAA TAATCATCAATCCGATTATAATTATTTATATATTTTCTATTTTC AAAGAAGTAAATCATGAGCTTTTCCAACTCAACATCTATTTTTTT TCTCTCAACCTTTTTCACATCTTAAGTAGTCTCACCCTTTATATA TATAACTTATTTCTTACCTTTTACATTATGTAACTTTTATCACCA AAACCAACAACTTTAAAATTTTATTAAATAGACTCCACAAGTAAC TTGACACTCTTACATTCATCGACATTAACTTTTATCTGTTTTATA AATATTATTGTATATAATTTAATCAAAATAACCACAAACTTTCA TAAAAGGTTCTTATTAAGCATGGCATTTAATAAGCAAAAACAACT CAATCACTTTCATATAGGAGGTAGCCTAAGTACGTACTCAAAATG CCAACAAATAAAAAAAAAGTTGCTTTAATAATGCCAAAACAAATT AATAAAACACTTACAACACCGGATTTTTTTAATTAAAATGTGCC ATTTAGGATAAATAGTTAATATTTTTAATAATTATTTAAAAAGCC GTATCTACTAAAATGATTTTTATTTGGTTGAAAATATTAATATGT TTAAATCAACACAATCTATCAAAATTAAACTAAAAAAAAAATAAG TGTACGTGGTTAACATTAGTACAGTAATATAAGAGGAAAATGAGA AATTAAGAAATTGAAAGCGAGTCTAATTTTTAAATTATGAACCTG CATATATAAAAGGAAAGAAAGAATCCAGGAAGAAAAGAAATGAAA CCATGCATGGTCCCCTCGTCATCACGAGTTTCTGCCATTTGCAAT AGAAACACTGAAACACCTTTCTCTTTGTCACTTAATTGAGATGCC GAAGCCACCTCACACCATGAACTTCATGAGGTGTAGCACCCAAGG CTTCCATAGCCATGCATACTGAAGAATGTCTCAAGCTCAGCACCC |

TABLE 11-continued

Sequences for exemplary introns, β-Lactoglobulin, ovalbumin, signal peptide, terminators, monomers, and promoters.

| | SEQ ID NO | Sequence |
|---|---|---|
| | | TACTTCTGTGACGTGTCCCTCATTCACCTTCCTCTCTTCCCTATA<br>AATAACCACGCCTCAGGTTCTCCGCTTCACAACTCAAACATTCTC<br>TCCATTGGTCCTTAAACACTCATCAGTCATCACC |
| GmSeed12 | 704 | CAACTATTATCGCATGATGATGTACGTTAAGTCATCATCATCTTT<br>AACTTTATATATTGTTAAAAGTAGAAAAAATAGGTGATGCATTAT<br>AAAATAATTTTATAACATCATTTAATTATAAATTATTTATAATAA<br>ATATTTGAGTTTTTATAGTAATTACCTAAACAATTATATCAAGAC<br>TAATGCCTGATTAGTTGACATGACGAAATTAAACTCATAAAAGTA<br>AAGATGTTTATGTGGAAAACTCTTATACAATTGAGCGGACTTTTT<br>TCCATGGTAGTTCAGTTTTCTTCTATTCAATTTATTTTTTTGGTT<br>TCCGCTCAGAATAAGAATAATTTGATAAATTCATTTTTAGGCAAT<br>TAAGAATATTTATTTGACTAACTTTTTAATTGAAATAAATTTACA<br>ATAAATACTCAATTTATCTTTCACAATCAAAAGATTGAGATGTTG<br>TAAGATCTCCGATAATATACTTATATCTTTTCATTTATTACGTTT<br>TCAAATTTGAATTTTAATGTGTGTTGTAAGTATAAATTTAAAATA<br>AAAATAAAAACAATTATTATATCAAAATGGCAAAAACATTTAATA<br>CGTATTATTTAAGAAAAAAATATGTAATAATATATTTATATTTTA<br>ATATCTATTCTTATGTATTTTTTAAAAATCTATTATATATTGATC<br>AACTAAAATATTTTTATATCTACACTTATTTTGCATTTTTATCAA<br>TTTTCTTGCGTTTTTTGGCATATTTAATAATGACTATTCTTTAAT<br>AATCAATCATTATTCTTACATGGTACATATTGTTGGAACCATATG<br>AAGTGTCCATTGCATTTGACTATGTGGATAGTGTTTTGATCCAGG<br>CCTCCATTTGCCGCTTATTAATTAATTTGGTAACAGTCCGTACTA<br>ATCAGTTACTTATCCTTCCTCCATCATAATTAATCTTGGTAGTCT<br>CGAATGCCACAACACTGACTAGTCTCTTGGATCATAAGAAAAAGC<br>CAAGGAACAAAAGAAGACAAAACACAATGAGAGTATCCTTTGCAT<br>AGCAATGTCTAAGTTCATAAAATTCAAACAAAAACGCAATCACAC<br>ACAGTGGACATCACTTATCCACTAGCTGATCAGGATCGCCGCGTC<br>AAGAAAAAAAACTGGACCCCAAAAGCCATGCACAACAACACGTA<br>CTCACAAAGGTGTCAATCGAGCAGCCCAAAACATTCACCAACTCA<br>ACCCATCATGAGCCCACACATTTGTTGTTTCTAACCCAACCTCAA<br>ACTCGTATTCTCTTCCGCCACCTCATTTTTGTTTATTTCAACACC<br>CGTCAAACTGCATGCCACCCCGTGGCCAAATGTCCATGCATGTTA<br>ACAAGACCTATGACTATAAATATCTGCAATCTCGGCCCAGGTTTT<br>CATCATCAAGAACCAGTTCAATATCCTAGTACACCGTATTAAAGA<br>ATTTAAGATATACT |
| PvPhas | 705 | CATTGTACTCCCAGTATCATTATAGTGAAAGTTTTGGCTCTCTCG<br>CCGGTGGTTTTTTACCTCTATTTAAAGGGGTTTTCCACCTAAAAA<br>TTCTGGTATCATTCTCACTTTACTTGTTACTTTAATTTCTCATAA<br>TCTTTGGTTGAAATTATCACGCTTCCGCACACGATATCCCTACAA<br>ATTTATTATTTGTTAAACATTTTCAAACCGCATAAAATTTTATGA<br>AGTCCCGTCTATCTTTAATGTAGTCTAACATTTTCATATTGAAAT<br>ATATAATTTACTTAATTTTAGCGTTGGTAGAAAGCATAATGATTT<br>ATTCTTATTCTTCTTCATATAAATGTTTAATATACAATATAAACA<br>AATTCTTTACCTTAAGAAGGATTTCCCATTTTATATTTTAAAAAT<br>ATATTTATCAAATATTTTTCAACCACGTAAATCACATAATAATAA<br>GTTGTTTCAAAAGTAATAAAATTTAACTCCATAATTTTTTTATTT<br>GACTGATCTTAAAGCAACACCCAGTGACACAACTAGCCATTTTTT<br>TCTTTGAATAAAAAAATCCAATTATCATTGTATTTTTTTTATACA<br>ATGAAAATTTCACCAAACAATGATTTGTGGTATTTCTGAAGCAAG<br>TCATGTTATGCAAAATTCTATAATTCCCATTTGACACTACGGAAG<br>TAACTGAAGATCTGCTTTTACATGCGAGACACATCTTCTAAAGTA<br>ATTTTAATAATAGTTACTATATTCAAGATTTCATATATCAAATAC<br>TCAATATTACTTCTAAAAAATTAATTAGATATAATTAAAATATTA<br>CTTTTTTAATTTTAAGTTTAATTGTTGAATTTGTGACTATTGATT<br>TATTATTCTACTATGTTTAAATTGTTTTATAGGTAGTTTAAAGTA<br>AATATAAGTAATGTAGTAGAGTGTTAGAGTGTTACCCTAAACCAT<br>AAACTATAAGATTTATGGTGGACTAATTTTCATATATTTCTTATT<br>GCTTTTACCTTTTCTTGGTATGTAAGTCCGTAACTGGAATTACTG<br>TGGGTTGCCATGACACTCTGTGGTCTT |
| BnNap | 706 | TTGGTTCATGCATGGATGCTTGCGCAAGAAAAAGACAAAGAACAA<br>AGAAAAAAGACAAAACAGAGAGACAAAACGCAATCACACAACCAA<br>CTCAAATTAGTCACTGGCTGATCAAGATCGCCGCGTCCATGTATG<br>TCTAAATGCCATGCAAAGCAACACGTGCTTAACATGCACTTTAAA<br>TGGCTCACCCATCCCAACCCACTCACAAACACATTGCCTTTTTCT<br>TCATCATCACCACAACCACCTGTATATATTCATTCTCTTCCGCCA<br>CCTCAATTTCTTCACTTCAACACACGTCAACCTGCATATGCGTGT<br>CATCCCATGCCCAAATCTCCATGCATGTTCCTACCACCTTCTCTC<br>TTATATAATACCCTATAAATACCTCTAATATCACTCACTTCTTTCA |

TABLE 11-continued

Sequences for exemplary introns, β-Lactoglobulin, ovalbumin, signal peptide, terminators, monomers, and promoters.

| | SEQ ID NO | Sequence |
|---|---|---|
| | | TCATCCATCCATCCAGAGTACTACTACTCTACTACTATAATACCC
CAACCCAACTCATATTCAATACTACTCTACTCATCGGTGATTGAT
TCCTTTAAAGACTTATGTTTCTTATCTTGCTTCTGAGGCAAGTAT
TCAGTTACCAGTTACCACTTATATTCTGGACTTTCTGACTGCATC
CTCATTTTTCCAACATTTTAAATTTCACTATTGGCTGAATGCTTC
TTCTTTGAGGAAGAAACAATTCAGATGGCAGAAATGTATCAACCA
ATGCATATATACAAATGTACCTCTTGTTCTCAAAACATCTATCGG
ATGGTTCCATTTGCTTTGTCATCCAATTAGTGACTACTTTATATT
ATTCACTCCTCTTTATTACTATTTTCATGCGAGGTTGCCATGTAC
ATTATATTTGTAAGGATTGACGCTATTGAGCGTTTTTCTTCAATT
TTCTTTATTTTAGACATGGGTATGAAATGTGTGTTAGAGTTGGGT
TGAATGAGATATACGTTCAAGTGAAGTGGCATACCGTTGTCGAGT
AAGGATGACCTACCCATTCTTGAGACAAATGTTACATTTTAGTAT
CAGAGTAAAATGTGTACCTATAACTCAAATTCGATTGACATGTAT
CCATTCAACATAAAATTAAACCAGCCTGCACCTGCATCCACATTT
CAAGTATTTTCAAACCGTTCGGCTCCTATCCACCGGGTGTAACAA
GACGGATTCCGAATTTGGAAGATTTTGACTCAAATTCCCAATTTA
TATTGACCGTGACTAAATCAACTTTAACTTCTATAATTCTGATTA
AGCTCCCAATTTATATTCCCAACGGCACTACCTCCAAAATTTATA
GACTCTCATCCCCTTTTAAACCAACTTAGTAAACGTTTTTTTTTT
TAATTTTATGAAGTTAAGTTTTTACCTTGTTTTTAAAAAGAATCC
TTCATAAGATGCCATGCCAGAACATTAGCTACACGTTACACATAG
CATGCAGCCGCGGAGAATTGTTTTTCTTCGCCACTTGTCACTCCC
TTCAAACACCTAAGAGCTTCTCTCTCACAGCACACACATACAATC
ACATGCGTGCATGCATTATTACACGTGATCGCCATGCAAATCTCC
TTTATAGCCTATAAATTAACTCATCCGCTTCACTCTTTACTCAAA
CCAAAACTCATCAATACAAACAAGATTAAAAACATA |

Signal peptides

| sig2 | 707 | ATGGCCAAGCTAGTTTTTTCCCTTTGTTTTCTGCTTTTCAGTGGC
TGCTGCTTCGCT |
| sig2 | 708 | MAKLVFSLCFLLFSGCCFA |
| sig10 | 709 | ATGGCTACTTCAAAGTTGAAAACCCAGAATGTGGTTGTATCTCTC
TCCCTAACCTTAACCTTGGTACTGGTGCTACTGACCAGCAAGGCA
AACTCA |
| sig10 | 710 | MATSKLKTQNVVVSLSLTLTLVLVLLTSKANS |
| sig11 | 711 | ATGATGAGAGCACGGTTCCCATTACTGTTGCTGGGACTTGTTTTC
CTGGCTTCAGTTTCTGTCTCA |
| sig11 | 712 | MMRARFPLLLLGLVFLASVSVS |
| sig12 | 713 | ATGATGAGAGCGCGGTTCCCATTACTGTTGCTGGGAGTTGTTTTC
CTGGCATCAGTTTCTGTCTCATTTGGC |
| sig12 | 714 | MMRARFPLLLLGVVFLASVSVSFG |
| coixss | 715 | ATGGCTACCAAGATATTTGCCCTCCTTGTGCTCCTTGCTCTTTCA
GCGAGCGCTACAACTGCG |
| coixss | 716 | MATKIFALLVLLALSASATTA |
| KDEL | 717 | AAGGATGAGCTT |
| KDEL | 616 | KDEL |

Terminators

| nosT | 718 | GATCGTTCAAACATTTGGCAATAAAGTTTCTTAAGATTGAATCCT
GTTGCCGGTCTTGCGATGATTATCATATAATTTCTGTTGAATTAC
GTTAAGCATGTAATAATTAACATGTAATGCATGACGTTATTTATG
AGATGGGTTTTTATGATTAGAGTCCCGCAATTATACATTTAATAC
GCGATAGAAAACAAAATATAGCGCGCAAACTAGGATAAATTATCG
CGCGCGGTGTCATCTATGTTACTAGATC |
| EU T | 719 | AAAGCAGAATGCTGAGCTAAAAGAAAGGCTTTTTCCATTTTCGAG
AGACAATGAGAAAGAAGAAGAAGAAGAAGAAGAAGAAGAAGAAG
AAAAGAGTAAATAATAAAGCCCCACAGGAGGCGAAGTTCTTGTAG |

TABLE 11-continued

Sequences for exemplary introns, β-Lactoglobulin, ovalbumin, signal peptide, terminators, monomers, and promoters.

| | SEQ ID NO | Sequence |
|---|---|---|
| | | CTCCATGTT ATCTAAGTTATTGATATTGTTGCCCTATATTTTATTTCTGTCAT TGTGTATGTTTTGTTCAGTTTCGATCTCCTTGCAAAATGCAGAGA TTATGAGATGAATAAACTAAGTTATATTATTATACGTGTTAATAT TCTCCTCCTCTCTCTAGCTAGCCTTTTGTTTTCTCTTTTTCTTAT TTGATTTTCTTTAAATCAATCCATTTTAGGAGAGGGCCAGGGAGT GATCCAGCAAAACATGAAGATTAGAAGAAACTTCCCTCTTTTTTT TCCTGAAAACAATTTAACGTCGAGATTTATCTCTTTTTGTAATGG AATCATTTCTACAGTTATGAC |
| StUbi3T | 720 | CTGATTTTAATGTTTAGCAAATGTCTTATCAGTTTTCTCTTTTTG TCGAACGGTAATTTAGAGTTTTTTTTGCTATATGGATTTTCGTTT TTGATGTATGTGACAACCCTCGGGATTGTTGATTTATTTCAAAAC TAAGAGTTTTTGTCTTATTGTTCTCGTCTATTTTGGAATATCAAT CTTAGTTTTATATCTTTTCTAGTTCTCTACGTGTTAAATGTTCAA CACACTAGCAATTTGGCCTGCCAGCGTATGGATTATGGAACTATC AAGTGTGTGGGATCGATAAATATGCTTCTCAGGAATTTGAGATTT TACAGTCTTTATGCTCATTGGGTTGAGTATAATATAGTAAAAAAA TAGTAAATTTAAGCAATAATGTTAGGTGCTATGTGTCTGTCGAGA CTATTGGCC |
| AtHSP T | 721 | ATATGAAGATGAAGATGAAATATTTGGTGTGTCAAATAAAAAGCT TGTGTGCTTAAGTTTGTGTTTTTTCTTGGCTTGTTGTGTTATGA ATTTGTGGCTTTTTCTAATATCAAATGAATGTAAGATCTCATTAT AATGAATAAACAAATGTTTCTATAATCCATTGTGAATGTTTTGTT GGATCTCTTCTGCAGCATATAACTACTGTATGTGCTATGGTATGG ACTATGGAATATGATTAAAGATAA |
| AtUbi10T | 722 | ATCTCGTCTCTGTTATGCTTAAGAAGTTCAATGTTTCGTTTCATG TAAAACTTTGGTGGTTTGTGTTTTGGGGCCTTGTATAATCCCTGA TGAATAAGTGTTCTACTATGTTTCCGTTCCTGTTATCTCTTTCTT TCTAATGACAAGTCGAACTTCTTCTTTATCATCGCTTCGTTTTTA TTATCTGTGCTTCTTTTGTTTAATACGCCTGCAAAGTGACTCGAC TCTGTTTAGTGCAGTTCTGCGAAACTTGTAAATAGTCCAATTGTT GGCCTCTAGTAATAGATGTAGCGAAAGTGTTGAGCTGTTGGGTTC TAAGGATGGCTTGAACATGTTAATCTTTTAGGTTCTGAGTATGAT GAACATTCGTTGTTGC |
| Rb7T | 723 | TAAAATGCGTCAATCTCTTTGTTCTTCCATATTCATATGTCAAAA TCTATCAAAATTCTTATATATCTTTTTCGAATTTGAAGTGAAATT TCGATAATTTAAAATTAAATAGAACATATCATTATTTAGGTATCA TATTGATTTTTATACTTAATTACTAAATTTGGTTAACTTTGAAAG TGTACATCAACGAAAAATTAGTCAAACGACTAAAATAAATAAATA TCATGTGTTATTAAGAAAATTCTCCTATAAGAATATTTTAATAGA TCATATGTTTGTAAAAAAAATTAATTTTTACTAACACATATATTT ACTTATCAAAAATTTGACAAAGTAAGATTAAAATAATATTCATCT AACAAAAAAAAACCAGAAAATGCTGAAAACCCGGCAAAACCGAA CCAATCCAAACCGATATAGTTGGTTTGGTTTGATTTTGATATAAA CC |
| TM6T | 724 | GAACCAACTCGGTCCATTTGCACCCCTAATCATAATAGCTTTAAT ATTTCAAGATATTATTAAGTTAACGTTGTCAATATCCTGGAAATT TTGCAAAATGAATCAAGCCTATATGGCTGTAATATGAATTTAAAA GCAGCTCGATGTGGTGGTAATATGTAATTTACTTGATTCTAAAAA AATATCCCAAGTATTAATAATTTCTGCTAGGAAGAAGGTTAGCTA CGATTTACAGCAAAGCCAGAATACAAAGAACCATAAAGTGATTGA AGCTCGAAATATACGAAGGAACAAATATTTTTAAAAAAATACGCA ATGACTTGGAACAAAAGAAAGTGATATATTTTTTGTTCTTAAACA AGCATCCCCTCTAAAGAATGGCAGTTTTCCTTTGCATGTAACTAT TATGCTCCCTTCGTTACAAAAATTTTGGACTACTATTGGGAACTT CTTCTGAAAATAGTGACATCCTAGGTTCAATCAAATTTTACTCGC ATATTGTAGACTTTATCCTTTTGTAATTGTTGCAAATTTCTTATA AAATTGATTATCTATATTTTAATCAAACATATATATACACTTCCA AATAATAAAATATAATGACAACAAAACAATCAAGCACAAAAAATG CCTATAACAAATAAAAATTACAACATACTTTTACCCTGATTCAAA TCTTCAAACACTATGCCAGACACCATAATCCTTCTGGATATAGGA TAAAAATTTAAAGTGATTTTTTACCAATTACTATTTCATAAATTG TTCAAATACAAAATATGATATTTAATTATTCCCAACTTTTTGAG CCTCCTATAACTAATCAATATAAAAAATAATTTATCGATTAAGA CTAAAGCAAAAATATTACCGATTTGAGTTACAATAAAAAGTTTT ATATCACGTTATGGTATTGTGAATTACTCTAACTTCCTAGTTCTT GGGTTCTAGCTTTTCTTGGCTCTCTGAATCTTCAAAACCTATATT |

TABLE 11-continued

Sequences for exemplary introns, β-Lactoglobulin, ovalbumin, signal peptide, terminators, monomers, and promoters.

| | SEQ ID NO | Sequence |
|---|---|---|
| | | TGATAAAGCCATAACATACACTAATGCTCCCATGCAAAGTGCTTC<br>TAAAACTCCTTAACTTGGTCTACGGTAAAATTTCTTCTAAAACAA<br>AAGCGACTATCAACTTCTAATCGTTGAACAAATAATTCATCTCCA<br>ATAAAGGATTTTAACAATAAATATGAAATAAGAAGTCTATTTCTA<br>GTTAAATAACCAACAATATCCCAAACATTTATGAAATCAATATAT<br>GACTGCATTACAATTTGATCCCAAAATGCAAAATAAAATTGCAT<br>CTCTATTATAGAGTAAAAATAATGCATCATCAATTACTAACCGAT<br>TTTACTAACACGAGAATCTAATTCTCTTCCACAAAGTAAAACTCA<br>ATGTCACCGTCAATTATTTAAGAATTTGAATTATATTCCAACAAC<br>TGAGTAAGAAACTATATAATTGTGGGGGAGGGGGGGCCAACCCT<br>AAAAGTTTACTTCTCATAAAAGGCTATTAGAAAGGAAAGGATACA<br>TAAAAAGAAGAGCAAAGAGAGATCGGAGAAGAGAGAAAAGTATA<br>TGAATTTATTAGAAGTACTTTTACTTATTAGAGGTAAGAGAGTTC<br>TAGACTGATTTGGATACCATATTAGAGTTATTACCGATATAAAAA<br>TCCTTGGTTATGTTAATTAAATTTCTAAATATTA |
| arcT | 725 | AATAAATAAAATGGGAGCAATAAATAAAATGGGAGCTCATATATT<br>TACACCATTTACACTGTCTATTATTCACCATGCCAATTATTACTT<br>CATAATTTTAAAATTATGTCATTTTTAAAAATTGCTTAATGATGG<br>AAAGGATTATTATAAGTTAAAAGTATAACATAGATAAACTAACCA<br>CAAAACAAATCAATATAAACTAACTTACTCTCCCATCTAATTTTT<br>ATTTAAATTTCTTTACACTTCTCTTCC<br>ATTTCTATTTCTACAACATTATTTAACATTTTTATTGTATTTTTC<br>TTACTTTCTAACTCTATTCATTTCAAAAATCAATATATGTTTATC<br>ACCACCTCTCTAAAAAAAACTTTACAATCATTGGTCCAGAAAGT<br>TAAATCACGAGATGGTCATTTTAGCATTAAAACAACGATTCTTGT<br>ATCACTATTTTCAGCATGTAGTCCATTCTCTTCAAACAAAGACA<br>GCGGCTATATAATCGTTGTGTTATATTCAGTCTAAAACAATTGTT<br>ATGGTAAAAGTCGTCATTTTACGCCTTTTTAAAAGATATAAAATG<br>ACAGTTATGTTAAAAGTCATCATGTTAGATCCTCCTTAAAGATA<br>TAAAATGACAGTTTTGGATAAAAAGTGGTCATTTTATACGCTCTT<br>GAAAGATATAAAACGACGGTTATGGTAAAAGCTGCCATTTTAAAT<br>GAAATATTTTTGTTTTAGTTCATTTTGTTTAATGCTAATCCCATT<br>TAAATTGACTTGTACAATTAAAACTCACCCACCCAGATACAATAT<br>AAACTAACTTACTCTCACAGCTAAGTTTTATTTAAATTTCTTTAC<br>ACTTCTTTTCCATTTCTATTTCTATGACATTAACTAACATTTTTC<br>TCGTAATTTTTTTTCTTATTTTCTAACTCTATCCATTTCAAATCG<br>ATATATGTTTATCACCACCACTTTAAAAAGAAAATTTACAATTTC<br>TCGTGCAAAAAAGCTAAATCATGACCGTCATTTTAGCATTAAAAC<br>AACGATTCTTGTATCGTTGTTTTTCAGCATGTAGTCCATTCTTTT<br>CAAGCAAAGACAACAGCTATATAATCATCGTGTTATATTCAGTCT<br>AAAACAACAGTAATGATAAAAGTCATCATTTTAGGCCTTTCTGAA<br>ATATATAGAACGACATTCATGGTAAAAAATCGTCATTTTAGATCC |

5'UTRs

| | | |
|---|---|---|
| soybean glutamine synthase | 726 | GAATTCTCTAAAAGAGATCTTTTTCTGCTCTTTGAAGAAAGAAGG<br>GTCTTTGCTTGATTTTGGAG |
| OVAL | 727 | ACATACAGCTAGAAAGCTGTATTGCCTTTAGCACTCAAGCTCAAA<br>AGACAACTCAGAGTTCACC |
| LG | 728 | CCCGAGCCCGCTGTCTCAGCCCTCCACTCCCTGCAGAGCTCAGAA<br>GCGTGACCCCAGCTGCAGCC |
| arcUTR | 729 | TGAATGCATGATC |

Monomer

| | | |
|---|---|---|
| Ubimonomer | 730 | ATGCAGATTTTCGTGAAGACCTTAACGGGGAAGACGATCACCCTA<br>GAGGTTGAGTCTTCCGACACCATCGACAATGTCAAAGCCAAGATC<br>CAGGACAAGGAAGGGATACCCCCAGACCAGCAGCGTTTGATTTC<br>GCCGGAAAGCAGCTTGAGGATGGTCGTACTCTTGCCGACTACAAC<br>ATCCAGAAGGAGTCAACTCTCCATCTCGTGCTCCGTCTCCGTGGT<br>GGTGGTTCC |
| Ubimonomer | 731 | MQIFVKTLTGKTITLEVESSDTIDNVKAKIQDKEGIPPDQQRLIF<br>AGKQLEDGRTLADYNIQKESTLHLVLRLRGGGS |

Selection and reporter gene cassette components: Promoter

| | | |
|---|---|---|
| CaMV35S | 785 | TCAGCGTGTCCTCTCCAAATGAAATGAACTTCCTTATATAGAGGA<br>AGGTCTTGCGAAGGATAGTGGGATTGTGCGTCATCCCTTACGTCA |

TABLE 11-continued

Sequences for exemplary introns, β-Lactoglobulin, ovalbumin, signal peptide, terminators, monomers, and promoters.

| | SEQ ID NO | Sequence |
|---|---|---|
| | | GTGGAGATATCACATCAATCCACTTGCTTTGAAGACGTGGTTGGA<br>ACGTCTTCTTTTTCCACGATGCTCCTCGTGGGTGGGGGTCCATCT<br>TTGGGACCACTGTCGGCAGAGGCATCTTGAACGATAGCCTTTCCT<br>TTATCGCAATGATGGCATTTGTAGGTGCCACCTTCCTTTTCTACT<br>GTCCTTTTGATGAAGTGACAGATAGCTGGGCAATGGAATCCGAGG<br>AGGTTTCCCGATATTACCCTTTGTTGAAAAGTCTCAATAGCCCTT<br>TGGTCTTCTGAGACTGTATCTTTGATATTCTTGGAGTAGACGAGA<br>GTGTCGTGCTCCACCATGTTATCACATCAATCCACTTGCTTTGAA<br>GACGTGGTTGGAACGTCTTCTTTTTCCACGATGCTCCTCGTGGGT<br>GGGGGTCCATCTTTGGGACCACTGTCGGCAGAGGCATCTTGAACG<br>ATAGCCTTTCCTTTATCGCAATGATGGCATTTGTAGGTGCCACCT<br>TCCTTTTCTACTGTCCTTTTGATGAAGTGACAGATAGCTGGGCAA<br>TGGAATCCGAGGAGGTTTCCCGATATTACCCTTTGTTGAAAAGTC<br>TCA |
| GmU3 | 786 | GGGCCCAATATAACAACGACGTCGTAACAGATAAAGCGAAGCTTG<br>AAGGTGCATGTGACTCCGTCAAGATTACGAAACCGCCAACTACCA<br>CGCAAATTGCAATTCTCAATTTCCTAGAAGGACTCTCCGAAAATG<br>CATCCAATACCAAATATTACCCGTGTCATAGGCACCAAGTGACAC<br>CATACATGAACACGCGTCACAATATGACTGGAGAAGGGTTCCACA<br>CCTTATGCTATAAAACGCCCCACACCCCTCCTCCTTCCTTCGCAG<br>TTCAATTCCAATATATTCCATTCTCTCTGTGTATTTCCCTACCTC<br>TCCCTTCAAGGTTAGTCGATTTCTTCTGTTTTTCTTCTTCGTTCT<br>TTCCATGAATTGTGTATGTTCTTTGATCAATACGATGTTGATTTG<br>ATTGTGTTTTGTTTGGTTTCATCGATCTTCAATTTTCATAATCAG<br>ATTCAGCTTTTATTATCTTTACAACAACGTCCTTAATTTGATGAT<br>TCTTTAATCGTAGATTTGCTCTAATTAGAGCTTTTTCATGTCAGA<br>TCCCTTTACAACAAGCCTTAATTGTTGATTCATTAATCGTAGATT<br>AGGGCTTTTTTCATTGATTACTTCAGATCCGTTAAACGTAACCAT<br>AGATCAGGGCTTTTTCATGAATTACTTCAGATCCGTTAAACAACA<br>GCCTTATTTTTATACTTCTGTGGTTTTTCAAGAAATTGTTCAGA<br>TCCGTTGACAAAAAGCCTTATTCGTTGATTCTATA<br>TCGTTTTTCGAGAGATATTGCTCAGATCTGTTAGCAACTGCCTTG<br>TTTGTTGATTCTATTGCCGTGGATTAGGGTTTTTTTTCACGAGAT<br>TGCTTCAGATCCGTACTTAAGATTACGTAATGGATTTTGATTCTG<br>ATTTATCTGTGATTGTTGACTCGACAG |
| StUbi3 | 787 | GGCCAAAGCACATAGTTATCGATTTAAATTTCATCGAAGAGATTA<br>ATATCGAATAATCATATACATACTTTAAATACATAACAAATTTTA<br>AATACATATATCTGGTATATAATTAATTTTTTAAAGTCATGAAGT<br>ATGTATCAAATACAAATATGGAAAAAATTAACTATTCATAATTTA<br>AAAAATAGAAAAGATACATCTAGTGAAATTAGGTGCATGTATCAA<br>ATACATTAGGAAAAGGGCATATATCTTGATCTAGATAATTAACGA<br>TTTTGATTTATGTATAATTTCCAAATGAAGGTTTATATCTACTTC<br>AGAAATAACAATATACTTTTATCAGAACATTCAACAAAGCAACAA<br>CCAACTAGAGTGAAAAATACACATTGTTCTCTAGACATACAAAAT<br>TGAGAAAAGAATCTCAAAATTTAGAGAAACAAATCTGAATTTCTA<br>GAAGAAAAAAATAATTATGCACTTTGCTATTGCTCGAAAAATAAA<br>TGAAAGAAATTAGACTTTTTTAAAAGATGTTAGACTAGATATACT<br>CAAAAGCTATTAAAGGAGTAATATTCTTCTTACATTAAGTATTTT<br>AGTTACAGTCCTGTAATTAAAGACACATTTTAGATTGTATCTAAA<br>CTTAAATGTATCTAGAATACATATATTTGATTGCATCATATCCAT<br>GTATCCGACACACCAATTCTCATAAAAAACGTAATATCCTAAACT<br>AATTTATCCTTCAAGTCAACCTAAGCCCAATATACATTTTCATCT<br>CTAAAGGCCCAAGTGGCACAAAATGTCAGGCCCAATTACGAAGAA<br>AAGGGCTTGTAAAACCCTAATAAAGTGGCACTGGCAGAGCTTACA<br>CTCTCATTCCATCAACAAAGAAACCCTAAAAGCCGCAGCGCCACT<br>GATTTCTCTCCTCCAGGCGAAG |

Data was bundled as shown in FIG. 1.

In the case of LG, a similar effect was seen in which RNA expression was lower (highest 0.14× glycinin) than expected under different promoters (FIG. 3A), however, unlike OVAL, protein accumulation was significant. GmSeed12: coixx (AR07-31), GmSeed12:sig12 (AR07-32), and PvPhas (AR07-33) showed the best results, producing the highest number of seeds with >100 TSP. Some seeds expressing transgene under control of the promoter GmSeed12: coixx (AR07-31) contained up to 2.53% TSP LG (FIG. 3, Table 12).

TABLE 12

Summary of RNA and protein quantification for exemplary LG designs

| Construct ID | Details | Highest RNA level | Max % TSP | # of all plants analyzed for ELISA | # of all seeds analyzed for ELISA | # of seeds below detection level | # of seeds with 0.063-1% TSP | # of seeds with over 1% TSP |
|---|---|---|---|---|---|---|---|---|
| AR07-28 | BnNap:sig11:OLG1:KDEL:nos | 0.03 | 0.00 | 1 | 8 | 8 | 0 | 0 |
| AR07-29 | GmSeed2:sig2:OLG1:KDEL:nos | 0.08 | 1.23 | 18 | 142 | 49 | 90 | 3 |
| AR07-31 | GmSeed12:coixss:OLG1:KDEL:nos | 0.12 | 2.53 | 15 | 128 | 32 | 88 | 8 |
| AR07-32 | GmSeed12:sig12:OLG1:KDEL:nos | 0.14 | 2.05 | 17 | 129 | 53 | 68 | 8 |
| AR07-33 | PvPhas:arcUTR:sig10:OLG1:KDEL:arc T | 0.07 | 2.38 | 17 | 136 | 47 | 79 | 10 |
| AR15-25 | GmSeed2:sig2:OLG2:KDEL:EUT:Rb7T | 0.78 | 4.18 | 8 | 64 | 15 | 25 | 24 |
| AR15-26 | GmSeed2:sig2:OLG3:KDEL:EUT:Rb7T | 0.60 | 1.79 | 10 | 76 | 10 | 53 | 13 |
| AR15-27 | GmSeed2:sig2:OLG4:KDEL:EUT:Rb7T | 0.14 | 1.05 | 2 | 13 | 1 | 11 | 1 |
| AR15-28 | GmSeed2:sig2:OLG2:EUT:Rb7T | All GOI silenced* | 2.66 | 8 | 45 | 20 | 23 | 2 |
| AR15-29 | GmSeed2 (intron 1):sig2:OLG2:KDEL:EUT:Rb7T | 0.11 | 1.21 | 10 | 61 | 27 | 33 | 1 |
| AR15-30 | GmSeed2:sig2:OLG2 (intron 1):KDEL:EUT:Rb7T | 0.55 | 3.58 | 9 | 59 | 16 | 25 | 18 |
| AR15-31 | GmSeed2:sig2:OLG2 (intron 2):KDEL:EUT:Rb7T | 0.80 | 6.33 | 9 | 69 | 17 | 17 | 35 |
| AR15-36 | GmSeed2:1gUTR:sig2:OLG2:KDEL:EUT:Rb7T | 0.32 | 1.82 | 9 | 72 | 41 | 26 | 5 |
| AR15-37 | GmSeed2:glnB1UTR:sig2:OLG2:KDEL:EUT:Rb7T | 0.55 | 2.81 | 9 | 72 | 20 | 28 | 24 |
| AR15-39 | GmSeed2:Ubimonomer:sig2:OLG2:KDEL:EUT:Rb7T | 0.52 | 0.92 | 9 | 76 | 22 | 54 | 0 |

*Three plants were analyzed for RNA levels for constructs AR15-28. No detectable transgene expression was observed.

Example 3: Use of Codon Optimization to Enhance Stability of RNA and Increase Protein Levels Codon usage bias can influence protein levels when recombinant proteins are expressed in host cells which do not natively express the protein. Initially, OVAL and LG were codon optimized (OOVAL1 and OLG1, respectively) using soybean's codon usage bias. When the different promoters were tested, the sequences were further optimized by analyzing the structure of the codon-optimized RNAs in silico, using the RNAfold program (rna.tbi.univie.ac.at//cgi-bin/RNAWebSuite/RNAfold.cgi?PAGE=3&ID=zsy5friDrE\). Different parameters were analyzed, including minimum free energy structures (MFE), base pair probabilities and energy mountain plot. In addition, the location of 5' and start codon within MFE structure were determined, and RNA structure analysis was focused within that region. By analyzing these different thermodynamic parameters, RNA stem loops were identified which could lead to a stable RNA structure. Specifically, the optimal length of the stem loop was about 4-8 bp, containing a tetraloop UUCG (SEQ ID NO: 615). Codon optimized sequences predicted to present pseudo-knots, such as large loops with no secondary structure of their own and loops of less than 4 and more than 8 bp, were predicted to be unstable. Based on several iterations of this analysis, it was predicted that version 2-4 of OVAL and LG would have the desired structural characteristics that are known to stabilize RNA. Accordingly, these codon optimized versions were chosen for soybean transformation.

In the case of OVAL, RNA expression was slightly improved in the codon optimized versions of OOVAL2 (0.11× glycinin) and OOVAL3 (0.08× glycinin). Additionally, the use of the double terminator EUT:Rb7T when compared to the control that is driven by the same promoter (AR07-23) that had an expression of 0.03× glycinin (FIG. 2A and Table 10). Surprisingly, the slight improvement in RNA expression led to a significant increase in protein accumulation with OOVAL2 and OOVAL3 producing seeds that contained up to 2.74 and 1.43% TSP (FIG. 2B and Table 10). There was limited RNA expression improvement in the plants expressing OOVAL4 and their protein analysis was not pursued.

In the case of LG, there was a significant improvement with the codon optimized versions of OLG2 (0.78× glycinin) and the use of the double terminator EUT:Rb7T when compared to the control that is driven by the same promoter (AR07-29), which had an expression level of 0.08× glycinin (FIG. 3A and Table 12). The increase in RNA expression translated into an increase in protein accumulation, with some seeds producing up to 4.18 and 1.79% TSP for OLG2 and OLG3, respectively.

Example 4: Addition or Removal of KDEL to Enhance Stability of RNA and Increase Protein Levels Proteins can be targeted to specific cellular compartments such as the endoplasmic reticulum (ER), vacuole, cytoplasm, protein storage vacuole (PSV) and apoplast, using specific peptide tags. The localization of recombinant proteins to different organelles offers a valuable strategy for recombinant protein production since a wide range of proteases are found in each of these organelles. Unlike the other organelles, the ER is a protective environment due to the low abundance of proteases. Accordingly, the ER is an optimal location to target recombinant proteins due to the abundance of chaperones that help in the folding thereof. Recombinant proteins can be targeted to the ER by the addition of the ER peptide tag KDEL (Lys-Asp-Glu-Leu (SEQ ID NO: 616) or AAGGAUGAGCUU (SEQ ID NO: 629) for RNA) at the N-terminus. Surprisingly, while analyzing the RNA expression levels, it was observed that the addition of AAGGAUGAGCUU (SEQ ID NO: 629) enhances the RNA stability, independent of its effects on protein targeting See Table 13, positive or negative.

TABLE 13

RNA expression levels with or without KDEL. Line averages of plant max RNA expression (out of 4 seeds per plant), excluding plants with no detectable transgene RNA.

| Transgene | KDEL status | RNA levels |
|---|---|---|
| OVAL | +KDEL | 0.044 |
|  | −KDEL | 0.120 |
| LG | +KDEL | 0.765 |
|  | −KDEL | <0.001 | significant improvement was obtained at the protein level. Interestingly, intron 1 and 2 had different effects on OVAL and LG. In the case of OVAL, intron 1 (AR15-21) had a greater effect leading to 64% of the seeds expressing at >1% TSP (control 8.7% of the seeds had >1% TSP (AR15-16)). Also, there was a significant increase in the Max % TSP from 2.74 (AR15-16) to 6.64% TSP (AR15-21). In the case of LG, intron 2 (AR15-31) had a pronounced effect, leading to 50% of the seeds expressing at >1% TSP (control 37% of the seeds had >1% TSP (AR15-25). Also, there was a noteworthy increase in the Max % TSP from 4.18 (AR15-25) to 6.33% TSP (AR15-31) in the designs that contained intron 2.

TABLE 14

Exemplary introns utilized

| Intron name | Intron/intron fragments | Glyma. Genebank | Length (bp) | IMEter score V2.1 | Percentile | Reference |
|---|---|---|---|---|---|---|
| Intron 1 | Intron 1 from Elongation factor 1A (Glycine max) | X56856.1 | 770 | 16.03 | 98 | DOI:10.1371/journal.pone.0166074 |
| Intron 2 | Intron 1 from Elongation factor 1A (Arabidopsis thaliana) | X16430.1 | 99 | 2.04 | 49 | — |

Figure 4:
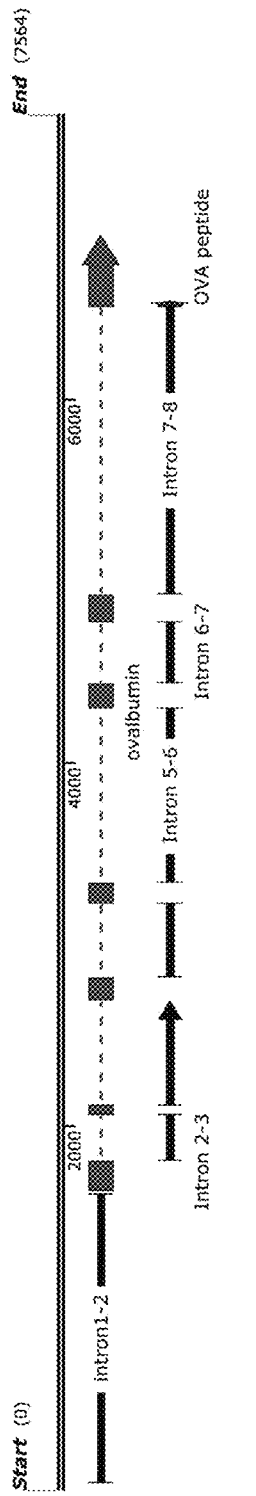
FIG. 4 is a graphic of modified *Gallus gallus* ovalbumin gene that was used in various constructs described herein. Plant intron 1 or 2 was placed in the location of native intron 2-3.
Figure 5:
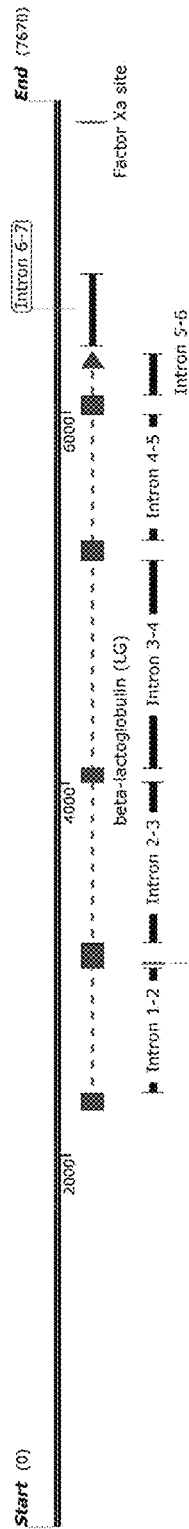
FIG. 5 is a graphic of modified *Bos taurus* β-Lactoglobulin gene that was used in various constructs described herein. Plant intron 1 or 2 was placed in the location of native intron 1-2.

Example 5: Use of Introns to Enhance Stability of RNA and Increase Protein Levels In this study, the effects of two introns were examined: Intron 1 and 2 from the Elongation Factor 1A (eF1A) gene from *Glycine max* or *Arabidopsis thaliana*, respectively (Table 14). Additionally, their effect on gene expression was analyzed by placing them in different locations within the DNA construct—either in the 5'UTR or within the coding sequence. For the designs with the intron at the 5' UTR, intron 1 was used and it was placed in between the GmSeed2 promoter and the start of either OVAL or LG (AR15-20 and AR15-29, respectively). In the designs wherein the intron was located within the coding region, OVAL's native intron 2-3 (FIG. 4) or LG's native intron 1-2 was replaced with either intron 1 or 2 (FIG. 5) (OVAL: AR15-21 and AR15-22 and LG: AR15-30 and AR15-31). The data provided herein shows that the use of intron 1 at the 5'UTR had a negative effect on both RNA and protein levels, for both OVAL and LG. When compared to the DNA construct designs lacking the intron (AR15-16 and AR15-25, OVAL and LG, respectively), the RNA expression dropped from 0.11 to 0.03× glycinin for OVAL and from 0.78 to 0.11× glycinin for LG, leading to low protein expression for LG (OVAL plants were not analyzed due to low RNA expression).

Figure 6:
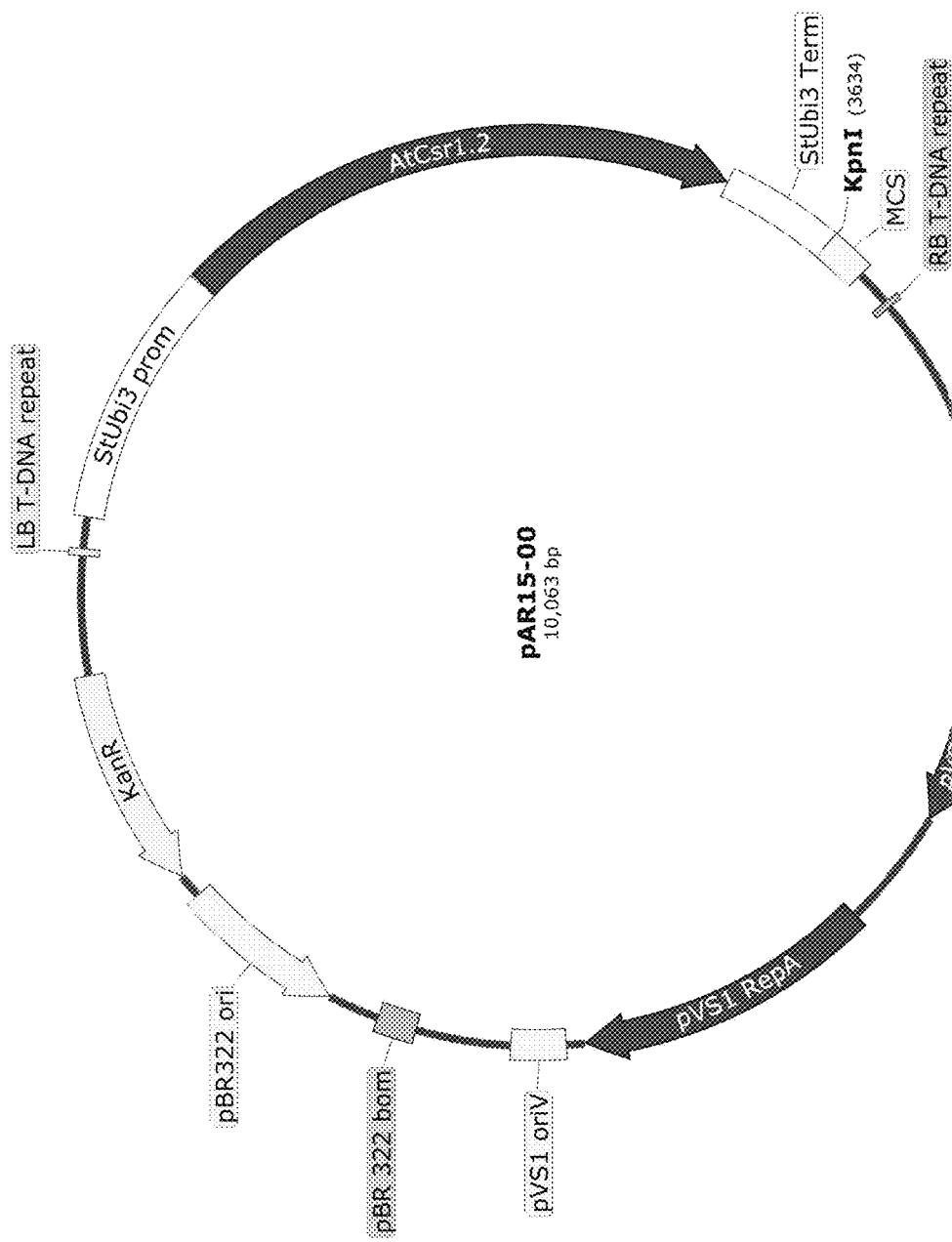
FIG. 6 is a graphic of the pAR15-00 cloning vector containing a selectable marker cassette conferring herbicide resistance. The pAR15-00 cloning vector is a modified binary pCAMBIA3300 vector containing the mutant acetolactate synthase gene (AtCsr1.2) of *Arabidopsis thaliana* driven by the StUbi3 promoter, which is followed by the StUbi3 terminator. A multiple cloning site (MCS) was included downstream of the selectable marker cassette. Within the MCS, a KpnI restriction enzyme site was available to insert the expression cassette into the pAR15-00 vector.

When the intron was placed within the coding sequence, a moderate change was observed at the RNA level, but a Example 6: Materials and Methods Utilized in the Present Examples Binary Vector Design The binary pCAMBIA3300 (Creative Biogene, VET1372) vector provides features such as high copy number in *E. coli* for high DNA yields, the pVS1 replicon for stable expression in *Agrobacterium*, a multiple cloning site to allow plasmid modifications and a kanamycin bacterial selection that permits the vector to move DNA from bacteria to the desired plant host. Therefore, this vector was customized to include a selectable marker suitable for soybean transformation and selection. In order to modify the vector, pCAMBIA3300 was digested with HindIII and AseI allowing the release of the vector backbone (LB T-DNA repeat_KanR_pBR322 ori_pBR322 bom_pVS1 oriV_pVs1 repA_pVS1 StaA_RB T-DNA repeat). The 6598 bp vector backbone was gel extracted and a synthesized multiple cloning site (MCS) was ligated via In-Fusion cloning (In-Fusion® HD Cloning System CE) to allow modular vector modifications and to create the vector backbone. A cassette containing the *Arabidopsis thaliana* Csr1.2 gene for acetolactate synthase was added to the vector backbone to be used as a marker for herbicide selection of transgenic plants. In order to build this cassette, the regulatory sequences from *Solanum tuberosum* ubiquitin/ribosomal fusion protein promoter (StUbi3 prom; −1 to −922 bp) and terminator (StUbi3 term; 414 bp) (accession no. L22576.1) were fused to the mutant (S653N) acetolactate synthase gene (Csr1.2; accession no. X51514.1) (Sathasivan et al 1990, Ding et al 2006) to generate imazapyr-resistant traits in soybean plants. The selectable marker cassette was introduced into the digested (EcoRI) modified vector backbone via In-Fusion cloning to form vector pAR15-00 (FIG. 6).

Vector pAR07-00 was assembled to include two cassettes, comprising an antibiotic selection and a reporter gene cassette. The antibiotic selection cassette contained the *E. coli* aadA gene for aminoglycoside adenylyltransferase (aadA; accession no. AB188259), which confers resistance to spectinomycin for the selection of transgenic plants. The regulatory elements in this cassette included the 35S promoter (enhanced) (35 s prom; 678 bp) from Cauliflower mosaic virus to promote expression of aadA gene, the 5-enolpyruvylshikimate-3-phosphate synthase (EPSPS) signal peptide (EPSPSss; 216 bp) (accession no. KJ787649.1) from *Petunia hybrida* for localization of aadA into the chloroplast, and the 35S poly(A) signal (35 s Term; 191 bp) from Cauliflower mosaic virus for aadA transcription stabilization. On the other hand, the selection marker cassette carried the mCherry fluorescent reporter gene from *Discosoma* sp. for rapid phenotypic selection of transgenic plants. The regulatory components for this cassette included the *Glycine max* Ubiquitin promoter (GmU3 prom; 917 bp) (accession no. EU310508) to promote the expression of mCherry, and the ribulose-1,5-bisphospate carboxylase small subunit termination sequence from *Pisum sativum* (RbcS-E9; 297 bp) (accession no. X00806.1) for mCherry transcription stabilization. Both cassettes were introduced into the digested vector backbone via In-Fusion cloning to form vector pAR07-00.

Vector pAR15-00 was constructed containing the *Arabidopsis thaliana* Csr1.2 gene for acetolactate synthase to be used as a marker for herbicide selection of transgenic plants. In order to build this cassette, the regulatory sequences from *Solanum tuberosum* ubiquitin/ribosomal fusion protein promoter (StUbi3 prom; −1 to −922 bp) and terminator (StUbi3 term; 414 bp) (accession no. L22576.1) were fused to the mutant (S653N) acetolactate synthase gene (Csr1.2; accession no. X51514.1) (Sathasivan et al 1990, Ding et al 2006) to generate imazapyr-resistant traits in soybean plants. The selectable marker cassette was introduced into the digested (EcoRI) modified vector backbone via In-Fusion cloning to form vector pAR15-00.

DNA Constructs

The components of each construct, see Table 15, were PCR amplified from either genomic DNA or synthesized fragments and assembled into a digested (KpnI) AR15-00 cloning vector using In-Fusion ligation (In-Fusion® HD Cloning System CE). Binary vectors were then transformed into *Agrobacterium* strain AGL1. Single colonies were verified for the presence of the vector via PCR using gene specific primers.

TABLE 15

Exemplary DNA constructs encoding ovalbumin or B-Lactoglobulin. Transcriptional Regulation (TR), Protein Stability (PS),

| Construct ID | SEQ ID NO | Details | Protein | Category |
| --- | --- | --- | --- | --- |
| AR07-22 | 752 | bnNap:sig11:OOVAL1:KDEL:nos | Ovalbumin | TR/Promoter |
| AR07-23 | 753 | gmSeed2:sig2:OOVAL1:KDEL:nos | Ovalbumin | TR/Promoter |
| AR07-25 | 754 | gmSeed12:coixss:OOVAL1:KDEL:nos | Ovalbumin | TR/Promoter |
| AR07-26 | 755 | gmSeed12:sig12:OOVAL1:KDEL:nos | Ovalbumin | TR/Promoter |
| AR07-27 | 756 | pvPhas:arcUTR:sig10:OOVAL1:KDEL:arcT | Ovalbumin | TR/Promoter |
| AR15-16 | 757 | GmSeed2:sig2:OOVAL2:KDEL:EUT:Rb7T | Ovalbumin | TR/Codon Optimized |
| AR15-17 | 758 | GmSeed2:sig2:OOVAL3:KDEL:EUT:Rb7T | Ovalbumin | TR/Codon Optimized |
| AR15-18 | 759 | GmSeed2:sig2:OOVAL4:KDEL:EUT:Rb7T | Ovalbumin | TR/Codon Optimized |
| AR15-19 | 760 | GmSeed2:sig2:OOVAL2:EUT: Rb7T | Ovalbumin | PS/No KDEL |
| AR15-20 | 761 | GmSeed2 (intron 1):sig2:OOVAL2:KDEL:EUT:Rb7T | Ovalbumin | TR/Intron |
| AR15-21 | 762 | GmSeed2:sig2:OOVAL2 (intron 1):KDEL:EUT:Rb7T | Ovalbumin | TR/Intron |
| AR15-22 | 763 | GmSeed2:sig2:OOVAL2 (intron 2):KDEL:EUT:Rb7T | Ovalbumin | TR/Intron |
| AR15-23 | 764 | GmSeed2:ovalUTR:sig2:OOVAL2:KDEL:EUT:Rb7T | Ovalbumin | TR/5'UTR |
| AR15-24 | 765 | GmSeed2:glnB1UTR:sig2:OOVAL2:KDEL:EUT:Rb7T | Ovalbumin | TR/5'UTR |
| AR15-38 | 766 | GmSeed2: Ubimonomer:sig2:OOVAL2:KDEL:EUT:Rb7T | Ovalbumin | TR/Monomer |
| AR07-28 | 767 | bnNap:sig11:OLG1:KDEL:nos | Betalactogobulin | TR/Promoter |
| AR07-29 | 768 | gm Seed2:sig2:OLG1:KDEL:nos | Betalactogobulin | TR/Promoter |
| AR07-31 | 769 | gm Seed12:coixss:OLG1:KDEL:nos | Betalactogobulin | TR/Promoter |
| AR07-32 | 770 | gmSeed12:sig12:OLG1:KDEL:nos | Betalactogobulin | TR/Promoter |
| AR07-33 | 771 | pvPhas:arcUTR:sig10:OLG1:KDEL:arcT | Betalactogobulin | TR/Promoter |
| AR15-25 | 772 | GmSeed2:sig2:OLG2:KDEL:EUT: Rb7T | Betalactogobulin | TR/Codon Optimized |
| AR15-26 | 773 | GmSeed2:sig2:OLG3:KDEL:EUT: Rb7T | Betalactogobulin | TR/Codon Optimized |
| AR15-27 | 774 | GmSeed2:sig2:OLG4:KDEL:EUT: Rb7T | Betalactogobulin | TR/Codon Optimized |
| AR15-28 | 775 | GmSeed2:sig2:OLG2:EUT:Rb7T | Betalactogobulin | PS/No KDEL |
| AR15-29 | 776 | GmSeed2 (intron 1):sig2:OLG2:KDEL:EUT:Rb7T | Betalactogobulin | TR/Intron |
| AR15-30 | 777 | GmSeed2:sig2:OLG2 (intron 1):KDEL:EUT:Rb7T | Betalactogobulin | TR/Intron |
| AR15-31 | 778 | GmSeed2:sig2:OLG2 (intron 2):KDEL:EUT:Rb7T | Betalactogobulin | TR/Intron |
| AR15-36 | 779 | GmSeed2:1gUTR:sig2:OLG2:KDEL:EUT:Rb7T | Betalactogobulin | TR/5'UTR |
| AR15-37 | 780 | GmSeed2:glnB1UTR:sig2:OLG2:KDEL:EUT:Rb7T | Betalactogobulin | TR/5'UTR |
| AR15-39 | 781 | GmSeed2: Ubimonomer:sig2:OLG2:KDEL:EUT:Rb7 | Betalactogobulin | TR/Monomer |
| AR15-00 | 782 | — | — | Plasmid |
| — | 783 | StUbi3:AtCsr1.2:StUbi3T | Acetolactate synthase | Selection marker in AR15-00 |

TABLE 15-continued

Exemplary DNA constructs encoding ovalbumin or B-Lactoglobulin. Transcriptional Regulation (TR), Protein Stability (PS),

| Construct ID | SEQ ID NO | Details | Protein | Category |
|---|---|---|---|---|
| AR07-00 | 784 | — | — | Plasmid |
| — | 788 | CaMV35S:ESPSss:aadA:35ST | Aminoglycoside adenylyltransferase | Selection marker in AR07-00 |
| — | 789 | GmU3:mCherry:RbcS-E9T | mCherry | Reporter gene in AR07-00 |

Plant Transformation: Bombardment

Pre-sterilized soybean seeds from soybean cultivar Jack were placed on an agar medium for germination. After an overnight incubation, embryonic axes (EAs) were aseptically isolated from seeds. The primary leaves of EAs were removed and the remaining EAs were treated with a solution containing BA (Benzyladenine) and GA (Gibberellic Acid) before they were wrapped in an aluminum foil and incubated in a growth chamber at 21° C. for up to 4 days.

On the day of transformation, gold particles coated with plasmid DNA that contains a mutated ALS (Acetolactate Synthase) gene and a gene coding for a recombinant protein were delivered into EAs using a Bio Rad biolistic apparatus. After the bombardment-mediated gene delivery, the targeted EAs were placed in a growth incubator for 1-3 days for recovery before they were transferred to a medium that contained 0.5 uM Imazapyr herbicide for shoot induction. Shoots which elongated from EAs were separated and were transferred to a rooting medium that contained 0.25 uM Imazapyr. Shoots that formed roots were transferred to Jiffy-7 peat pots for continuing development. Leaf tissues were collected and analyzed by ddPCR to evaluate the number of gene copies inserted.

Plant Transformation: *Agrobacterium*

Pre-sterilized soybean seeds from cultivar Jack were placed on an agar medium for germination. After incubation in a growth chamber overnight, embryonic axes (EAs) were isolated aseptically from seeds. The primary leaves of EAs were removed and the remaining EAs were then stored in a refrigerator until use in transformation.

Two days before transformation, transferred glycerol stock of *agrobacterium* that contains a mutated ALS gene, a visible marker gene (mCherry), and a gene coding for a casein protein to a culture tube containing 3 ml LB medium and 100 μg/mg of kanamycin (LB Kan100), and placed the culture on a shaker at 250 rpm at 28° C. overnight. One day before transformation, 15 μl of overnight grown *agrobacterium* solution was inoculated into 30 ml of LB Kan100 medium and grown for 24 more hours. On the day of transformation, the O.D. (optical density) was adjusted to 0.5 in 50 ml infection medium supplemented with acetosyringone and dithiothreitol.

On the day of transformation, EAs separated in several sterile petri plates were co-cultivated in an incubator at 22° C. for 3 days with 15 ml of *agrobacterium* suspension. After co-cultivation, EAs were transferred to a shoot induction medium that contains 300 μg/ml cefotaxime and 0.5 μM Imazapyr. Elongated shoots from EAs were separated and transferred to a rooting medium that contained 0.2 μM Imazapyr. Shoots that formed roots and expressed mCherry gene were transferred to Jiffy-7 peat pots for continuing development. Leaf tissues were collected and analyzed by ddPCR to evaluate the number of gene copies inserted.

DNA Extraction and ddPCR Analysis

Total soybean genomic DNA was isolated from the first trifoliate leaves of transgenic events using the PureGene tissue DNA isolation kit (product #158667: QIAGEN, Valencia, CA, USA). Trifoliates were frozen in liquid nitrogen and pulverized. Cells were lysed using the PureGene Cell Lysis Buffer, proteins were precipitated using the PureGene Protein Precipitation Buffer, and DNA was precipitated from the resulting supernatant using ethanol. The DNA pellets were washed with 70% ethanol and resuspended in water.

Genomic DNA was quantified by the Quant-iT PicoGreen (product #P7589: ThermoFisher Scientific, Waltham, MA, USA) assay as described by manufacturer, and 150 ng of DNA was digested overnight with EcoRI, HindIII, NcoI, and/or KpnI, 30 ng of which was used for a BioRad ddPCR reaction, including labelled FAM or HEX probes for the transgene and Lectin1 endogenous gene respectively. Transgene copy number was calculated by comparing the measured transgene concentration to the reference gene concentration.

RNA Isolation and Transcriptional Analysis

Transcript levels of transgenes in transgenic soybean seeds were determined by quantitative real-time PCR. Seeds were harvested at S1.09b stage (about 40 days after flowering), immediately frozen in liquid nitrogen and after grounding the RNA was isolated using the GeneJET Plant RNA purification kit (Catlog #K0802, Thermo Scientific). One microgram or less of RNA was treated with DNase I (Catlog #M0303S, NEB) prior to reverse transcription. Each RNA sample was diluted 25-fold and set up for SYBR green-based real-time quantitative PCR assays following the Luna® Universal One-Step RT-qPCR Kit (Catlog #E3005E, NEB). Real-time quantitative PCR assays were run in QuantStudio 6 Flex quantitative PCR system (Catlog #4485691, Applied Biosystems). For each transgenic event, four to six seeds were analyzed with 2 technical replicates.

The qPCR primer pairs were validated by building standard curves with four 10-fold serial dilutions. Only primer pairs showing over 90% amplification efficiency and generating a single peak in the dissociation curve were selected. The primers used are listed in Table 16. Gene expression levels were calculated using the Delta-Delta CT method (Vandesompele et al., 2002). Relative expressions of the seed storage gene GmGlyl to the constitutively expressed reference gene GmTUA5 were calculated as quality control. Samples showing less than one GmGly 1/GmTUA5 relative transcript expression indicated not mature seeds and those samples were excluded for further analysis. As our target gene expression cassettes are all driven by native seed storage gene promoters, we reported the transcript expressions of the target transgene in the format of "X native Glycinin1" by calculating the relative expression of transgene to the seed storage gene GmGlyl.

TABLE 16

Exemplary primer pairs utilized in qRT-PCR analysis

| Gene Name | Short Name | Forward Primer Sequence | Reverse Primer Sequence | Amplicon Size | Amplification Efficiency |
|---|---|---|---|---|---|
| Glycinin 1 | Seed2 | CTGAGTTTGGAT CTCTCCGC (SEQ ID NO: 732) | ACTTGTATCAATG CCCGTCC (SEQ ID NO: 733) | 103 bp | 91.11% |
| Alpha Tubulin 5 | TUA5 | GGATGTCAATGC TGCTGTTG (SEQ ID NO: 734) | AACCTTAGCAAG GTCACCAC (SEQ ID NO: 735) | 134 bp | 90.42% |
| Beta Lactoglobulin 1 | OLG1 | ACGAACAAGGCA TTGGCAGG (SEQ ID NO: 736) | AGGTGCTCGTACT GGACACT (SEQ ID NO: 737) | 101 bp | 91.99% |
| Beta Lactoglobulin 2 | OLG2 | TCGATGCTCTCA ACGAGAACA (SEQ ID NO: 738) | TCCTCACAAGGC ATTGGCAAAC (SEQ ID NO: 739) | 123 bp | 103.47% |
| Beta Lactoglobulin 3 | OLG3 | AGACCAAAATTC CTGCTGTGT (SEQ ID NO: 740) | TGATTGTTCTGGC TCTGCGC (SEQ ID NO: 741) | 125 bp | 100.83% |
| Beta Lactoglobulin 4 | OLG4 | CTGGTCCTCGAC ACTGATTATA (SEQ ID NO: 742) | AAGTGCCTCGTC ATCAACCTC (SEQ ID NO: 743) | 123 bp | 107.94% |
| Ovalbumin 1 | OOVA L1 | GCCGAGGAAAGA TACCCCAT (SEQ ID NO: 744) | TGTCTGGCTCTCT ACCCAAGA (SEQ ID NO: 745) | 141 bp | 95.95% |
| Ovalbumin 2 | OOVA L2 | AACGCTACCCTA TCCTGCCA (SEQ ID NO: 746) | TGGCTCTCGACCC AAGAATTG (SEQ ID NO: 747) | 130 bp | 92.40% |
| Ovalbumin 3 | OOVA L3 | CAGCAGACTGTA CGCAGAAG (SEQ ID NO: 748) | TCAGCTCACGAG CCTGATCT (SEQ ID NO: 749) | 128 bp | 97.30% |
| Ovalbumin 4 | OOVA L4 | AGGAGCTGCGTC TATGGAGT (SEQ ID NO: 750) | TGCACCCAAGTA AACCATGC (SEQ ID NO: 751) | 127 bp | 101.35% |

Protein Extraction and Detection: Preparation of Total Soluble Protein Samples

Total soluble soybean protein fractions were prepared from the seeds of transgenic events by bead beating seeds (seeds collected about 60-90 days after flowering) at 15000 rpm for 1 min. The resulting powder was resuspended in 50 mM Carbonate-Bicarbonate pH10.8, 1 mM DTT, 1×HALT Protease Inhibitor Cocktail (Product #78438 ThermoFisher Scientific). The resuspended powder was incubated at 4° C. for 15 minutes and then the supernatant collected after centrifuging twice at 4000 g, 20 min, 4° C. Protein concentration was measured using a modified Bradford assay (Thermo Scientific Pierce 660 nm assay; Product #22660 ThermoFisher Scientific) using a bovine serum albumin (BSA) standard curve.

Recombinant Protein Quantification via ELISA

Wells of microtiter plates were coated directly with crude plant protein extract diluted in pH 9.5 Bicarbonate-Bicarbonate buffer and incubated overnight at 4° C. Microtiter plates were blocked with 3% BSA in phosphate buffered saline with 0.05% Tween-20, washed with phosphate buffered saline with 0.05% Tween-20, reacted with antigen specific antibody and subsequently reacted with HRP-conjugated sheep anti rabbit IgG (Product #AB6795 Abcam, Cambridge, UK). The reaction was visualized by the addition of chromogenic substrate (TMB) and reaction was stopped with 2M Sulfuric acid and absorbance read at 450 nm using BMG ClarioStar plate reader (Ortenberg, Germany). Recombinant protein from the seeds of transgenic events was quantified by a standard curve prepared from commercial reference protein spike-in standards.

Example 7—Codon Variant Expression and RNA Secondary Structure

Results presented in earlier examples (including Example 3) revealed significant expression differences between codon-optimized variants of nucleic acids encoding for the same protein. For instance, Example 3 noted that β-lactoglobulin gene variant OLG 2 expressed at higher levels than other β-lactoglobulin codon variants.

It was initially hypothesized that increased expression of some codon variants may correlate with the nucleic acid taking on a specific RNA secondary structure. However, a comparison of predicted structures suggested significant structural differences, even amongst higher expressing variants. See e.g., FIG. 8. Therefore no clear correlation was identified between predicted structure and expression.

While conducting the structural analysis discuss above, the inventor(s) noticed that highly-expressing codon variants tended to have similar—if not identical—predicted structures across multiple RNA folding tools. For example, among the β-lactoglobulin codon variants discussed in this example, OLG2 and OLG3 exhibited the highest RNA expression, and also returned similar predicted secondary structures using the minimum free energy (MFE) and centroid models. See FIG. 9.

It was therefore hypothesized that RNA expression could be correlated to a codon variant exhibiting similar predicted secondary structures across multiple RNA folding models.

Example 8—Nucleic Acid Optimization Through Secondary Structure Modeling

Analyses conducted in Example 8 suggested that RNA expression could be associated with predicted secondary structures across multiple RNA folding models. This Example further tests this hypothesis and evaluates whether structural similarities among predicted secondary structures could be predictive of RNA expression.

To test this hypothesis, 3-4 codon optimized variants were produced for β-lactoglobulin (OLG), Ovalbumin (OOVAL), and Green Fluorescent Protein (eGFP). Each of these optimized codon variant nucleic acid sequences were then analyzed in silico to generate predicted secondary structures. Two secondary structures based on two different RNA folding models were generated for each nucleic acid sequence using the RNAfold program. The MFE generated secondary structure represents the optimal secondary structure. The centroid generated secondary structure represents the minimum total base pair distance to all the structures in the thermodynamic ensemble.

Structure Similarity by Visual Inspection

Figure 10B:
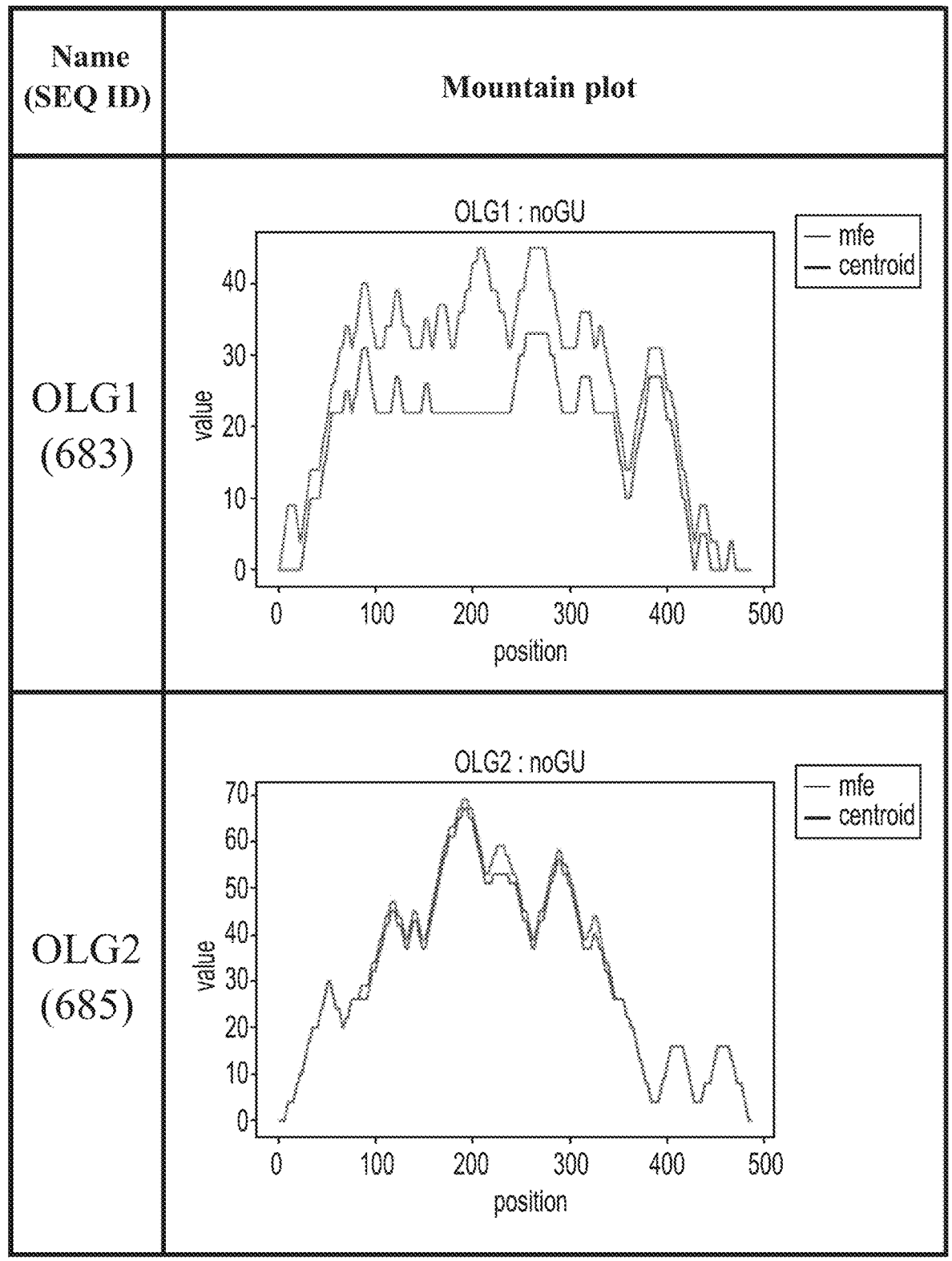
Figure 10E:
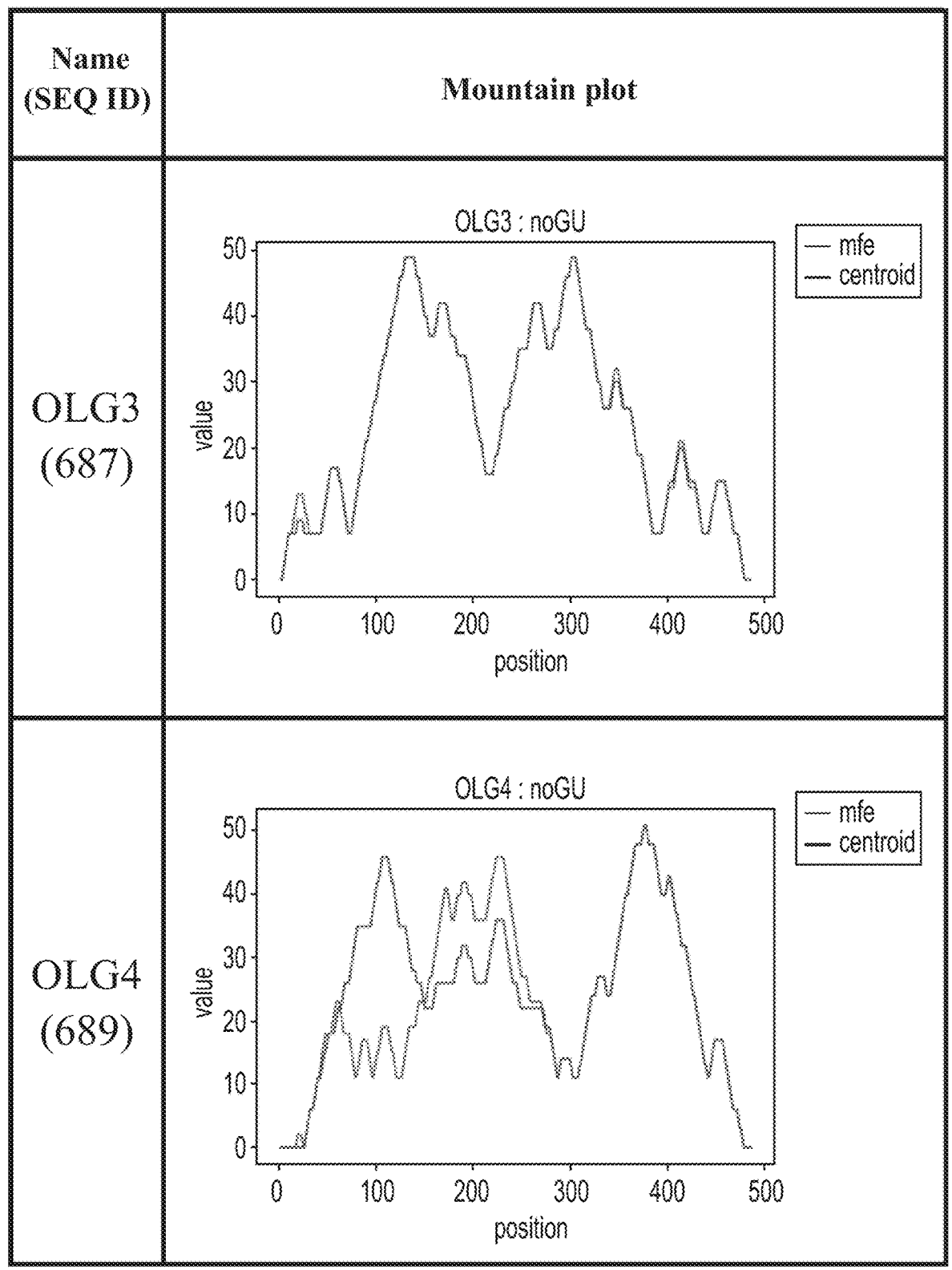
Figure 11B:
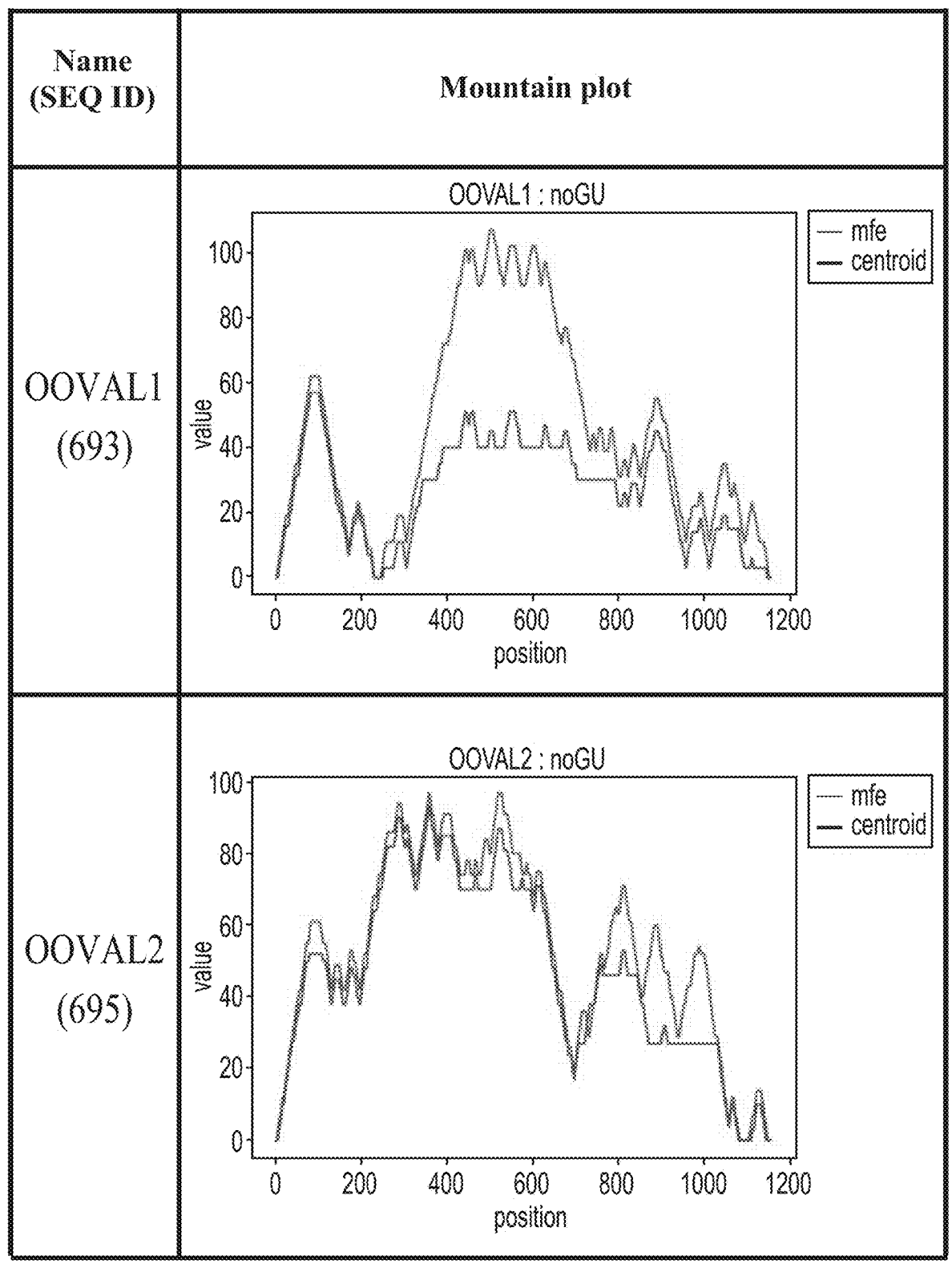
Figure 11E:
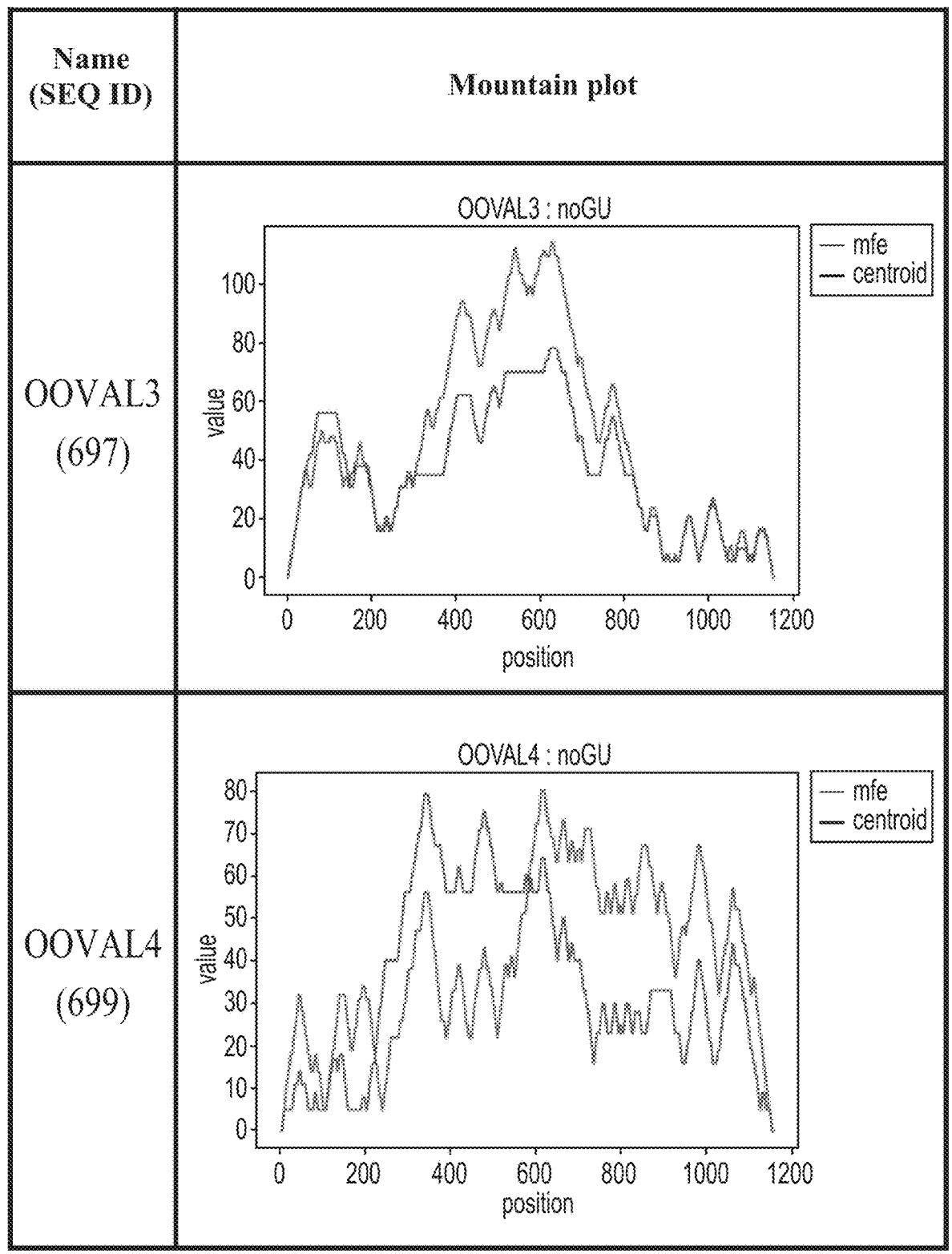
Figure 12B:
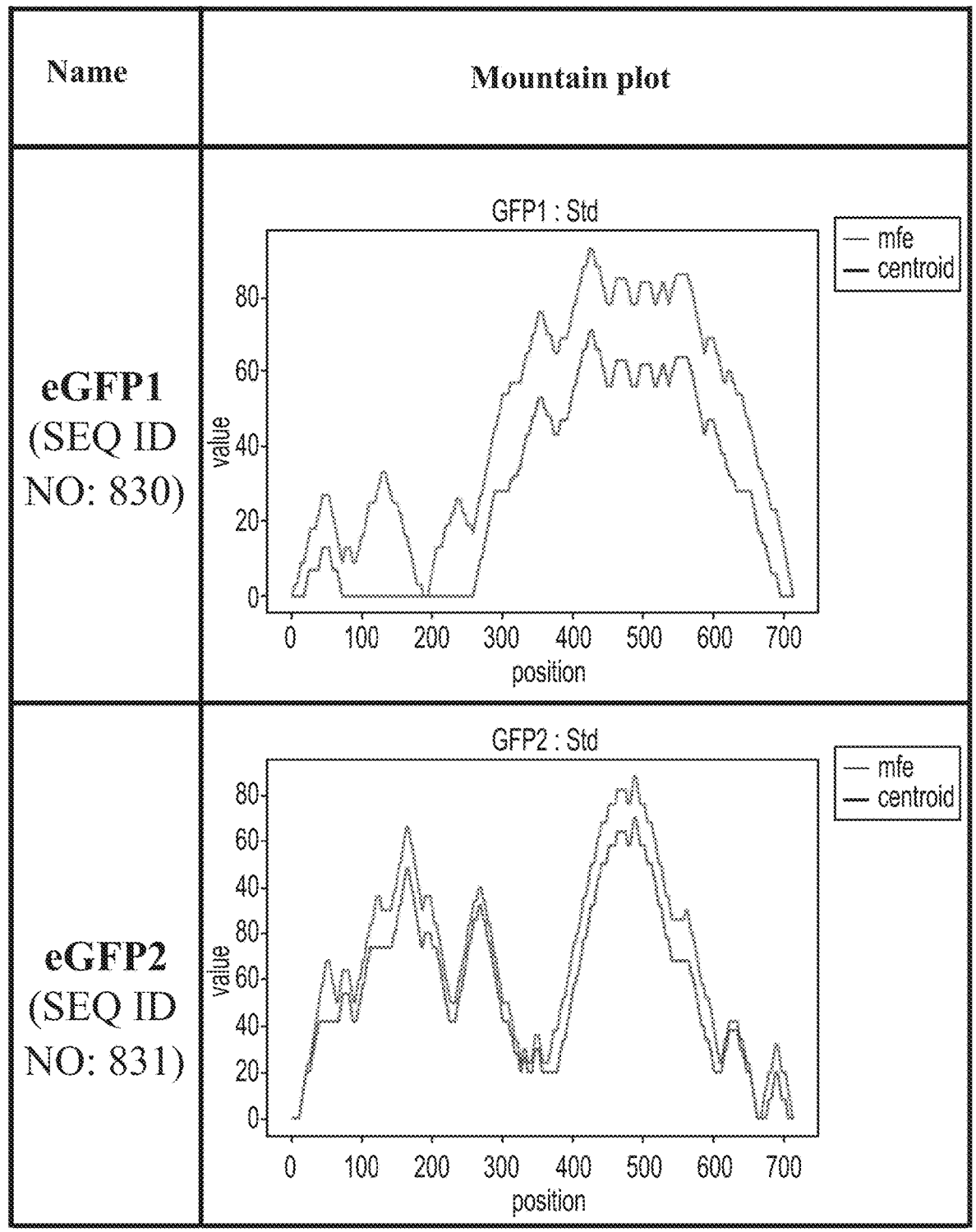
Figure 12E:
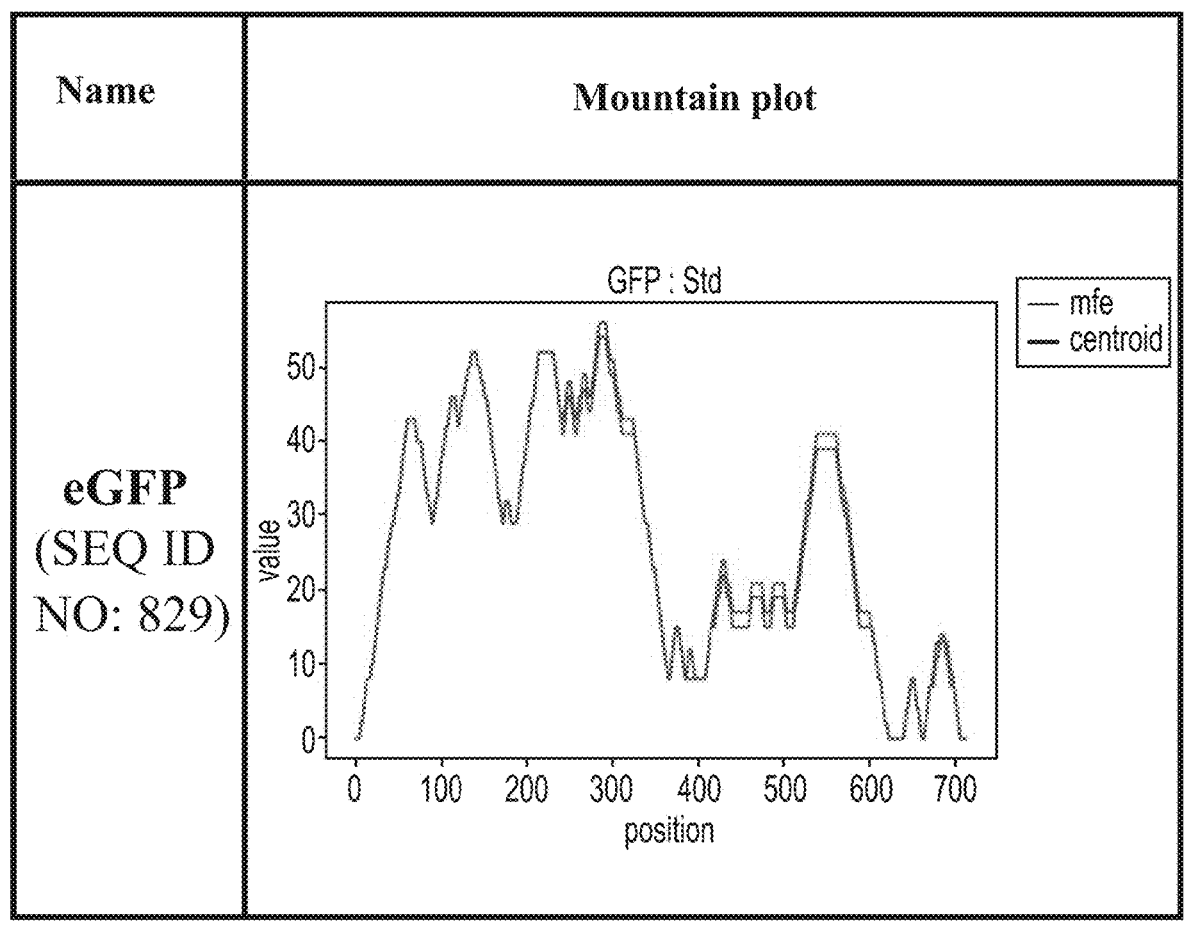

As an initial step, the similarity of the predicted MFE and centroid structures was visually compared and ranked according to perceived similarity. This similarity was assessed by stacking the secondary structure figures with 50% translucency in Microsoft Word and assessing the amount of overlap. Pictures of each of the predicted secondary structures, as well as the visual score for similarity of the two structures produced for each nucleic acid sequence is provided in FIGS. 10-12.

Structure Similarity In Silico

As an alternative to visual inspection, an in silico structural similarity score was developed. Specifically, similarity between the two predicted secondary structures was calculated using the ViennaRNA Package (version 2.5.0) (world wide web-tbi.univie.ac.at/RNA/) (Gruber, 2008) and similarity measures package (pypi.org/project/similaritymeasures/) (Jekel, 2019).

The MFE structure was predicted by the minimum free energy algorithm of (Zuker & Stiegler 1981). The centroid structure was predicted by the suboptimal folding algorithm of (Wuchty et. al 1999).

The ViennaRNA package was first used to convert each of the predicted secondary structures to a height versus position plot (mountain plot), where the vertical y-axis height m(k) is given by the number of base pairs enclosing the base position in the horizontal x-axis (k). In general, this visualization of secondary structure depicts hairpin loops as plateaus and helices as slopes. The mountain plots further assisted in visualizing structural differences, where similar structures were visualized as overlapping mountain plot curves for the MFE and centroid structures, whereas different portions of the secondary structure were visualized as non-overlapping curves. See FIGS. 10-12. These mountain plots also permitted for visual assessment of structure similarity, which largely corresponded with the visual assessment conducted earlier in the Example.

In order to obtain a purely in silico similarity score, the mountain plot curves generated above were further analyzed by the python package similaritymeasures 0.4.4 (pypi.org/project/similaritymeasures/) (Jekel, 2019). This package was used to assess the curve length of each mountain plot, quantifying the deviation between the curves produced by the MFE and centroid secondary structures. Lower curve length measures indicated high overlap between the two curves, suggesting increased similarity between the two plotted secondary structures. Higher curve length measures indicated lower overlap between the curves, suggesting lower similarity between the two plotted secondary structures. These scores were then saved and are presented in FIGS. 10-12.

Empirical Expression Measurement

The sequences in this example were then expressed in soybean using the methods described in Example 8. Briefly, each of the codon-optimized nucleic acid sequences were manufactured into nucleic acids and were cloned into expression vectors. The expression vectors were introduced into soybean, and RNA expression was measured via quantitative RT PCR.

Nucleic Acid Predicted Structure Similarity as Predictor of Expression

Figure 13A:
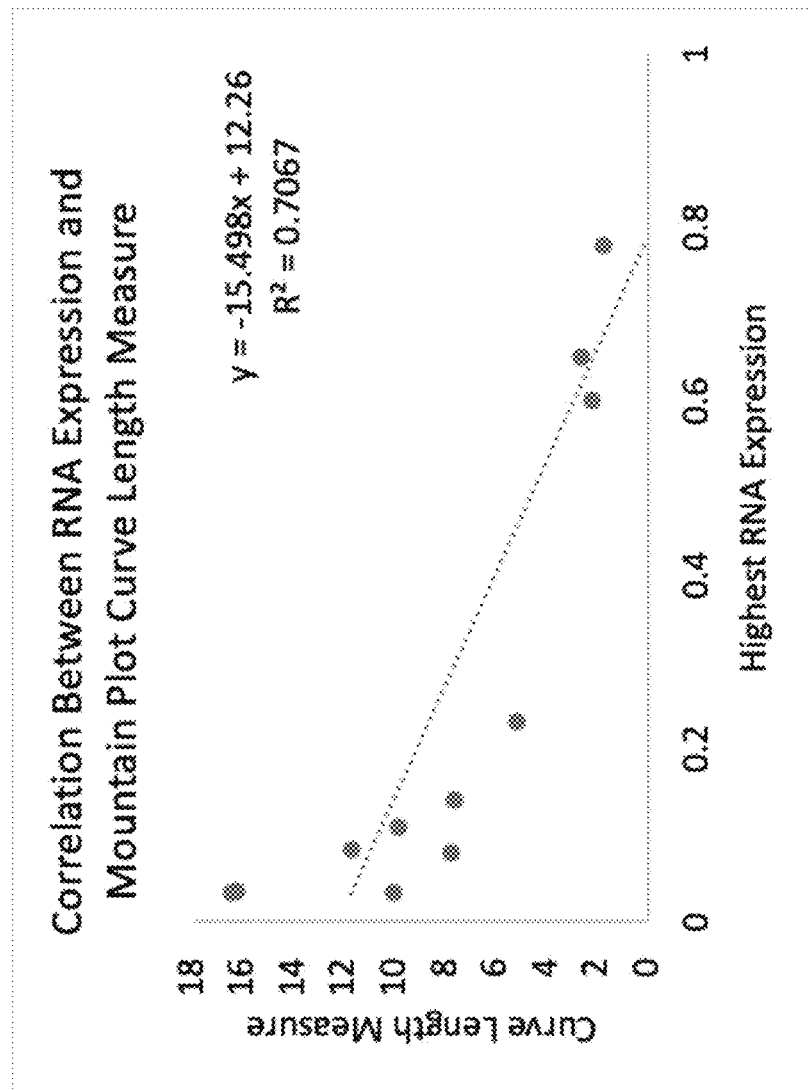
FIG. 13A-B—depicts a X-Y scatter plot of curve length measure between predicted secondary structures for each nucleic acid sequence created from different RNA folding models, and highest RNA expression from constructs comprising each nucleic acid sequence.
Figure 13B:
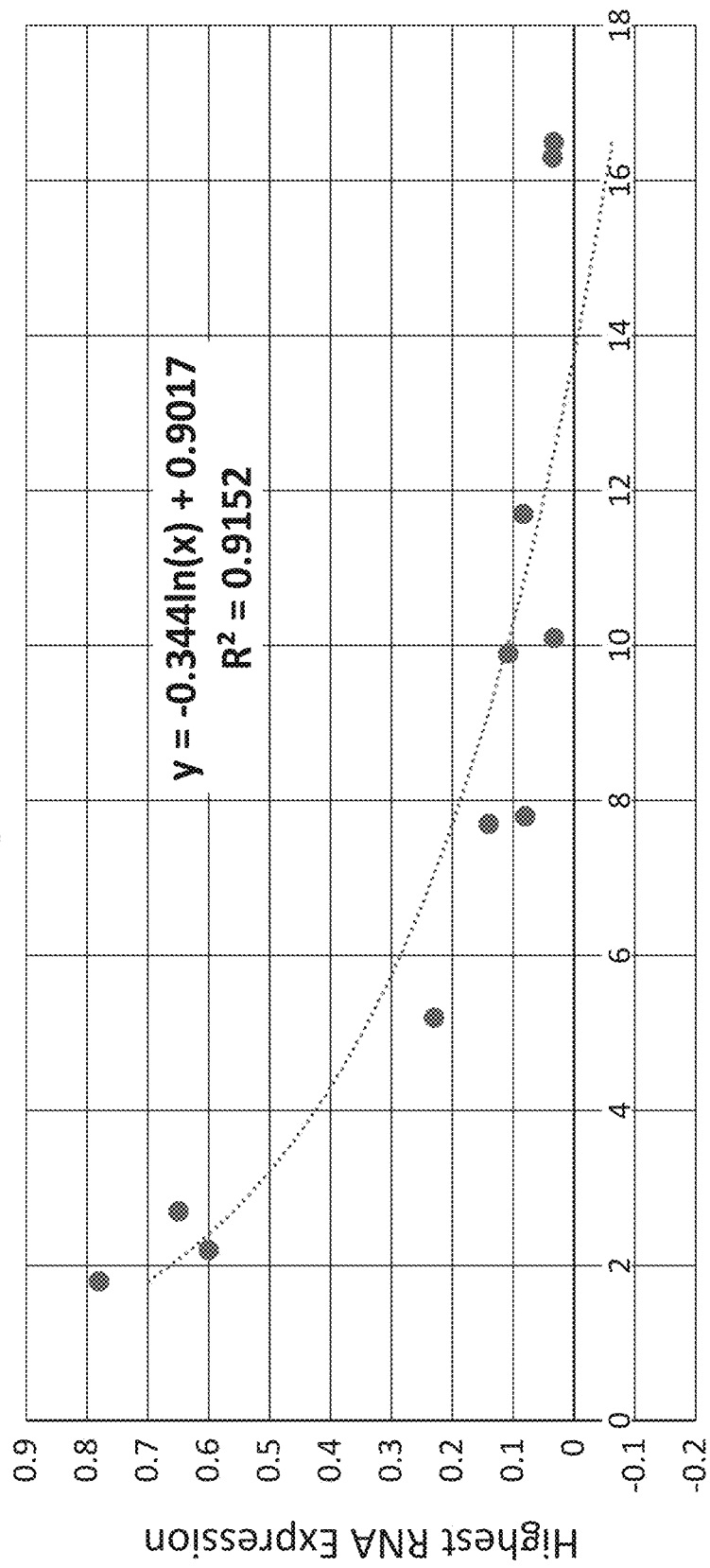
Figure 14:
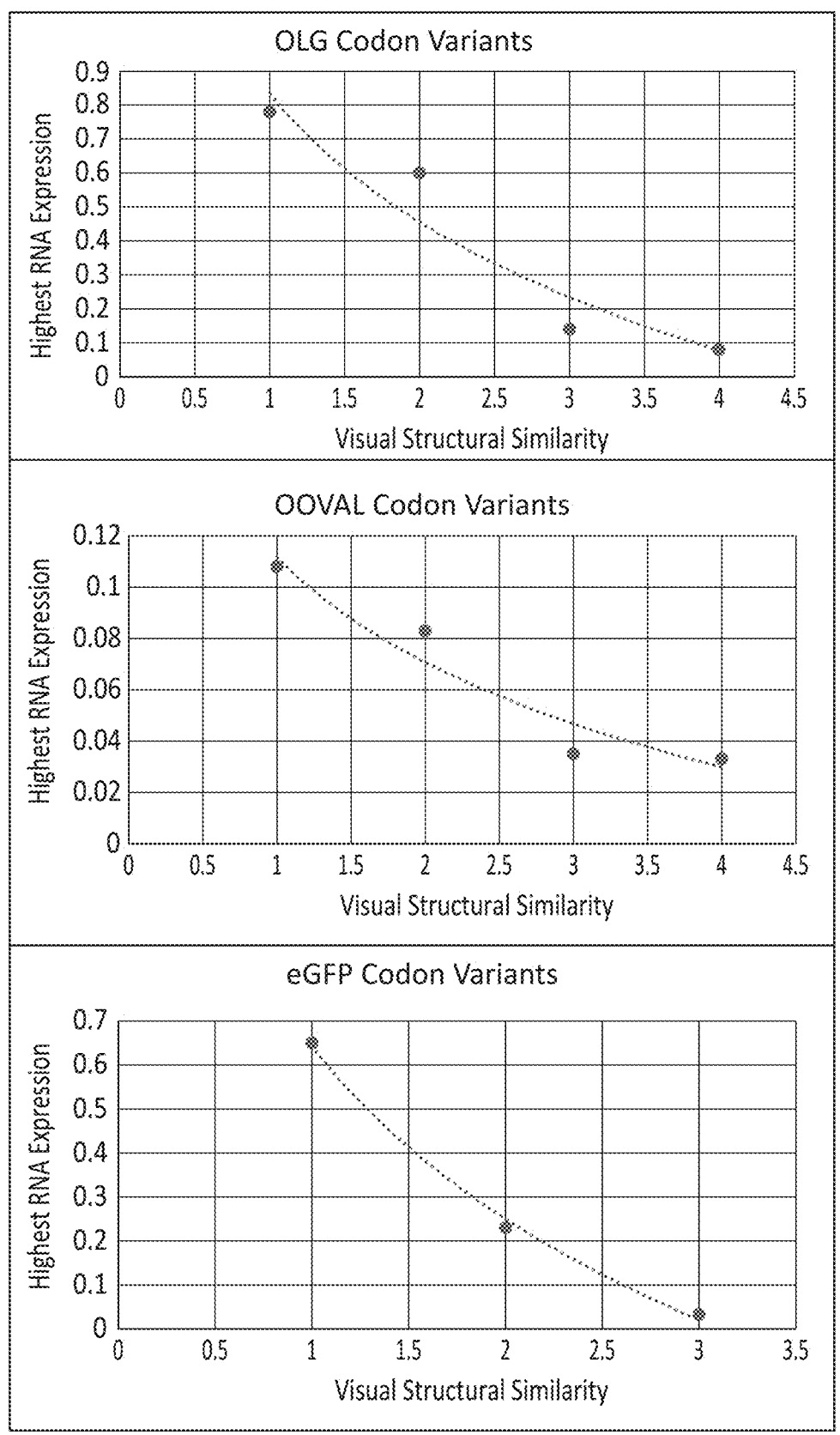
FIG. 14—depicts a X-Y scatter plots of curve length measure between predicted secondary structures for each nucleic acid sequence created from different RNA folding models, and highest RNA expression from constructs comprising each nucleic acid sequence. Separate plots for β-Lactoglobulin, Ovalbumin, and Green Fluorescent Protein are provided, each with trend lines showing correlation.

The in silico structural similarity scores measured above were plotted against the empirical expression data measured for each nucleic acid sequence (FIGS. 13A-B). The results demonstrated a strong correlation between structural similarity of predicted secondary structures and empirical expression. This correlation appeared to be logarithmic, with an $R^2$ correlation coefficient of 0.915. This correlation was measured across multiple codon variants and genes, demonstrating that it is not an artifact of any specific sequence. The general trend of correlation also held true for visual structural similarity scores, demonstrating that multiple structure similarity comparators can be used (FIG. 14).

Milk Protein Sequences

The following Table 17 describes various representative species of milk proteins exemplified in the disclosure.

TABLE 17

Exemplary Milk Protein Sequences of the Disclosure

| SEQ ID NO | Description | Genus/species | Accession Number |
|---|---|---|---|
| Kappa casein sequences | | | |
| 3 | Optimized kappa-casein truncated version 1 (OKC1-T) | Artificial (codon optimized *Bos taurus*) | |
| 4 | Optimized kappa-casein truncated version 1 (OKC1-T) | *Bos taurus* | |

TABLE 17-continued

Exemplary Milk Protein Sequences of the Disclosure

| SEQ ID NO | Description | Genus/species | Accession Number |
|---|---|---|---|
| 85 | Kappa casein | *Capra hircus* | |
| 86 | Kappa casein | *Ovis aries* | |
| 87 | Kappa casein | *Bubalus bubalis* | |
| 88 | Kappa casein | *Camelus dromedaries* | |
| 89 | Kappa casein | *Camelus bactrianus* | |
| 90 | Kappa casein | *Bos mutus* | |
| 91 | Kappa casein | *Equus caballus* | |
| 92 | Kappa casein | *Equus asinus* | |
| 93 | Kappa casein | *Rangifer tarandus* | |
| 94 | Kappa casein | *Alces alces* | |
| 95 | Kappa casein | *Vicugna pacos* | |
| 96 | Kappa casein | *Bos indicus* | |
| 97 | Kappa casein | *Lama glama* | |
| 98 | Kappa casein | *Homo sapiens* | |
| 148 | Kappa casein | *Bos taurus* | NP_776719.1 |
| 149 | | | AAI02121.1 |
| 150 | | | AAA30433.1 |
| 151 | | | AAB26704.1 |
| 152 | | | 1406275A |
| 153 | | | AAF72097.1 |
| 154 | | | AAD32139.1 |
| 155 | | | XP_024848756.1 |
| 156 | | | CAF03625.1 |
| 157 | | | ABN42697.1 |
| 158 | | | AAD32140.1 |
| 159 | | | ALC76014.1 |
| 160 | | | DAA28589.1 |
| 161 | | | ADT82665.1 |
| 162 | | | ADT82666.1 |
| 163 | | | CAH56573.1 |
| 164 | | | ADT82669.1 |
| 165 | Kappa casein | *Capra hircus* | QIZ03342.1 |
| 166 | | | AYN74373.1 |
| 167 | | | AAM12026.1 |
| 168 | | | AFZ92921.1 |
| 169 | | | NP_001272516.1 |
| 170 | | | AAM12027.1 |
| 171 | | | AAR06605.1 |
| 172 | | | AAL90873.1 |
| 173 | | | AFZ92919.1 |
| 174 | | | QIZ03345.1 |
| 175 | | | AAR91623.1 |
| 176 | | | AAK17010.1 |
| 177 | | | AAL93193.1 |
| 178 | | | AFZ92918.1 |
| 179 | | | AAL90872.1 |
| 180 | | | AFZ92917.1 |
| 181 | | | AAO39432.1 |
| 182 | | | AAL90871.1 |
| 183 | | | AAO39431.1 |
| 184 | Kappa casein | *Ovis aries* | NP_001009378.1 |
| 185 | | | AAP69943.1 |
| 186 | Kappa casein | *Bubalus bubalis* | NP_001277901.1 |
| 187 | | | AXE74388.1 |
| 188 | | | APQ30586.1 |
| 189 | | | AXE74385.1 |
| 190 | | | XP_006071184.1 |
| 191 | | | AXE74386.1 |
| 192 | Kappa casein | *Bos mutus* | XP_005897104.1 |
| 193 | | | XP_014334109.1 |
| 194 | | | MXQ92034.1 |
| 195 | Kappa casein | *Bos indicus* | XP_019818432.1 |
| 196 | | | ACF15188.1 |
| 197 | | | ACF15186.1 |
| 198 | | | ACF15190.1 |
| 199 | | | ABY81250.1 |
| 200 | | | ABY81251.1 |
| 201 | | | ADT82668.1 |
| 202 | | | ADT82663.1 |
| 203 | | | ADT82671.1 |
| 204 | | | ADT82670.1 |
| 205 | | | AAQ73171.1 |
| 206 | Kappa casein | *Jeotgalicoccus coquinae* | WP_188357548.1 |
| 207 | (Hypothetical Protein) | | WP_188357549.1 |
| 208 | Kappa casein isoform X1 | *Bison bison bison* | XP_010837415.1 |

TABLE 17-continued

Exemplary Milk Protein Sequences of the Disclosure

| SEQ ID NO | Description | Genus/species | Accession Number |
|---|---|---|---|
| 209 | | | XP_010837416.1 |
| 210 | Kappa casein | Bos grunniens | AFM93768.1 |
| 211 | | | AXE74296.1 |
| 212 | | | AAM25910.1 |
| 213 | | | ABU53615.1 |
| 214 | | | AAM25909.1 |
| 215 | | | AAF63191.1 |
| 216 | Kappa casein | Bos indicus × Bos taurus | AAF72096.1 |
| 217 | | | AAF72098.1 |
| 218 | Kappa casein (precursor) | Oreamnos americanus | P50423.1 |
| 219 | Kappa casein (precursor) | Naemorhedus goral | P50422.1 |
| 220 | Kappa casein | Odocoileus virginianus texanus | XP_020729185.1 |
| 221 | Kappa casein (precursor) | Capricornis sumatraensis | P50420.1 |
| 222 | Kappa casein (precursor) | Capricornis crispus | BAA03287.1 |
| 223 | | | P42156.1 |
| 224 | Kappa casein (precursor) | Capricornis swinhoei | P50421.1 |
| 225 | Kappa casein (precursor) | Saiga tatarica | P50425.1 |
| 226 | Kappa casein (precursor) | Rupicapra rupicapra | P50424.1 |
| 227 | Kappa casein (precursor) | Cervus nippon | P42157.1 |
| 228 | Kappa casein | Bos frontalis | ADF58295.1 |
| 229 | Kappa casein (hypothetical protein FD755 023011) | Muntiacus reevesi | KAB0354473.1 |
| 230 | Kappa casein (hypothetical protein FD754 018150) | Muntiacus muntjak | KAB0341224.1 |
| 231 | Kappa casein | Madoqua saltiana | AFY03578.1 |
| 232 | Kappa casein | Gazella dorcas | AFY03574.1 |
| 233 | Kappa casein | Gazella arabica | AFY03576.1 |
| 234 | Kappa casein | Capra ibex ibex | AAP80529.1 |
| 235 | Kappa casein | Ovis ammon severtzovi | ADB66396.1 |
| 236 | Kappa casein | Ovis orientalis gmelini | ADB66423.1 |
| 237 | | | ADB66420.1 |
| 238 | Kappa casein (hypothetical protein G4228 004474) | Cervus hanglu yarkandensis | KAF4013038.1 |
| 239 | Kappa casein | Procapra gutturosa | AFY03581.1 |
| 240 | | | AFY03580.1 |
| 1 | Optimized para-kappa-casein truncated version 1 (paraOKC1-T) | Artificial (codon optimized Bos taurus) | |
| 2 | Optimized para-kappa-casein truncated version 1 (paraOKC1-T) | Bos taurus | |
| 241 | Kappa casein isoform X1 | Bos taurus | AAA30433.1 |
| 242 | | | 1406275A |
| 243 | | | AAI02121.1 |
| 244 | | | NP_776719.1 |
| 245 | | | DAA28589.1 |
| 246 | | | AAB26704.1 |
| 247 | | | XP_024848756.1 |
| 248 | | | ABN42697.1 |
| 249 | | | AAF72097.1 |
| 250 | | | 721588A |
| 251 | | | AAD32139.1 |
| 252 | | | AAD32140.1 |
| 253 | | | CAF03625.1 |
| 254 | Kappa casein | Jeotgalicoccus coquinae | WP_188357548.1 |
| 255 | (hypothetical protein) | | WP_188357549.1 |
| 256 | Kappa casein isoform X1 | Bos mutus | XP_005897104.1 |
| 257 | | | XP_014334109.1 |
| 258 | | | MXQ92034.1 |
| 259 | Kappa casein | Bos indicus | XP_019818432.1 |
| 260 | | | ACF15188.1 |
| 261 | | | ABY81250.1 |
| 262 | | | ABY81251.1 |
| 263 | | | ACF15186.1 |
| 264 | | | ACF15190.1 |
| 265 | | | ADT82668.1 |
| 266 | Kappa casein | Bos grunniens | AXE74296.1 |
| 267 | | | AFM93768.1 |
| 268 | | | AAM25910.1 |
| 269 | | | AAM25909.1 |
| 270 | | | ABU53615.1 |
| 271 | Kappa casein isoform X1 | Bison bison bison | XP_010837415.1 |

TABLE 17-continued

Exemplary Milk Protein Sequences of the Disclosure

| SEQ ID NO | Description | Genus/species | Accession Number |
|---|---|---|---|
| 272 | | | XP_010837416.1 |
| 273 | Kappa casein (precursor) | Bubalus bubalis | NP_001277901.1 |
| 274 | | | XP_006071184.1 |
| 275 | | | AXE74388.1 |
| 276 | | | AXE74385.1 |
| 277 | | | APQ30586.1 |
| 278 | | | AXE74386.1 |
| 279 | Kappa casein (precursor) | Oreamnos americanus | P50423.1 |
| 280 | Kappa casein (precursor) | Capricornis swinhoei | P50421.1 |
| 281 | Kappa casein (precursor) | Naemorhedus goral | P50422.1 |
| 282 | Kappa casein (precursor) | Capricornis sumatraensis | P50420.1 |
| 283 | Kappa casein (precursor) | Capricornis crispus | BAA03287.1 |
| 284 | | | P42156.1 |
| 285 | Kappa casein (precursor) | Saiga tatarica | P50425.1 |
| 286 | Kappa casein | Bos indicus × Bos taurus | AAF72096.1 |
| 287 | | | AAF72098.1 |
| 288 | Kappa casein (precursor) | Capra hircus | NP_001272516.1 |
| 289 | | | AYN74373.1 |
| 290 | | | QIZ03345.1 |
| 291 | | | QIZ03342.1 |
| 292 | | | AFZ92921.1 |
| 293 | | | AAR06605.1 |
| 294 | | | AAM12026.1 |
| 295 | | | AAL93193.1 |
| 296 | | | AAR91623.1 |
| 297 | | | AFZ92917.1 |
| 298 | | | AAM12027.1 |
| 299 | | | AAL90873.1 |
| 300 | | | AFZ92918.1 |
| 301 | | | AAL90871.1 |
| 302 | | | AAL90872.1 |
| 303 | | | AAL31535.1 |
| 304 | | | AAL31534.1 |
| 305 | | | ABK59545.1 |
| 306 | | | AAO39432.1 |
| 307 | | | AFZ92919.1 |
| 308 | | | AAK17010.1 |
| 309 | | | AAO39431.1 |
| 310 | | | AAP80475.1 |
| 311 | Kappa casein | Odocoileus virginianus texanus | XP 020729185.1 |
| 312 | Kappa casein (precursor) | Rupicapra rupicapra | P50424.1 |
| 313 | Kappa casein (precursor) | Ovis aries | NP 001009378.1 |
| 314 | | | AAP69943.1 |
| 315 | Kappa casein (precursor) | Cervus nippon | P42157.1 |
| 316 | Kappa casein | Gazella arabica | AFY03576.1 |
| 317 | Kappa casein (hypothetical protein FD754 018150) | Muntiacus muntjak | KAB0341224.1 |
| 318 | Kappa casein (hypothetical protein FD755 023011) | Muntiacus reevesi | KAB0354473.1 |
| 319 | Kappa casein | Gazella dorcas | AFY03575.1 |
| 320 | Kappa casein | Procapra gutturosa | AFY03581.1 |
| 321 | | | AFY03580.1 |
| 322 | Kappa casein | Madoqua saltiana | AFY03578.1 |
| 323 | Kappa casein | Ammotragus lervia | QIN85723.1 |
| 324 | | | QIN85720.1 |
| 325 | | | QIN85721.1 |
| 326 | Kappa casein | Capra sibirica | AAP80568.1 |
| 327 | Kappa casein | Ovis canadensis canadensis | ADB66397.1 |
| 328 | | | ADB66402.1 |
| 329 | Kappa casein | Gazella subgutturosa marica | AFY03577.1 |
| 330 | Kappa casein | Antilope cervicapra | AFY03573.1 |
| 331 | Kappa casein | Capra ibex ibex | AAP80529.1 |
| 332 | Kappa casein | Ovis vignei arkal | ADB66436.1 |
| 333 | | | ADB66442.1 |
| 334 | Kappa casein | Ovis ammon collium | ADB66395.1 |
| 335 | Kappa casein | Ovis vignei blanfordi | ADB66445.1 |
| 336 | Kappa casein | Ovis orientalis gmelini | ADB66423.1 |
| 337 | | | ADB66420.1 |
| 338 | Kappa casein | Ovis orientalis × vignei | ADB66465.1 |
| 339 | Kappa casein | Ovis vignei vignei | ADB66456.1 |
| 340 | Kappa casein | Ovis ammon severtzovi | ADB66396.1 |

TABLE 17-continued

Exemplary Milk Protein Sequences of the Disclosure

| SEQ ID NO | Description | Genus/species | Accession Number |
|---|---|---|---|
| colspan="4" | Alpha S1 casein sequences | | |
| 7 | Optimized alpha S1-casein truncated version 1(OaS1-T) | Artificial (codon optimized *Bos taurus*) | |
| 8 | Optimized alpha S1-casein truncated version 1(OaS1-T) | *Bos taurus* | |
| 99 | Alpha S1 casein | *Capra hircus* | |
| 100 | Alpha S1 casein | *Ovis aries* | |
| 101 | Alpha S1 casein | *Bubalus bubalis* | |
| 102 | Alpha S1 casein | *Camelus dromedaries* | |
| 103 | Alpha S1 casein | *Camelus bactrianus* | |
| 104 | Alpha S1 casein | *Bos mutus* | |
| 105 | Alpha S1 casein | *Equus caballus* | |
| 106 | Alpha S1 casein | *Equus asinus* | |
| 107 | Alpha S1 casein | *Bos indicus* | |
| 108 | Alpha S1 casein | *Lama glama* | |
| 109 | Alpha S1 casein | *Homo sapiens* | |
| 341 | Alpha S1 casein | *Bos taurus* | ABW98943.1 |
| 342 | | | XP_024848771.1 |
| 343 | | | ABW98940.1 |
| 344 | | | ACG63494.1 |
| 345 | | | XP_015327132.1 |
| 346 | | | XP_024848772.1 |
| 347 | | | 1308122A |
| 348 | | | ABW98949.1 |
| 349 | | | AAA30429.1 |
| 350 | | | XP_015327135.1 |
| 351 | | | XP_015327134.1 |
| 352 | | | XP_024848773.1 |
| 353 | | | XP_015327133.1 |
| 354 | | | XP_024848774.1 |
| 355 | | | XP_015327136.1 |
| 356 | | | XP_024848775.1 |
| 357 | | | XP_005208084.1 |
| 358 | | | XP_024848776.1 |
| 359 | | | XP_015327137.1 |
| 360 | | | XP_015327138.1 |
| 361 | | | XP_024848777.1 |
| 362 | | | XP_024848778.1 |
| 363 | | | XP_015327139.1 |
| 364 | | | ABW98944.1 |
| 365 | | | XP_015327140.1 |
| 366 | | | XP_024848779.1 |
| 367 | | | XP_015327141.1 |
| 368 | | | XP_024848780.1 |
| 369 | | | XP_015327142.1 |
| 370 | | | ABW98945.1 |
| 371 | | | XP_024848782.1 |
| 372 | | | ABW98951.1 |
| 373 | | | XP_024848784.1 |
| 374 | | | XP_024848783.1 |
| 375 | | | ABW98950.1 |
| 376 | | | ABW98941.1 |
| 377 | | | XP_005208086.1 |
| 378 | | | ABW98942.1 |
| 379 | | | ABW98937.1 |
| 380 | | | ABW98952.1 |
| 381 | | | ABW98954.1 |
| 382 | | | ABW98953.1 |
| 383 | | | ABW98955.1 |
| 384 | | | ABW98957.1 |
| 385 | Alpha S1 casein | *Capra hircus* | XP_017904616.1 |
| 386 | | | QIZ03312.1 |
| 387 | | | ALJ30147.1 |
| 388 | | | P18626.2 |
| 389 | | | XP_017904617.1 |
| 390 | | | AFN44013.1 |
| 391 | | | QIZ03319.1 |
| 392 | | | CAA51022.1 |
| 393 | | | NP_001272624.1 |
| 394 | | | ALJ30148.1 |
| 395 | | | QIZ03317.1 |
| 396 | | | QIZ03310.1 |

TABLE 17-continued

Exemplary Milk Protein Sequences of the Disclosure

| SEQ ID NO | Description | Genus/species | Accession Number |
|---|---|---|---|
| 397 | | | QIZ03318.1 |
| 398 | | | XP_017904618.1 |
| 399 | | | XP_017904620.1 |
| 400 | | | XP_017904619.1 |
| 401 | | | XP_017904621.1 |
| 402 | | | XP_017904622.1 |
| 403 | Alpha S1 casein | Ovis aries | XP_012034747.1 |
| 404 | | | P04653.3 |
| 405 | | | AAB34797.1 |
| 406 | | | ACJ46472.1 |
| 407 | | | XP 027826521.1 |
| 408 | | | XP 027826520.1 |
| 409 | | | ACR58469.1 |
| 410 | | | ACJ46473.1 |
| 411 | | | AAB34798.1 |
| 412 | | | NP_001009795.1 |
| 413 | Alpha S1 casein | Bubalus bubalis | AAZ14098.1 |
| 414 | | | APQ30583.1 |
| 415 | | | O62823.2 |
| 416 | | | XP_006071187.1 |
| 417 | | | QCP57314.1 |
| 418 | | | XP_025145744.1 |
| 419 | | | QPO15022.1 |
| 420 | | | XP_025145745.1 |
| 421 | | | ACJ14317.1 |
| 422 | | | XP_006071188.1 |
| 423 | | | XP_025145747.1 |
| 424 | | | XP_025145746.1 |
| 425 | | | XP_025145748.1 |
| 426 | | | XP_025145749.1 |
| 427 | | | XP_025145750.1 |
| 428 | | | XP_025145751.1 |
| 429 | | | XP_025145752.1 |
| 430 | | | XP_025145753.1 |
| 431 | Alpha S1 casein | Bos mutus | XP_005902100.1 |
| 432 | Alpha S1 casein | Bos indicus | XP_019818428.1 |
| 433 | Alpha S1 casein | Jeotgalicoccus coquinae | WP_188357546.1 |
| 434 | (hypothetical protein) | | GGE26809.1 |
| 435 | Alpha S1 casein | Bison bison bison | XP_010850445.1 |
| 436 | Alpha S1 casein | Bos grunniens | AXE74293.1 |
| 437 | Alpha S1 casein | Jeotgalicoccus aerolatus | WP_188349304.1 |
| 438 | (hypothetical protein) | | WP_188352531.1 |
| 439 | Alpha S1 casein (hypothetical protein FD754 018154) | Muntiacus muntjak | KAB0341228.1 |
| 440 | Alpha S1 casein (hypothetical protein FD755 023008) | Muntiacus reevesi | KAB0354470.1 |
| Alpha S2 casein sequences | | | |
| 83 | Optimized alpha S2-casein truncated version 1(OaS2-T) | Artificial (codon optimized Bos taurus) | |
| 84 | Optimized alpha S2-casein truncated version 1(OaS2-T) | Bos taurus | |
| 110 | Alpha S2 casein | Capra hircus | |
| 111 | Alpha S2 casein | Ovis aries | |
| 112 | Alpha S2 casein | Bubalus bubalis | |
| 113 | Alpha S2 casein | Camelus dromedaries | |
| 114 | Alpha S2 casein | Camelus bactrianus | |
| 115 | Alpha S2 casein | Bos mutus | |
| 116 | Alpha S2 casein | Equus caballus | |
| 117 | Alpha S2 casein | Equus asinus | |
| 118 | Alpha S2 casein | Vicugna pacos | |
| 119 | Alpha S2 casein | Bos indicus | |
| 120 | Alpha S2 casein | Lama glama | |
| 441 | Alpha S2 casein | Bos taurus | AAI14774.1 |
| 442 | | | XP_024848786.1 |
| 443 | | | XP_015327143.1 |
| 444 | Alpha S2 casein | Capra hircus | QIS93310.1 |
| 445 | | | NP_001272514.1 |
| 446 | | | CAB94236.1 |
| 447 | | | QIS93322.1 |
| 448 | | | AAB32166.1 |

TABLE 17-continued

Exemplary Milk Protein Sequences of the Disclosure

| SEQ ID NO | Description | Genus/species | Accession Number |
|---|---|---|---|
| 449 | | | QIS93306.1 |
| 450 | | | XP_013820127.2 |
| 451 | | | QIS93323.1 |
| 452 | | | QIZ03322.1 |
| 453 | | | QIS93316.1 |
| 454 | | | CAB59920.1 |
| 455 | | | CAC21704.2 |
| 456 | | | QIS93307.1 |
| 457 | | | XP_013820130.2 |
| 458 | | | QIS93319.1 |
| 459 | | | QIS93321.1 |
| 460 | | | XP_013820128.2 |
| 46 | | | QIS93304.1 |
| 462 | | | XP_013820129.2 |
| 463 | | | QIS93305.1 |
| 464 | | | QIS93314.1 |
| 465 | | | QIS93317.1 |
| 466 | | | XP_013820132.2 |
| 467 | | | XP_013820131.2 |
| 468 | Alpha S2 casein | Ovis aries | ADB65931.1 |
| 469 | | | NP_001009363.1 |
| 470 | | | ADB65933.1 |
| 471 | | | ADB65935.1 |
| 472 | | | ADB65934.1 |
| 473 | | | ADB65932.1 |
| 474 | Alpha S2 casein | Bubalus bubalis | NP_001277794.1 |
| 475 | | | AAZ80050.1 |
| 476 | | | CAA06534.2 |
| 477 | | | AFB69498.1 |
| 478 | | | XP_006071185.2 |
| 479 | | | AAZ57423.1 |
| 480 | | | APQ30584.1 |
| 481 | | | XP_025145302.1 |
| 482 | | | XP_025145301.1 |
| 483 | Alpha S2 casein | Bos mutus | XP_014335716.1 |
| 484 | | | ELR51813.1 |
| 485 | Alpha S2 casein (hypothetical protein) | Jeotgalicoccus aerolatus | WP_188352530.1 |
| 486 | | | GGE08804.1 |
| 487 | Alpha S2 casein (hypothetical protein) | Jeotgalicoccus coquinae | WP_188357545.1 |
| 488 | Alpha S2 casein | Bos grunniens | AXE74294.1 |
| 489 | Alpha S2 casein | Bison bison bison | XP_010850447.1 |
| 490 | Alpha S2 casein | Bos indicus × Bos taurus | XP_027401112.1 |
| 491 | Alpha S2 casein | Odocoileus virginianus texanus | XP_020729187.1 |
| 492 | Alpha S2 casein (hypothetical protein FD754 018155) | Muntiacus muntjak | KAB0341229.1 |
| 493 | Alpha S2 casein (hypothetical protein FD755 022792) | Muntiacus reevesi | KAB0354254.1 |
| 494 | Alpha S2 casein (CSN1S2) | Cervus elaphus hippelaphus | OWK13818.1 |
| | | Beta-casein sequences | |
| 5 | Optimized beta-casein truncated version 2 (OBC-T2) | Artificial (codon optimized Bos taurus) | |
| 6 | Optimized beta-casein truncated version 2 (OBC-T2) | Bos taurus | |
| 121 | Beta casein | Capra hircus | |
| 122 | Beta casein | Ovis aries | |
| 123 | Beta casein | Bubalus bubalis | |
| 124 | Beta casein | Camelus dromedaries | |
| 125 | Beta casein | Camelus bactrianus | |
| 126 | Beta casein | Bos mutus | |
| 127 | Beta casein | Equus caballus | |
| 128 | Beta casein | Equus asinus | |
| 129 | Beta casein | Alces alces | |
| 130 | Beta casein | Vicugna pacos | |
| 131 | Beta casein | Bos indicus | |
| 132 | Beta casein | Lama glama | |
| 133 | Beta casein | Homo sapiens | |
| 495 | Beta casein | Bos taurus | AAB29137.1 |
| 496 | | | AAA30431.1 |

TABLE 17-continued

Exemplary Milk Protein Sequences of the Disclosure

| SEQ ID NO | Description | Genus/species | Accession Number |
|---|---|---|---|
| 497 | | | 1314242A |
| 498 | | | AGT56763.1 |
| 499 | | | AAI11173.1 |
| 500 | | | XP_010804480.2 |
| 501 | | | AAA30430.1 |
| 502 | | | XP_015327157.2 |
| 503 | | | ABR10906.1 |
| 504 | | | ABL74247.1 |
| 505 | | | QCI03091.1 |
| 50€ | | | QCI03090.1 |
| 507 | | | CAC37028.1 |
| 508 | Beta casein | Capra hircus | P33048.1 |
| 509 | | | QIZ03333.1 |
| 510 | | | CAB39200.1 |
| 511 | | | AAK97639.1 |
| 512 | | | XP_005681778.2 |
| 513 | | | QLI42602.1 |
| 514 | | | XP_013820153.1 |
| 515 | | | QLI42606.1 |
| 516 | | | QHN12643.1 |
| 517 | | | ABQ52487.1 |
| 518 | | | QHN12642.1 |
| 519 | | | CAB39313.1 |
| 520 | | | QHN12644.1 |
| 521 | | | AWN06750.1 |
| 522 | Beta casein | Ovis aries | P11839.3 |
| 523 | | | NP_001009373.1 |
| 524 | Beta casein | Bubalus bubalis | QHB80269.1 |
| 525 | | | APQ30585.1 |
| 526 | | | QHB80272.1 |
| 527 | | | QHB80273.1 |
| 528 | | | NP 001277808.1 |
| 529 | | | Q9TSI0.1 |
| 530 | | | XP 006071186.1 |
| 531 | | | CAA06535.1 |
| 532 | | | 1004269A |
| 533 | | | ADD31643.1 |
| 534 | | | ADD31644.1 |
| 535 | | | AAT09469.1 |
| 536 | | | ABL10285.1 |
| 537 | | | ABA41625.1 |
| 538 | | | ABA41623.1 |
| 539 | Beta casein | Bos mutus | MXQ92033.1 |
| 540 | | | XP_014335713.1 |
| 541 | | | XP_005902099.2 |
| 542 | | | XP_014335715.1 |
| 543 | | | XP_014335714.1 |
| 544 | Beta casein | Bos indicus | AQY78354.1 |
| 545 | | | AQY78355.1 |
| 546 | | | ABL75279.1 |
| 547 | | | ABY27644.1 |
| 548 | | | AWN06759.1 |
| 549 | | | AGZ84117.1 |
| 550 | Beta casein | Bison bison bison | XP_010850446.1 |
| 551 | Beta casein (hypothetical protein) | Jeotgalicoccus aerolatus | WP_188352529.1 |
| 552 | Beta casein (hypothetical protein) | Jeotgalicoccus coquinae | WP_188357544.1 |
| 553 | Beta casein (precursor) | Bos indicus × Bos taurus | ARU83745.1 |
| 554 | | | AWN06757.1 |
| 555 | | | AWN06758.1 |
| 556 | Beta casein | Bos grunniens | AXE74295.1 |
| 557 | | | AEY63644.1 |
| 558 | | | AEY63645.1 |
| 559 | | | AEC13563.1 |
| 560 | Beta casein | Neophocaena asiaeorientalis asiaeorientalis | XP_024597374.1 |
| 561 | Beta casein | Odocoileus virginianus texanus | XP_020729180.1 |
| 562 | Beta casein (hypothetical protein FD755_022863) | Muntiacus reevesi | KAB0354325.1 |
| 563 | Beta casein (hypothetical protein FD754_022431) | Muntiacus muntjak | KAB0345505.1 |

TABLE 17-continued

Exemplary Milk Protein Sequences of the Disclosure

| SEQ ID NO | Description | Genus/species | Accession Number |
|---|---|---|---|
| Beta-Lactoglobulin sequences | | | |
| 9 | Optimized Beta Lactoglobulin 1 (OLG1) | Artificial (codon optimized *Bos taurus*) | |
| 10 | Optimized Beta Lactoglobulin 1 (OLG1) | *Bos taurus* | |
| 11 | Optimized Beta Lactoglobulin 2 (OLG2) | Artificial (codon optimized *Bos taurus*) | |
| 12 | Optimized Beta Lactoglobulin 3 (OLG3) | Artificial (codon optimized *Bos taurus*) | |
| 13 | Optimized Beta Lactoglobulin 4 (OLG4) | Artificial (codon optimized *Bos taurus*) | |
| 564 | Beta Lactoglobulin | *Bos taurus* | 5K06_A |
| 565 | | | 1B0O_A |
| 566 | | | NP_776354.2 |
| 567 | | | 3PH5_A |
| 568 | | | 1BEB_A |
| 569 | | | 6QPD_A |
| 570 | | | 6QI7_A |
| 571 | | | DAA24277.1 |
| 572 | | | 5HTD_A |
| 573 | | | 6QPE_A |
| 574 | | | 6RWR_A |
| 575 | | | 1BSO_A |
| 576 | | | 6RWQ_A |
| 577 | | | ACG59280.1 |
| 578 | | | 5NUJ_A |
| 579 | | | 5NUM_A |
| 580 | | | 1UZ2_X |
| 581 | | | CAA32835.1 |
| 582 | | | 1CJ5_A |
| 583 | | | 5NUK_A |
| 584 | | | 5NUN_A |
| 585 | | | 732164A |
| 586 | | | XP_024854027.1 |
| 587 | | | AAA30411.1 |
| 588 | Beta Lactoglobulin | *Capra hircus* | 4OMW_A |
| 589 | | | NP_001272468.1 |
| 590 | | | ABQ51182.1 |
| 591 | Beta Lactoglobulin | *Ovis aries* | 4NLI_A |
| 592 | | | NP_001009366.1 |
| 593 | | | 4CK4_A |
| 594 | | | 4CK4_B |
| 595 | Beta Lactoglobulin | *Bubalus bubalis* | 0601265A |
| 596 | | | P02755.2 |
| 597 | | | NP_001277893.1 |
| 598 | | | QOQ34530.1 |
| 599 | | | APQ30587.1 |
| 600 | | | ABG78270.1 |
| 601 | Beta Lactoglobulin | *Bos mutus* | XP_005888577.1 |
| 602 | | | MXQ94840.1 |
| 603 | Beta Lactoglobulin | *Bos indicus* | XP_019826641.1 |
| 604 | Beta Lactoglobulin (lipocalin/fatty-acid binding family protein) | *Jeotgalicoccus coquinae* | WP_188357550.1 |
| 605 | Beta Lactoglobulin (lipocalin/fatty-acid binding family protein | *Jeotgalicoccus schoeneichii* | WP_188349305.1 |
| 606 | Beta Lactoglobulin | *Bison bison bison* | XP_010855058.1 |
| 607 | Beta Lactoglobulin | *Ovis* sp. | AAA31510.1 |
| 608 | Beta Lactoglobulin | *Ovis aries musimon* | P67975.1 |
| 609 | Beta Lactoglobulin | *Odocoileus virginianus texanus* | XP_020744123.1 |
| 610 | Beta Lactoglobulin, Chain A | *Rangifer tarandus* | 1YUP_A |
| 611 | Beta Lactoglobulin | *Rangifer tarandus tarandus* | AAZ57420.1 |
| 612 | Beta Lactoglobulin (hypothetical protein FD754 009020) | *Muntiacus muntjak* | KAB0364864.1 |
| 613 | Beta Lactoglobulin (hypothetical protein FD755 007442) | *Muntiacus reevesi* | KAB0379658.1 |
| 614 | Beta Lactoglobulin, Chain A | *Equus caballus* | 3KZA_A |

REFERENCES

Fox, P. F., and A. L. Kelly. "Chemistry and biochemistry of milk constituents." *Food Biochemistry and Food Processing* 2 (2006): 442-464.

Garbarino, Joan E., and William R. Belknap. "Isolation of a ubiquitin-ribosomal protein gene (ubi3) from potato and expression of its promoter in transgenic plants." *Plant molecular biology* 24, no. 1 (1994): 119-127.

Grey, Finn, Rebecca Tirabassi, Heather Meyers, Guanming Wu, Shannon McWeeney, Lauren Hook, and Jay A. Nelson. "A viral microRNA down-regulates multiple cell cycle genes through mRNA 5' UTRs." *PLoS Pathog* 6, no. 6 (2010): e1000967.

Laxa, Miriam. "Intron-mediated enhancement: a tool for heterologous gene expression in plants?." *Frontiers in plant science* 7 (2017): Orom, Ulf Andersson, Finn Cilius Nielsen, and Anders H. Lund. "MicroRNA-10a binds the 5' UTR of ribosomal protein mRNAs and enhances.

Ortega, Jose Luis, Olivia L. Wilson, and Champa Sengupta-Gopalan. "The 5' untranslated region of the soybean cytosolic glutamine synthetase β 1 gene contains prokaryotic translation initiation signals and acts as a translational enhancer in plants." *Molecular genetics and genomics* 287, no. 11 (2012): 881-893.

Strixner, T., & Kulozik, U. (2011). Egg proteins. In Handbook of food proteins (pp. 150-209). Woodhead publishing.

Tian, Li, and Samuel S M Sun. "Ubiquitin fusion expression and tissue-dependent targeting of hG-CSF in transgenic tobacco." *BMC biotechnology* 11, no. 1 (2011): 91.

Tschofen, Marc, Dietmar Knopp, Elizabeth Hood, and Eva Stoger. "Plant molecular farming: much more than medicines." *Annual Review of Analytical Chemistry* 9 (2016): 271-294.

Zou, Z., C. Eibl, and H-U. Koop. "The stem-loop region of the tobacco psbA 5' UTR is an important determinant of mRNA stability and translation efficiency." *Molecular genetics and genomics* 269, no. 3 (2003): 340-349.

EMBODIMENTS

Embodiment Set 1

1. A host cell that comprises an exogenous RNA sequence that encodes a chordate protein, wherein the exogenous RNA sequence is stabilized as determined by increased expression of the chordate protein as compared to an otherwise comparable host cell lacking the exogenous RNA sequence that is stabilized, and wherein the chordate protein is expressed in the amount of at least 1% or higher per total protein weight of soluble protein extractable from the host cell.
2. The host cell of embodiment 1, wherein the chordate is a vertebrate.
3. The host cell of embodiment 2, wherein the vertebrate is a mammal.
4. The host cell of embodiment 3, wherein the mammal is a bovine.
5. The host cell of embodiment 2, wherein the vertebrate is a bird.
6. The host cell of embodiment 5, wherein the bird is a chicken.
7. The host cell of any one of the preceding embodiments, wherein the chordate protein is an egg protein or a milk protein.
8. The host cell of embodiment 7, wherein the chordate protein is a milk protein.
9. The host cell of embodiment 8, wherein the milk protein is β-lactoglobulin.
10. The host cell of embodiment 7, wherein the chordate protein is an egg protein.
11. The host cell of embodiment 10, wherein the egg protein is ovalbumin.
12. The host cell of any one of the preceding embodiments, wherein the chordate protein is expressed in the amount of at least 2%, at least 3%, at least 4%, or at least 5% per total protein weight of soluble protein extractable from the host cell.
13. The host cell of any one of the preceding embodiments, wherein the chordate protein is expressed in the amount of about 1 to about 2%, about 2 to about 3%, or about 2 to about 5% per total protein weight of soluble protein extractable from the host cell.
14. A plant that comprises the host cell of any one of embodiments 1-13.
15. The plant of embodiment 14, wherein the plant is a soybean plant.
16. A DNA construct for expression of a transgene in a host cell, wherein the DNA construct comprises: a codon-optimized transgene sequence that comprises at least 90% identity to a sequence selected from the group consisting of SEQ ID NO: 1, 3, 5, 7, 9-13, 83, 617-621, 683-690, and 693-700; and an exogenous intron sequence, wherein the exogenous intron sequence comprises at least 90% identity to a sequence selected from the group consisting of: SEQ ID NO: 679-682.
17. The DNA construct of embodiment 16, wherein the codon-optimized transgene sequence comprises a sequence selected from SEQ ID NO: 1, 3, 5, 7, 9-13, 83, 617-621, 683-690, and 693-700.
18. The DNA construct of embodiment 16, wherein the exogenous intron sequence comprises a sequence selected from SEQ ID NO: 679-682.
19. A DNA construct for expression of a transgene in a host cell, wherein the DNA construct comprises: a codon-optimized transgene sequence that comprises at least 90% identity to a sequence selected from the group consisting of SEQ ID NO: 1, 3, 5, 7, 9-13, 83, 617-621, 683-690, and 693-700; and an exogenous intron sequence, wherein the exogenous intron sequence comprises at least 90% identity to a sequence selected from the group consisting of: SEQ ID NO: 679-682.
20. The DNA construct of embodiment 19, wherein the codon-optimized transgene sequence comprises a sequence selected from SEQ ID NO: 1, 3, 5, 7, 9-13, 83, 617-621, 683-690, and 693-700.
21. The DNA construct of embodiment 19, wherein the exogenous intron sequence comprises a sequence selected from SEQ ID NO: 679-682.
22. The DNA construct of any one of embodiments 16-21, wherein the DNA construct further comprises a signal peptide sequence.
23. The DNA construct of embodiment 22, wherein the signal peptide sequence is selected from the group consisting of: SEQ ID NO: 616, 707-717.
24. The DNA construct of any one of embodiments 16-23, wherein the DNA construct further comprises a sequence encoding a KDEL sequence.

25. The DNA construct of any one of embodiments 16-23, wherein the DNA construct further comprises a sequence encoding at least one of a 5' UTR and a 3' UTR.
26. The DNA construct of any one of embodiments 16-25, wherein the DNA construct further comprises a sequence encoding a ubiquitin monomer.
27. The DNA construct of any one of embodiments 16-26, wherein the DNA construct further comprises an exogenous promoter sequence.
28. The DNA construct of embodiment 27, wherein the exogenous promoter sequence is isolated or derived from a plant promoter sequence.
29. The DNA construct of embodiment 27, wherein the exogenous promoter sequence is isolated or derived from a seed promoter sequence.
30. The DNA construct of any one of embodiments 16-29, wherein the DNA construct further comprises an exogenous terminator sequence.
31. A composition that comprises the DNA construct of any one of embodiments 16-30.
32. A method of transforming a host cell, the method comprising contacting a host cell with the composition of embodiment 31, thereby transforming the host cell.
33. The method of embodiment 32, wherein the host cell is a plant cell.
34. The method of embodiment 33, wherein the method comprises bombardment or *agrobacterium*-mediated transformation.
35. The method of any one of embodiment 33-34, further comprising cultivating the plant cell after the transforming.
36. An RNA generated from the DNA construct of any one of embodiments 16-30.
37. A method of expressing ovalbumin or β-lactoglobulin in a plant, the method comprising: contacting at least a portion of a plant with the DNA construct of any one of embodiments 16-30, wherein the method is effective in increasing expression of the ovalbumin or β-lactoglobulin as compared to an otherwise comparable method lacking the contacting.
38. The method of embodiment 37, wherein the method is effective in increasing expression of the ovalbumin or β-lactoglobulin by at least about 1-fold as compared to an otherwise comparable method lacking the contacting.
39. A method of stably expressing a chordate protein in a plant cell, the method comprising: contacting a plant cell with a DNA construct that comprises at least 90% identity to a sequence selected from the group consisting of SEQ ID NO: 752-766, thereby generating a transformed plant cell; and cultivating a plant that comprises the transformed plant cell, thereby generating a transformed plant, wherein the chordate protein is expressed in the amount of 1% or higher per total protein weight of soluble protein extractable from the transformed plant cell.
40. The method of embodiment 39, wherein the DNA construct comprises at least 95%, at least 97%, or at least 99% identity to a sequence selected from the group consisting of SEQ ID NO: 752-766.
41. A method of stably expressing a chordate protein in a plant cell, the method comprising: contacting a plant cell with a DNA construct that comprises at least 90% identity to a sequence selected from the group consisting of SEQ ID NO: 767-781, thereby generating a transformed plant cell; and cultivating a plant that comprises the transformed plant cell, thereby generating a transformed plant, wherein the chordate protein is expressed in the amount of 1% or higher per total protein weight of soluble protein extractable from the transformed plant cell.
42. The method of embodiment 41, wherein the DNA construct comprises at least 95%, at least 97%, or at least 99% identity to a sequence selected from the group consisting of SEQ ID NO: 767-781.
43. The method of any one of embodiments 39-42, wherein the chordate protein is expressed in the amount of at least 1%, at least 2%, at least 3%, at least 4%, or at least 5% per total protein weight of soluble protein extractable from the transformed plant cell.
44. The method of any one of embodiments 39-43, wherein the plant cell is from a soybean plant.
45. The method of any one of embodiments 39-44, wherein the contacting comprises bombardment or *agrobacterium*-mediated transformation.
46. The method of any one of embodiments 39-45, wherein a level of a transcript of a transgene encoded by the DNA construct is increased by at least 1-fold as compared to an otherwise comparable method lacking the contacting.
47. The method of any one of embodiments 39-46, wherein a level of the chordate protein encoded by the DNA construct is increased by at least 1-fold as measured by ELISA and as compared to an otherwise comparable method lacking the contacting.
48. The method of embodiments 46 or 47, wherein the level is increased by at least 3-fold, at least 5-fold, at least 10-fold, at least 30-fold, or at least 50-fold.
49. The method of any one of embodiments 39-48, further comprising isolating a seed from the transformed plant.
50. A nutraceutical that comprises a chordate protein isolated from a transformed plant cell generated by the method of any one of embodiments 39-49.

Embodiment Set 2

1. A method for selecting a nucleic acid sequence, said method comprising the steps of: a) providing data on a plurality of nucleic acid sequences; b) predicting secondary structure of the plurality of nucleic acid sequences, with a plurality of RNA folding models, such that each nucleic acid sequence in the plurality of nucleic acid sequences is associated with at least two predicted secondary structures; c) determining a structural similarity score for the at least two predicted secondary structures associated with each nucleic acid sequence; and d) selecting a nucleic acid sequence with a higher structural similarity score than at least one other nucleic acid sequence in the plurality of nucleic acid sequences; wherein the selected nucleic acid sequence is predicted to accumulate at higher levels when expressed in a host cell.
2. A method for selecting a nucleic acid sequence, said method comprising the steps of: a) providing data on a plurality of nucleic acid sequences, each nucleic acid sequence in the plurality of nucleic acid sequences being associated with at least two predicted secondary structures from different RNA folding models; b) determining a structural similarity score for the at least two predicted secondary structures associated with each nucleic acid sequence; d) selecting a nucleic acid sequence with a higher structural similarity score than at least one other nucleic acid sequence in the plurality of nucleic acid sequences; wherein the selected nucleic acid sequence is predicted to accumulate at higher levels when expressed in a host cell.
3. The method of embodiment 1 or 2, wherein at least one of the RNA folding models employs machine learning.
4. The method of embodiment 1 or 2, wherein the plurality of nucleic acid sequences encode the same amino acid sequence.
4.1 The method of embodiment 1 or 2, wherein the plurality of nucleic acid sequences encode amino acids sharing at least 90%, 91%, 92%, 93%, 94%, 95%, 96%, 97%, 98%, or 99% sequence identity.
5. The method of any one of embodiments 1-4, comprising: manufacturing the selected nucleic acid sequence into a nucleic acid.
6. The method of any one of embodiments 1-5, comprising: expressing the selected nucleic acid sequence in a host cell.
7. The method of embodiment 5, comprising expressing the manufactured nucleic acid in a host cell.
8. The method of any one of embodiments 1-6, wherein the nucleic acid sequence encodes for a messenger RNA.
9. The method of any one of embodiments 1-8, wherein the RNA folding models comprise a model selected from the group consisting of Cocke-Younger Kasami model, inside and outside models, loop-based energy model, minimum free energy, suboptimal folding, centroid, and any combination thereof.
9.1 The method of any one of embodiments 1-8, wherein the RNA folding models comprise a model selected from Tables 1 or 2.
10. The method of any one of embodiments 1-8, wherein the at least two predicted secondary structures are a minimum free energy structure and a centroid structure.
11. The method of any one of embodiments 1-10, wherein the structural similarity score is determined via tool selected from the group consisting of Consan, Dynalign, PMcomp, Stemloc, Foldalign, locARNA, SPARSE, MARNA, FoldAlignM, Murlet, CARNA, RAF, RNAforester, RNAdistance, RNAStrAt, RNApdist, and any combination thereof.
12. The method of any one of embodiments 1-10, wherein the structure similarity score is based on visual inspection of the predicted secondary structures.
13. The method of embodiment 12, wherein the structure similarity score is a ranking of the plurality of nucleic acid sequences based on the relative similarity of each nucleic acid sequences' predicted secondary structures.
14. The method of any one of embodiments 1-10, wherein the similarity score is based on degree of curve overlap in a graph depicting number of base pairs at each position of the predicted secondary structures.
15. The method of any one of embodiments 1-10, wherein the similarity score is based on the degree of curve overlap of the predicted secondary structures plotted in a mountain plot.
16. The method of any one of embodiments 1-10, wherein the similarity score is based on the correlation of curves representing the predicted secondary structures in a graph depicting number of base pairs at each position.
17. The method of embodiment 16, wherein the degree of curve overlap is calculated by methodology selected from the group consisting of least squares, curve length measure, and any combination thereof.
18. A method of manufacturing a nucleic acid, said method comprising: a) manufacturing a selected nucleic acid sequence to produce a nucleic acid, wherein the selection of the nucleic acid sequence was based on the selected nucleic acid sequence having a higher structural similarity score than at least one other nucleic acid sequence in a plurality of nucleic acid sequences; wherein the structural similarity score is based on the structural similarity between at least two predicted secondary structures for each nucleic acid sequence, the predicted secondary structures produced by different RNA folding models.
19. The method of embodiment 18, wherein at least one of the RNA folding models employs machine learning.
20. The method of embodiment 18 or 19, wherein the plurality of nucleic acid sequences encode the same amino acid sequence.
20.1 The method of embodiment 18 or 19, wherein the plurality of nucleic acid sequences encode amino acids sharing at least 90%, 91%, 92%, 93%, 94%, 95%, 96%, 97%, 98%, or 99% sequence identity.
21. The method of any one of embodiments 18-20, comprising: expressing the manufactured nucleic acid in a host cell.
22. The method of 21, wherein the manufactured nucleic acid expresses at a higher level than other nucleic acids containing other nucleic acid sequences from the plurality of nucleic acid sequences.
23. The method of any one of embodiments 18-22, wherein the RNA folding models comprise a model selected from the group consisting of Cocke-Younger Kasami model, inside and outside models, loop-based energy model, minimum free energy, suboptimal folding, centroid, and any combination thereof.
24. The method of any one of embodiments 18-22, wherein the at least two predicted secondary structures are a minimum free energy structure and a centroid structure.
25. The method of any one of embodiments 18-24, wherein the structural similarity score is determined via tool selected from the group consisting of Consan, Dynalign, PMcomp, Stemloc, Foldalign, locARNA, SPARSE, MARNA, FoldAlignM, Murlet, CARNA, RAF, RNAforester, RNAdistance, RNAStrAt, RNApdist, and any combination thereof.
25.1 The method of any one of embodiments 18-24, wherein the RNA folding models comprise a model selected from Tables 1 or 2.
26. The method of any one of embodiments 18-24, wherein the structure similarity score is based on visual inspection of the predicted secondary structures.
27. The method of embodiment 26, wherein the structure similarity score is a ranking of the plurality of nucleic acid sequences based on the relative similarity of each nucleic acid sequences' predicted secondary structures.
28. The method of any one of embodiments 18-24, wherein the similarity score is based on degree of curve overlap in a graph depicting number of base pairs at each position of the predicted secondary structures.
29. The method of any one of embodiments 18-24, wherein the similarity score is based on the degree of curve overlap of the predicted secondary structures plotted in a mountain plot.
30. A nucleic acid comprising the nucleic acid sequence selected in the method of any one of embodiments 1-29.
31. A host cell comprising a nucleic acid comprising a sequence of Table 11, Table 12, or Table 15.

32. The host cell of embodiment 31, wherein the nucleic acid comprises a sequence selected from the group consisting of: SEQ ID NO: 757, 760, 762, 763, 765, 772, 773, 778, and 780.
33. A host cell comprising a nucleic acid encoding any one of SEQ ID NO: 685, 687, and 695.
34. An automated system for predicting relative expression strength of a plurality of nucleic acid sequences expression in vivo, the system comprising: i) a memory; and ii) a processor in communication with the memory, the processor configured to: a) define a plurality of nucleic acid sequences; b) predict secondary structure of the plurality of nucleic acid sequences, with a plurality of RNA folding models, such that each nucleic acid sequence in the plurality of nucleic acid sequences is associated with at least two predicted secondary structures; c) determine a structural similarity score for the at least two predicted secondary structures associated with each nucleic acid sequence; wherein nucleic acid sequences with similarity scores indicative of greater structure similarity are predicted to accumulate at higher levels than nucleic acid sequences with scores indicative of lower structural similarity, when expressed in a host cell.
35. The system of embodiment 34, wherein at least one of the RNA folding models employs machine learning.
36. The system of embodiment 34 or 35, wherein the plurality of nucleic acid sequences encode the same amino acid sequence.
37. The system of embodiment 34 or 35, wherein the plurality of nucleic acid sequences encode amino acids sharing at least 90%, 91%, 92%, 93%, 94%, 95%, 96%, 97%, 98%, or 99% sequence identity.
38. The system of any one of embodiments 34-37, wherein the processor is configured to manufacture a nucleic acid sequence from the plurality of nucleic acid sequences, into a nucleic acid.
39. The system of any one of embodiments 34-37, wherein the processor is configured to send instructions to automated liquid and particle handling robotics to cause the automated liquid and particle handling robotics to manipulate liquid or particles added to or removed from reactions to manufacture a nucleic acid with the nucleic acid sequence from the plurality of nucleic acid sequences.
40. The system of any one of embodiments 34-39, wherein the processor is configured to express a nucleic acid sequence from the plurality of nucleic acid sequences, in a host cell.
41. The system of embodiment 40, wherein the nucleic acid sequence expressed is the nucleic acid manufactured in embodiment 39.
42. The system of any one of embodiments 34-39, wherein the processor is configured to send instructions to automated liquid and particle handling robotics to cause the automated liquid and particle handling robotics to manipulate liquid or particles added to or removed from cultures having a base host cells to create an engineered host cell expressing a nucleic acid sequence from the plurality of nucleic acid sequences.
43. The system of any one of embodiments 34-42, wherein the nucleic acid sequence encodes for a messenger RNA.
44. The system of any one of embodiments 34-43, wherein the wherein the processor is configured to select a nucleic acid sequence from the plurality of nucleic acid sequences that is predicted to accumulate at 10%, 20%, 30%, 40%, 50% or more higher levels than at least on other nucleic acid in the plurality of nucleic acid sequences.
45. The system of any one of embodiments 34-44, wherein the RNA folding models comprise a model selected from the group consisting of Cocke-Younger Kasami model, inside and outside models, loop-based energy model, minimum free energy, suboptimal folding, centroid, and any combination thereof.
46. The system of any one of embodiments 34-44, wherein the at least two predicted secondary structures are a minimum free energy structure and a centroid structure.
47. The system of any one of embodiments 34-46, wherein the structural similarity score is determined via tool selected from the group consisting of Consan, Dynalign, PMcomp, Stemloc, Foldalign, locARNA, SPARSE, MARNA, FoldAlignM, Murlet, CARNA, RAF, RNAforester, RNAdistance, RNAStrAt, RNApdist, and any combination thereof.
47.1 The system of any one of embodiments 34-46, wherein the RNA folding models comprise a model selected from Tables 1 or 2.
48. A composition comprising or consisting of a sequence with at least about 80%, 85%, 90%, 95%, 96%, 97%, 98%, 99%, or 100% identity to any one of SEQ ID NO: 829-831.
49. A nucleic acid comprising or consisting of a sequence with at least about 80%, 85%, 90%, 95%, 96%, 97%, 98%, 99%, or 100% identity to any one of SEQ ID NO: 829-831.
50. A polypeptide encoded by a sequence with at least about 80%, 85%, 90%, 95%, 96%, 97%, 98%, 99%, or 100% identity to any one of SEQ ID NO: 829-831.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

The invention claimed is:

1. A method for selecting a nucleic acid sequence, said method comprising the steps of:
   a) providing data on a plurality of nucleic acid sequences that encode the same amino acid sequence;
   b) predicting secondary structure of the plurality of nucleic acid sequences with a plurality of RNA folding models, such that each nucleic acid sequence in the plurality of nucleic acid sequences is associated with at least two predicted secondary structures;
   c) determining a structural similarity score, the determining comprising quantifying differences between the at least two predicted secondary structures associated with each nucleic acid sequence, that were predicted in step b);
   d) selecting a nucleic acid sequence with a higher structural similarity score than at least one other nucleic acid sequence in the plurality of nucleic acid sequences wherein the selected nucleic acid sequence accumulates at higher levels when expressed in a host cell compared to accumulation of at least one of the other nucleic acids from the plurality of nucleic acids, said at least one other nucleic acid having a lower structural similarity score than the selected nucleic acid; and
   e) manufacturing the selected nucleic acid sequence.

2. The method of claim 1, wherein at least one of the plurality of RNA folding models employs machine learning.

3. The method of claim 1, wherein the plurality of nucleic acid sequences encode amino acids sharing at least 95% sequence identity.

4. The method of claim 1, comprising: f) transforming a host cell with the manufactured nucleic acid sequence.

5. The method of claim 1, comprising: f) expressing the manufactured nucleic acid in a host cell.

6. The method of claim 1, wherein the nucleic acid sequence encodes for a messenger RNA.

7. The method of claim 1, wherein the plurality of RNA folding models comprise an analysis selected from the group consisting of Cocke-Younger Kasami, inside and outside, loop-based energy, minimum free energy, suboptimal folding, centroid, and any combination thereof.

8. The method of claim 1, wherein the at least two predicted secondary structures are a minimum free energy structure and a centroid structure.

9. The method of claim 1, wherein the structural similarity score is determined via tool selected from the group consisting of Consan, Dynalign, PMcomp, Stemloc, Foldalign, locARNA, SPARSE, MARNA, FoldAlignM, Murlet, CARNA, RAF, RNAforester, RNAdistance, RNAStrAt, RNApdist, and any combination thereof.

10. The method of claim 1, wherein the structural similarity score is a ranking of the plurality of nucleic acid sequences based on the relative similarity of each nucleic acid sequences' predicted secondary structures.

11. The method of claim 1, wherein the structural similarity score is based on degree of curve overlap in a graph depicting number of base pairs at each position of the predicted secondary structures of each nucleic acid sequence.

12. The method of claim 1, wherein the structure similarity score is based on the degree of curve overlap of the predicted secondary structures of each nucleic acid sequence, plotted in a mountain plot.

13. The method of claim 1, wherein the structural similarity score is based on the correlation of curves representing the predicted secondary structures for each nucleic acid sequence in a graph depicting number of base pairs at each position.

14. The method of claim 11, wherein the degree of curve overlap is calculated by methodology selected from the group consisting of least squares, curve length measure, and any combination thereof.

* * * * *

SEQUENCE LISTING

```
Sequence total quantity: 831
SEQ ID NO: 1           moltype = DNA  length = 318
FEATURE                Location/Qualifiers
misc_feature           1..318
                       note = Optimized para-kappa-casein truncated version 1
                       (paraOKC1-T)
```

```
source                   1..318
                         mol_type = other DNA
                         organism = synthetic construct
SEQUENCE: 1
caagagcaga atcaagagca gccaatccgt tgtgagaagg acgagaggtt cttctcagac   60
aagatcgcca aatatatacc catacaatat gtactctcac gctaccctag ctacgggctt  120
aactactatc agcaaaaacc tgtagcactg ataaataacc agtttctccc ctatccctat  180
tatgctaaac ctgccgccgt gaggagtcca gcacaaatac ttcagtggca agtgctcagt  240
aacaccgtgc cagcaaaaag ctgccaggct cagcccacca caatggcccg tcatccccat  300
cctcacctta gcttcatg                                                318

SEQ ID NO: 2             moltype = AA  length = 106
FEATURE                  Location/Qualifiers
REGION                   1..106
                         note = Optimized para-kappa-casein truncated version 1
                           (paraOKC1-T)
source                   1..106
                         mol_type = protein
                         organism = synthetic construct
SEQUENCE: 2
QEQNQEQPIR CEKDERFFSD KIAKYIPIQY VLSRYPSYGL NYYQQKPVAL INNQFLPYPY   60
YAKPAAVRSP AQILQWQVLS NTVPAKSCQA QPTTMARHPH PHLSFM                 106

SEQ ID NO: 3             moltype = DNA  length = 507
FEATURE                  Location/Qualifiers
misc_feature             1..507
                         note = Optimized kappa-casein truncated version 1 (OKC1-T)
source                   1..507
                         mol_type = other DNA
                         organism = synthetic construct
SEQUENCE: 3
caagagcaga atcaagagca gccaatccgt tgtgagaagg acgagaggtt cttctcagac   60
aagatcgcca aatatatacc catacaatat gtactctcac gctaccctag ctacgggctt  120
aactactatc agcaaaaacc tgtagcactg ataaataacc agtttctccc ctatccctat  180
tatgctaaac ctgccgccgt gaggagtcca gcacaaatac ttcagtggca agtgctcagt  240
aacaccgtgc cagcaaaaag ctgccaggct cagcccacca caatggcccg tcatccccat  300
cctcacctta gcttcatggc aatcccacca agaagaatc aagacaagac cgaaatacct  360
accatcaaca caattgcatc tggagagcct accagtacac caacaactga ggcagtagag  420
tctactgttg ctacccttga ggacagcccc gaggttatag agtccccacc tgagataaat  480
accgtgcagg tgacaagtac cgccgta                                      507

SEQ ID NO: 4             moltype = AA  length = 169
FEATURE                  Location/Qualifiers
REGION                   1..169
                         note = Optimized kappa-casein truncated version 1 (OKC1-T)
source                   1..169
                         mol_type = protein
                         organism = synthetic construct
SEQUENCE: 4
QEQNQEQPIR CEKDERFFSD KIAKYIPIQY VLSRYPSYGL NYYQQKPVAL INNQFLPYPY   60
YAKPAAVRSP AQILQWQVLS NTVPAKSCQA QPTTMARHPH PHLSFMAIPP KKNQDKTEIP  120
TINTIASGEP TSTPTTEAVE STVATLEDSP EVIESPPEIN TVQVTSTAV              169

SEQ ID NO: 5             moltype = DNA  length = 627
FEATURE                  Location/Qualifiers
misc_feature             1..627
                         note = Optimized beta-casein truncated version 2 (OBC-T2)
source                   1..627
                         mol_type = other DNA
                         organism = synthetic construct
SEQUENCE: 5
cgcgaactgg aagagttgaa cgtaccagga gagattgtag aatcactgag ctcctcagag   60
gagtctatta ctcgtatcaa caagaagata gagaagttcc aatccgagga gcaacaacaa  120
acagaggacg aattgcagga caagatacat cctttcgcac agaccccagag cctcgtctat  180
cccctttccag gtccaatccc taactctctc cccagaata tcccacccttt gactcagact  240
cccgtggtcg tacccccttt cttgcaaccc gaggtgatgg gggtttctaa agtcaaagag  300
gctatggctc ctaaacataa ggaaatgcct tttcccaaat atccagtgga gccattcact  360
gagagccagt ctctgacact tacagatgtg gaaaacttgc acctgccctt gccacttttg  420
cagtcctgga tgcaccaacc acatcaaccc ttgcccccca cagtgatgtt tcctccacaa  480
tcagttctta gtctctccca aagcaaagtc cttccagtgc ctcagaaggc cgtcccctac  540
ccccagagag atatgccaat acaggcattc ttgctttacc aggaaccagt gctcggtcct  600
gtacgtggcc cattccctat catagtg                                      627

SEQ ID NO: 6             moltype = AA  length = 209
FEATURE                  Location/Qualifiers
REGION                   1..209
                         note = Optimized beta-casein truncated version 2 (OBC-T2)
source                   1..209
                         mol_type = protein
```

```
                            organism = synthetic construct
SEQUENCE: 6
RELEELNVPG EIVESLSSSE ESITRINKKI EKFQSEEQQQ TEDELQDKIH PFAQTQSLVY   60
PFPGPIPNSL PQNIPPLTQT PVVVPPFLQP EVMGVSKVKE AMAPKHKEMP FPKYPVEPFT  120
ESQSLTLTDV ENLHLPLPLL QSWMHQPHQP LPPTVMFPPQ SVLSLSQSKV LPVPQKAVPY  180
PQRDMPIQAF LLYQEPVLGP VRGPFPIIV                                   209

SEQ ID NO: 7                moltype = DNA   length = 597
FEATURE                     Location/Qualifiers
misc_feature                1..597
                            note = Optimized alpha S1-casein truncated version 1(OaS1-T)
source                      1..597
                            mol_type = other DNA
                            organism = synthetic construct
SEQUENCE: 7
cgcccaaaac atcccataaa acatcaagga ttgccccagg aagtactcaa cgagaatctc   60
ctccgttttt tcgttgctcc ttttccccgaa gtgttcggga aggaaaaagt aaacgagctt  120
tcaaaggaca tcggctctga aagtaccgag gatcaggcta tggaagatat caagcaaatg  180
gaggccgaat ctataagttc ttcagaagaa atagttccca actcagtgga gcagaagcac  240
attcagaaag aagacgtgcc cagcgagcgc tatctgggat atttggaaca gctgctcaga  300
ctgaaaaagt acaaggtgcc tcagctcgaa atcgtaccca atagtgctga gaaaggttg   360
cactcaatga aagaggggat tcacgcacaa caaaaagctg ctatgatcgg agtaaatcaa  420
gaactggcat acttttatcc cgagttgttt cgccaattct atcaactgga tgcctaccct  480
tccggtgcat ggtactacgt accctcggt actcaatata ccgatgctcc ctccttttcc  540
gacattccta atcctatagg ttccgagaat agcgaaaaga ccaccatgcc cttatgg    597

SEQ ID NO: 8                moltype = AA   length = 199
FEATURE                     Location/Qualifiers
REGION                      1..199
                            note = Optimized alpha S1-casein truncated version 1(OaS1-T)
source                      1..199
                            mol_type = protein
                            organism = synthetic construct
SEQUENCE: 8
RPKHPIKHQG LPQEVLNENL LRFFVAPFPE VFGKEKVNEL SKDIGSESTE DQAMEDIKQM   60
EAESISSSEE IVPNSVEQKH IQKEDVPSER YLGYLEQLLR LKKYKVPQLE IVPNSAEERL  120
HSMKEGIHAQ QKEPMIGVNQ ELAYFYPELF RQFYQLDAYP SGAWYYVPLG TQYTDAPSFS  180
DIPNPIGSEN SEKTTMPLW                                              199

SEQ ID NO: 9                moltype = DNA   length = 486
FEATURE                     Location/Qualifiers
misc_feature                1..486
                            note = Optimized Beta Lactoglobulin 1 (OLG1)
source                      1..486
                            mol_type = other DNA
                            organism = synthetic construct
SEQUENCE: 9
ttgatcgtaa cacagactat gaagggtctt gatatacaga aggtggccgg gacttggtac   60
agtttggcaa tggccgcatc cgacatctcc ttgttggacg cacaatcagc cccattgcgt  120
gtgtacgtag aagagcttaa accaactccc gaggggggatc tggaaattct gctccagaaa  180
tgggagaacg gtgagtgcgc ccagaagaag atcatcgaag aagaccaa aattccagca   240
gtattcaaaa tcgacgcatt gaacgaaaat aaggtgctcg tactggacac tgattataag  300
aagtatctcc ttttctgtat ggagaactca gcagagcctg aacagagtct tgcctgccaa  360
tgccttgttc gtaccccaga ggtagatgat gaagctctgg aaaagttcga taaggccctt  420
aaggctctgc ctatgcacat taggcttct ttcaatccaa ctcaacttga ggaacaatgt  480
cacatt                                                            486

SEQ ID NO: 10               moltype = AA   length = 162
FEATURE                     Location/Qualifiers
REGION                      1..162
                            note = Optimized Beta Lactoglobulin 1 (OLG1)
source                      1..162
                            mol_type = protein
                            organism = synthetic construct
SEQUENCE: 10
LIVTQTMKGL DIQKVAGTWY SLAMAASDIS LLDAQSAPLR VYVEELKPTP EGDLEILLQK   60
WENGECAQKK IIAEKTKIPA VFKIDALNEN KVLVLDTDYK KYLLFCMENS AEPEQSLACQ  120
CLVRTPEVDD EALEKFDKAL KALPMHIRLS FNPTQLEEQC HI                    162

SEQ ID NO: 11               moltype = DNA   length = 486
FEATURE                     Location/Qualifiers
misc_feature                1..486
                            note = Optimized Beta Lactoglobulin 2 (OLG2)
source                      1..486
                            mol_type = other DNA
                            organism = synthetic construct
SEQUENCE: 11
cttattgtga cccaaaccat gaagggcctc gacattcaaa aggttgccgg aacctggtac   60
tcccttgcta tggctgcttc cgatatctcc ttgctcgatg ctcaatccgc tccacttagg  120
```

```
gtgtacgtgg aagagttgaa gccaactcca gagggcgatc ttgagatctt gcttcaaaag    180
tgggagaacg atgagtgcgc ccagaagaag attatcgccg aaaagaccaa gattcccgcc    240
gtgttcaaga tcgatgctct caacgagaac aaggtgctcg tgctcgatac cgactacaag    300
aagtaccttc tcgtctgcat ggaaaactcc gctgagccag agcaatctct tgtttgccaa    360
tgccttgtga ggaccccaga ggttgacgat gaagctcttg agaagttcga caaggctctc    420
aaggctttgc ctatgcacat ccgccttagc ttcaacccaa ctcagcttga ggaacagtgc    480
cacatc                                                               486

SEQ ID NO: 12            moltype = DNA  length = 486
FEATURE                  Location/Qualifiers
misc_feature             1..486
                         note = Optimized Beta Lactoglobulin 3 (OLG3)
source                   1..486
                         mol_type = other DNA
                         organism = synthetic construct
SEQUENCE: 12
ctcattgtta cacaaaccat gaagggtctt gacattcaga aggttgctgg gacatggtat     60
tcactagcga tggctgcttc tgatatctcc ctgttggatg cacagtctgc ccccctgaga    120
gtgtatgttg aagaactgaa accgacacct gaaggagact tggaaatttt actccagaaa    180
tgggaaaatg atgagtgtgc ccaaaagaag ataatagccg agaagaccaa aattcctgct    240
gtgtttaaga ttgatgcttt gaatgagaac aaagtactag tcctcgacac tgattacaag    300
aaatacttat tagtgtgcat ggaaaacagc gcagagccag acaatcact tgtttgtcaa     360
tgtttggtcc gtactccaga ggtagatgat gaagcattgg agaaatttga taaagcattg    420
aaggcacttc caatgcatat aaggcttagt ttcaatccta ctcagcttga agagcaatgc    480
cacatc                                                               486

SEQ ID NO: 13            moltype = DNA  length = 486
FEATURE                  Location/Qualifiers
misc_feature             1..486
                         note = Optimized Beta Lactoglobulin 4 (OLG4)
source                   1..486
                         mol_type = other DNA
                         organism = synthetic construct
SEQUENCE: 13
cttatagtaa ctcaaaccat gaagggactt gatatccaaa aagttgcagg aacctggtac     60
tcactggcta tggcagcttc cgacatctcc ttgttggacg cacaatccgc accattgcgc    120
gtctacgttg aggagttgaa acctacacca gaggggatc ttgagatttt gctccagaaa    180
tgggagaacg acgagtgtgc ccagaaaaaa attatagcag agaagactaa aattcctgct    240
gttttttaaga ttgatgccct gaacgagaat aagtactgg tcctcgacac tgattataaa    300
aagtatttgc tggtgtgtat ggagaacagt gctgaacctg aacagagcct ggtctgtcaa    360
tgtcttgtaa ggacacctga ggttgatgac gaggcacttg aaaaattcga caaggccctt    420
aaggctctgc ctatgcacat ccgtctgagt ttcaaccca ctcagttgga ggaacaatgt     480
catatt                                                               486

SEQ ID NO: 14            moltype =      length =
SEQUENCE: 14
000

SEQ ID NO: 15            moltype =      length =
SEQUENCE: 15
000

SEQ ID NO: 16            moltype =      length =
SEQUENCE: 16
000

SEQ ID NO: 17            moltype =      length =
SEQUENCE: 17
000

SEQ ID NO: 18            moltype =      length =
SEQUENCE: 18
000

SEQ ID NO: 19            moltype =      length =
SEQUENCE: 19
000

SEQ ID NO: 20            moltype =      length =
SEQUENCE: 20
000

SEQ ID NO: 21            moltype =      length =
SEQUENCE: 21
000

SEQ ID NO: 22            moltype =      length =
SEQUENCE: 22
000
```

| | | |
|---|---|---|
| SEQ ID NO: 23 SEQUENCE: 23 | moltype = 000 | length = |
| SEQ ID NO: 24 SEQUENCE: 24 | moltype = 000 | length = |
| SEQ ID NO: 25 SEQUENCE: 25 | moltype = 000 | length = |
| SEQ ID NO: 26 SEQUENCE: 26 | moltype = 000 | length = |
| SEQ ID NO: 27 SEQUENCE: 27 | moltype = 000 | length = |
| SEQ ID NO: 28 SEQUENCE: 28 | moltype = 000 | length = |
| SEQ ID NO: 29 SEQUENCE: 29 | moltype = 000 | length = |
| SEQ ID NO: 30 SEQUENCE: 30 | moltype = 000 | length = |
| SEQ ID NO: 31 SEQUENCE: 31 | moltype = 000 | length = |
| SEQ ID NO: 32 SEQUENCE: 32 | moltype = 000 | length = |
| SEQ ID NO: 33 SEQUENCE: 33 | moltype = 000 | length = |
| SEQ ID NO: 34 SEQUENCE: 34 | moltype = 000 | length = |
| SEQ ID NO: 35 SEQUENCE: 35 | moltype = 000 | length = |
| SEQ ID NO: 36 SEQUENCE: 36 | moltype = 000 | length = |
| SEQ ID NO: 37 SEQUENCE: 37 | moltype = 000 | length = |
| SEQ ID NO: 38 SEQUENCE: 38 | moltype = 000 | length = |
| SEQ ID NO: 39 SEQUENCE: 39 | moltype = 000 | length = |
| SEQ ID NO: 40 SEQUENCE: 40 | moltype = 000 | length = |
| SEQ ID NO: 41 SEQUENCE: 41 | moltype = 000 | length = |
| SEQ ID NO: 42 SEQUENCE: 42 | moltype = | length = |

000

SEQ ID NO: 43         moltype =    length =
SEQUENCE: 43
000

SEQ ID NO: 44         moltype =    length =
SEQUENCE: 44
000

SEQ ID NO: 45         moltype =    length =
SEQUENCE: 45
000

SEQ ID NO: 46         moltype =    length =
SEQUENCE: 46
000

SEQ ID NO: 47         moltype =    length =
SEQUENCE: 47
000

SEQ ID NO: 48         moltype =    length =
SEQUENCE: 48
000

SEQ ID NO: 49         moltype =    length =
SEQUENCE: 49
000

SEQ ID NO: 50         moltype =    length =
SEQUENCE: 50
000

SEQ ID NO: 51         moltype =    length =
SEQUENCE: 51
000

SEQ ID NO: 52         moltype =    length =
SEQUENCE: 52
000

SEQ ID NO: 53         moltype =    length =
SEQUENCE: 53
000

SEQ ID NO: 54         moltype =    length =
SEQUENCE: 54
000

SEQ ID NO: 55         moltype =    length =
SEQUENCE: 55
000

SEQ ID NO: 56         moltype =    length =
SEQUENCE: 56
000

SEQ ID NO: 57         moltype =    length =
SEQUENCE: 57
000

SEQ ID NO: 58         moltype =    length =
SEQUENCE: 58
000

SEQ ID NO: 59         moltype =    length =
SEQUENCE: 59
000

SEQ ID NO: 60         moltype =    length =
SEQUENCE: 60
000

SEQ ID NO: 61         moltype =    length =
SEQUENCE: 61
000

SEQ ID NO: 62         moltype =    length =

| | | |
|---|---|---|
| SEQUENCE: 62<br>000 | | |
| SEQ ID NO: 63<br>SEQUENCE: 63<br>000 | moltype = | length = |
| SEQ ID NO: 64<br>SEQUENCE: 64<br>000 | moltype = | length = |
| SEQ ID NO: 65<br>SEQUENCE: 65<br>000 | moltype = | length = |
| SEQ ID NO: 66<br>SEQUENCE: 66<br>000 | moltype = | length = |
| SEQ ID NO: 67<br>SEQUENCE: 67<br>000 | moltype = | length = |
| SEQ ID NO: 68<br>SEQUENCE: 68<br>000 | moltype = | length = |
| SEQ ID NO: 69<br>SEQUENCE: 69<br>000 | moltype = | length = |
| SEQ ID NO: 70<br>SEQUENCE: 70<br>000 | moltype = | length = |
| SEQ ID NO: 71<br>SEQUENCE: 71<br>000 | moltype = | length = |
| SEQ ID NO: 72<br>SEQUENCE: 72<br>000 | moltype = | length = |
| SEQ ID NO: 73<br>SEQUENCE: 73<br>000 | moltype = | length = |
| SEQ ID NO: 74<br>SEQUENCE: 74<br>000 | moltype = | length = |
| SEQ ID NO: 75<br>SEQUENCE: 75<br>000 | moltype = | length = |
| SEQ ID NO: 76<br>SEQUENCE: 76<br>000 | moltype = | length = |
| SEQ ID NO: 77<br>SEQUENCE: 77<br>000 | moltype = | length = |
| SEQ ID NO: 78<br>SEQUENCE: 78<br>000 | moltype = | length = |
| SEQ ID NO: 79<br>SEQUENCE: 79<br>000 | moltype = | length = |
| SEQ ID NO: 80<br>SEQUENCE: 80<br>000 | moltype = | length = |
| SEQ ID NO: 81<br>SEQUENCE: 81<br>000 | moltype = | length = |

| | | |
|---|---|---|
| SEQ ID NO: 82 | moltype = length = | |
| SEQUENCE: 82 | | |
| 000 | | |

SEQ ID NO: 83 moltype = AA length = 621
FEATURE Location/Qualifiers
REGION 1..621
 note = Optimized alpha S2-casein truncated version 1(OaS2-T)
source 1..621
 mol_type = protein
 organism = synthetic construct
SEQUENCE: 83

```
AAGAATACTA TGGAACACGT AAGCTCAAGT GAAGAATCTA ATAATAAGTCA AGAGACATAT  60
AAGCAAGAGA AAAACATGGC AATAAATCCC TCCAAGGAGA ATCTTTGTAG CACTTTTTGC  120
AAAGAAGTTG TGAGAAATGC AAATGAGGAA GAATACTCAA TAGGCAGCTC TTCCGAAGAA  180
TCTGCTGAAG TCGCTACTGA AGAGGTCAAA ATAACAGTTG ACGACAAGCA TTATCAAAAA  240
GCCCTGAATG AAATAAACCA GTTCTACCAA AAATTTCCCC AATACCTCCA GTACCTTTAT  300
CAAGGACCCA TAGTCCTCAA CCCTTGGGAT CAGGTCAAGC GTAATGCTGT TCCAATAACA  360
CCAACACTCA ATCGTGAACA ACTGTCTACC TCAGAAGAAA ATTCCAAAAA AACTGTGGAT  420
ATGGAAAGTA CAGAAGTTTT TACTAAAAAG ACCAAGCTCA CCGAGGAGGA AAAAAATAGA  480
TTGAATTTTC TTAAGAAGAT CAGTCAACGC TATCAGAAGT TCGCCCTTCC ACAATACCTC  540
AAGACTGTAT ACCAACATCA GAAGGCCATG AAGCCTTGGA TTCAGCCCAA AACAAAGGTA  600
ATCCCCTATG TTAGATACTT G  621
```

SEQ ID NO: 84 moltype = AA length = 207
FEATURE Location/Qualifiers
REGION 1..207
 note = Optimized alpha S2-casein truncated version 1(OaS2-T)
source 1..207
 mol_type = protein
 organism = synthetic construct
SEQUENCE: 84

```
KNTMEHVSSS EESIISQETY KQEKNMAINP SKENLCSTFC KEVVRNANEE EYSIGSSSEE  60
SAEVATEEVK ITVDDKHYQK ALNEINQFYQ KFPQYLQYLY QGPIVLNPWD QVKRNAVPIT  120
PTLNREQLST SEENSKKTVD MESTEVFTKK TKLTEEEKNR LNFLKKISQR YQKFALPQYL  180
KTVYQHQKAM KPWIQPKTKV IPYVRYL  207
```

SEQ ID NO: 85 moltype = AA length = 171
FEATURE Location/Qualifiers
source 1..171
 mol_type = protein
 organism = Capra hircus
SEQUENCE: 85

```
QEQNQEQPIC CEKDERFFDD KIAKYIPIQY VLSRYPSYGL NYYQQRPVAL INNQFLPYPY  60
YAKPVAVRSP AQTLQWQVLP NTVPAKSCQD QPTTLARHPH PHLSFMAIPP KKDQDKTEVP  120
AINTIASAEP TVHSTPTTEA IVNTVDNPEA SSESIASASE TNTAQVTSTE V  171
```

SEQ ID NO: 86 moltype = AA length = 171
FEATURE Location/Qualifiers
source 1..171
 mol_type = protein
 organism = Ovis aries
SEQUENCE: 86

```
QEQNQEQRIC CEKDERFFDD KIAKYIPIQY VLSRYPSYGL NYYQQRPVAL INNQFLPYPY  60
YAKPVAVRSP AQTLQWQVLP NAVPAKSCQD QPTAMARHPH PHLSFMAIPP KKDQDKTEIP  120
AINTIASAEP TVHSTPTTEA VVNAVDNPEA SSESIASAPE TNTAQVTSTE V  171
```

SEQ ID NO: 87 moltype = AA length = 165
FEATURE Location/Qualifiers
source 1..165
 mol_type = protein
 organism = Bubalus bubalis
SEQUENCE: 87

```
QEQNQEQPIR CEKEERFFND KIAKYIPIQY VLSRYPSYGL NYYQQKPVAL INNQFLPYPY  60
YAKPAAVRSP AQILQWQVLP NTVPAKSCQA QPTTMTRHPH PHLSFMAIPP KKNQDKTEIP  120
TINTIVSVEP TSTPTTEAIE NTVATLEASS EVIESVPETN TAQVT  165
```

SEQ ID NO: 88 moltype = AA length = 162
FEATURE Location/Qualifiers
source 1..162
 mol_type = protein
 organism = Camelus dromedarius
SEQUENCE: 88

```
EVQNQEQPTC FEKVERLLNE KTVKYFPIQF VQSRYPSYGI NYYQHRLAVP INNQFIPYPN  60
YAKPVAIRLH AQIPQCQALP NIDPPTVERR PRPRPSFIAI PPKKTQDKTV NPAINTVATV  120
EPPVIPTAEP AVNTVVIAEA SSEFITTSTP ETTTVQITST EI  162
```

SEQ ID NO: 89 moltype = AA length = 162
FEATURE Location/Qualifiers

```
source                  1..162
                        mol_type = protein
                        organism = Camelus bactrianus
SEQUENCE: 89
EVQNQEQPTC CEKVERLLNE KTVKYFPIQF VQSRYPSYGI NYYQHRLAVP INNQFIPYPN    60
YAKPVAIRLH AQIPQCQALP NIDPPTVERR PRPRPSFIAI PPKKTQDKTV NPAINTVATV   120
EPPVIPTAEP AVNTVVIAEA SSEFITTSTP ETTTVQITST EI                     162

SEQ ID NO: 90           moltype = AA   length = 173
FEATURE                 Location/Qualifiers
source                  1..173
                        mol_type = protein
                        organism = Bos mutus
SEQUENCE: 90
QEQNQEQPIR CEKDERFFSD KIAKYIPIQY VLSRYPSYGL NYYQQKPVAL INNQFLPYPY    60
YAKPAAVRSP AQILQWQVLS NTVPAKSCQA QPTTMARHPH PHLSFMAIPP KKNQDKTEIP   120
TINTIASGEP TSTPTTEAVE STVATLEASP EASPEVIESP PEINTVQVTS TAV          173

SEQ ID NO: 91           moltype = AA   length = 165
FEATURE                 Location/Qualifiers
source                  1..165
                        mol_type = protein
                        organism = Equus caballus
SEQUENCE: 91
EVQNQEQPTC HKNDERFFDL KTVKYIPIYY VLNSSPRYEP IYYQHRLALL INNQHMPYQY    60
YARPAAVRPH VQIPQWQVLP NIYPSTVVRH PCPHPSFIAI PPKKLQEITV IPKINTIATV   120
EPTPIPTPEP TVNNAVIPDA SSEFIIASTP ETTTVPVTSP VVQKL                  165

SEQ ID NO: 92           moltype = AA   length = 162
FEATURE                 Location/Qualifiers
source                  1..162
                        mol_type = protein
                        organism = Equus asinus
SEQUENCE: 92
EVQNQEQPTC RKNDERFFDL KTVKYIPIYY VLNSSPRNEP IYYQHRLAVL INNQHMPYQY    60
YARPAAVRPH VQIPQWQVLP NIYPSTVVRH PRPHPSFIAI PPKKLQEKTV IPKINTIATV   120
EPTPIPTPEP TVNNAVIPDA SSEFIIASTP ETTTVPVTSP VV                     162

SEQ ID NO: 93           moltype = AA   length = 122
FEATURE                 Location/Qualifiers
source                  1..122
                        mol_type = protein
                        organism = Rangifer tarandus
SEQUENCE: 93
VALINNQFLP YPYYAKPGAV RSPAQILQWQ VLPNTVPAKS CQAQPTTLAR HPHPRLSFMA    60
IPPKKNQDKT DIPTINTIAT VESTITPTTE AIVDTVATLE ASSEVIESAP ETNTDQVTST   120
VV                                                                 122

SEQ ID NO: 94           moltype = AA   length = 141
FEATURE                 Location/Qualifiers
source                  1..141
                        mol_type = protein
                        organism = Alces alces
SEQUENCE: 94
KIVKYIPIQY ALSRYPSYGL SYYQHRPVAL INNQFLPYPY YAKPGAVRSP AQILQWQVLP    60
NTVPAKSCQA QPTTMARHPR PRLSFMAIPP KKNQDKTDIP TINTIATVES TITPTTEAIE   120
DNVATLEASS EVIESAPETN T                                            141

SEQ ID NO: 95           moltype = AA   length = 162
FEATURE                 Location/Qualifiers
source                  1..162
                        mol_type = protein
                        organism = Vicugna pacos
SEQUENCE: 95
EVQNQEQPTC CEKVERLLNE KTVKYFPIQF VQSRYPSYGI NYYQHRLAVP INNQFIPYPN    60
YAKPVAIRLH AQIPQCQALP NIDPPTVERR PRPRPSFIAI PPKKTQDKTV IPAINTVATA   120
EPPVIPTAEP VVNTVVIAEA SSEFITTSTP ETTTVQITST EI                     162

SEQ ID NO: 96           moltype = AA   length = 160
FEATURE                 Location/Qualifiers
source                  1..160
                        mol_type = protein
                        organism = Bos indicus
SEQUENCE: 96
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEDS PEVIESPPEI NTVQVTSTAV                        160

SEQ ID NO: 97           moltype = AA   length = 162
```

| FEATURE | Location/Qualifiers |
|---|---|
| source | 1..162<br>mol_type = protein<br>organism = Lama glama |

SEQUENCE: 97
```
EVQNQEQPTC CEKVERLLNE KTVKYFPIQF VQSRYPSYGI NYYQHRLAVP INNQFIPYPN   60
YAKPVAIRLH AQIPQCQALP NIDPPTVERR PRPRPSFIAI PPKKTQDKTV IPAINTVATV  120
EPPVIPTAEP VVNTVVIAEA SSEFITTSTP ETTTVQITST EI                    162
```

| SEQ ID NO: 98 | moltype = AA  length = 162 |
|---|---|
| FEATURE | Location/Qualifiers |
| source | 1..162<br>mol_type = protein<br>organism = Homo sapiens |

SEQUENCE: 98
```
EVQNQKQPAC HENDERPFYQ KTAPYVPMYY VPNSYPYYGT NLYQRRPAIA INNPYVPRTY   60
YANPAVVRPH AQIPQRQYLP NSHPPTVVRR PNLHPSFIAI PPKKIQDKII IPTINTIATV  120
EPTPAPATEP TVDSVVTPEA FSESIITSTP ETTTVAVTPP TA                    162
```

| SEQ ID NO: 99 | moltype = AA  length = 199 |
|---|---|
| FEATURE | Location/Qualifiers |
| source | 1..199<br>mol_type = protein<br>organism = Capra hircus |

SEQUENCE: 99
```
RPKHPINHRG LSPEVPNENL LRFVVAPFPE VFRKENINEL SKDIGSESTE DQAMEDAKQM   60
KAGSSSSSEE IVPNSAEQKY IQKEDVPSER YLGYLEQLLR LKKYNVPQLE IVPKSAEEQL  120
HSMKEGNPAH QKQPMIAVNQ ELAYFYPQLF RQFYQLDAYP SGAWYYLPLG TQYTDAPSFS  180
DIPNPIGSEN SGKTTMPLW                                              199
```

| SEQ ID NO: 100 | moltype = AA  length = 199 |
|---|---|
| FEATURE | Location/Qualifiers |
| source | 1..199<br>mol_type = protein<br>organism = Ovis aries |

SEQUENCE: 100
```
RPKHPIKHQG LSSEVLNENL LRFVVAPFPE VFRKENINEL SKDIGSESIE DQAMEDAKQM   60
KAGSSSSSEE IVPNSAEQKY IQKEDVPSER YLGYLEQLLR LKKYNVPQLE IVPKSAEEQL  120
HSMKEGNPAH QKQPMIAVNQ ELAYFYPQLF RQFYQLDAYP SGAWYYLPLG TQYTDAPSFS  180
DIPNPIGSEN SGKITMPLW                                              199
```

| SEQ ID NO: 101 | moltype = AA  length = 199 |
|---|---|
| FEATURE | Location/Qualifiers |
| source | 1..199<br>mol_type = protein<br>organism = Bubalus bubalis |

SEQUENCE: 101
```
RPKQPIKHQG LPQGVLNENL LRFFVAPFPE VFGKEKVNEL STDIGSESTE DQAMEDIKQM   60
EAESISSSEE IVPISVEQKH IQKEDVPSER YLGYLEQLLR LKKYNVPQLE IVPNLAEEQL  120
HSMKEGIHAQ QKEPMIGVNQ ELAYFYPQLF RQFYQLDAYP SGAWYYVPLG TQYPDAPSFS  180
DIPNPIGSEN SGKTTMPLW                                              199
```

| SEQ ID NO: 102 | moltype = AA  length = 154 |
|---|---|
| FEATURE | Location/Qualifiers |
| source | 1..154<br>mol_type = protein<br>organism = Camelus dromedarius |

SEQUENCE: 102
```
DTERKESGSS SSEEVVSSTT EQKDILKEDM PSQRYLEELH RLNKYKLLQL EAIRDQKLIP   60
RVKLSSHPYL EQLYRINEDN HPQLGEPVKV VTQEQAYFHL EPFPQFFQLG ASPYVAWYYP  120
PQVMQYIAHP SSYDTPEGIA SEDGGKTDVM PQWW                             154
```

| SEQ ID NO: 103 | moltype = AA  length = 207 |
|---|---|
| FEATURE | Location/Qualifiers |
| source | 1..207<br>mol_type = protein<br>organism = Camelus bactrianus |

SEQUENCE: 103
```
RPKYPLRYPE VFQNEPDSIE EVLNKRKILE LAVVSPIQFR QENIDELKDT RNEPTEDHIM   60
EDTERKESGS SSSEEVVSST TEQKDILKED MPSQRYLEEL HRLNKYKLLQ LEAIRDQKLI  120
PRVKLSSHPY LEQLYRINED NHPQLGEPVK VVTQPFPQFF QLGASPYVAW YYPPQVMQYI  180
AHPSSYDTPE GIASEDGGKT DVMPQWW                                     207
```

| SEQ ID NO: 104 | moltype = AA  length = 199 |
|---|---|
| FEATURE | Location/Qualifiers |
| source | 1..199<br>mol_type = protein<br>organism = Bos mutus |

SEQUENCE: 104

```
RPKHPIKHQG LPQEVLNENL LRFFVAPFPE VFGKEKVNEL SKDIGSESTE DQAMEDIKQM    60
EAESISSSEE IVPNSVEQKH IQKEDVPSEH YLGYLEQLLR LKKYKVPQLE IVPNSAEERL   120
HSMKEGIHAQ QKEPMIGVNQ ELAYFYPELF RQFYQLDAYP SGAWYYVPLG TQYTDAPSFS   180
DIPNPIGSEN SGKTTMPLW                                                199

SEQ ID NO: 105         moltype = AA  length = 226
FEATURE                Location/Qualifiers
source                 1..226
                       mol_type = protein
                       organism = Equus caballus
SEQUENCE: 105
REKEELNVSS ETVESLSSNE PDSSSEESIT HINKEKLQKF KHEGQQQREV ERQDKISRFV    60
QPQPVVYPYA EPVPYAVVPQ SILPLAQPPI LPFLQPEIME VSQAKETILP KRKVMPFLKS   120
PIVPFSERQI LNPTNGENLR LPVHLIQPFM HQVPQSLLQT LMLPSQPVLS PPQSKVAPFP   180
QPVVPYPQRD TPVQAFLLYQ DPRLGPTGEL DPATQPIVAV HNPVIV                  226

SEQ ID NO: 106         moltype = AA  length = 202
FEATURE                Location/Qualifiers
source                 1..202
                       mol_type = protein
                       organism = Equus asinus
SEQUENCE: 106
RPKLPHRHPE IIQNEQDSRE KVLKERKFPS FALHTPREEY INELNRQREL LKEKQKDEHK    60
EYLIEDPEQQ ESSSTSSSEE VVPINTEQKR IPREDMLYQH TLEQLRRLSK YNQLQLQAIY   120
AQEQLIRMKE NSQRKPMRVV NQEQAYFYLE PFQPSYQLDV YPYAAWFHPA QIMQHVAYSP   180
FHDTAKLIAS ENSEKTDIIP EW                                            202

SEQ ID NO: 107         moltype = AA  length = 199
FEATURE                Location/Qualifiers
VARIANT                84
                       note = X is any amino acid
source                 1..199
                       mol_type = protein
                       organism = Bos indicus
SEQUENCE: 107
RPKHPIKHQG LPQEVLNENL LRFFVAPFPE VFGKEKVNEL SKDIGSESTE DQAMEDIKQM    60
EAESISSSEE IVPNSVEQKH IQKXDVPSER YLGYLEQLLR LKKYKVPQLE IVPNSAEERL   120
HSMKEGIHAQ QKEPMIGVNQ ELAYFYPELF RQFYQLDAYP SGAWYYVPLG TQYTDAPSFS   180
DIPNPIGSEN SGKTTMPLW                                                199

SEQ ID NO: 108         moltype = AA  length = 215
FEATURE                Location/Qualifiers
source                 1..215
                       mol_type = protein
                       organism = Lama glama
SEQUENCE: 108
RPKYPLRYPE VFQNEPDSIQ EVLNKRKILE LAVVSPIQFR QENIDELKDT RNEPTEDHIM    60
EDTERTVSGS SSSEEVVSST TEQKDILKED MPSQRILEEL HRLNYKLLQ LEAIRDQKLI    120
PRVKLSSHPY LEQLYRINED NHPQLGEPVK VVTQEQAYFH LEPFQQFFQL GASPYVAWYY   180
PPQVMQYIAH PSSHDTPEGI ASEDGGKTDV MPQWW                              215

SEQ ID NO: 109         moltype = AA  length = 170
FEATURE                Location/Qualifiers
source                 1..170
                       mol_type = protein
                       organism = Homo sapiens
SEQUENCE: 109
RPKLPLRYPE RLQNPSESSE PIPLESREEY MNGMNRQRNI LREKQTDEIK DTRNESTQNC    60
VVAEPEKMES SISSSSEEMS LSKCAEQFCR LNEYNQLQLQ AAHAQEQIRR MNENSHVQVP   120
FQQLNQLAAY PYAVWYYPQI MQYVPFPPFS DISNPTAHEN YEKNNVMLQW              170

SEQ ID NO: 110         moltype = AA  length = 208
FEATURE                Location/Qualifiers
source                 1..208
                       mol_type = protein
                       organism = Capra hircus
SEQUENCE: 110
KHKMEHVSSS EEPINIFQEI YKQEKNMAIH PREKLCTTS CEEVVRNANE EEYSIRSSSE    60
ESAEVAPEEI KITVDDKHYQ KALNEINQFY QKFPQYLQYP YQGPIVLNPW DQVKRNAGPF   120
TPTVNREQLS TSEENSKKTI DMESTEVFTK KTKLTEEEKN RLNFLKKISQ YYQKFAWPQY   180
LKTVDQHQKA MKPWTQPKTN AIPYVRYL                                      208

SEQ ID NO: 111         moltype = AA  length = 208
FEATURE                Location/Qualifiers
source                 1..208
                       mol_type = protein
                       organism = Ovis aries
SEQUENCE: 111
KHKMEHVSSS EEPINISQEI YKQEKNMAIH PREKLCTTS CEEVVRNADE EEYSIRSSSE    60
```

```
ESAEVAPEEV KITVDDKHYQ KALNEINQFY QKFPQYLQYL YQGPIVLNPW DQVKRNAGPF    120
TPTVNREQLS TSEENSKKTI DMESTEVFTK KTKLTEEEKN RLNFLKKISQ YYQKFAWPQY    180
LKTVDQHQKA MKPWTQPKTN AIPYVRYL                                      208

SEQ ID NO: 112          moltype = AA  length = 207
FEATURE                 Location/Qualifiers
source                  1..207
                        mol_type = protein
                        organism = Bubalus bubalis
SEQUENCE: 112
KHTMEHVSSS EESIISQETY KQEKNMAIHP SKENLCSTFC KEVIRNANEE EYSIGSSSEE    60
SAEVATEEVK ITVDDKHYQK ALNEINQFYQ KFPQYLQYLY QGPIVLNPWD QVKRNAVPIT    120
PTLNREQLST SEENSKKTVD MESTEVITKK TKLTEEDKNR LNFLKKISQH YQKFTWPQYL    180
KTVYQYQKAM KPWTQPKTNV IPYVRYL                                       207

SEQ ID NO: 113          moltype = AA  length = 178
FEATURE                 Location/Qualifiers
source                  1..178
                        mol_type = protein
                        organism = Camelus dromedarius
SEQUENCE: 113
KHEMDQGSSS EESINVSQQK FKQVKKVAIH PSKEDICSTF CEEAVRNIKE VESAEVPTEN    60
KISQFYQKWK FLQYLQALHQ GQIVMNPWDQ GKTRAYPFIP TVNTEQLSIS EESTEVPTEE    120
STEVFTKKTE LTEEEKDHQK FLNKIYQYYQ TFLWPEYLKT VYQYQKTMTP WNHIKRYF     178

SEQ ID NO: 114          moltype = AA  length = 178
FEATURE                 Location/Qualifiers
source                  1..178
                        mol_type = protein
                        organism = Camelus bactrianus
SEQUENCE: 114
KHEMDQGSSS EESINVSQQK FKQVKKVAIH PSKEDICSTF CEEAVRNIKE VESAEVPTEN    60
KISQFYQKWK FLQYLQALHQ GQIVMNPWDQ GKTRAYPFIP TVNTEQLSIS EESTEVPTEE    120
STEVFNKKTE LTEEEKDHQK FLNKIYQYYQ TFLWPEYLKT VYQYQKTMTP WNHIKRYF     178

SEQ ID NO: 115          moltype = AA  length = 204
FEATURE                 Location/Qualifiers
source                  1..204
                        mol_type = protein
                        organism = Bos mutus
SEQUENCE: 115
KNTMEHVSSS EESIISQETY KQEKNMAINP SKGNLCSTFC KEVVRNANEE EYSIGSSSEE    60
SAEVATEEVK ITVDDKHYQK ALNEINQFYQ KFPQYLQYLY QGPIVLNPWD QVKRNAVPIT    120
PTLNREQLST SEENSKKTVD MESTEVFTKK TKLTEEEKNR LNFLKKISQR YQKFALPQYL    180
KTVYQHQKAM KPWIQPKTKV IPYV                                          204

SEQ ID NO: 116          moltype = AA  length = 216
FEATURE                 Location/Qualifiers
source                  1..216
                        mol_type = protein
                        organism = Equus caballus
SEQUENCE: 116
KHNMEHRSSS EDSVNISQEK FKQEKYVVIP TSKESICSTS CEEATRNINE MESAKFPTEV    60
YSSSSSSEES AKFPTEREEK EVEEKHHLKQ LNKINQFYEK LNFLQYLQAL RQPRIVLTPW    120
DQTKTGDSPF IPIVNTEQLF TSEEIPKKTV DMESTEVVTE KTELTEEEKN YLKLLYYEKF    180
TLPQYFKIVR QHQTTMDPRS HRKTNSYQII PVLRYF                             216

SEQ ID NO: 117          moltype = AA  length = 221
FEATURE                 Location/Qualifiers
source                  1..221
                        mol_type = protein
                        organism = Equus asinus
SEQUENCE: 117
KHNMEHRSSS EDSVNISQEK FKQEKYVVIP TSKESICSTS CEEATRNINE MESAKFPTEV    60
YSSSSSSEES AKFPTEREEK EVEEKHHLKQ LNKINQFYEK LNFLQYLQAL RQPRIVLTPW    120
DQTKTGASPF IPIVNTEQLF TSEEIPKKTV DMESTEVVTE KTELTEEEKN YLKLLNKINQ    180
YYEKFTLPQY FKIVHQHQTT MDPQSHSKTN SYQIIPVLRY F                       221

SEQ ID NO: 118          moltype = AA  length = 192
FEATURE                 Location/Qualifiers
source                  1..192
                        mol_type = protein
                        organism = Vicugna pacos
SEQUENCE: 118
KHEMDQGSSS EESINVSQQK LKQVKKVAIH PSKEDICSTF CEEAVRNIKE VESVEVPTEN    60
KISQFYQKWK FLQYLQALHQ GQIVMNPWDQ GKTMVYPFIP TVNTEQLSIS EESTEVPTEE    120
STEVFTKKTE LTEEEKDHQK FLNKIYQYYQ TFLWPEYLKT VYQYQKTMTP WNHIKVKAYQ    180
IIPNLVSSTF YL                                                       192
```

```
SEQ ID NO: 119              moltype = AA  length = 207
FEATURE                     Location/Qualifiers
source                      1..207
                            mol_type = protein
                            organism = Bos indicus
SEQUENCE: 119
KNTMEHVSSS EESIISQETY KQEKNMAINP SKENLCSTFC KEVVRNANEE EYSIGSSSEE   60
SAEVATEEVK ITVDDKHYQK ALNEINQFYQ KFPQYLQYLY QGPIVLNPWD QVKRNAVPIT  120
PTLNREQLST SEENSKKTVD MESTEVFTKK TKLTEEEKNR LNFLKKISQR YQKFALPQYL  180
KTVYQHQKAM KPWIQPKTKV IPYVRYL                                     207

SEQ ID NO: 120              moltype = AA  length = 187
FEATURE                     Location/Qualifiers
source                      1..187
                            mol_type = protein
                            organism = Lama glama
SEQUENCE: 120
KHEMDQGSSS EESINVSQQK LKQVKKVAIH PSKEDICSTF CEEAVRNIKE VESVEVPTEN   60
KISQFYQKWK FLQYLQALHQ GQIVMNPWDQ GKTMVYPFIP TVNTEQLSIS EESTEVPTEE  120
NSKKTVDTES TEVFTKKTEL TEEEKDHQKF LNKIYQYYQT FLWPEYLKTV YQYQKTMTPW  180
NHIKRYF                                                           187

SEQ ID NO: 121              moltype = AA  length = 207
FEATURE                     Location/Qualifiers
source                      1..207
                            mol_type = protein
                            organism = Capra hircus
SEQUENCE: 121
REQEELNVVG ETVESLSSSE ESITHINKKI EKFQSEEQQQ TEDELQDKIH PFAQAQSLVY   60
PFTGPIPNSL PQNILPLTQT PVVVPPFLQP EIMGVPKVKE TMVPKHKEMP FPKYPVEPFT  120
ESQSLTLTDV EKLHLPLPLV QSWMHQPPQP LSPTVMFPPQ SVLSLSQPKV LPVPQKAVPQ  180
RDMPIQAFLL YQEPVLGPVR GPFPILV                                     207

SEQ ID NO: 122              moltype = AA  length = 207
FEATURE                     Location/Qualifiers
source                      1..207
                            mol_type = protein
                            organism = Ovis aries
SEQUENCE: 122
REQEELNVVG ETVESLSSSE ESITHINKKI EKFQSEEQQQ TEDELQDKIH PFAQAQSLVY   60
PFTGPIPNSL PQNILPLTQT PVVVPPFLQP EIMGVPKVKE TMVPKHKEMP FPKYPVEPFT  120
ESQSLTLTDV EKLHLPLPLV QSWMHQPPQP LPPTVMFPPQ SVLSLSQPKV LPVPQKAVPQ  180
RDMPIQAFLL YQEPVLGPVR GPFPILV                                     207

SEQ ID NO: 123              moltype = AA  length = 209
FEATURE                     Location/Qualifiers
source                      1..209
                            mol_type = protein
                            organism = Bubalus bubalis
SEQUENCE: 123
RELEELNVPG EIVESLSSSE ESITHINKKI EKFQSEEQQQ MEDELQDKIH PFAQTQSLVY   60
PFPGPIPKSL PQNIPPLTQT PVVVPPFLQP EIMGVSKVKE AMAPKHKEMP FPKYPVEPFT  120
ESQSLTLTDV ENLHLPLPLL QSWMHQPPQP LPPTVMFPPQ SVLSLSQSKV LPVPQKAVPY  180
PQRDMPIQAF LLYQEPVLGP VRGPFPIIV                                   209

SEQ ID NO: 124              moltype = AA  length = 217
FEATURE                     Location/Qualifiers
source                      1..217
                            mol_type = protein
                            organism = Camelus dromedarius
SEQUENCE: 124
REKEEFKTAG EALESISSSE ESITHINKQK IEKFKIEEQQ QTEDEQQDKI YTFPQPQSLV   60
YSHTEPIPYP ILPQNFLPPL QPAVMVPFLQ PKVMDVPKTK ETIIPKRKEM PLLQSPVVPF  120
TESQSLTLTD LENLHLPLPL LQSLMYQIPQ PVPQTPMIPP QSLLSLSQFK VLPVPQQMVP  180
YPQRAMPVQA VLPFQEPVPD PVRGLHPVPQ PLVPVIA                          217

SEQ ID NO: 125              moltype = AA  length = 217
FEATURE                     Location/Qualifiers
source                      1..217
                            mol_type = protein
                            organism = Camelus bactrianus
SEQUENCE: 125
REKEEFKTAG EALESISSSE ESITHINKQK IEKFKIEEQQ QTEDEQQDKI YTFPQPQSLV   60
YSHTEPIPYP ILPQNFLPPL QPAVMVPFLQ PKVMDVPKTK ETIIPKRKEM PLLQSPVVPF  120
TESQSLTLTD LENLHLPLPL LQSLMYQIPQ PVPQTPMIPP QSLLSLSQFK VLPVPQQMVP  180
YPQRAIPVQA VLPFQEPVPD PVRGLHPVPQ PLVPVIA                          217

SEQ ID NO: 126              moltype = AA  length = 209
FEATURE                     Location/Qualifiers
```

```
source                  1..209
                        mol_type = protein
                        organism = Bos mutus
SEQUENCE: 126
RELEELNVPG EIVESLSSSE ESITRINKKI EKFQSEEQQQ TEDELQDKIH PFAQTQSLVY    60
PFPGPIPNSL PQNIPPLTQT PVVVPPFLQP EVMGVSKVKE AMAPKHKEMP FPKYPVEPFT   120
ESQSLTLTDV ENLHLPLPLL QSWMHQPHQP LPPTVMFPPQ SVLSLSQSKV LPVPQKAVPY   180
PQRDMPIQAF LLYQEPVLGP VRGPFPIIV                                    209

SEQ ID NO: 127          moltype = AA  length = 226
FEATURE                 Location/Qualifiers
source                  1..226
                        mol_type = protein
                        organism = Equus caballus
SEQUENCE: 127
REKEELNVSS ETVESLSSNE PDSSSEESIT HINKEKLQKF KHEGQQQREV ERQDKISRFV    60
QPQPVVYPYA EPVPYAVVPQ SILPLAQPPI LPFLQPEIME VSQAKETILP KRKVMPFLKS   120
PIVPFSERQI LNPTNGENLR LPVHLIQPFM HQVPQSLLQP LMLPSQPVLS PPQSKVAPFP   180
QPVVPYPQRD TPVQAFLLYQ DPRLGPTGEL DPATQPIVAV HNPVIV                  226

SEQ ID NO: 128          moltype = AA  length = 226
FEATURE                 Location/Qualifiers
source                  1..226
                        mol_type = protein
                        organism = Equus asinus
SEQUENCE: 128
REKEELNVSS ETVESLSSNE PDSSSEESIT HINKEKSQKF KHEGQQQREV EHQDKISRFV    60
QPQPVVYPYA EPVPYAVVPQ NILVLAQPPI VPFLQPEIME VSQAKETILP KRKVMPFLKS   120
PIVPFSERQI LNPTNGENLR LPVHLIQPFM HQVPQSLLQT LMLPSQPVLS PPQSKVAPFP   180
QPVVPYPQRD TPVQAFLLYQ DPQLGLTGEF DPATQPIVPV HNPVIV                  226

SEQ ID NO: 129          moltype = AA  length = 141
FEATURE                 Location/Qualifiers
VARIANT                 6
                        note = X is any amino acid
VARIANT                 17
                        note = X is any amino acid
VARIANT                 65
                        note = X is any amino acid
source                  1..141
                        mol_type = protein
                        organism = Alces alces
SEQUENCE: 129
IHPFAXTQSL VYPFTGXIPY SLPQNFLPLP QTPGMVPPFL QPEIMGVSEV KETMVPKNKE    60
MPFPXYPVEP FAEGQSLTLT DVENHLPLPL LQSWMHQTP QPLPPTVMFP PQSVLSLSQP   120
KVLSVPQKAV YPQRDMPIQ A                                             141

SEQ ID NO: 130          moltype = AA  length = 173
FEATURE                 Location/Qualifiers
source                  1..173
                        mol_type = protein
                        organism = Vicugna pacos
SEQUENCE: 130
DEQQDKIYTF PQPQSLVYSH TEPIPYPILP QNFLPPLQPA VMVPFLQPKV MDVPKTKEIV    60
IPKREMPLL QSPLVPFTES QSLTLTDLEN LHLPLPLLQS LMHQIPQQVP QTPMIPPQSL   120
LSLSQFKVLP VPQQMVPYPQ RAMPVQALLP FQEPIDPVR GLHPVPQLV PVI            173

SEQ ID NO: 131          moltype = AA  length = 209
FEATURE                 Location/Qualifiers
source                  1..209
                        mol_type = protein
                        organism = Bos indicus
SEQUENCE: 131
RELEELNVPG EIVESLSSSE ESITRINKKI EKFQSEEQQQ TEDELQDKIH PFAQTQSLVY    60
PFPGPIPNSL PQNIPPLTQT PVVVPPFLQP EVMGVSKVKE AMAPKHKEMP FPKYPVEPFT   120
ESQSLTLTDV ENLHLPLPLL QSWMHQPHQP LPPTVMFPPQ SVLSLSQSKV LPVPQKAVPY   180
PQRDMPIQAF LLYQEPVLGP VRGPFPIIV                                    209

SEQ ID NO: 132          moltype = AA  length = 217
FEATURE                 Location/Qualifiers
source                  1..217
                        mol_type = protein
                        organism = Lama glama
SEQUENCE: 132
REKEEFKTAG EAVESISSSE ESITHINKQK IEKFKIEEQQ QTEDEQQDKI YTFPQPQSLV    60
YSHTEPIPYP ILPQNFLPPL QPAVMVPFLQ PKVMDVPKTK EIVIPKRKEM PLLQSPLVPF   120
TESQSLTLTD LENLHLPLPL LQSLMHQIPQ PVPQTPMIPP QSLLSLSQFK VLPVPQQMVP   180
YPQRAMPVQA LLPFQEPIPD PVRGLHPVPQ PLVPVIA                            217
```

```
SEQ ID NO: 133         moltype = AA  length = 211
FEATURE                Location/Qualifiers
source                 1..211
                       mol_type = protein
                       organism = Homo sapiens
SEQUENCE: 133
RETIESLSSS EESITEYKQK VEKVKHEDQQ QGEDEHQDKI YPSFQPQPLI YPFVEPIPYG    60
FLPQNILPLA QPAVVLPVPQ PEIMEVPKAK DTVYTKGRVM PVLKSPTIPF FDPQIPKLTD   120
LENLHLPLPL LQPLMQQVPQ PIPQTLALPP QPLWSVPQPK VLPIPQQVVP YPQRAVPVQA   180
LLLNQELLLN PTHQIYPVTQ PLAPVHNPIS V                                 211

SEQ ID NO: 134         moltype =     length =
SEQUENCE: 134
000

SEQ ID NO: 135         moltype =     length =
SEQUENCE: 135
000

SEQ ID NO: 136         moltype =     length =
SEQUENCE: 136
000

SEQ ID NO: 137         moltype =     length =
SEQUENCE: 137
000

SEQ ID NO: 138         moltype =     length =
SEQUENCE: 138
000

SEQ ID NO: 139         moltype =     length =
SEQUENCE: 139
000

SEQ ID NO: 140         moltype =     length =
SEQUENCE: 140
000

SEQ ID NO: 141         moltype =     length =
SEQUENCE: 141
000

SEQ ID NO: 142         moltype =     length =
SEQUENCE: 142
000

SEQ ID NO: 143         moltype =     length =
SEQUENCE: 143
000

SEQ ID NO: 144         moltype =     length =
SEQUENCE: 144
000

SEQ ID NO: 145         moltype =     length =
SEQUENCE: 145
000

SEQ ID NO: 146         moltype =     length =
SEQUENCE: 146
000

SEQ ID NO: 147         moltype =     length =
SEQUENCE: 147
000

SEQ ID NO: 148         moltype = AA  length = 190
FEATURE                Location/Qualifiers
source                 1..190
                       mol_type = protein
                       organism = Bos taurus
SEQUENCE: 148
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPTTEAV ESTVATLEDS PEVIESPPEI   180
NTVQVTSTAV                                                         190

SEQ ID NO: 149         moltype = AA  length = 190
```

| FEATURE | Location/Qualifiers |
|---|---|
| source | 1..190<br>mol_type = protein<br>organism = Bos taurus |

SEQUENCE: 149
```
MMKSFFLVVT ILALTLPFLG AQEQNQEQPI RCEKDERFFS DKIAKYIPIQ YVLSRYPSYG   60
LNYYQQKPVA LINNQFLPYP YYAKPAAVRS PAQILQWQVL SNTVPAKSCQ AQPTTMARHP  120
HPHLSFMAIP PKKNQDKTEI PTINTIASGE PTSTPTIEAV ESTVATLEAS PEVIESPPEI  180
NTVQVTSTAV                                                         190
```

| SEQ ID NO: 150 | moltype = AA  length = 190 |
|---|---|
| FEATURE | Location/Qualifiers |
| source | 1..190<br>mol_type = protein<br>organism = Bos taurus |

SEQUENCE: 150
```
MMKSFFLVVT ILALTLPFLG AQEQNQEQPI RCEKDERFFS DKIAKYIPIQ YVLSRYPSYG   60
LNYYQQKPVA LINNQFLPYP YYAKPAAVRS PAQILQWQVL SNTVPAKSCQ AQPTTMARHP  120
HPHLSFMAIP PKKNQDKTEI PTINTIASGE PTSTPTIEAV ESTVATLEAS PEVTESPPEI  180
NTVQVTSTAV                                                         190
```

| SEQ ID NO: 151 | moltype = AA  length = 169 |
|---|---|
| FEATURE | Location/Qualifiers |
| source | 1..169<br>mol_type = protein<br>organism = Bos taurus |

SEQUENCE: 151
```
QEQNQEQPIR CEKDERFFSD KIAKYIPIQY VLSRYPSYGL NYYQQKPVAL INNQFLPYPY   60
YAKPAAVRSP AQILQWQVLS NTVPAKSCQA QPTTMAHHPH PHLSFMAIPP KKNQDKTEIP  120
TINTIASGEP TSTPITEAVE STVATLEASP EVIESPPEIN TVQVTSTAV              169
```

| SEQ ID NO: 152 | moltype = AA  length = 190 |
|---|---|
| FEATURE | Location/Qualifiers |
| source | 1..190<br>mol_type = protein<br>organism = Bos taurus |

SEQUENCE: 152
```
MMKSFFLVVT ILALTLPFLG AQEQNQEQPI RCEKDERFFS DKIAKYIPIQ YVLSRYPSYG   60
LNYYQQKPVA LINNQFLPYP YYAKPAAVRS PAQILQWQVL SNTVPAKSCQ AQPTTMARHP  120
HPHLSFMAIP PKKNQDKTGI PTINTIASGE PTSTPTIEAV ESTVATLEAS PEVTESPPEI  180
NTVQVTSTAV                                                         190
```

| SEQ ID NO: 153 | moltype = AA  length = 160 |
|---|---|
| FEATURE | Location/Qualifiers |
| source | 1..160<br>mol_type = protein<br>organism = Bos taurus |

SEQUENCE: 153
```
RCEKDERFFS DKIAKYIPIQ YVLSRYPSYG LNYYQQKPVA LINNQFLPYP YYAKPAAVRS   60
PAQILQWQVL SNTVPAKSCQ AQPTTMARHP HPHLSFMAIP PKKNQDKTEI PTINTIASGE  120
PTSTPITEAV ESTVATLEDS PEVIESPPEI NTVQVTSTAV                        160
```

| SEQ ID NO: 154 | moltype = AA  length = 160 |
|---|---|
| FEATURE | Location/Qualifiers |
| source | 1..160<br>mol_type = protein<br>organism = Bos taurus |

SEQUENCE: 154
```
HCEKDERFFS DKIAKYIPIQ YVLSRYPSYG LNYYQQKPVA LINNQFLPYP YYAKPAAVRS   60
PAQILQWQVL SNTVPAKSCQ AQPTTMARHP HPHLSFMAIP PKKNQDKTEI PTINTIASGE  120
PTSTPTTEAV ESTVATLEDS PEVIESPPEI NTVQVTSTAV                        160
```

| SEQ ID NO: 155 | moltype = AA  length = 179 |
|---|---|
| FEATURE | Location/Qualifiers |
| source | 1..179<br>mol_type = protein<br>organism = Bos taurus |

SEQUENCE: 155
```
MMKSFFLVVT ILALTLPFLR CEKDERFFSD KIAKYIPIQY VLSRYPSYGL NYYQQKPVAL   60
INNQFLPYPY YAKPAAVRSP AQILQWQVLS NTVPAKSCQA QPTTMARHPH PHLSFMAIPP  120
KKNQDKTEIP TINTIASGEP TSTPTIEAVE STVATLEASP EVIESPPEIN TVQVTSTAV   179
```

| SEQ ID NO: 156 | moltype = AA  length = 159 |
|---|---|
| FEATURE | Location/Qualifiers |
| source | 1..159<br>mol_type = protein<br>organism = Bos taurus |

SEQUENCE: 156
```
CEKDERFFSD KIAKYIPIQY VLSRYPSYGL NYYQQKPVAL INNQFLPYPY YAKPAAVRSP   60
```

```
AQILQWQVLS NTVPAKSCQA QPTTMAHHPH PHLSFMAIPP KKNQDKTEIP TINTIASGEP    120
TSTPTTEAVE STVATLEDSP EVIESPPEIN TVQVTSTAV                          159

SEQ ID NO: 157          moltype = AA   length = 160
FEATURE                 Location/Qualifiers
source                  1..160
                        mol_type = protein
                        organism = Bos taurus
SEQUENCE: 157
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE    120
PTSTPTIEAV ESTVATLEAS PEVIESPPEI NTVQVTSTAV                         160

SEQ ID NO: 158          moltype = AA   length = 160
FEATURE                 Location/Qualifiers
source                  1..160
                        mol_type = protein
                        organism = Bos taurus
SEQUENCE: 158
RCEKDERFFS DKIAKYIPIQ YVLSRYPSYG LNYYQQKPVA LINNQFLPYP YYAKPAAVRS    60
PAQILQWQVL SNTVPAKSCQ AQPTTMACHP HPHLSFMAIP PKKNQDKTEI PTINTIASGE    120
PTSTPITEAV ESTVATLEDS PEVIESPPEI NTVQVTSTAV                         160

SEQ ID NO: 159          moltype = AA   length = 145
FEATURE                 Location/Qualifiers
source                  1..145
                        mol_type = protein
                        organism = Bos taurus
SEQUENCE: 159
YIPIQYVLSR YPSYGLNYYQ QKPVALINNQ FLPYPYYAKP AAVRSPAQIL QWQVLSNTVP    60
AKSCQAQPTT MARHPHPHLS FMAIPPKKNQ DKTEIPTINT IASGEPTSTP TTEAVESTVA    120
TLEDSPEVIE SPPEINTVQV TSTAV                                         145

SEQ ID NO: 160          moltype = AA   length = 160
FEATURE                 Location/Qualifiers
source                  1..160
                        mol_type = protein
                        organism = Bos taurus
SEQUENCE: 160
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP    120
HPHLSFMAIP PKKNQDKTEI PTINTIASGE PTSTPTTEAV                         160

SEQ ID NO: 161          moltype = AA   length = 142
FEATURE                 Location/Qualifiers
source                  1..142
                        mol_type = protein
                        organism = Bos taurus
SEQUENCE: 161
IQYVLSRYPS YGLNYYQQKP VALINNQFLP YPYYAKPAAV RSPAQILQWQ VLSNTVPAKS    60
CQAQPTTMAR HPHPHLSFMA IPPKKNQDKT EIPTINTIAS GEPTSTPITE AVESTVATLE    120
DSPEVIESPP EINTVQVTST AV                                            142

SEQ ID NO: 162          moltype = AA   length = 141
FEATURE                 Location/Qualifiers
source                  1..141
                        mol_type = protein
                        organism = Bos taurus
SEQUENCE: 162
QYVLSRYPSY GLNYYQQKPV ALINNQFLPY PYYAKPAAVR SPAQILQWQV LSNTVPAKSC    60
QAQPTTMARH PHPHLSFMAI PPKKNQDKTE IPTINTIASG EPTSTPTTEA VESTVATLED    120
SPEVIEGPPE INTVQVTSTA V                                             141

SEQ ID NO: 163          moltype = AA   length = 139
FEATURE                 Location/Qualifiers
source                  1..139
                        mol_type = protein
                        organism = Bos taurus
SEQUENCE: 163
VLSRYPSYGL NYYQQKPVAL INNQFLPYPY YAKPAAVRSP AQILQWQVLS NTVPAKSCQA    60
QPTTMARHPH PHLSFMAIPP KKNQDKTEIP TINTIASGEP TSTPTTEAVE STVATLEDSP    120
EVIESPPEIN TVQVTSTAV                                                139

SEQ ID NO: 164          moltype = AA   length = 140
FEATURE                 Location/Qualifiers
source                  1..140
                        mol_type = protein
                        organism = Bos taurus
SEQUENCE: 164
```

```
YVLSRYPSYG LNYYQQKPVA LINNQFLPYP YYAKPAAVRS PAQILQWQVL SNTVPAKSCQ    60
AQPTTMARHP HPHLSFMAIP PKKNQDKTEI PTINTIASGE PTSTPTIEAV ESTVATLEAS   120
PEVIESPPEI NTVQVTSTAV                                              140

SEQ ID NO: 165              moltype = AA   length = 192
FEATURE                     Location/Qualifiers
source                      1..192
                            mol_type = protein
                            organism = Capra hircus
SEQUENCE: 165
MMKSFFLVVT ILALTLPFLG AQEQNQEQPI CCEKDERFFD DKIAKYIPIQ YVLSRYPSYG    60
LNYYRQRPVA LINNQFLPYP YYAKPIAVRS PAQTLQWQVL PNTVPAKSCQ DQPTTLARHP   120
HPHLSFMAIP PKKDQDKTEI PAINTIASAE PTVHSTPTTE AIVNTVDNPE ASSESIASAP   180
ETNTAQVTST EV                                                      192

SEQ ID NO: 166              moltype = AA   length = 192
FEATURE                     Location/Qualifiers
source                      1..192
                            mol_type = protein
                            organism = Capra hircus
SEQUENCE: 166
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTVPAKSCQ DQPTTLARHP   120
HPHLSFMAIP PKKDQDKTEI PAINTIASAE PTVHSTPTTE AIVNTVDNPE ASSESIASAS   180
ETNTAQVTST EV                                                      192

SEQ ID NO: 167              moltype = AA   length = 162
FEATURE                     Location/Qualifiers
source                      1..162
                            mol_type = protein
                            organism = Capra hircus
SEQUENCE: 167
CCEKDERFFD DKIAKYIPIQ YVLSRYPSYG LNYYQQRPVA LINNQFLPYP YYAKPVAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIASAP ETNTAQVTST EV                     162

SEQ ID NO: 168              moltype = AA   length = 161
FEATURE                     Location/Qualifiers
source                      1..161
                            mol_type = protein
                            organism = Capra hircus
SEQUENCE: 168
CEKDERFFDD KIAKYIPIQY VLSRYPSYGL NYYQQRPVAL INNQFLPYPY YAKPIAVRSP    60
AQTLQWQVLP NTVPAKSCQD QPTTLARHPH PHLSFMAIPP KKDQDKTEIP AINTIASAEP   120
TVHSTPTTEA IVNTVDNPEA SSESIASAPE TNTAQVTSTE V                      161

SEQ ID NO: 169              moltype = AA   length = 192
FEATURE                     Location/Qualifiers
source                      1..192
                            mol_type = protein
                            organism = Capra hircus
SEQUENCE: 169
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTVPAKSCQ DQPTTLARHP   120
HPHLSFMAIP PKKDQDKTEV PAINTIASAE PTVHSTPTTE AIVNTVDNPE ASSESIASAS   180
ETNTAQVTST EV                                                      192

SEQ ID NO: 170              moltype = AA   length = 162
FEATURE                     Location/Qualifiers
source                      1..162
                            mol_type = protein
                            organism = Capra hircus
SEQUENCE: 170
CCEKDERFFD DKIAKYIPIQ YVLSRYPSYG LNYYQQRPVA LINNQFLPYP YYAKPIAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIASAP ETNTAQVTST EV                     162

SEQ ID NO: 171              moltype = AA   length = 161
FEATURE                     Location/Qualifiers
source                      1..161
                            mol_type = protein
                            organism = Capra hircus
SEQUENCE: 171
CEKDERFFDD KIAKYIPIQY VLSRYPSYGL NYYQQRPVAL INNQFLPYPY YAKPIAVRSP    60
AQTLQWQVLP NTVPAKSCQD QPTTLARHPH PHLSFMAIPP KKDQDKTEIP AINTIASAEP   120
TVHSTPTTEA IVNTVDNPEA SSESIVSAPE TNTAQVTSTE V                      161

SEQ ID NO: 172              moltype = AA   length = 162
FEATURE                     Location/Qualifiers
```

```
source                    1..162
                          mol_type = protein
                          organism = Capra hircus
SEQUENCE: 172
CCEKDERFFD DKIAKYIPIQ YVLSRYPSYG LNYYQQRPVA LINNQFLPYP YYAKPIAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIVSAP ETNTAQVTST EV                      162

SEQ ID NO: 173            moltype = AA  length = 161
FEATURE                   Location/Qualifiers
source                    1..161
                          mol_type = protein
                          organism = Capra hircus
SEQUENCE: 173
CEKDERFFDD KIAKYIPIQY VLSRYPSYGL NYYQRPVAL INNQFLPYPY YAKPIAVRSP    60
AQTLQWQVLP NTVPAKSCQD QPTTLARHPH PHLSFMAIPP KKDQDKTEIP AINTIASAEP   120
TVHSTPTTEA IVNTVDNPEA SSESIASAPE TNTAQVTSTE V                       161

SEQ ID NO: 174            moltype = AA  length = 192
FEATURE                   Location/Qualifiers
source                    1..192
                          mol_type = protein
                          organism = Capra hircus
SEQUENCE: 174
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTVPAKSCQ DQPTTLARHP   120
HPHLSFMAIP PKKDQDKTEI PAINTIASAE PTVHSTPITE AIVNTVDNPE ASSESIASAS   180
ETNTAQVTST EV                                                       192

SEQ ID NO: 175            moltype = AA  length = 162
FEATURE                   Location/Qualifiers
source                    1..162
                          mol_type = protein
                          organism = Capra hircus
SEQUENCE: 175
CCEKDERFFD DKIAKYIPIQ YVLSRYPSYG LNYYQQRPVA LINNQFLPYP YYAKPVAVRS    60
PAQTLQWQVL PNTVPAKSCQ NQPTTLARHP HPHLSFMAIP PKKDQDKTEI PAINTIASAE   120
PTVHSTPTTE AIVNTADNPE ASSESIASAP ETNTAQVTST EV                      162

SEQ ID NO: 176            moltype = AA  length = 162
FEATURE                   Location/Qualifiers
source                    1..162
                          mol_type = protein
                          organism = Capra hircus
SEQUENCE: 176
CCEKDERFFD DKIAKYIPIQ YVLSRYPSYG LNYYRQRPVA LINNQFLPYP YYAKPIAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIASAP ETNTAQVTST EV                      162

SEQ ID NO: 177            moltype = AA  length = 162
FEATURE                   Location/Qualifiers
source                    1..162
                          mol_type = protein
                          organism = Capra hircus
SEQUENCE: 177
CCEKDERFFD DKIAKYIPIQ YVLSRYPSYG LNYYQQRPVA LINNQFLPYP YYAKPVAVRS    60
PAQTLQWQVL PNTVPAKSCQ GQPTTLARHP HPHLSFMAIP PKKDQDKTEI PAINTIASAE   120
PTVHSTPTTE AIVNTVDNPE ASSESIASAS ETNTAQVTST EV                      162

SEQ ID NO: 178            moltype = AA  length = 161
FEATURE                   Location/Qualifiers
source                    1..161
                          mol_type = protein
                          organism = Capra hircus
SEQUENCE: 178
CEKDERFFDD KIAKYIPIQY VLSRYPSYGL NYYQQRPVAL INNQFLPYPY YAKPVAVRSP    60
AQTLQWQVLP NTVPAKSCQD QPTTLARHPH PHLSFMAIPP KKDQDKTEIP AINTIASAEP   120
TVHSTPTTEA IVNTVDNPEA SSESIASASE TNTAQVTSTE V                       161

SEQ ID NO: 179            moltype = AA  length = 162
FEATURE                   Location/Qualifiers
source                    1..162
                          mol_type = protein
                          organism = Capra hircus
SEQUENCE: 179
CCEKDERFFD DKIAKYIPIQ YVLSRYPSYG LNYYQQRPVA LINNQFLPYP YYAKPVAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIASAS ETNTAQVTST EV                      162
```

```
SEQ ID NO: 180              moltype = AA   length = 161
FEATURE                     Location/Qualifiers
source                      1..161
                            mol_type = protein
                            organism = Capra hircus
SEQUENCE: 180
CEKDERFFDD KIAKYIPIQY VLSRYPSYGL NYYQQRPVAL INNQFLPYPY YAKPVAVRSP    60
AQTLQWQVLP NTVPAKSCQD QPTTLARHPH PHLSFMAIPP KKDQDKTEVP AINTIASAEP   120
TVHSTPTTEA IVNTVDNPEA SSESIASASE TNTAQVTSTE V                      161

SEQ ID NO: 181              moltype = AA   length = 162
FEATURE                     Location/Qualifiers
source                      1..162
                            mol_type = protein
                            organism = Capra hircus
SEQUENCE: 181
CCEKDERFFD DKIAKYIPIQ YVLSRYPSYG LNYYQQRPVA LINNQFLPYP YYAKPIAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIASAS ETNTAQVTST EV                     162

SEQ ID NO: 182              moltype = AA   length = 162
FEATURE                     Location/Qualifiers
source                      1..162
                            mol_type = protein
                            organism = Capra hircus
SEQUENCE: 182
CCEKDERFFD DKIAKYIPIQ YVLSRYPSYG LNYYQQRPVA LINNQFLPYP YYAKPVAVRS    60
PAQTLQWQVL PNTVPAKSCQ DQPTTLARHP HPHLSFMAIP PKKDQDKTEV PAINTIASAE   120
PTVHSTPTTE AIVNTVDNPE ASSESIASAS ETNTAQVTST EV                     162

SEQ ID NO: 183              moltype = AA   length = 162
FEATURE                     Location/Qualifiers
source                      1..162
                            mol_type = protein
                            organism = Capra hircus
SEQUENCE: 183
CCEKDERFFD DKIAKYIPIQ YVLSRYPSYG LNYYRQRPVA LINNQFLPYP YYAKPVAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIASAS ETNTAQVTST EV                     162

SEQ ID NO: 184              moltype = AA   length = 192
FEATURE                     Location/Qualifiers
source                      1..192
                            mol_type = protein
                            organism = Ovis aries
SEQUENCE: 184
MMKSFFLVVT ILALTLPFLG AQEQNQEQRI CCEKDERFFD DKIAKYIPIQ YVLSRYPSYG    60
LNYYQQRPVA LINNQFLPYP YYAKPVAVRS PAQTLQWQVL PNAVPAKSCQ DQPTAMARHP   120
HPHLSFMAIP PKKDQDKTEI PAINTIASAE PTVHSTPTTE AVVNAVDNPE ASSESIASAP   180
ETNTAQVTST EV                                                      192

SEQ ID NO: 185              moltype = AA   length = 162
FEATURE                     Location/Qualifiers
source                      1..162
                            mol_type = protein
                            organism = Ovis aries
SEQUENCE: 185
CCEKDERFFD DKIAKYIPIQ YVLSRYPSYG LNYYQQRPVA LINNQFLPYP YYAKPVAVRS    60
PAQTLQWQVL PNAVPAKSCQ DQPTAMARHP HPHLSFMAIP PKKDQDKTEI PAINTIASAE   120
PTVHSTPTTE AVVNAVDNPE ASSESIASAP ETNTAQVTST EV                     162

SEQ ID NO: 186              moltype = AA   length = 190
FEATURE                     Location/Qualifiers
source                      1..190
                            mol_type = protein
                            organism = Bubalus bubalis
SEQUENCE: 186
MMKSFFLVVT ILALTLPFLG AQEQNQEQPI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP   120
HPHLSFMAIP PKKNQDKTEI PTINTIVSVE PTSTPTTEAI ENTVATLEAS SEVIESVPET   180
NTAQVTSTVV                                                         190

SEQ ID NO: 187              moltype = AA   length = 190
FEATURE                     Location/Qualifiers
source                      1..190
                            mol_type = protein
                            organism = Bubalus bubalis
SEQUENCE: 187
MMKSFFLVVT ILALTLPFLG AQEQNQEQPI RCEKEERFFN DKIAKYIPIQ YVLSRYPSYG    60
```

```
LNYYQQKPVA LINNQFLPYP YYAKPAAVRS PAQILQWQVL PNTVPAKSCQ AQPTTMTRHP    120
HPHLSFMAIP PKKNQDKTEI PTINTIVSIE PTSTPTTEAI ENTVATLEAS SEVIESVPET    180
NTAQVTSTVV                                                           190

SEQ ID NO: 188           moltype = AA  length = 190
FEATURE                  Location/Qualifiers
source                   1..190
                         mol_type = protein
                         organism = Bubalus bubalis
SEQUENCE: 188
MMKSFFLVVT ILALTLPFLG AQEQNQEQPI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP    120
HPHLSFMAIP PKKNQDKTEI PTINTIVSVE PTSTPTTEAI ENTVATLEAS SDVIESVPET    180
NTAQVTSTVV                                                           190

SEQ ID NO: 189           moltype = AA  length = 190
FEATURE                  Location/Qualifiers
source                   1..190
                         mol_type = protein
                         organism = Bubalus bubalis
SEQUENCE: 189
MMKSFFLVVT ILALTLPFLG AQEQNQEQPI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP    120
HPHLSFMAIP PKKNQDKTEI PTINTIVSIE PTSTPTTEAI ENTVATLEAS SDVIESVPET    180
NTAQVTSTVV                                                           190

SEQ ID NO: 190           moltype = AA  length = 190
FEATURE                  Location/Qualifiers
source                   1..190
                         mol_type = protein
                         organism = Bubalus bubalis
SEQUENCE: 190
MMKSFFLVVT ILALTLPFLG AQEQNQEQPI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP    120
HPHLSFMAIP PKKNQDKTEI PTINTIVSVE PTSTPITEAI ENTVATLEAS SEVIESVPET    180
NTAQVTSTVV                                                           190

SEQ ID NO: 191           moltype = AA  length = 190
FEATURE                  Location/Qualifiers
source                   1..190
                         mol_type = protein
                         organism = Bubalus bubalis
SEQUENCE: 191
MMKSFFLVVT ILALTLPFLG AQEQNQEQLI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP    120
HPHLSFMAIP PKKNQDKTEI PTINTIVSVE PTSTPTTEAI ENTVATLEAS SDVIESVPET    180
NTAQVTSTVV                                                           190

SEQ ID NO: 192           moltype = AA  length = 194
FEATURE                  Location/Qualifiers
source                   1..194
                         mol_type = protein
                         organism = Bos mutus
SEQUENCE: 192
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP    120
HPHLSFMAIP PKKNQDKTEI PTINTIASGE PTSTPTTEAV ESTVATLEAS PEASPEVIES    180
PPEINTVQVT STAV                                                      194

SEQ ID NO: 193           moltype = AA  length = 183
FEATURE                  Location/Qualifiers
source                   1..183
                         mol_type = protein
                         organism = Bos mutus
SEQUENCE: 193
MMKSFFLVVT ILALTLPFLR CEKDERFFSD KIAKYIPIQY VLSRYPSYGL NYYQQKPVAL    60
INNQFLPYPY YAKPAAVRSP AQILQWQVLS NTVPAKSCQA QPTTMARHPH PHLSFMAIPP    120
KKNQDKTEIP TINTIASGEP TSTPTTEAVE STVATLEASP EASPEVIESP PEINTVQVTS    180
TAV                                                                  183

SEQ ID NO: 194           moltype = AA  length = 976
FEATURE                  Location/Qualifiers
source                   1..976
                         mol_type = protein
                         organism = Bos mutus
SEQUENCE: 194
MTSGTAVQRA DSSEEKRHRK RKKHHLIKSQ ILSYTEDRGF NEGQMKEDEQ EKADSSEEVR    60
HFHSLQKDKV NMKFFIFTCL LAVALAKNVK SLLKSKKHGT ITRTSFKVQE SHRENVDSQT    120
ISSICQNFII LDCRSSATRI LCKRFKITVD DKHYQKALNE INQFYQKFPQ YLQYLYQGPI    180
```

```
VLNPWDQVKR NAVPITPTLV IKLIFIFFFH KESTEVFTKK TKLTEEEKNR LNFLKKISQR    240
YQKFALPQYL KTVYQHQKAM KPWIQPKTKV IPYVDYSDNI GSPYPVNPSA SISYPVTPSA    300
SIPCPVNPSA SIPCPMPDRD FTPPVYLTKT NLPNDPAVPS NPLVFTALGA PLYSIAGLPI    360
SPFSGQLPPT GVFRLVPSS  RPIGPLYSPN EAAPSANTYI VEILVPPTTP PHTVPDVQPL   420
TITEPDEAEP AADALAAPEP QSSISFDQLI PQHLMSASNS NELLLNLNNA QLRPLQLQGP    480
FNPWIPPFPG ILQQQQQNQV PGLSPFSLST REWFAGLVPN QIFVPGQVSF AQGTQAGQLD   540
PSQPQTPQQT QRGPKNVMPS VFFKMPQEQA QMLQYYPVYM FLPWEQPQQT VAQSPPQTRE   600
QLFEEQMPFY TEFGYIPQQV EPVMPVEQQQ PVFDPFLGTA PEIAAMDRKA VIVITIKRQL   660
APFVRTILEP VTSISYNTIP EKDRTGKFEV SQDTEGEARS VSGSDELSSQ FFFPPYQYPR   720
SHYSRFLCPW WAYFYPPIPV PASVSATTPL NEKKKYQIHV NKVERPTEPT AKQELTVTRK   780
GAMMKSFFLV VTILALTLPF LGAQEQNQEQ PIRCEKDERF FSDKIAKYIP IQYVLSRYPS   840
YGLNYYQQKP VALINNQFLP YPYYAKPAAV RSPAQILQWQ VLSNTVPAKS CQAQPTTMAR   900
HPHPHLSFMA IPPKKNQDKT EIPTINTIAS GEPTSTPTTE AVESTVATLE ASPEASPEVI   960
ESPPEINTVQ VTSTAV                                                   976

SEQ ID NO: 195         moltype = AA  length = 190
FEATURE                Location/Qualifiers
source                 1..190
                       mol_type = protein
                       organism = Bos indicus
SEQUENCE: 195
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPITEAV ESTVATLEDS PEVIESPPEI   180
NTVQVTSTAV                                                          190

SEQ ID NO: 196         moltype = AA  length = 160
FEATURE                Location/Qualifiers
source                 1..160
                       mol_type = protein
                       organism = Bos indicus
SEQUENCE: 196
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTIEAV ESTVATLEDS PEVIESPPEI NTVQVTSTAV                         160

SEQ ID NO: 197         moltype = AA  length = 160
FEATURE                Location/Qualifiers
source                 1..160
                       mol_type = protein
                       organism = Bos indicus
SEQUENCE: 197
RCEKDERFFS DKIAKYIPIQ YVLSRYPSYG LNYYQQKPVA LINNQFLPYP YYAKPAAVRS    60
SAQILQWQVL SNTVPAKSCQ AQPTTMARHP HPHLSFMAIP PKKNQDKTEI PTINTIASGE   120
PTSTPTTEAV ESTVATLEDS PEVIESPPEI NTVQVTSTAV                         160

SEQ ID NO: 198         moltype = AA  length = 160
FEATURE                Location/Qualifiers
source                 1..160
                       mol_type = protein
                       organism = Bos indicus
SEQUENCE: 198
RCEKDERFFS DKIAKYIPIQ YVLSRYPSYG LNYYQQKPVA LINNQFLPYP YYAKPAAVRS    60
SAQILQWQVL SNTVPAKSCQ AQPTTMARHP HPHLSFMAIP PKKNQDKTEI PTINTIASGE   120
PTSTPTIEAV ESTVATLEAS PEVIESPPEI NTVQVTSTAV                         160

SEQ ID NO: 199         moltype = AA  length = 171
FEATURE                Location/Qualifiers
source                 1..171
                       mol_type = protein
                       organism = Bos indicus
SEQUENCE: 199
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPITEAV ESTVATLEDS PEVIESPPEI NTVQVRQLQS KNLRRHQRRQ R            171

SEQ ID NO: 200         moltype = AA  length = 171
FEATURE                Location/Qualifiers
source                 1..171
                       mol_type = protein
                       organism = Bos indicus
SEQUENCE: 200
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPITEAV ESTVATLEDS PEVIESPPEI NTVQVLNLQS KNLRRHQRRQ R            171

SEQ ID NO: 201         moltype = AA  length = 156
FEATURE                Location/Qualifiers
source                 1..156
```

```
                    mol_type = protein
                    organism = Bos indicus
SEQUENCE: 201
DERFFSDKIA KYIPIQYVLS RYPSYGLNYY QQKPVALINN QFLPYPYYAK PAAVRSPAQI    60
LQWQVLSNTV PAKSCQAQPT TMARHPHPHL SFMAIPPKKN QDKTEIPTIN TIASGEPTST   120
PTIEAVESTV ATLEASPEVI ESPPEINTVQ VTSTAV                             156

SEQ ID NO: 202          moltype = AA  length = 144
FEATURE                 Location/Qualifiers
source                  1..144
                        mol_type = protein
                        organism = Bos indicus
SEQUENCE: 202
IPIQYVLSRY PSYGLNYYQQ KPVALINNQF LPYPYYAKPA AVRSPAQILQ WQVLSNTVPA    60
KSCQAQPTTM ARHPHPHLSF MAIPPKKNQD KTEIPTINTI ASGEPTSTPT TEAVESTVAT   120
LEDSPEVIES PPEINTVQVT STAV                                          144

SEQ ID NO: 203          moltype = AA  length = 144
FEATURE                 Location/Qualifiers
source                  1..144
                        mol_type = protein
                        organism = Bos indicus
SEQUENCE: 203
IPIQYVLSRY PSYGLNYYQQ KPVALINNQF LPYPYYAKPA AVRSPAQILQ WQVLSNTVPA    60
KSCQAQPTTM ARHPHPHLSF MAIPPKKNQD KTEIPTINTI ASGEPTSTPI TEAVESTVAT   120
LEDSPEVIES PPEINTVQVT STAV                                          144

SEQ ID NO: 204          moltype = AA  length = 141
FEATURE                 Location/Qualifiers
source                  1..141
                        mol_type = protein
                        organism = Bos indicus
SEQUENCE: 204
QYVLSRYPSY GLNYYQQKPV ALINNQFLPY PYYAKPAAVR SPAQILQWQV LSNTVPAKSC    60
QAQPTTMARH PHPHLSFMAI PPKKNQDKTE IPTINTIASG EPTSTPTIEA VESTVATLEA   120
SPEVIESPPE INTVQVTSTA V                                             141

SEQ ID NO: 205          moltype = AA  length = 139
FEATURE                 Location/Qualifiers
source                  1..139
                        mol_type = protein
                        organism = Bos indicus
SEQUENCE: 205
VLSRYPSYGL NYYQQKPVAL INNQFLPYPY YAKPAAVRSP AQILQWQVLS NTVPAKSCQA    60
QPTTMARHPH PHLSFMAIPP KKNQDKTEIP TINTIASGEP TSTPITEAVE STVATLEDSP   120
EVIESPPEIN TVQVTSTAV                                                139

SEQ ID NO: 206          moltype = AA  length = 210
FEATURE                 Location/Qualifiers
source                  1..210
                        mol_type = protein
                        organism = Jeotgalicoccus coquinae
SEQUENCE: 206
MERPTEPTAK QELTVTRKGA MMKSFFLVVT ILALTLPFLG AQEQNQEQPI RCEKDERFFS    60
DKIAKYIPIQ YVLSRYPSYG LNYYQQKPVA LINNQFLPYP YYAKPAAVRS PAQILQWQVL   120
SNTVPAKSCQ AQPTTMARHP HPHLSFMAIP PKKNQDKTEI PTINTIASGE PTSTPTIEAV   180
ESTVATLEAS PEVIESPPEI NTVQVTSTAV                                    210

SEQ ID NO: 207          moltype = AA  length = 184
FEATURE                 Location/Qualifiers
source                  1..184
                        mol_type = protein
                        organism = Jeotgalicoccus coquinae
SEQUENCE: 207
LVVTILALTL PFLGAQEQNQ EQLIRCEKEE RFFNDKIAKY IPIQYVLSRY PSYGLNYYQQ    60
KPVALINNQF LPYPYYAKPA AVRSPAQILQ WQVLPNTVPA KSCQAQPTTM TRHPHPHLSF   120
MAIPPKKNQD KTEIPTINTI VSVEPTSTPT TEAIENTVAT LEASSEVIES VPETNTAQVT   180
STVV                                                                184

SEQ ID NO: 208          moltype = AA  length = 190
FEATURE                 Location/Qualifiers
source                  1..190
                        mol_type = protein
                        organism = Bison bison
SEQUENCE: 208
MMKSFFLVVT ILALTLPFLG AQEQNQEQPI RCEKDERFFS DKIAKYIPIQ YVLSRYPSYG    60
LNAYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPTTEAV ESTVATLEAS PEVIESPPEI   180
NTVQVTSTVV                                                          190
```

```
SEQ ID NO: 209          moltype = AA  length = 179
FEATURE                 Location/Qualifiers
source                  1..179
                        mol_type = protein
                        organism = Bison bison
SEQUENCE: 209
MMKSFFLVVT ILALTLPFLR CEKDERFFSD KIAKYIPIQY VLSRYPSYGL NAYQQKPVAL    60
INNQFLPYPY YAKPAAVRSP AQILQWQVLS NTVPAKSCQA QPTTMARHPH PHLSFMAIPP   120
KKNQDKTEIP TINTIASGEP TSTPTTEAVE STVATLEASP EVIESPPEIN TVQVTSTVV    179

SEQ ID NO: 210          moltype = AA  length = 190
FEATURE                 Location/Qualifiers
source                  1..190
                        mol_type = protein
                        organism = Bos grunniens
SEQUENCE: 210
MMKSFFLVVT ILALTLPFLG AQEQNQEQPI RCEKDERFFS DKIAKYIPIQ YVLSRYLSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE RTSTPTTEAV ESTVATLEAS PEVIESPPEI   180
NTVQVTSTAV                                                          190

SEQ ID NO: 211          moltype = AA  length = 194
FEATURE                 Location/Qualifiers
source                  1..194
                        mol_type = protein
                        organism = Bos grunniens
SEQUENCE: 211
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SSTVPAKSCQ AQPTTMARHP   120
HPHLSFMAIP PKKNQDKTEI PTINTIASGE PTSTPTTEAV ESTVATLEAS PEASPEVIES   180
PPEINTVQVT STAV                                                     194

SEQ ID NO: 212          moltype = AA  length = 160
FEATURE                 Location/Qualifiers
source                  1..160
                        mol_type = protein
                        organism = Bos grunniens
SEQUENCE: 212
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEAS PEVIESPPEI NTVQVTSTAV                         160

SEQ ID NO: 213          moltype = AA  length = 160
FEATURE                 Location/Qualifiers
source                  1..160
                        mol_type = protein
                        organism = Bos grunniens
SEQUENCE: 213
RCEKDERFFS DKIAKYIPIQ YVLSRYLSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEAS PEVIESPPEI NTVQVTSTAV                         160

SEQ ID NO: 214          moltype = AA  length = 164
FEATURE                 Location/Qualifiers
source                  1..164
                        mol_type = protein
                        organism = Bos grunniens
SEQUENCE: 214
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEAS PEASPEVIES PPEINTVQVT STAV                    164

SEQ ID NO: 215          moltype = AA  length = 160
FEATURE                 Location/Qualifiers
source                  1..160
                        mol_type = protein
                        organism = Bos grunniens
SEQUENCE: 215
RCEKDERFFS DKIAKYIPIQ YVLSRYLSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
RTSTPTTEAV ESTVATLEAS PEVIESPPEI NTVQVTSTAV                         160

SEQ ID NO: 216          moltype = AA  length = 160
FEATURE                 Location/Qualifiers
REGION                  1..160
                        note = Bos indicus x Bos taurus
source                  1..160
                        mol_type = protein
```

```
                        organism = unidentified
SEQUENCE: 216
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEDS PEVIESPPEI NTVQVTSTAV                         160

SEQ ID NO: 217          moltype = AA  length = 160
FEATURE                 Location/Qualifiers
REGION                  1..160
                        note = Bos indicus x Bos taurus
source                  1..160
                        mol_type = protein
                        organism = unidentified
SEQUENCE: 217
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLAFMAIP PKKNQDKTEI PTINTIASGE   120
PTSTPTTEAV ESTVATLEDS PEVIESPPEI NTVQVTSTAV                         160

SEQ ID NO: 218          moltype = AA  length = 192
FEATURE                 Location/Qualifiers
source                  1..192
                        mol_type = protein
                        organism = Oreamnos americanus
SEQUENCE: 218
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQILQWQVL PNTAPAKSCQ DQPTTMARHP   120
HPHLSFMAIP PKKDQDKTEI PTINTIASAE PTVHSTPTTE AIVNTVDNPE ASSESIVSAP   180
ETNTAQVTST EV                                                      192

SEQ ID NO: 219          moltype = AA  length = 192
FEATURE                 Location/Qualifiers
source                  1..192
                        mol_type = protein
                        organism = Naemorhedus goral
SEQUENCE: 219
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTAPAKSCQ DQPTTMARHP   120
HPHLSFMAIP PKKDQDKTEI PTINTIASAE PTVHSTPTTE AIVNTVDNPE ASSESIASAP   180
ETNTAQVTST EV                                                      192

SEQ ID NO: 220          moltype = AA  length = 190
FEATURE                 Location/Qualifiers
source                  1..190
                        mol_type = protein
                        organism = Odocoileus virginianus
SEQUENCE: 220
MMKSFSLVVT ILALTLPFLV AQEQNQEQPT GCEKDERFFN DKIVKYIPIQ YVLSRYPSYG    60
LSYYQHRPVA LINNQFLPYP YYAKPGAVRS PAQILQWQVL PNTVPAKSCQ AQPTTLARHP   120
HPRLSFMAIP PKKNQDKTDI PTINTIATVE STITPTTEAI VDTVATPEAS SEVIESAPET   180
KTDQVTSTVV                                                         190

SEQ ID NO: 221          moltype = AA  length = 192
FEATURE                 Location/Qualifiers
source                  1..192
                        mol_type = protein
                        organism = Capricornis sumatraensis
SEQUENCE: 221
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTAPAKSCQ DQPTTMARHP   120
HPHLSFMAIP PKKDQDKTEI PTINTIASAE PTVHSTPTTE AIVNTVDNPE ASSESIVSAP   180
ETNTAQVTST EV                                                      192

SEQ ID NO: 222          moltype = AA  length = 192
FEATURE                 Location/Qualifiers
source                  1..192
                        mol_type = protein
                        organism = Capricornis crispus
SEQUENCE: 222
MMKSFFLAVT ILALTLPFLG AQEQNQEQPI CCEKDETFFD DKIAKYIPIQ YVLSRYPSYG    60
LNYYQQRPVA LINNQFLPYP YYAKPVAVRS PAQTLQWQVL PNTAPAKSCQ DQPTTMARHP   120
HPHLSFMAIP PKKDQDKTEI PTINTIASAE PTVHSTPTTE AIVNTVDNPE ASSESIVSAP   180
ETNTAQVTST EV                                                      192

SEQ ID NO: 223          moltype = AA  length = 192
FEATURE                 Location/Qualifiers
source                  1..192
                        mol_type = protein
                        organism = Capricornis crispus
SEQUENCE: 223
```

```
MMKSFFLVVT ILALTLPFLG AQEQNQEQPI CCEKDETFFD DKIAKYIPIQ YVLSRYPSYG    60
LNYYQQRPVA LINNQFLPYP YYAKPVAVRS PAQTLQWQVL PNTVPAKSCQ DQPTTMARHP   120
HPHLSFMAIP PKKDQDKTEI PTINTIASAE PTVHSTPTTE AIVNTVDNPE ASSESIVSAP   180
ETNTAQVTST EV                                                      192

SEQ ID NO: 224         moltype = AA  length = 192
FEATURE                Location/Qualifiers
source                 1..192
                       mol_type = protein
                       organism = Capricornis swinhoei
SEQUENCE: 224
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTAPAKSCQ DQPTTMARHP   120
HPHLSFMAIP PKKDQDKTEI PTINTIASAE TTVHSTPTTE AIVNTVDNRE ASSESIVSAP   180
ETNTAQVTST EV                                                      192

SEQ ID NO: 225         moltype = AA  length = 202
FEATURE                Location/Qualifiers
source                 1..202
                       mol_type = protein
                       organism = Saiga tatarica
SEQUENCE: 225
MMKSFFLVVT ILALTLPFLD AQERNQEQPI CCEKDERFFN DRIAKYIPIQ YVLSRYPSYG    60
LNYYQQRPVA LINNQFLPYP YYAKPVAVRS PAQTLQWQVL PNTVPAKSCQ DQPTTMARHP   120
HPHLSFMAIP PKKDQDKTEI PTINTVASAE PASTPTTEAI VNTEAIVNTE AIVNTVDNPE   180
ASSEIIASVP ETNTAQVTST EV                                           202

SEQ ID NO: 226         moltype = AA  length = 192
FEATURE                Location/Qualifiers
source                 1..192
                       mol_type = protein
                       organism = Rupicapra rupicapra
SEQUENCE: 226
MMKSFFLVAT ILALTLPFLG AQEQNQEQSI CCEKDERFFE DKIAKYIPIQ YVLSRYPSYG    60
LNYYQQRPVA LINNQFLPYP YYAKPVAVRS PAQTLQWQVL PNTAPAKSCQ DQPTTMAHHP   120
HPHLSFMAIP PKKDQDKTEI PTINTIASAE PTVHSTPTTE AIVNTVDNPE ASSESIASAP   180
ETNTAQVTST EV                                                      192

SEQ ID NO: 227         moltype = AA  length = 190
FEATURE                Location/Qualifiers
source                 1..190
                       mol_type = protein
                       organism = Cervus nippon
SEQUENCE: 227
MMKSFFLAVT ILALTLPFLV AQEQIQEQPT GCEKDERFFN DKIVKYIPIQ YALSRYPSYG    60
LNYYQHRPVA LINNQFLPYP YYVKPGAVRS PAQILQWQVL PNTVPAKFCQ AQPTTMARHP   120
HPRLSFMAIP PKKNQDKTDI PSINTIATAE STITPTTEAI VDTVATQEAF SEVIESAPEA   180
KTDQVTSTVV                                                         190

SEQ ID NO: 228         moltype = AA  length = 139
FEATURE                Location/Qualifiers
source                 1..139
                       mol_type = protein
                       organism = Bos frontalis
SEQUENCE: 228
VLSRYPSYGL NYYQQKPVAL INNQFLPYPY YAKPAAVRSP AQILQWQVLS NTVPAKSCQA    60
QPTTMARHPH PHLSFMAIPP KKNQDKTEIP TINTIASGEP TSTPTTEAVE STVATLEASP   120
EVIESPPEIN TVQVTSTAV                                               139

SEQ ID NO: 229         moltype = AA  length = 170
FEATURE                Location/Qualifiers
source                 1..170
                       mol_type = protein
                       organism = Muntiacus reevesi
SEQUENCE: 229
AQELNQEQPT GCEKDERFFN DKIVKYIPIQ YALSRYPSYG LNYYQHRPVA LISNQFLPYP    60
YYAKPGAVRS PAQILQWQAL PNTVPATSCQ AQPATVARHP HPRLSFMAIP PKKSQDKTDH   120
PTINTIATVE STATPTTEAV VDTAATQEAS PEVIASAPEA STDQVTSTAV              170

SEQ ID NO: 230         moltype = AA  length = 170
FEATURE                Location/Qualifiers
source                 1..170
                       mol_type = protein
                       organism = Muntiacus muntjak
SEQUENCE: 230
AQELNQEQPT GCEKDERFFN DKIVKYIPIQ YALSRYPSYG LNYYQHRPVA LISNQFLPYP    60
YYAKPGAVRS PAQTLQWQAL PNTVPATSCQ AQPATMARHP HPRLSFMAIP PKKTQDKTDH   120
PTFNTIATAE STATPTTEAV VDTVATQEAS SEVTASAPEA NTDQVTSTAV              170
```

```
SEQ ID NO: 231           moltype = AA  length = 160
FEATURE                  Location/Qualifiers
source                   1..160
                         mol_type = protein
                         organism = Madoqua saltiana
SEQUENCE: 231
CCEKDERFFN DKIAKYIPIQ YVLSRYPSYG LNYYQQRPVA LINNQFLPYP YFAKPVAVRS    60
PAQTLQWQVL PNTVPAKSCQ DQPTTMARHP HPHLSFMAIP PKKDQDKPEI PTINTIASAE   120
LTSTPTTEAI VNTVDNPEAS SEIIASVPET NTAEVTSTEV                         160

SEQ ID NO: 232           moltype = AA  length = 172
FEATURE                  Location/Qualifiers
source                   1..172
                         mol_type = protein
                         organism = Gazella dorcas
SEQUENCE: 232
CCEKDERFFN DKIAKYIPIQ YVLSRYPSYG LNYYQQRPVA LINNQFLPYP YYAKPVAVRS    60
PAQTLQWQVL PNTVPAKSCQ DQPTTMARHP HPHLSFMAIP PKKDQDKTEI PTINTIASAE   120
PASTPTTEAI VNTEAIVNTE PIVNTVDNPE ASSEIIASVP ETNTAQVTST EV           172

SEQ ID NO: 233           moltype = AA  length = 178
FEATURE                  Location/Qualifiers
VARIANT                  178
                         note = X is any amino acid
source                   1..178
                         mol_type = protein
                         organism = Gazella arabica
SEQUENCE: 233
CCEKDERFFN DKIAKYIPIQ YVLSRYPSYG LNYYQQRPVA LINNQFLPYP YYAKPVAVRS    60
PAQTLQWQVL PNTVPAKSCQ DQPTTMARHP HPHLSFMAIP PKKDQDKTEI PTINTIASAE   120
PASTPTTEAI VNTEAVVNTE AIVNTEAIVN TVDNPEASSE IIASVPETNT AQVTSTEX     178

SEQ ID NO: 234           moltype = AA  length = 162
FEATURE                  Location/Qualifiers
source                   1..162
                         mol_type = protein
                         organism = Capra ibex
SEQUENCE: 234
CCEKDERFFD DKIAKYIPIQ YVLNRYPTYG LNYYQQRPVA LINNQFLPYP YYAKPVAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIASAP ETNTAQVTST EV                      162

SEQ ID NO: 235           moltype = AA  length = 162
FEATURE                  Location/Qualifiers
VARIANT                  73
                         note = X is any amino acid
source                   1..162
                         mol_type = protein
                         organism = Ovis ammon
SEQUENCE: 235
CCEKDERFFD DKIAKYIPIQ YVLSRYPSYG LNYYQQRPVA LINNQFLPYP YYAKPVAVRS    60
PAQTLQWQVL PNXVPAKSCQ DQPTAMARHP HPHLSFMAIP PKKDQDKTEI PAINTIASAE   120
PTVHSTPTTE AVVNAVDNPE ASSESIASAP ETNTAQVTST EV                      162

SEQ ID NO: 236           moltype = AA  length = 162
FEATURE                  Location/Qualifiers
source                   1..162
                         mol_type = protein
                         organism = Ovis orientalis
SEQUENCE: 236
CCEKDERFFD DKIAKYIPIQ YVLSRYPSYG LNYYQQRPVA LINNQFLPYP YYAKPVAVRS    60
PAQTLQWQVL PNTVPAKSCQ DQPTAMARHP HPHLSFMAIP PKKDQDKTEI PAINTIASAE   120
PTVHSTPTTE AVVNAVDNPE ASSESIASAP ETNTAQVTST EV                      162

SEQ ID NO: 237           moltype = AA  length = 162
FEATURE                  Location/Qualifiers
source                   1..162
                         mol_type = protein
                         organism = Ovis orientalis
SEQUENCE: 237
CCEKDERFFD DKIAKYIPIQ YVLSRYPSYG LNYYQQRPVA LINNQFLPYP YYAKPVAVRS    60
PAQTLQWQVL PNAVPAKSCQ DQPTAMARHP HPHLSFMAIP PKKDQDKTEI PAINTIASAE   120
PTVHSTPTTE AVVNAVDNPE ASSESIASAP ETNTAQITST EV                      162

SEQ ID NO: 238           moltype = AA  length = 463
FEATURE                  Location/Qualifiers
source                   1..463
                         mol_type = protein
                         organism = Cervus hanglu
```

```
SEQUENCE: 238
QEVKVTVDNK HYQKVLNEIS QFYQKFPQYL QYLYQGPIVM NPWEQVKRTA GPFIPTVVSA    60
APLYVSCLFG FLFKTKLTEE EKNRLNFLKK ISQYYQKFAW PQYLKTVYQY QKAMKPWTQP   120
KTNAIPYVLI PQRLMSASNS NELLLNLNNA QLQPLQLQGP FNSWIPPFPG ILQQQQQDQI   180
PGLSPFSLST LERFAGLVPN QIFVPGQVGF AQGTQAGQLD PSQPQTPQQT QRGPKNVMPS   240
LLSLKMPQEQ AQLLQYYPVY MFLPWEQPQQ TVAQSPPQTR LQLFEEQMPY YTEFGYIPQQ   300
VEPGCEKDER FFNDKIVKYI PIQYALSRYP SYGLNYYQHR PVALINNQFL PYPYYVKPGA   360
VRSPAQILQW QVLPNTVPAK FCQAQPTTMA RHPHPRLSFM AIPPKKNQDK TDIPSINTIA   420
TAESTITPTT EAIVDTVATQ EASSEVIESA PEAKTDQVTS TVV                    463

SEQ ID NO: 239          moltype = AA  length = 160
FEATURE                 Location/Qualifiers
source                  1..160
                        mol_type = protein
                        organism = Procapra gutturosa
SEQUENCE: 239
CCEKDERFFN DKIAKYIPIQ YVMSRYPSYG LNYYQQRPVA LINNQFLPYP YYAKPVAVRS    60
PAQTLQWQVL PNTVPAKSCQ DQPTTMARHP HPHLSFMAIP PKKDQDKTEI PTINTIASAE   120
PTSTPTTEAI VNTVDNPEAT SEIIASVPET NTAQVTSTEV                        160

SEQ ID NO: 240          moltype = AA  length = 160
FEATURE                 Location/Qualifiers
VARIANT                 111
                        note = X is any amino acid
VARIANT                 121
                        note = X is any amino acid
VARIANT                 125
                        note = X is any amino acid
VARIANT                 139
                        note = X is any amino acid
source                  1..160
                        mol_type = protein
                        organism = Procapra gutturosa
SEQUENCE: 240
CCEKDERFFN DKIAKYIPIQ YVMSRYPSYG LNYYQQRPVA LINNQFLPYP YYAKPVAVRS    60
PAQTLQWQVL PNTVPAKSCQ DQPTTMARHP HPHLSFMAIP PKKDQDKTEI XTINTIASAE   120
XTSTXTTEAI VNTVDNPEXT SEIIASVPET NTAQVTSTEV                        160

SEQ ID NO: 241          moltype = AA  length = 190
FEATURE                 Location/Qualifiers
source                  1..190
                        mol_type = protein
                        organism = Bos taurus
SEQUENCE: 241
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPTIEAV ESTVATLEAS PEVTESPPEI   180
NTVQVTSTAV                                                         190

SEQ ID NO: 242          moltype = AA  length = 190
FEATURE                 Location/Qualifiers
source                  1..190
                        mol_type = protein
                        organism = Bos taurus
SEQUENCE: 242
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTGI PTINTIASGE PTSTPTIEAV ESTVATLEAS PEVTESPPEI   180
NTVQVTSTAV                                                         190

SEQ ID NO: 243          moltype = AA  length = 190
FEATURE                 Location/Qualifiers
source                  1..190
                        mol_type = protein
                        organism = Bos taurus
SEQUENCE: 243
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPTIEAV ESTVATLEAS PEVIESPPEI   180
NTVQVTSTAV                                                         190

SEQ ID NO: 244          moltype = AA  length = 190
FEATURE                 Location/Qualifiers
source                  1..190
                        mol_type = protein
                        organism = Bos taurus
SEQUENCE: 244
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
```

```
HPHLSFMAIP PKKNQDKTEI PTINTIASGE PTSTPTTEAV ESTVATLEDS PEVIESPPEI    180
NTVQVTSTAV                                                           190

SEQ ID NO: 245          moltype = AA   length = 160
FEATURE                 Location/Qualifiers
source                  1..160
                        mol_type = protein
                        organism = Bos taurus
SEQUENCE: 245
MMKSFFLVVT ILALTLPFLG AQEQNQEQPI RCEKDERFFS DKIAKYIPIQ YVLSRYPSYG     60
LNYYQQKPVA LINNQFLPYP YYAKPAAVRS PAQILQWQVL SNTVPAKSCQ AQPTTMARHP    120
HPHLSFMAIP PKKNQDKTEI PTINTIASGE PTSTPTTEAV                          160

SEQ ID NO: 246          moltype = AA   length = 169
FEATURE                 Location/Qualifiers
source                  1..169
                        mol_type = protein
                        organism = Bos taurus
SEQUENCE: 246
QEQNQEQPIR CEKDERFFSD KIAKYIPIQY VLSRYPSYGL NYYQQKPVAL INNQFLPYPY     60
YAKPAAVRSP AQILQWQVLS NTVPAKSCQA QPTTMAHHPH PHLSFMAIPP KKNQDKTEIP    120
TINTIASGEP TSTPITEAVE STVATLEASP EVIESPPEIN TVQVTSTAV                169

SEQ ID NO: 247          moltype = AA   length = 179
FEATURE                 Location/Qualifiers
source                  1..179
                        mol_type = protein
                        organism = Bos taurus
SEQUENCE: 247
MMKSFFLVVT ILALTLPFLR CEKDERFFSD KIAKYIPIQY VLSRYPSYGL NYYQQKPVAL     60
INNQFLPYPY YAKPAAVRSP AQILQWQVLS NTVPAKSCQA QPTTMARHPH PHLSFMAIPP    120
KKNQDKTEIP TINTIASGEP TSTPIEAVE STVATLEASP EVIESPPEIN TVQVTSTAV      179

SEQ ID NO: 248          moltype = AA   length = 160
FEATURE                 Location/Qualifiers
source                  1..160
                        mol_type = protein
                        organism = Bos taurus
SEQUENCE: 248
RCEKDERFFS DKIAKYIPIQ YVLSRYPSYG LNYYQQKPVA LINNQFLPYP YYAKPAAVRS     60
PAQILQWQVL SNTVPAKSCQ AQPTTMARHP HPHLSFMAIP PKKNQDKTEI PTINTIASGE    120
PTSTPTIEAV ESTVATLEAS PEVIESPPEI NTVQVTSTAV                          160

SEQ ID NO: 249          moltype = AA   length = 160
FEATURE                 Location/Qualifiers
source                  1..160
                        mol_type = protein
                        organism = Bos taurus
SEQUENCE: 249
RCEKDERFFS DKIAKYIPIQ YVLSRYPSYG LNYYQQKPVA LINNQFLPYP YYAKPAAVRS     60
PAQILQWQVL SNTVPAKSCQ AQPTTMARHP HPHLSFMAIP PKKNQDKTEI PTINTIASGE    120
PTSTPITEAV ESTVATLEDS PEVIESPPEI NTVQVTSTAV                          160

SEQ ID NO: 250          moltype = AA   length = 106
FEATURE                 Location/Qualifiers
source                  1..106
                        mol_type = protein
                        organism = Bos taurus
SEQUENCE: 250
AEQQNEEEPI RCEKDERFFS DKIAKYIPIQ YVLSRYPSYG LNYYQQKPVA LINNQFLPYP     60
YYAKPAAVRS PAQILQWQVL SNTVPAKSCQ AQPTTMARHP PHHLSF                   106

SEQ ID NO: 251          moltype = AA   length = 160
FEATURE                 Location/Qualifiers
source                  1..160
                        mol_type = protein
                        organism = Bos taurus
SEQUENCE: 251
HCEKDERFFS DKIAKYIPIQ YVLSRYPSYG LNYYQQKPVA LINNQFLPYP YYAKPAAVRS     60
PAQILQWQVL SNTVPAKSCQ AQPTTMARHP HPHLSFMAIP PKKNQDKTEI PTINTIASGE    120
PTSTPTTEAV ESTVATLEDS PEVIESPPEI NTVQVTSTAV                          160

SEQ ID NO: 252          moltype = AA   length = 160
FEATURE                 Location/Qualifiers
source                  1..160
                        mol_type = protein
                        organism = Bos taurus
SEQUENCE: 252
RCEKDERFFS DKIAKYIPIQ YVLSRYPSYG LNYYQQKPVA LINNQFLPYP YYAKPAAVRS     60
```

```
PAQILQWQVL  SNTVPAKSCQ  AQPTTMACHP  HPHLSFMAIP  PKKNQDKTEI  PTINTIASGE   120
PTSTPITEAV  ESTVATLEDS  PEVIESPPEI  NTVQVTSTAV                          160

SEQ ID NO: 253          moltype = AA  length = 159
FEATURE                 Location/Qualifiers
source                  1..159
                        mol_type = protein
                        organism = Bos taurus
SEQUENCE: 253
CEKDERFFSD  KIAKYIPIQY  VLSRYPSYGL  NYYQQKPVAL  INNQFLPYPY  YAKPAAVRSP   60
AQILQWQVLS  NTVPAKSCQA  QPTTMAHHPH  PHLSFMAIPP  KKNQDKTEIP  TINTIASGEP  120
TSTPTTEAVE  STVATLEDSP  EVIESPPEIN  TVQVTSTAV                          159

SEQ ID NO: 254          moltype = AA  length = 210
FEATURE                 Location/Qualifiers
source                  1..210
                        mol_type = protein
                        organism = Jeotgalicoccus coquinae
SEQUENCE: 254
MERPTEPTAK  QELTVTRKGA  MMKSFFLVVT  ILALTLPFLG  AQEQNQEQPI  RCEKDERFFS   60
DKIAKYIPIQ  YVLSRYPSYG  LNYYQQKPVA  LINNQFLPYP  YYAKPAAVRS  PAQILQWQVL  120
SNTVPAKSCQ  AQPTTMARHP  HPHLSFMAIP  PKKNQDKTEI  PTINTIASGE  PTSTPTIEAV  180
ESTVATLEAS  PEVIESPPEI  NTVQVTSTAV                                    210

SEQ ID NO: 255          moltype = AA  length = 184
FEATURE                 Location/Qualifiers
source                  1..184
                        mol_type = protein
                        organism = Jeotgalicoccus coquinae
SEQUENCE: 255
LVVTILALTL  PFLGAQEQNQ  EQLIRCEKEE  RFFNDKIAKY  IPIQYVLSRY  PSYGLNYYQQ   60
KPVALINNQF  LPYPYYAKPA  AVRSPAQILQ  WQVLPNTVPA  KSCQAQPTTM  TRHPHPHLSF  120
MAIPPKKNQD  KTEIPTINTI  VSVEPTSTPT  TEAIENTVAT  LEASSEVIES  VPETNTAQVT  180
STVV                                                                  184

SEQ ID NO: 256          moltype = AA  length = 194
FEATURE                 Location/Qualifiers
source                  1..194
                        mol_type = protein
                        organism = Bos mutus
SEQUENCE: 256
MMKSFFLVVT  ILALTLPFLG  AQEQNQEQPI  RCEKDERFFS  DKIAKYIPIQ  YVLSRYPSYG   60
LNYYQQKPVA  LINNQFLPYP  YYAKPAAVRS  PAQILQWQVL  SNTVPAKSCQ  AQPTTMARHP  120
HPHLSFMAIP  PKKNQDKTEI  PTINTIASGE  PTSTPTTEAV  ESTVATLEAS  PEASPEVIES  180
PPEINTVQVT  STAV                                                      194

SEQ ID NO: 257          moltype = AA  length = 183
FEATURE                 Location/Qualifiers
source                  1..183
                        mol_type = protein
                        organism = Bos mutus
SEQUENCE: 257
MMKSFFLVVT  ILALTLPFLR  CEKDERFFSD  KIAKYIPIQY  VLSRYPSYGL  NYYQQKPVAL   60
INNQFLPYPY  YAKPAAVRSP  AQILQWQVLS  NTVPAKSCQA  QPTTMARHPH  PHLSFMAIPP  120
KKNQDKTEIP  TINTIASGEP  TSTPTTEAVE  STVATLEASP  EASPEVIESP  PEINTVQVTS  180
TAV                                                                   183

SEQ ID NO: 258          moltype = AA  length = 976
FEATURE                 Location/Qualifiers
source                  1..976
                        mol_type = protein
                        organism = Bos mutus
SEQUENCE: 258
MTSGTAVQRA  DSSEEKRHRK  RKKHHLIKSQ  ILSYTEDRGF  NEGQMKEDEQ  EKADSSEEVR   60
HFHSLQKDKV  NMKFFIFTCL  LAVALAKNVK  SLLKSKKHGT  ITRTSFKVQE  SHRENVDSQT  120
ISSICQNFII  LDCRSSATRI  LCKRFKITVD  DKHYQKALNE  INQFYQKFPQ  YLQYLYQGPI  180
VLNPWDQVKR  NAVPITPTLV  IKLIFIFFFH  KESTEVFTKK  TKLTEEEKNR  LNFLKKISQR  240
YQKFALPQYL  KTVYQHQKAM  KPWIQPKTKV  IPYVDYSDNI  GSPYPVNPSA  SISYPVTPSA  300
SIPCPVNPSA  SIPCPMPDRD  FTPPVYLTKT  NLPNDPAVPS  NPLVFTALGA  PLYSIAGLPI  360
SPFSGQLPPT  GVFRLVPVSS  RPIGPLYSPN  EAAPSANTYI  VEILVPPTTP  PHTVPDQPL   420
TITEPDEAEP  AADALAAPEP  QSSISFDQLI  PQHLMSASNS  NELLLNLNNA  QLRPLQLQGP  480
FNPWIPPFPG  ILQQQQQNQV  PGLSPFSLST  REWFAGLVPN  QIFVPGQVSF  AQGTQAGQLD  540
PSQPQTPQQT  QRGPKNVMPS  VFFKMPQEQA  QMLQYYPVYM  FLPWEQPQQT  VAQSPPQTRE  600
QLFEEQMPFY  TEFGYIPQQV  EPVMPVEQQQ  PVFDPPFLGTA  PEIAAMDRKA  VIVITIKRQL  660
APFVRTILEP  VTSISYNTIP  EKDRTGKFEV  SQDTEGEARS  VSGSDELSSQ  FFFPPYQYPR  720
SHYSRFLCPW  WAYFYPPIPV  PASVSATTPL  NEKKKYQIHV  NKVERPTEPT  AKQELTVTRK  780
GAMMKSFFLV  VTILALTLPF  LGAQEQNQEQ  PIRCEKDERF  FSDKIAKYIP  IQYVLSRYPS  840
YGLNYYQQKP  VALINNQFLP  YPYYAKPAAV  RSPAQILQWQ  VLSNTVPAKS  CQAQPTTMAR  900
HPHPHLSFMA  IPPKKNQDKT  EIPTINTIAS  GEPTSTPTTE  AVESTVATLE  ASPEASPEVI  960
```

```
ESPPEINTVQ VTSTAV                                                            976

SEQ ID NO: 259          moltype = AA   length = 190
FEATURE                 Location/Qualifiers
source                  1..190
                        mol_type = protein
                        organism = Bos indicus
SEQUENCE: 259
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPITEAV ESTVATLEDS PEVIESPPEI   180
NTVQVTSTAV                                                          190

SEQ ID NO: 260          moltype = AA   length = 160
FEATURE                 Location/Qualifiers
source                  1..160
                        mol_type = protein
                        organism = Bos indicus
SEQUENCE: 260
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTIEAV ESTVATLEDS PEVIESPPEI NTVQVTSTAV                         160

SEQ ID NO: 261          moltype = AA   length = 171
FEATURE                 Location/Qualifiers
source                  1..171
                        mol_type = protein
                        organism = Bos indicus
SEQUENCE: 261
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPITEAV ESTVATLEDS PEVIESPPEI NTVQVRQLQS KNLRRHQRRQ R            171

SEQ ID NO: 262          moltype = AA   length = 171
FEATURE                 Location/Qualifiers
source                  1..171
                        mol_type = protein
                        organism = Bos indicus
SEQUENCE: 262
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPITEAV ESTVATLEDS PEVIESPPEI NTVQVLNLQS KNLRRHQRRQ R            171

SEQ ID NO: 263          moltype = AA   length = 160
FEATURE                 Location/Qualifiers
source                  1..160
                        mol_type = protein
                        organism = Bos indicus
SEQUENCE: 263
RCEKDERFFS DKIAKYIPIQ YVLSRYPSYG LNYYQQKPVA LINNQFLPYP YYAKPAAVRS    60
SAQILQWQVL SNTVPAKSCQ AQPTTMARHP HPHLSFMAIP PKKNQDKTEI PTINTIASGE   120
PTSTPTTEAV ESTVATLEDS PEVIESPPEI NTVQVTSTAV                         160

SEQ ID NO: 264          moltype = AA   length = 160
FEATURE                 Location/Qualifiers
source                  1..160
                        mol_type = protein
                        organism = Bos indicus
SEQUENCE: 264
RCEKDERFFS DKIAKYIPIQ YVLSRYPSYG LNYYQQKPVA LINNQFLPYP YYAKPAAVRS    60
SAQILQWQVL SNTVPAKSCQ AQPTTMARHP HPHLSFMAIP PKKNQDKTEI PTINTIASGE   120
PTSTPTIEAV ESTVATLEAS PEVIESPPEI NTVQVTSTAV                         160

SEQ ID NO: 265          moltype = AA   length = 156
FEATURE                 Location/Qualifiers
source                  1..156
                        mol_type = protein
                        organism = Bos indicus
SEQUENCE: 265
DERFFSDKIA KYIPIQYVLS RYPSYGLNYY QQKPVALINN QFLPYPYYAK PAAVRSPAQI    60
LQWQVLSNTV PAKSCQAQPT TMARHPHPHL SFMAIPPKKN QDKTEIPTIN TIASGEPTST   120
PTIEAVESTV ATLEASPEVI ESPPEINTVQ VTSTAV                             156

SEQ ID NO: 266          moltype = AA   length = 194
FEATURE                 Location/Qualifiers
source                  1..194
                        mol_type = protein
                        organism = Bos grunniens
SEQUENCE: 266
```

```
MMKSFFLVVT ILALTLPFLG AQEQNQEQPI RCEKDERFFS DKIAKYIPIQ YVLSRYPSYG    60
LNYYQQKPVA LINNQFLPYP YYAKPAAVRS PAQILQWQVL SSTVPAKSCQ AQPTTMARHP   120
HPHLSFMAIP PKKNQDKTEI PTINTIASGE PTSTPTTEAV ESTVATLEAS PEASPEVIES   180
PPEINTVQVT STAV                                                    194

SEQ ID NO: 267          moltype = AA  length = 190
FEATURE                 Location/Qualifiers
source                  1..190
                        mol_type = protein
                        organism = Bos grunniens
SEQUENCE: 267
MMKSFFLVVT ILALTLPFLG AQEQNQEQPI RCEKDERFFS DKIAKYIPIQ YVLSRYLSYG    60
LNYYQQKPVA LINNQFLPYP YYAKPAAVRS PAQILQWQVL SNTVPAKSCQ AQPTTMARHP   120
HPHLSFMAIP PKKNQDKTEI PTINTIASGE RTSTPTTEAV ESTVATLEAS PEVIESPPEI   180
NTVQVTSTAV                                                         190

SEQ ID NO: 268          moltype = AA  length = 160
FEATURE                 Location/Qualifiers
source                  1..160
                        mol_type = protein
                        organism = Bos grunniens
SEQUENCE: 268
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEAS PEVIESPPEI NTVQVTSTAV                         160

SEQ ID NO: 269          moltype = AA  length = 164
FEATURE                 Location/Qualifiers
source                  1..164
                        mol_type = protein
                        organism = Bos grunniens
SEQUENCE: 269
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEAS PEASPEVIES PPEINTVQVT STAV                    164

SEQ ID NO: 270          moltype = AA  length = 160
FEATURE                 Location/Qualifiers
source                  1..160
                        mol_type = protein
                        organism = Bos grunniens
SEQUENCE: 270
RCEKDERFFS DKIAKYIPIQ YVLSRYLSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEAS PEVIESPPEI NTVQVTSTAV                         160

SEQ ID NO: 271          moltype = AA  length = 190
FEATURE                 Location/Qualifiers
source                  1..190
                        mol_type = protein
                        organism = Bison bison
SEQUENCE: 271
MMKSFFLVVT ILALTLPFLG AQEQNQEQPI RCEKDERFFS DKIAKYIPIQ YVLSRYPSYG    60
LNAYQQKPVA LINNQFLPYP YYAKPAAVRS PAQILQWQVL SNTVPAKSCQ AQPTTMARHP   120
HPHLSFMAIP PKKNQDKTEI PTINTIASGE PTSTPTTEAV ESTVATLEAS PEVIESPPEI   180
NTVQVTSTVV                                                         190

SEQ ID NO: 272          moltype = AA  length = 179
FEATURE                 Location/Qualifiers
source                  1..179
                        mol_type = protein
                        organism = Bison bison
SEQUENCE: 272
MMKSFFLVVT ILALTLPFLR CEKDERFFSD KIAKYIPIQY VLSRYPSYGL NAYQQKPVAL    60
INNQFLPYPY YAKPAAVRSP AQILQWQVLS NTVPAKSCQA QPTTMARHPH PHLSFMAIPP   120
KKNQDKTEIP TINTIASGEP TSTPTTEAVE STVATLEASP EVIESPPEIN TVQVTSTVV    179

SEQ ID NO: 273          moltype = AA  length = 190
FEATURE                 Location/Qualifiers
source                  1..190
                        mol_type = protein
                        organism = Bubalus bubalis
SEQUENCE: 273
MMKSFFLVVT ILALTLPFLG AQEQNQEQPI RCEKEERFFN DKIAKYIPIQ YVLSRYPSYG    60
LNYYQQKPVA LINNQFLPYP YYAKPAAVRS PAQILQWQVL PNTVPAKSCQ AQPTTMTRHP   120
HPHLSFMAIP PKKNQDKTEI PTINTIVSVE PTSTPTTEAI ENTVATLEAS SEVIESVPET   180
NTAQVTSTVV                                                         190

SEQ ID NO: 274          moltype = AA  length = 190
```

```
FEATURE                 Location/Qualifiers
source                  1..190
                        mol_type = protein
                        organism = Bubalus bubalis
SEQUENCE: 274
MMKSFFLVVT ILALTLPFLG AQEQNQEQPI RCEKEERFFN DKIAKYIPIQ YVLSRYPSYG      60
LNYYQQKPVA LINNQFLPYP YYAKPAAVRS PAQILQWQVL PNTVPAKSCQ AQPTTMTRHP     120
HPHLSFMAIP PKKNQDKTEI PTINTIVSVE PTSTPITEAI ENTVATLEAS SEVIESVPET     180
NTAQVTSTVV                                                            190

SEQ ID NO: 275          moltype = AA  length = 190
FEATURE                 Location/Qualifiers
source                  1..190
                        mol_type = protein
                        organism = Bubalus bubalis
SEQUENCE: 275
MMKSFFLVVT ILALTLPFLG AQEQNQEQPI RCEKEERFFN DKIAKYIPIQ YVLSRYPSYG      60
LNYYQQKPVA LINNQFLPYP YYAKPAAVRS PAQILQWQVL PNTVPAKSCQ AQPTTMTRHP     120
HPHLSFMAIP PKKNQDKTEI PTINTIVSIE PTSTPTTEAI ENTVATLEAS SEVIESVPET     180
NTAQVTSTVV                                                            190

SEQ ID NO: 276          moltype = AA  length = 190
FEATURE                 Location/Qualifiers
source                  1..190
                        mol_type = protein
                        organism = Bubalus bubalis
SEQUENCE: 276
MMKSFFLVVT ILALTLPFLG AQEQNQEQPI RCEKEERFFN DKIAKYIPIQ YVLSRYPSYG      60
LNYYQQKPVA LINNQFLPYP YYAKPAAVRS PAQILQWQVL PNTVPAKSCQ AQPTTMTRHP     120
HPHLSFMAIP PKKNQDKTEI PTINTIVSIE PTSTPTTEAI ENTVATLEAS SDVIESVPET     180
NTAQVTSTVV                                                            190

SEQ ID NO: 277          moltype = AA  length = 190
FEATURE                 Location/Qualifiers
source                  1..190
                        mol_type = protein
                        organism = Bubalus bubalis
SEQUENCE: 277
MMKSFFLVVT ILALTLPFLG AQEQNQEQPI RCEKEERFFN DKIAKYIPIQ YVLSRYPSYG      60
LNYYQQKPVA LINNQFLPYP YYAKPAAVRS PAQILQWQVL PNTVPAKSCQ AQPTTMTRHP     120
HPHLSFMAIP PKKNQDKTEI PTINTIVSVE PTSTPTTEAI ENTVATLEAS SDVIESVPET     180
NTAQVTSTVV                                                            190

SEQ ID NO: 278          moltype = AA  length = 190
FEATURE                 Location/Qualifiers
source                  1..190
                        mol_type = protein
                        organism = Bubalus bubalis
SEQUENCE: 278
MMKSFFLVVT ILALTLPFLG AQEQNQEQLI RCEKEERFFN DKIAKYIPIQ YVLSRYPSYG      60
LNYYQQKPVA LINNQFLPYP YYAKPAAVRS PAQILQWQVL PNTVPAKSCQ AQPTTMTRHP     120
HPHLSFMAIP PKKNQDKTEI PTINTIVSVE PTSTPTTEAI ENTVATLEAS SDVIESVPET     180
NTAQVTSTVV                                                            190

SEQ ID NO: 279          moltype = AA  length = 192
FEATURE                 Location/Qualifiers
source                  1..192
                        mol_type = protein
                        organism = Oreamnos americanus
SEQUENCE: 279
MMKSFFLVVT ILALTLPFLG AQEQNQEQPI CCEKDERFFD DKIAKYIPIQ YVLSRYPSYG      60
LNYYQQRPVA LINNQFLPYP YYAKPVAVRS PAQILQWQVL PNTAPAKSCQ DQPTTMARHP     120
HPHLSFMAIP PKKDQDKTEI PTINTIASAE PTVHSTPTTE AIVNTVDNPE ASSESIVSAP     180
ETNTAQVTST EV                                                         192

SEQ ID NO: 280          moltype = AA  length = 192
FEATURE                 Location/Qualifiers
source                  1..192
                        mol_type = protein
                        organism = Capricornis swinhoei
SEQUENCE: 280
MMKSFFLVVT ILALTLPFLG AQEQNQEQPI CCEKDERFFD DKIAKYIPIQ YVLSRYPSYG      60
LNYYQQRPVA LINNQFLPYP YYAKPVAVRS PAQTLQWQVL PNTAPAKSCQ DQPTTMARHP     120
HPHLSFMAIP PKKDQDKTEI PTINTIASAE TTVHSTPTTE AIVNTVDNRE ASSESIVSAP     180
ETNTAQVTST EV                                                         192

SEQ ID NO: 281          moltype = AA  length = 192
FEATURE                 Location/Qualifiers
source                  1..192
```

```
                        mol_type = protein
                        organism = Naemorhedus goral
SEQUENCE: 281
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTAPAKSCQ DQPTTMARHP   120
HPHLSFMAIP PKKDQDKTEI PTINTIASAE PTVHSTPTTE AIVNTVDNPE ASSESIASAP   180
ETNTAQVTST EV                                                      192

SEQ ID NO: 282          moltype = AA  length = 192
FEATURE                 Location/Qualifiers
source                  1..192
                        mol_type = protein
                        organism = Capricornis sumatraensis
SEQUENCE: 282
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTAPAKSCQ DQPTTMARHP   120
HPHLSFMAIP PKKDQDKTEI PTINTIASAE PTVHSTPTTE AIVNTVDNPE ASSESIVSAP   180
ETNTAQVTST EV                                                      192

SEQ ID NO: 283          moltype = AA  length = 192
FEATURE                 Location/Qualifiers
source                  1..192
                        mol_type = protein
                        organism = Capricornis crispus
SEQUENCE: 283
MMKSFFLAVT ILALTLPFLG AQEQNQEQPI CCEKDETFFD DKIAKYIPIQ YVLSRYPSYG    60
LNYYQQRPVA LINNQFLPYP YYAKPVAVRS PAQTLQWQVL PNTVPAKSCQ DQPTTMARHP   120
HPHLSFMAIP PKKDQDKTEI PTINTIASAE PTVHSTPTTE AIVNTVDNPE ASSESIVSAP   180
ETNTAQVTST EV                                                      192

SEQ ID NO: 284          moltype = AA  length = 192
FEATURE                 Location/Qualifiers
source                  1..192
                        mol_type = protein
                        organism = Capricornis crispus
SEQUENCE: 284
MMKSFFLVVT ILALTLPFLG AQEQNQEQPI CCEKDETFFD DKIAKYIPIQ YVLSRYPSYG    60
LNYYQQRPVA LINNQFLPYP YYAKPVAVRS PAQTLQWQVL PNTVPAKSCQ DQPTTMARHP   120
HPHLSFMAIP PKKDQDKTEI PTINTIASAE PTVHSTPTTE AIVNTVDNPE ASSESIVSAP   180
ETNTAQVTST EV                                                      192

SEQ ID NO: 285          moltype = AA  length = 202
FEATURE                 Location/Qualifiers
source                  1..202
                        mol_type = protein
                        organism = Saiga tatarica
SEQUENCE: 285
MMKSFFLVVT ILALTLPFLD AQERNQEQPI CCEKDERFFN DRIAKYIPIQ YVLSRYPSYG    60
LNYYQQRPVA LINNQFLPYP YYAKPVAVRS PAQTLQWQVL PNTVPAKSCQ DQPTTMARHP   120
HPHLSFMAIP PKKDQDKTEI PTINTVASAE PASTPTTEAI VNTEAIVNTE AIVNTVDNPE   180
ASSEIIASVP ETNTAQVTST EV                                           202

SEQ ID NO: 286          moltype = AA  length = 160
FEATURE                 Location/Qualifiers
REGION                  1..160
                        note = Bos indicus x Bos taurus
source                  1..160
                        mol_type = protein
                        organism = unidentified
SEQUENCE: 286
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLSFMAIP PKKNQDKTEI PTINTIASGE   120
PTSTPTTEAV ESTVATLEDS PEVIESPPEI NTVQVTSTAV                         160

SEQ ID NO: 287          moltype = AA  length = 160
FEATURE                 Location/Qualifiers
REGION                  1..160
                        note = Bos indicus x Bos taurus
source                  1..160
                        mol_type = protein
                        organism = unidentified
SEQUENCE: 287
RCEKDERFFS DKIAKYIPIQ YVLSRYPSYG LNYYQQKPVA LINNQFLPYP YYAKPAAVRS    60
PAQILQWQVL SNTVPAKSCQ AQPTTMARHP HPHLAFMAIP PKKNQDKTEI PTINTIASGE   120
PTSTPTTEAV ESTVATLEDS PEVIESPPEI NTVQVTSTAV                         160

SEQ ID NO: 288          moltype = AA  length = 192
FEATURE                 Location/Qualifiers
source                  1..192
```

```
                mol_type = protein
                organism = Capra hircus
SEQUENCE: 288
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTVPAKSCQ DQPTTLARHP   120
HPHLSFMAIP PKKDQDKTEV PAINTIASAE PTVHSTPTTE AIVNTVDNPE ASSESIASAS   180
ETNTAQVTST EV                                                      192

SEQ ID NO: 289          moltype = AA  length = 192
FEATURE                 Location/Qualifiers
source                  1..192
                        mol_type = protein
                        organism = Capra hircus
SEQUENCE: 289
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTVPAKSCQ DQPTTLARHP   120
HPHLSFMAIP PKKDQDKTEI PAINTIASAE PTVHSTPTTE AIVNTVDNPE ASSESIASAS   180
ETNTAQVTST EV                                                      192

SEQ ID NO: 290          moltype = AA  length = 192
FEATURE                 Location/Qualifiers
source                  1..192
                        mol_type = protein
                        organism = Capra hircus
SEQUENCE: 290
MMKSFFLVVT ILALTLPFLG AQEQNQEQPI CCEKDERFFD DKIAKYIPIQ YVLSRYPSYG    60
LNYYQQRPVA LINNQFLPYP YYAKPVAVRS PAQTLQWQVL PNTVPAKSCQ DQPTTLARHP   120
HPHLSFMAIP PKKDQDKTEI PAINTIASAE PTVHSTPITE AIVNTVDNPE ASSESIASAS   180
ETNTAQVTST EV                                                      192

SEQ ID NO: 291          moltype = AA  length = 192
FEATURE                 Location/Qualifiers
source                  1..192
                        mol_type = protein
                        organism = Capra hircus
SEQUENCE: 291
MMKSFFLVVT ILALTLPFLG AQEQNQEQPI CCEKDERFFD DKIAKYIPIQ YVLSRYPSYG    60
LNYYRQRPVA LINNQFLPYP YYAKPIAVRS PAQTLQWQVL PNTVPAKSCQ DQPTTLARHP   120
HPHLSFMAIP PKKDQDKTEI PAINTIASAE PTVHSTPTTE AIVNTVDNPE ASSESIASAP   180
ETNTAQVTST EV                                                      192

SEQ ID NO: 292          moltype = AA  length = 161
FEATURE                 Location/Qualifiers
source                  1..161
                        mol_type = protein
                        organism = Capra hircus
SEQUENCE: 292
CEKDERFFDD KIAKYIPIQY VLSRYPSYGL NYYQQRPVAL INNQFLPYPY YAKPIAVRSP    60
AQTLQWQVLP NTVPAKSCQD QPTTLARHPH PHLSFMAIPP KKDQDKTEIP AINTIASAEP   120
TVHSTPTTEA IVNTVDNPEA SSESIASAPE TNTAQVTSTE V                      161

SEQ ID NO: 293          moltype = AA  length = 161
FEATURE                 Location/Qualifiers
source                  1..161
                        mol_type = protein
                        organism = Capra hircus
SEQUENCE: 293
CEKDERFFDD KIAKYIPIQY VLSRYPSYGL NYYQQRPVAL INNQFLPYPY YAKPIAVRSP    60
AQTLQWQVLP NTVPAKSCQD QPTTLARHPH PHLSFMAIPP KKDQDKTEIP AINTIASAEP   120
TVHSTPTTEA IVNTVDNPEA SSESIVSAPE TNTAQVTSTE V                      161

SEQ ID NO: 294          moltype = AA  length = 162
FEATURE                 Location/Qualifiers
source                  1..162
                        mol_type = protein
                        organism = Capra hircus
SEQUENCE: 294
CCEKDERFFD DKIAKYIPIQ YVLSRYPSYG LNYYQQRPVA LINNQFLPYP YYAKPVAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIASAP ETNTAQVTST EV                     162

SEQ ID NO: 295          moltype = AA  length = 162
FEATURE                 Location/Qualifiers
source                  1..162
                        mol_type = protein
                        organism = Capra hircus
SEQUENCE: 295
CCEKDERFFD DKIAKYIPIQ YVLSRYPSYG LNYYQQRPVA LINNQFLPYP YYAKPVAVRS    60
PAQTLQWQVL PNTVPAKSCQ GQPTTLARHP HPHLSFMAIP PKKDQDKTEI PAINTIASAE   120
```

```
PTVHSTPTTE AIVNTVDNPE ASSESIASAS ETNTAQVTST EV                  162

SEQ ID NO: 296          moltype = AA  length = 162
FEATURE                 Location/Qualifiers
source                  1..162
                        mol_type = protein
                        organism = Capra hircus
SEQUENCE: 296
CCEKDERFFD DKIAKYIPIQ YVLSRYPSYG LNYYQQRPVA LINNQFLPYP YYAKPVAVRS  60
PAQTLQWQVL PNTVPAKSCQ NQPTTLARHP HPHLSFMAIP PKKDQDKTEI PAINTIASAE 120
PTVHSTPTTE AIVNTADNPE ASSESIASAP ETNTAQVTST EV                  162

SEQ ID NO: 297          moltype = AA  length = 161
FEATURE                 Location/Qualifiers
source                  1..161
                        mol_type = protein
                        organism = Capra hircus
SEQUENCE: 297
CEKDERFFDD KIAKYIPIQY VLSRYPSYGL NYYQQRPVAL INNQFLPYPY YAKPVAVRSP  60
AQTLQWQVLP NTVPAKSCQD QPTTLARHPH PHLSFMAIPP KKDQDKTEVP AINTIASAEP 120
TVHSTPTTEA IVNTVDNPEA SSESIASASE TNTAQVTSTE V                   161

SEQ ID NO: 298          moltype = AA  length = 162
FEATURE                 Location/Qualifiers
source                  1..162
                        mol_type = protein
                        organism = Capra hircus
SEQUENCE: 298
CCEKDERFFD DKIAKYIPIQ YVLSRYPSYG LNYYQQRPVA LINNQFLPYP YYAKPIAVRS  60
PAQTLQWQVL PNTVPAKSCQ DQPTTLARHP HPHLSFMAIP PKKDQDKTEI PAINTIASAE 120
PTVHSTPTTE AIVNTVDNPE ASSESIASAP ETNTAQVTST EV                  162

SEQ ID NO: 299          moltype = AA  length = 162
FEATURE                 Location/Qualifiers
source                  1..162
                        mol_type = protein
                        organism = Capra hircus
SEQUENCE: 299
CCEKDERFFD DKIAKYIPIQ YVLSRYPSYG LNYYQQRPVA LINNQFLPYP YYAKPIAVRS  60
PAQTLQWQVL PNTVPAKSCQ DQPTTLARHP HPHLSFMAIP PKKDQDKTEI PAINTIASAE 120
PTVHSTPTTE AIVNTVDNPE ASSESIVSAP ETNTAQVTST EV                  162

SEQ ID NO: 300          moltype = AA  length = 161
FEATURE                 Location/Qualifiers
source                  1..161
                        mol_type = protein
                        organism = Capra hircus
SEQUENCE: 300
CEKDERFFDD KIAKYIPIQY VLSRYPSYGL NYYQQRPVAL INNQFLPYPY YAKPVAVRSP  60
AQTLQWQVLP NTVPAKSCQD QPTTLARHPH PHLSFMAIPP KKDQDKTEIP AINTIASAEP 120
TVHSTPTTEA IVNTVDNPEA SSESIASASE TNTAQVTSTE V                   161

SEQ ID NO: 301          moltype = AA  length = 162
FEATURE                 Location/Qualifiers
source                  1..162
                        mol_type = protein
                        organism = Capra hircus
SEQUENCE: 301
CCEKDERFFD DKIAKYIPIQ YVLSRYPSYG LNYYQQRPVA LINNQFLPYP YYAKPVAVRS  60
PAQTLQWQVL PNTVPAKSCQ DQPTTLARHP HPHLSFMAIP PKKDQDKTEV PAINTIASAE 120
PTVHSTPTTE AIVNTVDNPE ASSESIASAS ETNTAQVTST EV                  162

SEQ ID NO: 302          moltype = AA  length = 162
FEATURE                 Location/Qualifiers
source                  1..162
                        mol_type = protein
                        organism = Capra hircus
SEQUENCE: 302
CCEKDERFFD DKIAKYIPIQ YVLSRYPSYG LNYYQQRPVA LINNQFLPYP YYAKPVAVRS  60
PAQTLQWQVL PNTVPAKSCQ DQPTTLARHP HPHLSFMAIP PKKDQDKTEI PAINTIASAE 120
PTVHSTPTTE AIVNTVDNPE ASSESIASAS ETNTAQVTST EV                  162

SEQ ID NO: 303          moltype = AA  length = 159
FEATURE                 Location/Qualifiers
source                  1..159
                        mol_type = protein
                        organism = Capra hircus
SEQUENCE: 303
CCEKDERFFD DKIAKYIPIQ YVLSRYPSYG LNYYQQRPVA LINNQFLPYP YYAKPVAVRS  60
```

```
PAQTLQWQVL PNTVPAKSCQ DQPTTLARHP HPHLSFMAIP PKKDQDKTEI PAINTIASAE    120
PTVHSTPTTE AIVNTVDNPE ASSESIASAS ETNTAQVTS                           159

SEQ ID NO: 304          moltype = AA  length = 159
FEATURE                 Location/Qualifiers
source                  1..159
                        mol_type = protein
                        organism = Capra hircus
SEQUENCE: 304
CCEKDERFFD DKIAKYIPIQ YVLSRYPSYG LNYYQQRPVA LINNQFLPYP YYAKPVAVRS    60
PAQTLQWQVL PNTVPAKSCQ DQPTTLARHP HPHLSFMAIP PKKDQDKTEV PAINTIASAE    120
PTVHSTPTTE AIVNTVDNPE ASSESIASAS ETNTAQVTS                           159

SEQ ID NO: 305          moltype = AA  length = 141
FEATURE                 Location/Qualifiers
VARIANT                 110
                        note = X is any amino acid
source                  1..141
                        mol_type = protein
                        organism = Capra hircus
SEQUENCE: 305
CCEKDERFFD DKIAKYIPIQ YVLSRYPSYG LNYYQQRPVA LINNQFLPYP YYAKPVAVRS    60
PAQTLQWQVL PNTVPAKSCQ DQPTTLARHP HPHLSFMAIP PKKDQDKTEX PAINTIASAE    120
PTVHSTPTTE AIVNTVDNPE A                                              141

SEQ ID NO: 306          moltype = AA  length = 162
FEATURE                 Location/Qualifiers
source                  1..162
                        mol_type = protein
                        organism = Capra hircus
SEQUENCE: 306
CCEKDERFFD DKIAKYIPIQ YVLSRYPSYG LNYYQQRPVA LINNQFLPYP YYAKPIAVRS    60
PAQTLQWQVL PNTVPAKSCQ DQPTTLARHP HPHLSFMAIP PKKDQDKTEI PAINTIASAE    120
PTVHSTPTTE AIVNTVDNPE ASSESIASAS ETNTAQVTST EV                       162

SEQ ID NO: 307          moltype = AA  length = 161
FEATURE                 Location/Qualifiers
source                  1..161
                        mol_type = protein
                        organism = Capra hircus
SEQUENCE: 307
CEKDERFFDD KIAKYIPIQY VLSRYPSYGL NYYRQRPVAL INNQFLPYPY YAKPIAVRSP    60
AQTLQWQVLP NTVPAKSCQD QPTTLARHPH PHLSFMAIPP KKDQDKTEIP AINTIASAEP    120
TVHSTPTTEA IVNTVDNPEA SSESIASAPE TNTAQVTSTE V                        161

SEQ ID NO: 308          moltype = AA  length = 162
FEATURE                 Location/Qualifiers
source                  1..162
                        mol_type = protein
                        organism = Capra hircus
SEQUENCE: 308
CCEKDERFFD DKIAKYIPIQ YVLSRYPSYG LNYYRQRPVA LINNQFLPYP YYAKPIAVRS    60
PAQTLQWQVL PNTVPAKSCQ DQPTTLARHP HPHLSFMAIP PKKDQDKTEI PAINTIASAE    120
PTVHSTPTTE AIVNTVDNPE ASSESIASAP ETNTAQVTST EV                       162

SEQ ID NO: 309          moltype = AA  length = 162
FEATURE                 Location/Qualifiers
source                  1..162
                        mol_type = protein
                        organism = Capra hircus
SEQUENCE: 309
CCEKDERFFD DKIAKYIPIQ YVLSRYPSYG LNYYRQRPVA LINNQFLPYP YYAKPVAVRS    60
PAQTLQWQVL PNTVPAKSCQ DQPTTLARHP HPHLSFMAIP PKKDQDKTEI PAINTIASAE    120
PTVHSTPTTE AIVNTVDNPE ASSESIASAS ETNTAQVTST EV                       162

SEQ ID NO: 310          moltype = AA  length = 162
FEATURE                 Location/Qualifiers
source                  1..162
                        mol_type = protein
                        organism = Capra hircus
SEQUENCE: 310
CCEKDERFFD DKIAKYIPIQ YVLSRYPSYG LNYYQQRPVA LINSQFLPYP YYAKPVAVRS    60
PAQTLQWQVL PNTVPAKSCQ DQPTTLARHP HPHLSFMAIP PKKDQDKTEI PAINTIASAE    120
PTVHSTPTTE AIVNTVDNPE ASSESIASAS ETNTAQVTST EV                       162

SEQ ID NO: 311          moltype = AA  length = 190
FEATURE                 Location/Qualifiers
source                  1..190
                        mol_type = protein
```

```
                        organism = Odocoileus virginianus
SEQUENCE: 311
MMKSFSLVVT ILALTLPFLV AQEQNQEQPT GCEKDERFFN DKIVKYIPIQ YVLSRYPSYG    60
LSYYQHRPVA LINNQFLPYP YYAKPGAVRS PAQILQWQVL PNTVPAKSCQ AQPTTLARHP   120
HPRLSFMAIP PKKNQDKTDI PTINTIATVE STITPTTEAI VDTVATPEAS SEVIESAPET   180
KTDQVTSTVV                                                         190

SEQ ID NO: 312          moltype = AA  length = 192
FEATURE                 Location/Qualifiers
source                  1..192
                        mol_type = protein
                        organism = Rupicapra rupicapra
SEQUENCE: 312
MMKSFFLVAT ILALTLPFLG AQEQNQEQSI CCEKDERFFE DKIAKYIPIQ YVLSRYPSYG    60
LNYYQQRPVA LINNQFLPYP YYAKPVAVRS PAQTLQWQVL PNTAPAKSCQ DQPTTMAHHP   120
HPHLSFMAIP PKKDQDKTEI PTINTIASAE PTVHSTPTTE AIVNTVDNPE ASSESIASAP   180
ETNTAQVTST EV                                                      192

SEQ ID NO: 313          moltype = AA  length = 192
FEATURE                 Location/Qualifiers
source                  1..192
                        mol_type = protein
                        organism = Ovis aries
SEQUENCE: 313
MMKSFFLVVT ILALTLPFLG AQEQNQEQRI CCEKDERFFD DKIAKYIPIQ YVLSRYPSYG    60
LNYYQQRPVA LINNQFLPYP YYAKPVAVRS PAQTLQWQVL PNAVPAKSCQ DQPTAMARHP   120
HPHLSFMAIP PKKDQDKTEI PAINTIASAE PTVHSTPTTE AVVNAVDNPE ASSESIASAP   180
ETNTAQVTST EV                                                      192

SEQ ID NO: 314          moltype = AA  length = 162
FEATURE                 Location/Qualifiers
source                  1..162
                        mol_type = protein
                        organism = Ovis aries
SEQUENCE: 314
CCEKDERFFD DKIAKYIPIQ YVLSRYPSYG LNYYQQRPVA LINNQFLPYP YYAKPVAVRS    60
PAQTLQWQVL PNAVPAKSCQ DQPTAMARHP HPHLSFMAIP PKKDQDKTEI PAINTIASAE   120
PTVHSTPTTE AVVNAVDNPE ASSESIASAP ETNTAQVTST EV                     162

SEQ ID NO: 315          moltype = AA  length = 190
FEATURE                 Location/Qualifiers
source                  1..190
                        mol_type = protein
                        organism = Cervus nippon
SEQUENCE: 315
MMKSFFLAVT ILALTLPFLV AQEQIQEQPT GCEKDERFFN DKIVKYIPIQ YALSRYPSYG    60
LNYYQHRPVA LINNQFLPYP YVKPGAVRS PAQILQWQVL PNTVPAKFCQ AQPTTMARHP   120
HPRLSFMAIP PKKNQDKTDI PSINTIATAE STITPTTEAI VDTVATQEAF SEVIESAPEA   180
KTDQVTSTVV                                                         190

SEQ ID NO: 316          moltype = AA  length = 178
FEATURE                 Location/Qualifiers
VARIANT                 178
                        note = X is any amino acid
source                  1..178
                        mol_type = protein
                        organism = Gazella arabica
SEQUENCE: 316
CCEKDERFFN DKIAKYIPIQ YVLSRYPSYG LNYYQQRPVA LINNQFLPYP YYAKPVAVRS    60
PAQTLQWQVL PNTVPAKSCQ DQPTTMARHP HPHLSFMAIP PKKDQDKTEI PTINTIASAE   120
PASTPTTEAI VNTEAVVNTE AIVNTEAIVN TVDNPEASSE IIASVPETNT AQVTSTEX     178

SEQ ID NO: 317          moltype = AA  length = 170
FEATURE                 Location/Qualifiers
source                  1..170
                        mol_type = protein
                        organism = Muntiacus muntjak
SEQUENCE: 317
AQELNQEQPT GCEKDERFFN DKIVKYIPIQ YALSRYPSYG LNYYQHRPVA LISNQFLPYP    60
YYAKPGAVRS PAQTLQWQAL PNTVPATSCQ AQPATMARHP HPRLSFMAIP PKKTQDKTDH   120
PTFNTIATAE STATPTTEAV VDTVATQEAS SEVTASAPEA NTDQVTSTAV              170

SEQ ID NO: 318          moltype = AA  length = 170
FEATURE                 Location/Qualifiers
source                  1..170
                        mol_type = protein
                        organism = Muntiacus reevesi
SEQUENCE: 318
AQELNQEQPT GCEKDERFFN DKIVKYIPIQ YALSRYPSYG LNYYQHRPVA LISNQFLPYP    60
```

```
YYAKPGAVRS PAQILQWQAL PNTVPATSCQ AQPATVARHP HPRLSFMAIP PKKSQDKTDH    120
PTINTIATVE STATPTTEAV VDTAATQEAS PEVIASAPEA STDQVTSTAV               170

SEQ ID NO: 319           moltype = AA  length = 172
FEATURE                  Location/Qualifiers
VARIANT                  136
                         note = X is any amino acid
VARIANT                  151
                         note = X is any amino acid
VARIANT                  154
                         note = X is any amino acid
VARIANT                  161
                         note = X is any amino acid
VARIANT                  168
                         note = X is any amino acid
source                   1..172
                         mol_type = protein
                         organism = Gazella dorcas
SEQUENCE: 319
CCEKDERFFN DKIAKYIPIQ YVLSRYPSYG LNYYQQRPVA LINNQFLPYP YYAKPVAVRS    60
PAQTLQWQVL PNTVPAKSCQ DQPTTMARHP HPHLSFMAIP PKKDQDKTEI PTINTIASAE    120
PASTPTTEAI VNTEPXVNTE PIVNTVDNPE XSSXIIASVP XTNTAQVXST EV            172

SEQ ID NO: 320           moltype = AA  length = 160
FEATURE                  Location/Qualifiers
source                   1..160
                         mol_type = protein
                         organism = Procapra gutturosa
SEQUENCE: 320
CCEKDERFFN DKIAKYIPIQ YVMSRYPSYG LNYYQQRPVA LINNQFLPYP YYAKPVAVRS    60
PAQTLQWQVL PNTVPAKSCQ DQPTTMARHP HPHLSFMAIP PKKDQDKTEI PTINTIASAE    120
PTSTPTTEAI VNTVDNPEAT SEIIASVPET NTAQVTSTEV                          160

SEQ ID NO: 321           moltype = AA  length = 160
FEATURE                  Location/Qualifiers
VARIANT                  111
                         note = X is any amino acid
VARIANT                  121
                         note = X is any amino acid
VARIANT                  125
                         note = X is any amino acid
VARIANT                  139
                         note = X is any amino acid
source                   1..160
                         mol_type = protein
                         organism = Procapra gutturosa
SEQUENCE: 321
CCEKDERFFN DKIAKYIPIQ YVMSRYPSYG LNYYQQRPVA LINNQFLPYP YYAKPVAVRS    60
PAQTLQWQVL PNTVPAKSCQ DQPTTMARHP HPHLSFMAIP PKKDQDKTEI XTINTIASAE    120
XTSTXTTEAI VNTVDNPEXT SEIIASVPET NTAQVTSTEV                          160

SEQ ID NO: 322           moltype = AA  length = 160
FEATURE                  Location/Qualifiers
source                   1..160
                         mol_type = protein
                         organism = Madoqua saltiana
SEQUENCE: 322
CCEKDERFFN DKIAKYIPIQ YVLSRYPSYG LNYYQQRPVA LINNQFLPYP YFAKPVAVRS    60
PAQTLQWQVL PNTVPAKSCQ DQPTTMARHP HPHLSFMAIP PKKDQDKPEI PTINTIASAE    120
LTSTPTTEAI VNTVDNPEAS SEIIASVPET NTAEVTSTEV                          160

SEQ ID NO: 323           moltype = AA  length = 155
FEATURE                  Location/Qualifiers
VARIANT                  138
                         note = X is any amino acid
source                   1..155
                         mol_type = protein
                         organism = Ammotragus lervia
SEQUENCE: 323
CCEKDERFFD DKIAKYIPIQ YVLSRYPSYG LNYYQQRPVA LINNQFLPYP YYAKPVAVRS    60
PAQTLQWQVL PNTAPAKSCQ DQPTTMARHP HPHLSFMAIP PKKDQDKTEI PAINTIASVE    120
PTVHSTPTAE AIVNTVDXPE ASSESIASAP ETNTA                               155

SEQ ID NO: 324           moltype = AA  length = 155
FEATURE                  Location/Qualifiers
source                   1..155
                         mol_type = protein
                         organism = Ammotragus lervia
SEQUENCE: 324
```

```
CCEKDERFFD DKIAKYIPIQ YVLSRYPSYG LNYYQQRPVA LINNQFLPYP YYAKPVAVRS    60
PAQTLQWQVL PNTAPAKSCQ DQPTTMARHP HPHLSFMAIP PKKDQDKTEI PAINTIASVE   120
PTVHSTPTAE AIVNTVDSPE ASSESIASAP ETNTA                              155

SEQ ID NO: 325          moltype = AA  length = 155
FEATURE                 Location/Qualifiers
source                  1..155
                        mol_type = protein
                        organism = Ammotragus lervia
SEQUENCE: 325
CCEKDERFFD DKIAKYIPIQ YVLSRYPSYG LNYYQQRPVA LINNQFLPYP YYAKPVAVRS    60
PAQTLQWQVL PNTAPAKSCQ DQPTTMARHP HPHLSFMAIP PKKDQDKTEI PAINTIASVE   120
PTVHSTPTAE AIVNTVDNPE ASSESIASAP ETNTA                              155

SEQ ID NO: 326          moltype = AA  length = 162
FEATURE                 Location/Qualifiers
source                  1..162
                        mol_type = protein
                        organism = Capra sibirica
SEQUENCE: 326
CCEKDERFFD DKIAKYIPIQ YVLSRYPSYG LNYYQQRPVA LINNQFLPYP YYAKPVAVRS    60
PAQTLQWQVL PNTVPAKSCQ DQPTTLARHP HPHLSFMAIP PKKDQDKTEV PAINTIASAE   120
PTVHSTPTTE AIVNTVDNPE ASSESIASAS ETNTGQVTST EV                      162

SEQ ID NO: 327          moltype = AA  length = 162
FEATURE                 Location/Qualifiers
source                  1..162
                        mol_type = protein
                        organism = Ovis canadensis
SEQUENCE: 327
CCEKDERFFD DKIAKYIPIQ YVLSRYPSYG LNYYQQRPVA LINNQFLPYP YYAKPVAVRS    60
PAQTLQWQVL PNTVPAKSCQ DQPTTMAHHP HPHLSFMAIP PKKDQDKTEI PAINTIASVE   120
PTVHSTPTTE AVVNTVDNPE ASSESIASAP ETNAAQVTTT EV                      162

SEQ ID NO: 328          moltype = AA  length = 162
FEATURE                 Location/Qualifiers
VARIANT                 155..156
                        note = X is any amino acid
source                  1..162
                        mol_type = protein
                        organism = Ovis canadensis
SEQUENCE: 328
CCEKDERFFD DKIAKYIPIQ YVLSRYPSYG LNYYQQRPVA LINNQFLPYP YYAKPVAVRS    60
PAQTLQWQVL PNTVPAKSCQ DQPTTMAHHP HPHLSFMAIP PKKDQDKTEI PAINTIASVE   120
PTVHSTPTTE AVVNTVDNPE ASSESIASAP ETNAXXVTTT EV                      162

SEQ ID NO: 329          moltype = AA  length = 178
FEATURE                 Location/Qualifiers
source                  1..178
                        mol_type = protein
                        organism = Gazella subgutturosa
SEQUENCE: 329
CCEKNERFFN DKIAKYIPIQ YVLSRYPSYG LNYYQQRPVA LINNQFLPYP YYVKPVAVRS    60
PAQTLQWQVL PNTVPAKSCQ DQPTTMARHP HPHLSFMAIP PKKDQDKTEI PTINTIASAE   120
PASTPTTEAI VNTEAVVNTE AIVNTEAIVN TVDNPEASSE IIASVPETNT AQVTSTEV     178

SEQ ID NO: 330          moltype = AA  length = 172
FEATURE                 Location/Qualifiers
VARIANT                 33
                        note = X is any amino acid
VARIANT                 135
                        note = X is any amino acid
source                  1..172
                        mol_type = protein
                        organism = Antilope cervicapra
SEQUENCE: 330
GCEKDERFFN DKIAKYIPIQ YVLSRYPSYG LNXYQQRPVA LINNQFLPYP YYVKPVAVRS    60
PAQTLQWQVL PNTVPAKSCQ DQPTTMARHP HPHLSFMAIP PKKDQDKTEI PTINTIASAE   120
PASTPTTEAI VNTEXIVNTE PIVNTVDNPE ASSEIIASVP ETNTAQVTST EV           172

SEQ ID NO: 331          moltype = AA  length = 162
FEATURE                 Location/Qualifiers
source                  1..162
                        mol_type = protein
                        organism = Capra ibex
SEQUENCE: 331
CCEKDERFFD DKIAKYIPIQ YVLNRYPTYG LNYYQQRPVA LINNQFLPYP YYAKPVAVRS    60
PAQTLQWQVL PNTVPAKSCQ DQPTTLARHP HPHLSFMAIP PKKDQDKTEI PAINTIASAE   120
PTVHSTPTTE AIVNTVDNPE ASSESIASAP ETNTAQVTST EV                      162
```

```
SEQ ID NO: 332           moltype = AA  length = 162
FEATURE                  Location/Qualifiers
source                   1..162
                         mol_type = protein
                         organism = Ovis vignei
SEQUENCE: 332
CCEKDERFFD DKIAKYIPIQ YVLSRYPSYG LNYYQQRPVA LINNQFLPYP YYAKPVAVRS   60
PAQTLQWQVL PNAVPAKSCQ DQPTAMARHP HPHLSFMAIP PKKDQDKTEI PAINTIASAE  120
PTVHSTPTTE AVVNAVDNPE ASSESIASAP ETNTAQVTST ES                     162

SEQ ID NO: 333           moltype = AA  length = 162
FEATURE                  Location/Qualifiers
VARIANT                  73
                         note = X is any amino acid
VARIANT                  162
                         note = X is any amino acid
source                   1..162
                         mol_type = protein
                         organism = Ovis vignei
SEQUENCE: 333
CCEKDERFFD DKIAKYIPIQ YVLSRYPSYG LNYYQQRPVA LINNQFLPYP YYAKPVAVRS   60
PAQTLQWQVL PNXVPAKSCQ DQPTAMARHP HPHLSFMAIP PKKDQDKTEI PAINTIASAE  120
PTVHSTPTTE AVVNAVDNPE ASSESIASAP ETNTAQVTST EX                     162

SEQ ID NO: 334           moltype = AA  length = 162
FEATURE                  Location/Qualifiers
VARIANT                  156
                         note = X is any amino acid
source                   1..162
                         mol_type = protein
                         organism = Ovis ammon
SEQUENCE: 334
CCEKDERFFD DKIAKYIPIQ YVLSRYPSYG LNYYQQRPVA LINNQFLPYP YYAKPVAVRS   60
PAQTLQWQVL PNAVPAKSCQ DQPTAMARHP HPHLSFMAIP PKKDQDKTEI PAINTIASAE  120
PTVHSTPTTE AVVNAVDNPE ASSESIASAP ETNTAXVTST EV                     162

SEQ ID NO: 335           moltype = AA  length = 162
FEATURE                  Location/Qualifiers
VARIANT                  112
                         note = X is any amino acid
source                   1..162
                         mol_type = protein
                         organism = Ovis vignei
SEQUENCE: 335
CCEKDERFFD DKIAKYIPIQ YVLSRYPSYG LNYYQQRPVA LINNQFLPYP YYAKPVAVRS   60
PAQTLQWQVL PNAVPAKSCQ DQPTAMARHP HPHLSFMAIP PKKDQDKTEI PXINTIASAE  120
PTVHSTPTTE AVVNAVDNPE ASSESIASAP ETNTAQVTST EV                     162

SEQ ID NO: 336           moltype = AA  length = 162
FEATURE                  Location/Qualifiers
source                   1..162
                         mol_type = protein
                         organism = Ovis orientalis
SEQUENCE: 336
CCEKDERFFD DKIAKYIPIQ YVLSRYPSYG LNYYQQRPVA LINNQFLPYP YYAKPVAVRS   60
PAQTLQWQVL PNTVPAKSCQ DQPTAMARHP HPHLSFMAIP PKKDQDKTEI PAINTIASAE  120
PTVHSTPTTE AVVNAVDNPE ASSESIASAP ETNTAQVTST EV                     162

SEQ ID NO: 337           moltype = AA  length = 162
FEATURE                  Location/Qualifiers
source                   1..162
                         mol_type = protein
                         organism = Ovis orientalis
SEQUENCE: 337
CCEKDERFFD DKIAKYIPIQ YVLSRYPSYG LNYYQQRPVA LINNQFLPYP YYAKPVAVRS   60
PAQTLQWQVL PNAVPAKSCQ DQPTAMARHP HPHLSFMAIP PKKDQDKTEI PAINTIASAE  120
PTVHSTPTTE AVVNAVDNPE ASSESIASAP ETNTAQITST EV                     162

SEQ ID NO: 338           moltype = AA  length = 162
FEATURE                  Location/Qualifiers
REGION                   1..162
                         note = Ovis orientalis x vignei
VARIANT                  107
                         note = X is any amino acid
source                   1..162
                         mol_type = protein
                         organism = unidentified
SEQUENCE: 338
```

```
CCEKDERFFD DKIAKYIPIQ YVLSRYPSYG LNYYQQRPVA LINNQFLPYP YYAKPVAVRS    60
PAQTLQWQVL PNAVPAKSCQ DQPTAMARHP HPHLSFMAIP PKKDQDXTEI PAINTIASAE   120
PTVHSTPTTE AVVNAVDNPE ASSESIASAP ETNTAQVTST EV                     162

SEQ ID NO: 339          moltype = AA  length = 162
FEATURE                 Location/Qualifiers
VARIANT                 154
                        note = X is any amino acid
source                  1..162
                        mol_type = protein
                        organism = Ovis vignei
SEQUENCE: 339
CCEKDERFFD DKIAKYIPIQ YVLSRYPSYG LNYYQQRPVA LINNQFLPYP YYAKPVAVRS    60
PAQTLQWQVL PNAVPAKSCQ DQPTAMARHP HPHLSFMAIP PKKDQDKTEI PAINTIASAE   120
PTVHSTPTTE AVVNAVDNPE ASSESIASAP ETNXAQVTST EV                     162

SEQ ID NO: 340          moltype = AA  length = 162
FEATURE                 Location/Qualifiers
VARIANT                 73
                        note = X is any amino acid
source                  1..162
                        mol_type = protein
                        organism = Ovis ammon
SEQUENCE: 340
CCEKDERFFD DKIAKYIPIQ YVLSRYPSYG LNYYQQRPVA LINNQFLPYP YYAKPVAVRS    60
PAQTLQWQVL PNXVPAKSCQ DQPTAMARHP HPHLSFMAIP PKKDQDKTEI PAINTIASAE   120
PTVHSTPTTE AVVNAVDNPE ASSESIASAP ETNTAQVTST EV                     162

SEQ ID NO: 341          moltype = AA  length = 205
FEATURE                 Location/Qualifiers
source                  1..205
                        mol_type = protein
                        organism = Bos taurus
SEQUENCE: 341
VSAALARPKH PIKHQGLPQE VLNENLLRFF VAPFPEVFGK EKVNELSKDI GSESTEDQAM    60
EDIKQMEAES ISSSEEIVPN SVEQKHIQKE DVPSERYLGY LEQLLRLKKY KVPQLEIVPN   120
SAEERLHSMK EGIHAQQKEP MIGVNQELAY FYPELFRQFY QLDAYPSGAW YYVPLGTQYT   180
DAPSFSDIPN PIGSENSEKT TMPLW                                        205

SEQ ID NO: 342          moltype = AA  length = 215
FEATURE                 Location/Qualifiers
source                  1..215
                        mol_type = protein
                        organism = Bos taurus
SEQUENCE: 342
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EQLLRLKKYK   120
VPQLEIVPNS AEERLHSMKE GIHAQQKEPM IGVNQELAYF YPELFRQFYQ LDAYPSGAWY   180
YVPLGTQYTD APSFSDIPNP IGSENSEKTT MPLWW                             215

SEQ ID NO: 343          moltype = AA  length = 206
FEATURE                 Location/Qualifiers
source                  1..206
                        mol_type = protein
                        organism = Bos taurus
SEQUENCE: 343
LVAVALARPK HPIKHQGLPQ EVLNENLLRF FVAPFPEVFG KEKVNELSKD IGSESTEDQA    60
MEDIKQMEAE SISSSEEIVP NSVEQKHIQK EDVPSERYLG YLEQLLRLKK YKVPQLEIVP   120
NSAEERLHSM KEGIHAQQKE PMIGVNQELA YFYPELFRQF YQLDAYPSGA WYYVPLGTQY   180
TDAPSFSDIP NPIGSENSEK TTMPLW                                       206

SEQ ID NO: 344          moltype = AA  length = 214
FEATURE                 Location/Qualifiers
source                  1..214
                        mol_type = protein
                        organism = Bos taurus
SEQUENCE: 344
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKDD VPSERYLGYL EQLLRLKKYK   120
VPQLEIVPNS AEERLHSMKE GIHAQQKEPM IGVNQELAYF YPELFRQFYQ LDAYPSGAWY   180
YVPLGTQYTD APSFSDIPNP IGSENSGKTT MPLW                              214

SEQ ID NO: 345          moltype = AA  length = 213
FEATURE                 Location/Qualifiers
source                  1..213
                        mol_type = protein
                        organism = Bos taurus
SEQUENCE: 345
MKLLILTCLV AVALARPKHP IKHQGLPQEV LNENLLRFFV APFPEVFGKE KVNELSKDIG    60
```

```
SESTEDQAME DIKQMEAESI SSSEEIVPNS VEKHIQKEDV PSERYLGYLE QLLRLKKYKV    120
PQLEIVPNSA EERLHSMKEG IHAQQKEPMI GVNQELAYFY PELFRQFYQL DAYPSGAWYY    180
VPLGTQYTDA PSFSDIPNPI GSENSEKTTM PLW                                213

SEQ ID NO: 346              moltype = AA   length = 214
FEATURE                     Location/Qualifiers
source                      1..214
                            mol_type = protein
                            organism = Bos taurus
SEQUENCE: 346
MKLLILTCLV AVALARPKHP IKHQGLPQEV LNENLLRFFV APFPEVFGKE KVNELSKDIG    60
SESTEDQAME DIKQMEAESI SSSEEIVPNS VEKHIQKEDV PSERYLGYLE QLLRLKKYKV    120
PQLEIVPNSA EERLHSMKEG IHAQQKEPMI GVNQELAYFY PELFRQFYQL DAYPSGAWYY    180
VPLGTQYTDA PSFSDIPNPI GSENSEKTTM PLWW                               214

SEQ ID NO: 347              moltype = AA   length = 214
FEATURE                     Location/Qualifiers
source                      1..214
                            mol_type = protein
                            organism = Bos taurus
SEQUENCE: 347
MKLLILTCLV AVALARPKHP IKHQGLPQEV LNENLLRFFV APFPEVFGKE KVNELSKDIG    60
SESTEDQAME DIKEMEAESI SSSGEIVPNS VEQKHIQKED VPSERYLGYL EQLLRLKKYK    120
VPQLEIVPNS AEERLHSMKE GIDAQQKEPM IGVNQELAYF YPELFRQFYQ LDAYPSGAWY    180
YVPLGTQYTD APSFSDIPNP IGSENSEKTT MPLW                               214

SEQ ID NO: 348              moltype = AA   length = 195
FEATURE                     Location/Qualifiers
source                      1..195
                            mol_type = protein
                            organism = Bos taurus
SEQUENCE: 348
PIKHQGLPQE VLNENLLRFF VAPFPEVFGK EKVNELSKDI GSESTEDQAM EDIKQMEAES    60
ISSSEEIVPN SVEQKHIQKE DVPSERYLGY LEQLLRLKKY KVPQLEIVPN SAEERLHSMK    120
EGIHAQQKEP MIGVNQELAY FYPELFRQFY QLDAYPSGAW YYVPLGTQYT DAPSFSDIPN    180
PIGSENSEKT TMPLW                                                    195

SEQ ID NO: 349              moltype = AA   length = 214
FEATURE                     Location/Qualifiers
source                      1..214
                            mol_type = protein
                            organism = Bos taurus
SEQUENCE: 349
MKLLILTCLV AVALARPKHP IKHQGLPQEV LNENLLRFFV ALFPEVFGKE KVNELSKDIG    60
SESTEDQAME DIKQMEAESI SSSEEIVPNS VEQKHIQKED VPSERYLGYL EQLLRLKKYK    120
VPQLEIVPNS AEERLHSMKE GIDAQQKEPM IGVNQELAYF YPELFRQFYQ LDAYPSGAWY    180
YVPLGTQYTD APSFSDIPNP IGSENSEKTT ISLW                               214

SEQ ID NO: 350              moltype = AA   length = 206
FEATURE                     Location/Qualifiers
source                      1..206
                            mol_type = protein
                            organism = Bos taurus
SEQUENCE: 350
MKLLILTCLV AVALARPKHP IKHQGLPQEV LNENLLRFFV APFPEVFGKE KVNELSKDIG    60
SESTEDQAME DIKQMEAESI SSSEQKHIQK EDVPSERYLG YLEQLLRLKK YKVPQLEIVP    120
NSAEERLHSM KEGIHAQQKE PMIGVNQELA YFYPELFRQF YQLDAYPSGA WYYVPLGTQY    180
TDAPSFSDIP NPIGSENSEK TTMPLW                                        206

SEQ ID NO: 351              moltype = AA   length = 206
FEATURE                     Location/Qualifiers
source                      1..206
                            mol_type = protein
                            organism = Bos taurus
SEQUENCE: 351
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EQLLRLKKYK    120
VPQLERLHSM KEGIHAQQKE PMIGVNQELA YFYPELFRQF YQLDAYPSGA WYYVPLGTQY    180
TDAPSFSDIP NPIGSENSEK TTMPLW                                        206

SEQ ID NO: 352              moltype = AA   length = 207
FEATURE                     Location/Qualifiers
source                      1..207
                            mol_type = protein
                            organism = Bos taurus
SEQUENCE: 352
MKLLILTCLV AVALARPKHP IKHQGLPQEV LNENLLRFFV APFPEVFGKE KVNELSKDIG    60
SESTEDQAME DIKQMEAESI SSSEQKHIQK EDVPSERYLG YLEQLLRLKK YKVPQLEIVP    120
NSAEERLHSM KEGIHAQQKE PMIGVNQELA YFYPELFRQF YQLDAYPSGA WYYVPLGTQY    180
```

```
TDAPSFSDIP NPIGSENSEK TTMPLWW                                              207

SEQ ID NO: 353           moltype = AA  length = 206
FEATURE                  Location/Qualifiers
source                   1..206
                         mol_type = protein
                         organism = Bos taurus
SEQUENCE: 353
MKLLILTCLV AVALARPKHP IKHQGLPQEV LNENLLRFFV APFPEVFGKE KVNELSKDIG           60
SESTEDQAME DIKQMEAESI SSSEEIVPNS VEQKHIQKED VPSERYLGYL EQLLRLKKYK          120
VPQLEIVPNS AEERLHSMKE GIHAQQKEPM IGVNQLFRQF YQLDAYPSGA WYYVPLGTQY          180
TDAPSFSDIP NPIGSENSEK TTMPLW                                              206

SEQ ID NO: 354           moltype = AA  length = 205
FEATURE                  Location/Qualifiers
source                   1..205
                         mol_type = protein
                         organism = Bos taurus
SEQUENCE: 354
MKLLILTCLV AVALARPKHP IKHQGLPQEV LNENLLRFFV APFPEVFGKE KVNELSKDIG           60
SESTEDQAME DIKQMEAESI SSSEEIVPNS VEKHIQKEDV PSERYLGYLE QLLRLKKYKV          120
PQLERLHSMK EGIHAQQKEP MIGVNQELAY FYPELFRQFY QLDAYPSGAW YYVPLGTQYT          180
DAPSFSDIPN PIGSENSEKT TMPLW                                               205

SEQ ID NO: 355           moltype = AA  length = 201
FEATURE                  Location/Qualifiers
source                   1..201
                         mol_type = protein
                         organism = Bos taurus
SEQUENCE: 355
MKLLILTCLV AVALARPKHP IKHQGLPQPF PEVFGKEKVN ELSKDIGSES TEDQAMEDIK           60
QMEAESISSS EEIVPNSVEQ KHIQKEDVPS ERYLGYLEQL LRLKKYKVPQ LEIVPNSAEE          120
RLHSMKEGIH AQQKEPMIGV NQELAYFYPE LFRQFYQLDA YPSGAWYYVP LGTQYTDAPS          180
FSDIPNPIGS ENSEKTTMPL W                                                   201

SEQ ID NO: 356           moltype = AA  length = 202
FEATURE                  Location/Qualifiers
source                   1..202
                         mol_type = protein
                         organism = Bos taurus
SEQUENCE: 356
MKLLILTCLV AVALARPKHP IKHQGLPQPF PEVFGKEKVN ELSKDIGSES TEDQAMEDIK           60
QMEAESISSS EEIVPNSVEQ KHIQKEDVPS ERYLGYLEQL LRLKKYKVPQ LEIVPNSAEE          120
RLHSMKEGIH AQQKEPMIGV NQELAYFYPE LFRQFYQLDA YPSGAWYYVP LGTQYTDAPS          180
FSDIPNPIGS ENSEKTTMPL WW                                                  202

SEQ ID NO: 357           moltype = AA  length = 200
FEATURE                  Location/Qualifiers
source                   1..200
                         mol_type = protein
                         organism = Bos taurus
SEQUENCE: 357
MKLLILTCLV AVALARPKHP IKHQGLPQEV LNENLLRFFV APFPEVFGKE KVNELSKDIG           60
SESTEDQAME DIKQMEAESI SSSEEIVPNS VEQKHIQKED VPSERYLGYL EIVPNSAEER          120
LHSMKEGIHA QQKEPMIGVN QELAYFYPEL FRQFYQLDAY PSGAWYYVPL GTQYTDAPSF          180
SDIPNPIGSE NSEKTTMPLW                                                     200

SEQ ID NO: 358           moltype = AA  length = 201
FEATURE                  Location/Qualifiers
source                   1..201
                         mol_type = protein
                         organism = Bos taurus
SEQUENCE: 358
MKLLILTCLV AVALARPKHP IKHQGLPQEV LNENLLRFFV APFPEVFGKE KVNELSKDIG           60
SESTEDQAME DIKQMEAESI SSSEEIVPNS VEQKHIQKED VPSERYLGYL EIVPNSAEER          120
LHSMKEGIHA QQKEPMIGVN QELAYFYPEL FRQFYQLDAY PSGAWYYVPL GTQYTDAPSF          180
SDIPNPIGSE NSEKTTMPLW W                                                   201

SEQ ID NO: 359           moltype = AA  length = 200
FEATURE                  Location/Qualifiers
source                   1..200
                         mol_type = protein
                         organism = Bos taurus
SEQUENCE: 359
MKLLILTCLV AVALARPKHP IKHQGLPQPF PEVFGKEKVN ELSKDIGSES TEDQAMEDIK           60
QMEAESISSS EEIVPNSVEK HIQKEDVPSE RYLGYLEQLL RLKKYKVPQL EIVPNSAEER          120
LHSMKEGIHA QQKEPMIGVN QELAYFYPEL FRQFYQLDAY PSGAWYYVPL GTQYTDAPSF          180
SDIPNPIGSE NSEKTTMPLW                                                     200
```

```
SEQ ID NO: 360            moltype = AA   length = 199
FEATURE                   Location/Qualifiers
source                    1..199
                          mol_type = protein
                          organism = Bos taurus
SEQUENCE: 360
MKLLILTCLV AVALARPKHP IKHQGLPQEV LNENLLRFFV APFPEVFGKE KVNELSKDIG    60
SESTEDQAME DIKQMEAESI SSSEEIVPNS VEKHIQKEDV PSERYLGYLE IVPNSAEERL   120
HSMKEGIHAQ QKEPMIGVNQ ELAYFYPELF RQFYQLDAYP SGAWYYVPLG TQYTDAPSFS   180
DIPNPIGSEN SEKTTMPLW                                                199

SEQ ID NO: 361            moltype = AA   length = 200
FEATURE                   Location/Qualifiers
source                    1..200
                          mol_type = protein
                          organism = Bos taurus
SEQUENCE: 361
MKLLILTCLV AVALARPKHP IKHQGLPQEV LNENLLRFFV APFPEVFGKE KVNELSKDIG    60
SESTEDQAME DIKQMEAESI SSSEEIVPNS VEKHIQKEDV PSERYLGYLE IVPNSAEERL   120
HSMKEGIHAQ QKEPMIGVNQ ELAYFYPELF RQFYQLDAYP SGAWYYVPLG TQYTDAPSFS   180
DIPNPIGSEN SEKTTMPLWW                                               200

SEQ ID NO: 362            moltype = AA   length = 198
FEATURE                   Location/Qualifiers
source                    1..198
                          mol_type = protein
                          organism = Bos taurus
SEQUENCE: 362
MKLLILTCLV AVALARPKHP IKHQGLPQEV LNENLLRFFV APFPEVFGKE KVNELSKDIG    60
SESTEDQAME DIKQMEAESI SSSEQKHIQK EDVPSERYLG YLEQLLRLKK YKVPQLERLH   120
SMKEGIHAQQ KEPMIGVNQE LAYFYPELFR QFYQLDAYPS GAWYYVPLGT QYTDAPSFSD   180
IPNPIGSENS EKTTMPLW                                                 198

SEQ ID NO: 363            moltype = AA   length = 198
FEATURE                   Location/Qualifiers
source                    1..198
                          mol_type = protein
                          organism = Bos taurus
SEQUENCE: 363
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EQLLRLKKYK   120
VPQLERLHSM KEGIHAQQKE PMIGVNQLFR QFYQLDAYPS GAWYYVPLGT QYTDAPSFSD   180
IPNPIGSENS EKTTMPLW                                                 198

SEQ ID NO: 364            moltype = AA   length = 214
FEATURE                   Location/Qualifiers
VARIANT                   111..124
                          note = X is any amino acid
source                    1..214
                          mol_type = protein
                          organism = Bos taurus
SEQUENCE: 364
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL XXXXXXXXXX   120
XXXXEIVPNS AEERLHSMKE GIHAQQKEPM IGVNQELAYF YPELFRQFYQ LDAYPSGAWY   180
YVPLGTQYTD APSFSDIPNP IGSENSEKTT MPLW                               214

SEQ ID NO: 365            moltype = AA   length = 193
FEATURE                   Location/Qualifiers
source                    1..193
                          mol_type = protein
                          organism = Bos taurus
SEQUENCE: 365
MKLLILTCLV AVALARPKHP IKHQGLPQPF EVFGKEKVN ELSKDIGSES TEDQAMEDIK     60
QMEAESISSS EEIVPNSVEQ KHIQKEDVPS ERYLGYLEQL LRLKKYKVPQ LERLHSMKEG   120
IHAQQKEPMI GVNQELAYFY PELFRQFYQL DAYPSGAWYY VPLGTQYTDA PSFSDIPNPI   180
GSENSEKTTM PLW                                                      193

SEQ ID NO: 366            moltype = AA   length = 194
FEATURE                   Location/Qualifiers
source                    1..194
                          mol_type = protein
                          organism = Bos taurus
SEQUENCE: 366
MKLLILTCLV AVALARPKHP IKHQGLPQPF EVFGKEKVN ELSKDIGSES TEDQAMEDIK     60
QMEAESISSS EQKHIQKEDV PSERYLGYLE QLLRLKKYKV PQLEIVPNSA EERLHSMKEG   120
IHAQQKEPMI GVNQELAYFY PELFRQFYQL DAYPSGAWYY VPLGTQYTDA PSFSDIPNPI   180
GSENSEKTTM PLWW                                                     194
```

```
SEQ ID NO: 367           moltype = AA   length = 192
FEATURE                  Location/Qualifiers
source                   1..192
                         mol_type = protein
                         organism = Bos taurus
SEQUENCE: 367
MKLLILTCLV AVALARPKHP IKHQGLPQEV LNENLLRFFV APFPEVFGKE KVNELSKDIG    60
SESTEDQAME DIKQMEAESI SSSEQKHIQK EDVPSERYLG YLEIVPNSAE ERLHSMKEGI   120
HAQQKEPMIG VNQELAYFYP ELFRQFYQLD AYPSGAWYYV PLGTQYTDAP SFSDIPNPIG   180
SENSEKTTMP LW                                                      192

SEQ ID NO: 368           moltype = AA   length = 193
FEATURE                  Location/Qualifiers
source                   1..193
                         mol_type = protein
                         organism = Bos taurus
SEQUENCE: 368
MKLLILTCLV AVALARPKHP IKHQGLPQEV LNENLLRFFV APFPEVFGKE KVNELSKDIG    60
SESTEDQAME DIKQMEAESI SSSEQKHIQK EDVPSERYLG YLEIVPNSAE ERLHSMKEGI   120
HAQQKEPMIG VNQELAYFYP ELFRQFYQLD AYPSGAWYYV PLGTQYTDAP SFSDIPNPIG   180
SENSEKTTMP LWW                                                     193

SEQ ID NO: 369           moltype = AA   length = 192
FEATURE                  Location/Qualifiers
source                   1..192
                         mol_type = protein
                         organism = Bos taurus
SEQUENCE: 369
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EIVPNSAEER   120
LHSMKEGIHA QQKEPMIGVN QLFRQFYQLD AYPSGAWYYV PLGTQYTDAP SFSDIPNPIG   180
SENSEKTTMP LW                                                      192

SEQ ID NO: 370           moltype = AA   length = 172
FEATURE                  Location/Qualifiers
source                   1..172
                         mol_type = protein
                         organism = Bos taurus
SEQUENCE: 370
FSEVFGKEKV NELSKDIGSE STEDQAMEDI KQMEAESISS SEEIVPNSVE QKHIQKEDVP    60
SERYLGYLEQ LLRLKKYKVP QLEIVPNSAE ERLHSMKEGI HAQQKEPMIG VNQELAYFYP   120
ELFRQFYQLD AYPSGAWYYV PLGTQYTDAP SFSDIPNPIG SENSEKTTMP LW           172

SEQ ID NO: 371           moltype = AA   length = 187
FEATURE                  Location/Qualifiers
source                   1..187
                         mol_type = protein
                         organism = Bos taurus
SEQUENCE: 371
MKLLILTCLV AVALARPKHP IKHQGLPQPF PEVFGKEKVN ELSKDIGSES TEDQAMEDIK    60
QMEAESISSS EEIVPNSVEQ KHIQKEDVPS ERYLGYLEIV PNSAEERLHS MKEGIHAQQK   120
EPMIGVNQEL AYFYPELFRQ FYQLDAYPSG AWYYVPLGTQ YTDAPSFSDI PNPIGSENSE   180
KTTMPLW                                                            187

SEQ ID NO: 372           moltype = AA   length = 166
FEATURE                  Location/Qualifiers
VARIANT                  118
                         note = X is any amino acid
source                   1..166
                         mol_type = protein
                         organism = Bos taurus
SEQUENCE: 372
KEKVNELSKD IGSESTEDQA MEDIKQMEAE SISSSEEIVP NSVEQKHIQK EDVPSERYLG    60
YLEQLLRLKK YKVPQLEIVP NSAEERLHSM KEGIHAQQKE PMIGVNQELA YFYPELFXQF   120
YQLDAYPSGA WYYVPLGTQY TDAPSFSDIP NPIGSENSEK TTMPLW                  166

SEQ ID NO: 373           moltype = AA   length = 177
FEATURE                  Location/Qualifiers
source                   1..177
                         mol_type = protein
                         organism = Bos taurus
SEQUENCE: 373
MKLLILTCLV AVALARPKHP IKHQGLPQEV LNENLLRFFV APFPEVFGKE KVNELSKDIG    60
SESTEDQAME DIKEQLLRLK KYKVPQLEIV PNSAEERLHS MKEGIHAQQK EPMIGVNQEL   120
AYFYPELFRQ FYQLDAYPSG AWYYVPLGTQ YTDAPSFSDI PNPIGSENSE KTTMPLW      177

SEQ ID NO: 374           moltype = AA   length = 178
FEATURE                  Location/Qualifiers
source                   1..178
```

```
                         mol_type = protein
                         organism = Bos taurus
SEQUENCE: 374
MKLLILTCLV AVALARPKHP IKHQGLPQEV LNENLLRFFV APFPEVFGKE KVNELSKDIG    60
SESTEDQAME DIKEQLLRLK KYKVPQLEIV PNSAEERLHS MKEGIHAQQK EPMIGVNQEL   120
AYFYPELFRQ FYQLDAYPSG AWYYVPLGTQ YTDAPSFSDI PNPIGSENSE KTTMPLWW    178

SEQ ID NO: 375           moltype = AA   length = 155
FEATURE                  Location/Qualifiers
source                   1..155
                         mol_type = protein
                         organism = Bos taurus
SEQUENCE: 375
GSESTEDQAM EDIKQMEAES ISSSEEIVPN SVEQKHIQKE DVPSERYLGY LEQLLRLKKY    60
KVPQLEIVPN SAEERLHSMK EGIHAQQKEP MIGVNQELAY FYPELFRQFY QLDAYPSGAW   120
YYVPLGTQYT DAPSFSDIPN PIGSENSEKT TMPLW                              155

SEQ ID NO: 376           moltype = AA   length = 163
FEATURE                  Location/Qualifiers
source                   1..163
                         mol_type = protein
                         organism = Bos taurus
SEQUENCE: 376
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EQLLRLKKYK   120
VPQLEIVPNS AEERLHSMKE GIHAQQKEPM IGVNQELAYF YPE                    163

SEQ ID NO: 377           moltype = AA   length = 177
FEATURE                  Location/Qualifiers
source                   1..177
                         mol_type = protein
                         organism = Bos taurus
SEQUENCE: 377
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EQLLRLKKYK   120
VPQLEIVPNS AEERLHSMKE GIHAQQKEPM IGVNQELAYF YPEKSQVNSE GLHSYGL     177

SEQ ID NO: 378           moltype = AA   length = 141
FEATURE                  Location/Qualifiers
source                   1..141
                         mol_type = protein
                         organism = Bos taurus
SEQUENCE: 378
QMEAESISSS EEIVPNSVEQ KHIQKEDVPS ERYLGYLEQL LRLKKYKVPQ LEIVPNSAEE    60
RLHSMKEGIH AQQKEPMIGV NQELAYFYPE LFRQFYQLDA YPSGAWYYVP LGTQYTDAPS   120
FSDIPNPIGS ENSEKTTMPL W                                            141

SEQ ID NO: 379           moltype = AA   length = 136
FEATURE                  Location/Qualifiers
source                   1..136
                         mol_type = protein
                         organism = Bos taurus
SEQUENCE: 379
SISSSEEIVP NSVEQKHIQK EDVPSERYLG YLEQLLRLKK YKVPQLEIVP NSAEERLHSM    60
KEGIHAQQKE PMIGVNQELA YFYPELFRQF YQLDAYPSGA WYYVPLGTQY TDAPSFSDIP   120
NPIGSENSEK TTMPLW                                                  136

SEQ ID NO: 380           moltype = AA   length = 138
FEATURE                  Location/Qualifiers
VARIANT                  10
                         note = X is any amino acid
VARIANT                  90
                         note = X is any amino acid
VARIANT                  128
                         note = X is any amino acid
source                   1..138
                         mol_type = protein
                         organism = Bos taurus
SEQUENCE: 380
AESISSSEEX VPNSVEQKHI QKEDVPSERY LGYLEQLLRL KKYKVPQLEI VPNSAEERLH    60
SMKEGIHAQQ KEPMIGVNQE LAYFYPELFX QFYQLDAYPS GAWYYVPLGT QYTDAPSFSD   120
IPNPIGSXNS EKTTMPLW                                                138

SEQ ID NO: 381           moltype = AA   length = 126
FEATURE                  Location/Qualifiers
source                   1..126
                         mol_type = protein
                         organism = Bos taurus
SEQUENCE: 381
```

```
NSVEQKHIQK EDVPSERYLG YLEQLLRLKK YKVPQLEIVP NSAEERLHSM KEGIHAQQKE    60
PMIGVNQELA YFYPELFRQF YQLDAYPSGA WYYVPLGTQY TDAPSFSDIP NPIGSENSEK   120
TTMPLW                                                             126

SEQ ID NO: 382          moltype = AA  length = 129
FEATURE                 Location/Qualifiers
VARIANT                 81
                        note = X is any amino acid
source                  1..129
                        mol_type = protein
                        organism = Bos taurus
SEQUENCE: 382
IVPNSVEQKH IQKEDVPSER YLGYLEQLLR LKKYKVPQLE IVPNSAEERL HSMKEGIHAQ    60
QKEPMIGVNQ ELAYFYPELF XQFYQPDAYP SGAWYYVPLG TQYTDAPSFS DIPNPIGSEN   120
SEKTTMPLW                                                          129

SEQ ID NO: 383          moltype = AA  length = 111
FEATURE                 Location/Qualifiers
source                  1..111
                        mol_type = protein
                        organism = Bos taurus
SEQUENCE: 383
ERYLGYLEQL LRLKKYKVPQ LEIVPNSAEE RLHSMKEGIH AQQKEPMIGV NQELAYFYPE    60
LFRQFYQLDA YPSGAWYYVP LGTQYTDAPS FSDIPNPIGS ENSEKTTMPL W           111

SEQ ID NO: 384          moltype = AA  length = 103
FEATURE                 Location/Qualifiers
source                  1..103
                        mol_type = protein
                        organism = Bos taurus
SEQUENCE: 384
QLLRLKKYKV PQLEIVPNSA EERLHSMKEG IHAQQKEPMI GVNQELAYFY PELFRQFYQL    60
DAYPSGAWYY VPLGTQYTDA PSFSDIPNPI GSENSEKTTM PLW                    103

SEQ ID NO: 385          moltype = AA  length = 214
FEATURE                 Location/Qualifiers
source                  1..214
                        mol_type = protein
                        organism = Capra hircus
SEQUENCE: 385
MKLLILTCLV AVALARPKHP INHQGLSPEV LNENLLRFVV APFPEVFRKE NINELSKDIG    60
SESTEDQAME DAKQMKAGSS SSSEEIVPNS AQQKYIQKED VPSERYLGYL EQLLRLKKYN   120
VPQLEIVPKS AEEQLHSMKE GNPAHQKQPM IAVNQELAYF YPQLFRQFYQ LDAYPSGAWY   180
YLPLGTQYTD APSFSDIPNP IGSENSGKTT MPLW                              214

SEQ ID NO: 386          moltype = AA  length = 214
FEATURE                 Location/Qualifiers
source                  1..214
                        mol_type = protein
                        organism = Capra hircus
SEQUENCE: 386
MKLLILTCLV AVALARPKHP INHQGLSPEV LNENLLRFVV APFPEVFRKE NINELSKDIG    60
SESTEDQAME DAKQMKAGSS SSSEEIVPNS AEQKYIQKED VPSERYLGYL EQLLKLKKYN   120
VPQLEIVPKS AEEQLHSMKE GNPAHQKQPM IAVNQELAYF YPQLFRQFYQ LDAYPSGAWY   180
YLPLGTQYTD APSFSDIPNP IGSENSGKTA MPLW                              214

SEQ ID NO: 387          moltype = AA  length = 213
FEATURE                 Location/Qualifiers
source                  1..213
                        mol_type = protein
                        organism = Capra hircus
SEQUENCE: 387
KLLILTCLVA VALARPKHPI NHQGLSPEVP NENLLRFVVA PFPEVFRKEN INELSKDIGS    60
ESTEDQAMED AKQMKAGSSS SEEIVPNSA EQKYIQKEDV PSERYLGYLE QLLRLKKYNV   120
PQLEIVPKSA EEQLHSMKEG NPAHQKQPMI AVNQELAYFY PQLFRQFYQL DAYPSGAWYY   180
LPLGTQYTDA PSFSDIPNPI GSENSGKTTM PLW                               213

SEQ ID NO: 388          moltype = AA  length = 214
FEATURE                 Location/Qualifiers
source                  1..214
                        mol_type = protein
                        organism = Capra hircus
SEQUENCE: 388
MKLLILTCLV AVALARPKHP INHRGLSPEV PNENLLRFVV APFPEVFRKE NINELSKDIG    60
SESTEDQAME DAKQMKAGSS SSSEEIVPNS AEQKYIQKED VPSERYLGYL EQLLRLKKYN   120
VPQLEIVPKS AEEQLHSMKE GNPAHQKQPM IAVNQELAYF YPQLFRQFYQ LDAYPSGAWY   180
YLPLGTQYTD APSFSDIPNP IGSENSGKTT MPLW                              214

SEQ ID NO: 389          moltype = AA  length = 213
```

```
FEATURE                 Location/Qualifiers
source                  1..213
                        mol_type = protein
                        organism = Capra hircus
SEQUENCE: 389
MKLLILTCLV AVALARPKHP INHQGLSPEV LNENLLRFVV APFPEVFRKE NINELSKDIG    60
SESTEDQAME DAKQMKAGSS SSSEEIVPNS AQKYIQKEDV PSERYLGYLE QLLRLKKYNV   120
PQLEIVPKSA EEQLHSMKEG NPAHQKPMI AVNQELAYFY PQLFRQFYQL DAYPSGAWYY   180
LPLGTQYTDA PSFSDIPNPI GSENSGKTTM PLW                                213

SEQ ID NO: 390          moltype = AA  length = 213
FEATURE                 Location/Qualifiers
source                  1..213
                        mol_type = protein
                        organism = Capra hircus
SEQUENCE: 390
MKLLILTCLV VVALARPKHP INHQGLSPEV LNENLLRFVV APFPEVFRKE NINELSKDIG    60
SESTEDQAME DAKQMKAGSS SSSEEIVPNS AQKYIQKEDV PSERYLGYLE QLLRLKKYNV   120
PQLEIVPKSA EEQLHSMKEG NPAHQKPMI AVNQELAYFY PQLFRQFYQL DAYPSGAWYY   180
LPLGTQYTDA PSFSDIPNPI GSENSGKTTM PLW                                213

SEQ ID NO: 391          moltype = AA  length = 214
FEATURE                 Location/Qualifiers
source                  1..214
                        mol_type = protein
                        organism = Capra hircus
SEQUENCE: 391
MKLLILTCLV AVALARPKHP INHQGLSPEV PNENLLRFVV APFPEVFRKE NINELSKDIG    60
SESTEDQAME DAKQMKAGSS SSSEEIVPNS AEQKYIQKED VPSERYLGYL EQLLKLKKYN   120
VPQLEIVPKS AEEQLHSMKE GNPAHQKPM IAVNQELAYF YPQLFRQFYQ LDAYPSGAWY   180
YLPLGTQYTD APSFSDIPNP IGSENSGKTA MPLW                               214

SEQ ID NO: 392          moltype = AA  length = 214
FEATURE                 Location/Qualifiers
source                  1..214
                        mol_type = protein
                        organism = Capra hircus
SEQUENCE: 392
MKLLILTCLV AVALARPKHP INHQGLSPEV PNENLLRFVV APFPEVFRKE NINELSKDIG    60
SESTEDQAME DAKQMKAGSS SSSEEIVPNS AEQKYIQKED VPSERYLGYL EQLLKLKKYN   120
VPQLEIVPKS AEEQLHSMKE GNPAHQKPM IAVNQELAYF YPQLFRQFYQ LDAYPSGAWY   180
YLPLGTQYTD APSFSDIPNP IGSENSGKAA MPLW                               214

SEQ ID NO: 393          moltype = AA  length = 213
FEATURE                 Location/Qualifiers
source                  1..213
                        mol_type = protein
                        organism = Capra hircus
SEQUENCE: 393
MKLLILTCLV AVALARPKHP INHQGLSPEV PNENLLRFVV APFPEVFRKE NINELSKDIG    60
SESTEDQAME DAKQMKAGSS SSSEEIVPNS AEKYIQKEDV PSERYLGYLE QLLRLKKYNV   120
PQLETVPNSA EEQLHSMKEG NPAHQKPMI AVNQELAYFY PQLFRQFYQL DAYPSGAWYY   180
LPLGTQYTDA PSFSDIPNPI GSENSGKTTM PLW                                213

SEQ ID NO: 394          moltype = AA  length = 212
FEATURE                 Location/Qualifiers
source                  1..212
                        mol_type = protein
                        organism = Capra hircus
SEQUENCE: 394
KLLILTCLVA VALARPKHPI NHQGLSPEVP NENLLRFVVA PFPEVFRKEN INELSKDIGS    60
ESTEDQAMED AKQMKAGSSS SSEEIVPNSA EKYIQKEDVP SERYLGYLEQ LLRLKKYNVP   120
QLEIVPKSAE EQLHSMKEGN PAHQKPMIA VNQELAYFYP QLFRQFYQLD AYPSGAWYYL   180
PLGTQYTDAP SFSDIPNPIG SENSGKTTMP LW                                 212

SEQ ID NO: 395          moltype = AA  length = 214
FEATURE                 Location/Qualifiers
source                  1..214
                        mol_type = protein
                        organism = Capra hircus
SEQUENCE: 395
MKLLILTCLV AVALARPKHP INIQGLSPEV PNENLLRFVV APFPEVFRKE NINELSKDIG    60
SESTEDQAME DAKQMKAGSS SSSEEIVPNS AEQKYIQKED VPSERYLGYL EQLLKLKKYN   120
VPQLEIVPKS AEEQLHSMKE GNPAHQKPM IAVNQELAYF YPQLFRQFYQ LDAYPSGAWY   180
YLPLGTQYTD APSFSDIPNP IGSENSGKTA MPLW                               214

SEQ ID NO: 396          moltype = AA  length = 215
FEATURE                 Location/Qualifiers
source                  1..215
```

```
                            mol_type = protein
                            organism = Capra hircus
SEQUENCE: 396
MKLLILTCLV AVALARPKHP INHQGLSPVS EVLNENLLRF VVAPFPEVFR RENINELSKD     60
IGSESTEDQA MEDAKQMKAG SSSSSEEIVP NSAQKYIQKE GVPSERYLGY LEQLLRLKKY    120
NVPQLEIVPK SAEEQLHSMK EGNPAHQKQP MIAVNQELAY FYPQLFRQFY QLDAYPSGAW    180
YYLPLGTQYT DAPSFSDIPN PIGSENSGKT TMPLW                               215

SEQ ID NO: 397              moltype = AA  length = 213
FEATURE                     Location/Qualifiers
source                      1..213
                            mol_type = protein
                            organism = Capra hircus
SEQUENCE: 397
MKLLILTCLV AVALARPKHP INIQGLSPEV PNENLLRFVV APFPEVFRKE NINELSKDIG     60
SESTEDQAME DAKQMKAGSS SSSEEIVPNS AEKYIQKEDV PSERYLGYLE QLLKLKKYNV    120
PQLEIVPKSA EEQLHSMKEG NPAHQKPMI AVNQELAYFY PQLFRQFYQL DAYPSGAWYY    180
LPLGTQYTDA PSFSDIPNPI GSENSGKTAM PLW                                 213

SEQ ID NO: 398              moltype = AA  length = 206
FEATURE                     Location/Qualifiers
source                      1..206
                            mol_type = protein
                            organism = Capra hircus
SEQUENCE: 398
MKLLILTCLV AVALARPKHP INHQGLSPEV LNENLLRFVV APFPEVFRKE NINELSKDIG     60
SESTEDQAME DAKQMKAGSS SSSEEIVPNS AQQKYIQKED VPSERYLGYL EQLLRLKKYN    120
VPQLEQLHSM KEGNPAHQKQ PMIAVNQELA YFYPQLFRQF YQLDAYPSGA WYYLPLGTQY    180
TDAPSFSDIP NPIGSENSGK TTMPLW                                         206

SEQ ID NO: 399              moltype = AA  length = 203
FEATURE                     Location/Qualifiers
source                      1..203
                            mol_type = protein
                            organism = Capra hircus
SEQUENCE: 399
MKLLILTCLV AVALARPEVL NENLLRFVVA PFPEVFRKEN INELSKDIGS ESTEDQAMED     60
AKQMKAGSSS SSEEIVPNSA QQKYIQKEDV PSERYLGYLE QLLRLKKYNV PQLEIVPKSA    120
EEQLHSMKEG NPAHQKQPMI AVNQELAYFY PQLFRQFYQL DAYPSGAWYY LPLGTQYTDA    180
PSFSDIPNPI GSENSGKTTM PLW                                            203

SEQ ID NO: 400              moltype = AA  length = 206
FEATURE                     Location/Qualifiers
source                      1..206
                            mol_type = protein
                            organism = Capra hircus
SEQUENCE: 400
MKLLILTCLV AVALARPKHP INHQGLSPEV LNENLLRFVV APFPEVFRKE NINELSKDIG     60
SESTEDQAME DAKQMKAGSS SSSEEIVPNS AQQKYIQKED VPSERYLGYL EQLLRLKKYN    120
VPQLEIVPKS AEEQLHSMKE GNPAHQKQPM IAVNQLFRQF YQLDAYPSGA WYYLPLGTQY    180
TDAPSFSDIP NPIGSENSGK TTMPLW                                         206

SEQ ID NO: 401              moltype = AA  length = 198
FEATURE                     Location/Qualifiers
source                      1..198
                            mol_type = protein
                            organism = Capra hircus
SEQUENCE: 401
MKLLILTCLV AVALARPKHP INHQGLSPEV LNENLLRFVV APFPEVFRKE NINELSKDIG     60
SESTEDQAME DAKQMKAGSS SSSEEIVPNS AQQKYIQKED VPSERYLGYL EQLLRLKKYN    120
VPQLEQLHSM KEGNPAHQKQ PMIAVNQLFR QFYQLDAYPS GAWYYLPLGT QYTDAPSFSD    180
IPNPIGSENS GKTTMPLW                                                  198

SEQ ID NO: 402              moltype = AA  length = 177
FEATURE                     Location/Qualifiers
source                      1..177
                            mol_type = protein
                            organism = Capra hircus
SEQUENCE: 402
MKLLILTCLV AVALARPKHP INHQGLSPEV LNENLLRFVV APFPEVFRKE NINELSKDIG     60
SESTEDQAME DAKEQLLRLK KYNVPQLEIV PKSAEEQLHS MKEGNPAHQK QPMIAVNQEL    120
AYFYPQLFRQ FYQLDAYPSG AWYYLPLGTQ YTDAPSFSDI PNPIGSENSG KTTMPLW       177

SEQ ID NO: 403              moltype = AA  length = 214
FEATURE                     Location/Qualifiers
source                      1..214
                            mol_type = protein
                            organism = Ovis aries
SEQUENCE: 403
```

```
MKLLILTCLV AVALARPKHP IKHQGLSPEV LNENLLRFVV APFPEVFRKE NINELSKDIG    60
SESIEDQAME DAKQMKAGSS SSSEEIVPNS AEQKYIQKED VPSERYLGYL EQLLRLKKYN   120
VPQLEIVPKS AEEQLHSMKE GNPAHQKQPM IAVNQELAYF YPQLFRQFYQ LDAYPSGAWY   180
YLPLGTQYTD APSFSDIPNP IGSENSGKTT MPLW                               214

SEQ ID NO: 404          moltype = AA   length = 214
FEATURE                 Location/Qualifiers
source                  1..214
                        mol_type = protein
                        organism = Ovis aries
SEQUENCE: 404
MKLLILTCLV AVALARPKHP IKHQGLSSEV LNENLLRFVV APFPEVFRKE NINELSKDIG    60
SESIEDQAME DAKQMKAGSS SSSEEIVPNS AEQKYIQKED VPSERYLGYL EQLLRLKKYN   120
VPQLEIVPKS AEEQLHSMKE GNPAHQKQPM IAVNQELAYF YPQLFRQFYQ LDAYPSGAWY   180
YLPLGTQYTD APSFSDIPNP IGSENSGKIT MPLW                               214

SEQ ID NO: 405          moltype = AA   length = 199
FEATURE                 Location/Qualifiers
source                  1..199
                        mol_type = protein
                        organism = Ovis aries
SEQUENCE: 405
RPKHPIKHQG LSSEVLNENL LRFVVAPFPE VFRKENINEL SKDIGSESIE DQAMEDAKQM    60
KAGSSSSSEE IVPNSAEQKY IQKEDVPSER YLGYLEQLLR LKKYNVPQLE IVPKSAEEQL   120
HSMKEGNPAH QKQPMIAVNQ ELAYFYPQLF RQFYQLDAYP SGAWYYLPLG TQYTDAPSFS   180
DIPNPIGSEN SGKITMPLW                                                199

SEQ ID NO: 406          moltype = AA   length = 214
FEATURE                 Location/Qualifiers
source                  1..214
                        mol_type = protein
                        organism = Ovis aries
SEQUENCE: 406
MKLLILTCLV AVALARPKHP IKHQGLSPEV LNENLLRFVV APFPEVFRKE NINELSKDIG    60
SESIEDQAME DAKQMKAGSS SSSEEIVPNS AEQKYIQKED VPSERYLGYL EQLLRLKKYN   120
VPQLEIVPKS AEEQLHSMKE GNPAHQKQPM IAVNQELAYF YPQLFRQFYQ LDAYPSGAWY   180
YLPLGTQYTD APSFSDIPNP IGSENSGKIT MPLW                               214

SEQ ID NO: 407          moltype = AA   length = 206
FEATURE                 Location/Qualifiers
source                  1..206
                        mol_type = protein
                        organism = Ovis aries
SEQUENCE: 407
MKLLILTCLV AVALARPKHP IKHQGLSPEV LNENLLRFVV APFPEVFRKE NINELSKDQA    60
MEDAKQMKAG SSSSSEEIVP NSAEQKYIQK EDVPSERYLG YLEQLLRLKK YNVPQLEIVP   120
KSAEEQLHSM KEGNPAHQKQ PMIAVNQELA YFYPQLFRQF YQLDAYPSGA WYYLPLGTQY   180
TDAPSFSDIP NPIGSENSGK TTMPLW                                        206

SEQ ID NO: 408          moltype = AA   length = 206
FEATURE                 Location/Qualifiers
source                  1..206
                        mol_type = protein
                        organism = Ovis aries
SEQUENCE: 408
MKLLILTCLV AVALARPKHP IKHQGLSPEV LNENLLRFVV APFPEVFRKE NINELSKDIG    60
SESIEQMKAG SSSSEEIVP NSAEQKYIQK EDVPSERYLG YLEQLLRLKK YNVPQLEIVP    120
KSAEEQLHSM KEGNPAHQKQ PMIAVNQELA YFYPQLFRQF YQLDAYPSGA WYYLPLGTQY   180
TDAPSFSDIP NPIGSENSGK TTMPLW                                        206

SEQ ID NO: 409          moltype = AA   length = 206
FEATURE                 Location/Qualifiers
source                  1..206
                        mol_type = protein
                        organism = Ovis aries
SEQUENCE: 409
MKLLILTCLV AVALARPKHP IKHQGLSPEV LNENLLRFVV APFPEVFRKE NINELSKDQA    60
MEDAKQMKAG SSSSSEEIVP NSAEQKYIQK EDVPSERYLG YLEQLLRLKK YNVPQLEIVP   120
KSAEEQLHSM KEGNPAHQKQ PMIAVNQELA YFYPQLFRQF YQLDAYPSGA WYYLPLGTQY   180
TDAPSFSDIP NPIGSENSGK ITMPLW                                        206

SEQ ID NO: 410          moltype = AA   length = 206
FEATURE                 Location/Qualifiers
source                  1..206
                        mol_type = protein
                        organism = Ovis aries
SEQUENCE: 410
MKLLILTCLV AVALARPKHP IKHQGLSPEV LNENLLRFVV APFPEVFRKE NINELSKDIG    60
SESIEQMKAG SSSSEEIVP NSAEQKYIQK EDVPSERYLG YLEQLLRLKK YNVPQLEIVP    120
```

```
KSAEEQLHSM KEGNPAHQKQ PMIAVNQELA YFYPQLFRQF YQLDAYPSGA WYYLPLGTQY    180
TDAPSFSDIP NPIGSENSGK ITMPLW                                         206

SEQ ID NO: 411             moltype = AA  length = 191
FEATURE                    Location/Qualifiers
source                     1..191
                           mol_type = protein
                           organism = Ovis aries
SEQUENCE: 411
RPKHPIKHQG LSSEVLNENL LRFVVAPFPE VFRKENINEL SKDIGSESIE DQAMEDAKQM    60
KAGSSSSSEE IVPNSAEQKY IQKEDVPSER YLGYLEQLLR LKKYNVPQLE IVPKSAEEQL    120
HSMKEGNPAH QKQPMIAVNQ LFRQFYQLDA YPSGAWYYLP LGTQYTDAPS FSDIPNPIGS    180
ENSGKITMPL W                                                         191

SEQ ID NO: 412             moltype = AA  length = 206
FEATURE                    Location/Qualifiers
source                     1..206
                           mol_type = protein
                           organism = Ovis aries
SEQUENCE: 412
MKLLILTCLV AVALARPKHP IKHQGLSPEV LNENLLRFVV APFPEVFRKE NINELSKDIG    60
SESIEDQAME DAKQMKAGSS SSSEEIVPNS AEQKYIQKED VPSERYLGYL EQLLRLKKYN    120
VPQLEIVPKS AEEQLHSMKE GNPAHQKQPM IAVNQLFRQF YQLDAYPSGA WYYLPLGTQY    180
TDAPSFSDIP NPIGSENSGK ITMPLW                                         206

SEQ ID NO: 413             moltype = AA  length = 214
FEATURE                    Location/Qualifiers
source                     1..214
                           mol_type = protein
                           organism = Bubalus bubalis
SEQUENCE: 413
MKLLILTCLV AVALARPKQP IKHQGLPQGV LNENLLRFFV APFPEVFGKE KVNELSTDIG    60
SESTEDQAME DIKQMEAESI SSSEEIVPIS VEQKHIQKED VPSERYLGYL EQLLRLKKYN    120
VPQLEIVPNL AEEQLHSMKE GIHAQQKEPM IGVNQELAYF YPQLFRQFYQ LDAYPSGAWY    180
YVPLGTQYPD APSFSDIPNP IGSENSEKTT MPLW                                214

SEQ ID NO: 414             moltype = AA  length = 214
FEATURE                    Location/Qualifiers
source                     1..214
                           mol_type = protein
                           organism = Bubalus bubalis
SEQUENCE: 414
MKLLVLTCLV AVALARPKQP IKHQGLPQGV LNENLLRFFV APFPEVFGKE KVNELSTDIG    60
SESTEDQAME DIKQMEAESI SSSEEIVPIS VEQKHIQKED VPSERYLGYL EQLLRLKKYN    120
VPQLEIVPNL AEEQLHSMKE GIHAQQKEPM IGVNQELAYF YPQLFRQFYQ LDAYPSGAWY    180
YVPLGTQYPD APSFSDIPNP IGSENSGKTT MPLW                                214

SEQ ID NO: 415             moltype = AA  length = 214
FEATURE                    Location/Qualifiers
source                     1..214
                           mol_type = protein
                           organism = Bubalus bubalis
SEQUENCE: 415
MKLLILTCLV AVALARPKQP IKHQGLPQGV LNENLLRFFV APFPEVFGKE KVNELSTDIG    60
SESTEDQAME DIKQMEAESI SSSEEIVPIS VEQKHIQKED VPSERYLGYL EQLLRLKKYN    120
VPQLEIVPNL AEEQLHSMKE GIHAQQKEPM IGVNQELAYF YPQLFRQFYQ LDAYPSGAWY    180
YVPLGTQYPD APSFSDIPNP IGSENSGKTT MPLW                                214

SEQ ID NO: 416             moltype = AA  length = 214
FEATURE                    Location/Qualifiers
source                     1..214
                           mol_type = protein
                           organism = Bubalus bubalis
SEQUENCE: 416
MKLLILTCLV AVALARPKQP IKHQGLPQGV LNENLLRFFV APFPEVFGKE KVNELSTDIG    60
SESTEDQAME DIKQMEAESI SSSEEIVPIS VEQKHIQKED VPSERYLGYL EQLLRLKKYN    120
VPQLEIVPNL AEEQLHSMKE GIHAQQKEPM IGVNQELAYF YPQLFRQFYQ LDAYPSGAWY    180
YVPLGTQYPD APLFSDIPNP IGSENSGKTT MPLW                                214

SEQ ID NO: 417             moltype = AA  length = 214
FEATURE                    Location/Qualifiers
source                     1..214
                           mol_type = protein
                           organism = Bubalus bubalis
SEQUENCE: 417
MKLLILTCLV AVALARPKQP IKHQGLPQGV LNENLLRFFV APFPEVFGKE KVNELSTDVG    60
SESTEDQAME DIKQMEAESI SSSEEIVPIS VEQKHIQKED VPSERYLGYL EQLLRLKKYN    120
VPQLEIVPNL AEEQLHSMKE GIHAQQKEPM IGVNQELAYF YPQLFRQFYQ LDAYPSGAWY    180
YVPLGTQYPD APSLSDIPNP IGSENSGKTT MPLW                                214
```

```
SEQ ID NO: 418            moltype = AA  length = 215
FEATURE                   Location/Qualifiers
source                    1..215
                          mol_type = protein
                          organism = Bubalus bubalis
SEQUENCE: 418
MKLLILTCLV AVALARPKQP IKHQGLPQGV LNENLLRFFV APFPEVFGKE KVNELSTDIG    60
SESTEDQAME DIKQMEAESI SSSEEIVPIS VEQKHIQKED VPSERYLGYL EQLLRLKKYN   120
VPQLEIVPNL AEEQLHSMKE GIHAQQKEPM IGVNQELAYF YPQLFRQFYQ LDAYPSGAWY   180
YVPLGTQYPD APLFSDIPNP IGSENSGKTT MPLWW                              215

SEQ ID NO: 419            moltype = AA  length = 214
FEATURE                   Location/Qualifiers
source                    1..214
                          mol_type = protein
                          organism = Bubalus bubalis
SEQUENCE: 419
MKLLILTCLV AVALARPKQP IKHQGLPQGV LNENLLRFFV APFPEMFGKE KVNELSTDVG    60
SESTEDQAME DIKQMEAESI SSSEEIVPIS VEQKHIQKED VPSERYLGYL EQLLRLKKYN   120
VPQLEIVPNL AEEQLHSMKE GIHAQQKEPM IGVNQELAYF YPQLFRQFYQ LDAYPSGAWY   180
YVPLGTQYPD APLFSDIPNP IGSENSGKTT MPLW                               214

SEQ ID NO: 420            moltype = AA  length = 214
FEATURE                   Location/Qualifiers
source                    1..214
                          mol_type = protein
                          organism = Bubalus bubalis
SEQUENCE: 420
MKLLILTCLV AVALARPKQP IKHQGLPQGV LNENLLRFFV APFPEVFGKE KVNELSTDIG    60
SESTEDQAME DIKQMEAESI SSSEEIVPIS VEQKHIQKEDV PSERYLGYLE QLLRLKKYNV   120
PQLEIVPNLA EEQLHSMKEG IHAQQKEPMI GVNQELAYFY PQLFRQFYQL DAYPSGAWYY   180
VPLGTQYPDA PLFSDIPNPI GSENSGKTTM PLWW                               214

SEQ ID NO: 421            moltype = AA  length = 206
FEATURE                   Location/Qualifiers
source                    1..206
                          mol_type = protein
                          organism = Bubalus bubalis
SEQUENCE: 421
MKLLILTCLV AVALARPKQP IKHQGLPQGV LNENLLRFFV APFPEMFGKD VGSESTEDQA    60
MEDIKQMEAE SISSSEEIVP ISVEQKHIQK EDVPSERYLG YLEQLLRLKK YNVPQLEIVP   120
NLAEEQLHSM KEGIHAQQKE PMIGVNQELA YFYPQLFRQF YQLDAYPSGA WYYVPLGTQY   180
PDAPSFSDIP NPIGSENSGK TTMPLW                                        206

SEQ ID NO: 422            moltype = AA  length = 206
FEATURE                   Location/Qualifiers
source                    1..206
                          mol_type = protein
                          organism = Bubalus bubalis
SEQUENCE: 422
MKLLILTCLV AVALARPKQP IKHQGLPQGV LNENLLRFFV APFPEVFGKD IGSESTEDQA    60
MEDIKQMEAE SISSSEEIVP ISVEQKHIQK EDVPSERYLG YLEQLLRLKK YNVPQLEIVP   120
NLAEEQLHSM KEGIHAQQKE PMIGVNQELA YFYPQLFRQF YQLDAYPSGA WYYVPLGTQY   180
PDAPLFSDIP NPIGSENSGK TTMPLW                                        206

SEQ ID NO: 423            moltype = AA  length = 207
FEATURE                   Location/Qualifiers
source                    1..207
                          mol_type = protein
                          organism = Bubalus bubalis
SEQUENCE: 423
MKLLILTCLV AVALARPKQP IKHQGLPQGV LNENLLRFFV APFPEVFGKD IGSESTEDQA    60
MEDIKQMEAE SISSSEEIVP ISVEQKHIQK EDVPSERYLG YLEQLLRLKK YNVPQLEIVP   120
NLAEEQLHSM KEGIHAQQKE PMIGVNQELA YFYPQLFRQF YQLDAYPSGA WYYVPLGTQY   180
PDAPLFSDIP NPIGSENSGK TTMPLWW                                       207

SEQ ID NO: 424            moltype = AA  length = 207
FEATURE                   Location/Qualifiers
source                    1..207
                          mol_type = protein
                          organism = Bubalus bubalis
SEQUENCE: 424
MKLLILTCLV AVALARPKQP IKHQGLPQGV LNENLLRFFV APFPEVFGKE KVNELSTDIG    60
SESTEDQAME DIKQMEAESI SSSEEIVPIS VEQKHIQKED VPSERYLGYL EQLLRLKKYN   120
VPQLEIVPNL AEEQLHSMKE GIHAQQKEPM IGVNQLFRQF YQLDAYPSGA WYYVPLGTQY   180
PDAPLFSDIP NPIGSENSGK TTMPLWW                                       207

SEQ ID NO: 425            moltype = AA  length = 207
```

```
FEATURE                 Location/Qualifiers
source                  1..207
                        mol_type = protein
                        organism = Bubalus bubalis
SEQUENCE: 425
MKLLILTCLV AVALARPKQP IKHQGLPQGV LNENLLRFFV APFPEVFGKE KVNELSTDQA   60
MEDIKQMEAE SISSSEEIVP ISVEQKHIQK EDVPSERYLG YLEQLLRLKK YNVPQLEIVP  120
NLAEEQLHSM KEGIHAQQKE PMIGVNQELA YFYPQLFRQF YQLDAYPSGA WYYVPLGTQY  180
PDAPLFSDIP NPIGSENSGK TTMPLWW                                     207

SEQ ID NO: 426          moltype = AA  length = 206
FEATURE                 Location/Qualifiers
source                  1..206
                        mol_type = protein
                        organism = Bubalus bubalis
SEQUENCE: 426
MKLLILTCLV AVALARPKQP IKHQGLPQGV LNENLLRFFV APFPEVFGKE KVNELSTDQA   60
MEDIKQMEAE SISSSEEIVP ISVEKHIQKE DVPSERYLGY LEQLLRLKKY NVPQLEIVPN  120
LAEEQLHSMK EGIHAQQKEP MIGVNQELAY FYPQLFRQFY QLDAYPSGAW YYVPLGTQYP  180
DAPLFSDIPN PIGSENSGKT TMPLWW                                      206

SEQ ID NO: 427          moltype = AA  length = 202
FEATURE                 Location/Qualifiers
source                  1..202
                        mol_type = protein
                        organism = Bubalus bubalis
SEQUENCE: 427
MKLLILTCLV AVALARPKQP IKHQGLPQPF PEVFGKEKVN ELSTDIGSES TEDQAMEDIK   60
QMEAESISSS EEIVPISVEQ KHIQKEDVPS ERYLGYLEQL LRLKKYNVPQ LEIVPNLAEE  120
QLHSMKEGIH AQQKEPMIGV NQELAYFYPQ LFRQFYQLDA YPSGAWYYVP LGTQYPDAPL  180
FSDIPNPIGS ENSGKTTMPL WW                                          202

SEQ ID NO: 428          moltype = AA  length = 194
FEATURE                 Location/Qualifiers
source                  1..194
                        mol_type = protein
                        organism = Bubalus bubalis
SEQUENCE: 428
MKLLILTCLV AVALARPKQP IKHQGLPQPF PEVFGKDIGS ESTEDQAMED IKQMEAESIS   60
SSEEIVPISV EQKHIQKEDV PSERYLGYLE QLLRLKKYNV PQLEIVPNLA EEQLHSMKEG  120
IHAQQKEPMI GVNQELAYFY PQLFRQFYQL DAYPSGAWYY VPLGTQYPDA PLFSDIPNPI  180
GSENSGKTTM PLWW                                                   194

SEQ ID NO: 429          moltype = AA  length = 194
FEATURE                 Location/Qualifiers
source                  1..194
                        mol_type = protein
                        organism = Bubalus bubalis
SEQUENCE: 429
MKLLILTCLV AVALARPKQP IKHQGLPQPF PEVFGKEKVN ELSTDQAMED IKQMEAESIS   60
SSEEIVPISV EQKHIQKEDV PSERYLGYLE QLLRLKKYNV PQLEIVPNLA EEQLHSMKEG  120
IHAQQKEPMI GVNQELAYFY PQLFRQFYQL DAYPSGAWYY VPLGTQYPDA PLFSDIPNPI  180
GSENSGKTTM PLWW                                                   194

SEQ ID NO: 430          moltype = AA  length = 178
FEATURE                 Location/Qualifiers
source                  1..178
                        mol_type = protein
                        organism = Bubalus bubalis
SEQUENCE: 430
MKLLILTCLV AVALARPKQP IKHQGLPQGV LNENLLRFFV APFPEVFGKE KVNELSTDIG   60
SESTEDQAME DIKEQLLRLK KYNVPQLEIV PNLAEEQLHS MKEGIHAQQK EPMIGVNQEL  120
AYFYPQLFRQ FYQLDAYPSG AWYYVPLGTQ YPDAPLFSDI PNPIGSENSG KTTMPLWW    178

SEQ ID NO: 431          moltype = AA  length = 214
FEATURE                 Location/Qualifiers
source                  1..214
                        mol_type = protein
                        organism = Bos mutus
SEQUENCE: 431
MKLLILTCLV AVALARPKHP IKHQGLPQEV LNENLLRFFV APFPEVFGKE KVNELSKDIG   60
SESTEDQAME DIKKMEAESI SSSEEIVPNS VEQKHIQKED VPSERYLGYL EQLLRLKKYK  120
VPQLEIVPNS AEERLHSMKE GIHAQQKEPM IGVNQELAYF YPELFRQFYQ LDAYPSGAWY  180
YVPLGTQYTD APSFSDIPNP IGSENSGKTT MPLW                             214

SEQ ID NO: 432          moltype = AA  length = 214
FEATURE                 Location/Qualifiers
VARIANT                 99
                        note = X is any amino acid
```

```
source                      1..214
                            mol_type = protein
                            organism = Bos indicus
SEQUENCE: 432
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKXD VPSERYLGYL EQLLRLKKYK   120
VPQLEIVPNS AEERLHSMKE GIHAQQKEPM IGVNQELAYF YPELFRQFYQ LDAYPSGAWY   180
YVPLGTQYTD APSFSDIPNP IGSENSGKTT MPLW                               214

SEQ ID NO: 433              moltype = AA  length = 205
FEATURE                     Location/Qualifiers
source                      1..205
                            mol_type = protein
                            organism = Jeotgalicoccus coquinae
SEQUENCE: 433
MAVALARPKH PIKHQGLPQE VLNENLLRFF VAPFPEVFGK EKVNELSKDI GSESTEDQAM    60
EDIKQMEAES ISSSEEIVPN SVEQKHIQKE DVPSERYLGY LEQLLRLKKY KVPQLEIVPN   120
SAEERLHSMK EGIHAQQKEP MIGVNQELAY FYPELFRQFY QLDAYPSGAW YYVPLGTQYT   180
DAPSFSDIPN PIGSENSEKT TMPLW                                        205

SEQ ID NO: 434              moltype = AA  length = 146
FEATURE                     Location/Qualifiers
source                      1..146
                            mol_type = protein
                            organism = Jeotgalicoccus coquinae
SEQUENCE: 434
MEDIKQMEAE SISSSEEIVP NSVEQKHIQK EDVPSERYLG YLEQLLRLKK YKVPQLEIVP    60
NSAEERLHSM KEGIHAQQKE PMIGVNQELA YFYPELFRQF YQLDAYPSGA WYYVPLGTQY   120
TDAPSFSDIP NPIGSENSEK TTMPLW                                       146

SEQ ID NO: 435              moltype = AA  length = 214
FEATURE                     Location/Qualifiers
source                      1..214
                            mol_type = protein
                            organism = Bison bison
SEQUENCE: 435
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EQLLRLKKYK   120
VPQLEIVPNS AEERLHSMKE GIHAQQKEPM IGVNQELAYF YPELFRQFYQ LDAYPSGAWY   180
YVPLGTQYTD APSFSDIPNP IGSENSGKTT MPLW                               214

SEQ ID NO: 436              moltype = AA  length = 214
FEATURE                     Location/Qualifiers
source                      1..214
                            mol_type = protein
                            organism = Bos grunniens
SEQUENCE: 436
MRLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSEHYLGYL EQLLRLKKYK   120
VPQLEIVPNS AEERLHSMKE GIHAQQKEPM IGVNQELAYF YPELFRQFYQ LDAYPSGAWY   180
YVPLGTQYTD APSFSDIPNP IGSENSGKTT MPLW                               214

SEQ ID NO: 437              moltype = AA  length = 214
FEATURE                     Location/Qualifiers
source                      1..214
                            mol_type = protein
                            organism = Jeotgalicoccus aerolatus
SEQUENCE: 437
MKLLILTCLV AVALARPKHP IKHQGLPQEV LNENLLRFFV APFPEVFGKE KVNELSKDIG    60
SESTEDQAME DIKQMEAESI SSSEEIVPNS VEQKHIQKED VPSERYLGYL EQLLRLKKYK   120
VPQLEIVPNS AEERLHSMKE GIHAQQKEPM IGVNQELAYF YPELFRQFYQ LDAYPSGAWY   180
YVPLGTQYTD APSFSDIPNP IGSENSEKTT MPLW                               214

SEQ ID NO: 438              moltype = AA  length = 196
FEATURE                     Location/Qualifiers
source                      1..196
                            mol_type = protein
                            organism = Jeotgalicoccus aerolatus
SEQUENCE: 438
LVAVALARPK QPIKHQGLPQ GVLNENLLRF FVAPFPEVFG KEKVNELSTD IGSESTEDQA    60
MEDIKQMEAE SISSSEEIVP ISVEQKHIQK EDVPSERYLG YLEQLLRLKK YNVPQLEIVP   120
NLAEEQLHSM KEGIHAQQKE PMIGVNQELA YFYPQLFRQF YQLDAYPSGA WYYVPLGTQY   180
PDAPSFSDIP NPIGSE                                                  196

SEQ ID NO: 439              moltype = AA  length = 229
FEATURE                     Location/Qualifiers
source                      1..229
                            mol_type = protein
                            organism = Muntiacus muntjak
```

-continued

```
SEQUENCE: 439
KHPIGHQGLP QEVLNENLLR LFVVPFPEVF GKESINELSK DTESESTEDH AMEDTKQVES    60
GSSSSSEEIV SNIAEQKQVQ KEDVPSERYL GYLEQLLKLQ KYNLPQLEQK IRSPRELLDY   120
FPPDMKHRFF VLPNYSKYNT ELNIFSKELL HSMKEGIHAQ QKKPMKGVSQ ELAYFYPQLF   180
RQFYQLDAYP SGAWYYLPLG IQYTDVPSFS DIPNPIGSEN SGKATMPLW               229

SEQ ID NO: 440          moltype = AA  length = 229
FEATURE                 Location/Qualifiers
source                  1..229
                        mol_type = protein
                        organism = Muntiacus reevesi
SEQUENCE: 440
KHPIGHQGLP QEVLNENLLR LFVVPFPEVF GKESISELSK DTESESTEDH AMEDTKQVES    60
GSSSSSEEIV SNIAEQKQVQ KEDVPSERYL GYLEQLLKLQ KYNLPQLEQK IRSPRELLDY   120
FPPDMKHRFF VLPNYSKYNT ELNIFSKELL HSMKEGIHAQ QKKPMKGVSQ ELAYFYPQLF   180
RQFYQLDAYP SGAWYYLPLG IQYTDAPSFS DIPNPIGSEN SGKATMPLW               229

SEQ ID NO: 441          moltype = AA  length = 222
FEATURE                 Location/Qualifiers
source                  1..222
                        mol_type = protein
                        organism = Bos taurus
SEQUENCE: 441
MKFFIFTCLL AVALAKNTME HVSSSEESII SQETYKQEKN MDINPSKENL CSTFCKEVVR    60
NANEEEYSIG SSSEESAEVA TEEVKITVDD KHYQKALNEI NQFYRKFPQY LQYLYQGPIV   120
LNPWDQVKRN AVPITPTLNR EQLSTSEENS KKTVDMESTE VFTKKTKLTE EEKNRLNFLK   180
KISQRYQKFA LPQYLKTVYQ HQKAMKPWIQ PKTKVIPYVR YL                      222

SEQ ID NO: 442          moltype = AA  length = 213
FEATURE                 Location/Qualifiers
source                  1..213
                        mol_type = protein
                        organism = Bos taurus
SEQUENCE: 442
MKFFIFTCLL AVALAKNTME HVSSSEESII SQETYKQEKN MAINPSKENL CSTFCKEVVR    60
NANEEEYSIG SSSEESAEVA TEEVKITVDD KHYQKALNEI NQFYQKFPQY LQYLYQGPIV   120
LNPWDQVKRN AVPITPTLNR EQLSTSEEST EVFTKKTKLT EEEKNRLNFL KKISQRYQKF   180
ALPQYLKTVY QHQKAMKPWI QPKTKVIPYV RYL                                213

SEQ ID NO: 443          moltype = AA  length = 213
FEATURE                 Location/Qualifiers
source                  1..213
                        mol_type = protein
                        organism = Bos taurus
SEQUENCE: 443
MKFFIFTCLL AVALAKNTME HVSSSEESII SQETYKQEKN MAINPSKEVV RNANEEEYSI    60
GSSSEESAEV ATEEVKITVD DKHYQKALNE INQFYQKFPQ YLQYLYQGPI VLNPWDQVKR   120
NAVPITPTLN REQLSTSEEN SKKTVDMEST EVFTKKTKLT EEEKNRLNFL KKISQRYQKF   180
ALPQYLKTVY QHQKAMKPWI QPKTKVIPYV RYL                                213

SEQ ID NO: 444          moltype = AA  length = 223
FEATURE                 Location/Qualifiers
source                  1..223
                        mol_type = protein
                        organism = Capra hircus
SEQUENCE: 444
MKFFIFTCLL AVALAKHKME HVSSSEEPIN ILQEIYKQEK NMAIHPRKEK LCTTSCEEVV    60
RNANEEEYSI RSSSEESAEV APEEIKITVD DKHYQKALNE INQFYQKFPQ YLQYPYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                     223

SEQ ID NO: 445          moltype = AA  length = 223
FEATURE                 Location/Qualifiers
source                  1..223
                        mol_type = protein
                        organism = Capra hircus
SEQUENCE: 445
MKFFIFTCLL AVALAKHKME HVSSSEEPIN IFQEIYKQEK NMAIHPRKEK LCTTSCEEVV    60
RNANEEEYSI RSSSEESAEV APEEIKITVD DKHYQKALNE INQFYQKFPQ YLQYPYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                     223

SEQ ID NO: 446          moltype = AA  length = 223
FEATURE                 Location/Qualifiers
source                  1..223
                        mol_type = protein
                        organism = Capra hircus
SEQUENCE: 446
MKFFIFTCLL AVALAKHKME HISSSEEPIN IFQEIYKQEK NMAIHPRKEK LCTTSCEEVV    60
```

```
RNANEEEYSI RSSSEESAEV APEEIKITVD DKHYQKALNE INQFYQKFPQ YLQYPYQGPI    120
VLNPWDQVKR NAGPFTPTVN REQLSTSEEN SKKTIDMEST EVFTKKTKLT EEEKNRLNFL    180
KKISQYYQKF AWPQYLKTVD QHQKAMKPWT QPKTNAIPYV RYL                      223

SEQ ID NO: 447           moltype = AA   length = 223
FEATURE                  Location/Qualifiers
source                   1..223
                         mol_type = protein
                         organism = Capra hircus
SEQUENCE: 447
MKFFIFTCLL AVALAKHKME HVSSSEEPIN IFQEIYKQEK NMAIHPRKEK LCTTSCEEVV     60
RNANEEEYSI RSSSEESAKV APEEIKITVD DKHYQKALNE INQFYQKFPQ YLQYPYQGPI    120
VLNPWDQVKR NAGPFTPTVN REQLSTSEEN SKKTIDMEST EVFTKKTKLT EEEKNRLNFL    180
KKISQYYQKF AWPQYLKTVD QHQKAMKPWT QPKTNAIPYV RYL                      223

SEQ ID NO: 448           moltype = AA   length = 223
FEATURE                  Location/Qualifiers
source                   1..223
                         mol_type = protein
                         organism = Capra hircus
SEQUENCE: 448
MKFFIFTCLL AVALAKHKME HVSSSEEPIN IFQEIYKQEK NMAIHPRKEK LCTTSCEEVV     60
RNANEEEYSI RSSSEESAEV APEEIKITVD DKHYQKALNE INQFYQKFPQ YLQYPYQGPI    120
VLNPWDQVKR NAGPFTPTVN REQLSTSEEN SKKTIDMEST EVFTKKTKLT EEEKNRLNFL    180
KIISQYYQKF AWPQYLKTVD QHQKAMKPWT QPKTNAIPYV RYL                      223

SEQ ID NO: 449           moltype = AA   length = 223
FEATURE                  Location/Qualifiers
source                   1..223
                         mol_type = protein
                         organism = Capra hircus
SEQUENCE: 449
MKFFIFTCLL AVALATHKME HVSSSEEPIN IFQEIYKQEK NMAIHPRKEK LCTTSCEEVV     60
RNANEEEYSI RSSSEESAKV APEEIKITVD DKHYQKALNE INQFYQKFPQ YLQYPYQGPI    120
VLNPWDQVKR NAGPFTPTVN REQLSTSEEN SKKTIDMEST EVFTKKTKLT EEEKNRLNFL    180
KKISQYYQKF AWPQYLKTVD QHQKAMKPWT QPKTNAIPYV RYL                      223

SEQ ID NO: 450           moltype = AA   length = 223
FEATURE                  Location/Qualifiers
source                   1..223
                         mol_type = protein
                         organism = Capra hircus
SEQUENCE: 450
MKFFIFTCLL AVALAKHKME HVSSSEEPIN IFQEIYKQEK NMAIHPRKEK LCTTSCEEVV     60
RNANEEEYSI RSSSEESAEV APEEIKITVD DKHYQKALNE INQFYQKFPQ YLQYPYQGPI    120
VLNPWDQVKR NAGAFTPTVN REQLSTSEEN SKKTIDMEST EVFTKKTKLT EEEKNRLNFL    180
KKISQYYQKF AWPQYLKTVD QHQKAMKPWT QPKTNAIPYV RYL                      223

SEQ ID NO: 451           moltype = AA   length = 223
FEATURE                  Location/Qualifiers
source                   1..223
                         mol_type = protein
                         organism = Capra hircus
SEQUENCE: 451
MKFFIFTCLL AVALAKHKME HVSSSEEPIN IFQEIYKQEK NMAIHPRKEK LCTTSCEEVV     60
RNANEEEYSI RSSSEESAEV APEEIKITVD DKHYQKALNE INQFYQKFPQ YLQYPYQGPI    120
VLNPWDQVKR NAGPFTPTVN REQLSTSEEN SKKTIDMEST EVFTKKAKLT EEEKNRLNFL    180
KIISQYYQKF AWPQYLKTVE QHQKAMKPWT QPKTNAIPYV RYL                      223

SEQ ID NO: 452           moltype = AA   length = 222
FEATURE                  Location/Qualifiers
source                   1..222
                         mol_type = protein
                         organism = Capra hircus
SEQUENCE: 452
MKFFIFTCLL AVALAKHMEH VSSSEEPINI FQEIYKQEKN MAIHPRKEKL CTTSCEEVVR     60
NANEEEYSIR SSSEESAEVA PEEIKITVDD KHYQKALNEI NQFYQKFPQY LQYPYQGPIV    120
LNPWDQVKRN AGAFTPTVNR EQLSTSEENS KKTIDMESTE VFTKKTKLTE EEKNRLNFLK    180
KISQYYQKFA WPQYLKTVDQ HQKAMKPWTQ PKTNAIPYVR YL                       222

SEQ ID NO: 453           moltype = AA   length = 223
FEATURE                  Location/Qualifiers
source                   1..223
                         mol_type = protein
                         organism = Capra hircus
SEQUENCE: 453
MKFFIFTCLL AVALAKHKME HVSSSEEPIN IFQEIYKQEK NMAIRPRKEK LCTTSCEEVV     60
RNANEEEYSI RSSSEESAEV APEEIKITVD DKHYQKALNE INQFYQKFPQ YLQYPYQGPI    120
VLNPWDQVKR NAGPFTPTVN REQLSTSEEN SKKTIDMEST EVFTKKTKLT EEEKNRLNFL    180
```

```
KKISQYYQKF AWPQYLKTVD QHQKAMKPRT QPKTNAIPYV RYL              223

SEQ ID NO: 454          moltype = AA   length = 223
FEATURE                 Location/Qualifiers
source                  1..223
                        mol_type = protein
                        organism = Capra hircus
SEQUENCE: 454
MKFFIFTCLL AVALAKHKME HVSSSEEPIN IFQEIYKQEK NMAIHPRKEK LCTTSCEEVV   60
RNANEEEYSI RSSSEESAEV APEEIKITVD DKHYQKALNE INQFYQKFPQ YLQYPYQGPI  120
VLNPWDQVKR NAGPFTPTVN REQLSTSEEN SKKTIDMEST EVFTKKTKLT EEEKNRLNFL  180
KIISQYYQKF AWPQYLKTVD QHQKAMKRWT QPKTNAIPYV RYL                   223

SEQ ID NO: 455          moltype = AA   length = 223
FEATURE                 Location/Qualifiers
source                  1..223
                        mol_type = protein
                        organism = Capra hircus
SEQUENCE: 455
MKFFIFTCLL AVALAKHKME HVSSSEEPIN IFQEIYKQEK NMAIHPRKEK LCTTSCEEVV   60
RNANEEEYSI RSSSEESAEV APEEIKITVD DKHYQKALNE INQFYQKFPQ YLQYPYQGPI  120
VLNPWDQVKR NAGPFTPTVN REQLSTSEEN SKKTIDMEST KVFTKKTKLT EEEKNRLNFL  180
KIISQYYQKF AWPQYLKTVD QHQKAMKRWT QPKTNAIPYV RYL                   223

SEQ ID NO: 456          moltype = AA   length = 215
FEATURE                 Location/Qualifiers
source                  1..215
                        mol_type = protein
                        organism = Capra hircus
SEQUENCE: 456
MKFFIFTCLL AVALAKHKME HVSSSEEPIN IFQEIYKQEK NMAIHPRKEK LCTTSCEEVV   60
RNANEEEYSI RSSSEEIKIT VDDKHYQKAL NEINQFYQKF PQYLQYPYQG PIVLNPWDQV  120
KRNAGPFTPT VNREQLSTSE ENSKKTIDME STEVFTKKTK LTEEEKNRLN FLKKISQYYQ  180
KFAWPQYLKT VDQHQKAMKP WTQPKTNAIP YVRYL                            215

SEQ ID NO: 457          moltype = AA   length = 214
FEATURE                 Location/Qualifiers
source                  1..214
                        mol_type = protein
                        organism = Capra hircus
SEQUENCE: 457
MKFFIFTCLL AVALAKHEPI NIFQEIYKQE KNMAIHPRKE KLCTTSCEEV VRNANEEEYS   60
IRSSSEESAE VAPEEIKITV DDKHYQKALN EINQFYQKFP QYLQYPYQGP IVLNPWDQVK  120
RNAGAFTPTV NREQLSTSEE NSKKTIDMES TEVFTKKTKL TEEEKNRLNF LKKISQYYQK  180
FAWPQYLKTV DQHQKAMKPW TQPKTNAIPY VRYL                             214

SEQ ID NO: 458          moltype = AA   length = 214
FEATURE                 Location/Qualifiers
source                  1..214
                        mol_type = protein
                        organism = Capra hircus
SEQUENCE: 458
MKFFIFTCLL AVALAKHKME HVSSSEEPIN IFQEIYKQEK NMAIHPRKEV VRNANEEEYS   60
IRSSSEESAE VAPEEIKITV DDKHYQKALN EINQFYQKFP QYLQYPYQGP IVLNPWDQVK  120
RNAGPFTPTV NREQLSTSEE NSKKTIDMES TEVFTKKTKL TEEEKNRLNF LKKISQYYQK  180
FAWPQYLKTV DQHQKAMKPW TQPKTNAIPY VRYL                             214

SEQ ID NO: 459          moltype = AA   length = 214
FEATURE                 Location/Qualifiers
source                  1..214
                        mol_type = protein
                        organism = Capra hircus
SEQUENCE: 459
MKFFIFTCLL AVALAKHEPI NIFQEIYKQE KNMAIHPRKE KLCTTSCEEV VRNANEEEYS   60
IRSSSEESAK VAPEEIKITV DDKHYQKALN EINQFYQKFP QYLQYPYQGP IVLNPWDQVK  120
RNAGPFTPTV NREQLSTSEE NSKKTIDMES TEVFTKKTKL TEEEKNRLNF LKKISQYYQK  180
FAWPQYLKTV DQYQKAMKPW TQPKTNAIPY VRYL                             214

SEQ ID NO: 460          moltype = AA   length = 215
FEATURE                 Location/Qualifiers
source                  1..215
                        mol_type = protein
                        organism = Capra hircus
SEQUENCE: 460
MKFFIFTCLL AVALAKHKME HVSSSEEPIN IFQEIYKQEK NMAIHPRKEK LCTTSCEEVV   60
RNANEEEYSI RSSSEEIKIT VDDKHYQKAL NEINQFYQKF PQYLQYPYQG PIVLNPWDQV  120
KRNAGAFTPT VNREQLSTSE ENSKKTIDME STEVFTKKTK LTEEEKNRLN FLKKISQYYQ  180
KFAWPQYLKT VDQHQKAMKP WTQPKTNAIP YVRYL                            215
```

```
SEQ ID NO: 461            moltype = AA  length = 214
FEATURE                   Location/Qualifiers
source                    1..214
                          mol_type = protein
                          organism = Capra hircus
SEQUENCE: 461
MKFFIFTCLL AVALAKHKME HVSSSEEPIN IFQEIYKQEK NMAIHPRKEV VRNANEEEYS    60
IRSSSEESAE VAPEEIKITV DDKHYQKALN EINQFYQKFP QYLQYPYQGP IVLNPWDQVK   120
RNAGPFTPTV NREQLSTSEE NSKKTIDMES TEVFTKKTKL TEEEKNRLNF LKIISQYYQK   180
FAWPQYLKTV DQHQKAMKPW TQPKTNAIPY VRYL                               214

SEQ ID NO: 462            moltype = AA  length = 214
FEATURE                   Location/Qualifiers
source                    1..214
                          mol_type = protein
                          organism = Capra hircus
SEQUENCE: 462
MKFFIFTCLL AVALAKHKME HVSSSEEPIN IFQEIYKQEK NMAIHPRKEV VRNANEEEYS    60
IRSSSEESAE VAPEEIKITV DDKHYQKALN EINQFYQKFP QYLQYPYQGP IVLNPWDQVK   120
RNAGAFTPTV NREQLSTSEE NSKKTIDMES TEVFTKKTKL TEEEKNRLNF LKKISQYYQK   180
FAWPQYLKTV DQHQKAMKPW TQPKTNAIPY VRYL                               214

SEQ ID NO: 463            moltype = AA  length = 214
FEATURE                   Location/Qualifiers
source                    1..214
                          mol_type = protein
                          organism = Capra hircus
SEQUENCE: 463
MKFFIFTCLL AVALAKHKME HVSSSEEPIN IFQEIYKQEK NMAIHPRKEV VRNANEEEYS    60
IRSSSEESAK VAPEEIKITV DDKHYQKALN EINQFYQKFL QYLQYPYQGP IVLNPWDQVK   120
RNAGPFTPTV NREQLSTSEE NSKKTIDMES TEVFTKKTKL TEEEKNRLNF LKKISQYYQK   180
FAWPQYLKTV DQHQKAMKPW TQPKTNAIPY VRYL                               214

SEQ ID NO: 464            moltype = AA  length = 214
FEATURE                   Location/Qualifiers
source                    1..214
                          mol_type = protein
                          organism = Capra hircus
SEQUENCE: 464
MKFFIFTCLL AVALAKHKME HVSSSEEPIN IFQEIYKQEK NMAIHPRKEV VRNANEEEYS    60
IRSSSEESAE VAPKEIKITV DDKHYQKALN EINQFYQKFP QYLQYPYQGP IVLNPWDQVK   120
RNAGPFTPTV NREQLSTSEE NSKKTIDMES TEVFTKKTKL TEEEKNRLNF LKIISQYYQK   180
FAWPQYLKTV DQHQKAMKAW TQPKTNAIPY VRYL                               214

SEQ ID NO: 465            moltype = AA  length = 214
FEATURE                   Location/Qualifiers
source                    1..214
                          mol_type = protein
                          organism = Capra hircus
SEQUENCE: 465
MKFFIFTCLL AVALAKHKME HVSSSEEPIN IFQEIYKQEK NMAIHPRKEK LCTTSCEEVV    60
RNANEEEYSI RSSSEESAEV APEEIKITVD DKHYQKALNE INQFYQKFPQ YLQYPYQGPI   120
VLNPWDQVKR NAGPFTPTVN REQLSTSEES TEVFTKKTKL TEEEKNRLNF LKIISRYYQK   180
FAWPQYLKTV DQHQKAMKPW TQPKTNAIPY VRYL                               214

SEQ ID NO: 466            moltype = AA  length = 205
FEATURE                   Location/Qualifiers
source                    1..205
                          mol_type = protein
                          organism = Capra hircus
SEQUENCE: 466
MKFFIFTCLL AVALAKHEPI NIFQEIYKQE KNMAIHPRKE VVRNANEEEY SIRSSSEESA    60
EVAPEEIKIT VDDKHYQKAL NEINQFYQKF PQYLQYPYQG PIVLNPWDQV KRNAGAFTPT   120
VNREQLSTSE ENSKKTIDME STEVFTKKTK LTEEEKNRLF LKKISQYYQ KFAWPQYLKT   180
VDQHQKAMKP WTQPKTNAIP YVRYL                                         205

SEQ ID NO: 467            moltype = AA  length = 206
FEATURE                   Location/Qualifiers
source                    1..206
                          mol_type = protein
                          organism = Capra hircus
SEQUENCE: 467
MKFFIFTCLL AVALAKHKME HVSSSEEPIN IFQEIYKQEK NMAIHPRKEV VRNANEEEYS    60
IRSSSEEIKI TVDDKHYQKA LNEINQFYQK FPQYLQYPYQ GPIVLNPWDQ VKRNAGAFTP   120
TVNREQLSTS EENSKKTIDM ESTEVFTKKT KLTEEEKNRL NFLKKISQYY QKFAWPQYLK   180
TVDQHQKAMK PWTQPKTNAI PYVRYL                                        206

SEQ ID NO: 468            moltype = AA  length = 223
FEATURE                   Location/Qualifiers
```

-continued

```
source                  1..223
                        mol_type = protein
                        organism = Ovis aries
SEQUENCE: 468
MKFFIFTCLL AVALAKHKME HVSSSEEPIN ISQEIYKQEK NMAIHPRKEK LCTTSCEEVV    60
RNANEEEYSI RSSSEESAEV APEEVKITVD DKHYQKALNE INQFYQKFPQ YLQYLYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                     223

SEQ ID NO: 469          moltype = AA   length = 223
FEATURE                 Location/Qualifiers
source                  1..223
                        mol_type = protein
                        organism = Ovis aries
SEQUENCE: 469
MKFFIFTCLL AVALAKHKME HVSSSEEPIN ISQEIYKQEK NMAIHPRKEK LCTTSCEEVV    60
RNADEEEYSI RSSSEESAEV APEEVKITVD DKHYQKALNE INQFYQKFPQ YLQYLYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                     223

SEQ ID NO: 470          moltype = AA   length = 223
FEATURE                 Location/Qualifiers
source                  1..223
                        mol_type = protein
                        organism = Ovis aries
SEQUENCE: 470
MKFFIFTCLL AVALAKHKME HVSSSEEPIN ISQEIYKQEK NMAIHPRKEK LCTTSCEEVI    60
RNSNEEEYSI RSSSEESAEV APEEVKITVD DKHYQKALNE INQFYQKFPQ YLQYLYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                     223

SEQ ID NO: 471          moltype = AA   length = 223
FEATURE                 Location/Qualifiers
source                  1..223
                        mol_type = protein
                        organism = Ovis aries
SEQUENCE: 471
MKFFIFTCLL AVALAKHKME HVSSSEEPIN ISQEIYKQEK NMAIHPRKEK LCTTSCEEVV    60
RNANEEEYSI RSSSEESAEV APEEVKITVD DKHYQKALNE INQFYQKFPQ YLQYLYQGPI   120
VLNPWDQVKR NAGPFTPTVN REQLSTSEEN SKKTIDMEST EVFTKKTKLT EEEKNHLNFL   180
KKISQYYQKF AWPQYLKTVD QHQKAMKPWT QPKTNAIPYV RYL                     223

SEQ ID NO: 472          moltype = AA   length = 223
FEATURE                 Location/Qualifiers
source                  1..223
                        mol_type = protein
                        organism = Ovis aries
SEQUENCE: 472
MKFFIFTCLL AVALAKHKME HVSSSEEPIN ISQEIYKQEK NMAIHPRKEK LCTTSCEEVV    60
SNANEEEYSI RSSSEESAEV APEEVKITVD DKHYQKALNE INQFYQKFPQ YLQYLYQGPI   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                     223

SEQ ID NO: 473          moltype = AA   length = 223
FEATURE                 Location/Qualifiers
source                  1..223
                        mol_type = protein
                        organism = Ovis aries
SEQUENCE: 473
MKFFIFTCLL AVALAKHKME HVSSSEEPIN ISQEIYKQEK NMAIHPRKEK LCTTSCEEVV    60
RNANEEEYSI RSSSEESAEV APEEVKITVY DKHYQKALNE INQFYQKFPQ YLQYLYQGPV   120
VLNPWDQVKR NAGPFTPTVN REQLSTSEEN SKKTIDMEST EVFTKKTKLT EEEKNRLNFL   180
KKISQYYQKF AWPQYLKTVD QHQKAMKPWT QPKTNAIPYV RYL                     223

SEQ ID NO: 474          moltype = AA   length = 222
FEATURE                 Location/Qualifiers
source                  1..222
                        mol_type = protein
                        organism = Bubalus bubalis
SEQUENCE: 474
MKFFIFTCLL AVALAKHTME HVSSSEESII SQETYKQEKN MAIHPSKENL CSTFCKEVIR    60
NANEEEYSIG SSSEESAEVA TEEVKITVDD KHYQKALNEI NQFYQKFPQY LQYLYQGPIV   120
LNPWDQVKRN AVPITPTLNR EQLSTSEENS KKTVDMESTE VFTKKTKLTE EDKNRLNFLK   180
KISQHYQKFA WPQYLKTVYQ YQKAMKPWTQ PKTNVIPYVR YL                      222

SEQ ID NO: 475          moltype = AA   length = 222
FEATURE                 Location/Qualifiers
source                  1..222
                        mol_type = protein
```

```
                                    organism = Bubalus bubalis
SEQUENCE: 475
MKFFIFTCLL AVALAKHTME HVSSSEESII SQETYKQEKN MAIHPSKENL CSTFCKEVIR    60
NANEEEYSIG SSSEESAEVA TEEVKITVDD KHYQKALNEI NQFYQKFPQY LQYLYQGPIV   120
LNPWDQVKRN AVPITPTLNR EQLSTSEENS KKTVDMESTE VITKKTKLTE EDKNRLNFLK   180
KISQHYQKFT WPQYLKTVYQ YQKAMKPWTQ PKTKVIPYVR YL                      222

SEQ ID NO: 476           moltype = AA  length = 210
FEATURE                  Location/Qualifiers
source                   1..210
                         mol_type = protein
                         organism = Bubalus bubalis
SEQUENCE: 476
ALAKHTMEHV SSSEESIISQ ETYKQEKNMA IHPSKENLCS TFCKEVIRNA NEEEYSIGSS    60
SEESAEVATE EVKITVDDKH YQKALNEINQ FYQKFPQYLQ YLYQGPIVLN PWDQVKRNAV   120
PITPTLNREQ LSTSEENSKK TVDMESTEVI TKKTKLTEED KNRLNFLKKI SQHYQKFTWP   180
QYLKTVYQYQ KAMKPWTQPK TNVIPYVRYL                                    210

SEQ ID NO: 477           moltype = AA  length = 215
FEATURE                  Location/Qualifiers
source                   1..215
                         mol_type = protein
                         organism = Bubalus bubalis
SEQUENCE: 477
CLLAVALAKH TMEHVSSSEE SIISQETYKQ EKNMAIHPSK ENLCSTFCKE VIRNANEEEY    60
SIGSSSEESA EVATEEVKIT VDDKHYQKAL NEINQFYQKF PQYLQYLYQG PIVLNPWDQV   120
KRNAVPITPT LNREQLSTSE ENSKKTVDME STEVITKKTK LTEEDKNRLN FLKKISQHYQ   180
KFTWPQYLKT VYQYQKAMKP WTQPKTNVIP YVRYL                              215

SEQ ID NO: 478           moltype = AA  length = 222
FEATURE                  Location/Qualifiers
source                   1..222
                         mol_type = protein
                         organism = Bubalus bubalis
SEQUENCE: 478
MKFFIFTCLL AVALAKHTME HVSSSEESII SQETYKQEKN MAIHPSKENL CSTFCKEVIR    60
NANEEEYSIG SSSEESAEVA TEEVKITVDD KHYQKALNEI NQFYQKFPQY LQYLYQGPIV   120
LNPWDQVKRN AVPITPTLNR EQLSTSEENS KKTVDMESTE VITKKTKLTE EDKNRLNFLK   180
KISQHYQKFT WPQYLKTVYQ YQKAMKPWTQ PKTNVIPYVR YL                      222

SEQ ID NO: 479           moltype = AA  length = 222
FEATURE                  Location/Qualifiers
source                   1..222
                         mol_type = protein
                         organism = Bubalus bubalis
SEQUENCE: 479
MKFFIFTCLL AVALAKHTME HVSSSEESII SQETYKQEKN MAIHPSKENL CSTFCKEVIR    60
NANEEEYSIG SSSEESAEVA TEEVKITVDD KHYQKALNEI NQFYQKFPQY LQYLYQGPIV   120
LNPWDQVERN AVPITPTLNR EQLSTSEENS KKTVDMESTE VITKKTKLTE EDKNRLNFLK   180
KISQHYQKFT WPQYLKTVYQ YQKAMKPWTQ PKTNVIPYVR YL                      222

SEQ ID NO: 480           moltype = AA  length = 213
FEATURE                  Location/Qualifiers
source                   1..213
                         mol_type = protein
                         organism = Bubalus bubalis
SEQUENCE: 480
MKFFIFTCLL AVALAKHTME HVSSSEESII SQETYKQEKN MAIHPSKENL CSTFCKEYSI    60
GSSSEESAEV ATEEVKITVD DKHYQKALNE INQFYQKFPQ YLQYLYQGPI VLNPWDQVKR   120
NAVPITPTLN REQLSTSEEN SKKTVDMEST EVFTKKTKLT EEDKNRLNFL KKISQHYQKF   180
AWPQYLKTVY QYQKAMKPWT QPKTNVIPYV RYL                                213

SEQ ID NO: 481           moltype = AA  length = 213
FEATURE                  Location/Qualifiers
source                   1..213
                         mol_type = protein
                         organism = Bubalus bubalis
SEQUENCE: 481
MKFFIFTCLL AVALAKHTME HVSSSEESII SQETYKQEKN MAIHPSKENL CSTFCKEVIR    60
NANEEEYSIG SSSEESAEVA TEEVKITVDD KHYQKALNEI NQFYQKFPQY LQYLYQGPIV   120
LNPWDQVKRN AVPITPTLNR EQLSTSEEST EVITKKTKLT EEDKNRLNFL KKISQHYQKF   180
TWPQYLKTVY QYQKAMKPWT QPKTNVIPYV RYL                                213

SEQ ID NO: 482           moltype = AA  length = 213
FEATURE                  Location/Qualifiers
source                   1..213
                         mol_type = protein
                         organism = Bubalus bubalis
SEQUENCE: 482
```

```
MKFFIFTCLL AVALAKHTME HVSSSEESII SQETYKQEKN MAIHPSKEVI RNANEEEYSI    60
GSSSEESAEV ATEEVKITVD DKHYQKALNE INQFYQKFPQ YLQYLYQGPI VLNPWDQVKR   120
NAVPITPTLN REQLSTSEEN SKKTVDMEST EVITKKTKLT EEDKNRLNFL KKISQHYQKF   180
TWPQYLKTVY QYQKAMKPWT QPKTNVIPYV RYL                                213

SEQ ID NO: 483          moltype = AA  length = 222
FEATURE                 Location/Qualifiers
source                  1..222
                        mol_type = protein
                        organism = Bos mutus
SEQUENCE: 483
MKFFIFTCLL AVALAKNTME HVSSSEESII SQETYKQEKN MAINPSKGNL CSTFCKEVVR    60
NANEEEYSIG SSSEESAEVA TEEVKITVDD KHYQKALNEI NQFYQKFPQY LQYLYQGPIV   120
LNPWDQVKRN AVPITPTLNR EQLSTSEENS KKTVDMESTE VFTKKTKLTE EEKNRLNFLK   180
KISQRYQKFA LPQYLKTVYQ HQKAMKPWIQ PKTKVIPYVR YL                      222

SEQ ID NO: 484          moltype = AA  length = 219
FEATURE                 Location/Qualifiers
source                  1..219
                        mol_type = protein
                        organism = Bos mutus
SEQUENCE: 484
MKFFIFTCLL AVALAKNTME HVSSSEESII SQETYKQEKN MAINPSKGNL CSTFCKEVVR    60
NANEEEYSIG SSSEESAEVA TEEVKITVDD KHYQKALNEI NQFYQKFPQY LQYLYQGPIV   120
LNPWDQVKRN AVPITPTLNR EQLSTSEENS KKTVDMESTE VFTKKTKLTE EEKNRLNFLK   180
KISQRYQKFA LPQYLKTVYQ HQKAMKPWIQ PKTKVIPYV                          219

SEQ ID NO: 485          moltype = AA  length = 222
FEATURE                 Location/Qualifiers
source                  1..222
                        mol_type = protein
                        organism = Jeotgalicoccus aerolatus
SEQUENCE: 485
MKFFIFTCLL AVALAKNTME HVSSSEESII SQETYKQEKN MAINPSKENL CSTFCKEVVR    60
NANEEEYSIG SSSEESAEVA TEEVKITVDD KHYQKALNEI NQFYQKFPQY LQYLYQGPIV   120
LNPWDQVKRN AVPITPTLNR EQLSTSEENS KKTVDMESTE VFTKKTKLTE EEKNRLNFLK   180
KISQRYQKFA LPQYLKTVYQ HQKAMKPWIQ PKTKVIPYVR YL                      222

SEQ ID NO: 486          moltype = AA  length = 182
FEATURE                 Location/Qualifiers
source                  1..182
                        mol_type = protein
                        organism = Jeotgalicoccus aerolatus
SEQUENCE: 486
MAINPSKENL CSTFCKEVVR NANEEEYSIG SSSEESAEVA TEEVKITVDD KHYQKALNEI    60
NQFYQKFPQY LQYLYQGPIV LNPWDQVKRN AVPITPTLNR EQLSTSEENS KKTVDMESTE   120
VFTKKTKLTE EEKNRLNFLK KISQRYQKFA LPQYLKTVYQ HQKAMKPWIQ PKTKVIPYVR   180
YL                                                                  182

SEQ ID NO: 487          moltype = AA  length = 237
FEATURE                 Location/Qualifiers
source                  1..237
                        mol_type = protein
                        organism = Jeotgalicoccus coquinae
SEQUENCE: 487
PGLLVFLLGN EDKVNMKFFI FTCLLAVALA KNTMEHVSSS EESIISQETY KQEKNMAINP    60
SKENLCSTFC KEVVRNANEE EYSIGSSSEE SAEVATEEVK ITVDDKHYQK ALNEINQFYQ   120
KFPQYLQYLY QGPIVLNPWD QVKRNAVPIT PTLNREQLST SEENSKKTVD MESTEVFTKK   180
TKLTEEEKNR LNFLKKISQR YQKFALPQYL KTVYQHQKAM KPWIQPKTKV IPYVRYL      237

SEQ ID NO: 488          moltype = AA  length = 222
FEATURE                 Location/Qualifiers
source                  1..222
                        mol_type = protein
                        organism = Bos grunniens
SEQUENCE: 488
MKFFIFTCLL AVALAKNTME HVSSSEESII SQETYKQEKN MAINPSKENL CSTFCKEVVR    60
NANEEEYSIG SSSEESAVVA TEEVKITVDD KHYQKALNEI NQFYQKFPQY LQYLYQGPIV   120
LNPWDQVKRN AVPITPTLNR EQLSTSEENS KKTVDMESTE VFTKKTKLTE EEKNRLNFLK   180
KISQRYQKFA LPQYLKTVYQ HQKAMEPWIQ PKTKVIPYVR YL                      222

SEQ ID NO: 489          moltype = AA  length = 222
FEATURE                 Location/Qualifiers
source                  1..222
                        mol_type = protein
                        organism = Bison bison
SEQUENCE: 489
MKFFIFTCLL AVALAKNTME HVSSSEESII SQETYKQEKN MAINPSKENL CSTFCKEVVR    60
NVNEEEYSIG SSSEESAEVA TEEVKITVDD KHYQKALNEI NQFYQKFPQY LQYLYQGPIV   120
```

```
LNPWDQVKRN AVPITPTLNR EQLSTSEENS KKTVDMESTE VFTKKTKLTE EEKNRLNFLK    180
KISQRYQKFA LPQYLKTVYQ RQKAMKPWIQ PKTKVIPYVR YL                      222

SEQ ID NO: 490           moltype = AA  length = 414
FEATURE                  Location/Qualifiers
REGION                   1..414
                         note = Bos indicus x Bos taurus
source                   1..414
                         mol_type = protein
                         organism = unidentified
SEQUENCE: 490
MKFFIFTCLL AVALAKNTME HVSSSEESII SQETYKQEKN MAINPSKENL CSTFCKEVVR    60
NANEEEYSIG SSSEESAEVA TEEVKITVDD KHYQKALNEI NQFYQKFPQY LQYLYQGPIV    120
LNPWDQVKRN AVPITPTLNR EQLSTSEENS KKTVDMESTE VFTKKTKLTE EEKNRLNFLK    180
KISQRYQKFA LPQYLKTVYQ HQKAMKPWIQ PKTKVIPYVD YSDNIGSPYP VNPSASISYP    240
VIPSASIPYP FNPSASISYP VTPSASIPCP VNPSASIPCP MPDRDFTPPV YLTKTNLPND    300
PAVPSNPLVF TALGAPLYSI AGLPISPFSG QLPPTGVFRL VPVSSRPIGP LYSPNEAAPS    360
ANTYIVEILV PPTTPPHTVP DVQPLTITEP DEAEPAADAL AAPEPQSSIS FDRE          414

SEQ ID NO: 491           moltype = AA  length = 222
FEATURE                  Location/Qualifiers
source                   1..222
                         mol_type = protein
                         organism = Odocoileus virginianus
SEQUENCE: 491
MKFFIFTCLL AVALAKHKME HVSSSEESIN IQETYKQEKN MAIHPSKENL CSTSCKEVVR    60
NANEEEYSIS SSSEESAEVA TEEVKVTVDD KHYQKILNEI SQFYQKFPQY LQYLYQGPIV    120
MNPWEQVKRT AVPFTPTVNR EQLSTSEENS EKIVDMESTE VFTKKTKLTE EEKNHLNLLK    180
KISQYYQKFA WPQYLKTVYQ YQKAMKPWTQ PKTNAIPYVK YL                      222

SEQ ID NO: 492           moltype = AA  length = 210
FEATURE                  Location/Qualifiers
source                   1..210
                         mol_type = protein
                         organism = Muntiacus muntjak
SEQUENCE: 492
MKNSAKHHKM EHVSSSEESI NIQETYKQEK NMAIHPSKEN LCSTSCKEVV RNANEEEYSI    60
SSSEESAEV ATEEVKVTVD DKHYQKVLNE ISQLYQKFPQ YLQYLYQGPI VMNPWEQVKR     120
TAGPFTPTVN RDHLSTSEEN SKKIVDMEST EVFTKKTKLT EEEKNRLNFL KKISQYYQKF    180
AWPQYLKTVY QYQKAMKPWT QPKTNAIPYV                                    210

SEQ ID NO: 493           moltype = AA  length = 210
FEATURE                  Location/Qualifiers
source                   1..210
                         mol_type = protein
                         organism = Muntiacus reevesi
SEQUENCE: 493
MKNSAKHHKM EHVSSSEESI NIQETYKQEK NMAIHPSKEN LCSTSCKEVV RNANEEEYSI    60
SSSSEESAEV ATEEAKVTVD DKHYQKVLNE ISQLYQKFPQ YLQYLYQGPI VMNPWEQVKR    120
TAGPFTPTVN RDHLSTSEEN SKKIVDMEST EVFTKKTKLT EEEKNRLNFL KKISQYYQKF    180
AWPQYLKTVY QYQKAMKPWT QPKTNAIPYV                                    210

SEQ ID NO: 494           moltype = AA  length = 235
FEATURE                  Location/Qualifiers
source                   1..235
                         mol_type = protein
                         organism = Cervus elaphus
SEQUENCE: 494
MKFFIFTCLL AVALAKHKME HVSSSEESIN IQETYKQEKN MAIHPSKEVV RNANEEESAD    60
VATEEVKVTV DNKHYQKVLN EISQFYQKFP QYLQYLYQGP IVMNPWEQVK RTAGPFIPTV    120
NRDHLSTSEE NSKKIVDMES TEVFTKKTKL TEEEKNRLNF LKKISQYYQK FAWPQYLKTV    180
YQYQKAMKPW TQPKTNAIPY VVELENLSST VSYLPLSTTS MFGVAHQQDK SQSIS         235

SEQ ID NO: 495           moltype = AA  length = 224
FEATURE                  Location/Qualifiers
source                   1..224
                         mol_type = protein
                         organism = Bos taurus
SEQUENCE: 495
MKVLILACLV ALALARELEE LNVPGEIVES LSSSEESITR INKKIEKFQS EEQQQTEDEL    60
QDKIHPFAQT QSLVYPFPGP IPNSLPQNIP PLTQTPVVVP PFLQPEVMGV SKVKEAMAPK    120
QKEMPFPKYP VEPFTESQSL TLTDVENLHL PLPLLQSWMH QHQPLPPTV MFPPQSVLSL     180
SQSKVLPVPQ KAVPYPQRDM PIQAFLLYQE PVLGPVRGPF PIIV                    224

SEQ ID NO: 496           moltype = AA  length = 224
FEATURE                  Location/Qualifiers
source                   1..224
                         mol_type = protein
                         organism = Bos taurus
```

```
SEQUENCE: 496
MKVLILACLV ALALARELEE LNVPGEIVES LSSSEESITR INKKIEKFQS EEQQQTEDEL    60
QDKIHPFAQT QSLVYPFPGP IHNSLPQNIP PLTQTPVVVP PFLQPEVMGV SKVKEAMAPK   120
HKEMPFPKYP VEPFTESQSL TLTDVENLHL PLPLLQSWMH QPHQPLPPTV MFPPQSVLSL   180
SQSKVLPVPQ KAVPYPQRDM PIQAFLLYQE PVLGPVRGPF PIIV                    224

SEQ ID NO: 497            moltype = AA  length = 209
FEATURE                   Location/Qualifiers
source                    1..209
                          mol_type = protein
                          organism = Bos taurus
SEQUENCE: 497
RELEELNVPG EIVESLSSSE ESITRINKKI EKFQSEEQQQ TEDELQDKIH PFAQTQSLVY    60
PFPGPIHNSL PQNIPPLTQT PVVVPPFLQP EVMGVSKVKE AMAPKHKEMP FPKYPVEPFT   120
ESQSLTLTDV ENLHLPLPLL QSWMHQPHQP LPPTVMFPPQ SVLSLSQSKV LPVPQKAVPY   180
PQRDMPIQAF LLYQEPVLGP VRGPFPIIV                                     209

SEQ ID NO: 498            moltype = AA  length = 224
FEATURE                   Location/Qualifiers
source                    1..224
                          mol_type = protein
                          organism = Bos taurus
SEQUENCE: 498
MKVLILACLV ALALARELEE LNVPGEIVES LSSSEESITR INKKIEKFQS EEQQQTEDEL    60
QDKIHPFAQT QSLVYPFPGP IPNSLPQNIP PLTQTPVVVP PFLQPEVMGV SKVKGAMAPK   120
HKEMPFPKYP VEPLTESQSL TLTDVENLHL PLPLLQSWMH QPHQPLPPTV MFPPQSVLSL   180
SQSKVLPVPQ KAVPYPQRDM PIQAFLLYQE PVLGPVRGPF PIIV                    224

SEQ ID NO: 499            moltype = AA  length = 224
FEATURE                   Location/Qualifiers
source                    1..224
                          mol_type = protein
                          organism = Bos taurus
SEQUENCE: 499
MKVLILACLV ALALARELEE LNVPGEIVES LSSSEESITR INKKIEKFQS EEQQQTEDEL    60
QDKIHPFAQT QSLVYPFPGP IHNSLPQNIP PLTQTPVVVP PFLQPEVMGV SKVKEAMAPK   120
HKEMPFPKYP VEPFTERQSL TLTDVENLHL PLPLLQSWMH QPHQPLPPTV MFPPQSVLSL   180
SQSKVLPVPQ KAVPYPQRDM PIQAFLLYQE PVLGPVRGPF PIIV                    224

SEQ ID NO: 500            moltype = AA  length = 259
FEATURE                   Location/Qualifiers
source                    1..259
                          mol_type = protein
                          organism = Bos taurus
SEQUENCE: 500
MPLNTIYKQP QNQIIIHSAP PSLLVLYFGK KELRAMKVLI LACLVALALA RELEELNVPG    60
EIVESLSSSE ESITRINKKI EKFQSEEQQQ TEDELQDKIH PFAQTQSLVY PFPGPIHNSL   120
PQNIPPLTQT PVVVPPFLQP EVMGVSKVKE AMAPKHKEMP FPKYPVEPFT ERQSLTLTDV   180
ENLHLPLPLL QSWMHQPHQP LPPTVMFPPQ SVLSLSQSKV LPVPQKAVPY PQRDMPIQAF   240
LLYQEPVLGP VRGPFPIIV                                                259

SEQ ID NO: 501            moltype = AA  length = 224
FEATURE                   Location/Qualifiers
source                    1..224
                          mol_type = protein
                          organism = Bos taurus
SEQUENCE: 501
MKVLILACLV ALALARELEE LNVPGEIVES LSSSEESITR INKKIEKFQS EEQQQTEDEL    60
QDKIHPFAQT QSLVYPFPGP IPNSLPQNIP PLTQTPVVVP PFLQPEVLGV SKVKEAMAPK   120
HKEMPFPKYP VEPFTESQSL TLTDVENLHL PPLLLQSWMH QPHQPLPPTV MFPPQSVLSL   180
SQSKVLPVPQ KAVPYPQRDM PIQAFLLYQQ PVLGPVRGPF PIIV                    224

SEQ ID NO: 502            moltype = AA  length = 216
FEATURE                   Location/Qualifiers
source                    1..216
                          mol_type = protein
                          organism = Bos taurus
SEQUENCE: 502
MKVLILACLV ALALARELEE LNVPGEIVES LSSSEKIEKF QSEEQQQTED ELQDKIHPFA    60
QTQSLVYPFP GPIHNSLPQN IPPLTQTPVV VPPFLQPEVM GVSKVKEAMA PKHKEMPFPK   120
YPVEPFTERQ SLTLTDVENL HLPLPLLQSW MHQPHQPLPP TVMFPPQSVL SLSQSKVLPV   180
PQKAVPYPQR DMPIQAFLLY QEPVLGPVRG PFPIIV                             216

SEQ ID NO: 503            moltype = AA  length = 166
FEATURE                   Location/Qualifiers
source                    1..166
                          mol_type = protein
                          organism = Bos taurus
SEQUENCE: 503
```

```
DELQDKIHPF AQTQSLVYPF PGPIPNSLPQ NIPPLTQTPV VVPPFLQPEV MGVSKVKEAM    60
APKHKEMPFP KYPVEPFTES QSLTLTDVEN LHLPLPLLQS WMHQPHQPLP PTVMFPPQSV   120
LSLSQSKVLP VPQKAVPYPQ RDMPIQAFLL YQEPALGPVR GPFPII                 166

SEQ ID NO: 504          moltype = AA  length = 165
FEATURE                 Location/Qualifiers
source                  1..165
                        mol_type = protein
                        organism = Bos taurus
SEQUENCE: 504
DELQDKIPPL PEQSLVYPFP GPIHNSLPQN IPPLTQTPVV VPPFLQPEVM GVSRVKEAMA    60
PKHKEMPFPK YPVEPFTESQ SLTLTDVENL HLPLPLLQSW MHQPHQPLPP TVMFPPQSVL   120
SLSQSKVLPV PQKAVPYPQR DMPIQAFLLY QEPVLGPVRG PFPII                  165

SEQ ID NO: 505          moltype = AA  length = 149
FEATURE                 Location/Qualifiers
source                  1..149
                        mol_type = protein
                        organism = Bos taurus
SEQUENCE: 505
DELQDKIHPF AQTQSLVYPF PGPIPNSLPQ NIPPLTQTPV VVPPFLQPEV MGVSKVKEAM    60
APKHKEMPFP KYPVEPFTES QSLTLTDVEN LHLPLPLLQS WMHQPHQPLP PTVMFPPQSV   120
LSLSQSKVLP VPQKAVPYPQ RDMPIQAFL                                    149

SEQ ID NO: 506          moltype = AA  length = 149
FEATURE                 Location/Qualifiers
source                  1..149
                        mol_type = protein
                        organism = Bos taurus
SEQUENCE: 506
DELQDKIHPF AQTQSLVYPF PGPIHNSLPQ NIPPLTQTPV VVPPFLQPEV MGVSKVKEAM    60
APKHKEMPFP KYPVEPFTES QSLTLTDVEN LHLPLPLLQS WMHQPHQPLP PTVMFPPQSV   120
LSLSQSKVLP VPQKAVPYPQ RDMPIQAFL                                    149

SEQ ID NO: 507          moltype = AA  length = 146
FEATURE                 Location/Qualifiers
source                  1..146
                        mol_type = protein
                        organism = Bos taurus
SEQUENCE: 507
KIHPFAQTQS LVYPFPGPIH NSLPQNIPPL TQTPVVVPPF LQPEVMGVSK VKEAMAPKHK    60
EMPFPKYPVE PFTERQSLTL TDVENLHLPL PLLQSWMHQP HQPLPPTVMF PPQSVLSLSQ   120
SKVLPVPQKA VPYPQRDMPI QAFLLV                                       146

SEQ ID NO: 508          moltype = AA  length = 222
FEATURE                 Location/Qualifiers
source                  1..222
                        mol_type = protein
                        organism = Capra hircus
SEQUENCE: 508
MKVLILACLV ALAIAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
SQPKVLPVPQ KAVPQRDMPI QAFLLYQEPV LGPVRGPFPI LV                     222

SEQ ID NO: 509          moltype = AA  length = 222
FEATURE                 Location/Qualifiers
source                  1..222
                        mol_type = protein
                        organism = Capra hircus
SEQUENCE: 509
MKVLILACLV ALAIAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
SQPKVLPVPQ KVVPQRDMPI QAFLLYQEPV LGPVRGPFPI LV                     222

SEQ ID NO: 510          moltype = AA  length = 222
FEATURE                 Location/Qualifiers
source                  1..222
                        mol_type = protein
                        organism = Capra hircus
SEQUENCE: 510
MKVLILACLV ALALAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
SQPKVLPVPQ KAVPQRDMPI QAFLLYQEPV LGPVRGPFPI LV                     222

SEQ ID NO: 511          moltype = AA  length = 223
FEATURE                 Location/Qualifiers
```

```
source                  1..223
                        mol_type = protein
                        organism = Capra hircus
SEQUENCE: 511
MKVLILACLV ALAIAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
SQPKVLPVPQ KVVPQRDMPI QAFLLYQEPV LGPVRGPFPI LVV                    223

SEQ ID NO: 512          moltype = AA  length = 257
FEATURE                 Location/Qualifiers
source                  1..257
                        mol_type = protein
                        organism = Capra hircus
SEQUENCE: 512
MPLNTIYKQP LNQIIIHSAS PSLLLLYFGK KESRAMKVLI LACLVALAIA REQEELNVVG    60
ETVESLSSSE ESITHINKKI EKFQSEEQQQ TEDELQDKIH PFAQAQSLVY PFTGPIPNSL   120
PQNILPLTQT PVVVPPFLQP EIMGVPKVKE TMVPKHKEMP FPKYPVEPFT ESQSLTLTDV   180
EKLHLPLPLV QSWMHQPPQP LSPTVMFPPQ SVLSLSQPKV LPVPQKVVPQ RDMPIQAFLL   240
YQEPVLGPVR GPFPILV                                                 257

SEQ ID NO: 513          moltype = AA  length = 222
FEATURE                 Location/Qualifiers
source                  1..222
                        mol_type = protein
                        organism = Capra hircus
SEQUENCE: 513
MKVLILACLV ALAIAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
SQPKVLPVPQ KVVPQRDMPI QAFLLYQEPV LGPVRGPFPI LN                     222

SEQ ID NO: 514          moltype = AA  length = 257
FEATURE                 Location/Qualifiers
source                  1..257
                        mol_type = protein
                        organism = Capra hircus
SEQUENCE: 514
MPLNTIYKQP LNQIIIHSAS PSLLLLYFGK KESRAMKVLI LACLVALAIA REQEELNVVG    60
ETVESLSSSE ESITHINKKI EKFQSEEQQQ TEDELQDKIH PFAQAQSLVY PFTGPIPNSL   120
PQNILPLTQT PVVVPPFLQP EIMGVPKVKE TMVPKHKEMP FPKYPVEPFT ESQSLTLTDV   180
EKLHLPLPLV QSWMHQPPQP LSPTVMFPPQ SVLSLSQPKV LPVPQKVVPQ RDMPIQAFLL   240
YQEPVLGPVR GPFPILN                                                 257

SEQ ID NO: 515          moltype = AA  length = 222
FEATURE                 Location/Qualifiers
source                  1..222
                        mol_type = protein
                        organism = Capra hircus
SEQUENCE: 515
MKVLILACLV ALDIAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
SQPKVLPVPQ KVVPQRDMPI QAFLLYQEPV LGPVRGPFPI LN                     222

SEQ ID NO: 516          moltype = AA  length = 160
FEATURE                 Location/Qualifiers
source                  1..160
                        mol_type = protein
                        organism = Capra hircus
SEQUENCE: 516
DELQDKIHPF AQAQSLVYPF TGPIPNSLPQ NILPLTQTPV VVPPFLQPEI MGVPKVKETM    60
VPKHKEMPFP KYPVEPFTES QSLTLTDVEK LHLPLPLVQS WMHQPPQPLS PTVMFPPQSV   120
LSLSQPKVLP VPQKAVPQRD MPIQAFLLYQ EPVLGPVRGP                        160

SEQ ID NO: 517          moltype = AA  length = 188
FEATURE                 Location/Qualifiers
source                  1..188
                        mol_type = protein
                        organism = Capra hircus
SEQUENCE: 517
MKVLILACLV ALALAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
SQPKVLPV                                                           188

SEQ ID NO: 518          moltype = AA  length = 160
FEATURE                 Location/Qualifiers
source                  1..160
```

```
                        mol_type = protein
                        organism = Capra hircus
SEQUENCE: 518
DELQDKIHPF AQAQSLVYPF TGPIPNSLPQ NILPLTQTPV VVPPFLQPEI MGVPKVKETM    60
VPKHKEMPFP KYPVEPFTES QSLTLTDVEK LHLPLPLVQS WMHQPPQPLS PTVMFPPQSV   120
LSLSQPKVLP VPQKVVPQRD MPIQAFLLYQ EPVLGPVRGP                         160

SEQ ID NO: 519          moltype = AA   length = 181
FEATURE                 Location/Qualifiers
source                  1..181
                        mol_type = protein
                        organism = Capra hircus
SEQUENCE: 519
MKVLILACLV ALAIAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLSPTV MFPPQSVLSL   180
S                                                                  181

SEQ ID NO: 520          moltype = AA   length = 149
FEATURE                 Location/Qualifiers
source                  1..149
                        mol_type = protein
                        organism = Capra hircus
SEQUENCE: 520
QAQSLVYPFT GPIPNSLPQN ILPLTQTPVV VPPFLQPEIM GVPKVKETMV PKHKEMPFPK    60
YPVEPFTESQ SLTLTDVEKL HLPLPLVQSW MHQPPQPLSP TVMFPPQSVL SLSQPKVLPV   120
PQKAVPQRDM PIQAFLLYQE PVLGPVRGP                                    149

SEQ ID NO: 521          moltype = AA   length = 148
FEATURE                 Location/Qualifiers
source                  1..148
                        mol_type = protein
                        organism = Capra hircus
SEQUENCE: 521
DEVQDKIHPF AQAQSLVYPF TGPIPNSLPQ NILPLTQTPV VVPPFLQPEI MGVPKVKETM    60
VPKHKEMPFP KYPVEPFTES QSLTLTDVEK LHLPLPLVQS WMHQPPQPLS PTVMFPPQSV   120
LSLSQPKVLP VPQKAVPQRD MPIQAFLL                                     148

SEQ ID NO: 522          moltype = AA   length = 222
FEATURE                 Location/Qualifiers
source                  1..222
                        mol_type = protein
                        organism = Ovis aries
SEQUENCE: 522
MKVLILACLV ALALAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLPPTV MFPPQSVLSL   180
SQPKVLPVPQ KAVPQRDMPI QAFLLYQEPV LGPVRGPFPI LV                      222

SEQ ID NO: 523          moltype = AA   length = 222
FEATURE                 Location/Qualifiers
VARIANT                 7
                        note = X is any amino acid
source                  1..222
                        mol_type = protein
                        organism = Ovis aries
SEQUENCE: 523
MKVLILXCLV ALALAREQEE LNVVGETVES LSSSEESITH INKKIEKFQS EEQQQTEDEL    60
QDKIHPFAQA QSLVYPFTGP IPNSLPQNIL PLTQTPVVVP PFLQPEIMGV PKVKETMVPK   120
HKEMPFPKYP VEPFTESQSL TLTDVEKLHL PLPLVQSWMH QPPQPLPPTV MFPPQSVLSL   180
SQPKVLPVPQ KAVPQRDMPI QAFLLYQEPV LGPVRGPFPI LV                      222

SEQ ID NO: 524          moltype = AA   length = 224
FEATURE                 Location/Qualifiers
source                  1..224
                        mol_type = protein
                        organism = Bubalus bubalis
SEQUENCE: 524
MKVLILACLV ALALARELEE LNVPGEIVES LSSSEESITH INKKIEKFQS EEQQQTEDEL    60
QDKIHPFAQT QSLVYPFPGP IPNSLPQNIP PLTQTPVVVP PFLQPEIMGV SKVKEAMAPK   120
HKEMPFPKYP VEPFTESQSL TLTDVENLHL PLPLLQSWMH QPPQPLPPTV MFPPQSVLSL   180
SQSKVLPVPQ KAVPYPQRDM PIQAFLLYQE PVLGPVRGPF PIIV                    224

SEQ ID NO: 525          moltype = AA   length = 259
FEATURE                 Location/Qualifiers
source                  1..259
                        mol_type = protein
                        organism = Bubalus bubalis
SEQUENCE: 525
```

```
MPLNTIYKQP QNQIIIHSAP PSLLVLYFGK KKLRVMKVLI LACLVALALA RELEELNVPG    60
EIVESLSSSE ESITHINKKI EKFQSEEQQQ TEDELQDKIH PFAQTQSLVY PFPGPIPNSL   120
PQNIPPLTQT PVVVPPFLQP EIMGVSKVKE AMAPKHKEMP FPKYPVEPFT ESQSLTLTDV   180
ENLHLPLPLL QSWMHQPPQP LPPTVMFPPQ SVLSLSQSKV LPVPQKAVPY PQRDMPIQAF   240
LLYQEPVLGP VRGPFPIIV                                                259

SEQ ID NO: 526          moltype = AA  length = 224
FEATURE                 Location/Qualifiers
source                  1..224
                        mol_type = protein
                        organism = Bubalus bubalis
SEQUENCE: 526
MKVLILACLV ALALARELEE LNVPGEIVES LSSSEESITH INKKIEKFQS EEQQQTEDEL    60
QDKIHPFAQT QSLVYPFPGP IPNSLPQNIP PLTQTPVVVP PFLQPEIMGV SKVKEAMAPK   120
HKEMPFPKYP FEPFTESQSL TLTDVENLHL PLPLLQSWMH QPPQPLPPTV MFPPQSVLSL   180
SQSKVLPVPQ KAVPYPQRDM PIQAFLLYQE PVLGPVRGPF PIIV                    224

SEQ ID NO: 527          moltype = AA  length = 224
FEATURE                 Location/Qualifiers
source                  1..224
                        mol_type = protein
                        organism = Bubalus bubalis
SEQUENCE: 527
MKVLILACLV ALALARELEE LNVPSEIVES LSSSEESITH INKKIEKFQS EEQQQTEDEL    60
QDKIHPFAQT QSLVYPFPGP IPNSLPQNIP PLTQTPVVVP PFLQPEIMGV SKVKEAMAPK   120
HKEMPFPKYP VEPFTESQSL TLTDVENLHL PLPLLQSWMH QPPQPLPPTV MFPPQSVLSL   180
SQSKVLPVPQ KAVPYPQRDM PIQAFLLYQE PVLGPVRGPF PIIV                    224

SEQ ID NO: 528          moltype = AA  length = 224
FEATURE                 Location/Qualifiers
source                  1..224
                        mol_type = protein
                        organism = Bubalus bubalis
SEQUENCE: 528
MKVLILACLV ALALARELEE LNVPSEIVES LSSSEESITH INKKIEKFQS EEQRQTEDEL    60
QDKIHPFAQT QSLVYPFPGP IPNSLPQNIP PLTQTPVVVP PFLQPEIMGV SKVKEAMAPK   120
HKEMPFPKYP VEPFTESQSL TLTDVENLHL PLPLLQSWMH QPPQPLPPTV MFPPQSVLSL   180
SQSKVLPVPQ KAVPYPQRDM PIQAFLLYQE PVLGPVRGPF PIIV                    224

SEQ ID NO: 529          moltype = AA  length = 224
FEATURE                 Location/Qualifiers
source                  1..224
                        mol_type = protein
                        organism = Bubalus bubalis
SEQUENCE: 529
MKVLILACLV ALALARELEE LNVPGEIVES LSSSEESITH INKKIEKFQS EEQQMEDEL     60
QDKIHPFAQT QSLVYPFPGP IPKSLPQNIP PLTQTPVVVP PFLQPEIMGV SKVKEAMAPK   120
HKEMPFPKYP VEPFTESQSL TLTDVENLHL PLPLLQSWMH QPPQPLPPTV MFPPQSVLSL   180
SQSKVLPVPQ KAVPYPQRDM PIQAFLLYQE PVLGPVRGPF PIIV                    224

SEQ ID NO: 530          moltype = AA  length = 259
FEATURE                 Location/Qualifiers
source                  1..259
                        mol_type = protein
                        organism = Bubalus bubalis
SEQUENCE: 530
MPLNTIYKQP QNQIIIHSAP PSLLVLYFGK KKLRAMKVLI LACLVALALA RELEELNVPG    60
EIVESLSSSE ESITHINKKI EKFQSEEQQQ MEDELQDKIH PFAQTQSLVY PFPGPIPKSL   120
PQNIPPLTQT PVVVPPFLQP EIMGVSKVKE AMAPKHKEMP FPKYPVEPFT ESQSLTLTDV   180
ENLHLPLPLL QSWMHQPPQP LPPTVMFPPQ SVLSLSQSKV LPVPQKAVPY PQRDMPIQAF   240
LLYQEPVLGP VRGPFPIIV                                                259

SEQ ID NO: 531          moltype = AA  length = 224
FEATURE                 Location/Qualifiers
source                  1..224
                        mol_type = protein
                        organism = Bubalus bubalis
SEQUENCE: 531
MKVLILACLV ALALARELEE LNVPGEIVES LSSSEESITH INKKIEKFQS EEQQQMEDEL    60
QDKIHPFAQT QSLVYPFPGP IPKSLPQNIP PLTQTPVVVP PFLQPEIMGV SKVKEATAPK   120
HKEMPFPKYP VEPFTESQSL TLTDVENLHL PLPLLQSWMH QPPQPLPPTV MFPPQSVLSL   180
SQSKVLPVPQ KAVPYPQRDM PIQAFLLYQE PVLGPVRGPF PIIV                    224

SEQ ID NO: 532          moltype = AA  length = 209
FEATURE                 Location/Qualifiers
source                  1..209
                        mol_type = protein
                        organism = Bubalus bubalis
SEQUENCE: 532
```

```
RELEELNVPG EIVESLSSSE ESITHINKKI EKFQSEEQQQ TEDELQDKIH PFAQTQSLVY    60
PFPGPIPKSL PQNIPPLTQT PVVVPPFLQP EIMGVSKVKE AMAPKHKEMP FPKYPVQPET   120
ESQSLTLTDV ENLHLPPLLL QSWMHQPHQP LPPTVMFPPQ SVLSLSQSKV LPVPEKAVPY   180
PQRDMPIQAF LLYQEPVLGP VRGPFPIIV                                    209

SEQ ID NO: 533           moltype = AA   length = 166
FEATURE                  Location/Qualifiers
source                   1..166
                         mol_type = protein
                         organism = Bubalus bubalis
SEQUENCE: 533
DELQDKIHPF AQTQSLVYPF PGPIPNSLPQ NIPPLTQTPV VVPPFLQPEI MGVSKVKEAM    60
APKHKEMPFP KYPVEPFTES QSLTLTDVEN LHLPLPLLQS WMHQPPQPLP PTVMFPPQSV   120
LSLSQSKVLP VPQKAVPYPQ RDMPIQAFLL YQEPVLGPVR GPFPII                 166

SEQ ID NO: 534           moltype = AA   length = 166
FEATURE                  Location/Qualifiers
source                   1..166
                         mol_type = protein
                         organism = Bubalus bubalis
SEQUENCE: 534
DELQDKIHPF AQTQSLVYPF PGPIPKSLPQ NIPPLTQTPV VVPPFLQPEI MGVSKVKEAM    60
APKHKEMPFP KYPVEPFTES QSLTLTDVEN LHLPLPLLQS WMHQPPQPLP PTVMFPPQSV   120
LSLSQSKVLP VPQKAVPYPQ RDMPIQAFLL YQEPVLGPVR GPFPII                 166

SEQ ID NO: 535           moltype = AA   length = 166
FEATURE                  Location/Qualifiers
source                   1..166
                         mol_type = protein
                         organism = Bubalus bubalis
SEQUENCE: 535
DELQDKNHPF AQTQSLVYPF PGPIPKSLPQ NIPPLTQTPV VVPPFLQPEI MGVSKVKEAM    60
APKHKEMPFP KYPVEPFTES QSLTLTDVEN LHLPLPLLQS WMHQPPQPLP PTVMFPPQSV   120
LSLSQSKVLP VPQKAVPYPQ RDMPIQAFLL YQEPVLGPVR GPFPII                 166

SEQ ID NO: 536           moltype = AA   length = 165
FEATURE                  Location/Qualifiers
source                   1..165
                         mol_type = protein
                         organism = Bubalus bubalis
SEQUENCE: 536
DELQDKIPPL PEQSLVYPFP APIPKSLPQN IPPLTQTPVV VPPFLQPEIM GVSKVKEAMA    60
PKHKEMPFPK YPVEPFTESQ SLTLTDVENL HLPLPLLQSW MHQPPQPLPP TVMFPPQSVL   120
SLSQSKVLPV PQKAVPYPQR DMPIQAFLLY QEPVLGPVRG PFPII                  165

SEQ ID NO: 537           moltype = AA   length = 155
FEATURE                  Location/Qualifiers
source                   1..155
                         mol_type = protein
                         organism = Bubalus bubalis
SEQUENCE: 537
IHPFAQTQSL VYPFPGPIPN SLPQNIPPLT QTPVVPPFL QPEIMGVSKV KEAMAPKHKE    60
MPFPKYPVEP FTESQSLTLT DVENLHLPLP LLQSWMHQPP QPLPPTVMFP PQSVLSLSQS   120
KVLPVPQKAV PYPQRDMPIQ AFLLYQEPVL GPVRG                             155

SEQ ID NO: 538           moltype = AA   length = 155
FEATURE                  Location/Qualifiers
source                   1..155
                         mol_type = protein
                         organism = Bubalus bubalis
SEQUENCE: 538
IHPFAQTQSL VYPFPGPIPK SLPQNIPPLT QTPVVPPFL QPEIMGVSKV KEAMAPKHKE    60
MPFPKYPVEP FTESQSLTLT DVENLHLPLP LLQSWMHQPP QPLPPTVMFP PQSVLSLSQS   120
KVLPVPQKAV PYPQRDMPIQ AFLLYQEPVL GPVRG                             155

SEQ ID NO: 539           moltype = AA   length = 235
FEATURE                  Location/Qualifiers
source                   1..235
                         mol_type = protein
                         organism = Bos mutus
SEQUENCE: 539
MKVLILACLV ALALARELEE LNVPGEIVES LSSSEESITR INKKIEKFQS EEQQQTEDEL    60
QDKIHPFAQT QSLVYPFPGP IPNSLPQNIP PLTQTPVVVP PFLQPEVMGV SKVKEAMAPK   120
HKEMPFPKYP VEPFTESQSL TLTDVENLHL PLPLLQSWMH QPHQPLPPTV MFPPQSVLSL   180
SQSKVLPVPQ KAVPYPQRDM PIQAFLLYQE PVLGPVRGPF PIIVSLNLLT VLFNF        235

SEQ ID NO: 540           moltype = AA   length = 270
FEATURE                  Location/Qualifiers
source                   1..270
```

```
                          mol_type = protein
                          organism = Bos mutus
SEQUENCE: 540
MPLNTIYKQP QNQIIIHSAP PSLLVLYFGK KELRAMKVLI LACLVALALA RELEELNVPG    60
EIVESLSSSE ESITRINKKI EKFQSEEQQQ TEDELQDKIH PFAQTQSLVY PPPGPIPNSL   120
PQNIPPLTQT PVVVPPFLQP EVMGVSKVKE AMAPKHKEMP FPKYPVEPFT ESQSLTLTDV   180
ENLHLPLPLL QSWMHQPHQP LPPTVMFPPQ SVLSLSQSKV LPVPQKAVPY PQRDMPIQAF   240
LLYQEPVLGP VRGPFPIIVS LNLLTVLFNF                                   270

SEQ ID NO: 541            moltype = AA   length = 259
FEATURE                   Location/Qualifiers
source                    1..259
                          mol_type = protein
                          organism = Bos mutus
SEQUENCE: 541
MPLNTIYKQP QNQIIIHSAP PSLLVLYFGK KELRAMKVLI LACLVALALA RELEELNVPG    60
EIVESLSSSE ESITRINKKI EKFQSEEQQQ TEDELQDKIH PFAQTQSLVY PPPGPIPNSL   120
PQNIPPLTQT PVVVPPFLQP EVMGVSKVKE AMAPKHKEMP FPKYPVEPFT ESQSLTLTDV   180
ENLHLPLPLL QSWMHQPHQP LPPTVMFPPQ SVLSLSQSKV LPVPQKAVPY PQRDMPIQAF   240
LLYQEPVLGP VRGPFPIIV                                               259

SEQ ID NO: 542            moltype = AA   length = 216
FEATURE                   Location/Qualifiers
source                    1..216
                          mol_type = protein
                          organism = Bos mutus
SEQUENCE: 542
MKVLILACLV ALALARELEE LNVPGEIVES LSSSEKIEKF QSEEQQQTED ELQDKIHPFA    60
QTQSLVYPFP GPIPNSLPQN IPPLTQTPVV VPPFLQPEVM GVSKVKEAMA PKHKEMPFPK   120
YPVEPFTESQ SLTLTDVENL HLPLLLQSW MHQPHQPLPP TVMFPPQSVL SLSQSKVLPV    180
PQKAVPYPQR DMPIQAFLLY QEPVLGPVRG PFPIIV                             216

SEQ ID NO: 543            moltype = AA   length = 227
FEATURE                   Location/Qualifiers
source                    1..227
                          mol_type = protein
                          organism = Bos mutus
SEQUENCE: 543
MKVLILACLV ALALARELEE LNVPGEIVES LSSSEKIEKF QSEEQQQTED ELQDKIHPFA    60
QTQSLVYPFP GPIPNSLPQN IPPLTQTPVV VPPFLQPEVM GVSKVKEAMA PKHKEMPFPK   120
YPVEPFTESQ SLTLTDVENL HLPLLLQSW MHQPHQPLPP TVMFPPQSVL SLSQSKVLPV    180
PQKAVPYPQR DMPIQAFLLY QEPVLGPVRG PFPIIVSLNL LTVLFNF                 227

SEQ ID NO: 544            moltype = AA   length = 224
FEATURE                   Location/Qualifiers
VARIANT                   197
                          note = X is any amino acid
source                    1..224
                          mol_type = protein
                          organism = Bos indicus
SEQUENCE: 544
MKVLILACLV ALALARELEE LNVPGEIVES LSSSEESITR INKKIEKFQS EEQQQTEDEL    60
QDKIHPFAQT QSLVYPFPGP IPNSLPQNIP PLTQTPVVVP PFLQPEVMGV SKVKEAMAPK   120
HKEMPFPKYP VEPFTESQSL TLTDVENLHL PLPLLQSWMH QPHQPLPPTV MFPPQSVLSL   180
SQSKVLPVPQ KAVPYPXRDM PIQAFLLYQE PVLGPVRGPF PIIV                    224

SEQ ID NO: 545            moltype = AA   length = 224
FEATURE                   Location/Qualifiers
VARIANT                   197
                          note = X is any amino acid
source                    1..224
                          mol_type = protein
                          organism = Bos indicus
SEQUENCE: 545
MKVLILACLV ALALARELEE LNVPGEIVES LSSSEESITR INKKIEKFQS EEQQQTEDEL    60
QDKIHPFAQT QSLVYPFPGP IHNSLPQNIP PLTQTPVVVP PFLQPEVMGV SKVKEAMAPK   120
HKEMPFPKYP VEPFTESQSL TLTDVENLHL PLPLLQSWMH QPHQPLPPTV MFPPQSVLSL   180
SQSKVLPVPQ KAVPYPXRDM PIQAFLLYQE PVLGPVRGPF PIIV                    224

SEQ ID NO: 546            moltype = AA   length = 165
FEATURE                   Location/Qualifiers
source                    1..165
                          mol_type = protein
                          organism = Bos indicus
SEQUENCE: 546
DELQDKIPPL PEQSLVYPFP GPIPNSLPQN IPPLTQTPVV VPPFLQPEVM GVSKVKEAMA    60
PKHKEMPFPK YPVEPFTESQ SLTLTDVENL HLPLPLLQSW MHQPHQPLPP TVMFPPQSVL   120
SLSQSKVLPV PQKAVPYPQR DMPIQAFLLY QEPVLGPVRG PFPII                   165
```

```
SEQ ID NO: 547            moltype = AA   length = 155
FEATURE                   Location/Qualifiers
source                    1..155
                          mol_type = protein
                          organism = Bos indicus
SEQUENCE: 547
IHPFAQTQSL VYPFPGPIPN SLPQNIPPLT QTPVVPPFL QPEVMGVSKV KEAMAPKHKE    60
MPFPKYPVEP FTESQSLTLT DVENLHLPLP LLQSWMHQPH QPLPPTVMFP PQSVLSLSQS  120
KVLPVPQKAV PYPQRDMPIQ AFLLYQEPVL GPVRG                             155

SEQ ID NO: 548            moltype = AA   length = 152
FEATURE                   Location/Qualifiers
source                    1..152
                          mol_type = protein
                          organism = Bos indicus
SEQUENCE: 548
QSLVYPFPGP IPNSLPQNIP PLTQTPVVVP PFLQPEVMGV SKVKEAMAPK HKEMPFPKYP   60
VEPFTESQSL TLTDVENLHL PLPLLQSWMH QPHQPLPPTV MFPPQSVLSL SQSKVLPVPQ  120
KAVPYPQRDM PIQAFLLYQE PVLGPVRGPF PI                                152

SEQ ID NO: 549            moltype = AA   length = 154
FEATURE                   Location/Qualifiers
source                    1..154
                          mol_type = protein
                          organism = Bos indicus
SEQUENCE: 549
LPDQSLVYPF PGPIPNSLPQ NIPPLTQTPV VVPPFLQPEV MGVSKVKEAM APKHKEMPFP   60
KYPVEPFTES QSLTLTDVEN LHLPLPLLQS WMHQPHQPLP PTVMFPPQSV LSLSQSKVLP  120
VPQKAVPYPQ RDMPIQAFLL YQEPVLGPVR GPFP                              154

SEQ ID NO: 550            moltype = AA   length = 224
FEATURE                   Location/Qualifiers
source                    1..224
                          mol_type = protein
                          organism = Bison bison
SEQUENCE: 550
MKVLILACLV ALALARELEE LNVPGEIVES LSSSEESITR INKKIEKFQS EEQQQTEDEL   60
QDKIHPFAQT QSLVYPFPGP IPNSLPQNIP PLTQTPVVVP PFLQPEVMGV SKVKEAMAPK  120
HKEMPFPKYP VEPFTESQSL TLTDVENLHL PLPLLQSWMH QPHQPLPPTV MFPPQSVLSL  180
SQSKVLPVPQ KAVPYPQRDM PIQAFLLYQE PVLGPVRGPF PIIV                   224

SEQ ID NO: 551            moltype = AA   length = 177
FEATURE                   Location/Qualifiers
source                    1..177
                          mol_type = protein
                          organism = Jeotgalicoccus aerolatus
SEQUENCE: 551
FQSEEQQQTE DELQDKIHPF AQTQSLVYPF PGPIPNSLPQ NIPPLTQTPV VVPPFLQPEV   60
MGVSKVKEAM APKHKEMPFP KYPVEPFTES QSLTLTDVEN LHLPLPLLQS WMHQPHQPLP  120
PTVMFPPQSV LSLSQSKVLP VPQKAVPYPQ RDMPIQAFLL YQEPVLGPVR GPFPIIV     177

SEQ ID NO: 552            moltype = AA   length = 240
FEATURE                   Location/Qualifiers
source                    1..240
                          mol_type = protein
                          organism = Jeotgalicoccus coquinae
SEQUENCE: 552
PPSLLVLYFG KKELRAMKVL ILACLVALAL ARELEELNVP GEIVESLSSS EESITRINKK   60
IEKFQSEEQQ QTEDELQDKI HPFAQTQSLV YPFPGPIPNS LPQNIPPLTQ TPVVVPPFLQ  120
PEVMGVSKVK EAMAPKHKEM PFPKYPVEPF TESQSLTLTD VENLHLPLPL LQSWMHQPHQ  180
PLPPTVMFPP QSVLSLSQSK VLPVPQKAVP YPQRDMPIQA FLLYQEPVLG PVRGPFPIIV  240

SEQ ID NO: 553            moltype = AA   length = 224
FEATURE                   Location/Qualifiers
REGION                    1..224
                          note = Bos indicus x Bos taurus
source                    1..224
                          mol_type = protein
                          organism = unidentified
SEQUENCE: 553
MKVLILACLV ALALARELEE LNVPGEIVES LSSSEESITR INKKIEKFQS EEQQQTEDEL   60
QEKIHPFAQT QSLVYPFPGP IPNSLPQNIP PLTQTPVVVP PFLQPEVMGV SKVKEAMAPK  120
HKEMPFPKYP VEPFTESQSL TLTDVENLHL PLPLLQSWMH QPHQPLPPTV MFPPQSVLSL  180
SQSKVLPVPQ KAVPYPQRDM PIQAFLLYQE PVLGPVRGPF PIIV                   224

SEQ ID NO: 554            moltype = AA   length = 153
FEATURE                   Location/Qualifiers
REGION                    1..153
                          note = Bos indicus x Bos taurus
```

```
source                          1..153
                                mol_type = protein
                                organism = unidentified
SEQUENCE: 554
QSLVYPFPGP IPNSLPQNIP PLTQTPVVVP PFLQPEVMGV SKVKEAMAPK HKEMPFPKYP    60
VEPFTESQSL TLTDVENLHL PLPLLQSWMH QPHQPLPPTV MFPPQSVLSL SQSKVLPVPQ   120
KAVPYPQRDM PIQAFLLYQE PVLGPVRGPF PIL                                153

SEQ ID NO: 555                  moltype = AA   length = 150
FEATURE                         Location/Qualifiers
REGION                          1..150
                                note = Bos indicus x Bos taurus
source                          1..150
                                mol_type = protein
                                organism = unidentified
SEQUENCE: 555
DEVQDKIHPF AQTQSLVYPF PGPIPNSLPQ NIPPLTQTPV VVPPFLQPEV MGVSKVKEAM    60
APKHKEMPFP KYPVEPFTES QSLTLTDVEN LHLPLPLLQS WMHQPHQPLP PTVMFPPQSV   120
LSLSQSKVLP VPQKAVPYPQ RDMPIQAFLL                                    150

SEQ ID NO: 556                  moltype = AA   length = 259
FEATURE                         Location/Qualifiers
source                          1..259
                                mol_type = protein
                                organism = Bos grunniens
SEQUENCE: 556
MPLNTIYKQP QNQIIIHSAP PSLLVLYFGK KELGAMKVLI LACLVALALA RELEELNVPG    60
EIVEGLSSSE ESITRINKKI EKFQSEEQQQ TEDGLQDKIH PFAQTQSLVY PFPGPIPNSL   120
PQNIPPLTQT PVVVPPFLQP EVMGVSKVKE AMAPKHKEMP FPKYPVEPFT ESQSLTLTDV   180
ENLHLPLPLL QSWMHQPHQP LPPTVMFPPQ SVLSLSQSKV LPVPQKAVPY PQRDMPIQAF   240
LLYQEPVLGP VRGPFPIIV                                                259

SEQ ID NO: 557                  moltype = AA   length = 166
FEATURE                         Location/Qualifiers
source                          1..166
                                mol_type = protein
                                organism = Bos grunniens
SEQUENCE: 557
DELQDKIHPF AQTQSLVYPF PGPIPNSLPQ NIPPLTQTPV VVPPFLQPEV MGVSKVKEAM    60
APKHKEMPFP KYPVEPFTES QSLTLTDVEN LHLPLPLLQS WMHQPHQPLP PTVMFPPQSV   120
LSLSQSKVLP VPQKAVPYPQ RDMPIQAFLL YQEPVLGPVR GPFPII                  166

SEQ ID NO: 558                  moltype = AA   length = 166
FEATURE                         Location/Qualifiers
source                          1..166
                                mol_type = protein
                                organism = Bos grunniens
SEQUENCE: 558
DELQDKIHPF AQTQSLVYPF PGPIPNSLPQ NIPPLTQTPV VVPPFLQPEV MGVSKVKEAM    60
APKHEEMPFP KYPVEPFTES QSLTLTDVEN LHLPLPLLQS WMHQPHQPLP PTVMFPPQSV   120
LSLSQSKVLP VPQKAVPYPQ RDMPIQAFLL YQEPVLGPVR GPFPII                  166

SEQ ID NO: 559                  moltype = AA   length = 155
FEATURE                         Location/Qualifiers
source                          1..155
                                mol_type = protein
                                organism = Bos grunniens
SEQUENCE: 559
QSLVYPFPGP IPNSLPQNIP PLTQTPVVVP PFLQPEVMGV SKVKEAMAPK HKEMPFPKYP    60
VEPFTESQSL TLTDVENLHL PLPLLQSWMH QPHQPLPPTV MFPPQSVLSL SQSKVLPVPQ   120
KAVPYPQRDM PIQAFLLYQE PVLGPVRGPF PIFVS                              155

SEQ ID NO: 560                  moltype = AA   length = 224
FEATURE                         Location/Qualifiers
source                          1..224
                                mol_type = protein
                                organism = Neophocaena asiaeorientalis
SEQUENCE: 560
MKVLILACLL ALALAREKEE LIVSGETVKS LSSSEESVTH INEKIEKFKH EEQQQTEDER    60
QDRIHHFSQP QPLVYSYTGP IPYPILPKNI LPLAQPPVVV PFQPEIMEV PKAKETILPK    120
HKEMRFPKSP VEPFIESQSL TLTDLENLHL PLPLLQSLMH QPPHRLPPTL MFPPQPLQSL   180
SQSKVLPIPQ QVVPYLQRDM PIQTLLLYQE PVLGPIQGLY PVIV                    224

SEQ ID NO: 561                  moltype = AA   length = 258
FEATURE                         Location/Qualifiers
source                          1..258
                                mol_type = protein
                                organism = Odocoileus virginianus
SEQUENCE: 561
```

```
MPLNTIYKQP QNQIIIHSGS PSLLVLYVGK EELRAMKVLI LACLVALALA KEEELNVSSE     60
IVESISSSEE SITHITKKIE KLQSEGQQQA EDELQDKIHP FAQTQSLVYP FTGPIPYSLP    120
QNFLPLPQTP VMVPPFLQPE IMGVSEVKET MVPKHKEMPF PKYPVEPFAE GQSLTLTEAE    180
NLHFPLPLPQ SWMHQTPQPL PPAVMFPPQS VLSLSQPKVL SVPQKAVPYP QRDMPIQAFL    240
LYQEPVPGPV RGPFPFIV                                                 258

SEQ ID NO: 562            moltype = AA  length = 222
FEATURE                   Location/Qualifiers
source                    1..222
                          mol_type = protein
                          organism = Muntiacus reevesi
SEQUENCE: 562
MKVLILACLV ALALAREEEL NVSGERLSSS SKAESITHIT KKIEKLQSEG QQQTEAELQD     60
KIHPFAQTQP LVYPFTGPIP YSLPQNFLPL PQTPMVVPPF LQPEIMGVSE VKETMVPKHK    120
EMPFPKYPVE PFAEGQSLTL TDVENLHLPL PVLQPWMHQT PQPLPPTVMF PPQSVLSLSQ    180
PKVLSVPQKA VPYPQREMPI QAFLLYQEPV PGPVPGPFPI IV                      222

SEQ ID NO: 563            moltype = AA  length = 230
FEATURE                   Location/Qualifiers
source                    1..230
                          mol_type = protein
                          organism = Muntiacus muntjak
SEQUENCE: 563
MKVLILACLV ALALAREEEL NVSGESRTLL KRLSSSSSSK AESITHITKK IEKLPSEGQQ     60
QTEAELQDKI HPFAQTQPLV YPFTGPIPYS LPQNFLPLPQ TPMVVPPFLQ PEIMGVSEVK    120
ETMVPKHKEM PFPKYPVEPF AEGQSLTLTD VENLHLPLPV LQPWMHQTPQ PLPPTVMFPP    180
QSVLSLSQPK VLSVPQKAVP YPQREMPIQA FLLYQEPVPG PVPGPFPIIV               230

SEQ ID NO: 564            moltype = AA  length = 163
FEATURE                   Location/Qualifiers
source                    1..163
                          mol_type = protein
                          organism = Bos taurus
SEQUENCE: 564
MLIVTQTMKG LDIQKVAGTW YSLAMAASDI SLLDAQSAPL RVYVEELKPT PEGDLEILLQ     60
KWENGECAQK KIIAEKTKIP AVFKIDALNE NKVLVLDTDY KKYLLFCMEN SAEPEQSLAC    120
QCLVRTPEVD DEALEKFDKA LKALPMHIRL SFNPTQLEEQ CHI                     163

SEQ ID NO: 565            moltype = AA  length = 162
FEATURE                   Location/Qualifiers
source                    1..162
                          mol_type = protein
                          organism = Bos taurus
SEQUENCE: 565
LIVTQTMKGL DIQKVAGTWY SLAMAASDIS LLDAQSAPLR VYVEELKPTP EGDLEILLQK     60
WENGECAQKK IIAEKTKIPA VFKIDALNEN KVLVLDTDYK KYLLFCMENS AEPEQSLACQ    120
CLVRTPEVDD EALEKFDKAL KALPMHIRLS FNPTQLEEQC HI                      162

SEQ ID NO: 566            moltype = AA  length = 178
FEATURE                   Location/Qualifiers
source                    1..178
                          mol_type = protein
                          organism = Bos taurus
SEQUENCE: 566
MKCLLLALAL TCGAQALIVT QTMKGLDIQK VAGTWYSLAM AASDISLLDA QSAPLRVYVE     60
ELKPTPEGDL EILLQKWENG ECAQKKIIAE KTKIPAVFKI DALNENKVLV LDTDYKKYLL    120
FCMENSAEPE QSLACQCLVR TPEVDDEALE KFDKALKALP MHIRLSFNPT QLEEQCHI     178

SEQ ID NO: 567            moltype = AA  length = 161
FEATURE                   Location/Qualifiers
source                    1..161
                          mol_type = protein
                          organism = Bos taurus
SEQUENCE: 567
IVTQTMKGLD IQKVAGTWYS LAMAASDISL LDAQSAPLRV YVEELKPTPE GDLEILLQKW     60
ENGECAQKKI IAEKTKIPAV FKIDALNENK VLVLDTDYKK YLLFCMENSA EPEQSLACQC    120
LVRTPEVDDE ALEKFDKALK ALPMHIRLSF NPTQLEEQCH I                       161

SEQ ID NO: 568            moltype = AA  length = 162
FEATURE                   Location/Qualifiers
source                    1..162
                          mol_type = protein
                          organism = Bos taurus
SEQUENCE: 568
LIVTQTMKGL DIQKVAGTWY SLAMAASDIS LLDAQSAPLR VYVEELKPTP EGDLEILLQK     60
WENGECAQKK IIAEKTKIPA VFKIDALNEN KVLVLDTDYK KYLLFCMENS AEPEQSLVCQ    120
CLVRTPEVDD EALEKFDKAL KALPMHIRLS FNPTQLEEQC HI                      162

SEQ ID NO: 569            moltype = AA  length = 162
```

```
FEATURE                 Location/Qualifiers
source                  1..162
                        mol_type = protein
                        organism = Bos taurus
SEQUENCE: 569
LIVTQTMKGL DIQKVAGTWY SLAMAASDIS LLDAQSAPLR VYVEELKPTP EGDLEFLLQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HI                      162

SEQ ID NO: 570          moltype = AA   length = 162
FEATURE                 Location/Qualifiers
source                  1..162
                        mol_type = protein
                        organism = Bos taurus
SEQUENCE: 570
LIVTQTMKGL DIQKVAGTWY SLAMAASDIS LLDAQSAPYR VYVEELKPTP EGDLEILLQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HI                      162

SEQ ID NO: 571          moltype = AA   length = 178
FEATURE                 Location/Qualifiers
source                  1..178
                        mol_type = protein
                        organism = Bos taurus
SEQUENCE: 571
MKCLLLALAL TCGAQALIVT QTMKGLDIQK VAGTWYSLAM AASDISLLDA QSAPLRVYVE    60
ELKPTPEGDL EILLQKWENG ECAQKKIIAE KTKIPAVFKI DALNENKVLV LDTDYKKYLL   120
FCMENSAEPE QSLVCQCLVR TPEVDDEALE KFDKALKALP MHIRLSFNPT QLEEQCHI    178

SEQ ID NO: 572          moltype = AA   length = 162
FEATURE                 Location/Qualifiers
source                  1..162
                        mol_type = protein
                        organism = Bos taurus
SEQUENCE: 572
ASVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HI                      162

SEQ ID NO: 573          moltype = AA   length = 162
FEATURE                 Location/Qualifiers
source                  1..162
                        mol_type = protein
                        organism = Bos taurus
SEQUENCE: 573
ASVTQTMKGL DIQKVAGTWY SLAMAASDIS LLDAQSAPLR VYVEELKPTP EGDLEILFQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HI                      162

SEQ ID NO: 574          moltype = AA   length = 162
FEATURE                 Location/Qualifiers
source                  1..162
                        mol_type = protein
                        organism = Bos taurus
SEQUENCE: 574
ASVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLFCLENS AEPEQSLACQ   120
CLVRTPEVDD EALEKFDKAL KALPMHIRLS FNPTQLEEQC HI                      162

SEQ ID NO: 575          moltype = AA   length = 162
FEATURE                 Location/Qualifiers
source                  1..162
                        mol_type = protein
                        organism = Bos taurus
SEQUENCE: 575
LIVTQTMKGL DIQKVAGTWY SLAMAASDIS LLDAQSAPLR VYVEELKPTP EGDLEILLQK    60
WENDECAQKK IIAEKTKIPA VFKIDALNEN KVLVLDTDYK KYLLFCMENS AEPEQSLVCQ   120
CLVRTPEVDD EALEKFDKAL KALPMHIRLS FNPTQLEEQC HI                      162

SEQ ID NO: 576          moltype = AA   length = 162
FEATURE                 Location/Qualifiers
source                  1..162
                        mol_type = protein
                        organism = Bos taurus
SEQUENCE: 576
ASVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLLCMENS AEPEQSLACQ   120
CLVRTPEVDD EALEKFDKAL KALPMHIRLS FNPTQLEEQC HI                      162
```

```
SEQ ID NO: 577            moltype = AA  length = 178
FEATURE                   Location/Qualifiers
source                    1..178
                          mol_type = protein
                          organism = Bos taurus
SEQUENCE: 577
MKCLLLALAL TCGAQALIVT QTMKGLDIQK VAGTWYSLAM AASDISLLDA QSAPLRVYVE     60
ELKPTPEGDL EILLQKWEND ECAQKKIIAE KTKIPAVFKI DALNENKVLV LDTDYKKYLL    120
FCMENSAEPE QSLVCQCLVR TPEVDDEALE KFDKALKALP MHIRLSFNPT QLEEQCHI     178

SEQ ID NO: 578            moltype = AA  length = 162
FEATURE                   Location/Qualifiers
source                    1..162
                          mol_type = protein
                          organism = Bos taurus
SEQUENCE: 578
ASVTQTMKGL DIQKVAGTWY SLAMAASDIS LLDAQSAPAR VYVEELKPTP EGDLEFLLQK     60
WENGECAQKK IIAEKTKIPA VFKIDALNEN KVLVLDTDYK KYLLFCMENS AEPEQSLACQ    120
CLVRTPEVDD EALEKFDKAL KALPMHIRLS FNPTQLEEQC HI                      162

SEQ ID NO: 579            moltype = AA  length = 162
FEATURE                   Location/Qualifiers
source                    1..162
                          mol_type = protein
                          organism = Bos taurus
SEQUENCE: 579
ASVTQTMKGL DIQKVAGTWY SLAMAASDIS LLDAQSAPAR VYVEELKPTP EGDLEILLQK     60
WENGECAQKK IIAEKTKIPA VFKIDALNEN KVLVLDTDYK KYLLLCMENS AEPEQSLACQ    120
CLVRTPEVDD EALEKFDKAL KALPMHIRLS FNPTQLEEQC HI                      162

SEQ ID NO: 580            moltype = AA  length = 162
FEATURE                   Location/Qualifiers
source                    1..162
                          mol_type = protein
                          organism = Bos taurus
SEQUENCE: 580
LIVTQTMKGL DIQKVAGTWY SLAMAASDIS LLDAQSAPLR VYVEELKPTP EGDLEILLQK     60
WENDECAQKK IIAEKTKIPA VFKIDALNEN KVLVLDTDYK KYLLFCMENS AEPEQSLVCQ    120
SLVRTPEVDD EALEKFDKAL KALPMHIRLS FNPTQLEEQC HI                      162

SEQ ID NO: 581            moltype = AA  length = 178
FEATURE                   Location/Qualifiers
source                    1..178
                          mol_type = protein
                          organism = Bos taurus
SEQUENCE: 581
MKCLLLALAL TCGAQALIVT QTMKGLDIQK VAGTWYSLAM AASDISLLDA QSAPLRVYVE     60
ELKPTPEGDL EILLQKWEND ECAQKKIIAE KTKIPAVFKI DALNENKVLV LDTDYKKYLL    120
VCMENSAEPE QSLVCQCLVR TPEVDDEALE KFDKALKALP MHIRLSFNPT QLEEQCHI     178

SEQ ID NO: 582            moltype = AA  length = 163
FEATURE                   Location/Qualifiers
source                    1..163
                          mol_type = protein
                          organism = Bos taurus
SEQUENCE: 582
AAYVTQTMKG LDIQKVAGTW YSLAMAASDI SLLDAQSAPL RVYVEELKPT PEGDLEILLQ     60
KWENDECAQK KIIAEKTKIP AVFKIDALNE NKVLVLDTDY KKYLLFCMEN SAEPEQSLVC    120
QCLVRTPEVD DEALEKFDKA LKALPMHIRL SFNPTQLEEQ CHI                     163

SEQ ID NO: 583            moltype = AA  length = 162
FEATURE                   Location/Qualifiers
source                    1..162
                          mol_type = protein
                          organism = Bos taurus
SEQUENCE: 583
ASVTQTMKGL DIQKVAGTWY SLAMAASDIS LLDAQSAPAR VYVEELKPTP EGDLEFLLQK     60
WENGECAQKK IIAEKTKIPA VFKIDALNEN KVLVLDTDYK KYLLFCFENS AEPEQSLACQ    120
CLVRTPEVDD EALEKFDKAL KALPMHIRLS FNPTQLEEQC HI                      162

SEQ ID NO: 584            moltype = AA  length = 162
FEATURE                   Location/Qualifiers
source                    1..162
                          mol_type = protein
                          organism = Bos taurus
SEQUENCE: 584
ASVTQTMKGL DIQKVAGTWY SLAMAASDIS LLDAQSAPAR VYVEELKPTP EGDLEILLQK     60
WENGECAQKK IIAEKTKIPA VFKIDALNEN KVLVLDTDYK KYLLLCFENS AEPEQSLACQ    120
CLVRTPEVDD EALEKFDKAL KALPMHIRLS FNPTQLEEQC HI                      162
```

```
SEQ ID NO: 585          moltype = AA  length = 162
FEATURE                 Location/Qualifiers
source                  1..162
                        mol_type = protein
                        organism = Bos taurus
SEQUENCE: 585
LIVTQTMKGL DIQKVAGTWY SLAMAASDIS LLDAQSAPLR VYVEELKPTP EGDLEILLQK     60
WENDECAQKK IIAEKTKIPA VFKLDAINEN KVLVLDTDYK KYLLFCMENS AEPEQSLVCQ    120
CLVRTPEVDD EALEKFDKAL KALPMHIRLS FNPTLQEEQC HI                       162

SEQ ID NO: 586          moltype = AA  length = 252
FEATURE                 Location/Qualifiers
source                  1..252
                        mol_type = protein
                        organism = Bos taurus
SEQUENCE: 586
MKCLLLALAL TCGAQALIVT QTMKGLDIQK VAGTWYSLAM AASDISLLDA QSAPLRVYVE     60
ELKPTPEGDL EILLQKWENG ECAQKKIIAE KTKIPAVFKI DALNENKVLV LDTDYKKYLL    120
FCMENSAEPE QSLACQCLVR TPEVDDEALE KFDKALKALP MHIRLSFNPT QLEGEHPGPT    180
LLLGQEATRP RTTSSHGDPQ LPRPPGRMET GCRAPRWPPP HPLPSSLCPG VSSPILTLPR    240
HGSPSPTEQC HI                                                        252

SEQ ID NO: 587          moltype = AA  length = 151
FEATURE                 Location/Qualifiers
source                  1..151
                        mol_type = protein
                        organism = Bos taurus
SEQUENCE: 587
IQKVAGTWYS LAMAASDISL LDAQSAPLRV YVEELKPTPE GDLEILLQKW ENDECAQKKI     60
IAEKTKIPAV FKIDALNENK VLVLDTDYKK YLLFCMENSA EPEQSLVCQC LVRTPEVDDE    120
ALEKFDKALK ALPMHIRLSF NPTQLEEQCH I                                   151

SEQ ID NO: 588          moltype = AA  length = 162
FEATURE                 Location/Qualifiers
source                  1..162
                        mol_type = protein
                        organism = Capra hircus
SEQUENCE: 588
IIVTQTMKGL DIQKVAGTWY SLAMAASDIS LLDAQSAPLR VYVEELKPTP EGNLEILLQK     60
WENGECAQKK IIAEKTKIPA VFKIDALNEN KVLVLDTDYK KYLLFCMENS AEPEQSLACQ    120
CLVRTPEVDK EALEKFDKAL KALPMHIRLA FNPTQLEGQC HV                       162

SEQ ID NO: 589          moltype = AA  length = 180
FEATURE                 Location/Qualifiers
source                  1..180
                        mol_type = protein
                        organism = Capra hircus
SEQUENCE: 589
MKCLLLALGL ALACGIQAII VTQTMKGLDI QKVAGTWYSL AMAASDISLL DAQSAPLRVY     60
VEELKPTPEG NLEILLQKWE NGECAQKKII AEKTKIPAVF KIDALNENKV LVLDTDYKKY    120
LLFCMENSAE PEQSLACQCL VRTPEVDKEA LEKFDKALKA LPMHIRLAFN PTQLEGQCHV    180

SEQ ID NO: 590          moltype = AA  length = 169
FEATURE                 Location/Qualifiers
source                  1..169
                        mol_type = protein
                        organism = Capra hircus
SEQUENCE: 590
MKCLLLALGL ALACGIQAII VTQTMKGLDI QKVAGTWYSL AMAASDISLL DAQSAPLRVY     60
VEELKPTPEG NLEILLQKWE NGECAQKKII AEKTKIPAVF KIDALNENKV LVLDTDYKKY    120
LLFCMENSAE PEQSLACQCL VRTPEVDKEA LEKFDKALKA LPMHIRLAF                169

SEQ ID NO: 591          moltype = AA  length = 162
FEATURE                 Location/Qualifiers
source                  1..162
                        mol_type = protein
                        organism = Ovis aries
SEQUENCE: 591
IIVTQTMKGL DIQKVAGTWY SLAMAASDIS LLDAQSAPLR VYVEELKPTP EGNLEILLQK     60
WENGECAQKK IIAEKTKIPA VFKIDALNEN KVLVLDTDYK KYLLFCMENS AEPEQSLACQ    120
CLVRTPEVDN EALEKFDKAL KALPMHIRLA FNPTQLEGQC HV                       162

SEQ ID NO: 592          moltype = AA  length = 180
FEATURE                 Location/Qualifiers
source                  1..180
                        mol_type = protein
                        organism = Ovis aries
SEQUENCE: 592
```

```
MKCLLLALGL ALACGVQAII VTQTMKGLDI QKVAGTWHSL AMAASDISLL DAQSAPLRVY    60
VEELKPTPEG NLEILLQKWE NGECAQKKII AEKTKIPAVF KIDALNENKV LVLDTDYKKY   120
LLFCMENSAE PEQSLACQCL VRTPEVDNEA LEKFDKALKA LPMHIRLAFN PTQLEGQCHV   180

SEQ ID NO: 593           moltype = AA   length = 161
FEATURE                  Location/Qualifiers
source                   1..161
                         mol_type = protein
                         organism = Ovis aries
SEQUENCE: 593
VTQTMKGLDI QKVAGTWYHS LAMAASDISL LDAQSAPLRV YVEELKPTPE GNLEILLQKW    60
ENGECAQKKI IAEKTKIPAV FKIDALNENK VLVLDTDYKK YLLFCMENSA EPEQSLACQC   120
LVRTPEVDNE ALEKFDKALK ALPMHIRLAF NPTQLEGQCH V                       161

SEQ ID NO: 594           moltype = AA   length = 162
FEATURE                  Location/Qualifiers
source                   1..162
                         mol_type = protein
                         organism = Ovis aries
SEQUENCE: 594
IIVTQTMKGL DIQKVAGTWY HSLAMAASDI SLLDAQSAPL RVYVEELKPT PEGNLEILLQ    60
KWEGECAQKK IIAEKTKIPA VFKIDALNEN KVLVLDTDYK KYLLFCMENS AEPEQSLACQ   120
CLVRTPEVDN EALEKFDKAL KALPMHIRLA FNPTQLEGQC HV                      162

SEQ ID NO: 595           moltype = AA   length = 162
FEATURE                  Location/Qualifiers
source                   1..162
                         mol_type = protein
                         organism = Bubalus bubalis
SEQUENCE: 595
IIVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HV                      162

SEQ ID NO: 596           moltype = AA   length = 180
FEATURE                  Location/Qualifiers
source                   1..180
                         mol_type = protein
                         organism = Bubalus bubalis
SEQUENCE: 596
MKCLLLALGL ALACAAQAII VTQTMKGLDI QKVAGTWYSL AMAASDISLL DAQSAPLRVY    60
VEELKPTPEG DLEILLQKWE NGECAQKKII AEKTKIPAVF KIDALNENKV LVLDTDYKKY   120
LLFCMENSAE PEQSLACQCL VRTPEVDDEA LEKFDKALKA LPMHIRLSFN PTQLEEQCHV   180

SEQ ID NO: 597           moltype = AA   length = 180
FEATURE                  Location/Qualifiers
source                   1..180
                         mol_type = protein
                         organism = Bubalus bubalis
SEQUENCE: 597
MKCLLLALGL ALACGAQAII VTQTMKGLDI QKVAGTWYSL AMAASDISLL DAQSAPLRVY    60
VEELKPTPEG DLEILLQKWE NGECAQKKII AEKTKIPAVF KIDALNENKV LVLDTDYKKY   120
LLFCMENSAE PEQSLACQCL VRTPEVDDEA LEKFDKALKA LPMHIRLSFN PTQLEEQCHV   180

SEQ ID NO: 598           moltype = AA   length = 180
FEATURE                  Location/Qualifiers
source                   1..180
                         mol_type = protein
                         organism = Bubalus bubalis
SEQUENCE: 598
MKCLLLALGL ALACGTQAII VTQTMKGLDI QKVAGTWYSL AMAASDISLL DAQSAPLRVY    60
VEELKPTPEG DLEILLQKWE NGECAQKKII AEKTKIPAVF KIDALNENKV LVLDTDYKKY   120
LLFCMENSAE PEQSLACQCL VRTPEVDDEA LEKFDKALKA LPMHIRLSFN PTQLEEQCHV   180

SEQ ID NO: 599           moltype = AA   length = 180
FEATURE                  Location/Qualifiers
source                   1..180
                         mol_type = protein
                         organism = Bubalus bubalis
SEQUENCE: 599
MKCLLLALGL ALACGTQAII VTQTMKGLDI QKVAGTWYSL AMAVSDISLL DAQSAPLRVY    60
VEELKPTPEG DLEILLQKWE NGECAQKKII AEKTKIPAVF KIDALNENKV LVLDTDYKKY   120
LLFCMENSAE PEQSLACQCL VRTPEVDDEA LEKFDKALKA LPMHIRLSFN PTQLEEQCHV   180

SEQ ID NO: 600           moltype = AA   length = 178
FEATURE                  Location/Qualifiers
source                   1..178
                         mol_type = protein
                         organism = Bubalus bubalis
```

```
SEQUENCE: 600
MKCLLLALAL ACGAQAIIVT QTMKGLDIQK VAGTWYSLAM AASDISLLDA QSAPLRVYVE    60
ELKPTPEGDL EILLQKWENG ECAQKKIIAE KTKIPAVFKI DALNENKVLV LDTDYKKYLL   120
FCMENSAEPE KAWPASAWVR TPEVDDEALE KFDKALKALP MHIRLSFNPT QLEEQCHI    178

SEQ ID NO: 601          moltype = AA  length = 178
FEATURE                 Location/Qualifiers
source                  1..178
                        mol_type = protein
                        organism = Bos mutus
SEQUENCE: 601
MKCLLLALAL TCGAQALIVT QTMKGLDIQK VAGTWYSLAM AASDISLLDA QSAPLRVYVE    60
ELKPTPEGDL EILLQKWENG ECAQKKIIAE KTKIPAVFKI DALNENKVLV LDTDYKKYLL   120
FCMENSAEPE QSLACQCLVR TPEVDDEALE KFDKALKALP MHIRLSFNPT QLEGQCHI    178

SEQ ID NO: 602          moltype = AA  length = 298
FEATURE                 Location/Qualifiers
source                  1..298
                        mol_type = protein
                        organism = Bos mutus
SEQUENCE: 602
MQLKVPPQVA GMWHTVAMAA SNMLLLDAES GPLRVYVEEL KPTPEGDLEI LLQKRENHEC    60
VEKTLMAQKT EDPAVFTPGP EMDDEAMEKF AGALASLLEH VQMVLGLRQG AELRSVTPAA   120
AMKCLLLALA LTCGAQALIV TQTMKGLDIQ KVAGTWYSLA MAASDISLLD AQSAPLRVYV   180
EELKPTPEGD LEILLQKWEN GECAQKKIIA EKTKIPAVFK IDALNENKVL VLDTDYKKYL   240
LFCMENSAEP EQSLACQCLV RTPEVDDEAL EKFDKALKAL PMHIRLSFNP TQLEGKPS    298

SEQ ID NO: 603          moltype = AA  length = 178
FEATURE                 Location/Qualifiers
VARIANT                 80
                        note = X is any amino acid
VARIANT                 134
                        note = X is any amino acid
source                  1..178
                        mol_type = protein
                        organism = Bos indicus
SEQUENCE: 603
MKCLLLALAL TCGAQALIVT QTMKGLDIQK VAGTWYSLAM AASDISLLDA QSAPLRVYVE    60
ELKPTPEGDL EILLQKWENX ECAQKKIIAE KTKIPAVFKI DALNENKVLV LDTDYKKYLL   120
FCMENSAEPE QSLXCQCLVR TPEVDDEALE KFDKALKALP MHIRLSFNPT QLEEQCHI    178

SEQ ID NO: 604          moltype = AA  length = 184
FEATURE                 Location/Qualifiers
source                  1..184
                        mol_type = protein
                        organism = Jeotgalicoccus coquinae
SEQUENCE: 604
MTPAAAMKCL LLALALTCGA QALIVTQTMK GLDIQKVAGT WYSLAMAASD ISLLDAQSAP    60
LRVYVEELKP TPEGDLEILL QKWENGECAQ KKIIAEKTKI PAVFKIDALN ENKVLVLDTD   120
YKKYLLFCME NSAEPEQSLA CQCLVRTPEV DDEALEKFDK ALKALPMHIR LSFNPTQLEE   180
QCHI                                                               184

SEQ ID NO: 605          moltype = AA  length = 181
FEATURE                 Location/Qualifiers
source                  1..181
                        mol_type = protein
                        organism = Jeotgalicoccus schoeneichii
SEQUENCE: 605
LRSVIPAAAM KCLLLALALT CGAQALIVTQ TMKGLDIQKV AGTWYSLAMA ASDISLLDAQ    60
SAPLRVYVEE LKPTPEGDLE ILLQKWENGE CAQKKIIAEK TKIPAVFKID ALNENKVLVL   120
DTDYKKYLLF CMENSAEPEQ SLACQCLVRT GVQDRCLERE QSPCAGHRLQ KVPALLHGEQ   180
C                                                                  181

SEQ ID NO: 606          moltype = AA  length = 178
FEATURE                 Location/Qualifiers
source                  1..178
                        mol_type = protein
                        organism = Bison bison
SEQUENCE: 606
MKCLLLALAL TCGAQALIVT QTMKGLDIQK VAGTWYSLAM AASDISLLDA QSAPLRVYVE    60
ELKPTPEGNL EILLQKWENG ECAQKKIIAE KTKVPAVFKI DALNENKVLV LDTDYKKYLL   120
FCMENSAEPE QSLACQCLVR TPEVDDEALE KFDKALKALP MHIRLSFNPT QLEGQCHI    178

SEQ ID NO: 607          moltype = AA  length = 180
FEATURE                 Location/Qualifiers
REGION                  1..180
                        note = Ovis sp.
source                  1..180
                        mol_type = protein
```

```
                              organism = unidentified
SEQUENCE: 607
MKCLLLALGL ALACGVQAII VTQTMKGLDI QKVAGTWYSL AMAASDISLL DAQSAPLRVY    60
VEELKPTPEG NLEILLQKWE NGECAQKKII AEKTKIPAVF KIDALNENKV LVLDTDYKKY   120
LLFCMENSAE PEQSLACQCL VRTPEVDNEA LEKFDKALKA LPMHIRLAFN PTQLEGQCHV   180

SEQ ID NO: 608           moltype = AA  length = 162
FEATURE                  Location/Qualifiers
source                   1..162
                         mol_type = protein
                         organism = Ovis aries
SEQUENCE: 608
IIVTQTMKGL DIQKVAGTWH SLAMAASDIS LLDAQSAPLR VYVEELKPTP EGNLEILLQK    60
WENGECAQKK IIAEKTKIPA VFKIDALNEN KVLVLDTDYK KYLLFCMENS AEPEQSLACQ   120
CLVRTPEVDN EALEKFDKAL KALPMHIRLA FNPTQLEGQC HV                      162

SEQ ID NO: 609           moltype = AA  length = 180
FEATURE                  Location/Qualifiers
source                   1..180
                         mol_type = protein
                         organism = Odocoileus virginianus
SEQUENCE: 609
MKCLLLALGL ALACGVQAAH IPQTAEDLDV RKVVGTWHVV AMAASDMSLL DAESGPLRVY    60
VEELKPTPQG DLEVLLQKRE NGKCAQKKII AEKTEIPAVF KIDALNENKV LVLDTDYKKY   120
LLFCMENSAE PEQSLACQCL VRTPEVDDEA MEKFDKALKA LPMHIRLSFN PTQLEEQCRI   180

SEQ ID NO: 610           moltype = AA  length = 162
FEATURE                  Location/Qualifiers
source                   1..162
                         mol_type = protein
                         organism = Rangifer tarandus
SEQUENCE: 610
IIVTQTMKDL DVQKVAGTWY SLAMAASDIS LLDAQSAPLR VYVEELKPTP GGDLEILLQK    60
WENGKCAQKK IIAEKTEIPA VFKIDALNEN KVLVLDTDYK KYLLFCMENS AEPEQSLACQ   120
CLVRTPEVDD EAMEKFDKAL KALPMHIRLS FNPTQLEEQC RV                      162

SEQ ID NO: 611           moltype = AA  length = 180
FEATURE                  Location/Qualifiers
source                   1..180
                         mol_type = protein
                         organism = Rangifer tarandus
SEQUENCE: 611
MKCLLITLGL ALACGAQAII VTQTMKDLDV QKVAGTWYSL AMAASDISLL DAQSAPLRVY    60
VEELKPTPGG DLEILLQKWE NGKCAQKKII AEKTEIPAVF KIDALNENKV LVLDTDYKKY   120
LLFCMENSAE PEQSLACQCL VRTPEVDDEA MEKFDKALKA LPMHIRLSFN PTQLEEQCRV   180

SEQ ID NO: 612           moltype = AA  length = 180
FEATURE                  Location/Qualifiers
source                   1..180
                         mol_type = protein
                         organism = Muntiacus muntjak
SEQUENCE: 612
MKCLLLALGL ALACGAQAIV VTQTMKDLDI QKVAGTWYSL AMAASDISLL DAQSAPLRVY    60
VEELKPTPEG DLEILLQKWE NGECAQKKIT AEKTEIPAVF KIDALNENEV LVLDTDYEKY   120
LLFCMDNSAE PEQSLACQCL VRTPEVDAEA MEKFDKALEA LPMHIRLSFN PTQLEEQCHV   180

SEQ ID NO: 613           moltype = AA  length = 180
FEATURE                  Location/Qualifiers
source                   1..180
                         mol_type = protein
                         organism = Muntiacus reevesi
SEQUENCE: 613
MKCLLLALGL ALACGAQAII VTQTMKDLDI QKVAGTWYSL AMAASDISLL DAQSAPLRVY    60
VEELKPTPEG DLEILLQKWE NGECAQKKIT AEKTEIPAVF KIDALNENNV LVLDTDYEKY   120
LLFCMDNSAE PEQSLACQCL VRTPEVDAEA MEKFDKALEA LPMHIRLSFN PTQLEEHCHV   180

SEQ ID NO: 614           moltype = AA  length = 162
FEATURE                  Location/Qualifiers
source                   1..162
                         mol_type = protein
                         organism = Equus caballus
SEQUENCE: 614
TNIPQTMQDL DLQEVAGTWY SLAMAASDIS LLDSESAPLR VYVEELKPTP EGDLEILLQK    60
WENKGCAQKK IIAEKTESPA EFKIDALDEN KVLVLDTDYK NYLLFCMENA ATPGQSLACQ   120
ALVRTQMVDD EALEKFDKAL QPLPMHIRLS FNPTRMAERC RI                      162

SEQ ID NO: 615           moltype =    length =
SEQUENCE: 615
000
```

```
SEQ ID NO: 616           moltype = AA   length = 4
FEATURE                  Location/Qualifiers
REGION                   1..4
                         note = ER peptide tag
source                   1..4
                         mol_type = protein
                         organism = synthetic construct
SEQUENCE: 616
KDEL                                                                    4

SEQ ID NO: 617           moltype = DNA  length = 1161
FEATURE                  Location/Qualifiers
misc_feature             1..1161
                         note = codon optimized ovalbumin
source                   1..1161
                         mol_type = other DNA
                         organism = synthetic construct
SEQUENCE: 617
atgggatcaa tcggtgctgc cagcatggag ttttgctttg atgtatttaa ggaactcaaa    60
gtacatcacg ctaacgaaaa tatttttctac tgtcctatag ctataatgtc cgcacttgct   120
atggtctatt tgggcgccaa ggattctaca cgcacccaga ttaataaggg ggttcgtttt   180
gacaaacttc caggctttgg tgattcaata gaggcccaat gtgggacaag tgtcaacgta   240
cacagctctt tgcgtgatat actcaaccaa ataactaaac ccaatgacgt gtatagtttt   300
tcccttgcct cccgtcttta tgctgaagaa cgttacccaa tattgcccga atacctccaa   360
tgtgtcaagg aactgtatcg cggcggactt gaaccactaa attttcagac cgcagccgat   420
caggccaggg agctcataaa ctcatgggtc gaaagtcaaa caaatgggat catacgtaat   480
gtgctccagc cttctagcgt tgattcacaa accgccatgg tgttggtcaa tgccatcgta   540
tttaaaggtc tctgggaaaa gacatttaag gatgaagata ctcaggcaat gccttttcgt   600
gtaaccgagc aggagtccaa acccgttcaa atgatgtacc agataggggt gtttagggta   660
gccagtatgg cctctgagaa aatgaagata ctgaattgc cctttgccag tggtaccatg   720
tccatgcttg tactgttgcc agatgaagtt tctggcctgg agcagcttga gtctataata   780
aacttcgaga agttgacaga gtggacatca tctaacgtta tggaagaacg taaaataaaa   840
gtgtatttgc ctcgcatgaa gatggaggag aaatacaacc ttaccagtgt actgatggca   900
atgggcataa ccgatgtttt ttctagttcc gcaaaccttt ctggtatctc ctcagcagaa   960
tctctgaaga tatcccaagc agttcatgca gcacacgcag aaataaacga ggcaggacgt  1020
gaagtggtag atcagccga ggcaggcgtt gatgcagcat ccgtgagcga agagtttcgt  1080
gccgatcacc cttttccttttt ctgcatcaaa acattgctta ccaatgccgt tcttttcttc  1140
gggcgctgtg tatcccctta a                                             1161

SEQ ID NO: 618           moltype = DNA  length = 2118
FEATURE                  Location/Qualifiers
misc_feature             1..2118
                         note = codon optimized ovotransferrin
source                   1..2118
                         mol_type = other DNA
                         organism = synthetic construct
SEQUENCE: 618
atgaaactga ttttgtgtac cgtcctgtca cttgggattg ccgcagtatg ttttgccgcc    60
ccacccaaga gtgttatccg ttggtgtacc atctctagcc tgaggagaa gaaatgtaac   120
aacctcaggg acttgaccca gcaagagagg ataagcctga catgtgtcca gaaggctacc   180
tatctcgact gtatcaaagc catagccaac aacgaggccg acgcaatatc ccttgatgga   240
ggacaggtgt tcgaggccgg acttgcccct tataaattga gcctatagc tgctgaaatc   300
tacgagcata ctgagggttc taccactagt tattatgccg tagccgtagt taaaaagggg   360
accgagttta cagtcaacga tctccagggt aaaaataagt gccatactgg tcttggtagg   420
agtgctgggt ggaatatacc tatcggtaca ctcctccact ggggcgctat cgagtgggga   480
ggtatcgaaa gtgtgaagcgt ggaacaggca gtcgctaagt tttttttccgc ctcttggcta   540
cccgcgcta ctatagagca gaaactttgc cgtcagtgca aggagatcc aagaccaag    600
tgtcccgta acgcccccta tagtggatat tccggcgctt tccactgctt gaaggatgga    660
aagggggacg tagccttcgt gaaacacact acagtgaatg aaaacgcccc cgatctcatt    720
gacgagtatg agttgcttg cctgatggt agtcgccaac cagtcgataa ttacaaaacc    780
tgtaactggg ctcgtgttgc tgcacatgcc gtcgttgcac gcgatgacaa taagtggag    840
gatatctggt cctttctgtc aaaagcccaa agcgattttg gcgtagatac caagtcagat    900
ttccatctgt ttgggccacc tggaaagaaa gacctgtgc ttaaggactt cttgttcaaa    960
gacagtgcca taatgctcaa acgcgttcct agccttatgg attctcaact gtatctcggg   1020
ttcgaatatt actcagccat acaatcaatg aggaaggacc agctcactcc tagccctaga   1080
gagaatagaa ttcaatggtg tgctgttgga aagacgaga atctaaatg cgaccgttgg   1140
agcgtcgtca gcaacggtga tgttgagtgt actgtagtgg atgaaactaa ggattgcatt   1200
attaagatta tgaagggggga ggccgatgcc gtcgcattga atggagggt ggttatacc   1260
gcaggtgtct gtggactggt gcctgtcatg gcagaaagat atgatgatga atcacaatgc   1320
agtaaaacag acgaacgtcc agcctcatat tttgctgtcg ccgtcgcccg caaggattcc   1380
aatgtgaatt ggaataattt gaagggaaaa aaatcctgcc acactgctgt agggcgtaca   1440
gcaggttggg tgatcccaat gggactgatt cacaatagga ccggtacttg caactttgat   1500
gaatattct ccgaggggtg tgctcccggt agccccccca acagccgctt gtgccagctg   1560
tgccaaggta gtgagggtat tccccctgag aaatgcgtcg cttcctctca cgagaaatac   1620
tttggttata ctggtgcctt gcgttgcctc gtagaaaaag gtgacgtcgc ttttatccaa   1680
cacagtactg tagaggagaa tacagggggg aagaacaaag ctgactggc taagaatctt   1740
cagatggacg atttcgaact gttgtgtacc gatggtagaa gggctaatgt tatggattat   1800
cgtgagtgca atcttgcaga agtaccaacc catgctgtag ttgtcagacc cgagaaagca   1860
```

```
aataaaatta gagacctttt ggagagacaa gagaaacgtt tcggtgtaaa cggctcagag   1920
aagtctaaat tcatgatgtt tgaaagtcaa aataaggatc tgttgttcaa agacttgact   1980
aaatgcctgt ttaaagtcag ggaaggcacc acttataaag aatttctggg agataaattc   2040
tacacagtaa taagcaactt gaaaacatgc aatccttccg atatcctgca aatgtgcagt   2100
ttccttgaag ggaaataa                                                 2118

SEQ ID NO: 619          moltype = DNA   length = 633
FEATURE                 Location/Qualifiers
misc_feature            1..633
                        note = codon optimized ovomucoid
source                  1..633
                        mol_type = other DNA
                        organism = synthetic construct
SEQUENCE: 619
atggctatgg ccggagtctt tgttcttttc tctttcgtgc tttgtggttt ttgcctgac    60
gccgccttcg gagccgaggt tgactgctct cgcttcccaa atgcaaccga taaagaggga   120
aaggacgttt tgtttgcaa caaggacctg cgtcctatct gtgggacaga tggcgttaca    180
tatactaacg actgcctttt gtgtgcatat tctattgaat ttggtactaa catatctaag   240
gagcatgatg gggaatgcaa agaaacagtt cccatgaact gtagttctta tgctaatacc   300
actagtgagg acggcaaggt catggtattg tgcaataggg ctttcaatcc tgtatgcggg   360
acagatggtg tcacttacga caatgaatgt tgctgtgtg ctcacaaggt cgaacaagga   420
gctttctgtcg ataagaggca tgatggggt tgcagaaaag aattggctgc agtatcagtt   480
gactgctctg agtatcccaa gccagattgc accgccgagg accgcccatt gtgtggaagc   540
gataataaga cttatggaaa taaatgcaac ttctgcaatg ccgttgtgga aagcaacggc   600
actctgactt tgagtcattt cggaaaatgc tga                                633

SEQ ID NO: 620          moltype = DNA   length = 444
FEATURE                 Location/Qualifiers
misc_feature            1..444
                        note = codon optimized lysozyme
source                  1..444
                        mol_type = other DNA
                        organism = synthetic construct
SEQUENCE: 620
atgaggagct tgttgatact gtgctttgt tccttcccc ttgcagcatt ggggaaagtt      60
ttcggtaggt gcgagcttgc cgccgcaatg aaaagacacg gcttgacaa ttatcgtgga   120
tactctctcg gcaattgggt ttgtgtagca aagttcgaga gcaattttaa cacccaggct   180
actaatagaa ataccgacgg atctaccgac tacgggattc tgcaaataaa cagccgctgg   240
tggtgtaatg acgggcgtac tccggtagc cgcaatctct gtaacatccc ctgtagtgca   300
ttgcttagtt ctgacattac agctagcgtg aactgtgcta aaagatagt ttctgacggt    360
aatgaatga gtgcttgggt tgcctggagg aacgttgta aggggaccga cgttcaagca     420
tggattagag ggtgtcgtct gtga                                          444

SEQ ID NO: 621          moltype = DNA   length = 321
FEATURE                 Location/Qualifiers
misc_feature            1..321
                        note = codon optimized apovitellenin-1
source                  1..321
                        mol_type = other DNA
                        organism = synthetic construct
SEQUENCE: 621
atggtacaat acagagcact cgtgattgcc gtaattttgc ttctttccac taccgtccct    60
gaggtacata gcaagtccat cattgacaga gaacgcaggg actggctggt gattcctgat   120
gctgctgctg cctatattta tgaagccgtc aacaaggtat caccacgcgc aggtcagttc   180
ttgctcgacg tttctcaaac cacagtcgtg tctggaatca ggaactttct catcaacgaa   240
acagctaggc ttactaagct ggccgagcaa cttatggaga aaattaagaa ccttttgctat   300
actaaagtgt tgggctacta g                                             321

SEQ ID NO: 622          moltype = AA    length = 386
FEATURE                 Location/Qualifiers
source                  1..386
                        mol_type = protein
                        organism = Gallus gallus
SEQUENCE: 622
MGSIGAASME FCFDVFKELK VHHANENIFY CPIAIMSALA MVYLGAKDST RTQINKVVRF    60
DKLPGFGDSI EAQCGTSVNV HSSLRDILNQ ITKPNDVYSF SLASRLYAEE RYPILPEYLQ   120
CVKELYRGGL EPINFQTAAD QARELINSWV ESQTNGIIRN VLQPSSVDSQ TAMVLVNAIV   180
FKGLWEKTFK DEDTQAMPFR VTEQESKPVQ MMYQIGLFRV ASMASEKMKI LELPFASGTM   240
SMLVLLPDEV SGLEQLESII NFEKLTEWTS SNVMEERKIK VYLPRMKMEE KYNLTSVLMA   300
MGITDVFSSS ANLSGISSAE SLKISQAVHA AHAEINEAGR EVVGSAEAGV DAASVSEEFR   360
ADHPFLFCIK HIATNAVLFF GRCVSP                                        386

SEQ ID NO: 623          moltype = AA    length = 705
FEATURE                 Location/Qualifiers
source                  1..705
                        mol_type = protein
                        organism = Gallus gallus
SEQUENCE: 623
MKLILCTVLS LGIAAVCFAA PPKSVIRWCT ISSPEEKKCN NLRDLTQQER ISLTCVQKAT    60
```

```
YLDCIKAIAN NEADAISLDG GQVFEAGLAP YKLKPIAAEI YEHTEGSTTS YYAVAVVKKG    120
TEFTVNDLQG KNSCHTGLGR SAGWNIPIGT LLHWGAIEWE GIESGSVEQA VAKFFSASCV    180
PGATIEQKLC RQCKGDPKTK CARNAPYSGY SGAFHCLKDG KGDVAFVKHT TVNENAPDLN    240
DEYELLCLDG SRQPVDNYKT CNWARVAAHA VVARDDNKVE DIWSFLSKAQ SDFGVDTKSD    300
FHLFGPPGKK DPVLKDFLFK DSAIMLKRVP SLMDSQLYLG FEYYSAIQSM RKDQLTPSPR    360
ENRIQWCAVG KDEKSKCDRW SVVSNGDVEC TVVDETKDCI IKIMKGEADA VALDGGLVYT    420
AGVCGLVPVM AERYDDESQC SKTDERPASY FAVAVARKDS NVNWNNLKGK KSCHTAVGRT    480
AGWVIPMGLI HNRTGTCNFD EYFSEGCAPG SPPNSRLCQL CQGSGGIPPE KCVASSHEKY    540
FGYTGALRCL VEKGDVAFIQ HSTVEENTGG KNKADWAKNL QMDDFELLCT DGRRANVMDY    600
RECNLAEVPT HAVVVRPEKA NKIRDLLERQ EKRFGVNGSE KSKFMMFESQ NKDLLFKDLT    660
KCLFKVREGT TYKEFLGDKF YTVISNLKTC NPSDILQMCS FLEGK                   705

SEQ ID NO: 624            moltype = AA  length = 210
FEATURE                   Location/Qualifiers
source                    1..210
                          mol_type = protein
                          organism = Gallus gallus
SEQUENCE: 624
MAMAGVFVLF SFVLCGFLPD AAFGAEVDCS RFPNATDKEG KDVLVCNKDL RPICGTDGVT     60
YTNDCLLCAY SIEFGTNISK EHDGECKETV PMNCSSYANT TSEDGKVMVL CNRAFNPVCG    120
TDGVTYDNEC LLCAHKVEQG ASVDKRHDGG CRKELAAVSV DCSEYPKPDC TAEDRPLCGS    180
DNKTYGNKCN FCNAVVESNG TLTLSHFGKC                                    210

SEQ ID NO: 625            moltype = AA  length = 147
FEATURE                   Location/Qualifiers
source                    1..147
                          mol_type = protein
                          organism = Gallus gallus
SEQUENCE: 625
MRSLLILVLC FLPLAALGKV FGRCELAAAM KRHGLDNYRG YSLGNWVCVA KFESNFNTQA     60
TNRNTDGSTD YGILQINSRW WCNDGRTPGS RNLCNIPCSA LLSSDITASV NCAKKIVSDG    120
NGMSAWVAWR NRCKGTDVQA WIRGCRL                                       147

SEQ ID NO: 626            moltype = AA  length = 106
FEATURE                   Location/Qualifiers
source                    1..106
                          mol_type = protein
                          organism = Gallus gallus
SEQUENCE: 626
MVQYRALVIA VILLLSTTVP EVHSKSIIDR ERRDWLVIPD AAAAYIYEAV NKVSPRAGQF     60
LLDVSQTTVV SGIRNFLINE TARLTKLAEQ LMEKIKNLCY TKVLGY                   106

SEQ ID NO: 627            moltype =     length =
SEQUENCE: 627
000

SEQ ID NO: 628            moltype =     length =
SEQUENCE: 628
000

SEQ ID NO: 629            moltype = RNA  length = 12
FEATURE                   Location/Qualifiers
misc_feature              1..12
                          note = ER peptide tag encoding sequence
source                    1..12
                          mol_type = other RNA
                          organism = synthetic construct
SEQUENCE: 629
aaggatgagc tt                                                        12

SEQ ID NO: 630            moltype =     length =
SEQUENCE: 630
000

SEQ ID NO: 631            moltype =     length =
SEQUENCE: 631
000

SEQ ID NO: 632            moltype = AA  length = 4
FEATURE                   Location/Qualifiers
REGION                    1..4
                          note = ER peptide tag
source                    1..4
                          mol_type = protein
                          organism = synthetic construct
SEQUENCE: 632
HDEF                                                                  4

SEQ ID NO: 633            moltype = AA  length = 4
```

```
FEATURE              Location/Qualifiers
REGION               1..4
                     note = ER peptide tag
source               1..4
                     mol_type = protein
                     organism = synthetic construct
SEQUENCE: 633
HDEL                                                                      4

SEQ ID NO: 634       moltype = AA  length = 4
FEATURE              Location/Qualifiers
REGION               1..4
                     note = ER peptide tag
source               1..4
                     mol_type = protein
                     organism = synthetic construct
SEQUENCE: 634
RDEF                                                                      4

SEQ ID NO: 635       moltype = AA  length = 4
FEATURE              Location/Qualifiers
REGION               1..4
                     note = ER peptide tag
source               1..4
                     mol_type = protein
                     organism = synthetic construct
SEQUENCE: 635
RDEL                                                                      4

SEQ ID NO: 636       moltype = AA  length = 4
FEATURE              Location/Qualifiers
REGION               1..4
                     note = ER peptide tag
source               1..4
                     mol_type = protein
                     organism = synthetic construct
SEQUENCE: 636
WDEL                                                                      4

SEQ ID NO: 637       moltype = AA  length = 4
FEATURE              Location/Qualifiers
REGION               1..4
                     note = ER peptide tag
source               1..4
                     mol_type = protein
                     organism = synthetic construct
SEQUENCE: 637
YDEL                                                                      4

SEQ ID NO: 638       moltype = AA  length = 4
FEATURE              Location/Qualifiers
REGION               1..4
                     note = ER peptide tag
source               1..4
                     mol_type = protein
                     organism = synthetic construct
SEQUENCE: 638
HEEF                                                                      4

SEQ ID NO: 639       moltype = AA  length = 4
FEATURE              Location/Qualifiers
REGION               1..4
                     note = ER peptide tag
source               1..4
                     mol_type = protein
                     organism = synthetic construct
SEQUENCE: 639
HEEL                                                                      4

SEQ ID NO: 640       moltype = AA  length = 4
FEATURE              Location/Qualifiers
REGION               1..4
                     note = ER peptide tag
source               1..4
                     mol_type = protein
                     organism = synthetic construct
SEQUENCE: 640
KEEL                                                                      4
```

```
SEQ ID NO: 641         moltype = AA  length = 4
FEATURE                Location/Qualifiers
REGION                 1..4
                       note = ER peptide tag
source                 1..4
                       mol_type = protein
                       organism = synthetic construct
SEQUENCE: 641
REEL                                                                    4

SEQ ID NO: 642         moltype = AA  length = 4
FEATURE                Location/Qualifiers
REGION                 1..4
                       note = ER peptide tag
source                 1..4
                       mol_type = protein
                       organism = synthetic construct
SEQUENCE: 642
KAEL                                                                    4

SEQ ID NO: 643         moltype = AA  length = 4
FEATURE                Location/Qualifiers
REGION                 1..4
                       note = ER peptide tag
source                 1..4
                       mol_type = protein
                       organism = synthetic construct
SEQUENCE: 643
KCEL                                                                    4

SEQ ID NO: 644         moltype = AA  length = 4
FEATURE                Location/Qualifiers
REGION                 1..4
                       note = ER peptide tag
source                 1..4
                       mol_type = protein
                       organism = synthetic construct
SEQUENCE: 644
KFEL                                                                    4

SEQ ID NO: 645         moltype = AA  length = 4
FEATURE                Location/Qualifiers
REGION                 1..4
                       note = ER peptide tag
source                 1..4
                       mol_type = protein
                       organism = synthetic construct
SEQUENCE: 645
KGEL                                                                    4

SEQ ID NO: 646         moltype = AA  length = 4
FEATURE                Location/Qualifiers
REGION                 1..4
                       note = ER peptide tag
source                 1..4
                       mol_type = protein
                       organism = synthetic construct
SEQUENCE: 646
KHEL                                                                    4

SEQ ID NO: 647         moltype = AA  length = 4
FEATURE                Location/Qualifiers
REGION                 1..4
                       note = ER peptide tag
source                 1..4
                       mol_type = protein
                       organism = synthetic construct
SEQUENCE: 647
KLEL                                                                    4

SEQ ID NO: 648         moltype = AA  length = 4
FEATURE                Location/Qualifiers
REGION                 1..4
                       note = ER peptide tag
source                 1..4
                       mol_type = protein
                       organism = synthetic construct
SEQUENCE: 648
KNEL                                                                    4
```

```
SEQ ID NO: 649          moltype = AA   length = 4
FEATURE                 Location/Qualifiers
REGION                  1..4
                        note = ER peptide tag
source                  1..4
                        mol_type = protein
                        organism = synthetic construct
SEQUENCE: 649
KQEL                                                                    4

SEQ ID NO: 650          moltype = AA   length = 4
FEATURE                 Location/Qualifiers
REGION                  1..4
                        note = ER peptide tag
source                  1..4
                        mol_type = protein
                        organism = synthetic construct
SEQUENCE: 650
KREL                                                                    4

SEQ ID NO: 651          moltype = AA   length = 4
FEATURE                 Location/Qualifiers
REGION                  1..4
                        note = ER peptide tag
source                  1..4
                        mol_type = protein
                        organism = synthetic construct
SEQUENCE: 651
KSEL                                                                    4

SEQ ID NO: 652          moltype = AA   length = 4
FEATURE                 Location/Qualifiers
REGION                  1..4
                        note = ER peptide tag
source                  1..4
                        mol_type = protein
                        organism = synthetic construct
SEQUENCE: 652
KVEL                                                                    4

SEQ ID NO: 653          moltype = AA   length = 4
FEATURE                 Location/Qualifiers
REGION                  1..4
                        note = ER peptide tag
source                  1..4
                        mol_type = protein
                        organism = synthetic construct
SEQUENCE: 653
KWEL                                                                    4

SEQ ID NO: 654          moltype = AA   length = 4
FEATURE                 Location/Qualifiers
REGION                  1..4
                        note = ER peptide tag
source                  1..4
                        mol_type = protein
                        organism = synthetic construct
SEQUENCE: 654
KYEL                                                                    4

SEQ ID NO: 655          moltype = AA   length = 4
FEATURE                 Location/Qualifiers
REGION                  1..4
                        note = ER peptide tag
source                  1..4
                        mol_type = protein
                        organism = synthetic construct
SEQUENCE: 655
KEDL                                                                    4

SEQ ID NO: 656          moltype = AA   length = 4
FEATURE                 Location/Qualifiers
REGION                  1..4
                        note = ER peptide tag
source                  1..4
                        mol_type = protein
                        organism = synthetic construct
SEQUENCE: 656
```

KIEL 4

SEQ ID NO: 657      moltype = AA   length = 4
FEATURE             Location/Qualifiers
REGION              1..4
                    note = ER peptide tag
source              1..4
                    mol_type = protein
                    organism = synthetic construct
SEQUENCE: 657
DKEL 4

SEQ ID NO: 658      moltype = AA   length = 4
FEATURE             Location/Qualifiers
REGION              1..4
                    note = ER peptide tag
source              1..4
                    mol_type = protein
                    organism = synthetic construct
SEQUENCE: 658
FDEL 4

SEQ ID NO: 659      moltype = AA   length = 4
FEATURE             Location/Qualifiers
REGION              1..4
                    note = ER peptide tag
source              1..4
                    mol_type = protein
                    organism = synthetic construct
SEQUENCE: 659
KDEF 4

SEQ ID NO: 660      moltype = AA   length = 4
FEATURE             Location/Qualifiers
REGION              1..4
                    note = ER peptide tag
source              1..4
                    mol_type = protein
                    organism = synthetic construct
SEQUENCE: 660
KKEL 4

SEQ ID NO: 661      moltype = AA   length = 4
FEATURE             Location/Qualifiers
REGION              1..4
                    note = ER peptide tag
source              1..4
                    mol_type = protein
                    organism = synthetic construct
SEQUENCE: 661
HADL 4

SEQ ID NO: 662      moltype = AA   length = 4
FEATURE             Location/Qualifiers
REGION              1..4
                    note = ER peptide tag
source              1..4
                    mol_type = protein
                    organism = synthetic construct
SEQUENCE: 662
HAEL 4

SEQ ID NO: 663      moltype = AA   length = 4
FEATURE             Location/Qualifiers
REGION              1..4
                    note = ER peptide tag
source              1..4
                    mol_type = protein
                    organism = synthetic construct
SEQUENCE: 663
HIEL 4

SEQ ID NO: 664      moltype = AA   length = 4
FEATURE             Location/Qualifiers
REGION              1..4
                    note = ER peptide tag
source              1..4
                    mol_type = protein
                    organism = synthetic construct

```
SEQUENCE: 664
HNEL                                                                    4

SEQ ID NO: 665          moltype = AA  length = 4
FEATURE                 Location/Qualifiers
REGION                  1..4
                        note = ER peptide tag
source                  1..4
                        mol_type = protein
                        organism = synthetic construct
SEQUENCE: 665
HTEL                                                                    4

SEQ ID NO: 666          moltype = AA  length = 4
FEATURE                 Location/Qualifiers
REGION                  1..4
                        note = ER peptide tag
source                  1..4
                        mol_type = protein
                        organism = synthetic construct
SEQUENCE: 666
KTEL                                                                    4

SEQ ID NO: 667          moltype = AA  length = 4
FEATURE                 Location/Qualifiers
REGION                  1..4
                        note = ER peptide tag
source                  1..4
                        mol_type = protein
                        organism = synthetic construct
SEQUENCE: 667
HVEL                                                                    4

SEQ ID NO: 668          moltype = AA  length = 4
FEATURE                 Location/Qualifiers
REGION                  1..4
                        note = ER peptide tag
source                  1..4
                        mol_type = protein
                        organism = synthetic construct
SEQUENCE: 668
NDEL                                                                    4

SEQ ID NO: 669          moltype = AA  length = 4
FEATURE                 Location/Qualifiers
REGION                  1..4
                        note = ER peptide tag
source                  1..4
                        mol_type = protein
                        organism = synthetic construct
SEQUENCE: 669
QDEL                                                                    4

SEQ ID NO: 670          moltype = AA  length = 4
FEATURE                 Location/Qualifiers
REGION                  1..4
                        note = ER peptide tag
source                  1..4
                        mol_type = protein
                        organism = synthetic construct
SEQUENCE: 670
REDL                                                                    4

SEQ ID NO: 671          moltype = AA  length = 4
FEATURE                 Location/Qualifiers
REGION                  1..4
                        note = ER peptide tag
source                  1..4
                        mol_type = protein
                        organism = synthetic construct
SEQUENCE: 671
RNEL                                                                    4

SEQ ID NO: 672          moltype = AA  length = 4
FEATURE                 Location/Qualifiers
REGION                  1..4
                        note = ER peptide tag
source                  1..4
                        mol_type = protein
```

-continued

```
                            organism = synthetic construct
SEQUENCE: 672
RTDL                                                                            4

SEQ ID NO: 673              moltype = AA   length = 4
FEATURE                     Location/Qualifiers
REGION                      1..4
                            note = ER peptide tag
source                      1..4
                            mol_type = protein
                            organism = synthetic construct
SEQUENCE: 673
RTEL                                                                            4

SEQ ID NO: 674              moltype = AA   length = 4
FEATURE                     Location/Qualifiers
REGION                      1..4
                            note = ER peptide tag
source                      1..4
                            mol_type = protein
                            organism = synthetic construct
SEQUENCE: 674
SDEL                                                                            4

SEQ ID NO: 675              moltype = AA   length = 4
FEATURE                     Location/Qualifiers
REGION                      1..4
                            note = ER peptide tag
source                      1..4
                            mol_type = protein
                            organism = synthetic construct
SEQUENCE: 675
TDEL                                                                            4

SEQ ID NO: 676              moltype = AA   length = 4
FEATURE                     Location/Qualifiers
REGION                      1..4
                            note = ER peptide tag
source                      1..4
                            mol_type = protein
                            organism = synthetic construct
SEQUENCE: 676
SKEL                                                                            4

SEQ ID NO: 677              moltype = AA   length = 4
FEATURE                     Location/Qualifiers
REGION                      1..4
                            note = ER peptide tag
source                      1..4
                            mol_type = protein
                            organism = synthetic construct
SEQUENCE: 677
STEL                                                                            4

SEQ ID NO: 678              moltype = AA   length = 4
FEATURE                     Location/Qualifiers
REGION                      1..4
                            note = ER peptide tag
source                      1..4
                            mol_type = protein
                            organism = synthetic construct
SEQUENCE: 678
EDEL                                                                            4

SEQ ID NO: 679              moltype = DNA   length = 770
FEATURE                     Location/Qualifiers
misc_feature                1..770
                            note = Intron 1
source                      1..770
                            mol_type = genomic DNA
                            organism = unidentified
SEQUENCE: 679
gttcgttatc taccaccgtt ctatggattt tattccttct attcgtgttt attctattgg              60
tttatgttgc ttgcaatatg ttttttctga atcgtcgtc gttgtcttca attttatcca              120
tgtttcagag atcaattttg tttgtgtagt atgtgcttat tcttcttctt ttcgttcgag              180
ttgttaataa cggtgctatg gtgttttcaa aagtgttttt tttattactt ttgatttaaa              240
gtttttttgg taaggctttt atttgcttgt tatattcaaa tctttggatc cagatcttat              300
ataagttttt ggttcaagaa agttttggt tactgatgaa tagatctatt aactgttact              360
ttaatcgatt caagctaaag ttttttggtt actgatgaat agatctatta tctgttactt              420
```

```
ttaatcggtt caagctcaag ttttttggtt actgatgaat agatctatat acgtcacagt    480
gtgctaaaca tgcccttgtt ttatctcgat cttatgtatg ggagtgccat aaattttgtt    540
atgtctatttt ttttatctgt tggaatcata ctgagtttga tgcgttacga ttgagcatac    600
ctattttttgg gcttgttgta tggtgggtat ttagatctta atcttttttat gcttatgaaa    660
ggttttgtaa tgacaaaggt cttaatgttg ttaaactttt attttttactt tatatggtgt    720
gttgatgtgt tatggttttg acaacttttt tttttctgg attttttgcag                770

SEQ ID NO: 680            moltype = DNA   length = 93
FEATURE                   Location/Qualifiers
misc_feature              1..93
                          note = Intron 2
source                    1..93
                          mol_type = genomic DNA
                          organism = unidentified
SEQUENCE: 680
gtaaccatat ctttcatctg ttatgtgact acacattgct tctcttttg tgttctgtct    60
cattaattgc ggtttgttac atgttgtttg tag                                 93

SEQ ID NO: 681            moltype = DNA   length = 85
FEATURE                   Location/Qualifiers
misc_feature              1..85
                          note = Intron 3
source                    1..85
                          mol_type = genomic DNA
                          organism = unidentified
SEQUENCE: 681
gtaagcaacc aacacaccat ctaatacgct agcaaattca atattatcat tatccttata    60
tttgtttccg cgcttgattt tatag                                          85

SEQ ID NO: 682            moltype = DNA   length = 269
FEATURE                   Location/Qualifiers
misc_feature              1..269
                          note = Intron 4
source                    1..269
                          mol_type = genomic DNA
                          organism = unidentified
SEQUENCE: 682
gtttgtattt actcaaatgt tgatcagtag tgtttttagg acattgatta agaaacccaa    60
aaaataatta ttttattga aacgcataaa tttatactag ccgtgactgt ttttatgtcc   120
ttatatgatc ttcgcaatat atattttcta ttataagttt cttaaccaat gcactaactt   180
actgttaaca agaccttatt attaaacatc atctatcact tggttaattg tattcatttg   240
atgcatggta atgcattaca tatatacag                                     269

SEQ ID NO: 683            moltype = DNA   length = 486
FEATURE                   Location/Qualifiers
misc_feature              1..486
                          note = OLG1
source                    1..486
                          mol_type = other DNA
                          organism = synthetic construct
SEQUENCE: 683
ttgatcgtaa cacagactat gaagggtctt gatatacaga aggtggccgg gacttggtac    60
agtttggcaa tggccgcatc cgacatctcc ttgttggacg cacaatcagc cccattgcgt   120
gtgtacgtag aagagcttaa accaactccc gaggggatc tggaaattct gctccagaaa   180
tgggagaacg gtgagtgcgc ccagaagaag atcatcgaag agaagaccaa aattccagca   240
gtattcaaaa tcgacgcatt gaacgaaaat aaggtgctcg tactggacac tgattataag   300
aagtatctcc ttttctgtat ggagaactca gcagagcctg aacagagtct tgcctgccaa   360
tgccttgttc gtaccccaga ggtagatgat gaagctctgg aaaagttcga taaggccctt   420
aaggctctgc ctatgcacat taggcttcct ttcaatccaa ctcaacttga ggaacaatgt   480
cacatt                                                              486

SEQ ID NO: 684            moltype = AA   length = 162
FEATURE                   Location/Qualifiers
REGION                    1..162
                          note = OLG1
source                    1..162
                          mol_type = protein
                          organism = synthetic construct
SEQUENCE: 684
LIVTQTMKGL DIQKVAGTWY SLAMAASDIS LLDAQSAPLR VYVEELKPTP EGDLEILLQK    60
WENGECAQKK IIAEKTKIPA VFKIDALNEN KVLVLDTDYK KYLLFCMENS AEPEQSLACQ   120
CLVRTPEVDD EALEKFDKAL KALPMHIRLS FNPTQLEEQC HI                       162

SEQ ID NO: 685            moltype = DNA   length = 486
FEATURE                   Location/Qualifiers
misc_feature              1..486
                          note = OLG2
source                    1..486
                          mol_type = other DNA
```

```
                        organism = synthetic construct
SEQUENCE: 685
cttattgtga cccaaaccat gaagggcctc gacattcaaa aggttgccgg aacctggtac    60
tcccttgcta tggctgcttc cgatatctcc ttgctcgatg ctcaatccgc tccacttagg   120
gtgtacgtgg aagagttgaa gccaactcca gagggcgatc ttgagatctt gcttcaaaag   180
tgggagaacg atgagtgcgc ccagaagaag attatcgccg aaaagaccaa gattcccgcc   240
gtgttcaaga tcgatgctct caacgagaac aaggtgctcg tgctcgatac cgactacaag   300
aagtaccttc tcgtctgcat ggaaaactcc gctgagccag agcaatctct tgtttgccaa   360
tgccttgtga ggaccccaga ggttgacgat gaagctcttg agaagttcga caaggctctc   420
aaggctttgc ctatgcacat ccgccttagc ttcaacccca ctcagcttga ggaacagtgc   480
cacatc                                                              486

SEQ ID NO: 686          moltype = AA   length = 162
FEATURE                 Location/Qualifiers
REGION                  1..162
                        note = OLG2
source                  1..162
                        mol_type = protein
                        organism = synthetic construct
SEQUENCE: 686
LIVTQTMKGL DIQKVAGTWY SLAMAASDIS LLDAQSAPLR VYVEELKPTP EGDLEILLQK    60
WENDECAQKK IIAEKTKIPA VFKIDALNEN KVLVLDTDYK KYLLVCMENS AEPEQSLVCQ   120
CLVRTPEVDD EALEKFDKAL KALPMHIRLS FNPTQLEEQC HI                      162

SEQ ID NO: 687          moltype = DNA   length = 486
FEATURE                 Location/Qualifiers
misc_feature            1..486
                        note = OLG3
source                  1..486
                        mol_type = other DNA
                        organism = synthetic construct
SEQUENCE: 687
ctcattgtta cacaaaccat gaagggtctt gacattcaga aggttgctgg acatggtat    60
tcactagcga tggctgcttc tgatatctcc ctgttggatg cacagtctgc cccctgaga   120
gtgtatgttg aagaactgaa accgacacct gaaggagact tgaaattttt actccagaaa   180
tgggaaaatg atgagtgtgc ccaaaagaag ataatagccg agaagaccaa aattcctgct   240
gtgtttaaga ttgatgcttt gaatgagaac aaagtactag tcctcgacac tgattacaag   300
aaatacttat tagtgtgcat ggaaaacagc gcagagccag aacaatcact tgtttgtcaa   360
tgtttggtcc gtactccaga ggtagatgat gaagcattgg agaaatttga taaagcattg   420
aaggcacttc caatgcatat aaggcttagt ttcaatccta ctcagcttga agagcaatgc   480
cacatc                                                              486

SEQ ID NO: 688          moltype = AA   length = 162
FEATURE                 Location/Qualifiers
REGION                  1..162
                        note = OLG3
source                  1..162
                        mol_type = protein
                        organism = synthetic construct
SEQUENCE: 688
LIVTQTMKGL DIQKVAGTWY SLAMAASDIS LLDAQSAPLR VYVEELKPTP EGDLEILLQK    60
WENDECAQKK IIAEKTKIPA VFKIDALNEN KVLVLDTDYK KYLLVCMENS AEPEQSLVCQ   120
CLVRTPEVDD EALEKFDKAL KALPMHIRLS FNPTQLEEQC HI                      162

SEQ ID NO: 689          moltype = DNA   length = 486
FEATURE                 Location/Qualifiers
misc_feature            1..486
                        note = OLG4
source                  1..486
                        mol_type = other DNA
                        organism = synthetic construct
SEQUENCE: 689
cttatagtaa ctcaaaccat gaagggactt gatatccaaa aagttgcagg aacctggtac    60
tcactggcta tggcagcttc cgacatctcc ttgttggacg cacaatccgc accttgcgc   120
gtctacgttg aggagttgaa acctacacca gagggggatc ttgagatttt gctccagaaa   180
tgggagaacg acgagtgtgc ccagaaaaaa attatagcag agaagactaa aattcctgct   240
gttttttaaga ttgatgccct gaacgagaat aaggtactgg tcctcgacac tgattataaa   300
aagtatttgc tggtgtgtat ggagaacagt gctgaacctg aacagagcct ggtctgtcaa   360
tgtcttgtaa ggacacctga ggttgatgac gaggcacttg aaaaattcga caaggccctt   420
aaggctctgc ctatgcacat ccgtctgagt ttcaacccta ctcagttgga ggaacaatgt   480
catatt                                                              486

SEQ ID NO: 690          moltype = AA   length = 162
FEATURE                 Location/Qualifiers
REGION                  1..162
                        note = OLG4
source                  1..162
                        mol_type = protein
                        organism = synthetic construct
```

```
SEQUENCE: 690
LIVTQTMKGL DIQKVAGTWY SLAMAASDIS LLDAQSAPLR VYVEELKPTP EGDLEILLQK   60
WENDECAQKK IIAEKTKIPA VFKIDALNEN KVLVLDTDYK KYLLVCMENS AEPEQSLVCQ  120
CLVRTPEVDD EALEKFDKAL KALPMHIRLS FNPTQLEEQC HI                    162

SEQ ID NO: 691          moltype = DNA   length = 1256
FEATURE                 Location/Qualifiers
misc_feature            1..1256
                        note = OLG2 (intron 1)
source                  1..1256
                        mol_type = other DNA
                        organism = synthetic construct
SEQUENCE: 691
cttattgtga cccaaaccat gaagggcctc gacattcaaa aggttcgtta tctaccaccg    60
ttctatggat tttattcctt ctattcgtgt ttattctatt ggtttatgtt gcttgcaata   120
tgttttttct gaatctgtcg tcgttgtctt caatttatc catgtttcag agatcaattt    180
tgtttgtgta gtatgtgctt attcttcttc ttttcgttcg agttgttaat aacggtgcta   240
tggtgttttc aaaagtgttt tttttattac ttttgattta aagttttttt ggtaaggctt   300
ttatttgctt gttatattca aatctttgga tccagatctt atataagttt ttggttcaag   360
aaagttttttg ttactgatga aatagatcta ttaactgtta ctttaatcga ttcaagctaa   420
agttttttgg ttactgatga atagatctat tatctgttac tttaatcgg ttcaagctca    480
agttttttgg ttactgatga atagatctat atacgtcaca gtgtgctaaa catgcccttg   540
ttttatctcg atcttatgta tgggagtgcc ataaattttg ttatgtctat ttttttatct   600
gttggaatca tactgagttt gatgcgttac gattgagcat acctattttt gggcttgttg   660
tatggtgggt atttagatct taatcttttt atgcttatga aaggttttgt aatgacaaag   720
gtcttaatgt tgttaaactt ttatttttac tttatatggt gtgttgatgt gttatggttt   780
tgacaacttt ttttttttct ggattttgc aggttgccgg aacctggtac tcccttgcta    840
tggctgcttc cgatatctcc ttgctcgatg ctcaatccgc tccacttagg gtgtacgtgg   900
aagagttgaa gccaactcca gagggcgatc ttgagatctt gcttcaaaag tgggagaacg   960
atgagtgcgc ccagaagaag attatcgccg aaaagaccaa gattcccgcc gtgttcaaga  1020
tcgatgctct caacgagaac aaggtgctcg tgctcgatac cgactacaag aagtaccttc  1080
tcgtctgcat ggaaaactcc gctgagcagc agcaatctct tgtttgccaa tgccttgtga  1140
ggaccccaga ggttgacgat gaagctcttg agaagttcga caaggctctc aaggctttgc  1200
ctatgcacat ccgccttagc ttcaacccaa ctcagcttga ggaacagtgc cacatc      1256

SEQ ID NO: 692          moltype = DNA   length = 579
FEATURE                 Location/Qualifiers
misc_feature            1..579
                        note = OLG2 (intron 2)
source                  1..579
                        mol_type = other DNA
                        organism = synthetic construct
SEQUENCE: 692
cttattgtga cccaaaccat gaagggcctc gacattcaaa aggtaaccat atctttcatc    60
tgttatgtga ctacacattg cttctctttt tgtgttctgt ctcattaatt gcggtttgtt   120
acatgttgtt tgtaggttgc cggaacctgg tactcccttg ctatggctgc ttccgatatc   180
tccttgctcg atgctcaatc cgctccactt agggtgtaga gagttgaagc caact        240
ccagagggcg atcttgagat cttgcttcaa aagtgggaga acgatgagtg cgcccagaag   300
aagattatcg ccgaaaagac caagattccc gccgtgttca agatcgatgc tctcaacgag   360
aacaaggtgc tcgtgctcga taccgactac aagaagtacc ttctcgtctg catggaaaac   420
tccgctgagc cagagcaatc tcttgtttgc caatgccttg taggacccc agaggttgac   480
gatgaagctc ttgagaagtt cgacaaggct ctcaaggctt tgcctatgca catccgcctt   540
agcttcaacc caactcagct tgaggaacag tgccacatc                          579

SEQ ID NO: 693          moltype = DNA   length = 1155
FEATURE                 Location/Qualifiers
misc_feature            1..1155
                        note = OOVAL1
source                  1..1155
                        mol_type = other DNA
                        organism = synthetic construct
SEQUENCE: 693
ggtagcattg gggctgcttc tatggaattt tgtttcgatg tctttaaaga acttaaggta    60
caccatgcaa atgagaacat tttctactgt cccatcgcta taatgtctgc acttgcaatg   120
gtttaccttg gggctaaaga cagtactcgt acacaaataa ataaagtagt gagattcgat   180
aagttgcctg ggtcggggga ttctatcgaa gctcaatgtg gaccagtgt taacgtacat    240
agctccttgc gcgatatctt gaatcaaata acaaagccta atgatgtata ctcatttca    300
ttggcctctc gcttgtatgc cgaggaaaga tacccattct gccagaata ccttcagtgc   360
gtcaaggaac tctaccgcgg aggactcgag cccataaatt tccagactgc agcagaccag   420
gccagggagc tgattaactc ttgggtagag agccagacaa atggcataat caggaatgtg   480
ctgcagccat catcagttga ttcacaaaca gctatggtgc tggttaatgc aatcgtcttc   540
aaagggttgt gggaaaaggc ttttaaggac gaagatactc aagctatgcc tttccgtgta   600
acagagcaag aaagcaagcc tgtacaaatg atgtatcaga ttggtctgtt tcgtgttgcc   660
tctatgggtt cagagaaaat gaagatactc gaacttccct tcgcatcagg gactatggc    720
atgtggtttt tgttgcctga tgaggtatct ggtttgaac agctggaatc aataatcaat   780
ttcgagaagt tgacagaatg gaccagttct aatgttatgg aagagcgtaa gataaaagta   840
tatttgcctc gtatgaaaat ggaagaaaag tacaatttga ccagcgtttt gatggctatg   900
gcatcactg acgtttttc atcttctgct aatctcagcg gcatatccag cgcagagagc   960
ctcaaaaatat cccaagccgt ccatgctgca catgcagaga taaatgaggc tggtaggaa  1020
```

```
gtggtcggga gcgctgaagc tggggtagat gcagccagtg taagtgaaga gttcagggct    1080
gaccatccct tcctgttctg cattaagcac attgcaacta acgcagtact cttttttgga    1140
cgttgcgtga gcccc                                                     1155

SEQ ID NO: 694          moltype = AA   length = 385
FEATURE                 Location/Qualifiers
REGION                  1..385
                        note = OOVAL1
source                  1..385
                        mol_type = protein
                        organism = synthetic construct
SEQUENCE: 694
GSIGAASMEF CFDVFKELKV HHANENIFYC PIAIMSALAM VYLGAKDSTR TQINKVVRFD     60
KLPGFGDSIE AQCGTSVNVH SSLRDILNQI TKPNDVYSFS LASRLYAEER YPILPEYLQC    120
VKELYRGGLE PINFQTAADQ ARELINSWVE SQTNGIIRNV LQPSSVDSQT AMVLVNAIVF    180
KGLWEKAFKD EDTQAMPFRV TEQESKPVQM MYQIGLFRVA SMASEKMKIL ELPFASGTMS    240
MLVLLPDEVS GLEQLESIIN FEKLTEWTSS NVMEERKIKV YLPRMKMEEK YNLTSVLMAM    300
GITDVFSSSA NLSGISSAES LKISQAVHAA HAEINEAGRE VVGSAEAGVD AASVSEEFRA    360
DHPFLFCIKH IATNAVLFFG RCVSP                                          385

SEQ ID NO: 695          moltype = DNA   length = 1155
FEATURE                 Location/Qualifiers
misc_feature            1..1155
                        note = OOVAL2
source                  1..1155
                        mol_type = other DNA
                        organism = synthetic construct
SEQUENCE: 695
ggatcaattg gcgccgcatc tatggagttc tgcttcgatg ttttttaaaga gcttaaagtg    60
caccatgcca acgagaatat cttctattgc ccaattgtca ttatgtctgc ccttgctatg    120
gtgtacttgg gtgctaaaga ctctactagg acccagataa acaaggtagt cagattcgac    180
aagctgcctg gtttggcga ctctattgaa gctcagtgtg gtacttctgt taatgtccac    240
tcatccctcc gcgacatact taatcaaatt acaaaaccaa atgatgtgta ctcatttagt    300
ctggccagcc gtttgtacgc agaggaacgc taccctatcc tgccagagta tttgcaatgt    360
gtgaaggaac tttacagggg tgggcttgag ccaataaact tccaaacagc agccgaccaa    420
gctagggagc ttatcaattc ttgggtcgag agccaaacta acggaatcat ccgcaacgtc    480
ctccagccaa gttccgttga ttcccagacc gctatggtac ttgtgaatgc cattgtcttc    540
aaggggcttt gggagaaggc atttaaagac gaggacactc aggcaatgcc ctttcgtgtg    600
accgagcagg agtcaaaacc tgttcaaatg atgtaccaaa ttgggctgtt cagagttgct    660
agtatggcct ctgagaaaat gaagatcctt gaactcccat ttgcctccgg gacaatgtct    720
atgcttgtcc tcctgccaga tgaagtcagt gggctcgaac agctcgaaag cataataaac    780
tttgagaaac ttaccgaatg gacttcttcc aatgttatgg aggagcgtaa aattaaggtc    840
tatctgcccc gcatgaaaat ggaggaaaag tataatctca ctagcgtcct catggctatg    900
ggaattactg atgtattctc ctctagcgct aatctgagtg gaatctccag cgccgagtct    960
ctcaagataa gccaggccgt gcacgctgct catgctgaaa tcaacgaagc cggcagagag   1020
gtggtggggt cagctgaggc aggtgtagat gcagccagtg tctctgagga atttagagcc   1080
gatcacccctt tcctttttg cattaaacat atcgctacaa atgccgtttt gttttcggtt   1140
cgttgcgtta gtcca                                                   1155

SEQ ID NO: 696          moltype = AA   length = 385
FEATURE                 Location/Qualifiers
REGION                  1..385
                        note = OOVAL2
source                  1..385
                        mol_type = protein
                        organism = synthetic construct
SEQUENCE: 696
GSIGAASMEF CFDVFKELKV HHANENIFYC PIAIMSALAM VYLGAKDSTR TQINKVVRFD     60
KLPGFGDSIE AQCGTSVNVH SSLRDILNQI TKPNDVYSFS LASRLYAEER YPILPEYLQC    120
VKELYRGGLE PINFQTAADQ ARELINSWVE SQTNGIIRNV LQPSSVDSQT AMVLVNAIVF    180
KGLWEKAFKD EDTQAMPFRV TEQESKPVQM MYQIGLFRVA SMASEKMKIL ELPFASGTMS    240
MLVLLPDEVS GLEQLESIIN FEKLTEWTSS NVMEERKIKV YLPRMKMEEK YNLTSVLMAM    300
GITDVFSSSA NLSGISSAES LKISQAVHAA HAEINEAGRE VVGSAEAGVD AASVSEEFRA    360
DHPFLFCIKH IATNAVLFFG RCVSP                                          385

SEQ ID NO: 697          moltype = DNA   length = 1155
FEATURE                 Location/Qualifiers
misc_feature            1..1155
                        note = OOVAL3
source                  1..1155
                        mol_type = other DNA
                        organism = synthetic construct
SEQUENCE: 697
gggtccatcg gtgccgcctc aatggaattc tgctttgacg tcttcaagga acttaaggta    60
catcatgcca acgagaatat ttttactgt ccaatagcta tcatgagtgc acttgctatg    120
gtgtaccttg gagccaaaga ctcaacccgt acccagatca caaggtggt ccgctttgac    180
aaactgccag ggtttgggga ttctattgag gcccaatgcg gaacaagtgt gaacgtccac    240
tctagcttgc gcgatatact taatcaaata actaaaccaa atgatgtgta ttcattctct    300
ctcgccagca gactgtacgc agaagaaagg tatcccattc tccccgagta cctccaatgc    360
```

-continued

```
gtaaaggagt tgtacagagg cggcctggaa cccataaatt tccaaactgc cgcagatcag    420
gctcgtgagc tgataaattc atgggtcgag agccaaacta acggtatcat tcgtaatgtc    480
cttcaaccct caagtgtgga cagtcagaca gccatggtcc tcgtcaatgc tatagtcttc    540
aaaggcctgt gggaaaagac ctttaaggat gaagatactc aagcaatgcc ctttagagtc    600
acagagcaag aaagccaaac cgtgcaaatg atgtatcaaa tcggctctt tcgtgttgca    660
tccatggcat ctgaaaagat gaagatattg aactcccct cgcctctgg aacaatgagt    720
atgttggtac ttctgcccga tgaggtctct gggttggaac agcttgaatc tattattaac    780
ttcgagaaac tgaccgagtg gactagtagt aatgtcatgg aggagagaaa gattaaggtt    840
tatttgccac gcatgaagat ggaagagaaa tataacttga catctgtact gatggcaatg    900
ggtataaccg acgtatttag cagtagcgca aatctgtcag ggatttcttc agccgaaagt    960
ctcaagattt ctcaggcagt tcacgcagcc catgcagaga taaacgaagc aggccgcgaa   1020
gttgtcggat ctgcagaagc cggcgtggat cagccagtg tctccgaaga gttcagagca   1080
gaccacccctt tcctcttctg cattaagcac atcgcaacca acgcagtact ttttttcgga   1140
cgttgcgtgt cccca                                                    1155

SEQ ID NO: 698           moltype = AA   length = 385
FEATURE                  Location/Qualifiers
REGION                   1..385
                         note = OOVAL3
source                   1..385
                         mol_type = protein
                         organism = synthetic construct
SEQUENCE: 698
GSIGAASMEF CFDVFKELKV HHANENIFYC PIAIMSALAM VYLGAKDSTR TQINKVVRFD     60
KLPGFGDSIE AQCGTSVNVH SSLRDILNQI TKPNDVYSFS LASRLYAEER YPILPEYLQC    120
VKELYRGGLE PINFQTAADQ ARELINSWVE SQTNGIIRNV LQPSSVDSQT AMVLVNAIVF    180
KGLWEKAFKD EDTQAMPFRV TEQESKPVQM MYQIGLFRVA SMASEKMKIL ELPFASGTMS    240
MLVLLPDEVS GLEQLESIIN FEKLTEWTSS NVMEERKIKV YLPRMKMEEK YNLTSVLMAM    300
GITDVFSSSA NLSGISSAES LKISQAVHAA HAEINEAGRE VVGSAEAGVD AASVSEEFRA    360
DHPFLFCIKH IATNAVLFFG RCVSP                                          385

SEQ ID NO: 699           moltype = DNA   length = 1155
FEATURE                  Location/Qualifiers
misc_feature             1..1155
                         note = OOVAL4
source                   1..1155
                         mol_type = other DNA
                         organism = synthetic construct
SEQUENCE: 699
ggttcaatag gagctgcgtc tatggagttt tgttttgatg tctttaagga actcaaagtc     60
caccacgcca atgaaaatat tttctattgc cctattgcaa tcatgagtgc gctagccatg    120
gtttacttgg gtgcaaaaga cagtacgcgt actcaaataa acaaggttgt tcgctttgac    180
aagcttcctg gatttggaga tagtattgaa gcacaatggt gaactagcgt aaacgtccac    240
agctcattga gggacattct taaccaaatt accaagccaa atgatgtata tagttttttcc    300
ttggcatcac gactgtatgc agaagaaaga tatcctatcc tcccggaata tcttcagtgc    360
gtgaaagaat tatacagagg tgggctagag ccaatcaatt tcaaaccgc tgctgatcaa    420
gctcgcgagt tgattaactc atgggttgag agccagacaa atgggataat aagaaatgtt    480
cttcaaccat ctagtgtgga ctctcaaaca gcaatggtgc tcgtcaatgc gatagttttt    540
aaaggcttgt gggagaaaac attcaaagat gaggatactc aggcaatgcc attccgtgta    600
actgaacagg aatctaagcc tgttcaaatg atgtatcaga ttggtttgtt cagagttgcc    660
tctatggcat ctgaaaaaat gaaaattttg gagcttccat ttgctagtgg aacaatgtca    720
atgttagttt tactgcctga tgaagtgtcc ggtttagaac aattggaatc aattatcaac    780
tttgaaaagt tgaccgagtg gacttcctcc aatgtgatgg aggagaggaa gattaaggtg    840
taccttccca gaatgaagat ggaagagaaa tataacctga cttcggtcct aatggctatg    900
gggatcacag atgtgtttc ttcctcggca aaccttttcag gcatatccaa cgccgagtca    960
ttgaaaattt cacaggctgt tcatgcagct catgctgaaa tcaatgaggc cggggcgggaa   1020
gttgtgggca gtgctgaagc tggagttgat gctgcctcag tgtctgagga atttagagca   1080
gatcatcctt tcctcttctg cattaagcat attgctacca atgctgtact gttcttcggt   1140
aggtgtgtta gcccc                                                    1155

SEQ ID NO: 700           moltype = AA   length = 385
FEATURE                  Location/Qualifiers
REGION                   1..385
                         note = OOVAL4
source                   1..385
                         mol_type = protein
                         organism = synthetic construct
SEQUENCE: 700
GSIGAASMEF CFDVFKELKV HHANENIFYC PIAIMSALAM VYLGAKDSTR TQINKVVRFD     60
KLPGFGDSIE AQCGTSVNVH SSLRDILNQI TKPNDVYSFS LASRLYAEER YPILPEYLQC    120
VKELYRGGLE PINFQTAADQ ARELINSWVE SQTNGIIRNV LQPSSVDSQT AMVLVNAIVF    180
KGLWEKTFKD EDTQAMPFRV TEQESKPVQM MYQIGLFRVA SMASEKMKIL ELPFASGTMS    240
MLVLLPDEVS GLEQLESIIN FEKLTEWTSS NVMEERKIKV YLPRMKMEEK YNLTSVLMAM    300
GITDVFSSSA NLSGISSAES LKISQAVHAA HAEINEAGRE VVGSAEAGVD AASVSEEFRA    360
DHPFLFCIKH IATNAVLFFG RCVSP                                          385

SEQ ID NO: 701           moltype = DNA   length = 1925
FEATURE                  Location/Qualifiers
misc_feature             1..1925
```

|  |  |  |
|---|---|---|
|  | note = OOVAL2 (intron 1) | |
| source | 1..1925 | |
|  | mol_type = other DNA | |
|  | organism = synthetic construct | |

SEQUENCE: 701

```
ggatcaattg gcgccgcatc tatggagttc tgcttcgatg tttttaaaga gcttaaagtg   60
caccatgcca acgagaatat cttctattgc ccaattgcca ttatgtctgc ccttgctatg  120
gtgtacttgg gtgctaaaga ctctactagg acccagataa acaaggttcg ttatctacca  180
ccgttctatg gattttattc cttctattcg tgtttattct attggtttat gttgcttgca  240
atatgttttt tctgaatctg tcgtcgttgt cttcaatttt atccatgttt cagagatcaa  300
ttttgtttgt gtagtatgtg cttattcttc ttcttttcgt tcgagttgtt aataacggtg  360
ctatggtgtt ttcaaaagtg ttttttttat tactttgat ttaaagtttt tttggtaagg  420
cttttatttg cttgttatat tcaaatcttt ggatccagat cttatataag ttttttggttc  480
aagaaagttt ttggttactg atgaatagat ctattcaagc tttcttttaat cgattcaagc  540
taaagttttt tggttactga tgaatagatc tattatctgt tacttttaat cggttcaagc  600
tcaagttttt tggttactga tgaatagatc tatatacgtc acagtgtgct aaacatgccc  660
ttgtttttatc tcgatcttat gtatgggagt gccataaatt ttgttatgtc tatttttta  720
tctgttggaa tcatactgag tttgatgcgt tacgattgag catacctatt tttgggcttg  780
ttgtatggtg ggtatttaga tcttaatctt tttatgctta tgaaaggttt tgtaatgaca  840
aaggtcttaa tgttgttaaa cttttatttt tactttatat ggtgtgttga tgtgttatgg  900
ttttgacaac ttttttttt tctggatttt tgcaggtagt cagattcgac aagctgcctg  960
ggtttggcga ctctattgaa gctcagtgtg gtacttcctc taatgtccac tcatccctcc 1020
gcgacatact taatcaaatt acaaaaccaa atgatgtgta ctcatttagt ctggccagcc 1080
gtttgtacgc agaggaacgc taccctatcc tgccagagta tttgcaatgt gtgaaggaac 1140
tttacagggg tgggcttgag ccaataaact ttcaaacagc agccgaccaa gctagggagc 1200
ttatcaattc ttgggtcgag agccaaacta acggaatcat ccgcaacgtc ctccagcaa 1260
gttccgttga ttcccagacc gctatggtac ttgtgaatgc cattgtcttc aaggggcttt 1320
gggagaaggc atttaaagac gaggacactc aggcaatgcc ctttcgtgtg accgagcagg 1380
agtcaaaacc tgttcaaatg atgtaccaaa ttgggctgtt cagagttgct agtatggcct 1440
ctgagaaaat gaagatcctt gaactcccat ttgcctccgg gacaatgtct atgcttgtcc 1500
tcctgccaga tgaagtcagt gggctcgaac agctcgaaag cataataaac tttgagaaac 1560
ttaccgaatg gacttcttcc aatgttatgg aggagcgtaa aattaaggtc tatctgcccc 1620
gcatgaaaat ggaggaaaag tataatctca ctagcgtcct catggctatg gaattactga 1680
atgtattctc ctctagcgct aatctgagtg aatctccag cgccgagtct ctcaagataa 1740
gccaggccgt gcacgctgct catgctgaaa tcaacgaagc cggcagagag gtggtggggt 1800
cagctgaggc aggtgtagat gcagccagtg tctctgagga atttagagcc gatcaccctt 1860
tccttttttg cattaaacat atcgctacaa atgccgtttt gttttccggt cgttgcgtta 1920
gtcca                                                              1925
```

| SEQ ID NO: 702 | moltype = DNA length = 1248 |
|---|---|
| FEATURE | Location/Qualifiers |
| misc_feature | 1..1248 |
|  | note = OOVAL2 (intron 2) |
| source | 1..1248 |
|  | mol_type = other DNA |
|  | organism = synthetic construct |

SEQUENCE: 702

```
ggatcaattg gcgccgcatc tatggagttc tgcttcgatg tttttaaaga gcttaaagtg   60
caccatgcca acgagaatat cttctattgc ccaattgcca ttatgtctgc ccttgctatg  120
gtgtacttgg gtgctaaaga ctctactagg acccagataa acaaggtaac catatctttc  180
atctgttatg tgactacaca ttgcttctct ttttgtgttc tgtctcatta attgcggttt  240
gttacatgtt gtttgtaggt agtcagattc gacaagctgc ctgggtttgg cgactctatt  300
gaagctcagt gtggtacttc tgttaatgtc cactcatccc tccgcgacat acttaatcaa  360
attacaaaaac caaatgatgt gtactcattt agtctggcca gccgtttgta cgcagaggaa  420
cgctacccta tcctgccaga gtatttgcaa tgtgtgaagg aactttacag gggtgggctt  480
gagccaataa actttcaaac agcagccgac caagctaggg agcttatcaa ttcttgggtc  540
gagagccaaa ctaacggaat catccgcaac gtcctccagc aagttccgtt gattcccag  600
accgctatgg tacttgtgaa tgccattgtc ttcaaggggc tttgggagaa ggcatttaaa  660
gacgaggaca ctcaggcaat gccctttcgt gtgaccgagc aggagtcaaa acctgttcaa  720
atgatgtacc aaattgggct gttcagagtt gctagtatgg cctctgagaa aatgaagatc  780
cttgaactcc catttgcctc cgggacaatg tctatgcttg tcctcctgcc agatgaagtc  840
agtgggctcg aacagctcga agcataata acttttgaga acttaccga atggacttct  900
tccaatgtta tggaggagcg taaaattaag gtctatctgc cccgcatgaa aatggaggaa  960
aagtataatc tcactagcgt cctcatggct atgggaatta ctgaatgtat tcctctagc 1020
gctaatctga gtgaatctc cagcgccgag tctctcaaga taagccaggc cgtgcacgct 1080
gctcatgctg aaatcaacga agccggcaga gaggtggtgg gtcagctga ggcaggtgta 1140
gatgcagcca gtgtctctga ggaatttaga gccgatcacc cttttccttttt ttgcattaaa 1200
catatcgcta caaatgccgt tttgttttc ggtcgttgcg ttagtcca              1248
```

| SEQ ID NO: 703 | moltype = DNA length = 1384 |
|---|---|
| FEATURE | Location/Qualifiers |
| misc_feature | 1..1384 |
|  | note = GmSeed2 promoter |
| source | 1..1384 |
|  | mol_type = genomic DNA |
|  | organism = unidentified |

SEQUENCE: 703

```
aacacaagct tcaagtttta aaggaaaaaa tgtcagccaa aaactttaaa taaaatggta   60
acaaggaaat tattcaaaaa ttacaaacct cgtcaaaata ggaaagaaaa aagtttagg  120
```

```
gatttagaaa aaacatcaat ctagttccac cttattttat agagagaaga aactaatata    180
taagaactaa aaaacagaag aatagaaaaa aaaagtattg acaggaaaga aaaagtagct    240
gtatgcttat aagtactttg aggatttgaa ttctctctta taaaacacaa acacaatttt    300
tagattttat ttaaataatc atcaatccga ttataattat ttatatattt ttctattttc    360
aaagaagtaa atcatgagct tttccaactc aacatctatt tttttctct caaccttttg     420
cacatcttaa gtagtctcac cctttatata tataacttat ttcttacctt ttacattatg    480
taacttttat caccaaaacc aacaacttta aaattttatt aaatagactc cacaagtaac    540
ttgacactct tacattcatc gacattaact tttatctgtt ttataaatat tattgtgata    600
taatttaatc aaaataacca caaactttca taaaaggttc ttattaagca tggcatttaa    660
taagcaaaaa caactcaatc acttccatat aggaggtagc ctaagtacgt actcaaaatg    720
ccaacaaata aaaaaaaagt tgctttaata atgccaaaac aaattaataa acacttaca     780
acaccggatt ttttttaatt aaaatgtgcc atttaggata aatagttaat attttttaata  840
attatttaaa aagccgtatc tactaaaatg attttttattt ggttgaaaat attaatatgt   900
ttaaatcaac acaatctatc aaaattaaac taaaaaaaaa ataagtgtac gtggttaaca   960
ttagtacagt aatataagag gaaaatgaga aattaagaaa ttgaaagcga gtctaatttt   1020
taaattatga acctgcatat ataaaaggaa agaaagaatc caggaagaaa agaaatgaaa  1080
ccatgcatgg tcccctcgtc atcacgagtt tctgccattt gcaatagaaa cactgaaaca  1140
cctttctctt tgtcacttaa ttgagatgcc gaagccacct cacaccatga acttcatgag  1200
gtgtagcacc caaggcttcc atagccatgc atactgaaga atgtctcaag ctcagcaccc  1260
tacttctgtg acgtgtccct cattcacctt cctctcttcc ctataaataa ccacgcctca  1320
ggttctccgc ttcacaactc aaacattctc tccattggtc cttaaacact catcagtcat  1380
cacc                                                                1384

SEQ ID NO: 704           moltype = DNA   length = 1454
FEATURE                  Location/Qualifiers
misc_feature             1..1454
                         note = GmSeed12 promoter
source                   1..1454
                         mol_type = genomic DNA
                         organism = unidentified
SEQUENCE: 704
caactattat cgcatgatga tgtacgttaa gtcatcatca tctttaactt tatatattgt    60
taaaagtaga aaaataggt gatgcattat aaaataattt tataacatca tttaattata    120
aattatttat aataaatatt tgagttttta tagtaattac ctaaacaatt atatcaagac   180
taatgcctga ttagttgaca tgacgaaatt aaactcataa aagtaaagat gtttatgtgg   240
aaaactctta tacaattgag cggacttttt tccatggtag ttcagttttc ttctattcaa   300
tttatttttt tggtttccgc tcagaataag aataatttga taaattcatt tttaggcaat   360
taagaatatt tatttgacta actttttaat tgaaataaat ttacaataaa tactcaattt   420
atctttcaca atcaaaagat tgagatgttg taagatctcc gataatatac ttatatcttt   480
tcatttatta cgtttttcaaa tttgaatttt aatgtgtgtt gtaagtataa atttaaaata  540
aaaataaaaa caattattat atcaaaatgg caaaaacatt taatacgtat tatttaagaa   600
aaaaatatgt aataatatat ttatatttta atatctattc ttatgtattt tttaaaaatc   660
tattatatat tgatcaacta aaatatttt atatctacac ttttttatcaa                720
ttttcttgcg ttttttggca tatttaataa tgactattct ttaataatca atcattattc   780
ttacatggta catattgttg gaaccatatg aagtgtccat tgcatttgac tatgtggata   840
gtgtttttgat ccaggcctcc atttgccgct tattaattaa tttggtaaca gtccgtacta   900
atcagttact tatccttcct ccatcataat taatcttggt agtctcgaat gccacaacac   960
tgactagtct cttggatcat aagaaaaagc caaggaacaa aagaagacaa acacaatga   1020
gagtatcctt tgcatagcaa tgtcaagtt cataaaattc aaacaaaaac gcaatcacac   1080
acagtggaca tcacttatcc actagctgat caggatcgcc gcgtcaagaa aaaaaaactg  1140
gacccaaaa gccatgcaca acacacgta ctcacaaagg tgtcaatcga gcagcccaaa    1200
acattcacca actcaaccca tcatgagccc acacatttgt tgtttctaac ccaacctcaa  1260
actcgtattc tcttccgcca cctcattttt gtttatttca acaccgtcaa actgcatgc   1320
cacccgtgg ccaaatgtcc atgcatgtta acaagaccta tgactataaa tatctgcaat   1380
ctcggcccag gttttcatca tcaagaacca gttcaatatc ctagtacacc gtattaaaga  1440
atttaagata tact                                                    1454

SEQ ID NO: 705           moltype = DNA   length = 1543
FEATURE                  Location/Qualifiers
misc_feature             1..1543
                         note = PvPhas promoter
source                   1..1543
                         mol_type = genomic DNA
                         organism = unidentified
SEQUENCE: 705
cattgtactc ccagtatcat tatagtgaaa gttttggctc tctcgccggt ggtttttac    60
ctctatttaa aggggtttc cacctaaaaa ttctggtatc attctcactt tacttgttac    120
tttaatttct cataatcttt ggttgaaatt atcacgcttc cgcacacgat atccctacaa   180
atttattatt tgttaaacat tttcaaaccg cataaaattt atgaagtcc cgtctatctt   240
taatgtagtc taacattttc atattgaaat atataattta cttaatttta gcgttggtag  300
aaagcataat gatttattct tattcttctt catataaatg tttaatatac aatataaaca   360
aattctttac cttaagaagg atttcccatt ttatatttta aaatatatt tatcaaatat    420
ttttcaacca cgtaaatcac ataataataa gttgtttcaa aagtaataaa atttaactcc  480
ataatttttt tatttgactg atcttaaagc aacaccagt gacacaacta gccattttt    540
tctttgaata aaaaaatcca attatcattg tatttttttt atacaatgaa aatttccacca  600
aacaatgatt tgtggtattt ctgaagcaag tcatgttatg caaaattcta taattcccat  660
ttgacactac ggaagtaact gaagatctgc ttttacatgc gagacacatc ttctaaagta  720
attttaataa tagttactat attcaagatt tcatatatca aatactcaat attacttcta  780
aaaaattaat tagatataat taaaatatta ctttttttaat tttaagttta attgttgaat  840
```

```
ttgtgactat tgatttatta ttctactatg tttaaattgt tttataggta gtttaaagta    900
aatataagta atgtagtaga gtgttagagt gttaccctaa accataaact ataagattta    960
tggtggacta attttcatat atttcttatt gcttttacct tttcttggta tgtaagtccg   1020
taactggaat tactgtgggt tgccatgaca ctctgtggtc ttttggttca tgcatggatg   1080
cttgcgcaag aaaaagacaa agaacaaaga aaaaagacaa aacagagaga caaaacgcaa   1140
tcacacaacc aactcaaatt agtcactggc tgatcaagat cgccgcgtcc atgtatgtct   1200
aaatgccatg caaagcaaca cgtgcttaac atgcacttta aatggctcac ccatcccaac   1260
ccactcacaa acacattgcc ttttcttca tcatcaccac aaccacctgt atatattcat    1320
tctcttccgc cacctcaatt tcttcacttc aacacacgtc aacctgcata tgcgtgtcat   1380
cccatgccca aatctccatg catgttccta ccaccttctc tcttatataa tacctataaa   1440
tacctctaat atcactcact tctttcatca tccatccatc cagagtacta ctactctact   1500
actataaatac cccaacccaa ctcatattca atactactct act                    1543

SEQ ID NO: 706           moltype = DNA   length = 1130
FEATURE                  Location/Qualifiers
misc_feature             1..1130
                         note = BnNap promoter
source                   1..1130
                         mol_type = genomic DNA
                         organism = unidentified
SEQUENCE: 706
catcggtgat tgattccttt aaagacttat gtttcttatc ttgcttctga ggcaagtatt     60
cagttaccag ttaccactta tattctggac tttctgactg catcctcatt tttccaacat    120
tttaaatttc actattggct gaatgcttct tctttgagga agaaacaatt cagatggcag    180
aaatgtatca accaatgcat atatacaaat gtacctcttg ttctcaaaac atctatcgga    240
tggttccatt tgctttgtca tccaattagt gactacttta tattattcac tcctctttat    300
tactattttc atgcgaggtt gccatgtaca ttatatttgt aaggattgac gctattgagc    360
gttttttcttc aatttctttt attttagaca tgggtatgaa atgtgtgtta gagttgggtt    420
gaatgagata tacgttcaag tgaagtggca taccgttgtc gagtaaggat gacctaccca    480
ttcttgagac aaatgttaca ttttagtatc agagtaaaat gtgtacctat aactcaaatt    540
cgattgacat gtatccattc aacataaaat taaaccagcc tgcacctgca tccacatttc    600
aagtattttc aaaccgttcg gctcctatcc accgggtgta acaagacgga ttccgaattt    660
ggaagattt gactcaaatt cccaatttat attgaccgtg actaaatcaa ctttaactc     720
tataattctg attaagctcc caatttat tcccaacggc actacctcca aaatttatag    780
actctcatcc ccttttaaac caacttagta aacgttttt ttttaattt tatgaagtta    840
agttttacc ttgttttaa aaagaatcgt tcataagatg ccatgccaga acattagcta    900
cacgttacac atagcatgca gccgcggaga attgttttc ttcgccactt gtcactccct    960
tcaaacacct aagagcttct ctctcacagc acacacatac aatcacatgc gtgcatgcat   1020
tattacacgt gatcgccatg caaatctcct ttatagccta taaattaact catccgcttc   1080
actctttact caaaccaaaa ctcatcaata caaacaagat taaaaacata                1130

SEQ ID NO: 707           moltype = DNA   length = 57
FEATURE                  Location/Qualifiers
misc_feature             1..57
                         note = sig2 signal peptide encoding sequence
source                   1..57
                         mol_type = other DNA
                         organism = unidentified
SEQUENCE: 707
atggccaagc tagttttttc cctttgtttt ctgcttttca gtggctgctg cttcgct       57

SEQ ID NO: 708           moltype = AA   length = 19
FEATURE                  Location/Qualifiers
REGION                   1..19
                         note = sig2 signal peptide
source                   1..19
                         mol_type = protein
                         organism = unidentified
SEQUENCE: 708
MAKLVFSLCF LLFSGCCFA                                                 19

SEQ ID NO: 709           moltype = DNA   length = 96
FEATURE                  Location/Qualifiers
misc_feature             1..96
                         note = sig10 signal peptide encoding sequence
source                   1..96
                         mol_type = other DNA
                         organism = unidentified
SEQUENCE: 709
atggctactt caaagttgaa aacccagaat gtggttgtat ctctctccct aaccttaacc    60
ttggtactgg tgctactgac cagcaaggca aactca                              96

SEQ ID NO: 710           moltype = AA   length = 32
FEATURE                  Location/Qualifiers
REGION                   1..32
                         note = sig10 signal peptide
source                   1..32
                         mol_type = protein
                         organism = unidentified
```

```
SEQUENCE: 710
MATSKLKTQN VVVSLSLTLT LVLVLLTSKA NS                                  32

SEQ ID NO: 711              moltype = DNA  length = 66
FEATURE                     Location/Qualifiers
misc_feature                1..66
                            note = sig11 signal peptide encoding sequence
source                      1..66
                            mol_type = other DNA
                            organism = unidentified
SEQUENCE: 711
atgatgagag cacggttccc attactgttg ctgggacttg ttttcctggc ttcagtttct   60
gtctca                                                              66

SEQ ID NO: 712              moltype = AA  length = 22
FEATURE                     Location/Qualifiers
REGION                      1..22
                            note = sig11 signal peptide
source                      1..22
                            mol_type = protein
                            organism = unidentified
SEQUENCE: 712
MMRARFPLLL LGLVFLASVS VS                                            22

SEQ ID NO: 713              moltype = DNA  length = 72
FEATURE                     Location/Qualifiers
misc_feature                1..72
                            note = sig12 signal peptide encoding sequence
source                      1..72
                            mol_type = other DNA
                            organism = unidentified
SEQUENCE: 713
atgatgagag cgcggttccc attactgttg ctgggagttg ttttcctggc atcagtttct   60
gtctcatttg gc                                                       72

SEQ ID NO: 714              moltype = AA  length = 24
FEATURE                     Location/Qualifiers
REGION                      1..24
                            note = sig12 signal peptide
source                      1..24
                            mol_type = protein
                            organism = unidentified
SEQUENCE: 714
MMRARFPLLL LGVVFLASVS VSFG                                          24

SEQ ID NO: 715              moltype = DNA  length = 63
FEATURE                     Location/Qualifiers
misc_feature                1..63
                            note = coixss signal peptide encoding sequence
source                      1..63
                            mol_type = other DNA
                            organism = unidentified
SEQUENCE: 715
atggctacca agatatttgc cctccttgtg ctccttgctc tttcagcgag cgctacaact   60
gcg                                                                 63

SEQ ID NO: 716              moltype = AA  length = 21
FEATURE                     Location/Qualifiers
REGION                      1..21
                            note = coixss signal peptide
source                      1..21
                            mol_type = protein
                            organism = unidentified
SEQUENCE: 716
MATKIFALLV LLALSASATT A                                             21

SEQ ID NO: 717              moltype = DNA  length = 12
FEATURE                     Location/Qualifiers
misc_feature                1..12
                            note = KDEL signal peptide encoding sequence
source                      1..12
                            mol_type = other DNA
                            organism = unidentified
SEQUENCE: 717
aaggatgagc tt                                                       12

SEQ ID NO: 718              moltype = DNA  length = 253
FEATURE                     Location/Qualifiers
misc_feature                1..253
```

```
                        note = nosT terminator
source                  1..253
                        mol_type = genomic DNA
                        organism = unidentified
SEQUENCE: 718
gatcgttcaa acatttggca ataaagtttc ttaagattga atcctgttgc cggtcttgcg     60
atgattatca tataatttct gttgaattac gttaagcatg taataattaa catgtaatgc    120
atgacgttat ttatgagatg ggtttttatg attagagtcc cgcaattata catttaatac    180
gcgatagaaa acaaaatata gcgcgcaaac taggataaat tatcgcgcgc ggtgtcatct    240
atgttactag atc                                                       253

SEQ ID NO: 719          moltype = DNA  length = 480
FEATURE                 Location/Qualifiers
misc_feature            1..480
                        note = EU T terminator
source                  1..480
                        mol_type = genomic DNA
                        organism = unidentified
SEQUENCE: 719
aaagcagaat gctgagctaa aagaaaggct ttttccattt tcgagagaca atgagaaaag     60
aagaagaaga agaagaagaa gaagaagaag aaaaagagta aataataaag cccacaggag    120
gcgaagttct tgtagctcca tgttatctaa gttattgtta ttgtttgccc tatattttat    180
ttctgtcatt gtgtatgttt tgttcagttt cgatctcctt gcaaaatgca gagattatga    240
gatgaataaa ctaagttata ttattatacg tgttaatatt ctcctcctct ctctagctag    300
cctttgtttt tctctttttc ttatttgatt ttctttaaat caatccattt taggagaggg    360
ccagggagtg atccagcaaa acatgaagat tagaagaaac ttccctcttt ttttttcctga   420
aaacaattta acgtcgagat ttatctcttt ttgtaatgga atcattccta cagttatgac    480

SEQ ID NO: 720          moltype = DNA  length = 414
FEATURE                 Location/Qualifiers
misc_feature            1..414
                        note = StUbi3T terminator
source                  1..414
                        mol_type = genomic DNA
                        organism = unidentified
SEQUENCE: 720
ctgattttaa tgtttagcaa atgtcttatc agttttctct ttttgtcgaa cggtaattta     60
gagtttttt tgctatatgg attttcgttt ttgatgtatg tgacaaccct cgggattgtt    120
gatttatttc aaaactaaga gttttttgtct tattgttctc gtctattttg gaatatcaat   180
cttagtttta tatcttttct agttctctac gtgttaaatg ttcaacacac tagcaatttg    240
gcctgccagc gtatggatta tggaactatc aagtgtgtgg gatcgataaa tatgcttctc    300
aggaatttga gattttacag tctttatgct cattgggttg agtataatat agtaaaaaaa    360
tagtaaattt aagcaataat gttaggtgct atgtgtctgt cgagactatt ggcc          414

SEQ ID NO: 721          moltype = DNA  length = 249
FEATURE                 Location/Qualifiers
misc_feature            1..249
                        note = AtHSP T terminator
source                  1..249
                        mol_type = genomic DNA
                        organism = unidentified
SEQUENCE: 721
atatgaagat gaagatgaaa tatttggtgt gtcaaataaa aagcttgtgt gcttaagttt     60
gtgtttttt cttggcttgt tgtgttatga atttgtggct ttttctaata tcaaatgaat    120
gtaagatctc attataatga ataaacaaat gtttctataa tccattgtga atgttttgtt    180
ggatctcttc tgcagcatat aactactgta tgtgctatgg tatggactat ggaatatgat    240
taaagataa                                                            249

SEQ ID NO: 722          moltype = DNA  length = 376
FEATURE                 Location/Qualifiers
misc_feature            1..376
                        note = AtUbi10T terminator
source                  1..376
                        mol_type = genomic DNA
                        organism = unidentified
SEQUENCE: 722
atctcgtctc tgttatgctt aagaagttca atgtttcgtt tcatgtaaaa ctttggtggt     60
ttgtgttttg gggccttgta taatccctga tgaataagtg ttctactatg tttccgttcc    120
tgttatctct ttctttctaa tgacaagtcg aacttctgtc ttatcatcgc ttcgttttta    180
ttatctgtgc ttcttttgtt taatacgcct gcaaagtgac tcgactcgt ttagtgcagt    240
tctgcgaaac ttgtaaatag tccaattgtt ggcctctagt aatagatgta gcgaaagtgt    300
tgagctgttg ggttctaagg atggcttgaa catgttaatc ttttaggttc tgagtatgat    360
gaacattcgt tgttgc                                                    376

SEQ ID NO: 723          moltype = DNA  length = 916
FEATURE                 Location/Qualifiers
misc_feature            1..916
                        note = Rb7T terminator
source                  1..916
```

```
                            mol_type = genomic DNA
                            organism = unidentified
SEQUENCE: 723
taaaatgcgt caatctcttt gttcttccat attcatatgt caaaatctat caaaattctt    60
atatatcttt ttcgaatttg aagtgaaatt tcgataattt aaaattaaat agaacatatc   120
attatttagg tatcatattg atttttatac ttaattacta aatttggtta acttgtgaaag  180
tgtacatcaa cgaaaaatta gtcaaacgac taaaataaaa aaatatcatg tgttattaag   240
aaaattctcc tataagaata ttttaataga tcatatgttt gtaaaaaaaa ttaattttta   300
ctaacacata tatttactta tcaaaaattt gacaaagtaa gattaaaata atattcatct   360
aacaaaaaaa aaaccagaaa atgctgaaaa cccggcaaaa ccgaaccaat ccaaaccgat   420
atagttggtt tggtttgatt ttgatataaa ccgaaccaac tcggtccatt tgcaccccta   480
atcataatag ctttaatatt tcaagatatt attaagttaa cgttgtcaat atcctggaaa   540
ttttgcaaaa tgaatcaagc ctatatggct gtaatatgaa tttaaaagca gctcgatgtg   600
gtggtaatat gtaatttact tgattctaaa aaaatatccc aagtattaat aaatttctgct  660
aggaagaagg ttagctacga tttacagcaa agccagaata caaagaacca taaagtgatt   720
gaagctcgaa atatacgaag gaacaaatat ttttaaaaaa atacgcaatg acttggaaca   780
aaagaaagtg atatatttt  tgttcttaaa caagcatccc ctctaaagaa tggcagtttt   840
cctttgcatg taactattat gctcccttcg ttacaaaaat tttggactac tattgggaac   900
ttcttctgaa aatagt                                                    916

SEQ ID NO: 724              moltype = DNA  length = 1190
FEATURE                     Location/Qualifiers
misc_feature                1..1190
                            note = TM6T terminator
source                      1..1190
                            mol_type = genomic DNA
                            organism = unidentified
SEQUENCE: 724
gacatcctag gttcaatcaa attttactcg catattgtag actttatcct tttgtaattg    60
ttgcaaattt cttataaaat tgattatcta tattttaatc aaacatatat atacacttcc   120
aaataataaa atataatgac aacaaaacaa tcaagcacaa aaaatgccta taacaaataa   180
aaattacaac atactttac  cctgattcaa atcttcaaac actatgccag acaccataat   240
ccttctggat ataggataaa aatttaaagt gattttttac caattactat ttcataaatt   300
gttcaaatac aaaatatgat atttttaatta ttcccaactt tttgagcctc ctataactaa   360
tcaatataaa aaaataattt atcgattaag actaaagcaa aaaatattac cgatttgagt   420
tacaataaaa agttttatat cacgttatgg tattgtgaat tactctaact tcctagttct   480
tgggttctag cttttcttgg ctctctgaat cttcaaaacc tatatttgat aaagccataa   540
catacactaa tgctcccatg caaagtgctt ctaaaactcc ttaacttggt ctacggtaaa   600
atttcttcta aaacaaaagc gactatcaac ttctaatcgt tgaacaaata attcatctcc   660
aataaaggat tttaacaata aatatgaaat aagaagtcta tttctagtta ataaccaac   720
aatatcccaa acatttatga aatcaatata tgactgcatt acaatttgat cccaaaatgc   780
aaaaataaaa ttgcatctct attatagagt aaaaataatg catcatcaat tactaaccga   840
ttttactaac acgagaatct aattctcttc cacaaagtaa aactcaatgt caccgtcaat   900
tatttaagaa tttgaattat attccaacaa ctgagtaaga aactatataa ttgtgggggg   960
agggggggcc aaccctaaaa gtttacttct cataaaaggc tattagaaag gaaaggatac  1020
ataaaaagaa gagcaaagag agatcggaga agagagaaaa agtatatgaa tttattgaa   1080
gtacttttac ttattagagg taagagagtt ctagactgat ttggatacca tattagagtt  1140
attaccgata taaaaatcct tggttatgtt aattaaattt ctaaatatta              1190

SEQ ID NO: 725              moltype = DNA  length = 1197
FEATURE                     Location/Qualifiers
misc_feature                1..1197
                            note = arcT terminator
source                      1..1197
                            mol_type = genomic DNA
                            organism = unidentified
SEQUENCE: 725
aataaataaa atgggagcaa taaataaaat gggagctcat atatttacac catttacact    60
gtctattatt caccatgcca attattactt cataattttta aaattatgtc atttttaaaa   120
attgcttaat gatggaaagg attattataa gttaaaagta taacatagat aaactaacca   180
caaacaaat  caatataaac taacttactc tcccatctaa ttttttattta aatttcttta   240
cacttctctt ccatttctat ttctacaaca ttatttaaca ttttttattgt attttttctta   300
ctttctaact ctattcattt caaaaatcaa tatatgttta tcaccacctc tctaaaaaaa   360
acttacaat cattggtcca gaaaagttaa atcacgagat ggtcatttta gcattaaaac   420
aacgattctt gtatcactat ttttcagcat gtagtccatt ctcttcaaac aaagacagcg   480
gctatataat cgttgtgtta tattcagtct aaaacaattg ttatggtaaa agtcgtcatt   540
ttacgccttt ttaaaagata taaatgaca  gttatggtta aaagtcatca tgttagatcc   600
tccttaaaga tataaaatga cagttttgga taaaaagtgg tcattttata cgctcttgaa   660
agatataaaa cgacggttat ggtaaaagct gccattttaa atgaaatatt tttgttttga   720
ttcattttgt ttaatgctaa tcccatttaa attgacttgt acaattaaaa ctcacccacc   780
cagatacaat ataaactaac ttactctcac agctaagttt tatttaaatt tctttacact   840
tcttttccat ttctatttct atgacattaa ctaacatttt tctcgtaatt tttttttctta   900
ttttctaact ctatccattt caaatcgata tatgtttatc accaccactt taaaagaaa   960
atttacaatt tctcgtgcaa aaaagctaaa tcatgacgat catttagca ttaaaacaac  1020
gattctgta tcgttgtttt tcagcatgta gtccattcct tcaagcaaaa gacaacagct   1080
atataatcat cgtgttatat tcagtctaaa acaacagtaa tgataaagt catcattta   1140
ggcctttctg aaatatatag aacgacattc atggtaaaaa atcgtcattt tagatcc       1197

SEQ ID NO: 726              moltype = DNA  length = 65
```

| FEATURE | Location/Qualifiers |
|---|---|
| misc_feature | 1..65 |
| | note = soybean glutamine synthase 5' UTR |
| source | 1..65 |
| | mol_type = genomic DNA |
| | organism = unidentified |

SEQUENCE: 726
```
gaattctcta aaagagatct ttttctgctc tttgaagaaa gaagggtctt tgcttgattt    60
tggag                                                                65
```

| SEQ ID NO: 727 | moltype = DNA   length = 64 |
|---|---|
| FEATURE | Location/Qualifiers |
| misc_feature | 1..64 |
| | note = OVAL 5' UTR |
| source | 1..64 |
| | mol_type = genomic DNA |
| | organism = unidentified |

SEQUENCE: 727
```
acatacagct agaaagctgt attgccttta gcactcaagc tcaaaagaca actcagagtt    60
cacc                                                                 64
```

| SEQ ID NO: 728 | moltype = DNA   length = 65 |
|---|---|
| FEATURE | Location/Qualifiers |
| misc_feature | 1..65 |
| | note = LG 5' UTR |
| source | 1..65 |
| | mol_type = genomic DNA |
| | organism = unidentified |

SEQUENCE: 728
```
cccgagcccg ctgtctcagc cctccactcc ctgcagagct cagaagcgtg accccagctg    60
cagcc                                                                65
```

| SEQ ID NO: 729 | moltype = DNA   length = 13 |
|---|---|
| FEATURE | Location/Qualifiers |
| misc_feature | 1..13 |
| | note = arcUTR 5' UTR |
| source | 1..13 |
| | mol_type = genomic DNA |
| | organism = unidentified |

SEQUENCE: 729
```
tgaatgcatg atc                                                       13
```

| SEQ ID NO: 730 | moltype = DNA   length = 234 |
|---|---|
| FEATURE | Location/Qualifiers |
| misc_feature | 1..234 |
| | note = Ubimonomer |
| source | 1..234 |
| | mol_type = other DNA |
| | organism = unidentified |

SEQUENCE: 730
```
atgcagattt tcgtgaagac cttaacgggg aagacgatca ccctagaggt tgagtcttcc    60
gacaccatcg acaatgtcaa agccaagatc caggacaagg aagggatacc cccagaccag   120
cagcgtttga ttttcgccgg aaaagcagct gaggatggtc gtactcttgc cgactacaac   180
atccagaagg agtcaactct ccatctcgtg ctccgtctcc gtggtggtgg ttcc         234
```

| SEQ ID NO: 731 | moltype = AA   length = 78 |
|---|---|
| FEATURE | Location/Qualifiers |
| REGION | 1..78 |
| | note = Ubimonomer |
| source | 1..78 |
| | mol_type = protein |
| | organism = unidentified |

SEQUENCE: 731
```
MQIFVKTLTG KTITLEVESS DTIDNVKAKI QDKEGIPPDQ QRLIFAGKQL EDGRTLADYN    60
IQKESTLHLV LRLRGGGS                                                  78
```

| SEQ ID NO: 732 | moltype = DNA   length = 20 |
|---|---|
| FEATURE | Location/Qualifiers |
| misc_feature | 1..20 |
| | note = Seed2 forward primer |
| source | 1..20 |
| | mol_type = other DNA |
| | organism = synthetic construct |

SEQUENCE: 732
```
ctgagtttgg atctctccgc                                                20
```

| SEQ ID NO: 733 | moltype = DNA   length = 20 |
|---|---|
| FEATURE | Location/Qualifiers |
| misc_feature | 1..20 |

-continued

```
                        note = Seed2 reverse primer
source                  1..20
                        mol_type = other DNA
                        organism = synthetic construct
SEQUENCE: 733
acttgtatca atgcccgtcc                                                   20

SEQ ID NO: 734          moltype = DNA  length = 20
FEATURE                 Location/Qualifiers
misc_feature            1..20
                        note = TUA5 forward primer
source                  1..20
                        mol_type = other DNA
                        organism = synthetic construct
SEQUENCE: 734
ggatgtcaat gctgctgttg                                                   20

SEQ ID NO: 735          moltype = DNA  length = 20
FEATURE                 Location/Qualifiers
misc_feature            1..20
                        note = TUA5 reverse primer
source                  1..20
                        mol_type = other DNA
                        organism = synthetic construct
SEQUENCE: 735
aaccttagca aggtcaccac                                                   20

SEQ ID NO: 736          moltype = DNA  length = 20
FEATURE                 Location/Qualifiers
misc_feature            1..20
                        note = OLG1 forward primer
source                  1..20
                        mol_type = other DNA
                        organism = synthetic construct
SEQUENCE: 736
acgaacaagg cattggcagg                                                   20

SEQ ID NO: 737          moltype = DNA  length = 20
FEATURE                 Location/Qualifiers
misc_feature            1..20
                        note = OLG1 reverse primer
source                  1..20
                        mol_type = other DNA
                        organism = synthetic construct
SEQUENCE: 737
aggtgctcgt actggacact                                                   20

SEQ ID NO: 738          moltype = DNA  length = 21
FEATURE                 Location/Qualifiers
misc_feature            1..21
                        note = OLG2 forward primer
source                  1..21
                        mol_type = other DNA
                        organism = synthetic construct
SEQUENCE: 738
tcgatgctct caacgagaac a                                                 21

SEQ ID NO: 739          moltype = DNA  length = 22
FEATURE                 Location/Qualifiers
misc_feature            1..22
                        note = OLG2 reverse primer
source                  1..22
                        mol_type = other DNA
                        organism = synthetic construct
SEQUENCE: 739
tcctcacaag gcattggcaa ac                                                22

SEQ ID NO: 740          moltype = DNA  length = 21
FEATURE                 Location/Qualifiers
misc_feature            1..21
                        note = OLG3 forward primer
source                  1..21
                        mol_type = other DNA
                        organism = synthetic construct
SEQUENCE: 740
agaccaaaat tcctgctgtg t                                                 21

SEQ ID NO: 741          moltype = DNA  length = 20
FEATURE                 Location/Qualifiers
```

```
misc_feature              1..20
                          note = OLG3 reverse primer
source                    1..20
                          mol_type = other DNA
                          organism = synthetic construct
SEQUENCE: 741
tgattgttct ggctctgcgc                                                    20

SEQ ID NO: 742            moltype = DNA  length = 22
FEATURE                   Location/Qualifiers
misc_feature              1..22
                          note = OLG4 forward primer
source                    1..22
                          mol_type = other DNA
                          organism = synthetic construct
SEQUENCE: 742
ctggtcctcg acactgatta ta                                                 22

SEQ ID NO: 743            moltype = DNA  length = 21
FEATURE                   Location/Qualifiers
misc_feature              1..21
                          note = OLG4 reverse primer
source                    1..21
                          mol_type = other DNA
                          organism = synthetic construct
SEQUENCE: 743
aagtgcctcg tcatcaacct c                                                  21

SEQ ID NO: 744            moltype = DNA  length = 20
FEATURE                   Location/Qualifiers
misc_feature              1..20
                          note = OOVAL1 forward primer
source                    1..20
                          mol_type = other DNA
                          organism = synthetic construct
SEQUENCE: 744
gccgaggaaa gatacccat                                                     20

SEQ ID NO: 745            moltype = DNA  length = 21
FEATURE                   Location/Qualifiers
misc_feature              1..21
                          note = OOVAL1 reverse primer
source                    1..21
                          mol_type = other DNA
                          organism = synthetic construct
SEQUENCE: 745
tgtctggctc tctacccaag a                                                  21

SEQ ID NO: 746            moltype = DNA  length = 20
FEATURE                   Location/Qualifiers
misc_feature              1..20
                          note = OOVAL2 forward primer
source                    1..20
                          mol_type = other DNA
                          organism = synthetic construct
SEQUENCE: 746
aacgctaccc tatcctgcca                                                    20

SEQ ID NO: 747            moltype = DNA  length = 21
FEATURE                   Location/Qualifiers
misc_feature              1..21
                          note = OOVAL2 reverse primer
source                    1..21
                          mol_type = other DNA
                          organism = synthetic construct
SEQUENCE: 747
tggctctcga cccaagaatt g                                                  21

SEQ ID NO: 748            moltype = DNA  length = 20
FEATURE                   Location/Qualifiers
misc_feature              1..20
                          note = OOVAL3 forward primer
source                    1..20
                          mol_type = other DNA
                          organism = synthetic construct
SEQUENCE: 748
cagcagactg tacgcagaag                                                    20

SEQ ID NO: 749            moltype = DNA  length = 20
```

```
FEATURE                 Location/Qualifiers
misc_feature            1..20
                        note = OOVAL3 reverse primer
source                  1..20
                        mol_type = other DNA
                        organism = synthetic construct
SEQUENCE: 749
tcagctcacg agcctgatct                                                   20

SEQ ID NO: 750          moltype = DNA  length = 20
FEATURE                 Location/Qualifiers
misc_feature            1..20
                        note = OOVAL4 forward primer
source                  1..20
                        mol_type = other DNA
                        organism = synthetic construct
SEQUENCE: 750
aggagctgcg tctatggagt                                                   20

SEQ ID NO: 751          moltype = DNA  length = 21
FEATURE                 Location/Qualifiers
misc_feature            1..21
                        note = OOVAL4 reverse primer
source                  1..21
                        mol_type = other DNA
                        organism = synthetic construct
SEQUENCE: 751
tgcacccaag taaaccatgg c                                                 21

SEQ ID NO: 752          moltype = DNA  length = 2625
FEATURE                 Location/Qualifiers
misc_feature            1..2625
                        note = Construct AR07-22
source                  1..2625
                        mol_type = other DNA
                        organism = synthetic construct
SEQUENCE: 752
catcggtgat tgattccttt aaagacttat gtttcttatc ttgcttctga ggcaagtatt       60
cagttaccag ttaccactta tattctggac tttctgactg catcctcatt tttccaacat      120
tttaaatttc actattggct gaatgcttct tctttgagga agaaacaatt cagatggcag      180
aaatgtatca accaatgcat atatacaaat gtacctcttg ttctcaaaac atctatcgga      240
tggttccatt tgctttgtca tccaattagt gactacttta tattattcac tcctctttat      300
tactattttc atgcgaggtt gccatgtaca ttatatttgt aaggattgac gctattgagc      360
gttttttcttc aatttctttt attttagaca tgggtatgaa atgtgtgtta gagttgggtt     420
gaatgagata tacgttcaag tgaagtggca taccgttgtc gagtaaggat gacctaccca      480
ttcttgagac aaatgttaca ttttagtatc agagtaaaat gtgtacctat aactcaaatt      540
cgattgacat gtatccattc aacataaaat taaaccgatc tgcacctgca tccacatttc      600
aagtattttc aaaccgttcg gctcctatcc accgggtgta acaagacgga ttccgaattt      660
ggaagatttt gactcaaatt cccaatttat attgaccgtg actaaatcaa ctttaacttc      720
tataattctg attaagctcc caattatat tcccaacggc actacctcca aaatttatag       780
actctcatcc cctttaaac caacttagta aacgttttt tttttaattt tatgaagtta       840
agttttttacc ttgttttttaa aaagaatcgt tcataagatg ccatgccaga acattagcta    900
cacgttacac atagcatgca gccgcgggaga attgtttttc ttcgccactt gtcactccct    960
tcaaacacct aagagcttct ctctcacagc acacacatac aatcacatgc gtgcatgcat     1020
tattacagtt gatcgccatg caaatctcct ttatagccta taaattaact catccgcttc    1080
actcttttact caaaccaaaa ctcatcaata caaacaagat taaaaacata atgatgagag    1140
cacggttccc attactgttg ctgggacttg ttttcctggc ttcagtttct gtctcaggta     1200
gcattggggc tgcttctatg gaattttgtt tcgatgtctt taaagaactt aaggtacacc    1260
atgcaaatga gaacattttc tactgtccca tcgctataat gtctgcactt gcaatggttt    1320
accttgggggc taaagacagt actcgtacac aaataaataa agtagtgaga ttcgataagt    1380
tgcctgggtt cggggattct atcgaagctc aatgtgggac cagtgttaac gtacatagct    1440
ccttgcgcga tatcttgaat caaataacaa agcctaatga tgtatactca ttttcattgg    1500
cctctcgctt gtatgccgag gaaagatacc ccattctgcc agaataccttc agtgcgtca    1560
aggaactcta ccgcggagga ctcgaccccaa taaatttcca gactgcagca gaccaggcca    1620
gggagctgat taactcttgg gtagagagcc agacaaatgg cataatcagg aatgtgctgc    1680
agccatcatc agttgattca caaacagcta tggtgctggt taatgcaatc gtcttcaaag    1740
ggttgtggga aaaggctttt aaggacgaag atactcaagc tatgccttc cgtgtaacag     1800
agcaagaaag caagcctgta caaatgatgt atcagattgt tctgttcgt gttgcctcta     1860
tggcttcaga gaaatgaag atactcgaac ttcccttcgc atcagggact atgagcatgt    1920
tggttttgtt gcctgatgag gtatctggtt tggaacagct ggaatcaata atcaatttcg    1980
agaagttgac agaatggacc agttctaatg ttatggaaga gcgtaagata aaagtatatt    2040
tgcctcgtat gaaaatggaa gaaaagtaca atttgaccag cgttttgatg gctatgggca    2100
tcactgacgt ttttttcatct tctgctaatc tcagcggcat atccagcgca gagagcctca    2160
aaatatccca agcctccat gctgcacatg cagagataaa tgaggctggt agggaagtgg    2220
tcggagcgct tgaagctggg gtagatgcag ccagtgtaag tgaagagttc agggctgacc    2280
atccttcct gttctgcatt aagcacattg caactaacgc agtactcttt tttgacgtt     2340
gcgtgagccc caaggatgag ctttaaagat ctgatcgttc aaacatttgg caataaagtt    2400
tcttaagatt gaatcctgtt gccggtcttg cgatgattat catataattt ctgttgaatt    2460
acgttaagca tgtaataatt aacatgtaat gcatgacgtt atttatgaga tgggtttta    2520
```

```
tgattagagt cccgcaatta tacatttaat acgcgataga aaacaaaata tagcgcgcaa    2580
actaggataa attatcgcgc gcggtgtcat ctatgttact agatc                   2625

SEQ ID NO: 753          moltype = DNA  length = 2870
FEATURE                 Location/Qualifiers
misc_feature            1..2870
                        note = Construct AR07-23
source                  1..2870
                        mol_type = other DNA
                        organism = synthetic construct
SEQUENCE: 753
aacacaagct tcaagtttta aaaggaaaaa tgtcagccaa aaactttaaa taaaatggta     60
acaaggaaat tattcaaaaa ttacaaacct cgtcaaaata ggaaagaaaa aaagtttagg    120
gatttagaaa aaacatcaat ctagttccac cttattttat agagagaaga aactaataa    180
taagaactaa aaaacagaag aatagaaaaa aaaagtattg acaggaaaga aaagtagct    240
gtatgcttat aagtactttg aggatttgaa ttctctctta taaacacaa acacaatttt    300
tagattttat ttaaataatc atcaatccga ttataattat ttatatattt ttctattttc    360
aaagaagtaa atcatgagct tttccaactc aacatctatt ttttttctct caacctttct    420
cacatcttaa gtagtctcac cctttatata tataacttat ttcttacctt ttacattatg    480
taactttttat caccaaaacc aacaacttta aaatttatt aaatagactc cacaagtaac    540
ttgacactct tacattcatc gacattaact tttatctgtt ttataaatat tattgtgata    600
taatttaatc aaaataacca caaactttca taaaaggttc ttaatttaa tggcatttaa    660
taagcaaaaa caactcaatc actttcatat aggaggtagc ctaagtacgt actcaaaatg    720
ccaacaaata aaaaaaaagt tgctttaata atgccaaaac aaattaataa aacacttaca    780
acaccggatt ttttttaatt aaaatgtgcc atttaggata aatagttaat atttttaata    840
attatttaaa aagccgtatc tactaaaatg atttttattt ggttgaaaat attaatatgt    900
ttaaatcaac acaatctatc aaaattaaac taaaaaaaaa ataagtgtac gtggttaaca    960
ttagtacagt aatataagag gaaaatgaga aattaagaaa ttgaaagcga gtctaatttt    1020
taaattatga acctgcatat ataaaggaa agaaagaatc caggaagaaa agaaatgaaa    1080
ccatgcatgg tcccctcgtc atcacgagtt tctgccattt gcaatagaaa cactgaaaca    1140
cctttctctt tgtcacttaa ttgagatgcc gaagccacct cacaccatga acttcatgag    1200
gtgtagcacc caaggcttcc atagccatgc atactgaaga atgtctcaag ctcagcaccc    1260
tacttctgtg acgtgtccct cattcacctt cctctcttcc ctataaataa ccacgcctca    1320
ggttctccgc ttcacaactc aaacattctc tccattggtc cttaaacact catcagtcat    1380
caccatggcc aagctagttt tttcccttg ttttctgctt ttcagtggct gctgcttcgc    1440
tggtagcatt gggctgctt ctatggaatt ttgtttcgat gtctttaaag aacttaaggt    1500
acaccatgca aatgagaaca ttttctactg tcccatcgct ataatgtctg cacttgcaat    1560
ggtttacctt ggggctaaag acagtactcg tacacaaata aataaagtag tgagattcga    1620
taagttgcct gggttcgggg attctatcga agctcaatgt gggaccagtg ttaacgtaca    1680
tagctccttg cgcgatatct tgaatcaaat aacaaagcct aatgatgtat actcattttc    1740
attggcctct cgcttgtatg ccgaggaaag atacccatt ctgccagaat accttcagtg    1800
cgtcaaggaa ctctaccgcg gaggactcga gcccataaat ttccagactg cagcagacca    1860
ggccagggag ctgattaact cttgggtaga gagccagaca aatggcataa tcaggaatgt    1920
gctgcagcca tcatcagttg attcacaaac agctatggtg ctggttaatg caatcgtctt    1980
caaagggttg tgggaaaagg cttttaagga cgaagatact caagctatgc ctttccgtgt    2040
aacagagcaa gaaagcaagc ctgtacaaat gatgtatcag attggtctgt ttcgtgttgc    2100
ctctatggct tcagagaaaa tgaagatact cgaacttccc ttcgcatcag ggactatgag    2160
catgttggtt ttgttgcctg atgaggtatc tggtttggaa cagctggaat caataatcaa    2220
tttcgagaag ttgacagaat ggaccagttc taatgttatg gaagagcgta agataaaagt    2280
atatttgcct cgtatgaaaa tggaagaaaa gtacaattg accagcgttt tgatggctat    2340
gggcatcact gacgtttttt catcttctgc taatctcaca gcatatcca gcgcagagag    2400
cctcaaaata tcccaagccg tccatgctgc acatgcagag ataaatgagg ctggtaggga    2460
agtggtcggg agcgctgaag ctggggtaga tgcagccagt gtaagtgaag agttcagggc    2520
tgaccatccc ttcctgttct gcattaagca cattgcaact aacgcagtac tcttttttgg    2580
acgttgcgtg agcccaagg atgagcttta aagatcgat cgttcaaaca tttggcaata    2640
aagtttctta agattgaatc ctgttgccgg tcttgcgatg attatcatat aatttctgtt    2700
gaattacgtt aagcatgtaa taattaacat gtaatgcatg acgttattta tgagatgggt    2760
ttttatgatt agagtcccgc aattatacat ttaatacgcg atagaaaaca aaatatagcg    2820
cgcaaactag gataaattat cgcgcgcggt gtcatctatg ttactagatc                2870

SEQ ID NO: 754          moltype = DNA  length = 2946
FEATURE                 Location/Qualifiers
misc_feature            1..2946
                        note = Construct AR07-25
source                  1..2946
                        mol_type = other DNA
                        organism = synthetic construct
SEQUENCE: 754
caactattat cgcatgatga tgtacgttaa gtcatcatca tctttaactt tatatattgt     60
taaaagtaga aaaataggt gatgcattat aaaataattt tataacatca tttaattata    120
aattatttat aataaatatt tgagttttta tagtaattac ctaaacaatt atatcaagac    180
taatgcctga ttagttgaca tgacgaaatt aaactcataa agtaaagat gtttatgtgg    240
aaaactctta tacaattgag cggactttt tccatggtaa ttcagttttc ttctattcaa    300
tttattttt tggtttccgc tcagaataag taaattcatt tttaggcaat    360
taagaatatt tatttgacta acttttaat tgaaataaat ttacaataaa tactcaattt    420
atctttcaca atcaaaagat tgagatgttg taagatctcc gataatatac ttatatcttt    480
tcatttatta cgttttcaaa tttgaatttt aatgtgtgtt gtaagtataa atttaaaata    540
aaaataaaaa caattattat atcaaaatgg caaaaacatt taatacgtat tatttaagaa    600
aaaaatatgt aataatatat ttatatttta atatctattc ttatgtattt tttaaaaatc    660
```

| | | | | |
|---|---|---|---|---|
| tattatatat | tgatcaacta | aaatatttt | atatctacac | ttattttgca | ttttatcaa | 720 |
| tttcttgcg | ttttttggca | tatttaataa | tgactattct | ttaataatca | atcattattc | 780 |
| ttacatggta | catattgttg | gaaccatatg | aagtgtccat | tgcatttgac | tatgtggata | 840 |
| gtgttttgat | ccaggcctcc | atttgccgct | tattaattaa | tttggtaaca | gtccgtacta | 900 |
| atcagttact | tatcctcct | ccatcataat | taatcttggt | agtctcgaat | gccacaacac | 960 |
| tgactagtct | cttggatcat | aagaaaaagc | caaggaacaa | aagaagacaa | aacacaatga | 1020 |
| gagtatcctt | tgcatagcaa | tgtctaagtt | cataaaattc | aaacaaaaac | gcaatcacac | 1080 |
| acagtggaca | tcacttatcc | actagctgat | caggatcgcc | gcgtcaagaa | aaaaaaactg | 1140 |
| gaccccaaaa | gccatgcaca | acaacacgta | ctcacaaagg | tgtcaatcga | gcagcccaaa | 1200 |
| acattcacca | actcaaccca | tcatgagccc | acacatttgt | tgtttctaac | ccaacctcaa | 1260 |
| actcgtattc | tcttccgcca | cctcattttt | gtttatttca | acaccgtca | aactgcatgc | 1320 |
| caccccgtgg | ccaaatgtcc | atgcatgtta | acaagaccta | tgactataaa | tatctgcaat | 1380 |
| ctcggcccag | gttttcatca | tcaagaacca | gttcaatatc | ctagtacacc | gtattaaaga | 1440 |
| atttaagata | tactatggct | accaagatat | ttgccctcct | tgtgctcctt | gctctttcag | 1500 |
| cgagcgctac | aactgcgggt | agcattgggg | ctgcttctat | ggaattttgt | ttcgatgtct | 1560 |
| ttaaagaact | taaggtacac | catgcaaatg | agaacatttt | ctactgtccc | atcgctataa | 1620 |
| tgtctgcact | tgcaatggtt | taccttgggg | ctaaagacag | tactcgtaca | caaataaata | 1680 |
| aagtagtgag | attcgataag | ttgcctgggt | tcggggattc | tatcgaagct | caatgtggga | 1740 |
| ccagtgttaa | cgtacatagc | tccttgcgcg | atatcttgaa | tcaaataaca | aagcctaatg | 1800 |
| atgtatactc | attttcattg | gcctctcgct | tgtatgccga | ggaaagatac | cccattctgc | 1860 |
| cagaatacct | tcagtgcgtc | aaggaactct | accgcgagg | actcgagccc | ataaatttcc | 1920 |
| agactgcagc | agaccaggcc | agggagctga | ttaactcttg | ggtagagagc | agacaaatg | 1980 |
| gcataatcag | gaatgtgctg | cagccatcat | cagttgattc | acaaacagct | atggtgctga | 2040 |
| ttaatgcaat | cgtcttcaaa | gggttgtggg | aaaaggcttt | taaggacgaa | gatactcaag | 2100 |
| ctatgccttt | ccgtgtaaca | gagcaagaaa | gcaagcctgt | acaaatgatg | tatcagattg | 2160 |
| gtctgtttcg | tgttgcctct | atggcttcag | agaaaatgaa | gatactgaca | cttcccttcg | 2220 |
| catcagggac | tatgagcatg | ttggttttgt | tgcctgatga | ggtatctggt | ttggaacagc | 2280 |
| tggaatcaat | aatcaatttc | gagaagttga | cagaatggac | cagttctaat | gttatggaag | 2340 |
| agcgtaagat | aaaagtatat | ttgcctcgta | tgaaaatgga | agaaaagtac | aatttgacca | 2400 |
| gcgttttgat | ggctatgggc | atcactgacg | ttttttcatc | ttctgctaat | ctcagccgca | 2460 |
| tatccagcgc | agagagcctc | aaaatatccc | aagccgtcca | tgctgcacat | gcagagataa | 2520 |
| atgaggctgg | tagggaagtg | gtcgggagcg | ctgaagctgg | ggtagatgca | gccagtgtaa | 2580 |
| gtgaagagtt | cagggctgac | catcccttcc | tgttctgcat | taagcacatt | gcaactaacg | 2640 |
| cagtactctt | ttttggacgt | tgcgtgagcc | ccaaggatga | gcttaaaga | tctgatcgtt | 2700 |
| caaacatttg | gcaataaagt | ttcttaagat | tgaatcctgt | tgccggtctt | gcgatgatta | 2760 |
| tcatataatt | tctgttgaat | tacgttaagc | atgtaataat | taacatgtaa | tgcatgacgt | 2820 |
| tatttatgag | atgggttttt | atgattagag | tcccgcaatt | atacatttaa | tacgcgatag | 2880 |
| aaaacaaaat | atagcgcgca | aactaggata | aattatcgcg | cgcggtgtca | tctatgttac | 2940 |
| tagatc | | | | | 2946 |

| | |
|---|---|
| SEQ ID NO: 755 | moltype = DNA length = 2955 |
| FEATURE | Location/Qualifiers |
| misc_feature | 1..2955 |
| | note = Construct AR07-26 |
| source | 1..2955 |
| | mol_type = other DNA |
| | organism = synthetic construct |

SEQUENCE: 755

| | | | | | |
|---|---|---|---|---|---|
| caactattat | cgcatgatga | tgtacgttaa | gtcatcatca | tctttaactt | tatatattgt | 60 |
| taaaagtaga | aaaaataggt | gatgcattat | aaaataattt | tataacatca | tttaattata | 120 |
| aattatttat | aataaatatt | tgagttttta | tagtaattac | ctaaacaatt | atatcaagac | 180 |
| taatgcctga | ttagttgaca | tgacgaaatt | aaactcataa | aagtaaagat | gtttatgtgg | 240 |
| aaaactctta | tacaattgag | cggacttttt | tccatggtag | ttcagttttc | ttctattcaa | 300 |
| tttatttttt | tggttccgc | tcagaataag | aataatttga | taaattcatt | tttaggcaat | 360 |
| taagaatatt | tatttgacta | acttttaat | tgaaataaat | ttacaataaa | tactcaattt | 420 |
| atctttcaca | atcaaaagat | tgagatgttg | taagatctcc | gataatatac | ttatatcttt | 480 |
| tcatttatta | cgttttcaaa | tttgaatttt | aatgtgtgtt | gtaagtataa | atttaaaata | 540 |
| aaaataaaaa | caattattat | atcaaatgg | caaaacatt | taatacgtat | tatttaagaa | 600 |
| aaaaatatgt | aataataat | ttatattta | atatctattc | ttatgtattt | tttaaaaatc | 660 |
| tattatatat | tgatcaacta | aaatatttt | atatctacac | ttattttgca | ttttatcaa | 720 |
| tttcttgcg | ttttttggca | tatttaataa | tgactattct | ttaataatca | atcattattc | 780 |
| ttacatggta | catattgttg | gaaccatatg | aagtgtccat | tgcatttgac | tatgtggata | 840 |
| gtgttttgat | ccaggcctcc | atttgccgct | tattaattaa | tttggtaaca | gtccgtacta | 900 |
| atcagttact | tatcctcct | ccatcataat | taatcttggt | agtctcgaat | gccacaacac | 960 |
| tgactagtct | cttggatcat | aagaaaaagc | caaggaacaa | aagaagacaa | aacacaatga | 1020 |
| gagtatcctt | tgcatagcaa | tgtctaagtt | cataaaattc | aaacaaaaac | gcaatcacac | 1080 |
| acagtggaca | tcacttatcc | actagctgat | caggatcgcc | gcgtcaagaa | aaaaaaactg | 1140 |
| gaccccaaaa | gccatgcaca | acaacacgta | ctcacaaagg | tgtcaatcga | gcagcccaaa | 1200 |
| acattcacca | actcaaccca | tcatgagccc | acacatttgt | tgtttctaac | ccaacctcaa | 1260 |
| actcgtattc | tcttccgcca | cctcattttt | gtttatttca | acaccgtca | aactgcatgc | 1320 |
| caccccgtgg | ccaaatgtcc | atgcatgtta | acaagaccta | tgactataaa | tatctgcaat | 1380 |
| ctcggcccag | gttttcatca | tcaagaacca | gttcaatatc | ctagtacacc | gtattaaaga | 1440 |
| atttaagata | tactatgatg | agagcgcggt | tcccattact | gttgctggga | gttgttttcc | 1500 |
| tggcatcagt | ttctgtctca | tttggcggta | gcattgggc | tgcttctatg | gaattttgtt | 1560 |
| tcgatgtctt | taaagaactt | aaggtacacc | atgcaaatga | gaacatttc | tactgtccca | 1620 |
| tcgctataat | gtctgcactt | gcaatggttt | accttgggc | taaagacagt | actcgtacac | 1680 |
| aaataaataa | agtagtgaga | ttcgataagt | tgcctgggtt | cggggattct | atcgaagctc | 1740 |
| aatgtgggac | cagtgttaac | gtacatagct | ccttgcgcga | tatcttgaat | caaataacaa | 1800 |
| agcctaatga | tgtatactca | ttttcattgg | cctctcgctt | gtatgccgag | gaaagatacc | 1860 |

```
ccattctgcc agaataccct cagtgcgtca aggaactcta ccgcggagga ctcgagccca  1920
taaatttcca gactgcagca gaccaggcca gggagctgat taactcttgg gtagagagcc  1980
agacaaatgg cataatcagg aatgtgctgc agccatcatc agttgattca caaacagcta  2040
tggtgctggt taatgcaatc gtcttcaaag ggttgtggga aaaggctttt aaggacgaag  2100
atactcaagc tatgcctttc cgtgtaacag agcaagaaag cctgta caaatgatgt  2160
atcagattgg tctgtttcgt gttgcctcta tggcttcaga gaaaatgaag atactcgaac  2220
ttcccttcgc atcagggact atgagcatgt tggttttgtt gcctgatgag gtatctggtt  2280
tggaacagct ggaatcaata atcaatttcg agaagttgac agaatggacc agttctaatg  2340
ttatggaaga gcgtaagata aaagtatatt tgcctcgtat gaaaatggaa gaaaagtaca  2400
atttgaccag cgtttttgatg gctatgggca tcactgacgt ttttttcatct tctgctaatc  2460
tcagcggcat atccagcgca gagagcctca aaatatccca agccgtccat gctgcacatg  2520
cagagataaa tgaggctggt agggaagtgg tcgggagcgc tgaagctggg gtagatgcag  2580
ccagtgtaag tgaagagttc agggctgacc atcccttcct gttctgcatt aagcacattg  2640
caactaacgc agtactcttt tttggacgtt gcgtgagcca caaggatgag ctttaaagat  2700
ctgatcgttc aaacatttgg caataaagtt tcttaagatt gaatcctgtt gccggtcttg  2760
cgatgattat catataattt ctgttgaatt acgttaagca tgtaataatt aacatgtaat  2820
gcatgacgtt atttatgaga tgggttttta tgattagagt cccgcaatta tacatttaat  2880
acgcgataga aaacaaaata tagcgcgcaa actaggataa attatcgcgc gcggtgtcat  2940
ctatgttact agatc                                                  2955

SEQ ID NO: 756      moltype = DNA  length = 4019
FEATURE             Location/Qualifiers
misc_feature        1..4019
                    note = Construct AR07-27
source              1..4019
                    mol_type = other DNA
                    organism = synthetic construct
SEQUENCE: 756
cattgtactc ccagtatcat tatagtgaaa gttttggctc tctcgccggt ggttttttac  60
ctctatttaa aggggttttc cacctaaaaa ttctggtatc attctcactt tacttgttac  120
tttaatttct cataatcttt ggttgaaatt atcacgcttc cgcacacgat atccctacaa  180
atttattatt tgttaaacat tttcaaaccg cataaaattt tatgaagtcc cgtctatctt  240
taatgtagtc taacattttc atattgaaat atataattta cttaatttta gcgttggtag  300
aaagcataat gatttattct tattcttctt catatataac aatataaaca  360
aattctttac cttaagaagg atttcccatt ttatattta aaaatatatt tatcaaatat  420
ttttcaacca cgtaaatcac ataataataa gttgtttcaa aagtaataaa atttaactcc  480
ataatttttt tatttgactg atcttaaagc aacacccagt gacacaacta gccattttt  540
tctttgaata aaaaaatcca attatcattg tattttttt atacaatgaa aatttcacca  600
aacaatgatt tgtggtattt ctgaagcaag tcatgttatg caaaattcta taattcccat  660
ttgacactac ggaagtaact gaagatctgc ttttacatgc gagacacatc ttctaaagta  720
attttaataa tagttactat attcaagatt tcatatatca aatactcaat attacttcta  780
aaaaattaat tagatataat taaaatatta cttttttaat tttaagttta attgttgaat  840
ttgtgactat tgatttatta ttctactatg tttaaaattgt tttataggta gttaaagta  900
aatataagta atgtagtaga gtgttagagt gttaccctaa accataaaact ataagattta  960
tggtggacta attttcatat atttcttatt gcttttacct tttcttggta tgtaagtccg  1020
taactggaat tactgtgggt tgccatgaca ctctgtggtc ttttggttca tgcatggatg  1080
cttgcgcaag aaaaagacaa agaacaaaga aaaaagacaa aacagagaga caaaacgcaa  1140
tcacacaacc aactcaaatt agtcactggc tgatcaagat cgccgcgtcc atgtatgtct  1200
aaatgccatg caaagcaaca cgtgcttaac atgcacttta aatggctcac ccatcccaac  1260
ccactcacaa acacattgcc ttttcttca tcatcaccac aaccacctgt atatattcat  1320
tctcttccgc cacctcaatt tcttcacttc aacacacgtc aacctgcata tgcgtgtcat  1380
cccatgccca aatctccatg catgttccta ccaccttctc tcttatataa tacctataaa  1440
tacctctaat atcactcact tctttcatca tccatccatc cagagtacta ctactctact  1500
actataatac cccaacccaa ctcatattca atactactct acttgaatgc atgatcatgg  1560
ctacttcaaa gttgaaaacc cagaatgtgg ttgtatctct ctcccttaacc ttaaccttgg  1620
tactggtgct actgaccagc aaggcaaact caggtagcat tggggctgct tctatgaat  1680
tttgtttcga tgtctttaaa gaacttaagg tacaccatgc aaatgagaac attttctact  1740
gtcccatcgc tataatgtct gcacttgcaa tggtttaccct tgggctaaa acagtactc  1800
gtacacaaat aaaatataagta gtgagattcg ataagttgcc tgggttcggg gattctatcg  1860
aagctcaatg tgggaccagt gttaacgtac atagctcctt gcgcgatatc ttgaatcaaa  1920
taacaaagcc taatgatgta tactcatttt cattggcctc tcgcttgtat gccgaggaaa  1980
gatacccccat tctgccagaa taccttcagt gcgtcaagga actctaccgc ggaggactcg  2040
agcccataaa tttccagact gcagcagacc aggccaggga gctgattaac tcttgggtag  2100
agagccagac aaatggcata atcaggaatg tgctgcagac atcatcagtt gattcacaaa  2160
cagctatggt gctggttaat gcaatcgtct tcaaagggtt gtgggaaaag gcttttaagg  2220
acgaagatac tcaagctatg cctttccgtg taacagagca agaaagcaag cctgtacaaa  2280
tgatgtatca gattggtctg tttcgtgttg cctctatggc ttcagagaaa atgaagatac  2340
tcgaacttcc cttcgcatca gggactatga gcatgttggt tttgttgcct gatgaggtat  2400
ctggtttgga acagctggaa tcaataatca tttcgaaa gttgacagaa tggaccagtt  2460
ctaatgttat ggaagagcgt aagataaaag tatatttgcc tcgtatgaaa atggaagaaa  2520
agtacaattt gaccagcgtt tttgatggcta tgggcatcac tgacgttttt tcatcttctg  2580
ctaatctcag cggcatatcc agcgcagaga gcctcaaaat atcccaagcc gtccatgctg  2640
cacatgcaga gataaatgag gctggtaggg aagtggtcgg gagcgctgaa gctggggtag  2700
atgcagccag tgtaagtgaa gagttcaggg ctgaccatcc cttcctgttc tgcattaagc  2760
acattgcaac taacgcagta ctcttttttg gacgttgcgt gagcccaag gatgagcttt  2820
aaaataaata aatgggagc aataaataaa atgggagctc atatttac accatttaca  2880
ctgtctatta ttcaccatgc caattattac ttcataattt taaaattatg tcatttttaa  2940
aaattgctta atgatggaaa ggattattat aagttaaaag tataacatag ataaactaac  3000
cacaaaacaa atcaatataa actaacttac tctcccatct aatttttatt taaatttctt  3060
```

```
tacacttctc ttccatttct atttctacaa cattatttaa catttttatt gtatttttct   3120
tactttctaa ctctattcat ttcaaaaatc aatatatgtt tatcaccacc tctctaaaaa   3180
aaactttaca atcattggtc cagaaaagtt aaatcacgag atggtcattt tagcattaaa   3240
acaacgattc ttgtatcact attttcagc atgtagtcca ttctcttcaa acaaagacag    3300
cggctatata atcgttgtgt tatattcagt ctaaaacaat tgttatggta aaagtcgtca   3360
ttttacgcct ttttaaaaga tataaaatga cagttatggt taaaagtcat catgttagat   3420
cctccttaaa gatataaaat gacagttttg gataaaagt ggtcatttta tacgctcttg    3480
aaagatataa aacgacggtt atggtaaaag ctgccatttt aaatgaaata tttttgtttt   3540
agttcatttt gtttaatgct aatcccattt aaattgactt gtacaattaa aactcaccca   3600
cccagataca atataaacta acttactctc acagctaagt tttatttaaa tttctttaca   3660
cttcttttcc atttctattt ctatgacatt aactaacatt tttctcgtaa ttttttttct   3720
tattttctaa ctctatccat ttcaaatcga tatatgttta tcaccaccac tttaaaaaga   3780
aaatttacaa tttctcgtgc aaaaaagcta aatcatgacc gtcattttag cattaaaaca   3840
acgattcttg tatcgttgtt tttcagcatg tagtccattc ttttcaagca aagacaacag   3900
ctatataatc atcgtgttat attcagtcta aaacaacagt aatgataaaa gtcatcatttt  3960
taggcctttc tgaaatatat agaacgacat tcatggtaaa aaatcgtcat tttagatcc    4019

SEQ ID NO: 757          moltype = DNA  length = 4259
FEATURE                 Location/Qualifiers
misc_feature            1..4259
                        note = Construct AR15-16
source                  1..4259
                        mol_type = other DNA
                        organism = synthetic construct
SEQUENCE: 757
aacacaagct tcaagtttta aaaggaaaaa tgtcagccaa aaactttaaa taaaatggta   60
acaaggaaat tattcaaaaa ttcaaacct cgtcaaaata ggaaagaaaa aaagtttagg    120
gatttagaaa aacatcaat ctagttccac cttatttat agagagaaga aactaatata    180
taagaactaa aaaacagaag aatagaaaaa aaagtattg acaggaaaga aaagtagct    240
gtatgcttat aagtactttg aggatttgaa ttctctctta taaaacacaa acacaattt    300
tagatttat ttaaataatc atcaatccga ttataattat ttatatattt ttctattttc   360
aaagaagtaa atcatgagct tttccaactc aacatctatt tttttctct caacctttt    420
cacatcttaa gtagtctcac cctttatata tataactat ttcttacctt ttacattatg   480
taacttttat caccaaaacc aacaacttta aaatttatt aaatagactc cacaagtaac   540
ttgacactct tacattcatc gacattaact tttatctgtt ttataaatat tattgtgata   600
taattaatc aaaataacca caaactttca taaaaggttc ttattaagca tggcatttaa   660
taagcaaaaa caactcaatc actttcatat aggaggtagc ctaagtacgt actcaaaatg   720
ccaacaaata aaaaaaagt tgctttaata atgccaaatc aattaataa aacacttaca    780
acaccggatt tttttaatt aaaatgtgcc atttaggata aatagttaat attttaata    840
attatttaaa aagccgtatc tactaaaatg attttattt ggttgaaaat attaatatgt    900
ttaaatcaac acaatctatc aaaattaaac taaaaaaaa ataagtgtac gtggttaaca   960
ttagtacagt aatataagag gaaatgaga aattaagaaa ttgaaagcga gtctaatttt   1020
taaattatga acctgcatat ataaaaggaa agaaagaatc caggaagaaa agaaatgaaa   1080
ccatgcatgg tccctcgtc atcacgagtt tctgccattt gcaatagaaa cactgaaaca   1140
cctttctctt tgtcacttaa ttgagatgcc gaagccacct cacaccatga acttcatgag   1200
gtgtagcacc caaggcttcc atagccatgc atactgaaga atgtctcaag ctcagcaccc   1260
tacttctgtg acgtgtccct cattcacctt cctctcttcc ctataaataa cccacgcctca   1320
ggttctccgc ttcacaactc aaacattctc tccattggtc cttaaacact catcagtcat   1380
caccatggcc aagctagttt ttttccctttg tttctgctt ttcagtggct gctgcttcgc   1440
tggatcaatt ggcgccgcat ctatggagtt ctgcttcgat gtttttaaag agcttaaagt   1500
gcaccatgcc aacgagaata tcttctattg cccaattgac attatgtctg cccttgctat   1560
ggtgtacttg ggtgctaaag actctactag gacccagata aacaaggtag tcagattcga   1620
caagctgcct gggtttggcg actctattga agctcagtgt ggtacttctg ttaatgtcca   1680
ctcatccctc cgcgacatac ttaatcaaat tacaaaacca aatgatgtgt actcatttag   1740
tctggccagc cgtttgtacg cagaggaacg ctacccatcc ctgccagagt atttgcaatg   1800
tgtgaaggaa ctttacaggg gtgggcttga gccaataaac tttcaaacag cagccgacca   1860
agctagggag cttatcaatt cttgggtcga gagccaaact aacggaatca tccgcaacgt   1920
cctccagcca agttccgttg attcccagac cgctatggta cttgtgaatg ccattgtctt   1980
caagggggctt tgggagaagg catttaaaga cgaggacact caggcaatgc cctttcgttg   2040
gaccgagcag gagtcaaaac ctgttcaaat gatgtaccaa attgggctgt tcagagttga   2100
tagtatggcc tctgagaaaa tgaagatcct tgaactccca tttgcctccg ggacaatgtc   2160
tatgcttgtc ctcctgccag atgaagtcag tgggctcgaa cagctcgaaa gcataataaa   2220
ctttgagaaa cttaccgaat ggacttcttc caatgttatg gaggagcgta aaattaaggt   2280
ctatctgccc cgcatgaaaa tggaggaaaa gtataatctc actagcgtcc tcatgctcat   2340
gggaattact gatgtattct cctctagcgc taatctgagt ggaatctcca gcgccgagtc   2400
tctcaagata agccaggccg tgcacgctgc tcatgctgaa atcaacgaag ccggcagaga   2460
ggtggtgggg tcagctgagg caggtgtaga tgcagccagt gtctctgagg aatttagagc   2520
cgatcaccct ttccttttttt gcattaaaca tatcgctaca aatgccgttt tgttttttcgg   2580
tcgttgcgtt agtccaaagg atgagcttta aaaagcagaa tgctgagcta aaagaaaggc   2640
ttttttccatt ttcgagagac aatgagaaaa gaagaagaag aagaagaaga agaagaagaa   2700
gaaaagagta aataataaag ccccacagga ggcgaagttc ttgtagctcc atgttatcta   2760
agttattgat attgtttgcc ctatatttta tttctgtcat tgtgtatgtt ttgttcagtt   2820
tcgatctcct tgcaaaatgc agagattatg agatgaataa actaagttat attatttac   2880
gtgttaatat ttcctcctc tctctagcta gcctttttgt ttctctttt cttatttgat   2940
tttcttttaaa tcaatccatt ttaggagagg gccagggagt gatccagcaa aacatgaaga   3000
ttagaagaaa cttccctctt ttttttcctg aaaacaattt aacgtcgaga tttatctctt   3060
tttgtaatgg aatcatttct acagttatga ctcgattaaa aatcccaatt atatttggtc   3120
taatttagtt tggtattgag taaaacaaat tcgaaccaaa ccaaaatata aatatatagt   3180
ttttatatat atgcctttaa gactttttat agaatttct ttaaaaaata tctagaaata   3240
```

```
tttgcgactc ttctggcatg taatatttcg ttaaatatga agtgctccat ttttattaac  3300
tttaaataat tggttgtacg atcactttct tatcaagtgt tactaaaatg cgtcaatctc  3360
tttgttcttc catattcata tgtcaaaatc tatcaaaatt cttatatatc tttttcgaat  3420
ttgaagtgaa atttcgataa tttaaaatta aatagaacat atcattattt aggtatcata  3480
ttgatttta tacttaatta ctaaatttgg ttaactttga aagtgtacat caacgaaaaa  3540
ttagtcaaac gactaaaata aataaatatc atgtgttatt aagaaaattc tcctataaga  3600
atatttaat agatcatatg tttgtaaaaa aaattaattt ttactaacac atatatttac  3660
ttatcaaaaa tttgacaaag taagattaaa ataatattca tctaacaaaa aaaaaccag  3720
aaaatgctga aaacccggca aaaccgaacc aatccaaacc gatatagttg gtttggtttg  3780
attttgatat aaaccgaacc aactcggtcc atttgcaccc ctaatcataa tagctttaat  3840
atttcaagat attattaagt taacgttgtc aatatcctgg aaattttgca aaatgaatca  3900
agcctatatg gctgtaatat gaatttaaaa gcagctcgat gtggtggtaa tatgtaattt  3960
acttgattct aaaaaaatat cccaagtatt aataatttct gctaggaaga aggttagcta  4020
cgatttacag caaagccaga ataaaagaa ccataaagtg attgaagctc gaaatatacg  4080
aaggaacaaa tatttttaaa aaaatacgca atgacttgga acaaaagaaa gtgatatatt  4140
ttttgttctt aaacaagcat cccctctaaa gaatggcagt tttcctttgc atgtaactat  4200
tatgctccct tcgttacaaa aattttggac tactattggg aacttcttct gaaaatagt   4259

SEQ ID NO: 758         moltype = DNA   length = 4259
FEATURE                Location/Qualifiers
misc_feature           1..4259
                       note = Construct AR15-17
source                 1..4259
                       mol_type = other DNA
                       organism = synthetic construct
SEQUENCE: 758
aacacaagct tcaagtttta aaaggaaaaa tgtcagccaa aaactttaaa taaaatggta   60
acaaggaaat tattcaaaaa ttacaaacct cgtcaaaata ggaaagaaaa aaagtttagg   120
gatttagaaa aaacatcaat ctagttccac cttattttat agagagaaga aactaatata   180
taagaactaa aaaacagaag aatagaaaaa aaaagtattg acaggaaaga aaaagtagct   240
gtatgcttat aagtactttg aggatttgaa ttctctctta taaacacaa acacaatttt   300
tagattttat ttaaataatc atcaatccga ttataattat ttatatattt ttctatttc   360
aaagaagtaa atcatgagct tttccaactc aacatctatt ttttttctct caaccttttt   420
cacatcttaa gtagtctcac cctttatata tataacttat ttcttacctt ttacattatg   480
taacttttat caccaaaacc aacaactttta aaatttatt aaatagactc cacaagtaac   540
ttgacactct tacattcatc gacattaact tttatctgtt ttataaatat tattgtgata   600
taatttaatc aaaataacca caaactttca taaaaggttc ttattaagca tggcatttaa   660
taagcaaaata caactcaatc actttctcat aggaggtagc ctaagtacgt actcaaaatg   720
ccaacaaata aaaaaaagt tgctttaata atgccaaaca aaattaataa aacacttaca   780
acaccggatt tttttttaatt aaaatgtgcc atttaggata aatagttaat attttttaata   840
attatttaaa aagccgtatc tactaaaatg atttttattt ggttgaaaat attaatatgt   900
ttaaatcaac acaatctatc aaaattaaac taaaaaaaaa ataagtgtac gtggttaaca   960
ttagtacagt aatataagag gaaaatgaga aattaagaaa ttgaaagcga gtctaatttt   1020
taaattatga acctgcatat ataaaagaa agaaagaatc caggaagaaa agaaatgaaa   1080
ccatgcatgg tcccctcgtc atcacgagtt tctgccattt gcaatagaaa cactgaaaca   1140
cctttctctt tgtcacttaa ttgagatgcc gaagccacct cacaccatga acttcatgag   1200
gtgtagcacc caaggcttcc atagccatgc atactgaaga atgtctcaag ctcagcaccc   1260
tacttctgtg acgtgtccct cattcacctt cctctcttcc ctataaataa ccacgcctca   1320
ggttctccgc ttcacaactc aaacattctc tccattggtc cttaaacact catcagtcat   1380
caccatggcc aagctagttt ttttccctttg ttttctgctt tcagtggct gctgcttcgc   1440
tgggtccatc ggtgccgcct caatggaatt ctgcttgac gtcttcaagg aacttaaggt   1500
acatcatgcc aacagagaata tttttttactg tccaatagct atcatgagtg cacttgctat   1560
ggtgtacctt ggagccaaag actcaaaccccg tacccagatc aacaaggtgg tccgctttga   1620
caaactgcca gggtttgggg attctattga ggcccaatgc ggaacaagtg tgaacgtcca   1680
ctctcagcttg cgcgatatac ttaatcaaat aactaaacca aatgatgtgt attcattctc   1740
tctcgccagc agactgtacg cagaagaaag gtatcccatt ctccccgagt acctccaatg   1800
cgtaaaggag ttgtacagag gcggcctgga acccataaat ttccaaactg ccgcagatca   1860
ggctcgtgag ctgataaatt catgggtcga gagccaaact aacggtatca ttcgtaatgt   1920
ccttcaaccc tcaagtgtgg acagtcagac agccatggtc ctcgtcaatg ctatagtctt   1980
caaaggcctg tgggaaagaa cctttaagga tgaagatact caagcaatgc ccttttagagt   2040
cacagagcaa gaaaagcaaac ccgtgcaaat gatgtatcaa atcgggctct ttcgtgttgc   2100
atccatggca tctgaaaaga tgaagatatt ggaactcccc ttcgcctctg gaacaatgag   2160
tatgttgta cttctgcccg atgaggtctc tgggttggaa cagcttgaat ctattattaa   2220
cttcgagaaa ttgaccgagt ggactagtag taatgtcatg gaggagagaa agattaaggt   2280
ttatttgcca cgcatgaaga tggaagagaa atataacttg acatctgtac tgatggcaat   2340
gggtataacc gacgtattta gcagtagcgc caatctgtca gggatttctt cagccgaaag   2400
tctcaagatt tctcaggcag ttcacgcagc ccatgcagag ataaacgaag caggccgcga   2460
agttgtcgga tctgcagaag ccggcgtgga tgcagccagt gtctccgaag agttcagagc   2520
agaccaccct ttcctcttct tgcattaagca catcgcaacc agcagtac tttttttgcg   2580
acgttgcgtg tccccaaagg atgagcttta aaaagcagaa tgctgagcta aagaaaggc   2640
ttttccatt ttcgagagac aatgagaaaa gaagaagaag aagaagaaga agaagaagaa   2700
gaaagagta ataataaag ccccacagga ggcgaagttc ttgtagctcc atgttatcta   2760
agttattgat attgtttgcc ctatatttta tttctgtcat tgtgtatgtt ttgttcagtt   2820
tcgatctcct tgcaaaatgc agagattatg agatgaataa actaagttat attattatac   2880
gtgttaatat tctcctcctc tctctagcta gcctttgtt ttctcttttt cttatttgat   2940
tttctttaaa tcaatccatt ttaggagagg gccagggagt gatccagcaa acatgaaga   3000
ttagaagaaa cttccctctt tttttttcctg aaaacaattt aacgtcgaga tttatctctt   3060
tttgtaatgg aatcattct acagttatga ctcgattaaa aatcccaatt atatttggtc   3120
taatttagtt tggtattgag taaaacaaat tcgaaccaaa ccaaaatata aatatatagt   3180
```

```
ttttatatat atgcctttaa gacttttat agaattttct ttaaaaaata tctagaaata  3240
tttgcgactc ttctggcatg taatatttcg ttaaatatga agtgctccat ttttattaac  3300
tttaaataat tggttgtacg atcactttct tatcaagtgt tactaaaatg cgtcaatctc  3360
tttgttcttc catattcata tgtcaaaatc tatcaaaatt cttatatatc tttttcgaat  3420
ttgaagtgaa atttcgataa tttaaaatta aatagaacat atcattattt aggtatcata  3480
ttgattttta tacttaatta ctaaatttgg ttaactttga aagtgtacat caacgaaaaa  3540
ttagtcaaac gactaaaata aataaatatc atgtgttatt aagaaaattc tcctataaga  3600
atattttaat agatcatatg tttgtaaaaa aaattaattt ttactaacac atatatttac  3660
ttatcaaaaa tttgacaaag taagattaaa ataattattca tctaacaaaa aaaaaaccag  3720
aaaatgctga aaacccggca aaaccgaacc aatccaaacc gatatagttg gtttggtttg  3780
attttgatat aaaccgaacc aactcggtcc atttgcaccc ctaatcataa tagctttaat  3840
atttcaagat attattaagt taacgttgtc aatatcctgg aaattttgca aaatgaatca  3900
agcctatatg gctgtaatat gaatttaaaa gcagctcgat gtggtggtaa tatgtaattt  3960
acttgattct aaaaaaatat cccaagtatt aataatttct gctaggaaga aggttagcta  4020
cgatttacag caaagccaga atacaaagaa ccataaagtg attgaagctc gaaatatacg  4080
aaggaacaaa tattttttaaa aaaatacgca atgacttgga acaaaagaaa gtgatatatt  4140
ttttgttctt aaacaagcat cccctctaaa gaatggcagt tttcctttgc atgtaactat  4200
tatgctccct tcgttacaaa aattttggac tactattggg aacttcttct gaaaatagt  4259

SEQ ID NO: 759       moltype = DNA  length = 4259
FEATURE              Location/Qualifiers
misc_feature         1..4259
                     note = Construct AR15-18
source               1..4259
                     mol_type = other DNA
                     organism = synthetic construct
SEQUENCE: 759
aacacaagct tcaagtttta aaaggaaaaa tgtcagccaa aaactttaaa taaaatggta   60
acaaggaaat tattcaaaaa ttacaaacct cgtcaaaata ggaaagaaaa aaagtttagg  120
gatttagaaa aaacatcaat ctagttccac cttatttat agagagaaga aactaataa   180
taagaactaa aaaacagaag aatagaaaaa aaaagtattg acaggaaaga aaaagtagct  240
gtatgcttat aagtactttg aggatttgaa ttctctctta taaacacaa acacaatttt  300
tagatttat ttaaataatc atcaatccga ttataattat ttatatattt ttctattttc  360
aaagaagtaa atcatgagct tttccaactc aacatctatt tttttctct caacctttct  420
cacatcttaa gtagtctcac cctttatata tataacttat ttcttacctt ttacattatg  480
taactttat caccaaaacc aacaacttta aatttatt aaatagactc cacaagtaac  540
ttgacactct tacattcatc gacattaact tttatctgtt ttataaatat tattgtgata  600
taatttaatc aaaaataacca caaactttca taaaagttc taaatagca tggcatttaa  660
taagcaaaaa caactcaatc acttttcatat aggaggtagc ctaagtacgt actcaaaatg  720
ccaacaaata aaaaaaaagt tgctttaata atgccaaaac aaattaataa aacacttaca  780
acaccggatt ttttttaatt aaaatgtgcc atttaggata aatagttaat attttttaata  840
attattttaaa aagccgtatc tactaaaatg attttttattt ggttgaaaat attaatatgt  900
ttaaatcaac acaatctatc aaaattaaac taaaaaaaaa ataagtgtac gtggttaaca  960
ttagtacagt aatataagag gaaaatgaga aattaagaaa ttgaaagcga gtctaatttt 1020
taaattatga acctgcatat ataaaaggaa agaaagaatc caggaagaaa agaaatgaaa 1080
ccatgcatgg tcccctcgtc atcacgagtt tctgccattt gcaatagaaa cactgaaaca 1140
cctttctctt tgtcacttaa ttgagatgcc gaagccactc cacaccatga acttcatgag 1200
gtgtagcacc caaggcttcc atagccatgc atactgaaga atgtctcaag ctcagcaccc 1260
tacttctgtg acgtgtccct cattcacctt cctctcttcc ctataaataa ccacgcctca 1320
ggttctccgc ttcacaactc aaacattctc tccattggtc cttaaacact catcagtcat 1380
caccatggcc aagctagttt tttccctttg ttttctgctt ttcagtggct gctgcttcgc 1440
tggttcaata ggagctgcgt ctatggagtt ttgttttgat gtctttaagg aactcaaagt 1500
ccaccacgcc aatgaaaata ttttctattg ccctattgca atcatgagtg cgctagccat 1560
ggtttacttg ggtgcaaaag acagtacgcg tactcaaata aacaaggttg ttcgctttga 1620
caagcttcct ggatttggag atagtattga agcacaagtt ggaactagcg taaacgtcca 1680
cagctcattg agggacattc ttaaccaaat taccaagcca aatgatgtat atagttttc 1740
cttggcatca cgactgtatg cagaagaaag atatcctatc ctcccggaat atcttcagtg 1800
cgtgaaagaa ttatacagag gtgggctaga gccaatcaat tttcaaaccg ctgctgatca 1860
agctcgcgag ttgattaact catggttga gagccagaca aatgataa taagaaatgt 1920
tcttcaacca tctagtgtgg actctcaaac agcaatgtg ctcgtcaatg cgatagtttt 1980
taaaggcttg tgggagaaaa cattcaaaga tgaggatact caggcaatgc cattccgtgt 2040
aactgaacag gaatcaagc ctgttcaaat gatgtatcag attggttgt tcagagttgc 2100
ctctatggca tctgaaaaa tgaaatttt ggagcttcca tttgctagtg gaacaatgtc 2160
aatgttagtt ttactgcctg atgaagtgtc cggttagaa caattggaat caattcaa 2220
cttgaaaag ttgaccgagt ggacttcctc caatgtgatg gaggagagga agattaaggt 2280
gtaccttccc agaatgaaga tggaagagaa atataacctg acttcggtcc taatggctat 2340
ggggatcaca gatgtgtttt cttcctcggc aaacctttca ggcatatcaa gcgccgagtc 2400
attgaaaaatt tcacaggctg ttcatgcagc tcatgctgaa acaatgaagg ccgggcggga 2460
ggttgtgggc agtgctgaag ctggagttga tgctgcctca gtgtctgagg aatttagagc 2520
agatcatcct ttcctcttct gcattaagca tattgctacc aatgctgtac tgttcttcgg 2580
taggtgtgtt agcccaagg atgagcttta aaaagcagaa tgctgagcta aaagaaaggc 2640
tttttccatt ttcgagagac aatgagaaaa gaagaagaag aagaagaaga agaagaagaa 2700
gaaaaggta aataataaaag ccccacagga ggcgaagttc ttgtagctcc atgttatcga 2760
gttttgat attgtttgcc ctatattta tcagttagt ttgttcagtt 2820
tcgatcctcct tgcaaatgc agagattatg agatgaataa actaagttat attattatac 2880
gtgttaatat tctcctcctc tctctagcta gccttttgtt tttcttttt cttatttgat 2940
tttctttaaa tcaatccatt ttaggagagg gccagggagt gatccagcaa acatgaaga 3000
ttagaagaaa cttccctctt tttttcctg aaaacaattt aacgtcgaga tttatctctt 3060
tttgtaatgg aatcattct acagttatga ctcgattaaa aatcccaatt atatttggtc 3120
```

```
taatttagtt tggtattgag taaaacaaat tcgaaccaaa ccaaaatata aatatatagt 3180
ttttatatat atgcctttaa gactttttat agaattttct ttaaaaaata tctagaaata 3240
tttgcgactc ttctggcatg taatatttcg ttaaatatga agtgctccat ttttattaac 3300
tttaaataat tggttgtacg atcactttct tatcaagtgt tactaaaatg cgtcaatctc 3360
tttgttcttc catattcata tgtcaaaatc tatcaaaatt cttatatatc ttttttcgaat 3420
ttgaagtgaa atttcgataa tttaaaatta aatagaacat atcattattt aggtatcata 3480
ttgattttta tacttaatta ctaaatttgg ttaactttga aagtgtacat caacgaaaaa 3540
ttagtcaaac gactaaaata aataaatatc atgtgttatt aagaaaattc tcctataaga 3600
atattttaat agatcatatg tttgtaaaaa aaattaattt ttactaacac atatatttac 3660
ttatcaaaaa tttgacaaag taagattaaa ataatattca tctaacaaaa aaaaaaccag 3720
aaaatgctga aaaccccggca aaaccgaacc aatccaaacc gatatagttg gtttggtttg 3780
attttgatat aaaccgaacc aactcggtcc atttgcaccc ctaatcataa tagctttaat 3840
atttcaagat attattaagt taacgttgtc aatatcctgg aaattttgca aaatgaatca 3900
agcctatatg gctgtaatat gaatttaaaa gcagctcgat gtggtggtaa tatgtaattt 3960
acttgattct aaaaaaatat cccaagtatt aataattcct gctaggaaga aggttagcta 4020
cgatttacag caaagccaga atacaaagaa ccataaagtg attgaagctc gaaatatacg 4080
aaggaacaaa tattttttaaa aaaatacgca atgacttgga acaaaagaaa gtgatatatt 4140
ttttgttctt aaacaagcat cccctctaaa gaatggcagt tttcctttgc atgtaactat 4200
tatgctccct tcgttacaaa aattttggac tactattggg aacttcttct gaaaatagt 4259

SEQ ID NO: 760          moltype = DNA  length = 4247
FEATURE                 Location/Qualifiers
misc_feature            1..4247
                        note = Construct AR15-19
source                  1..4247
                        mol_type = other DNA
                        organism = synthetic construct
SEQUENCE: 760
aacacaagct tcaagtttta aaaggaaaaa tgtcagccaa aaactttaaa taaaatggta 60
acaaggaaat tattcaaaaa ttacaaacct cgtcaaaata ggaaagaaaa aaagtttagg 120
gatttagaaa aaacatcaat ctagttccac cttattttat agagagaaga aactaataa 180
taagaactaa aaaacagaag aatagaaaaa aaagtattg acaggaaaga aaagtagct 240
gtatgcttat aagtactttg aggatttgaa ttctctctta taaacacaa acacaatttt 300
tagattttat ttaaataatc atcaatccga ttataattat ttatatattt ttctattttc 360
aaagaagtaa atcatgagct tttccaactc aacatctatt tttttctct caaccttttt 420
cacatcttaa gtagtctcac cctttatata tataacttat ttcttacctt ttacattatg 480
taacttttat caccaaaacc aacaacttta aattttatt aaatagactc cacaagtaac 540
ttgacactct tacattcatc gacattaact tttatctgtt ttataaatat tattgtgata 600
taatttaatc aaaataacca caaactttca taaaaggttc ttattaagca tggcatttaa 660
taagcaaaaa caactcaatc actttcatat aggaggtagc ctaagtacgt actcaaaatg 720
ccaacaaata aaaaaaaagt tgctttaata atgccaaaac aaattaataa aacacttaca 780
acaccggatt ttttttaatt aaaatgtgcc atttaggata aatagttaat attttttaata 840
attatttaaa aagccgtatc tactaaaatg attttttattt ggttgaaaat attaatatgt 900
ttaaatcaac acaatctatc aaaattaaac taaaaaaaaa ataagtgtac gtggttaaca 960
ttagtacagt aatataagag gaaaatgaga aattaagaaa ttgaaagcga gtctaatttt 1020
taaattatga acctgcatat ataaaggaa agaaagaatc caggaagaaa agaaatgaaa 1080
ccatgcatgg tcccctcgtc atcacgagtt tctgccattt gcaatagaaa cactgaaaca 1140
cctttctctt tgtcacttaa ttgagatgcc gaagccacct cacaccatga acttcatgag 1200
gtgtagcacc caaggcttcc atagccatgc atactgaaga atgtctcaag ctcagcaccc 1260
tacttctgtg acgtgtccct cattcacctt cctctcttcc ctataaataa ccacgcctca 1320
ggttctccgc ttcacaactc aaacattctc tccattggtc cttaaacact catcagtcat 1380
caccatggcc aagctagttt ttttccctttg ttttctgctt ttcagtggct gctgcttcgc 1440
tggatcaatt ggcgccgcat ctatggagtt ctgcttcgat gttttttaaag agcttaaagt 1500
gcaccatgcc aacgagaata tcttctattg cccaattgcc attatgtctg cccttgctat 1560
ggtgacttg ggtgctaaag actctactag gacccagata aacaaggtag tcagattcga 1620
caagctgcct gggtttggcg actctcattga agctcagtgt ggtacttctg ttaatgtcca 1680
ctcatccctc cgcgacatac ttaatcaaat tacaaaacca aatgatgtgt actcattttag 1740
tctggccagc cgtttgtacg cagaggaacg ctacccctatc ctgccagagt atttgcaatg 1800
tgtgaaggaa cttttacaggg gtgggcttga gccaataaac tttcaaacag cagccgacca 1860
agctagggag cttatcaatt cttgggtcga gagccaaact aacgaatca tccgcaacgt 1920
cctccagcca agttccgttg attcccgac cgctatggta cttgtgaatg ccattgtctt 1980
caaggggctt tgggagaagg catttaaaga cgaggacact caggcaatgc cctttcgtgt 2040
gaccgagcag gagtcaaaac ctgttcaaat gatgtaccaa atttgggctgt tcagagttgc 2100
tagtatggcc tctgagaaaa tgaagatcct tgaactccca tttgcctccg ggacaatgtc 2160
tatgcttgtc ctcctgccag atgaagtcag tgggctcgaa cagctcgaaa gcataaataa 2220
cttttgagaaa cttaccgaat ggacttcttc caatgttatg gaggagccgta aaattaaggt 2280
ctatctgccc cgcatgaaaa tggaggaaaa gtataatctc actagcgtcc tcatggctat 2340
gggaattact gatgtattct cctctagcgc taatctgagt ggaatctcca gcgccgagtc 2400
tctcaagata agccaggccg tgcacgctgc tcatgctgaa atcaacgagc cgggcagaga 2460
ggtggtgggg tcagctgagg caggtgtaga tgcagccagt gtctctgagg aatttagagc 2520
cgatcaccct ttcctttttt gcattaaaca tatcgctaca aatgccgttt tgttttttcgg 2580
tcgttgcgtt agtccataaa aagcagaatg ctgagctaaa agaaaggctt tttccatttt 2640
cgagagacaa tgagaaaaga agaagaagaa gaagaagaag aaagagtaaa 2700
taataaagcc ccacaggagg cgaagttctt gtagctccat gttatctaag ttattgatat 2760
tgtttgccct atatttttatt tctgtcattg tgtatgtttt gttcagtttc gatctccttg 2820
caaaatgcag agattatgag atgaataaac taagttatat tattatacgt gttaatattc 2880
tcctcctctc tctagctagc cttttgtttt ctcttttttct tatttgattt tctttaaatc 2940
aatccatttt aggagagggc cagggagtga tccagcaaaa catgaagatt agaagaaact 3000
tccctctttt ttttcctgaa aacaaatttaa cgtcgagatt tatctctttt tgtaatggaa 3060
```

```
tcatttctac agttatgact cgattaaaaa tcccaattat atttggtcta atttagtttg   3120
gtattgagta aaacaaattc gaaccaaacc aaaatataaa tatatagttt ttatatatat   3180
gcctttaaga cttttatag aattttcttt aaaaaatatc tagaaatatt tgcgactctt    3240
ctggcatgta atatttcgtt aaatatgaag tgctccattt ttattaactt taaataattg   3300
gttgtacgat cactttctta tcaagtgtta ctaaaatgcg tcaatctcct tgttcttcca   3360
tattcatatg tcaaaatcta tcaaaattct tatatatctt tttcgaattt gaagtgaaat   3420
ttcgataatt taaattaaa tagaacatat cattatttag gtatcatatt gattttata    3480
cttaattact aaatttggtt aactttgaaa gtgtacatca acgaaaaatt agtcaaacga   3540
ctaaaataaa taaatatcat gtgttattaa gaaaattctc ctataagaat attttaatag   3600
atcatatgtt tgtaaaaaaa attaattttt actaacacat atatttactt atcaaaaatt   3660
tgacaaagta agattaaaat aatattcatc taacaaaaaa aaaaccagaa aatgctgaaa   3720
acccggcaaa accgaaccaa tccaaaccga tatagttggt ttggtttgat tttgatataa   3780
accgaaccaa ctcggtccat ttgcaccect aatcataata gctttaatat ttcaagatat   3840
tattaagtta acgttgtcaa tatcctggaa attttgcaaa atgaatcaag cctatatggc   3900
tgtaatatga atttaaaagc agctcgatgt ggtggtaata tgtaatttac ttgattctaa   3960
aaaaatatcc caagtattaa taatttctgc taggaagaag gttagctacg atttacagca   4020
aagccagaat acaaagaacc ataaagtgat tgaagctcga aatatacgaa ggaacaaata   4080
ttttaaaaa aatacgcaat gacttggaac aaaagaaagt gatatatttt ttgttcttaa   4140
acaagcatcc cctctaaaga atggcagttt tcctttgcat gtaactatta tgctcccttc   4200
gttacaaaaa ttttggacta ctattgggaa cttcttctga aaatagt                4247

SEQ ID NO: 761           moltype = DNA    length = 5040
FEATURE                  Location/Qualifiers
misc_feature             1..5040
                         note = Construct AR15-20
source                   1..5040
                         mol_type = other DNA
                         organism = synthetic construct
SEQUENCE: 761
aacacaagct tcaagtttta aaaggaaaaa tgtcagccaa aaactttaaa taaaatggta   60
acaaggaaat tattcaaaaa ttcaaacct cgtcaaaata ggaaagaaaa aaagtttagg    120
gatttagaaa aaacatcaat ctagttccac cttattttat agagagaaga aactaatata   180
taagaactaa aaaacagaag aatagaaaaa aaaagtattg acaggaaaga aaagtagct    240
gtatgcttat aagtactttg aggatttgaa ttctctctta taaaacacaa acacaatttt   300
tagatttat ttaaataatc atcaatccga ttataattat ttatatattt ttctatttc    360
aaagaagtaa atcatgagct tttccaactc aacatctatt ttttttctct caaccttttt   420
cacatcttaa gtagtctcac cctttatata tataacttat ttcttacctt ttacattatg   480
taacttttat caccaaaacc aacaacttta aaattttaat aaatagactc cacaagtaac   540
ttgacactct tacattcatc gacattaact tttatctgtt ttataaatat tattgtgata   600
taatttaatc aaaataacca caaacttca taaaaggttc ttattaagca tggcatttaa    660
taagcaaaaa caactcaatc actttcatat aggaggtagc ctaagtacgt actcaaaatg   720
ccaacaaata aaaaaaaagt tgcttaata atgccaaaac aaattaataa aacacttaca    780
acaccggatt ttttttaatt aaaatgtgcc atttaggata aatagttaat atttttaata   840
attatttaaa aagccgtatc tactaaaatg attttttattt ggttgaaaat attaatatgt   900
ttaaatcaac acaatctatc aaaattaaac taaaaaaaaa ataagtgtac gtggttaaca   960
ttagtacagt aatataagag gaaatgaga aattaagaaa ttgaaagcga gtctaatttt    1020
taaattatga acctgcatat ataaaggaa agaaagaatc caggaagaaa agaaatgaaa    1080
ccatgcatgg tccctcgtc atcacgagtt tctgccattt gcaatagaaa cactgaaaca    1140
cctttctctt tgtcacttaa ttgagatgcc gaagccacct cacaccatga acttcatgag   1200
gtgtagcacc caaggcttcc atagccatgc atactgaaga atgtctcaag ctcagcaccc   1260
tacttctgtg acgtgtccct cattcaccct cctctcttcc ctataaataa ccacgcctca   1320
ggttctccgc ttcacaactc aaacattctc tccattggtc cttaaacact catcagtcat   1380
caccgttcgt tatctaccac cgttctatgg atttttattcc ttctattcgt gtttattcta   1440
ttggttatg ttgcttgcaa tatgtttttt ctgaatctgt cgtcgttgtc ttcaatttta    1500
tccatgtttc agagatcaat tttgtttgtg tagtatgtgc ttattcttct tctttttcgtt   1560
cgagttgtta ataacggtgc tatggtgttt tcaaagtgtt ttttttatt acttttgatt   1620
taaagttttc ttggtaaggc ttttatttgc ttgttatatt caaatctttg gatccagatc   1680
ttatataagt ttttggttca agaaagtttt tggttactga tgaatagatc tattaactgt   1740
tactttaatc gattcaagct aaagtttttt ggttactgat gaatagatct attatctgtt   1800
acttttaatc ggttcaagct caagtttttt ggttactga gaatagatct atatacgtca   1860
cagtgtgcta aacatgccct tgttttatct cgatcttatg tatgggagtg ccataaattt   1920
tgttatgtct atttttttat ctgttggaat catactgagt ttgatgcgtt acgattgagc   1980
atacctattt ttgggcttgt tgtatggtgg gtatttagat cttaatcttt ttatgcttat   2040
gaaaggtttt gtaatgacaa aggtcttaat gttgttaact tttatttt actttatatg    2100
gtgtgttgat gtgttatggt tttgacaact ttttttttt ctggattttt gcagatttaa    2160
ggaccatggc caagctagtt ttttcccttt gtttctgct tttcagtggc tgctgcttcg    2220
ctggatcaat tggcgccgca tctatggagt tctgcttcga tgttttttaaa gagcttaaag   2280
tgcaccatgc caacgagaat atcttctatt gcccaattgc cattatgtct gcccttgcta   2340
tggtgtactt gggtgctaaa gactctacta ggacccaagg ta gtcagattcg            2400
acaagctgcc tgggtttggc gactctattg aagctcagtg tggtacttct gttaatgtcc   2460
actcatccct ccgcgacata cttaatcaaa ttacaaaacc aaatgatgtg tactcattta   2520
gtctggccag ccgtttgtac gcagaggaac gctaccctat cctgccagag tatttgcaat   2580
gtgtgaagga actttcacagg ggtgggcttg agccaataaa ctttcaaaca gcagccgacc   2640
aagctaggga gcttatcaat tcttgggtcg agagccaaac taacgagatc atccgtaacg   2700
tcctccagcc aagttccgtt gattcccaga ccgctatggt acttgtgaat gccattgtct   2760
tcaaggggct tgggagaag gcatttaaag acgaggacac tcaggcaatg cccttttcgtg   2820
tgaccgagca ggagtcaaaa cctgttcaaa tgatgtacca aattgggctg ttcagagttg   2880
ctagtatggc ctctgagaaa atgaagatcc ttgaactccc atttgcctcc gggacaatgt   2940
ctatgcttgt cctcctgcca gatgaagtca gtgggctcga acagctcgaa agcataataa   3000
```

-continued

```
actttgagaa acttaccgaa tggacttctt ccaatgttat ggaggagcgt aaaattaagg   3060
tctatctgcc ccgcatgaaa atggaggaaa agtataatct cactagcgtc ctcatggcta   3120
tgggaattac tgatgtattc tcctctagcg ctaatctgag tggaatctcc agcgccgagt   3180
ctctcaagat aagccaggcc gtgcacgctg ctcatgctga aatcaacgaa gccggcagag   3240
aggtggtggg gtcagctgag gcaggtgtag atgcagccga tgtctctgag gaatttagag   3300
ccgatcaccc tttcctttt tgcattaaac atatcgctac aaatgccgtt ttgttttcg    3360
gtcgttgcgt tagtccaaag gatgagcttt aaaaagcaga atgctgagct aaaagaaagg   3420
cttttccat tttcgagaga caatgagaaa agaagaagaa gaagaagaag aagaagaaga    3480
agaaaagagt aaataataaa gccccacagg aggcgaagtt cttgtagctc catgttatct   3540
aagttattga tattgtttgc cctatatttt atttctgtca ttgtgtatgt tttgttcagt   3600
ttcgatctcc ttgcaaaatg cagagattat gagatgaata aactaagtta tattattata   3660
cgtgttaata ttctcctcct ctctctagct agccttttgt tttctctttt tcttatttga   3720
ttttctttaa atcaatccat tttaggagag ggccagggag tgatccagca aaacatgaag   3780
attagaagaa acttcccctct ttttttcct gaaaacaatt taacgtcgag atttatctct   3840
ttttgtaatg gaatcatttc tacagttatg actcgattaa aaatcccaat tatatttggt   3900
ctaatttagt ttggtattga gtaaaacaaa ttcgaaccaa accaaaatat aaatatatag   3960
tttttatata tatgccttta agactttta tagaattttc tttaaaaaat atctagaaat    4020
atttgcgact cttctggcat gtaatatttc gttaaatatg aagtgctcca tttttattaa   4080
cttaaaataa ttggttgtac gatcactttc ttatcaagtg ttactaaaat gcgtcaatct   4140
ctttgttctt ccatattcat atgtcaaaat ctatcaaaat tcttatatat cttttcgaa    4200
tttgaagtga aatttcgata atttaaatt aaatagaaca tatcattatt taggtatcat    4260
attgatttt atacttaatt actaaatttg gttaactttg aaagtgtaca tcaacgaaaa    4320
attagtcaaa cgactaaaat aaataaatat catgtgttat taagaaaatt ctcctataag   4380
aatattttaa tagatcatat gtttgtaaaa aaaattaatt tttactaaca catatattta   4440
cttatcaaaa atttgacaaa gtaagattaa aataatattc atctaacaaa aaaaaaacca   4500
gaaaatgctg aaaaaccggc aaaaccgaac caatccaaac cgatatagtt ggtttggttt   4560
gattttgata taaaccgaac caactcggtc catttgcacc cctaatcata atagcttaa    4620
tatttcaaga tattattaag ttaacgttgt caatatcctg gaattttgc aaaatgaatc    4680
aagcctatat ggctgtaata tgaatttaaa agcagctcga tgtggtggta atatgtaatt   4740
tacttgattc taaaaaaata tcccaagtat taataatttc tgctaggaag aaggttagct   4800
acgatttaca gcaaagccag aatacaaaga accataaagt gattgaagct cgaaatatac   4860
gaaggaacaa atattttaa aaaaatacgc aatgacttgg aacaaagaa agtgatatat     4920
ttttgttct taaacaagca tcccctctaa agaatggcag ttttcctttg catgtaacta   4980
ttatgctccc ttcgttacaa aaattttgga ctactattgg gaacttcttc tgaaaatagt   5040
```

SEQ ID NO: 762        moltype = DNA   length = 5029
FEATURE               Location/Qualifiers
misc_feature          1..5029
                      note = Construct AR15-21
source                1..5029
                      mol_type = other DNA
                      organism = synthetic construct
SEQUENCE: 762

```
aacacaagct tcaagtttta aaaggaaaaa tgtcagccaa aaactttaaa taaaatggta     60
acaaggaaat tattcaaaaa ttacaaacct cgtcaaaata ggaaagaaaa aaagtttagg    120
gatttagaaa aaacatcaat ctagttccac cttatttttt agagagaaga aactaatata    180
taagaactaa aaaacagaag aatagaaaaa acaggaaaga aaaagtagct                240
gtatgcttat aagtactttg aggattttgaa ttctctctta taaaacacaa acacaatttt   300
tagattttat ttaaataatc atcaatccga ttataattat ttatatattt ttctatttc    360
aaagaagtaa atcatgagct tttccaactc aacatctatt ttttttctct caaccttttt   420
cacatcttaa gtagtctcac cctttatata taaacttat ttcttacctt ttacattatg    480
taacttttat caccaaaacc aacaacttta aatttatt aaatagactc cacaagtaac     540
ttgacactct tacattcatc gacattaact tttatctgtt ttataaatat tattgtgata   600
taatttaatc aaaataacca caaactttca taaaggttc ttattaagca tggcatttaa    660
taagcaaaaa caactcaatc actttcatat aggaggtagc ctaagtacgt actcaaaatg   720
ccaacaaata aaaaaaagt tgctttaata atgccaaaac aaattaataa aacacttaca    780
acaccggatt ttttttaatt aaaatgtgcc atttaggata aatagttaat attttttaata  840
attatttaaa aagccgtatc tactaaaatg attttttattt ggttgaaaat attaatatgt   900
ttaaatcaac acaatctatc aaaattaaac taaaaaaaaa aaagtgtac gtggttaaca    960
ttagtacagt aatataagag gaaaatgaga aattaagaaa ttgaaagcga gtctaattt    1020
taaattatga acctgcatat ataaaggaa agaagaatc caggaagaaa agaaatgaaa     1080
ccatgcatgg tcccctcgtc atcacgagtt tctgccattt gcaatagaaa cactgaaaca   1140
cctttctctt tgtcacttaa ttgagatgcc gaagccacct cacaccatga acttcatgag   1200
gtgtagcacc caaggcttcc atagccatgc atactgaaga tgtctcaag ctcagcaccc    1260
tacttctgtg acgtgtccct cattcacctt cctctcttcc ctataaataa ccacgcctca   1320
ggttctccgc ttcacaactc aaacattctc tccattggtc cttaaacact catcagtcat   1380
caccatggcc aagctagttt tttccctttg ttttctgctt ttcagtggct gctgcttcgc   1440
tggatcaatt ggcgccgcat ctatggagtt ctgcttcgat gtttttaaag agcttaaagt   1500
gcaccatgcc aacgagaata tcttctattg cccaattgcc attatgtctg ccttgctat    1560
ggtgtacttg ggtgctaaag actactagag gacccagata aacaaggttc gttatctacc   1620
accgttctat ggattttatt ccttctattc gtgtttattc tattggttta tgttgcttgc   1680
aatatgttt ttctgaatct gtcgtcgttg tcttcaattt tatccatgtt tcagagatca    1740
attttgttg tgtagtatgt gcttattctt cttctttcg ttcgagttgt taataacggt     1800
tgctgtggtg ttcaaaagt gttttttta ttactttga tttaaagttt tttggtaag       1860
gcttttattt gcttgttata ttcaaatctt tggatccaga tcttatataa gttttggtt    1920
caagaaagtt tttggttact gatgaataga tctattaact gttacttaa tcgattcaag    1980
ctaaagtttt ttggttactg atgaatagat ctattatctg ttacttttaa tcggttcaag   2040
ctcaagtttt ttggttactg atgaatagat ctatatacgt cacagtgtgc taaacatgcc   2100
cttgttttat ctcgatctta tgtatgggag tgccataaat tttgttatgt ctatttttt    2160
```

```
atctgttgga atcatactga gtttgatgcg ttacgattga gcatacctat ttttgggctt   2220
gttgtatggt gggtatttag atcttaatct ttttatgctt atgaaaggtt ttgtaatgac   2280
aaaggtctta atgttgttaa acttttattt ttacttttata tggtgtgttg atgtgttatg  2340
gttttgacaa cttttttttt ttctggattt ttgcaggtag tcagattcga caagctgcct   2400
gggtttggcg actctattga agctcagtgt ggtacttctg ttaatgtcca ctcatccctc   2460
cgcgacatac ttaatcaaat tacaaaacca aatgatgtgt actcatttag tctggccagc   2520
cgtttgtacg cagaggaacg ctaccctatc ctgccagagt atttgcaatg tgtgaaggaa   2580
ctttacaggg gtgggcttga gccaataaac tttcaaacag cagccgacca agctagggag   2640
cttatcaatt cttgggtcga gagccaaact aacggaatca tccgcaacgt cctccagcca   2700
agttccgttg attcccagac cgctatggta cttgtgaatg ccattgtctt caagggcgtt   2760
tgggagaagg catttaaaga cgaggacact caggcaatgc cctttcgtgt gaccgagcag   2820
gagtcaaaac ctgttcaaat gatgtaccaa attgggctgt tcagagttgc tagtatggcc   2880
tctgagaaaa tgaagatcct tgaactccca tttgcctccg ggacaatgtc tatgcttgtc   2940
ctcctgccag atgaagtcag tgggctcgaa cagctcgaaa gcataataaa ctttgagaaa   3000
cttaccgaat ggacttcttc caatgttatg gaggagcgta aaattaaggt tctatctgccc  3060
cgcatgaaaa tggaggaaaa gtataatctc actagcgtcc tcatggctat gggaattact   3120
gatgtattct cctctagcgc taatctgagt ggaatctcca cgccgagtc tctcaagata    3180
agccaggccg tgcacgctgc tcatgctgaa atcaacgaag ccggcagaga ggtggtgggg   3240
tcagctgagg caggtgtaga tgcagccagt gtctctgagg aatttagagc cgatcaccct   3300
ttccttttttt gcattaaaca tatcgctaca aatgccgttt tgtttttcgg tcgttgcgtt  3360
agtccaaagg atgagcttta aaaagcagaa tgctgagcta aaagaaaggc ttttttccatt  3420
ttcgagagac aatgagaaga aagaagaag aagaagaaga gaaaagagta                3480
aataataaag ccccacagga ggcgaagttc ttgtagctcc atgttatcta agttattgat    3540
attgtttgcc ctatatttta tttctgtcat tgtgtatgtt ttgttcagtt tcgatctcct    3600
tgcaaaatgc agagattatg agatgaataa actaagttat attattatac gtgttaatat    3660
tctcctcctc tctctagcta gccttttgtt ttctcttttt cttatttgat tttctttaaa    3720
tcaatccatt ttaggagagg gccagggagt gatccagcaa aacatgaaga ttagaagaaa    3780
cttccctctt tttttttcctg aaaacaattt aacgtcgaga tttatctctt tttgtaatgg   3840
aatcatttct acagttatga ctcgattaaa atcccaatt atatttggtc taatttagtt     3900
tggtattgag taaaacaaat tcgaaccaaa ccaaaaatat aaatatagt ttttatatat     3960
atgcctttaa gacttttat agaatttct ttaaaaaata tctagaaata tttgcgactc      4020
ttctggcatg taatatttcg ttaaaatgaa agtgctccat ttttattaac tttaaataat    4080
tggttgtacg atcactttct tatcaagtgt tactaaaatg cgtcaatctc tttgttcttc    4140
catattcata tgtcaaaatc tatcaaaatt ctttatatc ttttttcgaat ttgaagtgaa    4200
atttcgataa tttaaaatta aatagaacat atcattattt aggtatcata ttgattttta   4260
tacttaatta ctaaatttgg ttaacttga aagtgtacat caacgaaaaa ttagtcaaac     4320
gactaaaata aataaatatc atgtgttatt aagaaaattc tcctataaga atattttaat    4380
agatcatatg tttgtaaaaa aaattaattt ttactaacaa atatatttac ttatcaaaaa    4440
tttgacaaag taagattaaa ataattatca tctaacaaaa aaaaaaccag aaaaatgctga   4500
aaacccggca aaaccgaacc aatccaaacc gatatagttg gtttggtttg attttgatat    4560
aaaccgaacc aactcggtcc atttgcaccc ctaatcataa tagctttaat atttcaagat    4620
attattaagt taacgttgtc aatatcctgg aaattttgca aaatgaatca agcctatatg    4680
gctgtaatat gaatttaaaa gcagctcgat gtggtggtaa tatgtaattt acttgattct    4740
aaaaaaaatat cccaagtatt aataatttct gctaggaaga aggttagcta cgatttcagg   4800
caaagccaga atacaagaa ccataaagtg attgaagctc gaaatatacg aaggaacaaa     4860
tatttttaaa aaaatacgca atgacttgga acaaagaaa gtgatatatt ttttgttctt     4920
aaacaagcat ccctctaaa gaatggcagt ttttcctttgc atgtaactat tatgctccct    4980
tcgttacaaa aatttttggac tactattggg aacttcttcc gaaaatagt                5029

SEQ ID NO: 763          moltype = DNA  length = 4352
FEATURE                 Location/Qualifiers
misc_feature            1..4352
                        note = Construct AR15-22
source                  1..4352
                        mol_type = other DNA
                        organism = synthetic construct
SEQUENCE: 763
aacacaagct tcaagtttta aaaggaaaaa tgtcagccaa aaactttaaa taaaatggta     60
acaaggaaat tattcaaaaa ttacaaacct cgtcaaaata ggaaagaaaa aaagtttagg    120
gatttagaaa aaacatcaat ctagttccac cttattttat agagagaaga aactaataa    180
taagaactaa aaaacagaag aatagaaaaa aaagtattg acaggaaaga aaagtagct     240
gtatgcttat aagtactttg aggatttgaa ttctctctta taaacacaa acacaatttt    300
tagatttttat ttaaataatc atcaatccga ttataattat ttatatattt ttctattttc  360
aaagaagtaa atcatgagct tttccaactc aacatctatt ttttttctct caacctttt    420
cacatcttaa gtagtctcac cctttatata tataacttat ttcttaccttt ttacattatg  480
taactttttat caccaaaacc aacaacttta aatttatt aaatagactc cacaagtaac    540
ttgacactct tacattcatc gacattaact tttatctgtt ttataaatat tattgtgata   600
taattaatc aaaataacca caaactttca taaaaggttc acttaagca tggcattttaa     660
taagcaaaaa caactcaatc acttttcatat aggaggtagc ctaagtacgt actcaaaatg  720
ccaacaaata aaaaaaaaagt tgctttaata atgccaaaac aaattaataa aacacttaca  780
acaccggatt ttttttaatt aaaaatgtgcc atttaggata aatagttaat attttttaata 840
attatttaaa aagccgtatc tactaaaatg attttttattt ggttgaaaat attaatatgt  900
ttaaatcaac acaatctatc aaaattaaac taaaaaaaaa ataagtgtac gtggttaaca   960
ttagtacagt aataagag gaaatgaga aattaaagtt tgaaagcga gtctaatttt       1020
taaattatga acctgcatat ataaaggaa agaagaatc aggaagaaa agaaatgaaa      1080
ccatgcatgg tcccctcgtc atcacgagtt tctgccattt gcaatagaaa cactgaaaca   1140
cctttctctt tgtcacttaa ttgagatgcc gaagccacct cacaccatga acttcatgag   1200
gtgtagcacc caaggcttcc atagccatgc atactgaaga atgtctcaag ctcagcaccc   1260
tacttctgtg acgtgtccct cattcacctt cctctcttcc ctataaataa ccacgcctca   1320
```

-continued

```
ggttctccgc ttcacaactc aaacattctc tccattggtc cttaaacact catcagtcat   1380
caccatggcc aagctagttt ttttccctttg ttttctgctt ttcagtggct gctgcttcgc   1440
tggatcaatt ggcgccgcat ctatggagtt ctgcttcgat gtttttaaag agcttaaagt   1500
gcaccatgcc aacgagaata tcttctattg cccaattgcc attatgtctg cccttgctat   1560
ggtgtacttg ggtgctaaag actctactag gacccagata aacaaggtaa ccatatcttt   1620
catctgttat gtgactacac attgcttctc tttttgtgtt ctgtctcatt aattgcggtt   1680
tgttacatgt tgtttgtagg tagtcagatt cgacaagctg cctgggtttg gcgactctat   1740
tgaagctcag tgtggtactt ctgttaatgt ccactcatcc ctccgcgaca tacttaatca   1800
aattacaaaa ccaaatgatg tgtactcatt tagtctggcc agccgttttgt acgcagagga   1860
acgctaccct atcctgccag agtatttgca atgtgtgaag aacttttaca ggggtgggct   1920
tgagccaata aactttcaaa cagcagccga ccaagctagg gagcttatca attcttgggt   1980
cgagagccaa actaacggaa tcatccgcaa cgtcctccag ccaagttccg ttgattccca   2040
gaccgctatg gtacttgtga atgccattgt cttcaagggg ctttgggaga aggcatttaa   2100
agacgaggac actcaggcaa tgcccttttcg tgtgaccgaa caggagtcaa aacctgttca   2160
aatgatgtac caaattgggc tgttcagagt tgctagtatg gcctctgaga aaatgaagat   2220
ccttgaactc ccatttgcct ccgggacaat gtctatgctt gtcctcctgc cagatgaagt   2280
cagtgggctc gaacagctcg aaagcataat aaactttgag aaacttaccg aatggacttc   2340
ttccaatgtt atggaggagc gtaaaattaa ggtctatctg ccccgcatga aaatggagga   2400
aaagtataat ctcactagcg tcctcatggc tatgggaatt actgatgtat tctcctctag   2460
cgctaatctg agtggaatct ccagcgccga gtctctcaag ataagccagg ccgtgcacgc   2520
tgctcatgct gaaatcaacg aagccggcag agaggtggtg gggtcagctg aggcaggtgt   2580
agatgcagcc agtgtctctg aggaatttag agccgatcac cctttccttt tttgcattaa   2640
acatatcgct acaaatgccg tttttgtttt cggtcgttgc gttagtccaa aggatgagct   2700
ttaaaaagca gaatgctgag ctaaaagaaa ggctttttcc attttcgaga gacaatgaga   2760
aaagaagaag aagaagaaga agaagaagaa gaagaaaaga gtaaataata aagccccaca   2820
ggaggcgaag ttcttgtagc tccatggttat ctaagttatt gatattgttt gccctatatt   2880
ttatttctgt cattgtgtat gttttgttca gttcgatct ccttgcaaaa tgcagagatt   2940
atgagatgaa taaactaagt tatattatta tacgtgttaa tattctcctc ctctctctag   3000
ctagcctttt gttttctctt tttcttattt gatttctttt aaatcaatcc attttaggag   3060
agggccaggg agtgatccag caaaacatga agattagaag aaacttccct cttttttttc   3120
ctgaaaacaa tttaacgtcg agatttatct ctttttgtaa tggaatcatt tctacagtta   3180
tgactcgatt aaaaatccca attatatttg gtctaattta gtttggtatt gagtaaaaca   3240
aattcgaacc aaaccaaaat ataaatatat agttttata tatatgcctt taagactttt   3300
tatagaattt tcttttaaaaa atatctagaa atatttgcga ctcttctggc atgtaatatt   3360
tcgttaaata tgaagtgctc cattttttatt aactttaaat aattggttgt acgatcactt   3420
tcttatcaag tgttactaaa atgcgtcaat ctctttgttc ttccatattc atatgtcaaa   3480
atctatcaaa attcttatat atcttttttcg aatttgaagt gaaatttcga aattttaaaa   3540
ttaaatagaa catatcatta tttaggtatc atattgattt ttatacttaa ttactaaatt   3600
tggttaactt tgaaagtgta catcaacgaa aaaattagtca aacgactaaa ataaataaat   3660
atcatgtgtt attaagaaaa ttctcctata agaatatttt aatagatcat atgtttgtaa   3720
aaaaaattaa ttttttactaa cacatatatt tacttatcaa aaatttgaca aagtaagatt   3780
aaaataatat tcatctaaca aaaaaaaaac cagaaaatgc tgaaacccg gcaaaaccga   3840
accaatccaa accgatatag ttggtttggt ttgattttga tataaccga accaactcgg   3900
tccattgca cccctaatca taatagcttt aatatttcaa gatattatta agttaacgtt   3960
gtcaatatcc tggaaatttt gcaaaatgaa tcaagcctat atggctgtaa tatgaattta   4020
aaagcagctc gatgtggtgg taatatgtaa tttacttgat tctaaaaaaa tatcccaagt   4080
attaataatt tctgctagga agaaggttag ctacgattta cagcaaagcc agaatacaaa   4140
gaaccataaa gtgattgaag ctcgaaatat acgaaggaac aaatattttt aaaaaaatac   4200
gcaatgactt ggaacaaaag aaagtgatat attttttgtt cttaaacaag catccctct   4260
aaagaatggc agtttttcctt tgcatgtaac tattatgctc ccttcgttac aaaaattttg   4320
gactactatt gggaacttct tctgaaaata gt                                 4352

SEQ ID NO: 764           moltype = DNA   length = 4323
FEATURE                  Location/Qualifiers
misc_feature             1..4323
                         note = Construct AR15-23
source                   1..4323
                         mol_type = other DNA
                         organism = synthetic construct
SEQUENCE: 764
aacacaagct tcaagtttta aaaggaaaaa tgtcagccaa aaactttaaa taaaatggta     60
acaaggaaat tattcaaaaa ttacaaacct cgtcaaaata ggaaagaaaa aaagtttagg   120
gatttagaaa aaacatcaat ctagttccac cttattttat agagaagaa aactaatata    180
taagaactaa aaacagaaga aatagaaaaa aaagtattg acaggaaaga aaagtagct    240
gtatgcttat aagtactttg aggatttgaa ttctctctta taaaacacaa acacaatttt   300
tagatttat ttaaataatc atcaatccga ttataattat ttatatattt ttctattttc    360
aaagaagtaa atcatgagct tttccaactc aacatctatt tttttttctct caacctttt    420
cacatcttaa gtagtctcac cctttatata taaacttat ttcttaccct ttacattatg    480
taacttttat caccaaaacc aacaacttta aaattttatt aaatagactc cacaagtaac   540
ttgacactct tacattcatc gacattaact tttatctgtt ttataaatat tattgtgata   600
taatttaatc aaaataacca caaactttca taaaaggttc ttattaagca tggcatttaa   660
taagcaaaaa caactcaatc actttcatat aggaggtagc ctaagtacgt actcaaaatg   720
ccaacaaata aaaaaaaagt tgcttaata atgccaaaac aaattaataa aacacttaca   780
acaccggatt ttttttaatt aaaatgtgcc atttaggata aatgttaat attttaata    840
attatttaaa aagccgtatc tactaaaatg atttttatt ggttgaaaat attaatatgt    900
ttaaatcaac acaatctatc aaaattaaac taaaaaaaaa ataagtgtac gtggttaaca   960
ttagtacagt aatataagag gaaatgaga attaagaaa ttgaaagcga gtctaatttt   1020
taaattatga acctgcatat ataaaggaa agaaagaatc caggaagaaa agaaatgaaa   1080
ccatgcatgg tcccctcgtc atcacgagtt tctgccattt gcaatagaaa cactgaaaca   1140
```

```
cctttctctt tgtcacttaa ttgagatgcc gaagccacct cacaccatga acttcatgag 1200
gtgtagcacc caaggcttcc atagccatgc atactgaaga atgtctcaag ctcagcaccc 1260
tacttctgtg acgtgtccct cattcacctt cctctcttcc ctataaataa ccacgcctca 1320
ggttctccgc ttcacaactc aaacattctc tccattggtc cttaaacact catcagtcat 1380
caccacatac agctagaaag ctgtattgcc tttagcactc aagctcaaaa gacaactcag 1440
agttcaccat ggccaagcta gttttttccc tttgttttct gcttttcagt ggctgctgct 1500
tcgctggatc aattggcgcc gcatctatgg agttctgctt cgatgttttt aaagagctta 1560
aagtgcacca tgccaacgag aatatcttct attgcccaat tgccattatg tctgcccttg 1620
ctatggtgta cttgggtgct aaagactcta ctaggaccca gataaacaag gtagtcagat 1680
tcgacaagct gcctgggttt ggcgactcta ttgaagctca gtgtggtact tctgttaatg 1740
tccactcatc cctccgcgac atacttaatc aaattacaaa accaaatgat gtgtactcat 1800
ttagtctggc cagccgtttg tacgcagagg aacgctaccc tatcctgcca gagtatttgc 1860
aatgtgtgaa ggaactttac aggggtgggc ttgagcaat aaactttcaa acagcagccg 1920
accaagctag ggagcttatc aattcttggg tcgagagcca aactaacgga atcatccgca 1980
acgtcctcca gccaagttcc gttgattccc agaccgctat ggtacttgtg aatgccattg 2040
tcttcaaggg gctttgggag aaggcattta agacgagga cactcaggca atgccctttc 2100
gtgtgaccga gcaggagtca aaacctgttc aaatgatgta ccaaattggg ctgttcagag 2160
ttgctagtat ggcctctgag aaaatgaaga tccttgaact cccatttgcc tccgggacaa 2220
tgtctatgct tgtcctcctg ccagatgaag tcagtgggcc cgaacagctc gaaagcataa 2280
taaactttga gaaacttacc gaatggactt cttccaatgt tatggaggag cgtaaaatta 2340
aggtctatct gccccgcatg aaaatggagg aaagtataa tctcactagc gtcctcatgg 2400
ctatgggaat tactgatgta ttctcctcta gcgctaatc gagtggaatc tccagcgccg 2460
agtctctcaa gataagccag gccgtgcacg ctgctcatgc tgaaatcaac gaagccggca 2520
gagaggtggt ggggtcagct gaggcaggtg tagatgcagc cagtgtctct gaggaattta 2580
gagccgatca ccctttcctt ttttgcatta acatatcgc tacaaatgcc gttttgtttt 2640
tcggtcgttg cgttagtcca aaggatgagc tttaaaaagc agaatgctga gctaaaagaa 2700
aggcttttc cattttcgag agacaatgag aaaagaagaa gaagaagaag aagaagaaga 2760
agaagaaaag agtaaataat aaagccccac aggaggcgaa gttcttgtag ctccatgtta 2820
tctaagttat tgatattgtt tgccctatat tttatttctg tcattgtgta tgttttgttc 2880
agtttcgatc tccttgcaaa atgcagagat tatgagatga ataaactaag ttatattatt 2940
atacgtgtta atattctcct cctctctcta gctagccttt tgttttctct ttttcttatt 3000
tgattttctt taaatcaatc cattttagga gaggccagg gagtgatcca gcaaaacatg 3060
aagattagaa gaaacttccc tcttttttttt cctgaaaaca atttaacgtc gagatttatc 3120
tcttttgta atggaatcat ttctacagtt atgactcgat taaaaatccc aattatattt 3180
ggtctaattt agtttggtat tgagtaaaac aaattcgaac caaaccaaaa tataaatata 3240
tagtttttat atatatgcct ttaagacttt ttatagaatt ttcttaaaa aatatctaga 3300
aatatttgcg actcttctgg catgtaatat ttcgttaaat atgaagtgct ccatttttat 3360
taactttaaa taattggttg tacgatcact ttcttatcaa gtgttactaa aatgcgtcaa 3420
tctctttgtt cttccatatt catatgtcaa aatctatcaa aattcttata tatctttttc 3480
gaatttgaag tgaaatttcg ataatttaaa attaaataga acatatcatt atttaggtat 3540
catattgatt tttatactta attactaaat ttggttaact ttgaaagtgt acatcaacga 3600
aaaattagtc aaacgactaa aataaataaa tatcatgtgt tattaagaaa attctcctat 3660
aagaatattt taatagatca tatgtttgta aaaaaaatta acacatatat 3720
ttacttatca aaaatttgac aaagtaagat taaaataata ttcatctaac aaaaaaaaa 3780
ccagaaaatg ctgaaaaccc ggcaaaaccg aaccaatcca aaccgatata gttggtttgg 3840
tttgattttg atataaaccg aaccaactcg gtccatttgc accctaatc ataatagctt 3900
taatatttca agatattatt aagttaacgt tgtcaatatc ctggaaattt tgcaaaatga 3960
atcaagccta tatggctgta atatgaattt aaaagcagct cgatgtggtg gtaaatatga 4020
atttacttga ttctaaaaaa atatcccaag tattaataat ttctgctagg aagaaggtta 4080
gctacgattt acagcaaagc cagaatacaa agaaccataa agtgattgaa gctcgaaata 4140
tacgaaggaa caaatatttt taaaaaaata cgcaatgact tggaacaaaa gaaagtgata 4200
tattttttgt tcttaaacaa gcatcccctc taaagaatgg cagttttcct ttgcatgtaa 4260
ctattatgct cccttcgtta caaaaatttt ggactactat tgggaacttc ttctgaaaat 4320
agt                                                                  4323

SEQ ID NO: 765        moltype = DNA   length = 4324
FEATURE               Location/Qualifiers
misc_feature          1..4324
                      note = Construct AR15-24
source                1..4324
                      mol_type = other DNA
                      organism = synthetic construct
SEQUENCE: 765
aacacaagct tcaagtttta aaaggaaaaa tgtcagccaa aaactttaaa taaaatggta  60
acaaggaaat tattcaaaaa ttacaaacct cgtcaaaata ggaaagaaaa aaagtttagg 120
gatttagaaa aaacatcaat ctagttccac cttatttat agagaagaa aactaatata 180
taagaactaa aaaacagaag aatagaaaaa aaagtattg acaggaaaga aaagtagct 240
gtatgcttat aagtactttg aggatttgaa ttctctctta taaaacacaa acacaatttt 300
tagattttat ttaaataatc atcaatccga ttataattat ttatatattt ttctatttc 360
aaagaagtaa atcatgagct tttccaactc aacatctatt tttttctct caaccttttt 420
cacatcttaa gtagtctcac cctttatata tataacttta ttcttacctt ttacattatg 480
taacttttat caccaaaacc aacaacttta aattttatt aaatagactc acaagtaac 540
ttgacactct tacattcatc gacattaact tttatctgtt ttaaatata tattgtgata 600
taatttaatc aaaataacca caaatttca taaaaggttc ttattaagca tggcatttaa 660
taagcaaaaa caactcaatc actttcatat aggaggtagc ctaagtacgt actcaaaatg 720
ccaacaaata aaaaaaagt tgctttaata atgccaaaac aaattaataa aacacttaca 780
acaccggatt tttttaatt aaaatgtgcc atttaggata aatagttaat attttttaata 840
attatttaaa aagccgtatc tactaaaatg atttttattt ggtgaaaat attaatatgt 900
ttaaatcaac acaatctatc aaaattaaac taaaaaaaaa ataagtgtac gtggttaaca 960
```

```
ttagtacagt aatataagag gaaaatgaga aattaagaaa ttgaaagcga gtctaatttt   1020
taaattatga acctgcatat ataaaaggaa agaaagaatc caggaagaaa agaaatgaaa   1080
ccatgcatgg tccccctcgtc atcacgagtt tctgccattt gcaatagaaa cactgaaaca   1140
cctttctctt tgtcacttaa ttgagatgcc gaagccacct cacaccatga acttcatgag   1200
gtgtagcacc caaggcttcc atagccatgc atactgaaga atgtctcaag ctcagcaccc   1260
tacttctgtg acgtgtccct cattcacctt cctctcttcc ctataaataa ccacgcctca   1320
ggttctccgc ttcacaactc aaacattctc tccattggtc cttaaacact catcagtcat   1380
caccgaattc tctaaaagag atcttttcct gctctttgaa gaaagaaggg tctttgcttg   1440
attttggaga tggccaagct agtttttcc ctttgtttc tgcttttcag tggctgctgc   1500
ttcgctggat caattggcgc cgcatctatg gagttctgct tcgatgtttt taaagagctt   1560
aaagtgcacc atgccaacga gaatatcttc tattgcccaa ttgccattat gtctgccctt   1620
gctatggtgt acttgggtgc taaagactct actaggaccc agataaacaa ggtagtcaga   1680
ttcgacaagc tgcctgggtt tggcgactct attgaagctc agtgtggtac ttctgttaat   1740
gtccactcat ccctccgcga catacttaat caaattacaa aaccaaatga tgtgtactca   1800
tttagtctgg ccagccgttt gtacgcgag gaacgctacc ctatcctgcc agagtatttg   1860
caatgtgtga aggaacttta cagggggtggg cttgagccaa taaactttca aacagcagcc   1920
gaccaagcta gggagcttat caattcttgg gtcgagagcc aaactaacgg aatcatccgc   1980
aacgtcctcc agccaagttc cgttgattcc cagaccgcta tggtacttgt gaatgccatt   2040
gtcttcaagg ggctttggga gaaggcattt aaagacgagg acactcaggc aatgccctt   2100
cgtgtgaccg agcaggagtc aaaacctgtt caaatgatgt accaaattgg gctgttcaga   2160
gttgctagta tggcctctga gaaatgaag atccttgaac tcccattgc ctccgggaca   2220
atgtctatgc ttgtcctcct gccagatgaa gtcagtgggc tgcaacagct cgaaagcata   2280
ataaactttg agaacttac cgaatggact tcttccaatg ttatggagga gcgtaaaatt   2340
aaggtctatc tgccccgcat gaaaatggag gaaagtata atctcactag cgtcctcatg   2400
gctatgggaa ttactgatgt attctcctct agcgctaatc tgagtggaat ctccagcgcc   2460
gagtctctca agataagcca ggccgtgcac gctgctcata ctgaaatcaa cgaagccggc   2520
agagaggtgg tggggtcagc tgaggcaggt gtagatgcag ccagtgtctc tgaggaattt   2580
agagccgatc ccccttttcct ttttttgcatt aaacatatcg ctacaaatgc cgttttgttt   2640
ttcggtcgtt gcgttagtcc aaaggatgag ctttaaaaag cagaatgctg agctaaaaga   2700
aaggctttt ccatttcga gagacaatga gaaaagaaga agaaggaaga gaagaagaag   2760
aagaagaaaa gagtaaataa taaagccca caggaggcga agttcttgta gctccatgtt   2820
atctaagtta ttgatattgt ttgccctata ttttattct gtcattgtgt atgttttgtt   2880
cagtttcgat ctccttgcaa aatgcagaga ttatgagatg aataaactaa gttatattat   2940
tatacgtgtt aatattctcc tcctctctct agctagcctt ttgttttctc tttttctttat   3000
ttgattttct ttaaatcaat ccattttagg agagggccag ggagtgatcc agcaaaacat   3060
gaagattaga agaaacttcc ctctttttt tcctgaaaac aatttaacgt cgagatttat   3120
ctcttttttgt aatggaatca tttctacagt tatgactcga ttaaaaatcc caattatatt   3180
tggtctaatt tagtttggta ttgagtaaaa caaattcgaa ccaaaccaaa atataaatat   3240
atagttttta tatatatgcc tttaagactt tttataaat ttttctttaaa aaatatctag   3300
aaatatttgc gactcttctg gcatgtaata tttcgttaaa tatgaagtgc tccattttta   3360
ttaactttaa ataattggtt gtacgatcac tttcttatca agtgttacta aaatgcgtca   3420
atctctttgt tcttccatat tcatatgtca aaatctatca aaattcttat atatctttt   3480
cgaatttgaa gtgaaatttc gataatttaa aattaaatag aacatatcat tatttaggta   3540
tcatattgat ttttatactt aattactaaa tttggttaac tttgaaagtg tacatcaacg   3600
aaaaattagt caaacgacta aaataaataa atatcatgtg ttattaagaa aattctccta   3660
taagaatatt ttaatagatc atatgttgt aaaaaaaatt aatttttact aacacatata   3720
tttacttatc aaaaatttga caaagtaaga ttaaaataat attcatctaa caaaaaaaa   3780
accagaaaat gctgaaaacc cggcaaaacc gaaccaatcc aaaccgatat agttggtttg   3840
gtttgatttt gatataaacc gaaccaactc ggtccatttg caccctaat cataatagct   3900
ttaatatttc aagatattat taagttaacg ttgtcaatat cctggaaatt ttgcaaaatg   3960
aatcaagcct atatggctgt aatatgaatt taaaagcagc tcgatgtggt ggtaatatg   4020
aatttacttg attctaaaa aatatccaa gtattaataa tttctgctag gaagaaggtt   4080
agctacgatt tacagcaaag ccagaataca aagaaccata aagtgattga agctcgaaat   4140
atacgaagga acaaatattt taaaaaat acgcaatgac ttgaacaaa agaaagtgat   4200
ataattttg ttcttaaaca agcatcccct ctaaagaatg gcagttttcc tttgcatgta   4260
actattatgc tcccttcgtt acaaaaattt tggactacta ttgggaactt cttctgaaaa   4320
tagt                                                               4324

SEQ ID NO: 766         moltype = DNA   length = 4493
FEATURE                Location/Qualifiers
misc_feature           1..4493
                       note = Construct AR15-38
source                 1..4493
                       mol_type = other DNA
                       organism = synthetic construct SEQUENCE: 766
aacacaagct tcaagtttta aaggaaaaa tgtcagccaa aaactttaaa taaaatggta    60
acaaggaaat tattcaaaaa ttacaaacct cgtcaaaata ggaaagaaaa aaagtttagg   120
gatttagaaa aaacatcaat ctagttccac cttattttat agagaagaaga aactaataa   180
taagaactaa aaaacagaag aatagaaaaa aaaagtattg acaggaaaga aaaagtagct   240
gtatgcttat aagtactttg aggatttgaa ttctctctta taaaacacaa acacaatttt   300
tagatttat ttaaataatc atcaatccga ttataattat ttatatattt ttctattttc   360
aaagaagtaa atcatgagct tttccaactc aacatctatt tttttttctct caaccttttt   420
cacatcttaa gtagtctcac cctttatata ataacttat ttcttaccctt ttacattatg   480
taactttat caccaaaacc aacaacttta aatttatt aaatagactc cacaagtaac   540
ttgcacactct tacattcatc gacattaact tttatctgtt ttataaatat tattgtgata   600
taatttaatc aaaataacca caaactttca taaaaggttc ttattaagca tggcatttaa   660
taagcaaaaa caactcaatc actttcatat aggaggtagc ctaagtacgt actcaaaatg   720
ccaacaaata aaaaaaagt tgctttaata atgccaaaac aaattaataa aacacttaca   780
```

```
acaccggatt ttttttaatt aaaatgtgcc atttaggata aatagttaat attttaata    840
attatttaaa aagccgtatc tactaaaatg attttattt ggttgaaat attaatatgt    900
ttaaatcaac acaatctatc aaaattaaac taaaaaaaaa ataagtgtac gtggttaaca   960
ttagtacagt aatataagag gaaatgaga aattaagaaa ttgaaagcga gtctaattc    1020
taaattatga acctgcatat ataaaaggaa agaaagaatc caggaagaaa agaaatgaaa  1080
ccatgcatgg tcccctcgtc atcacgagtt tctgccattt gcaatagaaa cactgaaaca  1140
cctttctctt tgtcacttaa ttgagatgcc gaagccacct cacaccatga acttcatgag  1200
gtgtagcacc caaggcttcc atagccatgc atactgaaga atgtctcaag ctcagcaccc  1260
tacttctgtg acgtgtccct cattcacctt cctctcttcc ctataaataa ccacgcctca  1320
ggttctccgc ttcacaactc aaacattctc tccattggtc cttaaacact catcagtcat  1380
caccatgcag attttcgtga agaccttaac ggggaagacg atcaccctag aggttgagtc  1440
ttccgacacc atcgacaatg tcaaagccaa gatccaggac aaggaaggga tacccccaga  1500
ccagcagcgt ttgattttcg ccggaaagca gcttgaggat ggtcgtactc ttgccgacta  1560
caacatccag aaggagtcaa ctctccatct cgtgctccgt ctccgtgggt gtggttccat  1620
ggccaagcta gttttttccc tttgttttct gcttttcagt ggctgctgct tcgctggatc  1680
aattggcgcc gcatctatgg agttctgctt cgatgttttt aaagagctta aagtgcacca  1740
tgccaacgag aatatcttct attgcccaat tgccattatg tctgcccttg ctatggtgta  1800
cttgggtgct aaagactcta ctaggaccca gataaacaag gtagtcagat tcgacaagct  1860
gcctgggttt ggcgactcta ttgaagctca gtgtggtact tctgttaatg tccactcatc  1920
cctccgcgac atacttaatc aaattacaaa accaaatgat gtgtactcat ttagtctggc  1980
cagccgtttg tacgcagagg aacgctaccc tatcctgcca gagtatttgc aatgtgtgaa  2040
ggaacttac aggggtgggc ttgagccaat aaactttcaa acagcagccg accaagctag  2100
ggagcttatc aattcttggg tcgagagcca aactaacgaa atcatccgca acgtcctcca  2160
gccaagttcc gttgattccc agaccgctat ggtacttgtg aatgccattg tcttcaaggg  2220
gctttgggag aaggcattta agacgagga cactcaggca atgcccttc gtgtgaccga   2280
gcaggagtca aaacctgttc aaatgatgta ccaaattggg ctgttcagag ttgctagtat  2340
ggcctctgag aaaatgaaga tccttgaact cccattgcc tccgggacaa tgtctatgct   2400
tgtcctcctg ccagatgaag tcagtgggct cgaacagctc gaaagcataa taaactttga  2460
gaaacttacc gaatggactt cttccaatgt tatggaggag cgtaaaatta aggtctatct  2520
gccccgcatg aaaatggagg aaaagtataa tctcactagc gtcctcatgg ctatgggaat  2580
tactgatgta ttctcctcta gcgctaatct gagtggaatc tccagcgccg agtctctcaa  2640
gataagccag gccgtgcacg ctgctcatgc tgaaatcaac gaagccggca gagaggtggt  2700
ggggtcagct gaggcaggtg tagatgcagc cagtgtctct gaggaattta gagccgatca  2760
cccttcctt ttttgcatta aacatatcgc tacaaatgcc gttttgttt tcggtcgttg    2820
cgttagtcca aaggatgagc tttaaaaagc agaatgctga gctaaaagaa aggcttttc   2880
cattttcgag agacaatgag aaaagaagaa gaagaagaag aagaagaaga agaagaaaag  2940
agtaaataat aaagccccac aggaggcgaa gttcttgtag ctccatgtta tctaagttat  3000
tgatattgtt tgccctatat tttatttctg tcattgtgta tgttttgttc agtttcgatc  3060
tccttgcaaa atgcagagat tatgagatga ataactaag ttatattatt atacgtgtta   3120
atattctcct cctctctcta gctagccttt tgtttctct ttttcttatt tgattttctt   3180
taaatcaatc cattttagga gagggccagg gagtgatcca gcaaaacatg aagattagaa  3240
gaaacttccc tctttttttt cctgaaaaca atttaacgtc gagatttatc tcttttgta   3300
atggaatcat ttctacagtt atgactcgat taaaaatccc aattatattt ggtctaattt  3360
agtttggtat tgagtaaaac aaaattcgaac caaaccaaaa tataaatata tagtttttat  3420
atatatgcct ttaagacttt ttatagaatt ttctttaaaa aatatctaga aatatttgcg  3480
actcttctgg catgtaatat ttcgttaaat atgaagtgct ccatttttat taactttaaa  3540
taattggttg tacgatcact ttcttatcaa gtgttactaa aatgcgtcaa tctcttttgt  3600
cttccatatt catatgtcaa aatctatcaa aattcttata tatctttttc gaatttgaag  3660
tgaaatttcg ataattaa attaaataga acatatcatt atttaggtat catattgatt    3720
tttatactta attactaaat ttggttaact ttgaaagtgt acatcaacga aaaattagtc  3780
aaacgactaa aataaataaa tatcatgtgt tattaagaaa attctcctat agaaatattt  3840
taatagatca tatgtttgta aaaaaaatta atttttacta acacatatat ttacttatca  3900
aaaatttgac aaagtaagat taaaataata ttcatctaac aaaaaaaaaa ccagaaaatg  3960
ctgaaaaccc ggcaaaaccg aaccaatcca aaccgatata gttggtttgg tttgattttg  4020
atataaaccg aaccaatcg gtccatttgc acccctaatc ataatagctt taatatttca   4080
agatattatt aagttaacgt tgtcaatatc ctggaaattt tgcaaaatga atcaagccta  4140
tatggctgta atatgaattt aaaagcagct cgatgtggtg gtaatatgta atttacttga  4200
ttctaaaaaa atatcccaag tattaataat ttctgctagg aagaaggtta gctacgattt  4260
acagcaaagc cagaatacaa agaaccataa agtgattgaa gctcgaaata tacgaaggaa  4320
caaatatttt taaaaaaata cgcaatgact tggaacaaaa gaaagtgata tatttttgt   4380
tcttaaacaa gcatcccctc taaagaatgg cagtttccct ttgcatgtaa ctattatgct  4440
cccttcgtta caaaaattt ggactactat tgggaacttc ttctgaaaat agt          4493
```

SEQ ID NO: 767   moltype = DNA   length = 1956
FEATURE          Location/Qualifiers
misc_feature     1..1956
                 note = Construct AR07-28
source           1..1956
                 mol_type = other DNA
                 organism = synthetic construct
SEQUENCE: 767

```
catcggtgat tgattccttt aaagacttat gtttcttatc ttgcttctga ggcaagtatt    60
cagttaccag ttaccactta tattctggac tttctgactg catcctcatt tttccaacat   120
tttaaatttc actattggct gaatgcttct ctttgagga agaaacaatt cagatggcag   180
aaatgtatca accaatgcat atatacaaat gtacctcttg ttctcaaaac atctatcgga   240
tggttccatt tgctttgtca tccaattagt gactactta tattattcac tcctctttat    300
tactattttc atgcgaggtt gccatgtaca ttatatttgt aaggattgac gctattgagc   360
gttttcttc aatttttctt attttagaca tgggtatgaa atgtgtgtta gagttgggtt    420
gaatgagata tacgttcaag tgaagtggca taccgttgtc gagtaaggat gacctaccca   480
```

```
ttcttgagac aaaatgttaca ttttagtatc agagtaaaat gtgtacctat aactcaaatt   540
cgattgacat gtatccattc aacataaaat taaaccagcc tgcacctgca tccacatttc   600
aagtattttc aaaccgttcg gctcctatcc accgggtgta acaagacgga ttccgaattt   660
ggaagatttt gactcaaatt cccaatttat attgaccgtg actaaatcaa ctttaacttc   720
tataattctg attaagctcc caatttatat tcccaacggc actacctcca aaatttatag   780
actctcatcc ccttttaaac caacttagta aacgtttttt tttttaattt tatgaagtta   840
agttttttacc ttgttttttaa aaagaatcgt tcataagatg ccatgccaga acattagcta   900
cacgttacac atagcatgca gccgcggaga attgttttc ttcgccactt gtcactccct   960
tcaaacacct aagagcttct ctctcacagc acacacatac aatcacatgc gtgcatgcat  1020
tattacacgt gatcgccatg caaatctcct ttatagccta taaattaact catccgcttc  1080
actctttact caaaccaaaa ctcatcaata caaacaagat taaaaacata atgatgagag  1140
cacggttccc attactgttg ctgggacttg ttttcctggc ttcagtttct gtctcattga  1200
tcgtaacaca gactatgaag ggtcttgata tacagaaggg ggccgggact tggtacagtt  1260
tggcaatgcc cgcatccgac atctccttgt tggacgcaca atcagcccca ttgcgtgtga  1320
acgtagaaga gcttaaacca actcccgagg gggatctgga aattctgctc cagaaatggg  1380
agaacggtga gtgcgcccag aagaagatca tcgcagagaa gaccaaaatt ccagcagtat  1440
tcaaaatcga cgcattgaac gaaaataagg tgctcgtact ggacactgat tataagaagt  1500
atctccttttt ctgtatggag aactcagcag agcctgaaca gagtcttgcc tgccaatgcc  1560
ttgttcgtac cccagaggta gatgatgaag ctctggaaaa gttcgataag gcccttaagg  1620
ctctgcctat gcacattagg ctttctttca atccaactca acttgaggaa caatgtcaca  1680
ttaaggatga gctttaaaga tctgatcgtt caaacatttg gcaataaagt ttcttaagat  1740
tgaatcctgt tgccggtctt gcgatgatta tcatataatt tctgttgact tacgttaagc  1800
atgtaataat taacatgtaa tgcatgacgt tatttatgag atgggttttt atgattagag  1860
tcccgcaatt atacatttaa tacgcgatag aaaacaaaat atagcgcgca aactaggata  1920
aattatcgcg cgcggtgtca tctatgttac tagatc                            1956

SEQ ID NO: 768         moltype = DNA  length = 2201
FEATURE                Location/Qualifiers
misc_feature           1..2201
                       note = Construct AR07-29
source                 1..2201
                       mol_type = other DNA
                       organism = synthetic construct
SEQUENCE: 768
aacacaagct tcaagtttta aaaggaaaaa tgtcagccaa aaactttaaa taaaatggta   60
acaaggaaat tattcaaaaa ttacaaacct cgtcaaaata ggaaagaaaa aaagtttagg  120
gatttagaaa aaacatcaat ctagttccac cttattttat agagagaaga aactaatata  180
taagaactaa aaaacagaag aatagaaaaa aaaagtattg acaggaaaga aaaagtagct  240
gtatgcttat aagtactttg aggatttgaa ttctctctta taaaacacaa acacaatttt  300
tagattttat ttaaataatc atcaatccga ttataattat ttatatattt ttctatttc   360
aaagaagtaa atcatgagct tttccaactc aacatctatt tttttctct caaccttttt  420
cacatcttaa gtagtctcac cctttatata tataacttat ttcttacctt ttacattatg  480
taacttttat caccaaaacc aacaacttta aaatttttatt aaatagactc cacaagtaac  540
ttgacactct tacattcatc gacattaact tttatctgtt ttataaatat tattgtgata  600
taatttaatc aaaataacca caaactttca taaaaggttc ttattaagca tggcatttaa  660
taagcaaaaa caactcaatc acttttcatat aggaggtagc ctaagtacgt actcaaaatg  720
ccaacaaata aaaaaaagt tgcttttaata atgccaaata aatacacttaca  780
acaccggatt ttttttaatt aaaaatgtgcc atttaggata aatagttaat attttttaata  840
attatttaaa aagccgtatc tactaaaatg attttttattt ggttgaaaat attaatatgt  900
ttaaatcaac acaatctatc aaaattaaac taaaaaaaaa ataagtgtac gtggttaaca  960
ttagtacagt aatataagag gaaaatgaga aattaagaaa ttgaaagcga gtctaatttt  1020
taaattatga acctgcatat ataaaaggaa agaaagaatc caggaagaaa agaaatgaaa  1080
ccatgcatgg tcccctcgtc atcacgagtt tctgccattt gcaatagaaa cactgaaaca  1140
cctttctctt tgtcacttaa ttgagatgcc gaagccacct cacaccatga acttcatgag  1200
gtgtagcacc caaggcttcc atagccatgc atactgaaga atgtctcaag ctcagcaccc  1260
tacttctgtg acgtgtccct cattcacctt cctctcttcc ctataaataa ccacgcctca  1320
ggttctccgc ttcacaactc aaacattctc tccattggtc cttaaacact catcagtcat  1380
caccatggcc aagctagttt tttcccttttg ttttctgctt tcagtggct gctgcttcgc  1440
tttgatcgta acacagacta tgaagggtct tgatatacag aaggtggccg ggacttggta  1500
cagtttggca atggccgcat ccgacatctc cttgttggac gcacaatcag ccccattgcg  1560
tgtgtacgta gaagagctta aaccaactcc cgagggggat ctggaaattc tgctccagaa  1620
atgggagaac ggtgagtgcg cccagaagaa gatcatcgca gagaagacca aaattccagc  1680
agtattcaaa atcgacgcat tgaacgaaaa taaggtgctc gtactggaca ctgattataa  1740
gaagtatctc ctttctgta tggagaactc agcagagtc ttgcctgcca  1800
atgccttgtt cgtaccccag aggtagatga tgaagctctg gaaaagttcg ataaggccct  1860
taaggctctg cctatgcaca ttaggctttc tttcaatcca actcaacttg aggaacaatg  1920
tcacattaag gatgagcttt aaagatctga tcgttcaaac atttggcaat aaagtttctt  1980
aagattgaat cctgttgccg gtcttgcgat gattatcata taatttctgt tgaattacgt  2040
taagcatgta ataattaaca tgtaatgcat gacgttattt atgagatgag ttttatgat  2100
tagagtcccg caattataca tttaatacgc gatagaaaac aaaatatagc gcgcaaacta  2160
ggataaatta tcgcgcgcgg tgtcatctat gttactagat c                      2201

SEQ ID NO: 769         moltype = DNA  length = 2277
FEATURE                Location/Qualifiers
misc_feature           1..2277
                       note = Construct AR07-31
source                 1..2277
                       mol_type = other DNA
                       organism = synthetic construct
```

```
SEQUENCE: 769
caactattat cgcatgatga tgtacgttaa gtcatcatca tctttaactt tatatattgt   60
taaaagtaga aaaaataggt gatgcattat aaaataattt tataacatca tttaattata  120
aattatttat aataaatatt tgagttttta tagtaattac ctaaacaatt atatcaagac  180
taatgcctga ttagttgaca tgacgaaatt aaactcataa aagtaaagat gtttatgtgg  240
aaaactctta tacaattgag cggacttttt tccatggtag ttcagttttc ttctattcaa  300
tttatttttt tggtttccgc tcagaataag aataatttga taaattcatt tttaggcaat  360
taagaatatt tatttgacta acttttaat tgaaataaat ttacaataaa tactcaattt  420
atctttcaca atcaaaagat tgagatgttg taagatctcc gataatatac ttatatcttt  480
tcatttatta cgttttcaaa tttgaatttt aatgtgtgtt gtaagtataa atttaaaata  540
aaaataaaaa caattattat atcaaaatgg caaaaacatt taatacgtat tatttaagaa  600
aaaaatatgt aataatatat ttatatttta atatctattc ttatgtattt tttaaaaatc  660
tattatatat tgatcaacta aaatattttt atatctacac ttattttgca ttttttatcaa  720
ttttcttgcg ttttttggca tatttaataa tgactattct ttaataatca atcattattc  780
ttacatggta catattgttg gaaccatatg aagtgtccat tgcatttgac tatgtggata  840
gtgtttttgat ccaggcctcc atttgccgct tattaattaa tttggtaaca gtccgtacta  900
atcagttact tatccttcct ccatcataat taatcttggt agtctcgaat gccacaacac  960
tgactagtct cttggatcat aagaaaaagc caaggaacaa aagaagacaa aacacaatga 1020
gagtatcctt tgcatagcaa tgtctaagtt cataaaattc aaacaaaaac gcaatcacac 1080
acagtggaca tcacttatcc actagctgat caggatcgcc gcgtcaagaa aaaaaaactg 1140
gaccccaaaa gccatgcaca acaacacgta ctcacaaagg tgtcaatcga gcagcccaaa 1200
acattcacca actcaaccca tcatgagccc acacattttgt tgtttctaac ccaacctcaa 1260
actcgtattc tcttccgcca cctcattttt gtttatttca acaccgtca aactgcatgc 1320
caccccgtgg ccaaatgtcc atgcatgtta acaagaccta tgactataaa tatctgcaat 1380
ctcggcccag gttttcatca tcaagaacca gttcaatatc ctagtacacc gtattaaaga 1440
atttaagata tactatggct accaagatat ttgccctcct tgtgctcctt gctcttcag 1500
cgagcgctac aactgcgttg atcgtaacac agactatgaa gggtcttgat atacagaagg 1560
tggccgggac ttggtacagt ttggcaatgg ccgcatccga catctccttg ttggacgcac 1620
aatcagcccc attgcgtgtg tacgtagaag agcttaaacc aactcccgag gggatctgg 1680
aaattctgct ccagaaatgg gagaacggtg agtgcgccca gaagaagatc atcgcagaga 1740
agaccaaaat tccagcagta tcaaaatcga acgcattgaa cgaaaataag gtgctcgtac 1800
tggacactga ttataagaag tatctccttt ctgtatggaa gaactcagca gagcctgaac 1860
agagtcttgc ctgccaatgc cttgttcgta ccccagaggt agatgatgaa gctctggaaa 1920
agttcgataa ggcccttaag gctctgcctca tgcacattag gctttcttc aatccaactc 1980
aacttggagga acaatgtcac attaaggatg agctttaaag atctgatcgt tcaaacatttt 2040
ggcaataaag tttcttaaga ttgaatcctg ttgccggtct tgcgatgatt atcatataat 2100
ttctgttgaa ttacgttaag catgtaataa ttaacatgta atgcatgacg ttatttatga 2160
gatgggtttt tatgattaga gtcccgcaat tatacattta atacgcgata gaaaacaaaa 2220
tatagcgcgc aaactaggat aaattatcgc gcgcggtgtc atctatgtta ctagatc     2277

SEQ ID NO: 770          moltype = DNA   length = 2286
FEATURE                 Location/Qualifiers
misc_feature            1..2286
                        note = Construct AR07-32
source                  1..2286
                        mol_type = other DNA
                        organism = synthetic construct
SEQUENCE: 770
caactattat cgcatgatga tgtacgttaa gtcatcatca tctttaactt tatatattgt   60
taaaagtaga aaaaataggt gatgcattat aaaataattt tataacatca tttaattata  120
aattatttat aataaatatt tgagttttta tagtaattac ctaaacaatt atatcaagac  180
taatgcctga ttagttgaca tgacgaaatt aaactcataa aagtaaagat gtttatgtgg  240
aaaactctta tacaattgag cggacttttt tccatggtag ttcagttttc ttctattcaa  300
tttatttttt tggtttccgc tcagaataag aataatttga taaattcatt tttaggcaat  360
taagaatatt tatttgacta acttttaat tgaaataaat ttacaataaa tactcaattt  420
atctttcaca atcaaaagat tgagatgttg taagatctcc gataatatac ttatatcttt  480
tcatttatta cgttttcaaa tttgaatttt aatgtgtgtt gtaagtataa atttaaaata  540
aaaataaaaa caattattat atcaaaatgg caaaaacatt taatacgtat tatttaagaa  600
aaaaatatgt aataatatat ttatatttta atatctattc ttatgtattt tttaaaaatc  660
tattatatat tgatcaacta aaatattttt atatctacac ttattttgca ttttttatcaa  720
ttttcttgcg ttttttggca tatttaataa tgactattct ttaataatca atcattattc  780
ttacatggta catattgttg gaaccatatg aagtgtccat tgcatttgac tatgtggata  840
gtgtttttgat ccaggcctcc atttgccgct tattaattaa tttggtaaca gtccgtacta  900
atcagttact tatccttcct ccatcataat taatcttggt agtctcgaat gccacaacac  960
tgactagtct cttggatcat aagaaaaagc caaggaacaa aagaagacaa aacacaatga 1020
gagtatcctt tgcatagcaa tgtctaagtt cataaaattc aaacaaaaac gcaatcacac 1080
acagtggaca tcacttatcc actagctgat caggatcgcc gcgtcaagaa aaaaaaactg 1140
gaccccaaaa gccatgcaca acaacacgta ctcacaaagg tgtcaatcga gcagcccaaa 1200
acattcacca actcaaccca tcatgagccc acacattttgt tgtttctaac ccaacctcaa 1260
actcgtattc tcttccgcca cctcattttt gtttatttca acaccgtca aactgcatgc 1320
caccccgtgg ccaaatgtcc atgcatgtta acaagaccta tgactataaa tatctgcaat 1380
ctcggcccag gttttcatca tcaagaacca gttcaatatc ctagtacacc gtattaaaga 1440
atttaagata tactatgatg agagcgcggt tcccattact gttgctggga gttgttttcc 1500
tggcatcagt ttctgtctca tttggcttga tcgtaacaca gactatgaag ggtcttgata 1560
tacagaaggt ggccgggact tggtacagtt tggcaatggc cgcatccgac atctccttgt 1620
tggacgcaca atcagcccca ttgcgtgtgt acgtagaaga gcttaaacca actcccgagg 1680
gggatctgga aattctgctc cagaaatggg agaacggtga gtgcgcccag aagaagatca 1740
tcgcagagaa gaccaaaatt ccagcagtat caaaatcgac gcattgaacg aaaataaggt 1800
gctcgtactg gacactgatt ataagaagta tctcctttct gtatggagaa actcagcag 1860
```

```
agcctgaaca gagtcttgcc tgccaatgcc ttgttcgtac cccagaggta gatgatgaag   1920
ctctggaaaa gttcgataag gcccttaagg ctctgcctat gcacattagg ctttctttca   1980
atccaactca acttgaggaa caatgtcaca ttaaggatga gctttaaaga tctgatcgtt   2040
caaacatttg gcataaaagt ttcttaagat tgaatcctgt tgccggtctt gcgatgatta   2100
tcatataatt tctgttgaat tacgttaagc atgtaataat taacatgtaa tgcatgacgt   2160
tatttatgag atgggttttt atgattagag tcccgcaatt atacatttaa tacgcgatag   2220
aaaacaaaat atagcgcgca aactaggata aattatcgcg cgcggtgtca tctatgttac   2280
tagatc                                                              2286

SEQ ID NO: 771         moltype = DNA   length = 3350
FEATURE                Location/Qualifiers
misc_feature           1..3350
                       note = Construct AR07-33
source                 1..3350
                       mol_type = other DNA
                       organism = synthetic construct
SEQUENCE: 771
cattgtactc ccagtatcat tatagtgaaa gttttggctc tctcgccggt ggttttttac   60
ctctatttaa aggggttttc cacctaaaaa ttctggtatc attctcactt tacttgttac   120
tttaatttct cataatcttt ggttgaaatt atcacgcttc cgcacacgat atccctacaa   180
atttattatt tgttaaacat tttcaaaccg cataaaattt tatgaagtcc cgtctatctt   240
taatgtagtc taacattttc atattgaaat atataattta cttaattttta gcgttggtag   300
aaagcataat gatttattct tattcttctt catataaatg tttaatatac aatataaaca   360
aattctttac cttaagaagg atttcccatt ttatatttta aaaatatatt tatcaaatat   420
ttttcaacca cgtaaatcac ataataataa gttgttcaa aagtaataaa atttaactcc   480
ataattttt tatttgactg atcttaaagc aacaccagt gacacaacta gccattttt   540
tctttgaata aaaaaatcca attatcattg tattttttt atacaatgaa aatttcacca   600
aacaatgatt tgtggtattt ctgaagcaag tcatgttatg caaaattcta taattcccat   660
ttgacactac ggaagtaact gaagatctgc ttttacatgc gagacacatc ttctaaagta   720
attttaataa tagttactat attcaagatt tcatatatca aatactcaat attacttcta   780
aaaaattaat tagatataat taaaatatta cttttttaat tttaagttta attgttgaat   840
ttgtgactat tgatttatta ttctactatg tttaaattgt tttataggta gtttaaagta   900
aatataagta atgtagtaga gtgttagagt gttaccctaa accataaact ataagattta   960
tggtggacta attttcatat atttcttatt gcttttacct tttcttggta tgtaagtccg   1020
taactggaat tactgtgggt tgccatgaca ctctgtggtc ttttggttca tgcatggatg   1080
cttgcgcaag aaaaagacaa agaacaaaga aaaagacaa aacagagaga caaaacgcaa   1140
tcacacaacc aactcaaatt agtcactggc tgatcaagat cgccgcgtcc atgtatgtct   1200
aaatgccatg caaagcaaca cgtgcttaac atgcacttta aatggctcac ccatcccaac   1260
ccactcacaa acacattgcc tttttcttca tcatcaccac aacacctgt atatattcat   1320
tctcttccgc cacctcaatt tcttcacttc aacacacgtc aacctgcata tgcgtgtcat   1380
cccatgccca aatctccatg catgttccta ccaccttctc tcttatataa tacctataaa   1440
tacctctaat atcactcact tctttcatca tccatccatc cagagtacta ctactctact   1500
actataatac cccaacccaa ctcatattca atactactct acttgaatgc atgatcatgg   1560
ctacttcaaa gttgaaaacc cagaatgtgg ttgtatctct ctccctaacc ttaaccttgg   1620
tactggtgct actgaccagc aaggcaaact cattgatcgt aacacagact atgaagggtc   1680
ttgatataca gaaggtggcc gggacttggt acagtttggc aatggccgca tccgacatct   1740
cctgttgga cgcacaatca gccccattgc gtgtgtacgt agaagagctt aaaaccaactc   1800
ccgaggggga tctggaaatt ctgctccaga aatgggagaa cggtgagtgc gcccagaaga   1860
agatcatcgc agagaagacc aaaattccag cagtattcaa aatcgacgca ttgaacgaaa   1920
ataaggtgct cgtactggac actgattata agaagtatct cctttctgt atggagaact   1980
cagcagagcc tgaacagagt cttgcctgcc aatgccttgt tcgtaccca gaggtagatg   2040
atgaagctct ggaaaagttc gataaggcc ttaaggctct gcctatgcac attaggcttt   2100
ctttcaatcc aactcaactt gaggaacaat gtcacattaa ggatgagctt taaaataaat   2160
aaaatgggag caataaataa aatgggagct catatattta caccatttac actgtctatt   2220
attcaccatg ccaattatta cttcataatt ttaaaattat gtcattttta aaaattgctt   2280
aatgatggaa aggattatta taagttaaaa gtataacata gataaactaa ccacaaaaca   2340
aatcaatata aactaactta ctctcccatc taattttat ttaaatttct ttacacttct   2400
cttccatttc tatttctaca acattattta acatttttat tgtatttttc ttactttcta   2460
actctattca tttcaaaaat caatatatgt ttatcaccac ctctctaaaa aaaactttac   2520
aatcattggt ccagaaaagt taaatcacga gatggtcatt ttagcattaa aacaacgatt   2580
cttgtatcac tattttcag catgtagtcc attctcttca aacaaagaca gcggctatat   2640
aatcgttgtg ttatattcag tctaaaacaa ttgttatggt aaaagtcgtc atttacgcc   2700
ttttaaaag atataaatg acagttatgg ttaaagtca tcatgttaga tcctcctaa   2760
agatataaaa tgcagttttt ggataaaaag tggtcattt atacgctctt gaaagtata   2820
aaacgacggt tatggtaaaa gctgccattt taaatgaaat attttgttt tagttcattt   2880
tgtttaatgc taatcccatt taaattgact tgtacaatta aaactcaccc acccagatac   2940
aatataaact aacttactct cacagctaag ttttatttaa atttctttac acttcttttc   3000
catttctatt tctatgacat taactaacat ttttctcgta tttatttttca   3060
actctatcca tttcaaatcg atatatgttt atcaccacca ctttaaaaag aaaatttaca   3120
atttctcgtg caaaaaagct aaatcatgac cgtcatttta gcattaaaac aacgattctt   3180
gtatcgttgt ttttcagcat gtagtccatt cttttcaagc aaagacaaca gctatataat   3240
catcgtgtta tattcagtct aaaacaacag taatgataaa agtcatcatt ttaggccttt   3300
ctgaaatata tagaacgaca ttcatggtaa aaaatcgtca ttttagatcc              3350

SEQ ID NO: 772         moltype = DNA   length = 3590
FEATURE                Location/Qualifiers
misc_feature           1..3590
                       note = Construct AR15-25
source                 1..3590
```

```
                    mol_type = other DNA
                    organism = synthetic construct
SEQUENCE: 772
aacacaagct tcaagtttta aaaggaaaaa tgtcagccaa aaactttaaa taaaatggta    60
acaaggaaat tattcaaaaa ttacaaacct cgtcaaaata ggaaagaaaa aaagtttagg   120
gatttagaaa aaacatcaat ctagttccac cttattttat agagagaaga aactaatata   180
taagaactaa aaaacagaag aatagaaaaa aaagtattg acaggaaaga aaaagtagct    240
gtatgcttat aagtactttg aggatttgaa ttctctctta taaaacacaa acacaatttt   300
tagatttat ttaaataatc atcaatccga ttataattat ttatatattt ttctatttc    360
aaagaagtaa atcatgagct tttccaactc aacatctatt tttttctct caacctttt    420
cacatcttaa gtagtctcac cctttatata tataacttat ttcttacctt ttacattatg   480
taactttat caccaaaacc aacaacttta aaattttatt aaatagactc cacaagtaac    540
ttgacactct tacattcatc gacattaact tttatctgtt ttataaatat tattgtgata   600
taatttaatc aaaataacca caaactttca taaaaggttc ttattaagca tggcatttaa   660
taagcaaaaa caactcaatc actttcatat aggaggtagc ctaagtacgt actcaaaatg   720
ccaacaaata aaaaaaaagt tgctttaata atgccaaaac aaattaataa aacacttaca   780
acaccggatt ttttttaatt aaaatgtgcc atttaggata aatagttaat attttaata   840
attatttaaa aagccgtatc tactaaaatg attttattt ggtgaaaat attaatatgt    900
ttaaatcaac acaatctatc aaaattaaac taaaaaaaaa ataagtgtac gtggttaaca   960
ttagtacagt aatataagag gaaaatgaga aattaagaaa ttgaaagcga gtctaatttt  1020
taaattatga acctgcatat ataaaggaa agaaagaatc caggaagaaa agaaatgaaa   1080
ccatgcatgg tcccctcgtc atcacgagtt tctgccattt gcaatagaac actgaaaca   1140
cctttctctt tgtcacttaa ttgagatgcc gaagccacct cacaccatga acttcatgag  1200
gtgtagcacc caaggcttcc atagccatgc atactgaaga atgtctcaag ctcagcaccc  1260
tacttctgtg acgtgtccct cattcacctt cctctcttcc ctataaataa ccacgcctca  1320
ggttcctccgc ttcacaactc aaacattctc tccattggtc cttaaacact catcagtcat 1380
caccatggcc aagctagttt tttcccttg ttttctgctt ttcagtggct gctgcttcgc   1440
tcttattgtg acccaaacca tgaagggcct cgacattcaa aaggttgccg gaacctggta  1500
ctcccttgct atggctgctt ccgatatctc cttgctcgat gctcaatccg ctccacttag  1560
ggtgtacgtg gaagagttga gccaactcc agagggcgat cttgagatct tgcttcaaaa  1620
gtgggagaac gatgagtgcg cccagaagaa gattatcgcc gaaaagacca agattcccgc  1680
cgtgttcaag atcgatgctc tcaacgagaa caaggtgctc gtgctcgata ccgactacaa  1740
gaagtacctt ctcgtctgca tggaaaactc cgctgagcca gagcaatctc ttgtttgcca  1800
atgccttgtg aggaccccag aggttgacga tgaagctctt gagaagttcg acaaggctct  1860
caaggctttg cctatgcaca tccgccttag cttcaaccca actcagcttg aggaacagtg  1920
ccacatcaag gatgagcttt aaaaagcaga atgctgagct aaaagaaagg ctttttccat  1980
tttcgagaga caatgagaaa agaagaagaa gaagaagaag aagaagaaga agaaaagagt  2040
aaataataaa gccccacagg aggcgaagtt cttgtagctc catgttatct aagttattga  2100
tattgtttgc cctatatttt atttctgtca ttgtgtatgt tttgttcagt ttcgatctcc  2160
ttgcaaaatg cagagattat gagatgaata aactaagtta tattattata cgtgttaata  2220
ttctcctcct ctctctagct agccttttgt tttctctttt tcttatttga ttttctttaa  2280
atcaatccat tttaggagag ggccaggag tgatccagca aaacatgaag attagaagaa   2340
acttccctct tttttttcct gaaaacaatt taacgtcgag atttatctct ttttgtaatg  2400
gaatcatttc tacagttatg actcgattaa aaatcccaat tatatttggt ctaatttagt  2460
ttggtattga gtaaaacaaa ttcgaaccaa accaaaatat aaatatatag ttttatata   2520
tatgcctta agactttta tagaatttc tttaaaaaat atctagaaat atttgcgact    2580
cttctggcat gtaatattc gttaaatatg aagtgctcca ttttattaa cttaaataa    2640
ttggttgtac gatcacttc ttatcaagtg ttactaaaat gcgtcaatct cttgttctt    2700
ccatattcat atgtcaaaat ctatcaaaat tcttatatat cttttcgaa tttgaagtga   2760
aatttcgata atttaaatt aaatagaaca tatcattatt taggtatcat attgattttt   2820
atacttaatt actaaatttg gttaactttg aaagtgtaca tcaacgaaaa attagtcaaa   2880
cgactaaaat aaaataaatat catgtgttat taagaaaatt ctcctataag aatattttaa  2940
tagatcatat gtttgtaaaa aaaattaatt tttactaaca catatattta cttatcaaaa  3000
atttgacaaa gtaagattaa aataatattc atctaacaaa aaaaaaacca gaaaatgctg  3060
aaaacccggc aaaaccgaac caatccaaac cgatatagtc ggtttggttt gattttgata  3120
taaaccgaac caactcggtc catttgcacc cctaatcata atagctttaa tatttcaaga  3180
tattattaag ttaacgttgt caatatcctg gaaattttgc aaaatgaatc aagcctatat  3240
ggctgtaata tgaatttaaa agcagctcga tgtggtggta atatgtaatt tacttgattc  3300
taaaaaaata tcccaagtat taataattc tgctaggaag aaggttagct acgatttaca  3360
gcaaagccag aatacaaaga accataaagt gattgaagct cgaaatatac gaaggaacaa  3420
atattttaa aaaaatacgc aatgacttgg aacaaaagaa agtgatatat tttttgttct  3480
taaacaagca tccctctaa agaatggcag ttttcctttg catgtaacta ttatgctccc   3540
ttcgttacaa aaattttgga ctactattgg gaacttcttc tgaaaatagt               3590

SEQ ID NO: 773        moltype = DNA   length = 3590
FEATURE               Location/Qualifiers
misc_feature          1..3590
                      note = Construct AR15-26
source                1..3590
                      mol_type = other DNA
                      organism = synthetic construct
SEQUENCE: 773
aacacaagct tcaagtttta aaaggaaaaa tgtcagccaa aaactttaaa taaaatggta    60
acaaggaaat tattcaaaaa ttacaaacct cgtcaaaata ggaaagaaaa aaagtttagg   120
gatttagaaa aaacatcaat ctagttccac cttattttat agagagaaga aactaatata   180
taagaactaa aaaacagaag aatagaaaaa aaagtattg acaggaaaga aaaagtagct    240
gtatgcttat aagtactttg aggatttgaa ttctctctta taaaacacaa acacaatttt   300
tagatttat ttaaataatc atcaatccga ttataattat ttatatattt ttctatttc    360
aaagaagtaa atcatgagct tttccaactc aacatctatt tttttctct caacctttt    420
```

```
cacatcttaa gtagtctcac cctttatata tataacttat ttcttacctt ttacattatg  480
taacttttat caccaaaacc aacaacttta aatttttatt aaatagactc cacaagtaac  540
ttgacactct tacattcatc gacattaact tttatctgtt ttataaatat tattgtgata  600
taatttaatc aaaataacca caaactttca taaaaggttc ttattaagca tggcatttaa  660
taagcaaaaa caactcaatc actttcatat aggaggtagc ctaagtacgt actcaaaatg  720
ccaacaaata aaaaaaaagt tgctttaata atgccaaaac aaattaataa aacacttaca  780
acaccggatt ttttttaatt aaaatgtgcc atttaggata aatagttaat attttttaata  840
attatttaaa aagccgtatc tactaaaatg attttttattt ggttgaaaat attaatatgt  900
ttaaatcaac acaatctatc aaaattaaac taaaaaaaaa ataagtgtac gtggttaaca  960
ttagtacagt aatataagag gaaaatgaga aattaagaaa ttgaaagcga gtctaatttt 1020
taaattatga acctgcatat ataaaaggaa agaagaatc caggaagaaa agaaatgaaa 1080
ccatgcatgg tccoctcgtc atcacgagtt tctgccattt gcaatagaaa cactgaaaca 1140
cctttctctt tgtcacttaa ttgagatgcc gaagccacct cacaccatga acttcatgag 1200
gtgtagcacc caaggcttcc atagccatgc atactgaaga atgtctcaag ctcagcaccc 1260
tacttctgtg acgtgtccct cattcacctt cctctcttcc ctataaataa ccacgcctca 1320
ggttctccgc ttcacaactc aaacattctc tccattggtc cttaaacact catcagtcat 1380
caccatggcc aagctagttt tttccctttg tttctgctt ttcagtggct gctgcttcgc 1440
tctcattgtt acacaaacca tgaagggtct tgacattcag aaggttgctg ggacatggta 1500
ttcactagcg atggctgctt ctgatatctc cctgttggat gcacagtctg cccccctgag 1560
agtgtatgtt gaagaactga aaccgacacc tgaaggagac ttggaaattt tactccagaa 1620
atgggaaaat gatgagtgtg cccaaaagaa gataatagcc gagaagacca aaattcctgc 1680
tgtgtttaag attgatgctt tgaatgagaa caagtacta gtcctcgaca ctgattacaa 1740
gaaatactta ttagtgtgca tggaaaacag cgcagagcca gaacaatcac ttgtttgtca 1800
atgtttggtc cgtactccag aggtagatga tgaagcattg gagaaatttg ataaagcatt 1860
gaaggcactt ccaatgcata taaggcttag tttcaatcct actcagcttg aagagcaatg 1920
ccacatcaag gatgagcttt aaaaagcaga atgctgaact aaaagaaagg cttttttccat 1980
tttcgagaga caatgagaaa agaagaagaa gaagaagaag aagaagaaga agaaaagagt 2040
aaataataaa gccccacagg aggcgaagtt cttgtagctc catgttatct aagttattga 2100
tattgtttgc cctatatttt atttctgtca ttgtgtatgt tttgttcagt ttcgatctcc 2160
ttgcaaaatg cagagattat gagatgaata aactaagtta tattattata cgtgttaata 2220
ttctcctcct ctctctagct agcctttgt tttctctttt tcttatttga ttttctttaa 2280
atcaatccat tttaggagag ggccagggag tgatccagca aaacatgaag attagaagaa 2340
acttccctct tttttttcct gaaaacaatt taacgtcgag atttatctct ttttgtaatg 2400
gaatcatttc tacagttatg actcgattaa aaatcccaat tatatttggt ctaatttagt 2460
ttggtattga gtaaaacaaa ttcgaaccaa accaaaatat aaatatatag ttttttatata 2520
tatgccttta agacttttta tagaattttc tttaaaaaat atctagaaat atttgcgact 2580
cttctggcat gtaatatttc gttaaaatatg aagtgctcca tttttattaa ctttaaataa 2640
ttggttgtac gatcactttc ttatcaagtg ttactaaaat gcgtcaatct ctttgttctt 2700
ccatattcat atgtcaaaat ctatcaaaat tcttatatat cttttcgaa tttgaagtga 2760
aatttcgata atttaaaatt aaatagaaca tatcattatt taggtatcat attgatttttt 2820
atacttaatt actaaatttg gttaacttttg aaagtgtaca tcaacgaaaa attagtcaaa 2880
cgactaaaat aaataaatat catgtgttat taagaaaatt ctcctataag aatatttttaa 2940
tagatcatat gtttgtaaaa aaaatttaatt tttactaaca catatattta cttatcaaaa 3000
atttgacaaa gtaagattaa aataatattc atctaacaaa aaaaaaacca gaaaatgctg 3060
aaaaccggc aaaaccgaac caatccaaac cgatatagtt ggtttggttt gattttgata 3120
taaaccgaac caactcggtc catttgcacc cctaatcata atagctttaa tatttcaaga 3180
tattattaag ttaacgttgt caatatcctg gaaattttgc aaaatgaatc aagcctatat 3240
ggctgtaata tgaattttaaa agcagctcga tgtggtggta atatgtaatt tacttgattc 3300
taaaaaaata tcccaagtat taataattc tgctaggaag aaggttagct acgatttaca 3360
gcaaagccaa aatacaaaga accataaagt gattgaagct cgaaatatac gaaggaacaa 3420
atattttaa aaaaaatacgc aatgacttgg aacaaaagaa agtgatatat tttttgttct 3480
taaacaagca tcccctctaa agaatggcag ttttcctttg catgtaacta ttatgctccc 3540
ttcgttacaa aaatttttgga ctactattgg gaacttcttc tgaaaatagt           3590
```

SEQ ID NO: 774        moltype = DNA  length = 3590
FEATURE               Location/Qualifiers
misc_feature       1..3590
                      note = Construct AR15-27
source                1..3590
                      mol_type = other DNA
                      organism = synthetic construct
SEQUENCE: 774

```
aacacaagct tcaagtttta aaaggaaaaa tgtcagccaa aaactttaaa taaaatggta   60
acaaggaaat tattcaaaaa ttacaaacct cgtcaaaata ggaaagaaaa aaagtttagg  120
gatttagaaa aaacatcaat ctagttccac cttattttat agagagaaga aactaatata  180
taagaactaa aaaacagaag aatagaaaaa aaagtattg acaggaaaga aaagtagct  240
gtatgcttat aagtactttg aggatttgaa ttctctctta taaacacaa acacaatttt  300
tagattttat ttaaataatc atcaatccga ttataattat ttatatattt ttctattttc  360
aaagaagtaa atcatgagct tttccaactc aacatctatt ttttttctct caaccttttt  420
cacatcttaa gtagtctcac cctttatata tataacttat ttcttacctt ttacattatg  480
taacttttat caccaaaacc aacaacttta aatttttatt aaatagactc cacaagtaac  540
ttgacactct tacattcatc gacattaact tttatctgtt ttataaatat tattgtgata  600
taatttaatc aaaataacca caaactttca taaaaggttc ttattaagca tggcatttaa  660
taagcaaaaa caactcaatc actttcatat aggaggtagc ctaagtacgt actcaaaatg  720
ccaacaaata aaaaaaaagt tgctttaata atgccaaaac aaattaataa aacacttaca  780
acaccggatt ttttttaatt aaaatgtgcc atttaggata aatagttaat attttttaata  840
attatttaaa aagccgtatc tactaaaatg attttttattt ggttgaaaat attaatatgt  900
ttaaatcaac acaatctatc aaaattaaac taaaaaaaaa ataagtgtac gtggttaaca  960
ttagtacagt aatataagag gaaaatgaga aattaagaaa ttgaaagcga gtctaatttt 1020
```

```
taaattatga acctgcatat ataaaaggaa agaaagaatc caggaagaaa agaaatgaaa 1080
ccatgcatgg tccccctcgtc atcacgagtt tctgccattt gcaatagaaa cactgaaaca 1140
cctttctctt tgtcacttaa ttgagatgcc gaagccacct cacaccatga acttcatgag 1200
gtgtagcacc caaggcttcc atagccatgc atactgaaga atgtctcaag ctcagcaccc 1260
tacttctgtg acgtgtccct cattcacctt cctctcttcc ctataaataa ccacgcctca 1320
ggttctccgc ttcacaactc aaacattctc tccattggtc cttaaacact catcagtcat 1380
caccatggcc aagctagttt tttcccttg ttttctgctt tcagtggct gctgcttcgc 1440
tcttatagta actcaaacca tgaagggact tgatatccaa aaagttgcag gaacctggta 1500
ctcactggct atggcagctt ccgacatctc cttgttggac gcacaatccg caccattgga 1560
cgtctacgtt gaggagttga aacctacacc agaggggat cttgagattt tgctccagaa 1620
atgggagaac gacgagtgtg cccagaaaaa aattatagca gagaagacta aaattcctgc 1680
tgttttaag attgatgccc tgaacgagaa taaggtactg gtcctcgaca ctgattataa 1740
aaagtatttg ctggtgtgta tggagaacag tgctgaacct gaacagagcc tggtctgtca 1800
atgtcttgta aggacacctg aggttgatga cgaggcactt gaaaaattcg acaaggccct 1860
taaggctctg cctatgcaca tccgtctgag tttcaaccct actcagttgg aggaacaatg 1920
tcatattaag gatgagcttt aaaaagcaga atgctgagct aaaagaaagg cttttttccat 1980
tttcgagaga caatgagaaa agaagaagaa gaagaagaag aagaagaaga agaaaagagt 2040
aaataataaa gccccacagg aggcgaagtt cttgtagctc catgttatct aagttattga 2100
tattgtttgc cctatatttt atttctgtca ttgtgtatgt tttgttcagt ttcgatctcc 2160
ttgcaaaatg cagagattat gagatgaata aactaagtta tattattata cgtgttaata 2220
ttctcctcct ctctctagct agccttttgt tttctctttt tcttatttga ttttctttaa 2280
atcaatccat tttaggagag ggccagggag tgatccagca aaacatgaag attagaagaa 2340
acttccctct tttttttcct gaaaacaatt taacgtcgag atttatctct ttttgtaatg 2400
gaatcatttc tacagttatg actcgattaa aaatcccaat tatatttggt ctaatttagt 2460
ttggtattga gtaaaacaaa ttcgaaccaa accaaaatat aaatatatag ttttttatata 2520
tatgcccttta agacttttta tagaattttc tttaaaaat atctagaatt atttgcgact 2580
cttctggcat gtaatatttc gttaaatatg aagtgctcca ttttattaa ctttaaataa 2640
ttggttgtac gatcactttc ttatcaagtg ttactaaaat gcgtcaatct cttgttctt 2700
ccatattcat atgtcaaaat ctatcaaaat tcttatatat cttttttcgaa tttgaagtga 2760
aatttcgata atttaaaatt aaatagaaca tatcattatt taggtatcat attgattttt 2820
atacttaatt actaaatttg gttaactttg aaagtgtaca tcaacgaaaa attagtcaaa 2880
cgactaaaat aaataaatat catgtgttat taagaaaatt ctcctataag aatattttaa 2940
tagatcatat gtttgtaaaa aaaattaatt tttactaaca catatattta cttatcaaaa 3000
atttgacaaa gtaagattaa aataatattc atctaacaaa aaaaaaaccca gaaaatgctg 3060
aaaaccccggc aaaaccgaac caatccaaac cgatatagtt ggtttggttt gattttgata 3120
taaaccgaac caactcggtc catttgcacc cctaatcata atagctttaa tatttcaaga 3180
tattattaag ttaacgttgt caatatcctg gaaatttgc aaaatgaatc aagcctatat 3240
ggctgtaata tgaatttaaa agcagctcga tgtggtggta atatgtaatt tacttgattc 3300
taaaaaaata tcccaagtat taataatttc tgctaggaag aaggttagct acgatttaca 3360
gcaaagccag aatacaaaga accataaagt gattgaagct cgaaatatac gaaggaacaa 3420
atattttaa aaaaatacgc aatgacttgg aacaaaagaa agtgatatat ttttgttct 3480
taaacaagca tccctcaa agaatggcag ttttcctttg catgtaacta ttatgctccc 3540
ttcgttacaa aaattttgga ctactattgg gaacttcttc tgaaaatagt     3590

SEQ ID NO: 775        moltype = DNA   length = 3578
FEATURE               Location/Qualifiers
misc_feature          1..3578
                      note = Construct AR15-28
source                1..3578
                      mol_type = other DNA
                      organism = synthetic construct
SEQUENCE: 775
aacacaagct tcaagtttta aaaggaaaaa tgtcagccaa aaactttaaa taaaatggta 60
acaaggaaat tattcaaaaa ttacaaacct cgtcaaaata ggaaagaaaa aaagtttagg 120
gatttagaaa aaacatcaat ctagttccac cttatttat agagagaaga aactaatata 180
taagaactaa aaaacagaag aatagaaaaa aaagtattg acaggaaaga aaaagtagct 240
gtatgcttat aagtactttg aggatttgaa ttctctctta taaacacaa acacaatttt 300
tagatttat ttaaataatc atcaatccga ttataattat ttatatattt ttctattttc 360
aaagaagtaa atcatgagct tttccaactc aacatctatt ttttttctct caaccttttt 420
cacatcttaa gtagtctcac cctttatata tataacttat ttcttacctt ttacattatg 480
taacttttat caccaaaacc aacaacttta aattttatt aaatagactc cacaagtaac 540
ttgacactct tacattcatc gacattaact tttatctgtt ttataaatat tattgtgata 600
taattaatc aaaaataacca caaacttttca taaaggttc ttattaagca tggcatttaa 660
taagcaaaaa caactcaatc actttcatat aggaggtagc ctaagtacgt actcaaaatg 720
ccaacaaata aaaaaaagt tgctttaata atgccaaaac aaattaataa aacacttaca 780
acaccggatt tttttaatt aaaatgtgcc atttaggata aatagttaat atttttaata 840
attatttaaa aagccgtatc tactaaaatg attttttattt ggttgaaaat attaatatgt 900
ttaaatcaac acaatctatc aaaattaaac taaaaaaaaa aataagtgtac gtggttaaca 960
ttagtacagt aatataagag gaaaatgaga aattaagaaa ttgaaagcga gtctaatttt 1020
taaattatga acctgcatat ataaaaggaa agaaagaatc caggaagaaa agaaatgaaa 1080
ccatgcatgg tccccctcgtc atcacgagtt tctgccattt gcaatagaaa cactgaaaca 1140
cctttctctt tgtcacttaa ttgagatgcc gaagccacct cacaccatga acttcatgag 1200
gtgtagcacc caaggcttcc atagccatgc atactgaaga atgtctcaag ctcagcaccc 1260
tacttctgtg acgtgtccct cattcacctt cctctcttcc ctataaataa ccacgcctca 1320
ggttctccgc ttcacaactc aaacattctc tccattggtc cttaaacact catcagtcat 1380
caccatggcc aagctagttt tttcccttg ttttctgctt tcagtggct gctgcttcgc 1440
tcttattgtg acccaaacca tgaagggcct cgacattcaa aaggttgccg gaacctggta 1500
ctccccttgct atggctgctt ccgatatctc cttgctcgat gctcaatccg ctccacttag 1560
ggtgtacgtg gaagagttga agccaactcc agagggcgat cttgagatct tgcttcaaaa 1620
```

-continued

```
gtgggagaac gatgagtgcg cccagaagaa gattatcgcc gaaaagacca agattcccgc   1680
cgtgttcaag atcgatgctc tcaacgagaa caaggtgctc gtgctcgata ccgactacaa   1740
gaagtacctt ctcgtctgca tggaaaactc cgctgagcca gagcaatctc ttgtttgcca   1800
atgccttgtg aggaccccag aggttgacga tgaagctctt gagaagttcg acaaggctct   1860
caaggctttg cctatgcaca tccgccttag cttcaaccca actcagcttg aggaacagtg   1920
ccacatctaa aaagcagaat gctgagctaa aagaaaggct ttttccattt tcgagagaca   1980
atgagaaaag aagaagaaga agaagaagaa gaagaagaag aaaagagtaa ataataaagc   2040
cccacaggag gcgaagttct tgtagctcca tgttatctaa gttattgata ttgtttgccc   2100
tatatttat ttctgtcatt gtgtatgttt tgttcagttt cgatctcctt gcaaaatgca    2160
gagattatga gatgaataaa ctaagttata ttattatacg tgttaatatt ctcctcctct   2220
ctctagctag cctttgttt tctctttttc ttatttgatt ttctttaaat caatccattt    2280
taggagaggg ccagggagtg atccagcaaa acatgaagat tagaagaaac ttccctcttt   2340
tttttcctga aaacaattta acgtcgagat ttatctcttt ttgtaatgga atcatttcta   2400
cagttatgac tcgattaaaa atcccaatta tatttggtct aatttagttt ggtattgagt   2460
aaaacaaatt cgaaccaaac caaaatataa atatatagtt tttatatata tgcctttaag   2520
actttttata gaattttctt taaaaaatat ctagaaatat ttgcgactct tctggcatgt   2580
aatatttcgt taaatatgaa gtgctccatt tttattaact ttaaataatt ggttgtacga   2640
tcactttctt atcaagtgtt actaaaatgc gtcaatctct tgttcttcc atattcatat    2700
gtcaaaatct atcaaaattc ttatatatct ttttcgaatt tgaagtgaaa tttcgataat   2760
ttaaaattaa atagaacata tcattattta ggtatcatat tgattttttat acttaattac  2820
taaatttggt taacttgaa agtgtacatc aacgaaaaat tagtcaaacg actaaaataa    2880
ataaatatca tgtgttatta agaaaattct cctataagaa tattttaata gatcatatgt   2940
ttgtaaaaaa aattaattttt tactaacaca tatatttact tatcaaaaat ttgacaaagt  3000
aagattaaaa taatattcat ctaacaaaaa aaaaaccaga aaatgctgaa aacccggcaa   3060
aaccgaacca atccaaaccg atatagttgg tttggtttga ttttgatata aaccgaacca   3120
actcggtcca tttgcacccc taatcataat agctttaata tttcaagata ttattaagtt   3180
aacgttgtca atatcctgga aattttgcaa aatgaatcaa gcctatatgg ctgtaatatg   3240
aatttaaaag cagctcgatg tggtggtaat atgtaattta cttgattcta aaaaaatatc   3300
ccaagtatta ataatttctg ctaggaagaa ggttagctac gatttacagc aaagccagaa   3360
tacaaagaac cataaagtga ttgaagctcg aaatatacga aggaacaaat attttttaaaa  3420
aaatacgcaa tgacttggaa caaaagaaag tgatatattt tttgttctta aacaagcatc   3480
ccctctaaag aatggcagtt ttcctttgca tgtaactatt atgctcccctt cgttacaaaa  3540
attttggact actattggga acttcttctg aaaatagt                           3578
```

```
SEQ ID NO: 776           moltype = DNA    length = 4371
FEATURE                  Location/Qualifiers
misc_feature             1..4371
                         note = Construct AR15-29
source                   1..4371
                         mol_type = other DNA
                         organism = synthetic construct
SEQUENCE: 776
aacacaagct tcaagtttta aaaggaaaaa tgtcagccaa aaactttaaa taaaatggta    60
acaaggaaat tattcaaaaa ttacaaacct cgtcaaaata ggaaagaaaa aaagtttagg   120
gatttagaaa aaacatcaat ctagttccac cttatttat agagagaaga aactaatata   180
taagaactaa aaaacagaag aatagaaaaa aaagtattg acaggaaaga aaagtagct    240
gtatgcttat aagtactttg aggattgaa ttctctctta taaaacacaa acacaattt    300
tagattttat ttaaataatc atcaatccga ttataattat ttatatattt ttctattttc   360
aaagaagtaa atcatgagct tttccaactc aacatctatt ttttttctct caacctttt    420
cacatcttaa gtagtctcac cctttatata taaacttat ttcttacctt ttacattatg    480
taactttat caccaaaacc aacaactta aaatttat aaatagactc cacaagtaa        540
ttgacactct tacattcatc gacattaact tttatctgtt ttataaatat tattgtgata   600
taatttaatc aaaataacca caaactttca taaaaggttc ttattaagca tggcatttaa   660
taagcaaaaa caactcaatc actttcatat aggaggtagc ctaagtacgt actcaaaatg   720
ccaacaaata aaaaaaaagt tgctttaata atgccaaata aacacttaca                780
acaccggatt ttttttaatt aaaatgtgcc atttaggata aatagttaat attttttaata   840
attattttaaa aagccgtatc tactaaaatg attttttattt ggttgaaat attaatatgt   900
ttaaatcaac acaatctatc aaaattaaac taaaaaaaaa ataagtgtac gtggttaaca   960
ttagtacagt aatataagag aaaatgagag aattaagaac ttgaaagcga gtctaatttt   1020
taaattatga acctgcatat ataaaaggaa agaagaatc caggaagaaa agaaatgaaa    1080
ccatgcatgg tcccctcgtc atcacgagtt tctgccattt gcaatagaaa cactgaaaca   1140
cctttctctt tgtcacttaa ttgagatgcc gaagccacct cacaccatga acttcatgag   1200
gtgtagcacc caaggcttcc atagccatgc atactgaaga atgtctcaag ctcagcaccc   1260
tacttcgtg acgtgtccct cattcacctt cctctcttcc ctataaataa cccgctctca    1320
ggttctccgc ttcacaactc aaacattctc tccattggtc cttaaacact catcagtcat   1380
caccgttcgt tatctaccac cgttctatgg attttattcc ttctattcgt gtttattcta   1440
ttggtttatg ttgcttgcaa tatgttttt ctgaatctgt cgtcgttgtc ttcaattta     1500
tccatgtttc agagatcaat tttgttttgtg tagtatgtc ttattcttct tcttttcgtt   1560
cgagttgtta ataacggtgc tatggtgttt tcaaaagtgt ttttttatt actttttgatt   1620
taaagttttt ttggtaaggc tttattttgc ttgttatatt caaatctttg gatccagatc    1680
ttatataagt ttttggttca agaaagtttt tggttactga tgaatagatc tattaactgt   1740
tactttaatc gattcaagct aaagtttttt ggttactgat gaatagatct attatctgtt   1800
acttttaatc ggttcaagct caagtttttt ggttactgat gaatagatct atatacgtca   1860
cagtgtgcta aacatgccct tgttttatct cgatcttaat tatgggagtg ccataaattt   1920
tgttatgtct atttttttat ctgttggaat catactgagt ttgatgcgtt acgattgagc   1980
ataccctattt ttgggcttgt tgtatggtgg gtatttagat cttaatctttt ttatgcttat  2040
gaaaggttt gtaatgacaa aggtcttaat gttgttaaac ttttatttttt actttatatg    2100
gtgtgttgat gtgttatggt tttgacaact ttttttttttt ctggattttt gcagatttaa   2160
ggaccatggc caagctagtt ttttcccttt gttttctgct tttcagtggc tgctgcttcg   2220
```

```
ctcttattgt gacccaaacc atgaagggcc tcgacattca aaaggttgcc ggaacctggt  2280
actcccttgc tatggctgct tccgatatct ccttgctcga tgctcaatcc gctccactta  2340
gggtgtacgt ggaagagttg aagccaactc cagagggcga tcttgagatc ttgcttcaaa  2400
agtgggagaa cgatgagtgc gcccagaaga agattatcgc cgaaaagacc aagattcccg  2460
ccgtgttcaa gatcgatgct ctcaacgaga acaaggtgct cgtgctcgat accgactaca  2520
agaagtacct tctcgtctgc atggaaaact ccgctgagcc agagcaatct cttgtttgcc  2580
aatgccttgt gaggacccca gaggttgacg atgaagctct tgagaagttc gacaaggctc  2640
tcaaggcttt gcctatgcac atccgcctta gcttcaaccc aactcagctt gaggaacagt  2700
gccacatcaa ggatgagctt taaaaagcag aatgctgagc taaaagaaag gcttttttcca  2760
ttttcgagag acaatgagaa aagaagaaga agaagaagaa gaagaagaag aagaaaagag  2820
taaataataa agcccacag gaggcgaagt cttgtagct ccatgttatc taagttattg  2880
atattgtttg ccctatattt tatttctgtc attgtgtatg ttttgttcag tttcgatctc  2940
cttgcaaaat gcagagatta tgatgaat aaactaagtt atattattat acgtgttaat  3000
attctcctcc tctctctagc tagccttttg ttttctcttt ttcttatttg attttctttta  3060
aatcaatcca ttttaggaga gggccaggga gtgatccagc aaaacatgaa gattagaaga  3120
aacttccctc tttttttttcc tgaaaacaat ttaacgtcga gatttatctc ttttttgtaat  3180
ggaatcattt ctacagttat gactcgatta aaaatcccaa ttatatttgg tctaatttag  3240
tttggtattg agtaaaacaa attcgaacca aaccaaata taaatatata gtttttatat  3300
atatgccttt aagacttttt atagaatttt ctttaaaaaa tatctagaaa tatttgcgac  3360
tcttctggca tgtaatattt cgttaaatat gaagtgctcc atttttattta actttaaata  3420
attggttgta cgatcacttt cttatcaagt gttactaaaa tgcgtcaatc tctttgttct  3480
tccatattca tatgtcaaaa tctatcaaaa ttcttatata tccttttcga atttgaagtg  3540
aaatttcgat aatttaaaat taaatagaac atatcattat ttaggtatca tattgatttt  3600
tatacttaat tactaaattt ggttaacttt gaaagtgtac atcaacgaaa aattagtcaa  3660
acgactaaaa taaataaata tcatgtgtta ttaagaaaat tctcctataa gaatattta  3720
atagatcata tgtttgtaaa aaaaattaat tttactaac acatatattt acttatcaaa  3780
aatttgacaa agtaagatta aaataatatt catctaacaa aaaaaaaacc agaaaatgct  3840
gaaaacccgg caaaaccgaa ccaatccaaa ccgatatagt tggtttggtt tgattttgat  3900
ataaaccgaa ccaactcggt ccatttgcac ccctaatcat aatagcttta atatttcaag  3960
atattattaa gttaacgttg tcaatatcct ggaaattttg caaaatgaat caagcctata  4020
tggctgtaat atgaatttaa aagcagctcg atgtggtggt aatatgtaat ttacttgatt  4080
ctaaaaaaat atcccaagta ttaataattt ctgctaggaa gaaggttagc tacgatttac  4140
agcaaagcca gaatacaaag aaccataaag tgattgaagc tcgaaatata cgaaggaaca  4200
aatatttttta aaaaaatacg caatgacttg gaacaaaaga aagtgatata ttttttgttc  4260
ttaaacaagc atccctcta aagaatggca gttttccttt gcatgtaact attatgctcc  4320
cttcgttaca aaaattttgg actactattg ggaacttctt ctgaaaatag t              4371
```

```
SEQ ID NO: 777         moltype = DNA   length = 4360
FEATURE                Location/Qualifiers
misc_feature           1..4360
                       note = Construct AR15-30
source                 1..4360
                       mol_type = other DNA
                       organism = synthetic construct
SEQUENCE: 777
aacacaagct tcaagtttta aaaggaaaaa tgtcagccaa aaactttaaa taaaatggta    60
acaaggaaat tattcaaaaa ttacaaacct cgtcaaaata ggaaagaaaa aaagtttagg   120
gatttagaaa aaacatcaat ctagttccac cttattttat agagagaaga aactaatata   180
taagaactaa aaaacagaag aatagaaaaa aaagtattg acaggaaaga aaagtagct     240
gtatgcttat aagtactttg aggatttgaa ttctctctta taaacacaa acacaatttt   300
tagattttat ttaaataatc atcaatccga ttataattat ttatatattt ttctatttta  360
aaagaagtaa atcatgagct tttccaactc aacatctatt tttttttctct caaccttttt  420
cacatcttaa gtagtctcac cctttatata tataactttat ttcttacctt ttacattatg  480
taactttttat caccaaaacc aacaactta aaattttatt aaatagactc cacaagtaac  540
ttgacactct tacattcatc gacattaact tttatctgtt ttataaatat tattgtgata  600
taatttaatc aaaataacca caaactttca taaaaggttc ttattaagca tggcatttaa  660
taagcaaaaa caactcaatc actttcatat aggaggtagc ctaagtacgt actcaaaatg  720
ccaacaaata aaaaaaagt tgctttaata atgccaaaac aaattaataa aacacttaca  780
acaccggatt ttttttaatt aaaatgtgcc atttaggata aatagttaat attttaata   840
attatttaaa aagccgtatc tactaaaatg attttttattt ggttgaaaat attaatatgt  900
ttaaatcaac acaatctatc aaaattaaac taaaaaaaaa ataagtgtac gtggttaaca  960
ttagtacagt aatataagag gaaatgaga attaagaaa ttgaaagcga gtctaatttt    1020
taaattatga acctgcatat ataaaggaa agaaagaatc caggaagaaa agaaatgaaa   1080
ccatgcatgg tcccctcgtc atcacgagtt tctgccattt gcaatagaaa cactgaaaca  1140
cctttctctt tgtcacttaa ttgagatgcc gaagccacct cacaccatga acttcatgag  1200
gtgtagcacc caaggcttcc atagccatgc atactgaaga atgtctcaag ctcagcaccc  1260
tacttctgtg acgtgtccct cattcacctt cctctcttcc ctataaataa ccacgcctca  1320
ggttctccgc ttcacaactc aaacattctc tccattggtc cttaaacact catcagtcat  1380
caccatggcc aagctagttt tttccctttg tttctgctt ttcagttgct gctgcttcgc  1440
tcttattgtg acccaaacca tgaagggcct cgacattcaa aaggttcgtt atctaccacc  1500
gttctatgga ttttattcct tctattcgtg tttattctat tggtttatgt tgcttgcaat  1560
atgttttttc tgaatctgtc gtcgttgtct tcaattttat ccatgtttca gagatcaatt  1620
ttgttgtgt agtatgtgct tattcttctt cttttcgttc gagttgttaa taacggtgct  1680
gttttttt caaaagtgtt ttttttatta ctttttatta tggtaaggct  1740
tttatttgct tgttatattc aaatctttgg atccagatct tatataagtt tttggttcaa  1800
gaaagtttttt ggttactgat gaatagatct attaactgtt actttaatcg attcaagcta  1860
aagtttttgt gttactgatg aatagatcta ttatctgtta ctttataatcg gttcaagctc  1920
aagtttttgt gttactgatg aatagatcta tatacgtcac agtgtgctaa acatgccctt  1980
gttttatctc gatcttatgt atgggagtgc ataaaatttgg ttatgtcta tttttttatc  2040
```

```
tgttggaatc atactgagtt tgatgcgtta cgattgagca tacctatttt tgggcttgtt  2100
gtatggtggg tatttagatc ttaatccttt tatgcttatg aaaggttttg taatgacaaa  2160
ggtcttaatg ttgttaaact tttattttta ctttatatgg tgtgttgatg tgttatggtt  2220
ttgacaactt ttttttttc tggattttgt caggttgccg gaacctggta ctcccttgct  2280
atggctgctt ccgatatctc cttgctcgat gctcaatccg ctccacttag ggtgtacgtg  2340
gaagagttga agccaactcc agagggcgat cttgagatct tgcttcaaaa gtgggagaac  2400
gatgagtgcg cccagaagaa gattatcgcc gaaaagacca agattcccgc cgtgttcaag  2460
atcgatgctc tcaacgagaa caaggtgctc gtgctcgata ccgactacaa gaagtaccttc  2520
ctcgtctgca tggaaaactc cgctgagcca gagcaatctc ttgtttgcca atgccttgga  2580
aggacccag aggttgacga tgaagctctt gagaagttcg acaaggctct caaggctttg  2640
cctatgcaca tccgccttag cttcaaccca actcagcttg aggaacagtg ccacatcaag  2700
gatgagcttt aaaagcaga atgctgagct aaaagaaagg cttttccat tttcgagaga  2760
caatgagaaa agaagaagaa gaagaagaag aagaagaaga agaaaagagt aaataataaa  2820
gccccacagg aggcgaagtt cttgtagctc catgttatct aagttattga tattgtttgc  2880
cctatatttt atttctgtca ttgtgtatgt tttgttcagt ttcgatctcc ttgcaaaatg  2940
cagagattat gagatgaata aactaagtta tattattata cgtgttaata ttctcctcct  3000
ctctctagct agcctttgt tttctctttt tcttatttga ttttctttaa atcaatccat  3060
tttaggagag ggccagggag tgatccagca aaacatgaag attagaagaa acttccctct  3120
tttttttcct gaaacaatt taacgtcgag atttatctct ttttgtaatg gaatcatttc  3180
tacagttatg actcgattaa aaatcccaat tatatttggt ctaatttagt ttggtattga  3240
gtaaaacaaa ttcgaaccaa accaaaatat aaatatatag ttttatata tatgcctttta  3300
agacttttta tagaatttt tttaaaaat atctagaaaat atttgcgact cttctggcat  3360
gtaatatttc gttaaatatg aagtgctcca tttttattaa cttttaaataa ttggttgtac  3420
gatcactttc ttatcaagtg ttactaaaat gcgtcaatct ctttgttctt ccatattcat  3480
atgtcaaaat ctatcaaaat tcttatatat ctttttcgaa tttgaagtga aatttcgata  3540
atttaaaatt aaatagaaca tatcattatt taggtatcat attgattttt atacttaatt  3600
actaaatttg gttaacttg aaagtgtaca tcaacgaaaa attagtcaaa cgactaaaat  3660
aaataaatat catgtgttat taagaaaatt ctcctataag aatatttaa tagatcatat  3720
gtttgtaaaa aaaattaatt tttactaaca catatattta cttatcaaaa atttgacaaa  3780
gtaagattaa aataaatc atctaacaaa aaaaaaacca gaaaatgctg aaaacccggc  3840
aaaaccgaac caatccaaac cgatatagtt ggtttggttt gattttgata taaaccgaac  3900
caactcggtc catttgcacc cctaatcata atagctttaa tatttcaaga tattattaag  3960
ttaacgttgt caatatcctg gaaattttgc aaaatgaatc aagcctatat ggctgtaata  4020
tgaatttaaa agcagctcga tgtggtggta atatgtaatt tacttgattc taaaaaaata  4080
tcccaagtat taataatttc tgctaggaag aaggttagct acgatttaca gcaaagccaa  4140
aatacaaaga accataaagt gattgaagct cgaaatatac gaaggaacaa atattttaa  4200
aaaaatacgc aatgacttgg aacaaaagaa agtgatatat tttttgttct taaacaagca  4260
tccctctaa agaatggcag ttttccttg catgtaacta ttatgctccc ttcgttacaa  4320
aaattttgga ctactattgg gaacttcttc tgaaaatagt                        4360
```

SEQ ID NO: 778        moltype = DNA   length = 3683
FEATURE               Location/Qualifiers
misc_feature       1..3683
                      note = Construct AR15-31
source             1..3683
                      mol_type = other DNA
                      organism = synthetic construct
SEQUENCE: 778

```
aacacaagct tcaagtttta aaaggaaaaa tgtcagccaa aaactttaaa taaaatggta   60
acaaggaaat tattcaaaaa ttacaaacct cgtcaaaata ggaaagaaaa aaagtttagg  120
gatttagaaa aaacatcaat ctagttccac cttatttat agagagaaga aactaatata  180
taagaactaa aaaacagaag aatagaaaaa aaaagtattg acaggaaaga aaaagtagct  240
gtatgcttat aagtactttg aggatttgaa ttctctctta taaacacaa acacaatttt  300
tagattttat ttaaataatc atcaatccga ttataattat ttatatattt ttctatttc  360
aaagaagtaa atcatgagct tttccaactc aacatctatt tttttctct caacctttt  420
cacatcttaa gtagtctcac cctttatata taaacttta ttcttacctt ttacattatg  480
taactttat caccaaaacc aacaacttta aatttatt aaatagactc cacaagtaac  540
ttgacactct tacattcatc gacattaact tttatctgtt ttataaatat tattgtgata  600
taatttaatc aaaataacca caaactttca taaaaggttc ttattaagca tggcatttaa  660
taagcaaaaa caactcaatc actttcatat aggaggtagc ctaagtacgt actcaaaatg  720
ccaacaaata aaaaaaagt tgctttaata atgccaaaac aaattaataa acacttaca  780
acaccggatt ttttttaatt aaaatgtgcc atttaggata aatagttaat attttttaata  840
attatttaaa aagccgtatc tactaaaatg attttttattt ggttgaaaat attaatatgt  900
ttaaatcaac acaatctatc aaaattaaac taaaaaaaaa aaagtgtac gtggttaaca  960
ttagtacagt aatataagag gaaatgaga aattaagaaa ttgaaagcga gtctaatttt  1020
taaattatga acctgcatat ataaaggaa agaaagaatc caggaagaaa agaaatgaaa  1080
ccatgcatgg tccctcgtc atcacgagtt tctgccattt gcaatagaaa cactgaaaca  1140
cctttctctt tgtcacttaa ttgagatgcc gaagccatga cacaccatga acttcatgag  1200
gtgtagcacc caaggcttcc atagccatgc atactgaaga atgtctcaag ctcagcaccc  1260
tacttctgtg acgtgtccct cattcacctt cctctcttcc ctataaataa ccacgcctca  1320
ggttctccgc ttcacaactc aaacattctc tccattggtc cttaaacact catcagtcat  1380
caccatggcc aagctagttt tttcccttg ttttctgctt tcagtggct gctgcttcgc  1440
tcttattgtg acccaaacca tgaagggcct cgacattcaa aaggtaacca tctttcat  1500
ctgttatgtg actacacatt gcttctcttt ttgtgttcta ttcattaat tgcggtttgt  1560
tacatgttgt ttgtaggttg ccggaacctg gtactccctt gctatggctg cttccgatat  1620
ctccttgctc gatgctcaat ccgctccact taggtgtac gtggaagagt tgaagccaac  1680
tccagagggc gatcttgaga tcttgcttca aaagtgggag aacgatgagt gcgcccagaa  1740
gaagattatc gccgaaaaga ccaagattcc cgccgtgttc aagatcgatg ctctcaacga  1800
gaacaaggtg ctcgtgctcg ataccgacta caagaagtac cttctcgtct gcatggaaaa  1860
```

```
ctccgctgag ccagagcaat ctcttgtttg ccaatgcctt gtgaggaccc cagaggttga  1920
cgatgaagct cttgagaagt tcgacaaggc tctcaaggct ttgcctatgc acatccgcct  1980
tagcttcaac ccaactcagc ttgaggaaca gtgccacatc aaggatgagc tttaaaaagc  2040
agaatgctga gctaaaagaa aggcttttc catttttcgag agacaatgag aaaagaagaa  2100
gaagaagaag aagaagaaga agaagaaaag agtaaataat aaagccccac aggaggcgaa  2160
gttcttgtag ctccatgtta tctaagttat tgatattgtt tgccctatat tttatttctg  2220
tcattgtgta tgttttgttc agtttcgatc tccttgcaaa atgcagagat tatgagatga  2280
ataaactaag ttatattatt atacgtgtta atattctcct cctctctcta gctagccttt  2340
tgttttctct tttcttatt tgattttctt taaatcaatc cattttagga gagggccagg  2400
gagtgatcca gcaaaacatg aagattagaa gaaacttccc tcttttttt cctgaaaaca  2460
atttaacgtc gagatttatc tctttttgta atggaatcat ttctacagtt atgactcgat  2520
taaaaatccc aattatattt ggtctaattt agtttggtat tgagtaaaac aaattcgaac  2580
caaaccaaaa tataaatata tagttttat atatatgcct ttaagactt ttatagaatt  2640
ttctttaaaa aatatctaga aatatttgcg actcttctgg catgtaatat ttcgttaaat  2700
atgaagtgct ccattttat taactttaaa taattggttg tacgatcact ttcttatcaa  2760
gtgttactaa aatgcgtcaa tctctttgtt cttccatatt catatgtcaa aatctatcaa  2820
aattcttata tatcttttc gaatttgaag tgaaatttcg ataatttaaa attaaataga  2880
acatatcatt atttaggtat catattgatt tttatactta attactaaat ttggttaact  2940
ttgaaagtgt acatcaacga aaaattagtc aaacgactaa aataaataaa tatcatgtgt  3000
tattaagaaa attctcctat aagaatattt taatagatca tatgtttgta aaaaaaatta  3060
attttttacta acacatatat ttacttatca aaaatttgac aaagtaagat taaaataata  3120
ttcatctaac aaaaaaaaaa ccagaaaatg ctgaaaaccc ggcaaaaccg aaccaatcca  3180
aaccgatata gttggtttgg tttgattttg atataaaccg aaccaactcg gtccatttgc  3240
accctaatc ataatagctt taatatttca agatattatt aagttaacgt tgtcaatatc  3300
ctggaaattt tgcaaaatga atcaagccta tatggctgta atatgaattt aaaagcagct  3360
cgatgtggtg gtaatatgta atttacttga ttctaaaaaa cagaataca agaaccataa  3420
ttctgctagg aagaaggtta gctacgattt acagcaaagc cagaatacaa agaaccataa  3480
agtgattgaa gctcgaaata tacgaaggaa caaatatttt taaaaaaata cgcaatgact  3540
tggaacaaaa gaaagtgata tatttttgt tcttaaacaa gcatcccctc taagaatgg  3600
cagtttctcct ttgcatgtaa ctattatgct cccttcgtta caaaaatttt ggactactat  3660
tgggaacttc ttctgaaaat agt                                         3683

SEQ ID NO: 779           moltype = DNA  length = 3655
FEATURE                  Location/Qualifiers
misc_feature             1..3655
                         note = Construct AR15-36
source                   1..3655
                         mol_type = other DNA
                         organism = synthetic construct
SEQUENCE: 779
aacacaagct tcaagtttta aaaggaaaaa tgtcagccaa aaactttaaa taaaatggta  60
acaaggaaat tattcaaaaa ttcaaaacct cgtcaaaata ggaaagaaaa aagtttagg   120
gatttagaaa aaacatcaat ctagttccac cttattttat agagagaaga aactaataa   180
taagaactaa aaaacagaag aatagaaaaa aaagtattg acaggaaaga aaaagtagct  240
gtatgcttat aagtactttg aggatttgaa ttctctctta taaaacacaa acacaatttt  300
tagattttat ttaaataatc atcaatccga ttataattat ttatatattt ttctattttc  360
aaagaagtaa atcatgagct tttccaactc aacatctatt ttttttctct caaccttttt  420
cacatcttaa gtagtctcac ccttatata tataacttat ttcttacctt ttacattatg  480
taactttta caccaaaacc aacaactta aaattttatt aaatagactc cacaagtaac  540
ttgacactct tacattcatc gacattaact tttatctgtt ttataaatat tattgtgata  600
taatttaatc aaaataacca caaactttca taaaaggttc ttattaagca tggcatttaa  660
taagcaaaaa caactcaatc acttttcatat aggaggtagc ctaagtacgt actcaaaatg  720
ccaacaaata aaaaaaaagt tgctttaata atgccaaaac aaattaataa acacttaca   780
acaccggatt ttttttaatt aaaatgtgcc atttaggata aatagttaat atttttaata  840
attattttaaa aagccgtatc tactaaaatg atttttatt ggttgaaaat attaatatgt  900
ttaaatcaac acaatctatc aaaattaaac taaaaaaaaa ataagtgtac gtggttaaca  960
ttagtacagt aatataagag gaaaatgaga aattaagaaa ttgaaagcga gtctaatttt  1020
taaattatga acctgcatat ataaaaggaa agaaagaatc caggaagaaa agaaatgaaa  1080
ccatgcatgg tccccctcgtc atcacgagtt tctgccattt gcaataaaga cactgaaaca  1140
cctttctctt tgtcacttaa ttgagatgcc gaagccacct cacaccatga acttcatgag  1200
gtgtagcacc caaggcttcc atagccatgc atactgaaga atgtctcaag ctcagcaccc  1260
tacttctgtg acgtgtccct cattcacctt cctctcttcc ctataaataa ccacgcctca  1320
ggttctccgc ttcacaactc aaacattctc tccattggtc cttaaacact catcagtcat  1380
caccccgag cccgctgtct cagccctcca ctcctgcag agctcagaag cgtgacccca  1440
gctgcagcca tggccaagct agtttttcc ctttgtttc tgcttttcag tggctgctgc  1500
ttcgctctta ttgtgaccca aaccatgaag ggcctcgaca ttcaaaaggt tgccggaacc  1560
tggtactccc ttgctatggc tgcttccgat atctccttgc tcgatgctca atccgctcca  1620
cttagggtgt acgtggaaga gttgaagcca actccagagg gcgatcttga gatcttgctt  1680
caaaagtgga gaacgatga gtgcgcccag aagaagatta tgccgaaaa gaccaagatt  1740
cccgccgtgt tcaagatcga tgctctcaac gagaacaagg tgctcgtgct cgataccgac  1800
tacaagaagt accttctcgt ctgcatgaaa aactccgctg agccagagca atctcttgtt  1860
tgccaatgcc ttgtgaggac cccagaggtt gacgatgaag ctcttgagaa gttcgacaag  1920
gctctcaagg ctttgcctat gcacatccgc cttagcttca acccaactca gcttgaggaa  1980
cagtgccaca tcaaggatga gctttaaaaa gcagaatgct gagctaaaga aaggcttttt  2040
ccatttttcg agagacaatg agaaaagaag aagaagaaga agaagaagaa gaagaagaaa  2100
agagtaaata ataaagcccc acaggaggcg aagttcttgt agctccatgt tatctaagtt  2160
attgatattg tttgccctat attttattc tgtcattgtg tgttttgt tcagtttcga  2220
tctccttgca aaatgcagag attatgagat gaataaacta agttatatta ttacgtgt   2280
taatattctc ctctctctc tagctagcct tttgttttct cttttcttaa tttgattttc  2340
```

```
tttaaatcaa tccattttag gagagggcca gggagtgatc cagcaaaaca tgaagattag    2400
aagaaacttc cctctttttt ttcctgaaaa caatttaacg tcgagattta tctcttttg    2460
taatggaatc atttctacag ttatgactcg attaaaaatc ccaattatat ttggtctaat    2520
ttagtttggt attgagtaaa acaaattcga accaaaccaa aatataaata tatagttttt    2580
atatatatgc ctttaagact ttttatagaa ttttctttaa aaaatatcta gaaatatttg    2640
cgactcttct ggcatgtaat atttcgttaa atatgaagtg ctccattttt attaactta     2700
aataattggt tgtacgatca cttcttatc aagtgttact aaaatgcgtc aatctctttg    2760
ttcttccata ttcatatgtc aaaatctatc aaaattctta tatatcttt tcgaatttga    2820
agtgaaattt cgataattta aaattaaata gaacatatca ttatttaggt atcatattga   2880
tttttatact taattactaa atttggttaa ctttgaaagt gtacatcaac gaaaaattga   2940
tcaaacgact aaaataaata aatatcatgt gttattaaga aaattctcct ataagaatat   3000
tttaatagat catatgttg taaaaaaaat taattttac taacacatat atttacttat    3060
caaaaatttg acaaagtaag attaaaataa tattcatcta acaaaaaaaa aaccagaaaa   3120
tgctgaaaac ccggcaaaac cgaaccaatc caaaccgata tagttggttt ggtttgattt   3180
tgatataaac cgaaccaact cggtccattt gcaccctaa tcataatagc tttaatattt    3240
caagatatta ttaagttaac gttgtcaata tcctggaaat tttgcaaaat gaatcaagcc   3300
tatatggctg taatatgaat ttaaaagcag ctcgatgtgg tggtaatatg taatttactt   3360
gattctaaaa aaatatccca tgattaata atttctgcta ggaagaaggt tagctacgat   3420
ttacagcaaa gccagaatac aaagaaccat aaagtgattg aagctcgaaa tatacgaagg   3480
aacaaatatt tttaaaaaaa tacgcaatga cttggaacaa aagaaagtga tatatttttt   3540
gttcttaaac aagcatcccc tctaaagaat ggcagttttc ctttgcatgt aactattatg   3600
ctcccttcgt tacaaaaatt ttggactact attgggaact tcttctgaaa atagt         3655
```

SEQ ID NO: 780          moltype = DNA   length = 3655
FEATURE                Location/Qualifiers
misc_feature         1..3655
                        note = Construct AR15-37
source                 1..3655
                        mol_type = other DNA
                        organism = synthetic construct
SEQUENCE: 780

```
aacacaagct tcaagtttta aaaggaaaaa tgtcagccaa aaactttaaa taaaatggta     60
acaaggaaat tattcaaaaa ttacaaacct cgtcaaaata ggaaagaaaa aaagtttagg    120
gatttagaaa aaacatcaat ctagttccac cttatttat agagagaaga aactaatata    180
taagaactaa aaaacagaag aatagaaaaa aaaagtattg acaggaaaga aaaaagtagct   240
gtatgcttat aagtactttg aggatttgaa ttctctctta taaaacacaa acacaatttt   300
tagatttat ttaaataatc atcaatccga ttataattat ttatatattt ttctattttc    360
aaagaagtaa atcatgagct tttccaactc aacatctatt tttttctct caacctttt    420
cacatcttaa gtagtctcac cctttatata tataacttat ttcttaccctt ttacattatg   480
taactttat caccaaaacc aacaacttta aaatttatt aaatagactc cacaagtaac    540
ttgacactct tacattcatc gacattaact tttatctgtt ttataaatat tattgtgata   600
taatttaatc aaaaataacca caaactttca taaaaggttc ttattaagca tggcatttaa   660
taagcaaaaa caactcaatc actttcatat aggaggtagc ctaagtacgt actcaaaatg   720
ccaacaaata aaaaaaaagt tgctttaata atgccaaaac aaattaataa aacacttaca   780
acaccggatt tttttaatt aaaatgtgcc atttaggata aatagttaat atttttaata    840
attatttaaa aagccgtatc tactaaaatg atttttattt ggttgaaaat attaatatgt   900
ttaaatcaac acaatctatc aaaattaaac taaaaaaaaa taaagtgtac gtggttaaca   960
ttagtacagt aatataagag gaaaatgaga aattaagaaa ttgaaagcga gtctaatttt   1020
taaattatga acctgcatat ataaaaggaa agaaagaatc caggaagaaa agaaatgaaa   1080
ccatgcatgg tcccctcgtc atcacgagtt tctgccattt gcaatagaaa cactgaaaca   1140
cctttctctt tgtcacttaa ttgagatgcc gaagccaatc cacaccatga acttcatgag   1200
gtgtagcacc caaggcttcc atagccatgc atactgaaga atgtctcaag ctcagcaccc   1260
tacttctgtg acgtgtccct cattcacctt cctctcttcc ctataaataa ccacgcctca   1320
ggttctccgc ttcacaactc aaacattctc tccattggtc cttaaacact catcagtcat   1380
caccgaattc tctaaaagag atcttttct gctctttgaa gaaagaaggg tctttgcttg   1440
attttggaga tggccaagct agttttttcc ctttgttttc tgcttttcag tggctgctgc   1500
ttcgctctta ttgtgaccca aaccatgaag ggctcgaca ttcaaaaggt tgccggaacc    1560
tggtactccc ttgctatggc tgcttccgat atctccttgc tcgatgctca atccgctcca   1620
cttagggtgt agtggaaga gttgaagcca actccagagg gcgatcttga gatcttgctt   1680
caaagtgggg agaacgatga gtgcgcccag aagaagatta tcgccgaaaa gaccaagatt   1740
cccgccgtgt tcaagatcga tgctctcaac gagaacaagg tgctcgtgct cgataccgac   1800
tacaagaagt accttctcgt ctgcatgaa aactccgctg agccagagca atctcttgtt   1860
tgccaatgcc ttgtgaggac cccagaggtt gacgatgaag ctcttgagaa gttcgacaag   1920
gctctcaagg ctttgcctat gcacatccgc ttagcttca acccaactca gcttgaggaa   1980
cagtgccaca tcaaggatga gcttaaaaaa gcagaatgct gagctaaaag aaaggctttt   2040
tccattttcg agagacaatg agaaagaag aagaagaga agaagaagaa gaagaagaaa    2100
agagtaaata ataaagcccc acaggaggcg aagttcttgt agctccatgt tatctaagtt   2160
attgatattg tttttatttc atttttattc tgtcattgtg tatgttttgt tcagtttcga   2220
tctccttgca aaatgcagag attatgagat gaataaacta agttatatta ttatacgtcga   2280
taatattctc ctcctctctc tagctagcct tttgttttct cttttcttaa tttgattttc   2340
tttaaatcaa tccatttag gagagggcca gggagtgatc cagcaaaaca tgaagattag   2400
aagaaacttc cctctttttt ttcctgaaaa caatttaacg tcgagattta tctcttttg    2460
taatggaatc atttctacag ttatgactcg attaaaaatc ccaattatat ttggtctaat   2520
ttagtttggt attgagtaaa acaaattcga accaaaccaa aatataaata tatagttttt   2580
atatatatgc ctttaagact ttttataaa ttttctttaa aaaatatcta gaaatatttg    2640
cgactcttct ggcatgtaat atttcgttaa atatgaagtg ctccattttt attaactta    2700
aataattggt tgtacgatca cttcttatc aagtgttact aaaatgcgtc aatctctttg    2760
ttcttccata ttcatatgtc aaaatctatc aaaattctta tatatcttt tcgaatttga    2820
agtgaaattt cgataattta aaattaaata gaacatatca ttatttaggt atcatattga   2880
```

```
tttttatact taattactaa atttggttaa ctttgaaagt gtacatcaac gaaaaattag 2940
tcaaacgact aaaataaata aatatcatgt gttattaaga aaattctcct ataagaatat 3000
tttaatagat catatgtttg taaaaaaaat taatttttac taacacatat atttacttat 3060
caaaaatttg acaagtaag attaaaataa tattcatcta acaaaaaaaa aaccagaaaa 3120
tgctgaaaac ccggcaaaac cgaaccaatc caaaccgata tagttggttt ggtttgattt 3180
tgatataaac cgaaccaact cggtccattt gcacccctaa tcataatagc tttaatattt 3240
caagatatta ttaagttaac gttgtcaata tcctggaaat tttgcaaaat gaatcaagcc 3300
tatatgcgtg taatatgaat ttaaaagcag ctcgatgtgg tggtaatatg taatttactt 3360
gattctaaaa aaatatccca agtattaata atttctgatg ggaagaaggt tagctacgat 3420
ttacagcaaa gccagaatac aagaaccat aaagtgattg aagctcgaaa tatacgaagg 3480
aacaaatatt tttaaaaaaa tacgcaatga cttggaacaa aagaaagtga tatattttt 3540
gttcttaaac aagcatcccc tctaaagaat ggcagttttc ctttgcatgt aactattatg 3600
ctcccttcgt tacaaaatt ttggactact attgggaact tcttctgaaa atagt 3655

SEQ ID NO: 781          moltype = DNA  length = 3824
FEATURE                 Location/Qualifiers
misc_feature            1..3824
                        note = Construct AR15-39
source                  1..3824
                        mol_type = other DNA
                        organism = synthetic construct
SEQUENCE: 781
aacacaagct tcaagtttta aaaggaaaaa tgtcagccaa aaactttaaa taaaatggta 60
acaaggaaat tattcaaaaa ttacaaacct cgtcaaaata ggaaagaaaa aaagtttagg 120
gatttagaaa aaacatcaat ctagttccac cttattttat agagaagaa aactaatata 180
taagaactaa aaaacagaag aatagaaaaa aaaagtaattg acaggaaaga aaagtagct 240
gtatgcttat aagtactttg aggatttgaa ttctctctta taaaacacaa acacaatttt 300
tagattttat ttaaataatc atcaatccga ttataattat ttatatattt ttctattttc 360
aaagaagtaa atcatgagct tttccaactc aacatctatt ttttttctct caacctttt 420
cacatcttaa gtagtctcac cctttatata taaacttat ttcttacctt ttacattatg 480
taacttttat caccaaaacc aacaacttta aattttatt aaatagactc cacaagtaac 540
ttgacactct tacattcatc gacattaact tttatctgtt ttataaatat tattgtgata 600
taatttaatc aaaataacca caaactttca taaaaggttc ttattaagca tggcatttaa 660
taagcaaaaa caactcaatc actttcatat aggaggtagc ctaagtacgt actcaaaatg 720
ccaacaaata aaaaaaagt tgctttaata atgccaaaac aaattaataa aacacttaca 780
acaccggatt ttttttaatt aaaatgtgcc atttaggata aatagttaat attttttaata 840
attatttaaa aagccgtatc tactaaaatg atttttattt ggttgaaaat attaatatgt 900
ttaaatcaac acaatctatc aaaattaaac taaaaaaaaaa ataagtgtac gtggttaaca 960
ttagtacagt aatataagag gaaaatgaga aattaagaaa ttgaaagcga gtctaatttt 1020
taaattatga acctgcatat ataaaggaa agaagaatc caggaagaaa agaaatgaaa 1080
ccatgcatgg tcccctcgtc atcacgagtt tctgccattt gcaatagaaa cactgaaaca 1140
cctttctctt tgtcacttaa ttgagatgcc gaagccacct cacaccatga acttcatgag 1200
gtgtagcacc caaggcttcc atagccatgc atactgaaga atgtctcaag ctcagcacc 1260
tacttctgtg acgtgtccct cattcaccctt cctctcttcc ctataataaa ccacgcctca 1320
ggttctccgc ttcacaactc aaacattctc tccattggtc cttaaacact catcagtcat 1380
caccatgcag attttcgtga agaccttaac ggggaagacg atcaccctag aggttgagtc 1440
ttccgacacc atcgacaatg tcaaagccaa gatcccagga aaggaaggga taccccagga 1500
ccagcagcgt ttgatttcg ccggaaagca gcttgaggat ggtcgtactc ttgccgacta 1560
caacatccag aaggagtcaa ctctccatct cgtgctccgt ctccgtggtg gtggttccat 1620
ggccaagcta gttttttccc tttgtttcct gcttttcagt ggctgctgct tcgctcttat 1680
tgtgacccaa accatgaagg gcctcgacat tcaaaaggtt gccggaacct ggtactcctc 1740
tgctatggct gcttccgata tctccttgct cgatgctcaa tccgctccac ttagggtgta 1800
cgtgaaagag ttgaagccaa ctccagaggg cgatcttgag atcttgcttc aaaagtggga 1860
gaacgatgag tgcgcccaga gaagattat cgccgaaaag accaagattc cgcgcgtgtt 1920
caagatcgat gctctcaacg agaacaaggt gctcgtgctc gataccgact acaagaagta 1980
ccttctcgtc tgcatggaaa actccgctga gccagagcaa tctccttgttt gccaatgcct 2040
tgtgaggacc ccagaggttg acgatgaagc tcttgagaag ttcgacaagg ctctcaaggc 2100
tttgcctatg cacatccgcc ttagcttcaa cccaactcag cttgaggaac agtgccacat 2160
caaggatgag ctttaaaaag cagaatgctg agctaaaaga aaggctttt ccattttcga 2220
gagacaatga gaaaagaaga agaagaagaa gaagaagaag aagaagaaaa gagtaaataa 2280
taaagcccca caggaggcga agttcttgta gctccatgtt atctaagtta ttgatattgt 2340
ttgccctata ttttatttct gtcattgtgt atgtttttgtt cagttcgat ctccttgcaa 2400
aatgcagaga ttatgagatg aataaactaa gttatattat tatacgtgtt aatattctcc 2460
tcctctctct agctagcttt ttgttttctc ttttttcttt ttgattttct ttaaatcaat 2520
ccatttttagg agagggccag ggagtgatcc agcaaaacat gaagattaga agaaacttcc 2580
ctctttttt tcctgaaaac aatttaacgt cgagatttat ctctttttgt aatgaaatca 2640
tttctacagt tatgactcga ttaaaaatcc caattatatt tggtctaatt tagttggtta 2700
ttgagtaaaa caaattcgaa ccaaaccaaa atataaaat atagttttta tatatatgcc 2760
tttaagactt tttatagaat tttctttaaa aaatatctag aaatatttgc gactcttctg 2820
gcatgtaata tttcgttaaa tatgaagtgc tccattttta ttaacttta ataattggtt 2880
gtacgatcac tttcttatca agtgttacta aaatgcgtca atctctttgt tcttccat 2940
tcatatgtca aaatctatca aaattcttat atatctttt cgaatttgaa gtgaaatttc 3000
gataatttaa aattaaatag aacatatcat tatttaggta tcatattgat ttttatactt 3060
aattactaaa tttggttaac tttgaaagt tacactcaacg aaaaattgat caacgacta 3120
aaataaataa atatcatgtg ttattaagaa aattctccta taagaatatt ttaatagtc 3180
atatgtttgt aaaaaaaatt aatttttact aacacatata tttacttatc aaaaatttga 3240
caaagtaaga ttaaaataat attcatctaa caaaaaaaaa accagaaat gctgaaaacc 3300
cggcaaaacc gaaccaatcc aaaccgatat agttggtttg gttgatttt gatataaacc 3360
gaaccaactc ggtccatttg caccctaat cataatagct ttaatatttc aagatattat 3420
```

```
taagttaacg ttgtcaatat cctggaaatt ttgcaaaatg aatcaagcct atatggctgt  3480
aatatgaatt taaaagcagc tcgatgtggt ggtaatatgt aatttacttg attctaaaaa  3540
aatatcccaa gtattaataa tttctgctag gaagaaggtt agctacgatt tacagcaaag  3600
ccagaataca aagaaccata aagtgattga agctcgaaat atacgaagga acaaatattt  3660
ttaaaaaaat acgcaatgac ttggaacaaa agaaagtgat atatttttg ttcttaaaca   3720
agcatcccct ctaaagaatg gcagttttcc tttgcatgta actattatgc tcccttcgtt  3780
acaaaaattt tggactacta ttgggaactt cttctgaaaa tagt                   3824

SEQ ID NO: 782          moltype = DNA  length = 10063
FEATURE                 Location/Qualifiers
misc_feature            1..10063
                        note = Construct AR15-00
source                  1..10063
                        mol_type = other DNA
                        organism = synthetic construct
SEQUENCE: 782
gcagacaagc ccgtcagggc gcgtcagcgg gtgttggcgg gtgtcggggc gcagccatga   60
cccagtcacg tagcgatagc ggagtgtata ctggcttaac tatgcggcat cagagcagat  120
tgtactgaga gtgcaccata tgcggtgtga aataccgcac agatgcgtaa ggagaaaata  180
ccgcatcagg cgctcttccg cttcctcgct cactgactcg ctgcgctcgg tcgttcggct  240
gcggcgagcg gtatcagctc actcaaaggc ggtaatacgg ttatccacag aatcagggga  300
taacgcagaa aagaacatgt gagcaaaagg ccagcaaaag gccaggaacc gtaaaaaggc  360
cgcgttgctg gcgtttttcc ataggctccg cccccctgac gagcatcaca aaaatcgacg  420
ctcaagtcag aggtggcgaa acccgacagg actataaaga taccaggcgt ttccccctgg  480
aagctccctc gtgcgctctc ctgttccgac cctgccgctt accggatacc tgtccgcctt  540
tctcccttcg ggaagcgtgg cgctttctca tagctcacgc tgtaggtatc tcagttcggt  600
gtaggtcgtt cgctccaagc tgggctgtgt gcacgaaccc cccgttcagc ccgaccgctg  660
cgccttatcc ggtaactatc gtcttgagtc aacccggta agacacgact tatcgccact   720
ggcagcagc actggtaaca ggattagcag agcgaggtat gtaggcggtg ctacagagtt   780
cttgaagtgg tggcctaact acggctacac tagaaggaca gtatttggta tctgcgctct  840
gctgaagcca gttaccttcg gaaaaagagt tggtagctct tgatccggca aacaaaccac  900
cgctggtagc ggtggttttt tgtttgcaa gcagcagatt acgcgcagaa aaaaggatc   960
tcaagaagat cctttgatct tttctacggg gtctgacgct cagtggaacg aaaactcacg  1020
ttaagggatt ttggtcatgc attctaggta ctaaaacaat tcatccagta aaatataata  1080
ttttatttc tcccaatcag gcttgatccc cagtaagtca aaaaatagct cgacatactg   1140
ttcttccccg atatcctccc tgatcgaccg gacgcagaag gcaatgtcat accacttgtc  1200
cgccctgccg cttctcccaa gatcaataaa gccacttact ttgccatctt tcacaaagat  1260
gttgctgtct cccaggtcgc cgtgggaaaa gacaagttcc tcttcgggct tttccgtctt  1320
taaaaaatca tacagctcgc gcggatcttt aaatgagtg tcttcttccc agttttcgca  1380
atccacatcg gccagatcgt tattcagtaa gtaatccaat tcggctaagc ggctgtctaa  1440
gctattcgta tagggacaat ccgatatgtc gatggagtga agagcctga tgcactccgc   1500
atacagctcg ataatctttt cagggctttg ttcatcttca tactcttccg agcaaaggac  1560
gccatcggcc tcactcatga gcagattgct ccagccatca tgccgttcaa agtgcaggac  1620
ctttggaaca ggcagctttc cttccagcca tagcatcatg tccttttccc gttccacatc  1680
ataggtggtc cctttatacc ggctgtccgt cattttaaaa tataggtttt cattttctcc  1740
caccagctta tatccttag caggagacat tccttccgta tcttttacgc agcggtattt   1800
ttcgatcagt ttttcaatt ccggtgatat tctcatttta gccatttatt atttccttcc   1860
tcttttctac agtatttaaa gatacccaa gaagctaatt ataacaagac gaactccaat   1920
tcactgttcc ttgcattcta aaaccttaaa taccagaaaa cagctttttc aaagttgttt  1980
tcaaagttgg cgtataacat agtatcgacg gagccgattt tgaaaccgcg gtgatcacag  2040
gcagcaacgc tctgtcatcg ttacaatcaa catgctaccc tccgcgagat catccgtgtt  2100
tcaaacccgg cagcttagtt gccgttcttc cgaatagcat cggtaacatg agcaaagtct  2160
gccgccttac aacggctctc ccgctgacgc cgtcccggac tgatgggctg cctgtatcga  2220
gtggtgattt tgtgccgagc tgccggtcgg ggagctgttg gctggctggt ggcaggatat  2280
attgtggtgt aaacaaattg acgcttagac aacttaataa cacattgcgg acgtttttaa  2340
tgtactgaat taacgcccga tcggtttaaa ccacacagga aacagctatg acatgattac  2400
gaattcggcc aaagcacata gttatcgatt taaatttcat cgaagagatt aatatcgaat  2460
aatcatatac atactttaaa tacataacaa attttaaata catatatctg gtatataatt  2520
aattttttaa agtcatgaag tatgtatcaa atacaaatat ggaaaaaatt aactattcat  2580
aatttaaaaa atagaaaaga tacatctagt gaaattaggt gcatgtatca aatacattag  2640
gaaaagggca tatatcttga tctagataat taacgatttt gatttatgta aatttccaa   2700
atgaaggttt atatctactt cagaaataac aatatacttt tatcagaaca ttcaacaaag  2760
caacaaccaa ctagagtgaa aaatacacat tgttctctag acatacaaaa ttgagaaaag  2820
aatctcaaaa tttagagaaa caaatctgaa tttctagaaa aaaaataa ttatgcaatt   2880
tgctattgct cgaaaaataa atgaaagaaa ttagactttt taaaagatg ttagactaga   2940
tatactcaaa agctattaaa ggagtaatat tcttcttaca ttaagtattt tagttacagt  3000
cctgtaatta aagacacatt ttagattgta tctaaactta aatgtatcta gaatacatat  3060
atttgattgc atcatatcca tgtatccgac acaccaattc tcataaaaaa cgtaatatcc  3120
taaactaatt tatccttcaa gtcaacctaa gcccaatata catttcatc tctaaaggcc   3180
caagtggcac aaaatgtcag gcccaattac gaagaaaagg gcttgtaaaa ccctaataaa  3240
gtggcactgg cagagcttac actctcattc catcaacaaa gaaacccaa aagccgcagc   3300
gccactgatt tctctcctcc aggcgaagtg atcaatggcg gcggcaacaa caacaacaac  3360
aacatctttct tcgatctcct tctccaccaa accatctcct tcctcctcca aatcaccatt  3420
accaatctcc agattctccc tcccattctc cctaaacccc aacaaatcat cctcctcctc  3480
ccgccgccgc ggtatcaaat ccagctctcc ctcctccatc tccgccgtgc tcaacacaac  3540
caccaatgtc acaccactc cctctccaac caaacctacc aaaccgaaa cattcatctc   3600
ccgattcgct ccagatcaac cccgcaaagg cgctgatatc ctcgtcgaag ctttagaacg  3660
tcaaggcgta gaaaccgtat tcgcttaccc tggaggtgca tcaatggaga ttcaccaagc  3720
cttaacccgc tcttcctcaa tccgtaacgt ccttcctcgt cacgaacaag gaggtgtatt  3780
```

```
cgcagcagaa ggatacgctc gatcctcagg taaaccaggt atctgtatag ccacttcagg   3840
tcccggagct acaaatctcg ttagcggatt agccgatgcg ttgttagata gtgttcctct   3900
tgtagcaatc acaggacaag tccctcgtcg tatgattggt acagatgcgt ttcaagagac   3960
tccgattgtt gaggtaacgc gttcgattac gaagcataac tatcttgtga tggatgttga   4020
agatatccct aggattattg aggaagcttt cttttagct acttctggta gacctggacc   4080
tgttttggtt gatgttccta aagatattca acaacagctt gcgattccta attgggaaca   4140
ggctatgaga ttacctggtt atatgtctag gatgcctaaa cctccggaag attctcattt   4200
ggagcagatt gttaggttga tttctgagtc taagaagcct gtgttgtatg ttggtggtgg   4260
ttgtttgaat tctagcgatg aattgggtag gtttgttgag cttacgggga tccctgttgg   4320
gagtacgttg atggggctgg gatcttatcc ttgtgatgat gagttgtcgt tacatatgct   4380
tggaatgcat gggactgtgt atgcaaatta cgctgtggag catagtgatt tgttgttggc   4440
gtttggggta aggtttgatg atcgtgtcac gggtaagctt gaggcttttg ctagtagggc   4500
taagattgtt catattgata ttgactcggc tgagattggg aagaataaga ctcctcatgt   4560
gtctgtgtgt ggtgatgtta agctggcttt gcaagggatg aataaggttc ttgagaaccg   4620
agcggaggag cttaagcttg attttggagt ttggaggaat gagttgaacg tacagaaaca   4680
gaagtttccg ttgagcttta agacgtttgg ggaagctatt cctccacagt atgcgattaa   4740
ggtccttgat gagttgactg atggaaaagc cataataagt actggtgtcg ggcaacatca   4800
aatgtgggcg gcgcagttct acaattacaa gaaaccaagg cagtggctat catcaggagg   4860
ccttggagct atgggatttg gacttcctgc tgccgattgga gcgtctgttg ctaacctga   4920
tgcgatagtt gtggatattg acggagatgg aagctttata atgaatgtgc aagagctagc   4980
cactattcgt gtagagaatc ttccagtgaa ggtactttta ttaaacaacc agcatcttgg   5040
catggttatg caatgggaag atcggttcta caaagctaac cgagctcaca catttctcgg   5100
ggatccggct caggaggacg agatattccc gaacatgttg ctgtttgcag cagcttgcgg   5160
gattccagcg cgagggtgaa caaagaaagc agatctccga gaagctattc agacaatgct   5220
ggatacacca ggaccttacc tgttggatgt gatttgtccg caccaagaac atgtgttgcc   5280
gatgatcccg aatggtggca cttttcaacga tgtcataacg gaaggagatg gccggattaa   5340
atactgatca ctgattttaa tgtttagcaa atgtcttatc agtttctct ttttgtcgaa   5400
cggtaattta gagttttttt tgctatatgg attttcgttt ttgatgtatg tgacaacct   5460
cgggattgtt gatttatttc aaaactaaga gtttttgtct tattgttctc gtctattttg   5520
gaatatcaat cttagttta tatcttttct agttctctac ggttttaaatg ttcaacacac   5580
tagcaatttg gcctgccagc gtatggatta tggaactatc aagtgtgtgg gatcgataaa   5640
tatgcttctc aggaatttga gatttacag tctttatgct cattgggttg agtataata   5700
agtaaaaaaa tagtaaattt aagcaataat gttaggtgct atgtgtctgt cgagactatt   5760
ggccggtacc cggggatcct ctagagtcga cctgcaggca tgcaagctag ggataacgag   5820
gtaatagctt ggcactggcc gtcgttttac aacgtcgtga ctgggaaaac cctggcgtta   5880
cccaacttaa tcgccttgca gcacatccc ctttcgccag ctggcgtaat agcgaagagg   5940
cccgcaccga tcgcccttcc caacagttgc gcagcctgaa tggcgaatgc tagagcagct   6000
tgagcttgga tcagattgtc gtttcccgcc ttcagtttaa actatcagtg tttgacagga   6060
tatattggcg ggtaaaccta agagaaaaga gcgttttatt gaataatcgg atatttaaa   6120
gggcgtgaaa aggtttatcc gttcgtccat ttgtatgtgc atgccaacca cagggttccc   6180
ctcgggatca aagtactttg atccaacccc tccgctgcta agtgcagtc ggcttctgac   6240
gttcagtgca gccgtcttct gaaaacgaca tgtcgcacaa gtcctaagtt acgcgacagg   6300
ctgccgccct gcccttttcc tggcgttttc ttgtcgcgtg ttttagtcgt ataaagtaga   6360
atacttgcga ctagaaccgg agacattacg ccatgaacaa gagcgccgcc gctggcctgc   6420
tgggctatgc ccgcgtcagc accgacgacc aggacttgac caaccaacgg gccgaactgc   6480
acgcggccgg ctgcaccaag ctgttttccg agaagatcac cggcaccagg cgcgaccgcc   6540
cggagctggc caggatgctt gaccacctac gccctggcgt cgttgtgaca gtgaccaggc   6600
tagaccgcct ggcccgcagc acccgcgacc tactggacat tgccgagcgc atccaggagg   6660
ccggcgcggg cctgcgtagc ctggcagagc cgtgggccga caccaccacg ccggccggcc   6720
gcatggtgtt gaccgtgttc gccggcattg ccgagttcga gcgttcccta atcatcgacc   6780
gcacccggag cgggcgcgag gccgccaagg cccgaggcgt gaagtttggc ccccgccta   6840
ccctcacccc ggcacagatc gcgcacgccc gcgagctgat cgaccaggaa ggccgcaccg   6900
tgaaagaggc ggctgcactg cttggcgtgc atcgctcgac cctgtaccgc gcacttgagc   6960
gcagcgagga agtgacgccc accgaggcca ggcggcgcgg tgccttccgt gaggacgcat   7020
tgaccgagcg cgacgccctg ggccgccgcg agaatgaacg ccaagaggaa caagcatgaa   7080
accgcaccag gacggccagg acgaaccgtt tttcattacc gaagagatcg aggcggagat   7140
gatcgcggcc gggtacgtgt tcgagccgcc cgcgcacgtc tcaacgtgc ggctgcatga   7200
aatcctggcc ggtttgtctg atgccaagct ggcggcctgg ccggcagct tggccgctga   7260
agaaaccgag cgccgccgtc taaaaaggtg atgtgtattt gagtaaaaca gcttgcgtca   7320
tgcggtcgct gcgtatatga tgcgatgagt aaataaacaa atacgcaagg ggaacgcatg   7380
aaggttatcg ctgtacttaa ccagaaaggc gggtcaggca agacgaccat cgcaacccat   7440
ctagcccgcg ccctgcaact cgccgggcc gatgttctgt tagtcgattc cgatcccag   7500
ggcagtgccc gcgattgggc ggccgtgcgg gaagatcaac cgctaaccgt tgtcggcatc   7560
gaccgcccga cgattgaccg cgacgtgaag gccatcggcc ggcgcgactt ctgtagtgatc   7620
gacgagcgc cccaggcggc ggacttggct gtgtccgcga tcaaggcagc cgacttcgtg   7680
ctgattccgg tgcagccaag cccttacgac atatgggcca ccgccgacct ggtggagctg   7740
gttaagcagc gcattgaggt cacgatgga aggctacaag cggcctttgt cgtgtcgcgg   7800
gcgatcaaag gcacgcgcat cggcggtgag gttgccgagg cgctggccgg gtacgagctg   7860
cccattcttg agtcccgtat cacgcagcgc gtgagctacc caggcactgc cgccgccggc   7920
acaaccgttc ttgaatcaga acccgagggc gacgctgccc gcgaggtcca ggcgctggcc   7980
gctgaaatta atcaaaact catttgagtt aatgaggtaa agagaaaatg agcaaaagca   8040
caaacacgct aagtgccggc cgtccgagcg cacgcagcag caaggctgca acgttggcca   8100
gcctggcaga cacgccagcc atgaagcggg tcaacttca gttgccggcg gaggatcaca   8160
ccaagctgaa gatgtacgcg gtacgccaag gcaagaccat taccgagctg ctatctgaat   8220
acatcgcgca gctaccagag taaatgagca aatgaataaa tgagtagatg aattttagcg   8280
gctaaaggag gcggcatgga aaatcaagaa caaccaggca ccgacgccgt ggaatgcccc   8340
atgtgtggag gaacgggcgg ttggccaggc gtaagcggct gggttgtctg ccggccctgc   8400
aatggcactg gaacccccaa gcccgaggaa tcggcgtgag cggtcgcaaa ccatccggcc   8460
cggtacaaat cggcgcggcg ctgggtgatg acctggtgga gaagttgaag gccgcgcagg   8520
```

-continued

```
ccgcccagcg gcaacgcatc gaggcagaag cacgcccggg tgaatcgtgg caagcggccg  8580
ctgatcgaat ccgcaaagaa tcccggcaac cgccggcagc cggtgcgccg tcgattagga  8640
agccgcccaa gggcgacgag caaccagatt ttttcgttcc gatgctctat gacgtgggca  8700
cccgcgatag tcgcagcatc atggacgtgg ccgttttccg tctgtcgaag cgtgaccgac  8760
gagctggcga ggtgatccgc tacgagcttc cagacgggca cgtagaggtt ccgcagggc   8820
cggccggcat ggccagtgtg tgggattacg acctggtact gatggcggtt cccatcctaa  8880
ccgaatccat gaaccgatac cgggaaggga agggagacaa gcccggccgc gtgttccgtc  8940
cacacgttgc ggacgtactc aagttctgcc ggcgagccga tggcggaaag cagaaagacg  9000
acctggtaga aacctgcatt cggttaaaca ccacgcacgt tgccatgcag cgtacgaaga  9060
aggccaagaa cggccgcctg gtgacggtat ccgagggtga agccttgatt agccgctaca  9120
agatcgtaaa gagcgaaacc gggcggccgg agtacatcga gatcgagcta gctgattgga  9180
tgtaccgcga gatcacagaa ggcaagaacc cggacgtgct gacggttcac cccgattact  9240
tttttgatcga tcccggcatc ggccgttttc tctaccgcct ggcacgccgc gccgcaggcg  9300
aggcagaagc cagatggttg ttcaagacga tctacgaacg cagtggcagc gccggagagt  9360
tcaagaagtt ctgtttcacc gtgcgcaagc tgatcgggtc aaatgacctg ccggagtacg  9420
atttgaagga ggaggcgggg caggctggcc cgatcctagt catgcgctac cgcaacctga  9480
tcgagggcga agcatccgcc ggttcctaat gtacggagca gatgctaggg caaattgccc  9540
tagcaggaga aaaaggtcga aaaggtctct ttcctgtgga tagcacgtac attgggaacc  9600
caaagccgta cattgggaac cggaacccgt acattgggaa cccaaagccg tacattggga  9660
accggtcaca catgtaagtg actgatataa aagagaaaaa aggcgatttt ccgcctaaaa  9720
actctttaaa acttattaaa actcttaaaa cccgcctggc ctgtgcataa ctgtctggcc  9780
agcgcacagc cgaagagctg caaaaagcgc ctacccttcg gtcgctgcgg tccctacgcc  9840
ccgccgcttc gcgtcggcct atcgcggccg ctggccgctc aaaaatggct ggcctacggc  9900
caggcaatct accagggcgc ggacaagccg cgccgtcgcc actcgaccgc cggcgcccac  9960
atcaaggcac cctgcctcgc gcgtttcggt gatgacggtg aaaacctctg acacatgcag 10020
ctcccggaga cggtcacagc ttgtctgtaa gcggatgccg gga                   10063
```

SEQ ID NO: 783          moltype = DNA   length = 3358
FEATURE                 Location/Qualifiers
misc_feature            1..3358
                        note = Selection marker in AR15-00
source                  1..3358
                        mol_type = other DNA
                        organism = synthetic construct SEQUENCE: 783
```
ggccaaagca catagttatc gatttaaatt tcatcgaaga gattaatatc gaataatcat    60
atacatactt taaatacata acaaatttta aatacatata tctggtatat aattaatttt   120
ttaaagtcat gaagtatgta tcaaatacaa atatggaaaa aattaactat tcataatttc   180
aaaaatagaa aagtacatc tagtgaaatt aggtgcatgt atcaaataca ttaggaaaag   240
ggcatatatc ttgatctaga taattaacga ttttgattta tgtataattt ccaaatgaag   300
gtttatatct acttcagaaa taacaatata cttttatcag aacattcaac aaagcaacaa   360
ccaactagag tgaaaaatac acattgttct ctagacatac aaaattgaga aaagaatctc   420
aaaatttaga gaaacaaatc tgaatttcta gaagaaaaaa ataattatgc actttgctc    480
tgctcgaaaa ataatgaaa gaaattagac ttttttaaaa gatgttagac tagatatact   540
caaaagctat taaggagta atattcttct tacattaagt atttttagtta cagtcctgta   600
attaaagaca catttagat tgtatctaaa cttaaatgta tctagaatac atatatttga   660
ttgcatcata tccatgtatc cgacacacca atttctcataa aaaacgtaat atcctaaact   720
aatttatcct tcaagtcaac ctaagcccaa tatacatttt catctctaaa ggcccaagtg   780
gcacaaaatg tcaggcccaa ttacgaagaa aagggcttgt aaaacccctaa taagtggca   840
ctggcagagc ttacactctc attccatcaa caaagaaacc ctaaaagccg cagcgccact   900
gatttctctc ctcaaggcga agtgatcaat ggcggcggca acaacaacaa caacaacatc   960
ttcttcgatc tccttctcca ccaaaccatc tccttcctcc tccaaatcac cattaccaat  1020
ctccagattc tccctcccat tctccctaaa ccccaacaaa tcatcctcct cctcccgccg  1080
ccgcggtatc aaatccagct ctccctcctc catctccgcc gtgctcaaca caaccaccaa  1140
tgtcacaaac actccctctc caaccaaacc taccaaaacc gaaacattca tctcccgatt  1200
cgctccagat caaccccgca aaggcgctga tatcctcgtc gaagctttag aacgtcaagg  1260
cgtagaaaacc gtattcgctt acctggagg tgcatcaatg gagattcacc aagcttaac   1320
ccgctcttcc tcaatccgta acgtcctttcc tcgtcacgaa caaggaggtg tattcgcagc  1380
agaaggatac gctcgatcct caggtaaaacc aaggtatctgt atagccactt caggtcccga  1440
agctacaaat tcgttagcg gattagccga tgcgttgtta gatagtgttc ctcttgtagc  1500
aatcacagga caagtccctc gtcgtatgat tggtacagat gcgtttcaag agactccgat  1560
tgttgaggta acgcgttcga ttacgaagca taactatctt gtgatggatg ttgaagatat  1620
ccctaggatt attgaggaag cttttcttttt agctactcct ggtagacctg gacctgtttt  1680
ggttgatgtt cctaaagata ttcaacaaca gcttgcgatt cctaattggg aacaggctat  1740
gagattacct ggttatatgt ctaggatgcc taaaacctccg gaagattctc atttggagca  1800
gattgttagg ttgatttctg agtctaagaa gcctgtgttg tatgttggtg gtggttgttt  1860
gaattctagc gatgaattgg gtaggtttgt tgagcttacg gggatccctg ttgcgagtac  1920
gttgatgggg ctgggatctt atccttgtga tgatgagtag tcgttacata tgcctggaat  1980
gcatgggact gtgtatgcaa attacgctgt ggagcatagt cagttgttgt tggcgtttgg  2040
ggtaaggttt tgatgatcgtg tcacgggtaa gcttgaggct tttgctagta gggctaagat  2100
tgttcatatt gatattgact cggctgagat tgggaagaat aagactcctc atgtgtctgt  2160
gtgtggtgat gttaagctgg ctttgcaagg gatgaataag gttcttgaga ccgagcgga  2220
ggagcttaag cttgattttg gagtttggag gaatgagttg aacgtacaga aacagaagtt  2280
tccgttgagc tttaagacgt ttgggggaac tattcctcca cagtatgcga ttaaggtcct  2340
tgatgagttg actgatgaa aagccataat aagtactggt gtcgggcaac atcaaatgtg  2400
ggcggcgcag ttctacaatt acaagaaacc aaggcagtgg ctatcatcag gaggccttgg  2460
agctatggga tttggacttc ctgctgcgat tggagcgtct gttgctaacc ctgatgcgat  2520
agttgtggat attgacggag atggaagctt tataatgaat gtgcaagagc tagccactat  2580
tcgtgtagag aatcttccag tgaaggtact tttattaaac aaccagcatc ttggcatggt  2640
```

```
tatgcaatgg gaagatcggt tctacaaagc taaccgagct cacacatttc tcggggatcc  2700
ggctcaggag gacgagatat tcccgaacat gttgctgttt gcagcagctt gcgggattcc  2760
agcggcgagg gtgacaaaga aagcagatct ccgagaagct attcagacaa tgctggatac  2820
accaggacct tacctgttgg atgtgatttg tccgcaccaa gaacatgtgt tgccgatgat  2880
cccgaatggt ggcactttca acgatgtcat aacggaagga gatggccgga ttaaatactg  2940
atcactgatt ttaatgttta gcaaatgtct tatcagtttt ctcttttttgt cgaacggtaa  3000
tttagagttt tttttgctat atggattttc gtttttgatg tatgtgacaa ccctcgggat  3060
tgttgattta tttcaaaact aagagttttt gtcttattgt tctcgtctat tttggaatat  3120
caatcttagt tttatatctt ttctagttct ctacgtgtta aatgttcaac acactagcaa  3180
tttggcctgc cagcgtatgg attatggaac tatcaagtgt gtgggatcga taaatatgct  3240
tctcaggaat ttgagatttt acagtcttta tgctcattgg gttgagtata atatagtaaa  3300
aaaatagtaa atttaagcaa taatgttagg tgctatgtgt ctgtcgagac tattggcc   3358
```

SEQ ID NO: 784          moltype = DNA   length = 10676
FEATURE                 Location/Qualifiers
misc_feature            1..10676
                        note = Construct AR07-00
source                  1..10676
                        mol_type = other DNA
                        organism = synthetic construct
SEQUENCE: 784

```
aattctaatt cgggggatct ggattttagt actggatttt ggttttagga attagaaatt    60
ttattgatag aagtatttta caaatacaaa tacatactaa gggtttctta tatgctcaac   120
acatgagcga aacccatag gaaccctaat tcccttatct gggaactact cacacattat    180
tatgagaaa atagagcttg tcgatcgtta attaattatt tgccgactac cttggtgatc    240
tcgcctttca cgtagtggac aaattcttcc aactgatctg cgcgcgaggc caagcgatct   300
tcttcttgtc caagataagc ctgtctagct tcaagtatga cgggctgata ctgggccggc   360
aggcgctcca ttgcccagtc ggcagcgaca tccttcggcg cgattttgcc ggttactgcg   420
ctgtaccaaa tgcgggacaa cgtaagcact acatttcgct catcgccagc ccagtcgggc   480
ggcgagttcc atagccgttaa ggtttcattt agccgcctcaa atagatcctg ttcaggaacc   540
ggatcaaaga gttcctccgc cgctggacct accaaggcaa cgctatgttc tcttgctttt   600
gtcagcaaga tagccagatc aatgtcgatc gtggctggct cgaagatacc tgcaagaatg   660
tcattgcgct gccattctcc aaattgcagt cgcgcttag ctggtaacg ccacggaatg   720
atgtcgtcgt gcacaacaat ggtgacttct acagcgcgga gaatctcgct ctctccaggg   780
gaagccgaag tttccaaaag gtcgttgatc aaagctcgcc gcgttgtttc atcaagcgtt   840
acggtcaccg taaccagcaa atcaatatca ctgtgtggct tcaggccgcc atccactgcg   900
gagccgtaca aatgtacggc cagcaacgtc ggttcgagat ggcgctcgat gacgccaact   960
acctctgata gttgagtcga tacttcggcg atcaccgctt ccctcatgca tgcagtggcc  1020
acggaagcag aaattctgaa tgaacgaaac ttttgcatga agattgaatc tttcttaagc  1080
accaacatag aattagcaga gttcttcaac ttcttggaac cgaagacaag aaagctagag  1140
cttttaggaa cctgtggctt atggaaatta gagttgggat tgagagtctg gatgccttgt  1200
gccatattgt taatctgggc catggtagac tcgagagaga tagatttgta gagagagact  1260
ggtgatttca gcgtgtcctc tccaaatgaa atgaacttct ttatatagag gaaggtcttg  1320
cgaaggatag tgggattgtg cgtcatccct tacgtcagtg gagatatcac atcaatccac  1380
ttgctttgaa gacgtggttg gaacgtcttc ttttccacg atgctcctcg tgggtggggg  1440
tccatctttg ggaccactgt cggcagaggc atcttgaacg atagcctttc ctttatcgca  1500
atgatggcat ttgtaggtgc caccttcctt ttctactgtc cttttgatga agtgacagat  1560
agctgggcaa tggaatccga ggaggttccc cgatattacc cttgttgaa aagtctcaat  1620
agcccttttgg tcttctgaga ctgtatcttt gatattcttg gagtagacga gagtgtcgtg  1680
ctccaccatg ttatcacatc aatccacttg ctttgaagac gtggtggaa cgtcttcttt  1740
ttccacgatg ctcctcgtgg gtggggtcc atctttggga ccactgtcgg cagaggcatc  1800
ttgaacgata gcctttcctt tatcgcaatg atgcatttg taggtgccac cttcctttc  1860
tactgtcctt ttgatgaagt gacagatagc tgggcaatgg aatccgagga ggtttcccga  1920
tattacccctt tgttgaaaag tctcaatagc cctttggtct tctgagactg tatctttgat  1980
attcttggag tagacgagag tgtcgtgctc caccatgttg cgggtacccg gggatcctc  2040
agagtcgacc tgcaggcatg caagctaggg ataacagggt aatgggccca atataacaac  2100
gacgtcgtaa cagataaagc gaagcttgaa ggtgcatgtg actccgtcaa gattacgaaa  2160
ccgccaacta ccacgcaaat tgcaattctc aatttcctag aaggactctc cgaaaatgca  2220
tccaataccca aatattaccc cgtcataggg caccaagtga caccatacat gaacacgcgt  2280
cacaatatga ctggagaagg gttccacacc ttatgctata aaacgcccca caccctcct  2340
ccttccttcg cagttcaatt ccaatatatt ccattctctc tgtgtatttc cctacctctc  2400
ccttcaaggt tagtcgattt cttctgtttt tcttcttcgt tctttccatg aattgtgtat  2460
gttctttgat caatacgatg ttgatttgat tgtgttttgt ttggtttcat cgatcttcaa  2520
ttttcataat cagattcagc ttttattatc tttacaacaa cgtccttaat ttgatgattc  2580
tttaatcgta gatttgctct aattagagct ttttcatgtc agatcccttt acaacaagcc  2640
ttaattgttg attcattaat cgtagattag ggctttttttc attgattact tcagatccgt  2700
taaacgtaac catagatcag ggcttttttca tgaattactt cagatccgtt aaacaacagc  2760
cttatttttt atacttctgt ggttttttcaa gaaattgttc agatccgttg acaaaaagcc  2820
ttattcgttg attctatatc gttttttcgag agatattgct cagatctgtt agcaactgtc  2880
ttgtttgttg attctattgc cgtggattag ggttttttttt cacgagattg cttcagatcc  2940
gtacttaaga ttacgtaatg gattttgatt ctgatttatc tgtgattgtt gactcgacag  3000
gtcgacatgt gagcaaggg cgaggaggat aacatggcca tcatcaagga gttcatgcgc  3060
ttcaaggtgc acatggaggg ctccgtgaac ggccacgagt cgagatcga gggcgaggc  3120
gagggcgcc ctacgagggg cacccagacc gccaagctga aggtgaccaa gggtggccc  3180
ctgcccttcg cctgggacat cctgtcccct cagttcatgt acggctccaa ggcctacgtg  3240
aagcaccccg ccgacatccc cgactacttg aagctgtcct tccccgaggg cttcaagtgg  3300
gagcgcgtga tgaacttcga ggacggcggc gtggtgaccg tgacccagga ctcctccctg  3360
caggacgcg agttcatcta caaggtgaag ctgcgcggca ccaacttccc ctccgacggc  3420
cccgtaatgc agaagaagac catgggctgg gaggcctcct ccgagcggat gtaccccgag  3480
```

```
gacggcgccc tgaagggcga gatcaagcag aggctgaagc tgaaggacgg cggccactac   3540
gacgctgagg tcaagaccac ctacaaggcc aagaagcccg tgcagctgcc cggcgcctac   3600
aacgtcaaca tcaagttgga catcacctcc cacaacgagg actacaccat cgtgggaacag  3660
tacgaacgcg ccgagggccg ccactccacc ggcggcatgg acgagctgta caagtaaccc   3720
ggggttcgag tattatgtgca ttgggaaaaac tgttttttctt gtaccatttg ttgtgcttgt 3780
aatttactgt gttttttatt cggttttcgc tatcgaactg tgaaatgaaa atggatggag   3840
aagagttaat gaatgatatg gtcctttttgt tcattctcaa attaatatta tttgtttttt   3900
ctcttatttg ttgtgtgttg aatttgaaat tataagagat atgcaaacat tttgttttga   3960
gtaaaaatgt gtcaaatcgt ggcctctaat gaccgaagtt aatatgagga gtaaaaacact  4020
agggataaca gggtaatagc ttggcactgg ccgtcgtttt acaacgtcgt gactgggaaa   4080
accctggcgt tacccaactt aatcgccttg cagcacatcc cctttcgcc agctggcgta    4140
atagcgaaga ggcccgcacc gatcgccctt cccaacagtt cgcagcctg aatggcgaat    4200
gctagagcag cttgagcttg gatcagattg tcgtttcccg ccttcagttt aaactatcag   4260
tgtttgacag gatatattgg cgggtaaacc taagagaaaa gagcgttttat tagaataacg   4320
gatatttaaa agggcgtgaa aaggtttatc cgttcgtcca tttgtatgtg catgccaacc   4380
acagggttcc cctcgggatc aaagtacttt gatccaaccc ctccgctgct atagtgcagt   4440
cggcttctga cgttcagtgc agccgtcttc tgaaaacgac atgtcgcaca agtcctaagt   4500
tacgcgacag gctgccgccc tgcccttttc ctggcgtttt cttgtcgcgt gttttagtcg   4560
cataaagtag aatacttgcg actagaaccg gagacattac gccatgaaca agagcgccgc   4620
cgctggcctg ctgggctatg cccgcgtcag caccgacgac caggacttga ccaaccaacg   4680
ggccgaactg cacgcggccg gctgcaccaa gctgttttcc gagaagatca ccggcaccag   4740
gcgcgaccgc ccggagctgg cagatgct tgaccaccta cgccctggcg acgttgtgac    4800
agtgaccagg ctagaccgcc tggcccgcag caccccgcga ctactggaca ttgccgagct   4860
catccaggag gccggcgcgg gcctgcgtag cctggcagag ccgtgggccg acaccaccac   4920
gccggccggc cgcatggtgt tgaccgtgtt cgccggcatt gccgagttcg agcgttccct   4980
aatcatcgac cgcacccgga gcggcgcga ggccgcaag cccgaggcg tgaagtttgg      5040
cccccgccct accctcaccc cggcacagat cgcgcacgcc cgcgagctga tcgaccagga   5100
aggccgcacc gtgaaagagg cggctgcact gcttggcgtg catcgctcga ccctgtaccg   5160
cgcacttgag cgcagcgagg aagtgacgcc caccgaggcc aggcggcgcg gtgccttccg   5220
tgaggacgca ttgaccgagg ccgacgccct gccggccgca gagaatgaac gccaagagga   5280
acaagcatga aaccgcacca ggacggccag gacgaaccgt ttttcattac cgaagagatc   5340
gaggcggaga tgatcgcggc cgggtacgtg ttcgagccgc ccgcgcacgt ctcaaccgtg   5400
cggctgcatg aaatcctggc cggttttgtct gatgccaagc tggcggcctg gccggccagc   5460
ttggccgctg aagaaaccga gcgccgccgt ctaaaaaggt gatgtgtatt tgagtaaaac   5520
agcttgcgtc atgcggtcgc tgcgtatatg atgcgatgag taaataaaca aatacgcaag   5580
gggaacgcat gaaggttatc gctgtactta accagaaagg cgggtcaggc aagacgacca   5640
tcgcaaccca tctagcccgc gccctgcaac tcgccggggc cgatgttctg ttagtcgatt   5700
ccgatcccca gggcagtgcc cgcgattggg cggccgtgcg ggaagatcaa ccgctaaccg   5760
ttgtcggcat cgaccgcccg acgattgacc gcgacgtgaa ggccatcgac cggcgcgact   5820
tcgtagtgat cgacggagcg cccaggcgg cggacttggc tgtgtccgcg atcaaggcag   5880
ccgacttcgt gctgattccg gtgcagccaa gcccttacga catatgggcc accgccgacc   5940
tggtggagct ggttaagcag cgcattgagg tcacggatgg aaggctacaa gcggccttttg   6000
tcgtgtcgcg ggcgatcaaa ggcacgcgca tcggcggtga ggttgccgag gcgctggcgg   6060
ggtacgagct gcccattctt gagtcccgta tcacgcagcg cgtgagctac ccaggcactg   6120
ccgccgccgg cacaaccgtt cttgaatcag aacccgaggg cgacgctgcc cgcgaggtcc   6180
aggcgctggc cgctgaaatt aaatcaaaac tcatttgagt taatgaggta aagagaaaat   6240
gagcaaaagc acaaacacgc taagtgccgg ccgtccgagc gcacgcagca gcaaggctgc   6300
aacgttggcc agcctggcag acacgccagc catgaagcgg gtcaactttc agttgccggc   6360
ggaggatcac accaagctga agatgtacgc ggtacgccaa gcaagacca ttaccgagct    6420
gctatctgaa tacatcgcgc agctaccaga gtaaatgagc aaatgaataa atgagtagat   6480
gaattttagc ggctaaagga ggcggcatgg aaaatcaaca accaggc accgacgccg      6540
tggaatgccc catgtgtgga ggaacgggcg gttggccagg cgtaagcggc tgggttgtct   6600
gccgccctg caatggcact ggaaccccca agcccgagga tcggcgtga gcggtcgcaa      6660
accatccggc ccgtacaaa tcggcgcggc gctgggtgat gacctggtgg agaagttgaa    6720
ggccgcgcag gccgcccac ggcaacgcat cgaggcagaa gcagccccg gtgaatcgtg      6780
gcaagcggcc gctgatcgaa tccgcaaaga atcccggcaa ccgccggcag ccggtgcgcc    6840
gtcgattagg aagccgccca agggcgacga gcaaccagat ttttttcgttc cgatgctcta   6900
tgacgtgggc acccgcgata gtcgcagcat catggacgtg gccgttttcc gtctgtcgaa   6960
gcgtgaccga cgagctggcg aggtgatccg ctacgagctt ccagacgggc acgtagaggt   7020
ttccgcaggg ccggccgca tggccagtgt gtgggattac gacctggtac tgatgccggt    7080
ttccatcta accgaatcca tgaaccgata ccgggaaggg aagggagaca agcccggccg    7140
cgtgttccgt ccacacgttg cggacgtact caagttctgc cggcgagccg atggcggaaa   7200
gcagaaagac gacctggtag aaacctgcat tcggttaaac accacgcacg ttgccatgca   7260
ggtacgaag aaggccaaga acggcccgct ggtgacgtta tccgagggtg aagccttgat    7320
tagccgctac aagatcgtaa agagcgaaac cgggcggccg gagtacatcg agatcgagct   7380
agctgattgg atgtaccgcg agatcacaga aggcaagaac ccggacgtgc tgacggttca   7440
ccccgattac ttttttgatcg atcccggcat cggccgtttt ctctaccgcc tggcacgccg    7500
cgccgcaggc aaggcagaag ccagatggtt gttcaagacg atctacgaac gcagtggcag   7560
cgccggagag ttcaagaagt tctgtttcac cgtgcgcaag ctgatcgact caaatgaccct   7620
gccgagtac gatttgaagg aggaggcggg gcaggctggc ccgatcctag tcatgcgcta   7680
ccgcaacctg atcgagggcg aagcatccgc cggttcctaa tgtacggagc agatgctagg   7740
gcaaattgcc ctagcagggg aaaaaggtcg aaaaggtctc tttcctgtgg atagcacgta   7800
cattgggaac ccaaagccgt acattgggaa ccggaacccg tacattggga acccaaagcc   7860
gtacattggg aaccggtcac acatgtaagt gactgatata aaagagaaaa aaggcgattt   7920
ttccgcctaa aactctttaa aacttattaa aactcttaaa acccgcctgg cctgtgcata   7980
actgtctggc cagcgcacag ccgaagagct gcaaaaagcg cctacccttc ggtcgctgcg   8040
ctccctacgc cccgccgctt cgcgtcgcc tatcgcggcc gctggccgct caaaaatggc    8100
tggcctacgg ccaggcaatc taccagggcg cggacaagcc gcgccgtcgc cactcgaccg   8160
ccggcgccca catcaaggca ccctgcctcg cgcgtttcgg tgatgacggt gaaaacctct   8220
```

```
gacacatgca gctcccggag acggtcacag cttgtctgta agcggatgcc gggagcagac    8280
aagcccgtca gggcgcgtca gcgggtgttg gcgggtgtcg gggcgcagcc atgacccagt    8340
cacgtagcga tagcggagtg tatactggct taactatgcg gcatcagagc agattgtact    8400
gagagtgcac catatgcggt gtgaaatacc gcacagatgc gtaaggagaa ataccgcat    8460
caggcgctct tccgcttcct cgctcactga ctcgctgcgc tcggtcgttc ggctgcggcg    8520
agcggtatca gctcactcaa aggcggtaat acggttatcc acagaatcag gggataacgc    8580
aggaaagaac atgtgagcaa aaggccagca aaaggccagg aaccgtaaaa aggccgcgtt    8640
gctggcgttt ttccataggc tccgcccccc tgacgagcat cacaaaaatc gacgctcaag    8700
tcagaggtgg cgaaacccga caggactata aagataccag gcgtttcccc ctggaagctc    8760
cctcgtgcgc tctcctgttc cgaccctgcc gcttaccgga tacctgtccg cctttctccc    8820
ttcgggaagc gtggcgcttt ctcatagctc acgctgtagg tatctcagtt cggtgtaggt    8880
cgttcgctcc aagctgggct gtgtgcacga accccccgtt cagcccgacc gctgcgcctt    8940
atccggtaac tatcgtcttg agtccaaccc ggtaagacac gacttatcgc cactggcagc    9000
agccactggt aacaggatta gcagagcgag gtatgtaggc ggtgctacag agttcttgaa    9060
gtggtggcct aactacggct acactagaag gacagtattt ggtatctgcg ctctgctgaa    9120
gccagttacc ttcggaaaaa gagttggtag ctcttgatcc ggcaaacaaa ccaccgctgg    9180
tagcggtggt ttttttgttt gcaagcagca gattacgcgc agaaaaaaag gatctcaaga    9240
agatcctttg atcttttcta cggggtctga cgctcagtgg aacgaaaact cacgttaagg    9300
gattttggtc atgcattcta ggtactaaaa caattcatcc agtaaaatat aatatttat    9360
tttctcccaa tcaggcttga tccccagtaa gtcaaaaaat agctcgacat actgttcttc    9420
cccgatatcc tccctgatcg accggacgca gaaggcaatg tcataccact tgtccgccct    9480
gccgcttctc ccaagatcaa taaagccact tactttgcca tcttttcacaa atgattgttgct    9540
gtctcccagg tcgccgtggg aaaagacaag ttcctcttcg gcttttttccg tctttaaaaa    9600
atcatacagc tcgcgcggat cttta aatgg agtgtcttct tccagtttt cgcaatccac    9660
atcggccaga tcgttattca gtaagtaatc caattcggct aagcggctgt ctaagctatt    9720
cgtataggga caatccgata tgtcgatgga gtgaaagacc ctgatgcact ccgcatacag    9780
ctcgataatc ttttcagggc tttgttcatc ttcatactct tccgagcaaa ggacgccatc    9840
ggcctcactc atgagcagat tgctccagcc atcatgccgt tcaaagtgca ggaccttgg    9900
aacaggcagc tttccttcca gccatagcat catgtccttt tcccgttcca catcataggt    9960
ggtccctta taccggctgt ccgtcatttt taaatataagg ttttcatttt ctcccaccag  10020
cttatatacc ttagcaggag acattccttc cgtatctttt acgcagcggt attttttcgat  10080
cagttttttc aattccggtg atattctcat tttagccatt tattatttcc ttcctctttt  10140
ctacagtatt taaagatacc ccaagaagct aattataaca agacgaactc caattcactg  10200
ttccttgcat tctaaaacct taaataccag aaaacagctt tttcaaagtt gtttttcaaag  10260
ttggcgtata acatagtatc gacggagccg attttgaaac cgcggtgatc acaggcagca  10320
acgctctgtc atcgttacaa tcaacatgct accctccgcg agatcatccg tgtttcaaac  10380
ccggcagctt agttgccgtt cttccgaata gcatcggtaa catgagcaaa gtctgccgcc  10440
ttacaacggc tctcccgctg acgccgtccc ggactgatgg gctgcctgta tcgagtggtg  10500
attttgtgcc gagctgccgg tcgggggagct gttggctggc tggttgccag atatattggg  10560
gtgtaaacaa attgacgctt agacaactta ataacacatt gcggacgttt ttaatgtact  10620
gaattaacgc cgatcggtt taaaccacac aggaaacagc tatgaccatg attacg       10676

SEQ ID NO: 785          moltype = DNA   length = 678
FEATURE                 Location/Qualifiers
misc_feature            1..678
                        note = CaMV35S promoter
source                  1..678
                        mol_type = other DNA
                        organism = synthetic construct
SEQUENCE: 785
tcagcgtgtc ctctccaaat gaaatgaact tccttatata gaggaaggtc ttgcgaagga     60
tagtgggatt gtgcgtcatc ccttacgtca gtggagatat cacatcaatc cacttgcttt    120
gaagacgtgg ttggaacgtc ttctttttcc acgatgctcc tcgtgggtgg gggtccatct    180
ttgggaccac tgtcggcaga ggcatcttga acgatagcct tcctttatc gcaatgatgg    240
catttgtagg tgccaccttc ctttttctact gtccttttga tgaagtgaca gatagctggg    300
caatggaatc cgaggaggtt tcccgatatt acccttttgt gaaaagtctc aatagccctt    360
tggtcttctg agactgtatc tttgatattt tggagtagac gagagtgtc gtgctccacc     420
atgttatcac atcaatccac ttgctttgaa gacgtggttg gaacgtcttc tttttccacg    480
atgctcctcg tgggtggggg tccatctttg gaccactgt cggcagaggc atcttgaacg    540
atagcctttc ctttatcgca atgatggcat ttgtaggtgc caccttcctt ttctactacc    600
cttttgatga agtgacagat agctgggcaa tggaatccga ggagtttccc cgatattacc    660
ctttgttgaa aagtctca                                                 678

SEQ ID NO: 786          moltype = DNA   length = 917
FEATURE                 Location/Qualifiers
misc_feature            1..917
                        note = GmU3 promoter
source                  1..917
                        mol_type = other DNA
                        organism = synthetic construct
SEQUENCE: 786
gggcccaata taacaacgac gtcgtaacag ataaagcgaa gcttgaaggt gcatgtgact     60
ccgtcaagat tacgaaaccg ccaactacca cgcaaattgc aattctcaat ttcctagaag    120
gactctccga aaatgcatcc aataccaaat attacccgtg tcataggcac caagtgacac    180
catacatgaa cacgcgtcac aatatgactg gagaagggtt ccacacctta tgctataaaa    240
cgccccacac ccctcctcct tccttcgcag ttcaattcca atatattcca ttctctctgt    300
gtatttccct acctctccct tcaaggttag tcgatttctt ctgttttttct tcttcgttcct    360
ttccatgaat tgtgtatgtt ctttgatcaa tacgatgttg atttgattgt gttttgtttg    420
gtttcatcga tcttcaattt tcataatcag attcagcttt tattatcttt acaacaacgt    480
```

```
ccttaatttg atgattcttt aatcgtagat ttgctctaat tagagctttt tcatgtcaga    540
tccctttaca acaagcctta attgttgatt cattaatcgt agattagggc ttttttcatt    600
gattacttca gatccgttaa acgtaaccat agatcagggc ttttttcatga attacttcag   660
atccgttaaa caacagcctt attttttata cttctgtggt ttttcaagaa attgttcaga    720
tccgttgaca aaaagcctta ttcgttgatt ctatatcgtt tttcgagaga tattgctcag    780
atctgttagc aactgccttg tttgttgatt ctattgccgt ggattagggt tttttttcac    840
gagattgctt cagatccgta cttaagatta cgtaatggat tttgattctg atttatctgt    900
gattgttgac tcgacag                                                    917

SEQ ID NO: 787          moltype = DNA  length = 922
FEATURE                 Location/Qualifiers
misc_feature            1..922
                        note = StUbi3 promoter
source                  1..922
                        mol_type = other DNA
                        organism = synthetic construct
SEQUENCE: 787
ggccaaagca catagttatc gatttaaatt tcatcgaaga gattaatatc gaataatcat    60
atacatactt taaatacata acaaatttta aatacatata tctggtatat aattaatttt   120
ttaaagtcat gaagtatgta tcaaatacaa atatggaaaa aattaactat tcataattta   180
aaaaatagaa aagatacatc tagtgaaatt aggtgcatgt atcaaataca ttaggaaaag   240
ggcatatatc ttgatctaga taattaacga ttttgattta tgtataattt ccaaatgaag   300
gtttatatct acttcagaaa taacaatata cttttatcag aacattcaac aaagcaacaa   360
ccaactagag tgaaaaatac acattgttct ctagacatac aaaattgaga aaagaatctc   420
aaaatttaga gaaacaaatc tgaatttcta gaagaaaaaa ataattatgc actttgctat   480
tgctcgaaaa ataaatgaaa gaaattagac tttttaaaga gatgttagac tagatatact   540
caaaagctat taaaggagta atattcttct tacattaagt attttagtta cagtcctgta    600
attaaagcaca catttagat tgtatctaaa cttaaatgta tctagaatac atatatttga   660
ttgcatcata tccatgtatc cgacacacca attctcataa aaaacgtaat atcctaaact   720
aatttatcct tcaagtcaac ctaagcccaa tatcatttt catctctaaa ggccaagtg    780
gcacaaaatg tcaggcccaa ttacgaagaa aagggcttgt aaaaccctaa taaagtggca   840
ctggcagagc ttacactctc attccatcaa caaagaaacc ctaaaagccg cagcgccact   900
gatttctctc ctccaggcga ag                                             922

SEQ ID NO: 788          moltype = DNA  length = 1940
FEATURE                 Location/Qualifiers
misc_feature            1..1940
                        note = Selection marker in AR07-00
source                  1..1940
                        mol_type = other DNA
                        organism = synthetic construct
SEQUENCE: 788
taattcgggg gatctggatt ttagtactgg attttggttt taggaattag aaattttatt     60
gatagaagta ttttacaaat acaaatacat actaagggtt tcttatatgc tcaacacatg    120
agcgaaaccc tataggaacc ctaattccct tatctgggaa ctactcacac attattatgg    180
agaaaataga gcttgtcgat cgttaattaa ttatttgccg actaccttgg tgatctcgcc    240
tttcacgtag tggacaaatt cttccaactg atctgcgcgc gaggccaagc gatcttcttc    300
ttgtccaaga taagcctgtc tagcttcaag tatgacgggc tgatactggg ccggcaggcc    360
ctccattgcc cagtcggcag cgacatcctt cggcgcgatt ttgccggtta ctgcgctgta    420
ccaaatgcgg gacaacgtaa gcactacatt tcgctcatcg ccagcccagt cgggcggcga    480
gttccatagc gttaaggttt catttagcgc ctcaaataga tcctgttcag gaaccggatc    540
aaagagttcc tccgccgctg gacctaccaa ggcaacgcta tgttctcttg cttttgtcag    600
caagatagcc agatcaatgt cgatcgtggc tggctcgaag atacctgcaa gaatgtcatt    660
gcgctgccat tctccaaatt gcagttcgcg cttagctgga taacgccacg gaatgatgtc    720
gtcgtgcaca acaatggtga cttctacagc gcggagaatc tcgctctctc caggggaagc    780
cgaagtttcc aaaaggtcgt tgatcaaagc tcgccgcgtt gtttcatcaa gccttacggt    840
caccgtaacc agcaaatcaa tatcactgtg tggcttcagg ccgccatcca ctgcggagcc    900
gtacaaatgt acgccagca acgtcggttc gagatggcgc tcgatgacgc caactacctc    960
tgatagttga gtcgatactt cggcgatcac cgcttccctc atgcatgag tggccacgga   1020
agcagaaatt ctgaatgaac agaacttttg catgaagatt gaatcttct taagcaccaa   1080
catagaatta gcagagttct tcaacttctg gaaccgaag acaagaaagc tagagctttt   1140
aggaacctgt ggcttatgga aattagagtt gggattgaga gtctggatgc cttgtgccat   1200
attgttaatc tgggccatgg tagactcgag agagatagat ttgtagagag agactggtga   1260
tttcagcgtg tcctcctcaa atgaaatgaa cttccttata tagaggaagg tcttgcgaag   1320
gatagtggga ttgtgcgtca tcccttacgt cagtggagat atcacatcaa tcccacttgct  1380
ttgaagacgt ggttggaacg tcttctttt ccacgatgct cctcgtgggt gggggtccat   1440
ctttgggacc actgtcggca gaggcatctt gaacgatagc ctttccttta tcgcaatgat  1500
ggcatttgta ggtgccaacct tccttttcta ctgtccttt gatgaagtga cagatagctg  1560
ggcaatggaa tccgaggagg tttcccgata ttaccctttg ttgaaaagtc tcaatagccc  1620
tttggtcttc tgagactgta tctttgatat tcttggagta gacgagagtg tcgtgctcca  1680
ccatgttatc acatcaatcc acttgctttg aagacgtggt tggaacgtct tctttttcca   1740
cgatgctcct cgtgggtggg ggtccatctt tgggaccact gtcggcagag gcatcttgaa   1800
cgatagcctt tcctttatcg caatgatggc atttgtaggt gccaccttcc ttttctactg   1860
tccttttgat gaagtgacag atagctgggc aatggaatcc gaggagggtt cccgatatta   1920
cccttttgttg aaaagtctca                                              1940

SEQ ID NO: 789          moltype = DNA  length = 1937
FEATURE                 Location/Qualifiers
misc_feature            1..1937
```

|  | note = Reporter gene in AR07-00 |
|---|---|
| source | 1..1937 |
|  | mol_type = other DNA |
|  | organism = synthetic construct |

SEQUENCE: 789
```
gggcccaata taacaacgac gtcgtaacag ataaagcgaa gcttgaaggt gcatgtgact   60
ccgtcaagat tacgaaaccg ccaactacca cgcaaattgc aattctcaat ttcctagaag  120
gactctccga aaatgcatcc aataccaaat attacccgtg tcataggcac caagtgacac  180
catacatgaa cacgcgtcac aatatgactg gagaagggtt ccacacctta tgctataaaa  240
cgccccacac ccctcctcct tccttcgcag ttcaattcca atatattcca ttctctctgt  300
gtatttccct acctctccct tcaaggttag tcgatttctt ctgttttct tcttcgttct   360
ttccatgaat tgtgtatgtt ctttgatcaa tacgatgttg atttgattgt gttttgtttg  420
gtttcatcga tcttcaattt tcataatcag attcagcttt tattatcttt acaacaacgt  480
ccttaatttg atgattcttt aatcgtagat ttgctctaat tagagctttt tcatgtcaga  540
tccctttaca acaagcctta attgttgatt cattaatcgt agattagggc ttttttcatt  600
gattacttca gatccgttaa acgtaaccat agatcagggc ttttttcatga attacttcag  660
atccgttaaa caacagcctt attttttata cttctgtggt ttttcaagaa attgttcaga  720
tccgttgaca aaaagcctta ttcgttgatt ctatatcgtt tttcgagaga tattgctcag  780
atctgttagc aactgccttg tttgttgatt ctattgccgt ggattagggt tttttttcac  840
gagattgctt cagatccgta cttaagatta cgtaatggat tttgattctg atttatctgt  900
gattgttgac tcgacaggtc gacatggtga gcaagggcga ggaggataac atggccatca  960
tcaaggagtt catgcgcttc aaggtgcaca tggagggctc cgtgaacggc cacgagttcg 1020
agatcgaggg cgagggcgag ggcgcccct acgagggcac ccagaccgcc aagctgaagg 1080
tgaccaaggt tggccccctg cccttcgcct gggacatcct gtcccctcag ttcatgtacg 1140
gctccaaggc ctacgtgaag cacccgccg acatccccga ctacttgaag ctgtccttcc 1200
ccgagggctt caagtgggag cgcgtgatga acttcgagga cggcggcgtg gtgaccgtga 1260
cccaggactc ctcccctgcag gacggcgagt tcatctacaa ggtgaagctg cgcggcacca 1320
acttcccctc cgacggcccc gtaatgcaga gaagaccat gggctgggag gcctcctccg 1380
agcggatgta ccccgaggac ggcgccctga agggcgagat caagcagagg ctgaagctga 1440
aggacggcgg ccactacgac gctgaggtca agaccaccta caagcccagg aagcccggc 1500
agctgcccgg cgcctacaac gtcaacatca gttggacat cacctcccac aacgaggact 1560
acaccatcgt ggaacagtac gaacgcgccg agggccgcca ctccaccggc ggcatggacg 1620
agctgtacaa gtaacccggg gttcgagtat tatggcattg ggaaaactgt ttttcttgta 1680
ccatttgttg tgcttgtaat ttactgtgtt ttttattcgg ttttcgctat cgaactgtga 1740
aatggaaatg gatggagaag agttaatgaa tgatatggtc cttttgttca ttctcaaatt 1800
aatattattt gttttttctc ttatttgttg tgtgttgaat ttgaaattat aagagatatg 1860
caaacatttt gttttgagta aaaatgtgtc aaatcgtggc ctctaatgac cgaagttaat 1920
atgaggagta aaacact                                                1937
```

SEQ ID NO: 790        moltype =     length =
SEQUENCE: 790
000

SEQ ID NO: 791        moltype =     length =
SEQUENCE: 791
000

SEQ ID NO: 792        moltype =     length =
SEQUENCE: 792
000

SEQ ID NO: 793        moltype =     length =
SEQUENCE: 793
000

SEQ ID NO: 794        moltype =     length =
SEQUENCE: 794
000

SEQ ID NO: 795        moltype =     length =
SEQUENCE: 795
000

SEQ ID NO: 796        moltype =     length =
SEQUENCE: 796
000

SEQ ID NO: 797        moltype =     length =
SEQUENCE: 797
000

SEQ ID NO: 798        moltype =     length =
SEQUENCE: 798
000

SEQ ID NO: 799        moltype =     length =
SEQUENCE: 799
000

```
SEQ ID NO: 800          moltype =         length =
SEQUENCE: 800
000

SEQ ID NO: 801          moltype =         length =
SEQUENCE: 801
000

SEQ ID NO: 802          moltype =         length =
SEQUENCE: 802
000

SEQ ID NO: 803          moltype =         length =
SEQUENCE: 803
000

SEQ ID NO: 804          moltype =         length =
SEQUENCE: 804
000

SEQ ID NO: 805          moltype =         length =
SEQUENCE: 805
000

SEQ ID NO: 806          moltype =         length =
SEQUENCE: 806
000

SEQ ID NO: 807          moltype =         length =
SEQUENCE: 807
000

SEQ ID NO: 808          moltype =         length =
SEQUENCE: 808
000

SEQ ID NO: 809          moltype =         length =
SEQUENCE: 809
000

SEQ ID NO: 810          moltype = AA    length = 386
FEATURE                 Location/Qualifiers
source                  1..386
                        mol_type = protein
                        organism = Meleagris gallopavo
SEQUENCE: 810
MGSIGAVSME FCFDVFKELK VHHANENIFY SPFTIISALA MVYLGAKDST RTQINKVVRF    60
DKLPGFGDSV EAQCGTSVNV HSSLRDILNQ ITKPNDVYSF SLASRLYAEE TYPILPEYLQ   120
CVKELYRGGL ESINFQTAAD QARGLINSWV ESQTNGMIKN VLQPSSVDSQ TAMVLVNAIV   180
FKGLWEKAFK DEDTQAIPFR VTEQESKPVQ MMYQIGLFKV ASMASEKMKI LELPFASGTM   240
SMWVLLPDEV SGLEQLETTI SFEKMTEWIS SNIMEERRIK VYLPRMKMEE KYNLTSVLMA   300
MGITDLFSSS ANLSGISSAG SLKISQAVHA AYAEIYEAGR EVIGSAEAGA DATSVSEEFR   360
VDHPFLYCIK HNLTNSILFF GRCISP                                       386

SEQ ID NO: 811          moltype = AA    length = 386
FEATURE                 Location/Qualifiers
source                  1..386
                        mol_type = protein
                        organism = Meleagris gallopavo
SEQUENCE: 811
MGSIGAVSME FCFDVFKELK VHHANENIFY SPFTIISALA MVYLGAKDST RTQINKVVRF    60
DKLPGFGDSV EAQCGTSVNV HSSLRDILNQ ITKPNDVYSF SLASRLYAEE TYPILPEYLQ   120
CVKELYRGGL ESINFQTAAD QARGLINSWV ESQTNGMIKN VLQPSSVDSQ TAMVLVNAIV   180
FKGLWEKAFK DEDTQAIPFR VTEQESKPVQ MMYQIGLFKV ASMASEKMKI LELPFASGTM   240
SMWVLLPDEV SGLEQLETTI SFEKMTEWIS SNIMEERRIK VYLPRMKMEE KYNLTSVLMA   300
MGITDLFSSS ANLSGISSAG SLKISQAAHA AYAEIYEAGR EVIGSAEAGA DATSVSEEFR   360
VDHPFLYCIK HNLTNSILFF GRCISP                                       386

SEQ ID NO: 812          moltype = AA    length = 383
FEATURE                 Location/Qualifiers
source                  1..383
                        mol_type = protein
                        organism = Coturnix japonica
SEQUENCE: 812
MGSIGAASME FCFDVFKELK VHHANDNMLY SPFAILSTLA MVFLGAKDST RTQINKVVHF    60
DKLPGFGDSI EAQCGTSVNV HSSLRDILNQ ITKQNDAYSF SLASRLYAQE TYTVVPEYLQ   120
CVKELYRGGL ESVNFQTAAD QARGLINAWV ESQTNGIIRN ILQPSSVDSQ TAMVLVNAIA   180
FKGLWEKAFK AEDTQTIPFR VTEQESKPVQ MMYQIGSFKV ASMASEKMKI LELPFASGTM   240
SMLVLLPDDV SGLEQLESII SFEKLTEWTS SSIMEERKVK VYLPRMKMEE KYNLTSLLMA   300
```

```
MGITDLFSSS ANLSGISSVG SLKISQAVHA AHAEINEAGR DVVGSAEAGV DATEEFRADH    360
PFLFCVKHIE TNAILLFGRC VSP                                            383

SEQ ID NO: 813           moltype = AA  length = 417
FEATURE                  Location/Qualifiers
source                   1..417
                         mol_type = protein
                         organism = Bambusicola thoracicus
SEQUENCE: 813
YYRVPCMVLC TAFHPYIFIV LLFALDNSEF TMGSIGAVSM EFCFDVFKEL RVHHPNENIF     60
FCPFAIMSAM AMVYLGAKDS TRTQINKVIR FDKLPGFGDS TEAQCGKSAN VHSSLKDILN    120
QITKPNDVYS FSLASRLYAD ETYSIQSEYL QCVNELYRGG LESINFQTAA DQARELINSW    180
VESQTNGIIR NVLQPSSVDS QTAMVLVNAI VFRGLWEKAF KDEDTQTMPF RVTEQESKPV    240
QMMYQIGSFK VASMASEKMK ILELPLASGT MSMLVLLPDE VSGLEQLETT ISFEKLTEWT    300
SSNVMEERKI KVYLPRMKME EKYNLTSVLM AMGITDLFRS SANLSGISLA GNLKISQAVH    360
AAHAEINEAG RKAVSSAEAG VDATSVSEEF RADRPFLFCI KHIATKVVFF FGRYTSP       417

SEQ ID NO: 814           moltype = AA  length = 386
FEATURE                  Location/Qualifiers
source                   1..386
                         mol_type = protein
                         organism = Numida Meleagris
SEQUENCE: 814
MASIGAVSTE FCVDVYKELR VHHANENIFY SPFTIISTLA MVYLGAKDST RTQINKVVRF     60
DKLPGFGDSI EAQCGTSVNV HSSLRDILNQ ITKPNDVYSF SLASRLYAEE TYPILPEYLQ    120
CVKELYRGGL ESINFQTAAD QARELINSWV ESQTSGIIKN VLQPSSVDSQ TAMVLVNAIY    180
FKGLWERAFK DEDTQAIPFR VTEQESKPVQ MMSQIGSFKV ASVASEKVKI LELPFVSGTM    240
SMLVLLPDEV SGLEQLESTI STEKLTEWTS SSIMEERKIK VFLPRMRMEE KYNLTSVLMA    300
MGMTDLFSSS ANLSGISSAE SLKISQAVHA AYAEIYEAGR EVVSSAEAGV DATSVSEEFR    360
VDHPFLLCIK HNPTNSILFF GRCISP                                         386

SEQ ID NO: 815           moltype = AA  length = 411
FEATURE                  Location/Qualifiers
source                   1..411
                         mol_type = protein
                         organism = Numida Meleagris
SEQUENCE: 815
MALCKAFHPY IFIVLLFDVD NSAFTMASIG AVSTEFCVDV YKELRVHHAN ENIFYSPFTI     60
ISTLAMVYLG AKDSTRTQIN KVVRFDKLPG FGDSIEAQCG TSVNVHSSLR DILNQITKPN    120
DVYSFSLASR LYAEETYPIL PEYLQCVKEL YRGGLESINF QTAADQAREL INSWVESQTS    180
GIIKNVLQPS SVNSQTAMVL VNAIYFKGLW ERAFKDEDTQ AIPFRVTEQE SKPVQMMSQI    240
GSFKVASVAS EKVKILELPF VSGTMSMLVL LPDEVSGLEQ LESTISTEKL TEWTSSSIME    300
ERKIKVFLPR MRMEEKYNLT SVLMAMGMTD LFSSSANLSG ISSAESLKIS QAVHAAYAEI    360
YEAGREVVSS AEAGVDATSV SEEFRVDHPF LLCIKHNPTN SILFFGRCIS P             411

SEQ ID NO: 816           moltype = AA  length = 411
FEATURE                  Location/Qualifiers
source                   1..411
                         mol_type = protein
                         organism = Odontophorus gujanensis
SEQUENCE: 816
RILCMAFHPY IFIVLLFAPD NSEFTMGSIG AVSTEFCFDV FKELKVHHAN ENIFYSPFTI     60
ISALAMVYLG AKDSTRTQIN KVVRFDKLPG FGDSIEAQCG TSVNVHSSLR DILNQITKPN    120
DFYSFSLASR LYADEAYPIL PEYLQCVKEL YRGGLESINF QTAADQAREL INSWVESQTS    180
GIIRNVLQPS SVDSQTAIVL VNAIYFKALW KKGFKNEDTQ AIPFRVTEQE SKSVQMMQQI    240
GTFKVASVAS EKMKILELPF ASGTMSMWVL LPDEVSDLEQ LETTISFEKL TEWTSSNIME    300
ERKIKVFLPR MKMEEKYNLT SVLMAMGMTD LFSSSANLSG ISSAESLKIS QAVHAAYAEI    360
YEAGSEVVGS AEAGVDATSA TEEFRVDRPF LFCIKHNPTN SILFFGRCIS P             411

SEQ ID NO: 817           moltype = AA  length = 383
FEATURE                  Location/Qualifiers
source                   1..383
                         mol_type = protein
                         organism = Coturnix japonica
SEQUENCE: 817
MGSIGAASME FCFDVFKELK VHHANDNMLY SPFAILSTLA MVFLGAKDST RTQINKVVHF     60
DKLPGFGDSI EAQCGTSANV HSSLRDILNQ ITKQNDAYSF SLASRLYAQE TYTVVPEYLQ    120
CVKELYRGGL ESVNFQTAAD QARGLINAWV ESQTNGIIKN ILQPSSVDSQ TAMVLVNAIA    180
FKGLWEKAFK AEDTQTIPFR VTEQESKPVQ MMHQIGSFKV ASMASEKMKI LELPFASGTM    240
SMLVLLPDDV SGLEQLESTI SFEKLTEWTS SSIMEERKVK VYLPRMKMEE KYNLTSLLMA    300
MGITDLFSSS ANLSGISSVG SLKISQAVHA AYAEINEAGR DVVGSAEAGV DATEEFRADH    360
PFLFCVKHIE TNAILLFGRC VSP                                            383

SEQ ID NO: 818           moltype = AA  length = 408
FEATURE                  Location/Qualifiers
source                   1..408
                         mol_type = protein
                         organism = Coturnix japonica
SEQUENCE: 818
```

```
MGLCTAFHPY IFIVLLFALD NSEFTMGSIG AASMEFCFDV FKELKVHHAN DNMLYSPFAI    60
LSTLAMVFLG AKDSTRTQIN KVVHFDKLPG FGDSIEAQCG TSANVHSSLR DILNQITKQN   120
DAYSFSLASR LYAQETYTVV PEYLQCVKEL YRGGLESVNF QTAADQARGL INAWVESQTN   180
GIIRNILQPS SVDSQTAMVL VNAIAFKGLW EKAFKAEDTQ TIPFRVTEQE SKPVQMMHQI   240
GSFKVASMAS EKMKILELPF ASGTMSMLVL LPDDVSGLEQ LESTISFEKL TEWTSSSIME   300
ERKVKVYLPR MKMEEKYNLT SLLMAMGITD LFSSSANLSG ISSVGSLKIS QAVHAAYAEI   360
NEAGRDVVGS AEAGVDATEE FRADHPFLFC VKHIETNAIL LFGRCVSP                408

SEQ ID NO: 819          moltype = AA   length = 383
FEATURE                 Location/Qualifiers
source                  1..383
                        mol_type = protein
                        organism = Coturnix coturnix
SEQUENCE: 819
MGSIGAASME FCFDVFKELK VHHANDNMLY SPFAILSTLA MVFLGAKDST RTQINKVVHF    60
DKLPGFGDSI EAQCGTSANV HSSLRDILNQ ITKQNDAYSF SLASRLYAQE TYTVVPEYLQ   120
CVKELYRGGL ESVNFQTAAD QARGLINAWV ESQTNGIIRN ILQPSSVDSQ TAMVLVNAIA   180
FKGLWEKAFK AEDTQTIPFR VTEQESKPVQ MMHQIGSFKV ASMASEKMKI LELPFASGTM   240
SMLVLLPDDV SGLEQLESTI SFEKLTEWTS SSIMEERKVK VYLPRMKMEE KYNLTSLLMA   300
MGITDLFSSS ANLSGISSVG SLKIPQAVHA AYAEINEAGR DVVGSAEAGV DATEEFRADH   360
PFLFCVKHIE TNAILLFGRC VSP                                          383

SEQ ID NO: 820          moltype = AA   length = 388
FEATURE                 Location/Qualifiers
source                  1..388
                        mol_type = protein
                        organism = Phasianus colchicus
SEQUENCE: 820
MGSIGAVSME FCFDVLKELK VHHANENYFY APFTMFSALA MIYLGAKDST RAQINKVVRF    60
DKLPGFGDSI EAQCGTSADP QVHSSLRDIL NQITKPNDAY SFSLASRLYA DEKYSIVPEY   120
LKCVKELYRG DVESINFQTA ADQARGLINS WVESQTNGMI KNVLQPSSVD SQTAMVLVNA   180
VVFKGLWEKA FKEEDTQAIP FRVTEQESKP VQMMHQIGLF KVASVPSEKM KILELPFASG   240
TMSMWVLLPD EVSGLEQLET TISFEKMTEW TSSNIMEERK IRVYLPRMKM EEKYNLTSIL   300
MAMGMTDLFS SSANLSGISS VGSLKISQAV HAAYAEIYEA GREVAGSAEA AMDATSVSEE   360
FRVDHPFLYC IKHNPSNTLL FLGRCIFP                                     388

SEQ ID NO: 821          moltype = AA   length = 413
FEATURE                 Location/Qualifiers
source                  1..413
                        mol_type = protein
                        organism = Phasianus colchicus
SEQUENCE: 821
MALCTAFHPY VFIILLFALD NSEFTMGSIG AVSMEFCFDV LKELKVHHAN ENYFYAPFTM    60
FSALAMIYLG AKDSTRAQIN KVVRFDKLPG FGDSIEAQCG TSADPQVHSS LRDILNQITK   120
PNDAYSFSLA SRLYADEKYS IVPEYLKCVK ELYRGDVESI NFQTAADQAR GLINSWVESQ   180
TNGMIKNVLQ PSSVDSQTAM VLVNAVVFKG LWEKAFKEED TQAIPFRVTE QESKPVQMMH   240
QIGLFKVASV PSEKMKILEL PFASGTMSMW VLLPDEVSGL EQLETTISFE KMTEWTSSNI   300
MEERKIRVYL PRMKMEEKYN LTSILMAMGM TDLFSSSANL SGISSVGSLK ISQAVHAAYA   360
EIYEAGREVA GSAEAAMDAT SVSEEFRVDH PFLYCIKHNP SNTLLFLGRC IFP          413

SEQ ID NO: 822          moltype = AA   length = 411
FEATURE                 Location/Qualifiers
source                  1..411
                        mol_type = protein
                        organism = Penelope pileate
SEQUENCE: 822
IALRTAYPPY IVIVLLFALD NSEFTMASIG AVSTEFCFNV FRELKVQHAN ENIFYCPFTI    60
FSALAFAYLG AKENTRTQIN KVAHFDKLPG FGDSIEAQCG TSANVHSSLR DILNQITKPS   120
DNYSLSLASR LYVDERYPIL PEYLQCVKEL YRGGVEPITF QTAADQAREL INSWVESQTN   180
GMIKNILQPS SVDSQTAMVL VNAVYFKGMW QKAFKNEDTQ EMPFRITENE SKPVQMMHQI   240
GSFKIATVAS EKLKILELPY ASGMMSMLVL LPDQASGLEQ LENTISFEKL NEWTSSNMVE   300
ERRIKVYLPR MKMEEKYNLT AVLTALGITD LFSPSANLSG ISSAASLKIS QAVHAAYAEI   360
YEAGRDVVGS AEAGVDATSV TDEFRVDHPF LFCMKHNPSN SIVFLGKCVS P            411

SEQ ID NO: 823          moltype = AA   length = 409
FEATURE                 Location/Qualifiers
source                  1..409
                        mol_type = protein
                        organism = Anseranas semipalmata
SEQUENCE: 823
CTAFHHYIVI VLLLFALDNS DFTMGSIGAA SAEFCFDVFK ELKVHHANEN ICYSPLSIIS    60
ALAMVYLGAR DNTRTQIDKV VHFDQIPGFG ESIESQCGTS VSVHSSLTDI LTQITKPSDN   120
YSFSLASRLY AEETYPILPE YLQCVKELYK GGLESISFQT AADQARELIN SWVESQTNGI   180
IKNILQPSSV DSQTAMVLVN AIYFKGMWEK AFKDENTQEM PFRVTEQESK PVQMMFQFGS   240
FKVATVASEK VKILELPYAS GMISMCVLLP DEVSGLEQIE NTISLEKLTE WTSSNMEER    300
RMKVYLPRMK LEEQYNLTSV LMALGMTDLS SPSANLSGIS SAESLKISEA VHAAYVEIYE   360
AGREVVGSAE AGMDVSSVSE EFRVDHPFLF LIKHNPSNSI LFFGRLISP               409

SEQ ID NO: 824          moltype = AA   length = 412
```

```
FEATURE              Location/Qualifiers
source               1..412
                     mol_type = protein
                     organism = Chauna torquata
SEQUENCE: 824
HYVCTAFHHH TVIVLLLFAL DNSDFTMGSI GAASTEFCFD VFKELKVQHV NGNIFYSPLS    60
IISALAMVYL GARDNTRTQI DKVVHFDKIP GFGESIEAQC GTSESVHSSL KDILTQITKP   120
SDNFSLSLAS RLYAEETYPI LPEYLQCVKE LYKGGLESVS FQTAADQARE LISSWVESQT   180
NGIIKNILQP SSVDSQTEMV LVNAIYFKGM WEKAFKDEDT QTMPFRITEQ ESKPMQMMYQ   240
VGSFKVAVVA SEKMKILELP YASGMMSMWV LLPDEVSGLE QLETTISFEK LTEWTSSNMM   300
EERRMKVYLP RMKMEEKYNL TSVLIALGMT DLFSSSANLS GISSAESLKM SEAVHAAYVE   360
IYEAGREVVG SAEAGMDVTS VSEEFKADRP FLFLIKHNPT NSILFFGRWI SP           412

SEQ ID NO: 825       moltype = AA  length = 386
FEATURE              Location/Qualifiers
source               1..386
                     mol_type = protein
                     organism = Anas platyrhynchos
SEQUENCE: 825
MGSIGAASTE FCFDVFRELR VQHVNENIFY SPFSIISALA MVYLGARDNT RTQIDKVVHF    60
DKLPGFGESM EAQCGTSVSV HSSLRDILTQ ITKPSDNFSL SFASRLYAEE TYAILPEYLQ   120
CVKELYKGGL ESISFQTAAD QARELINSWV ESQTNGIIKN ILQPSSVDSQ TTMVLVNAIY   180
FKGMWEKAFK DEDTQAMPFR MTEQESKPVQ MMYQVGSFKV AMVTSEKMKI LELPFASGMM   240
SMFVLLPDEV SGLEQLESTI SFEKLTEWTS STMMEERRMK VYLPRMKMEE KYNLTSVFMA   300
LGMTDLFSSS ANMSGISSTV SLKMSEAVHA ACVEIFEAGR DVVGSAEAGM DVTSVSEEFR   360
ADHPLFFFIK HNPTNSILFF GRWMSP                                        386

SEQ ID NO: 826       moltype = AA  length = 386
FEATURE              Location/Qualifiers
VARIANT              45
                     note = X is any amino acid
source               1..386
                     mol_type = protein
                     organism = Anas platyrhynchos
SEQUENCE: 826
MGSIGAASTE FCFDVFRELR VQHVNENIFY SPFSIISALA MVYLXARDNT RTQIDKVVHF    60
DKLPGFGESM EAQCGTSVSV HSSLRDILTQ ITKPSDNFSL SFASRLYAEE TYAILPEYLQ   120
CVKELYKGGL ESISFQTAAD QARELINSWV ESQTNGIIKN ILQPSSVDSQ TTMVLVNAIY   180
FKGMWEKAFK DEDTQAMPFR MTEQESKPVQ MMYQVGSFKV AMVTSEKMKI LELPFASGMM   240
SMFVLLPDEV SGLEQLESTI SFEKLTEWTS STMMEERRMK VYLPRMKMEE KYNLTSVFMA   300
LGMTDLFSSS ANMSGISSTV SLKMSEAVHA ACVEIFEAGR DVVGSAEAGM DVTSVSEEFR   360
ADHPLFFFIK HNPTNSILFF GRWMSP                                        386

SEQ ID NO: 827       moltype = AA  length = 386
FEATURE              Location/Qualifiers
source               1..386
                     mol_type = protein
                     organism = Cygnus atratus
SEQUENCE: 827
MGSIGAASTE FCFDVFRELK VQHVNENIFY SPLSIISALA MVYLGARDNT RAQIDKVVHF    60
DKIPGFGESM ESQCGTSVSV HSSLRDILTE ITKPSDNFSL SFASRLYAEE TYTILPEYLQ   120
CVKELYKGGL ESISFQTAAD QARELINSWV ESQTNGIIKN ILQPSSVDSQ TTMVLVNAIY   180
FKGMWEKAFK DEDTQTMPFR MTEQESKPVQ MMYQVGSFKV ATVTSEKVKI LELPFASGMM   240
SMCVLLPDEV SGLEQLETTI SFEKLTEWTS STMMEERRMK VYLPRMKMEE KYNLTSVFMA   300
LGMTDLFSSS ANMSGISSTV SLKMSEAVHA ACVEIFEAGR DVVGSAEAGM DVTSVSEEFR   360
ADHPLFFFIK HNPTNSILFF GRWISP                                        386

SEQ ID NO: 828       moltype = AA  length = 386
FEATURE              Location/Qualifiers
source               1..386
                     mol_type = protein
                     organism = Anser cygnoides
SEQUENCE: 828
MGSIGAASTE FCFDVFRELK VQHVNENIFY SPLSIISALA MVYLGARDNT RTQIDQVVHF    60
DKIPGFGESM EAQCGTSVSV HSSLRDILTE ITKPSDNFSL SFASRLYAEE TYTILPEYLQ   120
CVKELYKGGL ESISFQTAAD QARELINSWV ESQTNGIIKN ILQPSSVDSQ TTMVLVNAIY   180
FKGMWEKAFK DEDTQTMPFR MTEQESKPVQ MMYQVGSFKL ATVTSEKVKI LELPFASGMM   240
SMCVLLPDEV SGLEQLETTI SFEKLTEWTS STMMEERRMK VYLPRMKMEE KYNLTSVFMA   300
LGMTDLFSSS ANMSGISSTV SLKMSEAVHA ACVEIFEAGR DVVGSAEAGM DVTSVSEEFR   360
ADHPLFFFIK HNPSNSILFF GRWISP                                        386

SEQ ID NO: 829       moltype = DNA  length = 714
FEATURE              Location/Qualifiers
misc_feature         1..714
                     note = eGFP
source               1..714
                     mol_type = other DNA
                     organism = synthetic construct
SEQUENCE: 829
```

```
gtgagcaagg gcgaggagct gttcaccggg gtggtgccca tcctggtcga gctggacggc  60
gacgtaaacg gccacaagtt cagcgtgtcc ggcgagggcg agggcgatgc cacctacggc 120
aagctgaccc tgaagttcat ctgcaccacc ggcaagctgc ccgtgccctg gcccaccctc 180
gtgaccacct tcacctacgg cgtgcagtgc ttcagccgct accccgacca catgaagcag 240
cacgacttct tcaagtccgc catgcccgaa ggctacgtcc aggagcgcac catcttcttc 300
aaggacgacg gcaactacaa gacccgcgcc gaggtgaagt tcgagggcga caccctggtg 360
aaccgcatcg agctgaaggg catcgacttc aaggaggacg gcaacatcct ggggcacaag 420
ctggagtaca actacaacag ccacaacgtc tatatcatgg ccgacaagca gaagaacggc 480
atcaaggtga acttcaagat ccgccacaac atcgaggacg gcagcgtgca gctcgccgac 540
cactaccagc agaacacccc catcggcgac ggccccgtgc tgctgcccga caaccactac 600
ctgagcaccc agtccgccct gagcaaagac cccaacgaga gcgcgatca catggtcctg 660
ctggagttcg tgaccgccgc cgggatcact cacggcatgg acgagctgta caag        714

SEQ ID NO: 830          moltype = DNA  length = 714
FEATURE                 Location/Qualifiers
misc_feature            1..714
                        note = eGFP1
source                  1..714
                        mol_type = other DNA
                        organism = synthetic construct
SEQUENCE: 830
gtgagtaagg gtgaagagct gttcacaggc gtcgttccca tccttgttga gttggatgga  60
gacgtgaacg gccataagtt ctctgtgagt ggtgagggag agggtgatgc aacttatggc 120
aaattgacat tgaagttcat atgtactact ggcaaattgc ccgtgccttg gcccaccttg 180
gtaaccacat tcacttatgg ggttcaatgt ttctccaggt atccagatca catgaagcag 240
catgatttct ttaagtccgc tatgcctgaa ggttacgtcc aggagcgcac tatattttt  300
aaagacgatg gaaactataa gacccagggct gaggtgaagt ttgaaggtga cactctcgtc 360
aaccgtatag aactgaaagg gatagacttc aaggaggatg gaaacatttt ggggcataag 420
ttggaataca attataactc ccataatgtc tatataatgg cagataagca gaagaatggc 480
attaaagtaa acttcaaaat aagacataac attgaagacg gctcagtcca gctcgccgac 540
cattaccaac aaaacacacc cataggagac ggtcctgtcc tgcttcccga caatcactac 600
ctgtcaactc agtccgccct gtccaaggac ccaaatgaaa agagagacca tatggtgctt 660
ctggaatttg tcacagccgc aggaatcaca catggcatgg atgaacttta taag        714

SEQ ID NO: 831          moltype = DNA  length = 714
FEATURE                 Location/Qualifiers
misc_feature            1..714
                        note = eGFP2
source                  1..714
                        mol_type = other DNA
                        organism = synthetic construct
SEQUENCE: 831
gtgtccaaag gagaagaact gttcactggt gtagtcccta ttctcgttga actggacggc  60
gatgtgaatg gacataaatt ttccgtttcc ggggagggtg aaggagatgc aacctacggt 120
aaactgactc ttaaatttat atgtactaca gggaagttgc cagtaccctg gccaaccctt 180
gttacaacct tcacatatgg tgtacaatgt ttctcccgct atcccgatca tatgaagcag 240
catgattttt tcaagagtgc tatgccagaa ggttacgttc aggaaagaac catcttcttc 300
aaagacgacg ggaactacaa gaccagggca gaagtcaaat tcgaagggga tacttttgta 360
aatcgtattg agctgaaagg tattgatttc aaggaggacg gtaacattct tggtcacaaa 420
ttggaatata actataactc acataacgtg tatataatgg ccgataagca gaagaacgga 480
attaaggtaa actttaagat tagacacaac ataggaggatg gttcagtcca attggcagat 540
cattatcaac agaacacacc cataggagac ggtcccgtcc tgctgcctga taaccactac 600
ctctcaacac agtccgcact cagtaaagac ccaaatgaga aacgtgacca catggttctt 660
ctcgaatttg tgacagctgc tggtatcact catggtatgg atgagcttta caag        714
```